US009783601B2

(12) United States Patent
Garcia-Martinez et al.

(10) Patent No.: US 9,783,601 B2
(45) Date of Patent: *Oct. 10, 2017

(54) METHODS OF PREVENTING INFLAMMATION AND TREATING PAIN USING ANTI-NGF COMPOSITIONS

(75) Inventors: Leon F. Garcia-Martinez, Woodinville, WA (US); Benjamin H. Dutzar, Seattle, WA (US); Ethan W. Ojala, Snohomish, WA (US); Jeffrey T. L. Smith, Bellevue, WA (US); John A. Latham, Seattle, WA (US)

(73) Assignee: ALDERBIO HOLDINGS LLC, Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/308,831

(22) Filed: Dec. 1, 2011

(65) Prior Publication Data

US 2012/0141484 A1 Jun. 7, 2012

Related U.S. Application Data

(60) Provisional application No. 61/418,832, filed on Dec. 1, 2010.

(51) Int. Cl.

| | |
|---|---|
| ***A61K 39/395*** | (2006.01) |
| ***C07K 16/22*** | (2006.01) |
| ***A61K 51/10*** | (2006.01) |
| ***C07K 16/28*** | (2006.01) |
| ***A61K 45/06*** | (2006.01) |
| *A61K 39/00* | (2006.01) |

(52) U.S. Cl.

CPC .......... *C07K 16/22* (2013.01); *A61K 39/3955* (2013.01); *A61K 45/06* (2013.01); *A61K 51/1021* (2013.01); *C07K 16/2875* (2013.01); *A61K 2039/505* (2013.01); *C07K 2317/24* (2013.01); *C07K 2317/41* (2013.01); *C07K 2317/55* (2013.01); *C07K 2317/565* (2013.01); *C07K 2317/622* (2013.01); *C07K 2317/76* (2013.01); *C07K 2317/92* (2013.01); *C07K 2317/94* (2013.01)

(58) Field of Classification Search

CPC .......................... A61K 38/185; A61K 2121/00

See application file for complete search history.

(56) References Cited

U.S. PATENT DOCUMENTS

| | | | |
|---|---|---|---|
| 4,230,691 | A | 10/1980 | Young |
| 5,180,820 | A | 1/1993 | Barde et al. |
| 5,453,361 | A | 9/1995 | Yancopoulos et al. |
| 5,604,202 | A | 2/1997 | Kessler et al. |
| 5,653,975 | A | 8/1997 | Baetge et al. |
| 5,656,435 | A | 8/1997 | Nakahama et al. |
| 5,656,481 | A | 8/1997 | Baetge et al. |
| 5,672,683 | A | 9/1997 | Friden et al. |
| 5,683,894 | A | 11/1997 | Edwards et al. |
| 5,688,911 | A | 11/1997 | Schneider et al. |
| 5,712,100 | A | 1/1998 | Nakahama et al. |
| 5,731,284 | A | 3/1998 | Williams |
| 5,753,225 | A | 5/1998 | Clary et al. |
| 5,795,790 | A | 8/1998 | Schinstine et al. |
| 5,830,462 | A | 11/1998 | Crabtree et al. |
| 5,844,092 | A | 12/1998 | Presta et al. |
| 5,869,337 | A | 2/1999 | Crabtree et al. |
| 5,877,016 | A | 3/1999 | Presta et al. |
| 5,908,623 | A | 6/1999 | Baetge et al. |
| 5,977,307 | A | 11/1999 | Friden et al. |
| 5,990,129 | A | 11/1999 | Bryant et al. |
| 6,011,004 | A | 1/2000 | Kessler et al. |
| 6,017,878 | A | 1/2000 | Saragovi et al. |
| 6,024,734 | A | 2/2000 | Brewitt |
| 6,043,082 | A | 3/2000 | Crabtree et al. |
| 6,046,047 | A | 4/2000 | Crabtree et al. |
| 6,063,768 | A | 5/2000 | First |
| 6,096,716 | A | 8/2000 | Hayes et al. |
| 6,140,120 | A | 10/2000 | Crabtree et al. |
| 6,153,189 | A | 11/2000 | Presta et al. |
| 6,165,787 | A | 12/2000 | Crabtree et al. |
| 6,211,142 | B1 | 4/2001 | Hammonds et al. |
| 6,262,239 | B1 | 7/2001 | Wallach et al. |
| 6,271,205 | B1 | 8/2001 | Ross et al. |
| 6,280,732 | B1 | 8/2001 | Caras et al. |
| 6,291,247 | B1 | 9/2001 | Riopelle et al. |
| 6,299,895 | B1 | 10/2001 | Hammang et al. |
| 6,333,310 | B1 | 12/2001 | Presta et al. |

(Continued)

FOREIGN PATENT DOCUMENTS

| | | |
|---|---|---|
| CN | 101633694 | 1/2010 |
| JP | 2007320967 | 12/2007 |

(Continued)

OTHER PUBLICATIONS

Jackowski, British Journal of Neurosurgery 9: 303-317 (1995).*
Geysen et al., Journal of Molecular Recognition 1: 32-41 (1988).*
Giusti et al., Proc. Natl. Acad. Sci. USA 84(9):2926-2930 (1987).*
Winkler et al., J. Imm. 265:4505-4514 (2000).*
Chien et al., Proc. Natl. Acad. Sci. USA 86(14): 5532-5536 (1989).*
Caldas et al., Mol. Immunol. 39(15): 941-952 (2003).*
Halvorson KG, et al. "A blocking antibody to nerve growth factor attenuates skeletal pain induced by prostate tumor cells growing in bone," Cancer Res. Oct. 15, 2005;65(20):9426-35.
Hongo JS, et al. "Antibody binding regions on human nerve growth factor identified by homolog- and alanine-scanning mutagenesis," Hybridoma. Jun. 2000;19(3):215-27.
Lane NE, et al. "Tanezumab Relieves Moderate to Severe Pain Due to Osteoarthritis (OA) of the Knee: A Phase 2 Trial," Internet Citation, Jan. 2008, p. 1, XP007916873; URL: https://acr.confex.com/acr/2008/webprogram/Paper3546.html.
MacCallum RM, et al. "Antibody-antigen interactions: contact analysis and binding site topography," J Mol Biol. Oct. 11, 1996;262(5):732-45.

(Continued)

*Primary Examiner* — Robert C Hayes

(74) *Attorney, Agent, or Firm* — Robin L. Teskin; LeClairRyan, A Professional Corporation

(57) ABSTRACT

Monovalent agents, including Fab fragments and monovalent monoclonal antibodies analogous to MetMab, having binding specificity to human Nerve Growth Factor ("NGF"), and methods treating pain in an individual wherein there is no substantial increase in the inflammatory response of the individual following administration of the monovalent agents.

19 Claims, 96 Drawing Sheets

(56) References Cited

U.S. PATENT DOCUMENTS 6,355,858 B1 3/2002 Gibbins
6,365,373 B2 4/2002 Presta et al.
6,391,312 B1 5/2002 Kishino et al.
6,417,159 B1 7/2002 Riopelle et al.
6,428,579 B1 8/2002 Valentini
6,440,928 B1 8/2002 Ishii
6,485,480 B1 11/2002 Brewitt
6,503,713 B1 1/2003 Rana
6,503,728 B1 1/2003 Urfer et al.
6,548,062 B2 4/2003 Buchkovich et al.
6,555,111 B2 4/2003 Wallach et al.
6,596,269 B1 7/2003 Iadarola et al.
6,610,500 B1 8/2003 Saragovi et al.
6,630,478 B2 10/2003 Diamond et al.
6,630,490 B2 10/2003 Diamond et al.
6,652,864 B1 11/2003 Webb et al.
6,656,465 B2 12/2003 Clary et al.
6,680,292 B1 1/2004 Guillemin et al.
6,719,970 B1 4/2004 Costantino et al.
6,806,251 B2 10/2004 Lamb
6,866,842 B1 3/2005 Chancellor et al.
6,887,861 B1 5/2005 Hill et al.
6,919,426 B2 7/2005 Boone et al.
7,144,983 B1 12/2006 Urfer et al.
7,169,568 B2 1/2007 Chao et al.
7,205,387 B2 4/2007 Wang et al.
7,252,822 B2 8/2007 Shelton et al.
7,255,860 B2 8/2007 Shelton et al.
7,282,482 B2 10/2007 Bartke et al.
7,342,146 B2 3/2008 Tsai et al.
7,425,329 B2 9/2008 Shelton et al.
7,449,616 B2 11/2008 Pons et al.
7,452,863 B1 11/2008 Presta et al.
7,459,156 B2 12/2008 Clary et al.
7,569,364 B2 8/2009 Rosenthal et al.
7,601,352 B1 10/2009 Novak
7,601,818 B2 10/2009 Wild, Jr. et al.
7,612,181 B2 11/2009 Wu et al.
7,615,383 B2 11/2009 Devaux et al.
7,655,231 B2 2/2010 Shelton et al.
7,655,232 B2 2/2010 Pons et al.
7,678,378 B2 3/2010 Webb et al.
7,718,605 B2 5/2010 Webb et al.
7,727,527 B2 6/2010 Shelton
7,750,122 B2 7/2010 Cho et al.
7,785,588 B2 8/2010 Klein et al.
7,795,413 B2 9/2010 Wild, Jr. et al.
7,846,891 B2 12/2010 Ellis-Behnke et al.
7,922,999 B2 4/2011 Bankiewicz
7,935,671 B2 5/2011 Urfer et al.
7,988,966 B2 8/2011 Pavone et al.
7,988,967 B2 8/2011 Macdonald et al.
8,007,800 B2 8/2011 Shelton et al.
8,034,346 B2 10/2011 Shelton et al.
8,088,384 B2 1/2012 Pons et al.
8,101,571 B2 1/2012 Presta et al.
8,106,167 B2 1/2012 Wild, Jr. et al.
8,124,724 B2 2/2012 Boone et al.
8,148,107 B2 4/2012 Macdonald et al.
8,163,018 B2 4/2012 Trieu
8,168,169 B2 5/2012 Cataldo et al.
8,183,219 B2 5/2012 Burright
8,198,410 B2 6/2012 Wild, Jr. et al.
8,226,951 B2 7/2012 Shelton et al.
8,246,956 B2 8/2012 Cattaneo et al.
8,257,696 B2 9/2012 Steindler et al.
8,257,710 B2 9/2012 Cattaneo et al.
8,258,268 B2 9/2012 Wu et al.
8,296,079 B2 10/2012 Cattaneo et al.
8,309,088 B2 11/2012 Macdonald et al.
8,420,779 B2 4/2013 Walker et al.
8,425,907 B2 4/2013 Macdonald et al.
8,426,673 B2 4/2013 Tanahashi et al.
8,435,523 B2 5/2013 Powell et al.
8,460,657 B2 6/2013 NykjæR et al.
8,461,110 B2 6/2013 Vitagliano et al.
8,475,788 B2 7/2013 Sing et al.
8,481,036 B2 7/2013 Shelton
8,486,401 B2 7/2013 Novak
8,513,241 B2 8/2013 Cervi et al.
8,540,990 B2 9/2013 Rosenthal et al.
8,557,245 B2 10/2013 Shelton et al.
8,591,898 B2 11/2013 Mills et al.
8,598,140 B2 12/2013 Schneider et al.
8,613,927 B2 12/2013 MacDonald et al.
8,637,031 B2 1/2014 MacDonald et al.
8,642,040 B2 2/2014 Mi et al.
8,674,071 B2 3/2014 Chan et al.
8,691,221 B2 4/2014 Pavone et al.
8,715,666 B2 5/2014 Pavone et al.
8,716,450 B2 5/2014 Ghayur et al.
8,722,019 B2 5/2014 Jefferies et al.
8,728,473 B2 5/2014 Garcia-Martinez et al.
2001/0019833 A1 9/2001 Wallach et al.
2001/0046959 A1 11/2001 Buchkovich et al.
2002/0004061 A1 1/2002 Panayotatos
2002/0012914 A1 1/2002 Bureau et al.
2002/0037280 A1 3/2002 Lieber et al.
2002/0045576 A1 4/2002 Rosenthal
2002/0051974 A1 5/2002 Dodge et al.
2002/0061327 A1 5/2002 Hammang et al.
2002/0086015 A1 7/2002 Gold
2002/0090682 A1 7/2002 Willson et al.
2002/0104104 A1 8/2002 Games et al.
2002/0110525 A1 8/2002 Adjei et al.
2002/0110526 A1 8/2002 Zhu et al.
2002/0110527 A1 8/2002 Zhu et al.
2002/0110528 A1 8/2002 Zhu et al.
2002/0110539 A1 8/2002 Zhu et al.
2002/0115173 A1 8/2002 Ben-Sasson
2002/0119117 A1 8/2002 Zhu et al.
2002/0128179 A1 9/2002 Tacon et al.
2002/0137126 A1 9/2002 Cares et al.
2002/0146416 A1 10/2002 Presta et al.
2002/0164333 A1 11/2002 Nemerow et al.
2002/0168338 A1 11/2002 Baird
2002/0177120 A1 11/2002 Elliott et al.
2002/0187551 A1 12/2002 Yoon
2002/0194630 A1 12/2002 Manning, Jr. et al.
2003/0008394 A1 1/2003 Yoon
2003/0008807 A1 1/2003 Levine et al.
2003/0027779 A1 2/2003 Neuman et al.
2003/0059945 A1 3/2003 Dzekunov et al.
2003/0073238 A1 4/2003 Dzekunov et al.
2003/0073653 A1 4/2003 Bureau et al.
2003/0082234 A1 5/2003 Seo et al.
2003/0096753 A1 5/2003 Robertson et al.
2003/0097667 A1 5/2003 Robertson et al.
2003/0143693 A1 7/2003 Silbiger et al.
2003/0152562 A1 8/2003 Mitrani
2003/0157099 A1 8/2003 Presta et al.
2003/0203383 A1 10/2003 Rosenthal
2003/0228312 A1 12/2003 Wallach et al.
2003/0232419 A1 12/2003 Kolodkin et al.
2003/0235580 A1 12/2003 Zhang
2004/0009149 A1 1/2004 Altman et al.
2004/0009589 A1 1/2004 Levenberg et al.
2004/0029169 A1 2/2004 He et al.
2004/0058393 A1 3/2004 Fukishima et al.
2004/0063610 A1 4/2004 Gold
2004/0071701 A1 4/2004 Delafoy et al.
2004/0077540 A1 4/2004 Quay
2004/0077545 A1 4/2004 Lipps et al.
2004/0097456 A1 5/2004 Paulista et al.
2004/0105840 A1 6/2004 Kinstler et al.
2004/0115671 A1 6/2004 Zlokovic et al.
2004/0131615 A1 7/2004 Shelton et al.
2004/0138155 A1 7/2004 Baird et al.
2004/0142388 A1 7/2004 Lamping et al.
2004/0185113 A1 9/2004 Mizushima et al.
2004/0197883 A1 10/2004 Dzekunov et al.
2004/0209801 A1 10/2004 Brand et al.
2004/0219144 A1 11/2004 Shelton
2004/0228862 A1 11/2004 Shelton et al.

(56) References Cited

U.S. PATENT DOCUMENTS

2004/0237124 A1 11/2004 Pons et al.
2004/0242847 A1 12/2004 Fukushima et al.
2004/0253244 A1 12/2004 Shelton et al.
2004/0258684 A1 12/2004 Fukushima et al.
2005/0008624 A1 1/2005 Peled et al.
2005/0027110 A1 2/2005 Russell et al.
2005/0037493 A1 2/2005 Mandalam et al.
2005/0054097 A1 3/2005 Peled et al.
2005/0069549 A1 3/2005 Herman
2005/0074435 A1 4/2005 Casper et al.
2005/0074821 A1 4/2005 Wild et al.
2005/0074865 A1 4/2005 Afeyan et al.
2005/0079200 A1 4/2005 Rathenow et al.
2005/0085417 A1 4/2005 Wickstrom et al.
2005/0119712 A1 6/2005 Shafer
2005/0123526 A1 6/2005 Shafer
2005/0142539 A1 6/2005 Herman
2005/0143336 A1 6/2005 Ramesh et al.
2005/0169882 A1 8/2005 Lowe et al.
2005/0220774 A1 10/2005 Peled et al.
2005/0221368 A1 10/2005 Rana
2005/0226871 A1 10/2005 Gold
2005/0260711 A1 11/2005 Datta et al.
2005/0265994 A1 12/2005 Shelton et al.
2005/0281781 A1 12/2005 Ostroff
2006/0050596 A1 3/2006 Abassi et al.
2006/0051818 A1 3/2006 Adriaenssens et al.
2006/0068469 A1 3/2006 Payne et al.
2006/0088936 A1 4/2006 Warrington et al.
2006/0093589 A1 5/2006 Warrington et al.
2006/0104973 A1 5/2006 He et al.
2006/0106203 A1 5/2006 Winter et al.
2006/0115874 A1 6/2006 Garrard et al.
2006/0140934 A1 6/2006 Gegg et al.
2006/0147450 A1 7/2006 Shelton
2006/0147932 A1 7/2006 Davies et al.
2006/0159666 A1 7/2006 Willing et al.
2006/0182724 A1 8/2006 Riordan
2006/0185025 A1 8/2006 Oshimura et al.
2006/0193825 A1 8/2006 Musso et al.
2006/0211619 A1 9/2006 Steward et al.
2006/0216751 A1 9/2006 Boschetti et al.
2006/0240007 A1 10/2006 Sanders
2006/0269478 A1 11/2006 Panayotatos
2006/0275290 A1 12/2006 Barbeito et al.
2006/0292114 A1 12/2006 Klein et al.
2006/0293240 A1 12/2006 Ron
2007/0015248 A1 1/2007 Anton et al.
2007/0020696 A1 1/2007 Zerial et al.
2007/0036751 A1 2/2007 Lode et al.
2007/0036797 A1 2/2007 Kim et al.
2007/0041972 A1 2/2007 Rother et al.
2007/0071675 A1 3/2007 Wu et al.
2007/0081992 A1 4/2007 Pardridge et al.
2007/0086942 A1 4/2007 Chang et al.
2007/0092968 A1 4/2007 Ji et al.
2007/0122904 A1 5/2007 Nordon
2007/0154524 A1 7/2007 Kauper et al.
2007/0160605 A1 7/2007 Shelton et al.
2007/0212357 A1 9/2007 Pons et al.
2007/0243132 A1 10/2007 Russell-Jones et al.
2007/0253907 A1 11/2007 Cattaneo et al.
2007/0264195 A1 11/2007 Nykiaer et al.
2007/0264265 A1 11/2007 Goldenberg et al.
2007/0269369 A1 11/2007 Gegg et al.
2007/0275412 A1 11/2007 Gama et al.
2008/0008999 A1 1/2008 Hankins
2008/0009537 A1 1/2008 Sakai
2008/0019940 A1 1/2008 Papisov
2008/0025968 A1 1/2008 Wallach et al.
2008/0025978 A1 1/2008 Hempstead et al.
2008/0033157 A1 2/2008 Wild et al.
2008/0038717 A1 2/2008 Garrard et al.
2008/0044428 A1 2/2008 Schofield
2008/0081040 A1 4/2008 Shelton et al.
2008/0095767 A1 4/2008 Jennings et al.
2008/0107658 A1 5/2008 Franks et al.
2008/0132427 A1 6/2008 Zhuang et al.
2008/0138855 A1 6/2008 Wang
2008/0138877 A1 6/2008 Dzekunov et al.
2008/0139790 A1 6/2008 Jennings et al.
2008/0182978 A1 7/2008 Rosenthal et al.
2008/0187966 A1 8/2008 Simmons
2008/0233088 A1 9/2008 Guha et al.
2008/0233140 A1 9/2008 Banchereau et al.
2008/0241170 A1 10/2008 Zurawski et al.
2008/0254044 A1 10/2008 Zurawski
2008/0254047 A1 10/2008 Banchereau et al.
2008/0255343 A1 10/2008 Jennings et al.
2008/0260757 A1 10/2008 Holt et al.
2008/0274077 A1 11/2008 Benowitz et al.
2008/0311078 A1 12/2008 Gokarn et al.
2008/0313749 A1 12/2008 Timmerman et al.
2008/0318314 A1 12/2008 Fulga et al.
2009/0004742 A1 1/2009 Mitchell et al.
2009/0012272 A1 1/2009 Gegg et al.
2009/0022683 A1 1/2009 Song et al.
2009/0022744 A1 1/2009 Gegg et al.
2009/0023901 A1 1/2009 Steward et al.
2009/0030308 A1 1/2009 Bradford et al.
2009/0030364 A1 1/2009 Harmon et al.
2009/0035257 A1 2/2009 Moseley et al.
2009/0035836 A1 2/2009 Datta et al.
2009/0041717 A1 2/2009 MacDonald et al.
2009/0041768 A1 2/2009 Gegg et al.
2009/0042229 A1 2/2009 Folkman et al.
2009/0047348 A1 2/2009 Song et al.
2009/0053786 A1 2/2009 Kao et al.
2009/0060864 A1 3/2009 Lode et al.
2009/0074779 A1 3/2009 Bock et al.
2009/0093024 A1 4/2009 Bowers et al.
2009/0123464 A1 5/2009 Pavone et al.
2009/0123468 A1 5/2009 Khan
2009/0148908 A1 6/2009 Paciotti et al.
2009/0155274 A1 6/2009 Wild, Jr. et al.
2009/0162380 A1 6/2009 Glaser et al.
2009/0175847 A1 7/2009 Barghorn et al.
2009/0181088 A1 7/2009 Song et al.
2009/0202433 A1 8/2009 Chang et al.
2009/0208490 A1 8/2009 Pavone et al.
2009/0220466 A1 9/2009 Ratajczak et al.
2009/0226439 A1 9/2009 Sanders
2009/0227655 A1 9/2009 Khan
2009/0232801 A1 9/2009 Hillen et al.
2009/0234104 A1 9/2009 Gegg et al.
2009/0252744 A1 10/2009 Shelton et al.
2009/0269346 A1 10/2009 Starr et al.
2009/0281286 A1 11/2009 Gregg et al.
2009/0286964 A1 11/2009 Gegg et al.
2009/0300780 A1 12/2009 Cattaneo et al.
2009/0304580 A1 12/2009 Goldenberg et al.
2009/0304693 A1 12/2009 Ghayur et al.
2009/0311253 A1 12/2009 Ghayur et al.
2009/0311718 A1 12/2009 Fukushima et al.
2010/0003679 A1 1/2010 Ichii et al.
2010/0009997 A1 1/2010 Oppenheimer et al.
2010/0011454 A1 1/2010 Kakeda et al.
2010/0016836 A1 1/2010 Makower et al.
2010/0034818 A1 2/2010 Wild, Jr. et al.
2010/0035236 A1 2/2010 Garrard et al.
2010/0047239 A1 2/2010 Wu et al.
2010/0048461 A1 2/2010 Saragovi
2010/0055109 A1 3/2010 Barbeito et al.
2010/0068137 A1 3/2010 Chang et al.
2010/0074900 A1 3/2010 Ghayur et al.
2010/0081172 A1 4/2010 Liu et al.
2010/0081794 A1 4/2010 Liu et al.
2010/0104652 A1 4/2010 Biris et al.
2010/0111970 A1 5/2010 Pons et al.
2010/0119492 A1 5/2010 Hans et al.
2010/0143355 A1 6/2010 Shelton et al.
2010/0166700 A1 7/2010 Charles
2010/0168625 A1 7/2010 Swain et al.
2010/0168720 A1 7/2010 Swain et al.

(56) References Cited

U.S. PATENT DOCUMENTS

| | | | |
|---|---|---|---|
| 2010/0168870 | A1 | 7/2010 | Swain et al. |
| 2010/0172871 | A1 | 7/2010 | Flannery et al. |
| 2010/0179515 | A1 | 7/2010 | Swain et al. |
| 2010/0189641 | A1 | 7/2010 | Chang et al. |
| 2010/0196266 | A1 | 8/2010 | Goldenberg et al. |
| 2010/0203044 | A1 | 8/2010 | Nikolaev et al. |
| 2010/0209447 | A1 | 8/2010 | Kumar-Singh et al. |
| 2010/0210523 | A1 | 8/2010 | Andersen et al. |
| 2010/0221250 | A1 | 9/2010 | Kim et al. |
| 2010/0254990 | A1 | 10/2010 | Shelton |
| 2010/0260775 | A1 | 10/2010 | Mills et al. |
| 2010/0260853 | A1 | 10/2010 | Basran et al. |
| 2010/0266496 | A1 | 10/2010 | Hansen et al. |
| 2010/0267573 | A1 | 10/2010 | Keene et al. |
| 2010/0267934 | A1 | 10/2010 | Van De Winkel et al. |
| 2010/0272636 | A1 | 10/2010 | Byrd et al. |
| 2010/0278839 | A1 | 11/2010 | Powell et al. |
| 2010/0291083 | A1 | 11/2010 | Pavone et al. |
| 2010/0330115 | A1 | 12/2010 | Zurawski et al. |
| 2011/0008251 | A1 | 1/2011 | Chang et al. |
| 2011/0014189 | A1 | 1/2011 | Soula et al. |
| 2011/0014208 | A1 | 1/2011 | Macdonald et al. |
| 2011/0033447 | A1 | 2/2011 | Rosenthal et al. |
| 2011/0033463 | A1 | 2/2011 | Thakker et al. |
| 2011/0034383 | A1 | 2/2011 | Arenzana et al. |
| 2011/0038865 | A1 | 2/2011 | Shin et al. |
| 2011/0040076 | A1 | 2/2011 | Wild, Jr. et al. |
| 2011/0044901 | A1 | 2/2011 | Seed et al. |
| 2011/0053221 | A1 | 3/2011 | Chen et al. |
| 2011/0059095 | A1 | 3/2011 | Macdonald et al. |
| 2011/0064653 | A1 | 3/2011 | Hansen et al. |
| 2011/0070188 | A1 | 3/2011 | Fowers et al. |
| 2011/0070607 | A1 | 3/2011 | Wang |
| 2011/0071216 | A1 | 3/2011 | Fowers et al. |
| 2011/0091463 | A1 | 4/2011 | Ghayur et al. |
| 2011/0091476 | A1 | 4/2011 | Wild, Jr. et al. |
| 2011/0091936 | A1 | 4/2011 | Gawlitzek et al. |
| 2011/0097341 | A1 | 4/2011 | Shelton |
| 2011/0104164 | A1 | 5/2011 | Cattaneo et al. |
| 2011/0105728 | A1 | 5/2011 | Cattaneo et al. |
| 2011/0110851 | A1 | 5/2011 | Chang et al. |
| 2011/0110852 | A1 | 5/2011 | Miller et al. |
| 2011/0123480 | A1 | 5/2011 | Wallach |
| 2011/0129462 | A1 | 6/2011 | Maggio |
| 2011/0145941 | A1 | 6/2011 | Benigni et al. |
| 2011/0151515 | A1 | 6/2011 | Heifetz et al. |
| 2011/0158905 | A1 | 6/2011 | Goldenberg et al. |
| 2011/0160439 | A1 | 6/2011 | Munck Petersen et al. |
| 2011/0171126 | A1 | 7/2011 | Burton et al. |
| 2011/0171217 | A1 | 7/2011 | Badkar et al. |
| 2011/0182912 | A1 | 7/2011 | Evans et al. |
| 2011/0189083 | A1 | 8/2011 | Chang et al. |
| 2011/0189206 | A1 | 8/2011 | Barbas, Iii |
| 2011/0191872 | A1 | 8/2011 | Cattaneo et al. |
| 2011/0195020 | A1 | 8/2011 | Chang et al. |
| 2011/0195124 | A1 | 8/2011 | Jin |
| 2011/0198286 | A1 | 8/2011 | Niazi |
| 2011/0206682 | A1 | 8/2011 | Novak |
| 2011/0212094 | A1 | 9/2011 | Ghayur et al. |
| 2011/0243841 | A1 | 10/2011 | Chang et al. |
| 2011/0243893 | A1 | 10/2011 | Axtell et al. |
| 2011/0243961 | A1 | 10/2011 | Shelton et al. |
| 2011/0250130 | A1 | 10/2011 | Benatuil et al. |
| 2011/0250206 | A1 | 10/2011 | Axtell et al. |
| 2011/0256053 | A1 | 10/2011 | Chang et al. |
| 2011/0256135 | A1 | 10/2011 | Fraunhofer et al. |
| 2011/0256150 | A1 | 10/2011 | Watts et al. |
| 2011/0256587 | A1 | 10/2011 | Macdonald et al. |
| 2011/0268725 | A1 | 11/2011 | Shelton |
| 2011/0268776 | A1 | 11/2011 | Schapira et al. |
| 2011/0293607 | A1 | 12/2011 | Labrijn et al. |
| 2012/0004643 | A1 | 1/2012 | Zurawski et al. |
| 2012/0009205 | A1 | 1/2012 | Gegg et al. |
| 2012/0014957 | A1 | 1/2012 | Ghayur et al. |
| 2012/0014968 | A1 | 1/2012 | Walsh et al. |
| 2012/0027847 | A1 | 2/2012 | Kusk et al. |
| 2012/0087858 | A1 | 4/2012 | Ghayur et al. |
| 2012/0093824 | A1 | 4/2012 | Macdonald et al. |
| 2012/0095193 | A1 | 4/2012 | Burden et al. |
| 2012/0141484 | A1 | 6/2012 | Garcia-Martinez et al. |
| 2012/0141485 | A1 | 6/2012 | Garcia-Martinez et al. |
| 2012/0148490 | A1 | 6/2012 | Dutzar et al. |
| 2012/0164067 | A1 | 6/2012 | Latham et al. |
| 2012/0164688 | A1 | 6/2012 | Macdonald et al. |
| 2012/0195900 | A1 | 8/2012 | Ghayur et al. |
| 2012/0201746 | A1 | 8/2012 | Liu et al. |
| 2012/0213784 | A1 | 8/2012 | Pavone et al. |
| 2012/0252717 | A1 | 10/2012 | Besman et al. |
| 2012/0315271 | A1 | 12/2012 | Shelton et al. |
| 2013/0004495 | A1 | 1/2013 | Shelton |
| 2013/0028892 | A1 | 1/2013 | Macdonald et al. |
| 2013/0058873 | A1 | 3/2013 | Jefferies et al. |
| 2013/0101601 | A1 | 4/2013 | King et al. |
| 2013/0183311 | A1 | 7/2013 | Nielsen et al. |
| 2013/0295112 | A1 | 11/2013 | Powell et al. |
| 2013/0302325 | A1 | 11/2013 | Rosenthal et al. |
| 2013/0330348 | A1 | 12/2013 | Lacy et al. |
| 2013/0336964 | A1 | 12/2013 | Rovati et al. |
| 2013/0336975 | A1 | 12/2013 | Dutzar et al. |
| 2013/0344064 | A1 | 12/2013 | Blein et al. |
| 2013/0344068 | A1 | 12/2013 | Garcia-Martinez et al. |
| 2014/0004115 | A1 | 1/2014 | Latham et al. |
| 2014/0004116 | A1 | 1/2014 | Garcia-Martinez et al. |
| 2014/0017235 | A1 | 1/2014 | Rosenthal et al. |
| 2014/0099254 | A1 | 4/2014 | Chang et al. |
| 2014/0147439 | A1 | 5/2014 | Gearing |
| 2014/0155582 | A1 | 6/2014 | Kamohara et al. |
| 2014/0170136 | A1 | 6/2014 | Gearing |

FOREIGN PATENT DOCUMENTS

| | | |
|---|---|---|
| WO | WO 2006/019266 | 3/2005 |
| WO | WO 2005/111077 | 11/2005 |
| WO | 2006031878 | 3/2006 |
| WO | WO 2006/077441 | 7/2006 |
| WO | WO 2006/110883 | 10/2006 |
| WO | WO 2006/131951 | 12/2006 |
| WO | WO 2009041643 | 4/2009 |

OTHER PUBLICATIONS

De Pascalis R, et al. "Grafting of "abbreviated" complementarity-determining regions containing specificity-determining residues essential for ligand contact to engineer a less immunogenic humanized monoclonal antibody," J Immunol. Sep. 15, 2002;169(6):3076-84.

Casset F, et al. "A peptide mimetic of an anti-CD4 monoclonal antibody by rational design," Biochem Biophys Res Commun. Jul. 18, 2003;307(1):198-205.

Chen Y, et al. "Selection and analysis of an optimized anti-VEGF antibody: crystal structure of an affinity-matured Fab in complex with antigen," J Mol Biol. Nov. 5, 1999;293(4):865-81.

Wu H, et al. "Humanization of a murine monoclonal antibody by simultaneous optimization of framework and CDR residues," J Mol Biol. Nov. 19, 1999;294(1):151-62.

Rudikoff S, et al. "Single amino acid substitution altering antigen-binding specificity," Proc Natl Acad Sci U S A. Mar. 1982;79(6):1979-83.

Colman PM, "Effects of amino acid sequence changes on antibody-antigen interactions," Res Immunol. Jan. 1994;145 (1):33-6.

Kobayashi N, et al. "Two-step in vitro antibody affinity maturation enables estradiol-17beta assays with more than 10-fold higher sensitivity," Anal Chem. Feb. 1, 2010;82(3):1027-38.

Hefti FF, et al. "Novel class of pain drugs based on antagonism of NGF," Trends Pharmacol Sci. Feb. 2006;27(2):85-91.

Yang TT, et al. "Optimized codon usage and chromophore mutations provide enhanced sensitivity with the green fluorescent protein," Nucleic Acids Res. Nov. 15, 1996;24(22):4592-3.

Hamdan FF, et al. "Codon optimization improves heterologous expression of a Schistosoma mansoni cDNA in HEK293 cells," Parasitol Res. Jun. 2002;88(6):583-6.

(56) References Cited

OTHER PUBLICATIONS

Sinclair G, et al. "Synonymous codon usage bias and the expression of human glucocerebrosidase in the methylotrophic yeast, Pichia pastoris," Protein Expr Purif. Oct. 2002;26(1):96-105.
Outchkourov NS, et al. "Optimization of the expression of equistatin in Pichia pastoris," Protein Expr Purif. Feb. 2002;24(1):18-24.
Giusti AM, et al. "Somatic diversification of S107 from an antiphosphocholine to an anti-DNA autoantibody is due to a single base change in its heavy chain variable region," Proc Natl Acad Sci U S A. May 1987;84(9):2926-30.
Winkler K, et al. "Changing the antigen binding specificity by single point mutations of an anti-p24 (HIV-1) antibody," J Immunol. Oct. 15, 2000;165(8):4505-14.
Chien NC, et al. "Significant structural and functional change of an antigen-binding site by a distant amino acid substitution: proposal of a structural mechanism," Proc Nati Acad Sci U S A. Jul. 1989;86(14):5532-6.
Caldas C, et al. "Humanization of the anti-CD18 antibody 6.7: an unexpected effect of a framework residue in binding to antigen," Mol Immunol. May 2003;39(15):941-52.
Steidl S, et al. "In vitro affinity maturation of human GM-CSF antibodies by targeted CDR-diversification," Mol Immunol. Nov. 2008;46(1):135-44.

* cited by examiner

Heavy_chain full length protein sequence.

QSLEESGGRLVTPGTPLTLTCTVSGFSLSSYAMSWVRQAPGKGLEWIGVITSIGSTVYAS
WAKGRFTISKTSTTVDLKITSPTTEDTATYFCARGYDDYDEMTYFNIWGQGTLVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYAST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO:4)

Variable_region heavy_chain protein sequence.

QSLEESGGRLVTPGTPLTLTCTVSGFSLSSYAMSWVRQAPGKGLEWIGVITSIGSTVYAS
WAKGRFTISKTSTTVDLKITSPTTEDTATYFCARGYDDYDEMTYFNIWGQGTLVTVSS
(SEQ ID NO:3)

Variable_region heavy_chain protein sequence. CDR1:Bold; CDR2: Underline; CDR3:Italics.

QSLEESGGRLVTPGTPLTLTCTVSGFSLSSYAMSWVRQAPGKGLEWIGVITSIGSTVYAS
WAKGRFTISKTSTTVDLKITSPTTEDTATYFCAR*GYDDYDEMTYFNI*WGQGTLVTVSS
(SEQ ID NOS: 8, 9, 10, respectively)

Variable_region heavy_chain DNA sequence. CDR1:Bold; CDR2: Underline; CDR3:Italics.

CAGTCGCTGGAGGAGTCCGGGGGTCGCCTGGTCACGCCTGGGACACCCCTGACACTCACC
TGCACAGTCTCTGGCTTCTCCCTCAGTAGCTATGCAATGAGCTGGGTCCGCCAGGCTCCA
GGGAAGGGGCTGGAATGGATCGGAGTCATTACTAGTATTGGTAGCACAGTCTACGCGAGC
TGGGCGAAAGGCCGATTCACCATCTCCAAAACCTCGACCACGGTGGATCTGAAAATCACC
AGTCCGACAACCGAGGACACGGCCACCTATTTCTGTGCCAGA*GGCTACGATGACTATGAT*
*GAGATGACCTACTTTAACATC*TGGGGCCAGGGGACCCTCGTCACCGTCTCGAGC (SEQ
ID NO: 203)

Heavy_chain Full length DNA sequence.

CAGTCGCTGGAGGAGTCCGGGGGTCGCCTGGTCACGCCTGGGACACCCCTGACACTCACC
TGCACAGTCTCTGGCTTCTCCCTCAGTAGCTATGCAATGAGCTGGGTCCGCCAGGCTCCA
GGGAAGGGGCTGGAATGGATCGGAGTCATTACTAGTATTGGTAGCACAGTCTACGCGAGC
TGGGCGAAAGGCCGATTCACCATCTCCAAAACCTCGACCACGGTGGATCTGAAAATCACC
AGTCCGACAACCGAGGACACGGCCACCTATTTCTGTGCCAGAGGCTACGATGACTATGAT
GAGATGACCTACTTTAACATCTGGGGCCAGGGGACCCTCGTCACCGTCTCGAGCGCCTCC
ACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAAATCT
TGTGACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGAGGTC
ACATGCGTGGTGGTGGACGTGAGCCACGAAGACCCTGAGGTCAAGTTCAACTGGTACGTG

FIG. 1B

GACGGCGTGGAGGTGCATAATGCCAAGACAAAGCCGCGGGAGGAGCAGTACGCCAGCACG
TACCGTGTGGTCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGAGGAGATGACC
AAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACGCAGAAG
AGCCTCTCCCTGTCTCCGGGTAAATGA (SEQ ID NO: 204)

Light_chain Full length protein sequence.

ALVMTQTPSSVSAAVGGTVTINCQASQNIYSNLAWYQQRPGQRPKLLIYGASNLDAGVPS
RFRGSGSGTEYTLTISDLECDDVGTYYCQSAFDSDSTENTFGGGTEVVVKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:2)

Variable_region_light_chain protein sequence.

ALVMTQTPSSVSAAVGGTVTINCQASQNIYSNLAWYQQRPGQRPKLLIYGASNLDAGVPS
RFRGSGSGTEYTLTISDLECDDVGTYYCQSAFDSDSTENTFGGGTEVVVKR (SEQ ID NO:1)

Variable region light chain protein sequence. CDR1:Bold; CDR2: Underline; CDR3:Italics.

ALVMTQTPSSVSAAVGGTVTINCQASQNIYSNLAWYQQRPGQRPKLLIY<u>GASNLDA</u>GVPS
RFRGSGSGTEYTLTISDLECDDVGTYYC*QSAFDSDSTENT*FGGGTEVVVKR (SEQ ID NOS: 5, 6, 7, respectively)

Variable region light chain DNA sequence. CDR1:Bold; CDR2: Underline; CDR3:Italics.

GCCCTTGTGATGACCCAGACTCCATCCTCCGTGTCTGCAGCTGTGGGAGGCACAGTCACC
ATCAATTGCCAGGCCAGTCAGAACATTTACAGCAATTTAGCCTGGTATCAACAGAGACCA
GGGCAGCGTCCCAAGCTCCTGATCTAT<u>GGTGCATCCAATCTGGATGCT</u>GGGGTCCCATCG
CGGTTCAGAGGCAGTGGATCTGGGACAGAGTACACTCTCACCATCAGCGACCTGGAGTGT
GACGATGTTGGCACTTACTACTGT*CAAAGTGCTTTTGATAGTGATAGTACTGAAAATACT*
TTCGGCGGAGGGACCGAGGTGGTGGTCAAACGT (SEQ ID NO: 201)

Light_chain Full length DNA sequence.

GCCCTTGTGATGACCCAGACTCCATCCTCCGTGTCTGCAGCTGTGGGAGGCACAGTCACC
ATCAATTGCCAGGCCAGTCAGAACATTTACAGCAATTTAGCCTGGTATCAACAGAGACCA
GGGCAGCGTCCCAAGCTCCTGATCTATGGTGCATCCAATCTGGATGCTGGGGTCCCATCG
CGGTTCAGAGGCAGTGGATCTGGGACAGAGTACACTCTCACCATCAGCGACCTGGAGTGT
GACGATGTTGGCACTTACTACTGTCAAAGTGCTTTTGATAGTGATAGTACTGAAAATACT
TTCGGCGGAGGGACCGAGGTGGTGGTCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ ID NO: 202)

Heavy_chain Full length protein sequence.

EVQLVESGGGLVQPGGSLRLSCAASGFTVSSYAMSWVRQAPGKGLEWVGVITSIGSTVYA
SSAKGRFTISRDNSKNTLYLQMNSLRAEDTAVYYCARGYDDYDEMTYFNIWGQGTLVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCDKTHTCPPCPAPELLG
GPSVFLFPPKPKDTLMISRTPEVTCVVVDVSHEDPEVKFNWYVDGVEVHNAKTKPREEQY
ASTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO:14)

Variable_region_heavy_chain protein sequence.

EVQLVESGGGLVQPGGSLRLSCAASGFTVSSYAMSWVRQAPGKGLEWVGVITSIGSTVYA
SSAKGRFTISRDNSKNTLYLQMNSLRAEDTAVYYCARGYDDYDEMTYFNIWGQGTLVTVS
S (SEQ ID NO:13)

Variable_region_heavy_chain protein sequence. CDR1:Bold; CDR2: Underline; CDR3:Italics.

EVQLVESGGGLVQPGGSLRLSCAASGFTVSSYAMSWVRQAPGKGLEWVG<u>VITSIGSTVYA</u>
<u>SSAKG</u>RFTISRDNSKNTLYLQMNSLRAEDTAVYYCAR*GYDDYDEMTYFNI*WGQGTLVTVS
S (SEQ ID NOS: 18, 19, 20, respectively)

Variable_region_heavy_chain DNA sequence. CDR1:Bold; CDR2: Underline; CDR3:Italics.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTAGCTATGCAATGAGCTGGGTCCGTCAGGCT
CCAGGGAAGGGGCTGGAGTGGGTCGGA<u>GTCATTACTAGTATTGGTAGCACAGTCTACGCG</u>
<u>AGCAGCGCGAAAGGC</u>CGATTCACCATCTCCAGAGACAATTCCAAGAACACCCTGTATCTT
CAAATGAACAGCCTGAGAGCTGAGGACACTGCTGTGTATTACTGTGCTAGA*GGCTACGAT*
*GACTATGATGAGATGACCTACTTTAACATCT*GGGGCCAAGGGACCCTCGTCACCGTCTCG
AGC (SEQ ID NO: 213)

Heavy_chain Full length DNA sequence.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTAGCTATGCAATGAGCTGGGTCCGTCAGGCT
CCAGGGAAGGGGCTGGAGTGGGTCGGAGTCATTACTAGTATTGGTAGCACAGTCTACGCG
AGCAGCGCGAAAGGCCGATTCACCATCTCCAGAGACAATTCCAAGAACACCCTGTATCTT
CAAATGAACAGCCTGAGAGCTGAGGACACTGCTGTGTATTACTGTGCTAGAGGCTACGAT
GACTATGATGAGATGACCTACTTTAACATCTGGGGCCAAGGGACCCTCGTCACCGTCTCG
AGCGCCTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAGAGTTGAG
CCCAAATCTTGTGACAAAACTCACACATGCCCACCGTGCCCAGCACCTGAACTCCTGGGG
GGACCGTCAGTCTTCCTCTTCCCCCCAAAACCCAAGGACACCCTCATGATCTCCCGGACC
CCTGAGGTCACATGCGTGGTGGTGGACGTGAGCCACGAAGACCCTGAGGTCAAGTTCAAC

FIG. 2B

TGGTACGTGGACGGCGTGGAGGTGCATAATGCCAAGACAAAGCCGCGGGAGGAGCAGTAC
GCCAGCACGTACCGTGTGGTCAGCGTCCTCACCGTCCTGCACCAGGACTGGCTGAATGGC
AAGGAGTACAAGTGCAAGGTCTCCAACAAAGCCCTCCCAGCCCCCATCGAGAAAACCATC
TCCAAAGCCAAAGGGCAGCCCCGAGAACCACAGGTGTACACCCTGCCCCCATCCCGGGAG
GAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTAC
ACGCAGAAGAGCCTCTCCCTGTCTCCGGGTAAATGA (SEQ ID NO: 214)

Light_chain Full length protein sequence.

DIQMTQSPSTLSASVGDRVTITCQASQNIYSNLAWYQQKPGKAPKLLIYGASNLDAGVPS
RFSGSGSGTEYTLTISSLQPDDFATYYCQSAFDSDSTENTFGGGTKVEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:12)

Variable_region Light_chain protein sequence.

DIQMTQSPSTLSASVGDRVTITCQASQNIYSNLAWYQQKPGKAPKLLIYGASNLDAGVPS
RFSGSGSGTEYTLTISSLQPDDFATYYCQSAFDSDSTENTFGGGTKVEIKR (SEQ ID
NO:11)

Variable_region Light_chain protein sequence. CDR1:Bold; CDR2: Underline; CDR3:Italics.

DIQMTQSPSTLSASVGDRVTITCQASQNIYSNLAWYQQKPGKAPKLLIY<u>GASNLDA</u>GVPS
RFSGSGSGTEYTLTISSLQPDDFATYYC*QSAFDSDSTENT*FGGGTKVEIKR (SEQ ID
NOS: 15, 16, 17, respectively)

Variable_region Light_chain DNA sequence. CDR1:Bold; CDR2: Underline; CDR3:Italics.

GACATCCAGATGACCCAGTCTCCTTCCACCCTGTCTGCATCTGTAGGAGACAGAGTCACC
ATCACTTGCCAGGCCAGTCAGAACATTTACAGCAACTTAGCCTGGTATCAGCAGAAACCA
GGAAAAGCCCCTAAGCTCCTGATCTAT<u>GGTGCATCCAATCTGGATGCT</u>GGAGTCCCATCA
AGGTTCTCTGGCAGTGGATCTGGGACAGAGTACACTCTCACCATCAGCAGCCTGCAGCCT
GATGATTTTGCAACTTACTACTGC*CAAAGTGCTTTTGATAGTGATAGTACTGAAAACACT*
TTCGGCGGAGGAACCAAGGTGGAAATCAAACGT (SEQ ID NO: 211)

Light_chain Full length DNA sequence.

GACATCCAGATGACCCAGTCTCCTTCCACCCTGTCTGCATCTGTAGGAGACAGAGTCACC
ATCACTTGCCAGGCCAGTCAGAACATTTACAGCAACTTAGCCTGGTATCAGCAGAAACCA
GGAAAAGCCCCTAAGCTCCTGATCTATGGTGCATCCAATCTGGATGCTGGAGTCCCATCA
AGGTTCTCTGGCAGTGGATCTGGGACAGAGTACACTCTCACCATCAGCAGCCTGCAGCCT
GATGATTTTGCAACTTACTACTGCCAAAGTGCTTTTGATAGTGATAGTACTGAAAACACT
TTCGGCGGAGGAACCAAGGTGGAAATCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ
ID NO: 212)

Heavy_chain Full length protein sequence.

QSVEESGGRLVTPGTPLTLTCTVSGFSLSSYVMIWVRQAPGKGLEYIGITWSAGTYYASW
AKGRFTISKTSSTTVDLKITSPTTEDTATYFCAGGGGSIYDIWGPGTLVTVSSASTKGPS
VFPLAPSSKSTSGGTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYASTYRVVS
VLTVLHQDWLNGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDKSRWQQGNVFS
CSVMHEALHNHYTQKSLSLSPGK (SEQ ID NO:24)

Variable_region_heavy_chain protein sequence.

QSVEESGGRLVTPGTPLTLTCTVSGFSLSSYVMIWVRQAPGKGLEYIGITWSAGTYYASW
AKGRFTISKTSSTTVDLKITSPTTEDTATYFCAGGGGSIYDIWGPGTLVTVSS (SEQ
ID NO:23)

Variable_region_heavy_chain protein sequence. CDR1:Bold; CDR2: Underline; CDR3:Italics.

QSVEESGGRLVTPGTPLTLTCTVSGFSLSSYVMIWVRQAPGKGLEYIGITWSAGTYYASW
AKGRFTISKTSSTTVDLKITSPTTEDTATYFCAG*GGGSIYDI*WGPGTLVTVSS (SEQ
ID NOS: 28, 29, 30, respectively)

Variable_region_heavy_chain DNA sequence. CDR1:Bold; CDR2: Underline; CDR3:Italics.

CAGTCGGTGGAGGAGTCCGGGGGTCGCCTGGTCACGCCTGGGACACCCCTGACACTCACC
TGCACAGTCTCTGGATTCTCCCTCAGTAGCTATGTAATGATCTGGGTCCGCCAGGCTCCA
GGGAAGGGGCTGGAATACATCGGAATCACTTGGAGTGCTGGTACATACTACGCGAGCTGG
GCGAAAGGCCGATTCACCATCTCCAAAACCTCGTCGACCACGGTGGATCTGAAAATCACC
AGTCCGACAACCGAGGACACGGCCACCTATTTCTGTGCCGGA*GGTGGTGGTAGTATTTAT*
*GATATT*TGGGGCCCGGGCACCCTGGTCACCGTCTCGAGC (SEQ ID NO: 223)

Heavy_chain Full length DNA sequence.

CAGTCGGTGGAGGAGTCCGGGGGTCGCCTGGTCACGCCTGGGACACCCCTGACACTCACC
TGCACAGTCTCTGGATTCTCCCTCAGTAGCTATGTAATGATCTGGGTCCGCCAGGCTCCA
GGGAAGGGGCTGGAATACATCGGAATCACTTGGAGTGCTGGTACATACTACGCGAGCTGG
GCGAAAGGCCGATTCACCATCTCCAAAACCTCGTCGACCACGGTGGATCTGAAAATCACC
AGTCCGACAACCGAGGACACGGCCACCTATTTCTGTGCCGGAGGTGGTGGTAGTATTTAT
GATATTTGGGGCCCGGGCACCCTGGTCACCGTCTCGAGCGCCTCCACCAAGGGCCCATCG
GTCTTCCCCCTGGCACCCTCCTCCAAGAGCACCTCTGGGGGCACAGCGGCCCTGGGCTGC
CTGGTCAAGGACTACTTCCCCGAACCGGTGACGGTGTCGTGGAACTCAGGCGCCCTGACC
AGCGGCGTGCACACCTTCCCGGCTGTCCTACAGTCCTCAGGACTCTACTCCCTCAGCAGC
GTGGTGACCGTGCCCTCCAGCAGCTTGGGCACCCAGACCTACATCTGCAACGTGAATCAC
AAGCCCAGCAACACCAAGGTGGACAAGAGAGTTGAGCCCAAATCTTGTGACAAAACTCAC
ACATGCCCACCGTGCCCAGCACCTGAACTCCTGGGGGGACCGTCAGTCTTCCTCTTCCCC
CCAAAACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTGGAGGTG
CATAATGCCAAGACAAAGCCGCGGGAGGAGCAGTACGCCAGCACGTACCGTGTGGTCAGC

FIG. 3B

GTCCTCACCGTCCTGCACCAGGACTGGCTGAATGGCAAGGAGTACAAGTGCAAGGTCTCC
AACAAAGCCCTCCCAGCCCCCATCGAGAAAACCATCTCCAAAGCCAAAGGGCAGCCCCGA
GAACCACAGGTGTACACCCTGCCCCCATCCCGGGAGGAGATGACCAAGAACCAGGTCAGC
CTGACCTGCCTGGTCAAAGGCTTCTATCCCAGCGACATCGCCGTGGAGTGGGAGAGCAAT
GGGCAGCCGGAGAACAACTACAAGACCACGCCTCCCGTGCTGGACTCCGACGGCTCCTTC
TTCCTCTACAGCAAGCTCACCGTGGACAAGAGCAGGTGGCAGCAGGGGAACGTCTTCTCA
TGCTCCGTGATGCATGAGGCTCTGCACAACCACTACACGCAGAAGAGCCTCTCCCTGTCT
CCGGGTAAATGA (SEQ ID NO: 224)

Light chain Full length protein sequence.

AVLTQTPSPVSAAMGDTVTIKCQSSQSVYKNNYLSWYQQKPGQPPRLLIYDASNLPSGVP
SRFSGSGSGTQFTLTISGVQCDDAATYYCLGDYDDDADNAFGGGTEVVVKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:22)

Variable_region_light_chain protein sequence.

AVLTQTPSPVSAAMGDTVTIKCQSSQSVYKNNYLSWYQQKPGQPPRLLIYDASNLPSGVP
SRFSGSGSGTQFTLTISGVQCDDAATYYCLGDYDDDADNAFGGGTEVVVKR (SEQ ID NO:21)

Variable_region_light_chain protein sequence. CDR1:Bold; CDR2: Underline; CDR3:Italics.

AVLTQTPSPVSAAMGDTVTIKCQSSQSVYKNNYLSWYQQKPGQPPRLLIY<u>DASNLPS</u>GVP
SRFSGSGSGTQFTLTISGVQCDDAATYYC*LGDYDDDADNA*FGGGTEVVVKR (SEQ ID NOS: 25, 26, 27, respectively)

Variable_region_light_chain DNA sequence. CDR1:Bold; CDR2: Underline; CDR3:Italics.

GCAGCCGTGCTGACCCAGACACCATCGCCCGTGTCTGCAGCTATGGGAGACACAGTCACC
ATCAAGTGCCAGTCCAGTCAGAGTGTTTATAAGAACAACTACTTATCCTGGTATCAGCAG
AAACCAGGGCAGCCTCCCAGGCTCCTGATCTAT<u>GATGCATCCAATCTGCCATCT</u>GGGGTC
CCATCACGGTTCAGCGGCAGTGGATCTGGGACACAGTTCACTCTCACCATCAGCGGCGTG
CAGTGTGACGATGCTGCCACTTACTACTGT*CTAGGCGATTATGATGATGATGCTGATAAT*
*GCT*TTCGGCGGAGGGACCGAGGTGGTGGTCAAACGT (SEQ ID NO: 221)

Light_chain Full length DNA sequence.

GCAGCCGTGCTGACCCAGACACCATCGCCCGTGTCTGCAGCTATGGGAGACACAGTCACC
ATCAAGTGCCAGTCCAGTCAGAGTGTTTATAAGAACAACTACTTATCCTGGTATCAGCAG
AAACCAGGGCAGCCTCCCAGGCTCCTGATCTATGATGCATCCAATCTGCCATCTGGGGTC
CCATCACGGTTCAGCGGCAGTGGATCTGGGACACAGTTCACTCTCACCATCAGCGGCGTG
CAGTGTGACGATGCTGCCACTTACTACTGTCTAGGCGATTATGATGATGATGCTGATAAT
GCTTTCGGCGGAGGGACCGAGGTGGTGGTCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 222)

Heavy_chain Full length protein sequence.

EVQLVESGGGLVQPGGSLRLSCAASGFTVSSYVMIWVRQAPGKGLEYIGITWSAGTYYAS
SAKGRFTISRDNSKNTLYLQMNSLRAEDTAVYYCAGGGGSIYDIWGQGTLVTVSSASTKG
PSVFPLAPSSKSTSGGTAALGCLVKDYFPEPVTVSWNSGALTSGVHTFPAVLQSSGLYSL
SSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYASTYRV
VSVLTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQGNV
FSCSVMHEALHNHYTQKSLSLSPGK (SEQ ID NO:34)

Variable_region_heavy_chain protein sequence.

EVQLVESGGGLVQPGGSLRLSCAASGFTVSSYVMIWVRQAPGKGLEYIGITWSAGTYYAS
SAKGRFTISRDNSKNTLYLQMNSLRAEDTAVYYCAGGGGSIYDIWGQGTLVTVSS (SEQ ID NO:33)

Variable_region_heavy_chain protein sequence. CDR1:Bold; CDR2: Underline; CDR3:Italics.

EVQLVESGGGLVQPGGSLRLSCAASGFTVSSYVMIWVRQAPGKGLEYIGITWSAGTYYAS
SAKGRFTISRDNSKNTLYLQMNSLRAEDTAVYYCAG*GGGSIYDI*WGQGTLVTVSS (SEQ ID NOS: 38, 39, 40, respectively)

Variable_region_heavy_chain DNA sequence. CDR1:Bold; CDR2: Underline; CDR3:Italics.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTAGCTATGTAATGATCTGGGTCCGTCAGGCT
CCAGGGAAGGGGCTGGAGTACATCGGAATCACTTGGAGTGCTGGTACATACTACGCGAGC
AGTGCGAAAGGCCGATTCACCATCTCCAGAGACAATTCCAAGAACACCCTGTATCTTCAA
ATGAACAGCCTGAGAGCTGAGGACACTGCTGTGTATTACTGTGCTGGA*GGTGGTGGTAGT*
*ATCTATGATATT*TGGGGCCAAGGGACCCTCGTCACCGTCTCGAGC (SEQ ID NO: 233)

Heavy_chain Full length DNA sequence.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTAGCTATGTAATGATCTGGGTCCGTCAGGCT
CCAGGGAAGGGGCTGGAGTACATCGGAATCACTTGGAGTGCTGGTACATACTACGCGAGC
AGTGCGAAAGGCCGATTCACCATCTCCAGAGACAATTCCAAGAACACCCTGTATCTTCAA
ATGAACAGCCTGAGAGCTGAGGACACTGCTGTGTATTACTGTGCTGGAGGTGGTGGTAGT
ATCTATGATATTTGGGGCCAAGGGACCCTCGTCACCGTCTCGAGCGCCTCCACCAAGGGC
CCATCGGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACTCAGGCGCC
CTGACCAGCGGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACATCTGCAACGTG
AATCACAAGCCCAGCAACACCAAGGTGGACAAGAGAGTTGAGCCCAAATCTTGTGACAAA
ACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTG
GTGGTGGACGTGAGCCACGAAGACCCTGAGGTCAAGTTCAACTGGTACGTGGACGGCGTG

FIG. 4B

GAGGTGCATAATGCCAAGACAAAGCCGCGGGAGGAGCAGTACGCCAGCACGTACCGTGTG
GTCAGCGTCCTCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGCCAAAGGGCAG
CCCCGAGAACCACAGGTGTACACCCTGCCCCCATCCCGGGAGGAGATGACCAAGAACCAG
GTCAGCCTGACCTGCCTGGTCAAAGGCTTCTATCCCAGCGACATCGCCGTGGAGTGGGAG
AGCAATGGGCAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAGGGGAACGTC
TTCTCATGCTCCGTGATGCATGAGGCTCTGCACAACCACTACACGCAGAAGAGCCTCTCC
CTGTCTCCGGGTAAATGA (SEQ ID NO: 234)

Light_chain Full length protein sequence.

DIQMTQSPSTLSASVGDRVTITCQSSQSVYKNNYLSWYQQKPGKAPKLLIYDASNLPSGV
PSRFSGSGSGTEFTLTISSLQPDDFATYYCLGDYDDDADNAFGGGTKVEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO:32)

Variable_region_Light_chain protein sequence.

DIQMTQSPSTLSASVGDRVTITCQSSQSVYKNNYLSWYQQKPGKAPKLLIYDASNLPSGV
PSRFSGSGSGTEFTLTISSLQPDDFATYYCLGDYDDDADNAFGGGTKVEIKR (SEQ ID NO:31)

Variable_region_Light_chain protein sequence. CDR1:Bold; CDR2: Underline; CDR3:Italics.

DIQMTQSPSTLSASVGDRVTITCQSSQSVYKNNYLSWYQQKPGKAPKLLIY<u>DASNLPS</u>GV
PSRFSGSGSGTEFTLTISSLQPDDFATYYC*LGDYDDDADNA*FGGGTKVEIKR (SEQ ID NOS: 35, 36, 37, respectively)

Variable_region_Light_chain DNA sequence. CDR1:Bold; CDR2: Underline; CDR3:Italics.

GACATCCAGATGACCCAGTCTCCTTCCACCCTGTCTGCATCTGTAGGAGACAGAGTCACC
ATCACTTGCCAGTCCAGTCAGAGTGTCTATAAGAACAACTACTTATCCTGGTATCAGCAG
AAACCAGGAAAAGCCCCTAAGCTCCTGATCTAT<u>GATGCATCCAATCTGCCATCT</u>GGAGTC
CCATCAAGGTTCAGCGGCAGTGGATCTGGAACAGAATTCACTCTCACCATCAGCAGCCTG
CAGCCTGATGATTTTGCAACTTATTACTGC*CTAGGCGATTATGATGATGATGCTGATAAT
GCT*TTCGGCGGAGGAACCAAGGTGGAAATCAAACGT (SEQ ID NO: 231)

Light_chain Full length DNA sequence.

GACATCCAGATGACCCAGTCTCCTTCCACCCTGTCTGCATCTGTAGGAGACAGAGTCACC
ATCACTTGCCAGTCCAGTCAGAGTGTCTATAAGAACAACTACTTATCCTGGTATCAGCAG
AAACCAGGAAAAGCCCCTAAGCTCCTGATCTATGATGCATCCAATCTGCCATCTGGAGTC
CCATCAAGGTTCAGCGGCAGTGGATCTGGAACAGAATTCACTCTCACCATCAGCAGCCTG
CAGCCTGATGATTTTGCAACTTATTACTGCCTAGGCGATTATGATGATGATGCTGATAAT
GCTTTCGGCGGAGGAACCAAGGTGGAAATCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 232)

Heavy_chain Full length protein sequence.

QSVEESGGRLVTPGTPLTLTCTVSGFSLSNYAVGWVRQAPGKGLEWIGIIGRNGNTWYAS
WARGRFTISKTSTTVDLKITSPTSEDTATYFCARGYGRSVAYYVFNIWGPGTLVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYAST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO:44)

Variable_region_heavy_chain protein sequence.

QSVEESGGRLVTPGTPLTLTCTVSGFSLSNYAVGWVRQAPGKGLEWIGIIGRNGNTWYAS
WARGRFTISKTSTTVDLKITSPTSEDTATYFCARGYGRSVAYYVFNIWGPGTLVTVSS
(SEQ ID NO:43)

Variable_region_heavy_chain protein sequence. CDR1:Bold; CDR2: Underline; CDR3:Italics.

QSVEESGGRLVTPGTPLTLTCTVSGFSLSNYAVGWVRQAPGKGLEWIGIIGRNGNTWYAS
WARGRFTISKTSTTVDLKITSPTSEDTATYFCAR*GYGRSVAYYVFNI*WGPGTLVTVSS
(SEQ ID NOS: 48, 49, 50, respectively)

Variable_region_heavy_chain DNA sequence. CDR1:Bold; CDR2: Underline; CDR3:Italics.

CAGTCGGTGGAGGAGTCCGGGGGTCGCCTGGTCACGCCTGGGACACCCCTGACACTCACC
TGCACAGTCTCTGGATTCTCCCTCAGTAACTATGCAGTGGGCTGGGTCCGCCAGGCTCCA
GGGAAGGGGCTGGAATGGATCGGAATCATTGGTCGTAATGGTAACACATGGTACGCGAGC
TGGGCAAGAGGCCGATTCACCATCTCCAAAACCTCGACCACGGTGGATCTGAAAATCACC
AGTCCGACAAGCGAGGACACGGCCACATATTTCTGTGCCAGA*GGATATGGCCGTAGTGTT*
*GCTTATTACGTCTTTAACATC*TGGGGCCCAGGCACCCTCGTCACCGTCTCGAGC (SEQ
ID NO: 243)

Heavy_chain Full length DNA sequence.

CAGTCGGTGGAGGAGTCCGGGGGTCGCCTGGTCACGCCTGGGACACCCCTGACACTCACC
TGCACAGTCTCTGGATTCTCCCTCAGTAACTATGCAGTGGGCTGGGTCCGCCAGGCTCCA
GGGAAGGGGCTGGAATGGATCGGAATCATTGGTCGTAATGGTAACACATGGTACGCGAGC
TGGGCAAGAGGCCGATTCACCATCTCCAAAACCTCGACCACGGTGGATCTGAAAATCACC
AGTCCGACAAGCGAGGACACGGCCACATATTTCTGTGCCAGAGGATATGGCCGTAGTGTT
GCTTATTACGTCTTTAACATCTGGGGCCCAGGCACCCTCGTCACCGTCTCGAGCGCCTCC
ACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAAATCT
TGTGACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGAGGTC
ACATGCGTGGTGGTGGACGTGAGCCACGAAGACCCTGAGGTCAAGTTCAACTGGTACGTG

FIG. 5B

GACGGCGTGGAGGTGCATAATGCCAAGACAAAGCCGCGGGAGGAGCAGTACGCCAGCACG
TACCGTGTGGTCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGAGGAGATGACC
AAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACGCAGAAG
AGCCTCTCCCTGTCTCCGGGTAAATGA (SEQ ID NO: 244)

Light chain Full length protein sequence.

AYDMTQTPASVEVAVGGTVTIKCQASQSIYSNLAWYQQRPGQPPKLLIYDASTLESGVPS
RFKGSGSGTEYTLTISGVECADAASYYCQQGFTVSDIDNAFGGGTEVVVKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:42)

Variable_region_light_chain protein sequence.

AYDMTQTPASVEVAVGGTVTIKCQASQSIYSNLAWYQQRPGQPPKLLIYDASTLESGVPS
RFKGSGSGTEYTLTISGVECADAASYYCQQGFTVSDIDNAFGGGTEVVVKR (SEQ ID NO:41)

Variable_region_light_chain protein sequence. CDR1:Bold; CDR2: Underline; CDR3:Italics.

AYDMTQTPASVEVAVGGTVTIKCQASQSIYSNLAWYQQRPGQPPKLLIYDASTLESGVPS
RFKGSGSGTEYTLTISGVECADAASYYC*QQGFTVSDIDNA*FGGGTEVVVKR (SEQ ID NOS: 45, 46, 47, respectively)

Variable_region_light_chain DNA sequence. CDR1:Bold; CDR2: Underline; CDR3:Italics.

GCCTATGATATGACCCAGACTCCAGCCTCTGTGGAGGTAGCTGTGGGAGGCACAGTCACC
ATCAAGTGCCAGGCCAGTCAGAGCATTTACAGCAATTTAGCCTGGTATCAGCAGAGACCA
GGGCAGCCTCCCAAGCTCCTGATCTATGATGCATCCACTCTGGAATCTGGGGTCCCATCG
CGGTTCAAAGGCAGTGGATCTGGGACAGAGTACACTCTCACCATCAGCGGCGTGGAGTGT
GCCGATGCTGCCTCTTACTACTGT*CAACAGGGTTTTACTGTTAGTGATATTGATAATGCT*
TTCGGCGGAGGGACCGAGGTGGTGGTCAAACGT (SEQ ID NO: 241)

Light_chain Full length DNA sequence.

GCCTATGATATGACCCAGACTCCAGCCTCTGTGGAGGTAGCTGTGGGAGGCACAGTCACC
ATCAAGTGCCAGGCCAGTCAGAGCATTTACAGCAATTTAGCCTGGTATCAGCAGAGACCA
GGGCAGCCTCCCAAGCTCCTGATCTATGATGCATCCACTCTGGAATCTGGGGTCCCATCG
CGGTTCAAAGGCAGTGGATCTGGGACAGAGTACACTCTCACCATCAGCGGCGTGGAGTGT
GCCGATGCTGCCTCTTACTACTGTCAACAGGGTTTTACTGTTAGTGATATTGATAATGCT
TTCGGCGGAGGGACCGAGGTGGTGGTCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ ID NO: 242)

Heavy_chain Full length protein sequence.

EVQLVESGGGLVQPGGSLRLSCAASGFTVSNYAVGWVRQAPGKGLEWVGIIGRNGNTWYA
SSARGRFTISRDNSKNTLYLQMNSLRAEDTAVYYCARGYGRSVAYYVFNIWGPGTLVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCDKTHTCPPCPAPELLG
GPSVFLFPPKPKDTLMISRTPEVTCVVVDVSHEDPEVKFNWYVDGVEVHNAKTKPREEQY
ASTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO:54)

Variable_region_heavy_chain protein sequence.

EVQLVESGGGLVQPGGSLRLSCAASGFTVSNYAVGWVRQAPGKGLEWVGIIGRNGNTWYA
SSARGRFTISRDNSKNTLYLQMNSLRAEDTAVYYCARGYGRSVAYYVFNIWGPGTLVTVS
S (SEQ ID NO:53)

Variable_region_heavy_chain protein sequence. CDR1:Bold; CDR2: Underline; CDR3:Italics.

EVQLVESGGGLVQPGGSLRLSCAASGFTVSNYAVGWVRQAPGKGLEWVGIIGRNGNTWYA
SSARGRFTISRDNSKNTLYLQMNSLRAEDTAVYYCAR*GYGRSVAYYVFNI*WGPGTLVTVS
S (SEQ ID NOS: 58, 59, 60, respectively)

Variable_region_heavy_chain DNA sequence. CDR1:Bold; CDR2: Underline; CDR3:Italics.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTAACTATGCAGTGGGCTGGGTCCGTCAGGCT
CCAGGGAAGGGGCTGGAGTGGGTCGGAATCATTGGTCGTAATGGTAACACATGGTACGCG
AGCTCTGCAAGAGGCCGATTCACCATCTCCAGAGACAATTCCAAGAACACCCTGTATCTT
CAAATGAACAGCCTGAGAGCTGAGGACACTGCTGTGTATTACTGTGCTAGA*GGATATGGC*
*CGTAGTGTTGCTTATTACGTCTTTAACATC*TGGGGCCCAGGGACCCTCGTCACCGTCTCG
AGC (SEQ ID NO: 253)

Heavy_chain Full length DNA sequence.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTAACTATGCAGTGGGCTGGGTCCGTCAGGCT
CCAGGGAAGGGGCTGGAGTGGGTCGGAATCATTGGTCGTAATGGTAACACATGGTACGCG
AGCTCTGCAAGAGGCCGATTCACCATCTCCAGAGACAATTCCAAGAACACCCTGTATCTT
CAAATGAACAGCCTGAGAGCTGAGGACACTGCTGTGTATTACTGTGCTAGAGGATATGGC
CGTAGTGTTGCTTATTACGTCTTTAACATCTGGGGCCCAGGGACCCTCGTCACCGTCTCG
AGCGCCTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAGAGTTGAG
CCCAAATCTTGTGACAAAACTCACACATGCCCACCGTGCCCAGCACCTGAACTCCTGGGG
GGACCGTCAGTCTTCCTCTTCCCCCCAAAACCCAAGGACACCCTCATGATCTCCCGGACC
CCTGAGGTCACATGCGTGGTGGTGGACGTGAGCCACGAAGACCCTGAGGTCAAGTTCAAC

FIG. 6B

TGGTACGTGGACGGCGTGGAGGTGCATAATGCCAAGACAAAGCCGCGGGAGGAGCAGTAC
GCCAGCACGTACCGTGTGGTCAGCGTCCTCACCGTCCTGCACCAGGACTGGCTGAATGGC
AAGGAGTACAAGTGCAAGGTCTCCAACAAAGCCCTCCCAGCCCCCATCGAGAAAACCATC
TCCAAAGCCAAAGGGCAGCCCCGAGAACCACAGGTGTACACCCTGCCCCCATCCCGGGAG
GAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTAC
ACGCAGAAGAGCCTCTCCCTGTCTCCGGGTAAATGA (SEQ ID NO: 254)

Light_chain Full length protein sequence.

DIQMTQSPSTLSASVGDRVTITCQASQSIYSNLAWYQQKPGKAPKLLIYDASTLESGVPS
RFSGSGSGTEYTLTISSLQPDDFATYYCQQGFTVSDIDNAFGGGTKVEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:52)

Variable_region_Light_chain protein sequence.

DIQMTQSPSTLSASVGDRVTITCQASQSIYSNLAWYQQKPGKAPKLLIYDASTLESGVPS
RFSGSGSGTEYTLTISSLQPDDFATYYCQQGFTVSDIDNAFGGGTKVEIKR (SEQ ID
NO:51)

Variable_region_Light_chain protein sequence. CDR1:Bold; CDR2: Underline; CDR3:Italics.

DIQMTQSPSTLSASVGDRVTITCQASQSIYSNLAWYQQKPGKAPKLLIY<u>DASTLES</u>GVPS
RFSGSGSGTEYTLTISSLQPDDFATYYC*QQGFTVSDIDNA*FGGGTKVEIKR (SEQ ID
NOS: 55, 56, 57, respectively)

Variable_region_Light_chain DNA sequence. CDR1:Bold; CDR2: Underline; CDR3:Italics.

GACATCCAGATGACCCAGTCTCCTTCCACCCTGTCTGCATCTGTAGGAGACAGAGTCACC
ATCACTTGCCAGGCCAGTCAGAGCATTTACAGCAATCTTGCCTGGTATCAGCAGAAACCA
GGAAAAGCCCCTAAGCTCCTGATCTAT<u>GATGCATCCACTCTGGAATCT</u>GGAGTCCCATCA
AGGTTCAGCGGCAGTGGATCTGGGACAGAGTACACTCTCACCATCAGCAGCCTGCAGCCT
GATGATTTTGCAACTTACTACTGC*CAACAGGGTTTTACTGTTAGTGATATTGATAATGCT*
TTCGGCGGAGGAACCAAGGTGGAAATCAAACGT (SEQ ID NO: 251)

Light_chain Full length DNA sequence.

GACATCCAGATGACCCAGTCTCCTTCCACCCTGTCTGCATCTGTAGGAGACAGAGTCACC
ATCACTTGCCAGGCCAGTCAGAGCATTTACAGCAATCTTGCCTGGTATCAGCAGAAACCA
GGAAAAGCCCCTAAGCTCCTGATCTATGATGCATCCACTCTGGAATCTGGAGTCCCATCA
AGGTTCAGCGGCAGTGGATCTGGGACAGAGTACACTCTCACCATCAGCAGCCTGCAGCCT
GATGATTTTGCAACTTACTACTGCCAACAGGGTTTTACTGTTAGTGATATTGATAATGCT
TTCGGCGGAGGAACCAAGGTGGAAATCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ
ID NO: 252)

Heavy_chain Full length protein sequence.

QEQLKESGGRLVTPGTPLTLTCTVSGFSLSSYAMIWVRQAPGKGLEYIGYIDTDTSAYYA
SWVKGRFTISRTSTTVDLKITSPTTEDTATYFCARSYAAYGGYPATFDPWGPGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO:64)

Variable_region_heavy_chain protein sequence.

QEQLKESGGRLVTPGTPLTLTCTVSGFSLSSYAMIWVRQAPGKGLEYIGYIDTDTSAYYA
SWVKGRFTISRTSTTVDLKITSPTTEDTATYFCARSYAAYGGYPATFDPWGPGTLVTVSS
(SEQ ID NO:63)

Variable_region_heavy_chain protein sequence. CDR1:Bold; CDR2: Underline; CDR3:Italics.

QEQLKESGGRLVTPGTPLTLTCTVSGFSLSSYAMIWVRQAPGKGLEYIGYIDTDTSAYYA
SWVKGRFTISRTSTTVDLKITSPTTEDTATYFCAR*SYAAYGGYPATFDP*WGPGTLVTVSS
(SEQ ID NOS: 68, 69, 70, respectively)

Variable_region_heavy_chain DNA sequence. CDR1:Bold; CDR2: Underline; CDR3:Italics.

CAGGAGCAGCTGAAGGAGTCCGGGGGTCGCCTGGTCACGCCTGGGACACCCCTGACACTC
ACCTGTACAGTCTCTGGATTCTCCCTCAGTAGCTATGCAATGATCTGGGTCCGCCAGGCT
CCAGGGAAGGGGCTGGAATACATCGGATACATTGATACTGATACTAGCGCATACTACGCG
AGCTGGGTGAAAGGCCGATTCACCATCTCCAGAACCTCGACCACGGTGGATCTCAAAATC
ACTAGTCCGACAACCGAGGACACGGCCACCTATTTCTGTGCCAGA*TCTTATGCTGCTTAT*
*GGTGGTTATCCTGCTACTTTT*GATCCCTGGGGCCCAGGCACCCTGGTCACCGTCTCGAGC
(SEQ ID NO: 263)

Heavy_chain Full length DNA sequence.

CAGGAGCAGCTGAAGGAGTCCGGGGGTCGCCTGGTCACGCCTGGGACACCCCTGACACTC
ACCTGTACAGTCTCTGGATTCTCCCTCAGTAGCTATGCAATGATCTGGGTCCGCCAGGCT
CCAGGGAAGGGGCTGGAATACATCGGATACATTGATACTGATACTAGCGCATACTACGCG
AGCTGGGTGAAAGGCCGATTCACCATCTCCAGAACCTCGACCACGGTGGATCTCAAAATC
ACTAGTCCGACAACCGAGGACACGGCCACCTATTTCTGTGCCAGATCTTATGCTGCTTAT
GGTGGTTATCCTGCTACTTTTGATCCCTGGGGCCCAGGCACCCTGGTCACCGTCTCGAGC
GCCTCCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGG

FIG. 7B

TACGTGGACGGCGTGGAGGTGCATAATGCCAAGACAAAGCCGCGGGAGGAGCAGTACGCC
AGCACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATCTCC
AAAGCCAAAGGGCAGCCCCGAGAACCACAGGTGTACACCCTGCCCCCATCCCGGGAGGAG
ATGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACG
CAGAAGAGCCTCTCCCTGTCTCCGGGTAAATGA (SEQ ID NO: 264)

Light_chain Full length protein sequence.

ADVVMTQTPASVSQPVGGTVTIKCQASEDIYNLLAWYQQKPGQPPKLLIYSASTLASGVP
SRFKGSGSGTEYTLTISGLECADAATYYCQNNYLVTTYGVAFGGGTEVVVKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO:62)

Variable_region_light_chain protein sequence.

ADVVMTQTPASVSQPVGGTVTIKCQASEDIYNLLAWYQQKPGQPPKLLIYSASTLASGVP
SRFKGSGSGTEYTLTISGLECADAATYYCQNNYLVTTYGVAFGGGTEVVVKR (SEQ ID NO:61)

Variable_region_light_chain protein sequence. CDR1:Bold; CDR2: Underline; CDR3:Italics.

ADVVMTQTPASVSQPVGGTVTIKCQASEDIYNLLAWYQQKPGQPPKLLIY<u>SASTLAS</u>GVP
SRFKGSGSGTEYTLTISGLECADAATYYC*QNNYLVTTYGVA*FGGGTEVVVKR (SEQ ID NOS: 65, 66, 67, respectively)

Variable_region_light_chain DNA sequence. CDR1:Bold; CDR2: Underline; CDR3:Italics.

GCCGATGTTGTGATGACCCAGACTCCAGCCTCCGTGTCTCAACCTGTGGGAGGCACAGTC
ACCATCAAGTGCCAGGCCAGTGAGGACATTTATAACTTATTGGCCTGGTATCAGCAGAAA
CCAGGGCAGCCTCCCAAGCTCCTGATCTAT<u>TCTGCATCCACTCTGGCATCT</u>GGGGTCCCA
TCGCGGTTCAAAGGCAGTGGATCTGGGACAGAGTACACTCTCACCATCAGCGGCCTGGAG
TGTGCCGATGCTGCCACTTACTACTGT*CAAAACAATTATCTTGTTACTACTTATGGTGTT*
*GCT*TTCGGCGGAGGGACCGAGGTGGTGGTCAAACGT (SEQ ID NO: 261)

Light_chain Full length DNA sequence.

GCCGATGTTGTGATGACCCAGACTCCAGCCTCCGTGTCTCAACCTGTGGGAGGCACAGTC
ACCATCAAGTGCCAGGCCAGTGAGGACATTTATAACTTATTGGCCTGGTATCAGCAGAAA
CCAGGGCAGCCTCCCAAGCTCCTGATCTATTCTGCATCCACTCTGGCATCTGGGGTCCCA
TCGCGGTTCAAAGGCAGTGGATCTGGGACAGAGTACACTCTCACCATCAGCGGCCTGGAG
TGTGCCGATGCTGCCACTTACTACTGTCAAAACAATTATCTTGTTACTACTTATGGTGTT
GCTTTCGGCGGAGGGACCGAGGTGGTGGTCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 262)

Heavy_chain Full length protein sequence.

QVQLVESGGGVVQPGRSLRLSCAASGFTFSSYAMIWVRQAPGKGLEYIGYIDTDTSAYYA
SSVKGRFTISRDNSKNTLYLQMSSLRAEDTAVYYCARSYAAYGGYPATFDPWGQGTLVTV
SSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPELL
GGPSVFLFPPKPKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDKS
RWQQGNVFSCSVMHEALHNHYTQKSLSLSPGK (SEQ ID NO:74)

Variable_region_heavy_chain protein sequence.

QVQLVESGGGVVQPGRSLRLSCAASGFTFSSYAMIWVRQAPGKGLEYIGYIDTDTSAYYA
SSVKGRFTISRDNSKNTLYLQMSSLRAEDTAVYYCARSYAAYGGYPATFDPWGQGTLVTV
SS (SEQ ID NO:73)

Variable_region_heavy_chain protein sequence. CDR1:Bold; CDR2: Underline; CDR3:Italics.

QVQLVESGGGVVQPGRSLRLSCAASGFTFSSYAMIWVRQAPGKGLEYIGYIDTDTSAYYA
SSVKGRFTISRDNSKNTLYLQMSSLRAEDTAVYYCAR*SYAAYGGYPATFDP*WGQGTLVTV
SS (SEQ ID NOS: 78, 79, 80, respectively)

Variable_region_heavy_chain DNA sequence. CDR1:Bold; CDR2: Underline; CDR3:Italics.

CAGGTACAGCTGGTGGAGTCTGGTGGAGGCGTGGTCCAGCCTGGGAGGTCCCTGAGACTC
TCCTGTGCAGCTTCTGGATTCACCTTCAGTAGCTATGCAATGATCTGGGTCCGCCAGGCT
CCAGGGAAGGGGCTGGAATACATCGGATACATTGATACTGATACTAGCGCATACTACGCA
AGCAGTGTGAAAGGCCGATTCACCATCTCCAGAGACAATTCCAAGAACACGCTGTACCTG
CAAATGTCTAGCCTGAGAGCCGAGGACACGGCTGTGTATTACTGTGCTAGA*TCTTATGCT*
*GCTTATGGTGGTTATCCTGCTACTTTTGATCCC*TGGGGCCAAGGTACCCTCGTCACCGTC
TCGAGC (SEQ ID NO: 273)

Heavy_chain Full length DNA sequence.

CAGGTACAGCTGGTGGAGTCTGGTGGAGGCGTGGTCCAGCCTGGGAGGTCCCTGAGACTC
TCCTGTGCAGCTTCTGGATTCACCTTCAGTAGCTATGCAATGATCTGGGTCCGCCAGGCT
CCAGGGAAGGGGCTGGAATACATCGGATACATTGATACTGATACTAGCGCATACTACGCA
AGCAGTGTGAAAGGCCGATTCACCATCTCCAGAGACAATTCCAAGAACACGCTGTACCTG
CAAATGTCTAGCCTGAGAGCCGAGGACACGGCTGTGTATTACTGTGCTAGATCTTATGCT
GCTTATGGTGGTTATCCTGCTACTTTTGATCCCTGGGGCCAAGGTACCCTCGTCACCGTC
TCGAGCGCCTCCACCAAGGGCCCATCGGTCTTCCCCCTGGCACCCTCCTCCAAGAGCACC
TCTGGGGGCACAGCGGCCCTGGGCTGCCTGGTCAAGGACTACTTCCCCGAACCGGTGACG
GTGTCGTGGAACTCAGGCGCCCTGACCAGCGGCGTGCACACCTTCCCGGCTGTCCTACAG
TCCTCAGGACTCTACTCCCTCAGCAGCGTGGTGACCGTGCCCTCCAGCAGCTTGGGCACC
CAGACCTACATCTGCAACGTGAATCACAAGCCCAGCAACACCAAGGTGGACAAGAGAGTT
GAGCCCAAATCTTGTGACAAAACTCACACATGCCCACCGTGCCCAGCACCTGAACTCCTG
GGGGGACCGTCAGTCTTCCTCTTCCCCCCAAAACCCAAGGACACCCTCATGATCTCCCGG
ACCCCTGAGGTCACATGCGTGGTGGTGGACGTGAGCCACGAAGACCCTGAGGTCAAGTTC

FIG. 8B

AACTGGTACGTGGACGGCGTGGAGGTGCATAATGCCAAGACAAAGCCGCGGGAGGAGCAG
TACGCCAGCACGTACCGTGTGGTCAGCGTCCTCACCGTCCTGCACCAGGACTGGCTGAAT
GGCAAGGAGTACAAGTGCAAGGTCTCCAACAAAGCCCTCCCAGCCCCCATCGAGAAAACC
ATCTCCAAAGCCAAAGGGCAGCCCCGAGAACCACAGGTGTACACCCTGCCCCCATCCCGG
GAGGAGATGACCAAGAACCAGGTCAGCCTGACCTGCCTGGTCAAAGGCTTCTATCCCAGC
GACATCGCCGTGGAGTGGGAGAGCAATGGGCAGCCGGAGAACAACTACAAGACCACGCCT
CCCGTGCTGGACTCCGACGGCTCCTTCTTCCTCTACAGCAAGCTCACCGTGGACAAGAGC
AGGTGGCAGCAGGGGAACGTCTTCTCATGCTCCGTGATGCATGAGGCTCTGCACAACCAC
TACACGCAGAAGAGCCTCTCCCTGTCTCCGGGTAAATGA (SEQ ID NO: 274)

Light_chain Full length protein sequence.

DIQMTQSPSSLSASVGDRVTITCQASEDIYNLLAWYQQKPGKVPKLLIYSASTLASGVPS
RFSGSGSGTDYTLTISSLQPEDVATYYCQNNYLVTTYGVAFGGGTKVEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:72)

Variable_region_Light_chain protein sequence.

DIQMTQSPSSLSASVGDRVTITCQASEDIYNLLAWYQQKPGKVPKLLIYSASTLASGVPS
RFSGSGSGTDYTLTISSLQPEDVATYYCQNNYLVTTYGVAFGGGTKVEIKR (SEQ ID NO:71)

Variable_region_Light_chain protein sequence. CDR1:Bold; CDR2: Underline; CDR3:Italics.

DIQMTQSPSSLSASVGDRVTITCQASEDIYNLLAWYQQKPGKVPKLLIY<u>SASTLAS</u>GVPS
RFSGSGSGTDYTLTISSLQPEDVATYYC*QNNYLVTTYGVA*FGGGTKVEIKR (SEQ ID NOS: 75, 76, 77, respectively)

Variable_region_Light_chain DNA sequence. CDR1:Bold; CDR2: Underline; CDR3:Italics.

GACATCCAGATGACCCAGTCTCCATCCTCCCTGTCTGCATCTGTAGGAGACAGAGTCACC
ATCACTTGCCAGGCCAGTGAGGACATTTACAACTTATTGGCCTGGTATCAGCAGAAACCA
GGGAAAGTCCCTAAGCTCCTGATCTAT<u>TCTGCATCCACTCTGGCATCT</u>GGGGTCCCATCT
CGTTTCAGTGGCAGTGGATCTGGGACAGATTACACTCTCACCATCAGCAGCCTGCAGCCT
GAAGATGTTGCAACTTATTACTGT*CAAAACAACTATCTTGTTACTACTTATGGTGTTGCT*
TTCGGCGGAGGAACCAAGGTGGAAATCAAACGT (SEQ ID NO: 271)

Light_chain Full length DNA sequence.

GACATCCAGATGACCCAGTCTCCATCCTCCCTGTCTGCATCTGTAGGAGACAGAGTCACC
ATCACTTGCCAGGCCAGTGAGGACATTTACAACTTATTGGCCTGGTATCAGCAGAAACCA
GGGAAAGTCCCTAAGCTCCTGATCTATTCTGCATCCACTCTGGCATCTGGGGTCCCATCT
CGTTTCAGTGGCAGTGGATCTGGGACAGATTACACTCTCACCATCAGCAGCCTGCAGCCT
GAAGATGTTGCAACTTATTACTGTCAAAACAACTATCTTGTTACTACTTATGGTGTTGCT
TTCGGCGGAGGAACCAAGGTGGAAATCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ ID NO: 272)

Heavy_chain Full length protein sequence.

QSVEESGGRLVTPGTPLTLTCTVSGIDLSMYSMGWVRQAPGKGLEYIGWISYGGTAYYAS
WAKGRFTISKTSTTVELKITSPTIEDTATYFCARETPVNYYLDIWGQGTLVTVSSASTKG
PSVFPLAPSSKSTSGGTAALGCLVKDYFPEPVTVSWNSGALTSGVHTFPAVLQSSGLYSL
SSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYASTYRV
VSVLTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQGNV
FSCSVMHEALHNHYTQKSLSLSPGK (SEQ ID NO:84)

Variable_region heavy_chain protein sequence.

QSVEESGGRLVTPGTPLTLTCTVSGIDLSMYSMGWVRQAPGKGLEYIGWISYGGTAYYAS
WAKGRFTISKTSTTVELKITSPTIEDTATYFCARETPVNYYLDIWGQGTLVTVSS (SEQ
ID NO:83)

Variable_region heavy_chain protein sequence. CDR1:Bold; CDR2: Underline; CDR3:Italics.

QSVEESGGRLVTPGTPLTLTCTVSGIDLSMYSMGWVRQAPGKGLEYIGWISYGGTAYYAS
WAKGRFTISKTSTTVELKITSPTIEDTATYFCAR*ETPVNYYLDI*WGQGTLVTVSS (SEQ
ID NOS: 88, 89, 90, respectively)

Variable_region heavy_chain DNA sequence. CDR1:Bold; CDR2: Underline; CDR3:Italics.

CAGTCGGTGGAGGAGTCCGGGGGTCGCCTGGTCACGCCTGGGACACCCCTGACACTCACC
TGCACAGTCTCTGGAATCGACCTCAGTATGTATTCAATGGGCTGGGTCCGCCAGGCTCCA
GGGAAGGGGCTGGAATACATCGGATGGATTAGTTATGGTGGTACTGCATATTACGCGAGC
TGGGCGAAGGGCCGATTCACCATCTCCAAAACCTCGACCACGGTGGAGCTGAAGATCACC
AGTCCGACAATCGAGGACACGGCCACCTATTTCTGTGCCAGA*GAGACTCCTGTTAATTAT*
*TATTTGGACATT*TGGGGCCAGGGGACCCTCGTCACCGTCTCGAGC (SEQ ID NO:
283)

Heavy_chain Full length DNA sequence.

CAGTCGGTGGAGGAGTCCGGGGGTCGCCTGGTCACGCCTGGGACACCCCTGACACTCACC
TGCACAGTCTCTGGAATCGACCTCAGTATGTATTCAATGGGCTGGGTCCGCCAGGCTCCA
GGGAAGGGGCTGGAATACATCGGATGGATTAGTTATGGTGGTACTGCATATTACGCGAGC
TGGGCGAAGGGCCGATTCACCATCTCCAAAACCTCGACCACGGTGGAGCTGAAGATCACC
AGTCCGACAATCGAGGACACGGCCACCTATTTCTGTGCCAGAGAGACTCCTGTTAATTAT
TATTTGGACATTTGGGGCCAGGGGACCCTCGTCACCGTCTCGAGCGCCTCCACCAAGGGC
CCATCGGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACTCAGGCGCC
CTGACCAGCGGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACATCTGCAACGTG
AATCACAAGCCCAGCAACACCAAGGTGGACAAGAGAGTTGAGCCCAAATCTTGTGACAAA
ACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTG
GTGGTGGACGTGAGCCACGAAGACCCTGAGGTCAAGTTCAACTGGTACGTGGACGGCGTG

FIG. 9B

GAGGTGCATAATGCCAAGACAAAGCCGCGGGAGGAGCAGTACGCCAGCACGTACCGTGTG
GTCAGCGTCCTCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGCCAAAGGGCAG
CCCCGAGAACCACAGGTGTACACCCTGCCCCCATCCCGGGAGGAGATGACCAAGAACCAG
GTCAGCCTGACCTGCCTGGTCAAAGGCTTCTATCCCAGCGACATCGCCGTGGAGTGGGAG
AGCAATGGGCAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAGGGGAACGTC
TTCTCATGCTCCGTGATGCATGAGGCTCTGCACAACCACTACACGCAGAAGAGCCTCTCC
CTGTCTCCGGGTAAATGA (SEQ ID NO: 284)

Light_chain Full length protein sequence.

AYDMTQTPASVSAAVGGTVTIKCQASENIGSYLAWYQQKPGQPPELLIYRASTLASGVPS
RFKGSGSGTQFTLTISGVECADAATYYCQQGYNSENLDNAFGGGTEVVVKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:82)

Variable_region_light_chain protein sequence.

AYDMTQTPASVSAAVGGTVTIKCQASENIGSYLAWYQQKPGQPPELLIYRASTLASGVPS
RFKGSGSGTQFTLTISGVECADAATYYCQQGYNSENLDNAFGGGTEVVVKR (SEQ ID
NO:81)

Variable_region_light_chain protein sequence. CDR1:Bold; CDR2: Underline; CDR3:Italics.

AYDMTQTPASVSAAVGGTVTIKCQASENIGSYLAWYQQKPGQPPELLIY<u>RASTLAS</u>GVPS
RFKGSGSGTQFTLTISGVECADAATYYC*QQGYNSENLDNA*FGGGTEVVVKR (SEQ ID
NOS: 85, 86, 87, respectively)

Variable_region_light_chain DNA sequence. CDR1:Bold; CDR2: Underline; CDR3:Italics.

GCCTATGATATGACCCAGACTCCAGCCTCCGTGTCTGCAGCTGTGGGAGGCACAGTCACC
ATCAAGTGCCAGGCCAGTGAGAACATTGGTAGCTACTTAGCCTGGTATCAGCAGAAACCA
GGGCAGCCTCCCGAACTCCTGATCTAC<u>AGGGCGTCCACTCTGGCATCT</u>GGGGTCCCATCG
CGGTTCAAAGGCAGTGGATCTGGGACACAGTTCACTCTCACCATCAGCGGCGTGGAGTGT
GCCGATGCTGCCACTTACTACTGT*CAACAGGGTTATAATAGTGAGAATCTTGATAATGCT*
TTCGGCGGAGGGACCGAGGTGGTGGTCAAACGT (SEQ ID NO: 281)

Light_chain Full length DNA sequence.

GCCTATGATATGACCCAGACTCCAGCCTCCGTGTCTGCAGCTGTGGGAGGCACAGTCACC
ATCAAGTGCCAGGCCAGTGAGAACATTGGTAGCTACTTAGCCTGGTATCAGCAGAAACCA
GGGCAGCCTCCCGAACTCCTGATCTACAGGGCGTCCACTCTGGCATCTGGGGTCCCATCG
CGGTTCAAAGGCAGTGGATCTGGGACACAGTTCACTCTCACCATCAGCGGCGTGGAGTGT
GCCGATGCTGCCACTTACTACTGTCAACAGGGTTATAATAGTGAGAATCTTGATAATGCT
TTCGGCGGAGGGACCGAGGTGGTGGTCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ
ID NO: 282)

Heavy_chain Full length protein sequence.

QVQLVESGGGVVQPGRSLRLSCAASGFTFSMYSMGWVRQAPGKGLEYIGWISYGGTAYYA
SSAKGRFTISRDNSKNTLYLQMSSLRAEDTAVYYCARETPVNYYLDIWGQGTLVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYAST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 94)

Variable_region_heavy_chain protein sequence.

QVQLVESGGGVVQPGRSLRLSCAASGFTFSMYSMGWVRQAPGKGLEYIGWISYGGTAYYA
SSAKGRFTISRDNSKNTLYLQMSSLRAEDTAVYYCARETPVNYYLDIWGQGTLVTVSS
(SEQ ID NO: 93)

Variable_region_heavy_chain protein sequence. CDR1:Bold; CDR2: Underline; CDR3:Italics.

QVQLVESGGGVVQPGRSLRLSCAASGFTFSMYSMGWVRQAPGKGLEYIGWISYGGTAYYA
SSAKGRFTISRDNSKNTLYLQMSSLRAEDTAVYYCAR*ETPVNYYLDI*WGQGTLVTVSS
(SEQ ID NOS: 98, 99, 100, respectively)

Variable_region_heavy_chain DNA sequence. CDR1:Bold; CDR2: Underline; CDR3:Italics.

CAGGTACAGCTGGTGGAGTCTGGTGGAGGCGTGGTCCAGCCTGGGAGGTCCCTGAGACTC
TCCTGTGCAGCTTCTGGATTCACCTTCAGTATGTATTCAATGGGCTGGGTCCGCCAGGCT
CCAGGGAAGGGGCTGGAATACATCGGATGGATTAGTTATGGTGGTACTGCATACTACGCT
AGCAGCGCTAAGGGCCGATTCACCATCTCCAGAGACAATTCCAAGAACACGCTGTACCTG
CAAATGTCTAGCCTGAGAGCCGAGGACACGGCTGTGTATTACTGTGCTAGA*GAGACTCCT*
*GTTAATTACTACTTGGACATT*TGGGGCCAAGGTACCCTCGTCACCGTCTCGAGC (SEQ
ID NO: 293)

Heavy_chain Full length DNA sequence.

CAGGTACAGCTGGTGGAGTCTGGTGGAGGCGTGGTCCAGCCTGGGAGGTCCCTGAGACTC
TCCTGTGCAGCTTCTGGATTCACCTTCAGTATGTATTCAATGGGCTGGGTCCGCCAGGCT
CCAGGGAAGGGGCTGGAATACATCGGATGGATTAGTTATGGTGGTACTGCATACTACGCT
AGCAGCGCTAAGGGCCGATTCACCATCTCCAGAGACAATTCCAAGAACACGCTGTACCTG
CAAATGTCTAGCCTGAGAGCCGAGGACACGGCTGTGTATTACTGTGCTAGAGAGACTCCT
GTTAATTACTACTTGGACATTTGGGGCCAAGGTACCCTCGTCACCGTCTCGAGCGCCTCC
ACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAAATCT
TGTGACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGAGGTC
ACATGCGTGGTGGTGGACGTGAGCCACGAAGACCCTGAGGTCAAGTTCAACTGGTACGTG

FIG. 10B

GACGGCGTGGAGGTGCATAATGCCAAGACAAAGCCGCGGGAGGAGCAGTACGCCAGCACG
TACCGTGTGGTCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGAGGAGATGACC
AAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACGCAGAAG
AGCCTCTCCCTGTCTCCGGGTAAATGA (SEQ ID NO: 294)

Light_chain Full length protein sequence.

AYDMTQSPSSLSASVGDRVTITCQASENIGSYLAWYQQKPGKVPKLLIYRASTLASGVPS
RFSGSGSGTDFTLTISSLQPEDVATYYCQQGYNSENLDNAFGGGTKVEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO: 92)

Variable_region_Light_chain protein sequence.

AYDMTQSPSSLSASVGDRVTITCQASENIGSYLAWYQQKPGKVPKLLIYRASTLASGVPS
RFSGSGSGTDFTLTISSLQPEDVATYYCQQGYNSENLDNAFGGGTKVEIKR (SEQ ID NO: 91)

Variable_region_Light_chain protein sequence. CDR1:Bold; CDR2: Underline; CDR3:Italics.

AYDMTQSPSSLSASVGDRVTITCQASENIGSYLAWYQQKPGKVPKLLIYRASTLASGVPS
RFSGSGSGTDFTLTISSLQPEDVATYYC*QQGYNSENLDNA*FGGGTKVEIKR (SEQ ID NOS: 95, 96, 97, respectively)

Variable_region_Light_chain DNA sequence. CDR1:Bold; CDR2: Underline; CDR3:Italics.

GCCTATGATATGACCCAGTCTCCATCCTCCCTGTCTGCATCTGTAGGAGACAGAGTCACC
ATCACTTGCCAGGCCAGTGAGAACATTGGTAGCTACTTAGCCTGGTATCAGCAGAAACCA
GGGAAAGTCCCTAAGCTCCTGATCTATAGGGCTTCCACTCTGGCATCTGGGGTCCCATCT
CGTTTCAGTGGCAGTGGATCTGGGACAGATTTCACTCTCACCATCAGCAGCCTGCAGCCT
GAAGATGTTGCAACTTATTACTGT*CAACAGGGTTACAATAGTGAGAATCTTGATAATGCT*
TTCGGCGGAGGAACCAAGGTGGAAATCAAACGT (SEQ ID NO: 291)

Light_chain Full length DNA sequence.

GCCTATGATATGACCCAGTCTCCATCCTCCCTGTCTGCATCTGTAGGAGACAGAGTCACC
ATCACTTGCCAGGCCAGTGAGAACATTGGTAGCTACTTAGCCTGGTATCAGCAGAAACCA
GGGAAAGTCCCTAAGCTCCTGATCTATAGGGCTTCCACTCTGGCATCTGGGGTCCCATCT
CGTTTCAGTGGCAGTGGATCTGGGACAGATTTCACTCTCACCATCAGCAGCCTGCAGCCT
GAAGATGTTGCAACTTATTACTGTCAACAGGGTTACAATAGTGAGAATCTTGATAATGCT
TTCGGCGGAGGAACCAAGGTGGAAATCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ ID NO: 292)

Heavy_chain Full length protein sequence.

QSLEESGGRLVTPGTPLTLTCTASGFSLSGYDMSWVRQAPGKGLEYIGLISYDGNTYYAT
WAKGRFTISKTSTTVDLKITSPTTEDTATYFCARSLYAGPNAGIGPFNIWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 104)

Variable_region_heavy_chain protein sequence.

QSLEESGGRLVTPGTPLTLTCTASGFSLSGYDMSWVRQAPGKGLEYIGLISYDGNTYYAT
WAKGRFTISKTSTTVDLKITSPTTEDTATYFCARSLYAGPNAGIGPFNIWGQGTLVTVSS
(SEQ ID NO: 103)

Variable_region_heavy_chain protein sequence. CDR1:Bold; CDR2: Underline; CDR3:Italics.

QSLEESGGRLVTPGTPLTLTCTASGFSLSGYDMSWVRQAPGKGLEYIG<u>LISYDGNTYYAT</u>
<u>WAKG</u>RFTISKTSTTVDLKITSPTTEDTATYFCAR*SLYAGPNAGIGPFNI*WGQGTLVTVSS
(SEQ ID NOS: 108, 109, 110, respectively)

Variable_region_heavy_chain DNA sequence. CDR1:Bold; CDR2: Underline; CDR3:Italics.

CAGTCGCTGGAGGAGTCCGGGGGTCGCCTGGTCACGCCTGGGACACCCCTGACACTCACC
TGCACAGCCTCTGGATTCTCCCTCAGTGGCTACGACATGAGCTGGGTCCGCCAGGCTCCA
GGAAAGGGGCTGGAATACATCGGA<u>CTCATTAGTTATGATGGTAACACATACTACGCGACC</u>
<u>TGGGCGAAAGGC</u>CGATTCACCATCTCCAAAACCTCGACCACGGTGGATCTGAAAATCACC
AGTCCGACAACCGAGGACACGGCCACCTATTTCTGTGCCAGA*AGTCTTTATGCTGGTCCT*
*AATGCTGGTATCGGACCGTTTAACATC*TGGGGCCAGGGGACCCTCGTCACCGTCTCGAGC
(SEQ ID NO: 303)

Heavy_chain Full length DNA sequence.

CAGTCGCTGGAGGAGTCCGGGGGTCGCCTGGTCACGCCTGGGACACCCCTGACACTCACC
TGCACAGCCTCTGGATTCTCCCTCAGTGGCTACGACATGAGCTGGGTCCGCCAGGCTCCA
GGAAAGGGGCTGGAATACATCGGACTCATTAGTTATGATGGTAACACATACTACGCGACC
TGGGCGAAAGGCCGATTCACCATCTCCAAAACCTCGACCACGGTGGATCTGAAAATCACC
AGTCCGACAACCGAGGACACGGCCACCTATTTCTGTGCCAGAAGTCTTTATGCTGGTCCT
AATGCTGGTATCGGACCGTTTAACATCTGGGGCCAGGGGACCCTCGTCACCGTCTCGAGC
GCCTCCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGG

FIG. 11B

TACGTGGACGGCGTGGAGGTGCATAATGCCAAGACAAAGCCGCGGGAGGAGCAGTACGCC
AGCACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATCTCC
AAAGCCAAAGGGCAGCCCCGAGAACCACAGGTGTACACCCTGCCCCCATCCCGGGAGGAG
ATGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACG
CAGAAGAGCCTCTCCCTGTCTCCGGGTAAATGA (SEQ ID NO: 304)

Light_chain Full length protein sequence.

AFELTQTPSSVEAAVGGTVTIKCQASQNIVTNLAWYQQKPGQPPKLLIYGASTLASGVSS
RFKGSGSGTQFTLTISDLECADAATYFCQSYDGFNSAGFGGGTEVVVKRTVAAPSVFIFP
PSDEQLKSGTASVVCLLNNFYPREAKVQWKVDNALQSGNSQESVTEQDSKDSTYSLSSTL
TLSKADYEKHKVYACEVTHQGLSSPVTKSFNRGEC (SEQ ID NO: 102)

Variable_region_light_chain protein sequence.

AFELTQTPSSVEAAVGGTVTIKCQASQNIVTNLAWYQQKPGQPPKLLIYGASTLASGVSS
RFKGSGSGTQFTLTISDLECADAATYFCQSYDGFNSAGFGGGTEVVVKR (SEQ ID NO: 101)

Variable_region_light_chain protein sequence. CDR1:Bold; CDR2: Underline; CDR3:Italics.

AFELTQTPSSVEAAVGGTVTIKCQASQNIVTNLAWYQQKPGQPPKLLIY<u>GASTLAS</u>GVSS
RFKGSGSGTQFTLTISDLECADAATYFC*QSYDGFNSAG*FGGGTEVVVKR (SEQ ID NOS: 105, 106, 107, respectively)

Variable_region_light_chain DNA sequence. CDR1:Bold; CDR2: Underline; CDR3:Italics.

GCATTCGAATTGACCCAGACTCCATCCTCCGTGGAGGCAGCTGTGGGAGGCACAGTCACC
ATCAAGTGCCAGGCCAGTCAGAACATTGTTACCAATTTAGCCTGGTATCAACAGAAACCA
GGGCAGCCTCCCAAGCTCCTGATCTAT<u>GGTGCATCCACTCTGGCATCT</u>GGGGTCTCATCG
CGGTTCAAAGGCAGTGGATCTGGGACACAGTTCACTCTCACCATCAGCGACCTGGAGTGT
GCCGATGCTGCCACTTATTTCTGT*CAGAGCTATGATGGTTTTAATAGTGCTGGG*TTCGGC
GGAGGGACCGAGGTGGTGGTCAAACGT (SEQ ID NO: 301)

Light_chain Full length DNA sequence.

GCATTCGAATTGACCCAGACTCCATCCTCCGTGGAGGCAGCTGTGGGAGGCACAGTCACC
ATCAAGTGCCAGGCCAGTCAGAACATTGTTACCAATTTAGCCTGGTATCAACAGAAACCA
GGGCAGCCTCCCAAGCTCCTGATCTATGGTGCATCCACTCTGGCATCTGGGGTCTCATCG
CGGTTCAAAGGCAGTGGATCTGGGACACAGTTCACTCTCACCATCAGCGACCTGGAGTGT
GCCGATGCTGCCACTTATTTCTGTCAGAGCTATGATGGTTTTAATAGTGCTGGGTTCGGC
GGAGGGACCGAGGTGGTGGTCAAACGTACGGTGGCTGCACCATCTGTCTTCATCTTCCCG
CCATCTGATGAGCAGTTGAAATCTGGAACTGCCTCTGTTGTGTGCCTGCTGAATAACTTC
TATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTG
ACGCTGAGCAAAGCAGACTACGAGAAACACAAAGTCTACGCCTGCGAAGTCACCCATCAG
GGCCTGAGCTCGCCCGTCACAAAGAGCTTCAACAGGGGAGAGTGTTAG (SEQ ID NO: 302)

Heavy chain Full length protein sequence.

QVQLVESGGGVVQPGRSLRLSCAASGFSLSGYDMSWVRQAPGKGLEWVGLISYDGNTYYA
TSAKGRFTISRDNSKNTLYLQMSSLRAEDTAVYYCARSLYAGPNAGIGPFNIWGQGTLVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKRVEPKSCDKTHTCPPCPAPEL
LGGPSVFLFPPKPKDTLMISRTPEVTCVVVDVSHEDPEVKFNWYVDGVEVHNAKTKPREE
QYASTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDK
SRWQQGNVFSCSVMHEALHNHYTQKSLSLSPGK (SEQ ID NO: 114)

Variable region heavy chain protein sequence.

QVQLVESGGGVVQPGRSLRLSCAASGFSLSGYDMSWVRQAPGKGLEWVGLISYDGNTYYA
TSAKGRFTISRDNSKNTLYLQMSSLRAEDTAVYYCARSLYAGPNAGIGPFNIWGQGTLVT
VSS (SEQ ID NO: 113)

Variable region heavy chain protein sequence. CDR1:Bold; CDR2: Underline; CDR3:Italics.

QVQLVESGGGVVQPGRSLRLSCAASGFSLSGYDMSWVRQAPGKGLEWVG<u>LISYDGNTYYA</u>
<u>TSAKG</u>RFTISRDNSKNTLYLQMSSLRAEDTAVYYCAR*SLYAGPNAGIGPFNI*WGQGTLVT
VSS (SEQ ID NOS: 118, 119, 120, respectively)

Variable region heavy chain DNA sequence. CDR1:Bold; CDR2: Underline; CDR3:Italics.

CAGGTACAGCTGGTGGAGTCTGGTGGAGGCGTGGTCCAGCCTGGGAGGTCCCTGAGACTC
TCCTGTGCAGCTTCTGGATTCTCCCTCAGTGGCTACGACATGAGCTGGGTCCGTCAGGCT
CCAGGCAAGGGACTGGAGTGGGTGGGA<u>CTCATTAGTTATGATGGTAACACATACTACGCG</u>
<u>ACCTCCGCGAAAGGC</u>CGATTCACCATCTCCAGAGACAATTCCAAGAACACGCTGTACCTG
CAAATGTCTAGCCTGAGAGCCGAGGACACGGCTGTGTATTACTGTGCTAGA*AGTCTTTAT*
*GCTGGTCCTAATGCTGGTATCGGACCGTTTAACATC*TGGGGCCAAGGTACCCTCGTCACC
GTCTCGAGC (SEQ ID NO: 313)

Heavy chain Full length DNA sequence.

CAGGTACAGCTGGTGGAGTCTGGTGGAGGCGTGGTCCAGCCTGGGAGGTCCCTGAGACTC
TCCTGTGCAGCTTCTGGATTCTCCCTCAGTGGCTACGACATGAGCTGGGTCCGTCAGGCT
CCAGGCAAGGGACTGGAGTGGGTGGGACTCATTAGTTATGATGGTAACACATACTACGCG
ACCTCCGCGAAAGGCCGATTCACCATCTCCAGAGACAATTCCAAGAACACGCTGTACCTG
CAAATGTCTAGCCTGAGAGCCGAGGACACGGCTGTGTATTACTGTGCTAGAAGTCTTTAT
GCTGGTCCTAATGCTGGTATCGGACCGTTTAACATCTGGGGCCAAGGTACCCTCGTCACC
GTCTCGAGCGCCTCCACCAAGGGCCCATCGGTCTTCCCCCTGGCACCCTCCTCCAAGAGC
ACCTCTGGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCTGTCCTA
CAGTCCTCAGGACTCTACTCCCTCAGCAGCGTGGTGACCGTGCCCTCCAGCAGCTTGGGC
ACCCAGACCTACATCTGCAACGTGAATCACAAGCCCAGCAACACCAAGGTGGACAAGAGA
GTTGAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATCTCC
CGGACCCCTGAGGTCACATGCGTGGTGGTGGACGTGAGCCACGAAGACCCTGAGGTCAAG

FIG. 12B

TTCAACTGGTACGTGGACGGCGTGGAGGTGCATAATGCCAAGACAAAGCCGCGGGAGGAG
CAGTACGCCAGCACGTACCGTGTGGTCAGCGTCCTCACCGTCCTGCACCAGGACTGGCTG
AATGGCAAGGAGTACAAGTGCAAGGTCTCCAACAAAGCCCTCCCAGCCCCCATCGAGAAA
ACCATCTCCAAAGCCAAAGGGCAGCCCCGAGAACCACAGGTGTACACCCTGCCCCCATCC
CGGGAGGAGATGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTACAAGACCACG
CCTCCCGTGCTGGACTCCGACGGCTCCTTCTTCCTCTACAGCAAGCTCACCGTGGACAAG
AGCAGGTGGCAGCAGGGGAACGTCTTCTCATGCTCCGTGATGCATGAGGCTCTGCACAAC
CACTACACGCAGAAGAGCCTCTCCCTGTCTCCGGGTAAATGA (SEQ ID NO: 314)

Light_chain Full length protein sequence.

AFQMTQSPSSLSASVGDRVTITCQASQNIVTNLAWYQQKPGKVPKLLIYGASTLASGVPS
RFSGSGSGTDFTLTISSLQPEDVATYYCQSYDGFNSAGFGGGTKVEIKRTVAAPSVFIFP
PSDEQLKSGTASVVCLLNNFYPREAKVQWKVDNALQSGNSQESVTEQDSKDSTYSLSSTL
TLSKADYEKHKVYACEVTHQGLSSPVTKSFNRGEC (SEQ ID NO: 112)

Variable_region Light_chain protein sequence.

AFQMTQSPSSLSASVGDRVTITCQASQNIVTNLAWYQQKPGKVPKLLIYGASTLASGVPS
RFSGSGSGTDFTLTISSLQPEDVATYYCQSYDGFNSAGFGGGTKVEIKR (SEQ ID
NO: 111)

Variable_region Light_chain protein sequence. CDR1:Bold; CDR2: Underline; CDR3:Italics.

AFQMTQSPSSLSASVGDRVTITCQASQNIVTNLAWYQQKPGKVPKLLIY<u>GASTLAS</u>GVPS
RFSGSGSGTDFTLTISSLQPEDVATYYC*QSYDGFNSAG*FGGGTKVEIKR (SEQ ID
NOS: 115, 116, 117, respectively)

Variable_region Light_chain DNA sequence. CDR1:Bold; CDR2: Underline; CDR3:Italics.

GCATTCCAGATGACCCAGTCTCCATCCTCCCTGTCTGCATCTGTAGGAGACAGAGTCACC
ATCACTTGCCAGGCCAGTCAGAACATTGTTACCAACTTAGCCTGGTATCAGCAGAAACCA
GGGAAAGTCCCTAAGCTCCTGATCTAT<u>GGTGCATCCACTCTGGCATCT</u>GGGGTCCCATCT
CGTTTCAGTGGCAGTGGATCTGGGACAGATTTCACTCTCACCATCAGCAGCCTGCAGCCT
GAAGATGTTGCAACTTATTACTGT*CAGAGCTATGATGGTTTCAATAGTGCTGGT*TTCGGC
GGAGGAACCAAGGTGGAAATCAAACGT (SEQ ID NO: 311)

Light_chain Full length DNA sequence.

GCATTCCAGATGACCCAGTCTCCATCCTCCCTGTCTGCATCTGTAGGAGACAGAGTCACC
ATCACTTGCCAGGCCAGTCAGAACATTGTTACCAACTTAGCCTGGTATCAGCAGAAACCA
GGGAAAGTCCCTAAGCTCCTGATCTATGGTGCATCCACTCTGGCATCTGGGGTCCCATCT
CGTTTCAGTGGCAGTGGATCTGGGACAGATTTCACTCTCACCATCAGCAGCCTGCAGCCT
GAAGATGTTGCAACTTATTACTGTCAGAGCTATGATGGTTTCAATAGTGCTGGTTTCGGC
GGAGGAACCAAGGTGGAAATCAAACGTACGGTGGCTGCACCATCTGTCTTCATCTTCCCG
CCATCTGATGAGCAGTTGAAATCTGGAACTGCCTCTGTTGTGTGCCTGCTGAATAACTTC
TATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTG
ACGCTGAGCAAAGCAGACTACGAGAAACACAAAGTCTACGCCTGCGAAGTCACCCATCAG
GGCCTGAGCTCGCCCGTCACAAAGAGCTTCAACAGGGGAGAGTGTTAG (SEQ ID NO:
312)

Heavy_chain Full length protein sequence.

QSVEASGGRLVTPGTPLTLTCTASGFSLSTYWMSWVRQAPGKGLEWIGDIYFSNEETNYA
SWAKGRFTISKTSTTVDLNVISPTTEDTATYFCARGSPDVDIGIDMWGPGTLVTVSSAST
KGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSV
FLFPPKPKDTLMISRTPEVTCVVVDVSHEDPEVKFNWYVDGVEVHNAKTKPREEQYASTY
RVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQG
NVFSCSVMHEALHNHYTQKSLSLSPGK (SEQ ID NO: 124)

Variable_region_heavy_chain protein sequence.

QSVEASGGRLVTPGTPLTLTCTASGFSLSTYWMSWVRQAPGKGLEWIGDIYFSNEETNYA
SWAKGRFTISKTSTTVDLNVISPTTEDTATYFCARGSPDVDIGIDMWGPGTLVTVSS
(SEQ ID NO: 123)

Variable_region_heavy_chain protein sequence. CDR1:Bold; CDR2: Underline; CDR3:Italics.

QSVEASGGRLVTPGTPLTLTCTASGFSLSTYWMSWVRQAPGKGLEWIGDIYFSNEETNYA
SWAKGRFTISKTSTTVDLNVISPTTEDTATYFCAR*GSPDVDIGIDM*WGPGTLVTVSS
(SEQ ID NOS: 128, 129, 130, respectively)

Variable_region_heavy_chain DNA sequence. CDR1:Bold; CDR2: Underline; CDR3:Italics.

CAGTCGGTGGAGGCGTCCGGGGGTCGCCTGGTCACGCCTGGGACACCCCTGACACTCACC
TGCACAGCCTCTGGATTCTCCCTCAGTACCTACTGGATGAGCTGGGTCCGCCAGGCTCCA
GGGAAGGGGCTGGAATGGATCGGAGACATTTATTTTAGTAATGAAGAAACAAACTACGCG
AGCTGGGCGAAAGGCCGATTTACCATCTCCAAAACCTCGACCACGGTGGATCTGAATGTC
ATCAGTCCGACAACCGAGGACACGGCCACCTATTTCTGTGCCAGA*GGTTCTCCTGATGTT*
*GATATTGGTATAGATATG*TGGGGCCCGGGCACCCTCGTCACCGTCTCGAGC (SEQ ID
NO: 323)

Heavy_chain Full length DNA sequence.

CAGTCGGTGGAGGCGTCCGGGGGTCGCCTGGTCACGCCTGGGACACCCCTGACACTCACC
TGCACAGCCTCTGGATTCTCCCTCAGTACCTACTGGATGAGCTGGGTCCGCCAGGCTCCA
GGGAAGGGGCTGGAATGGATCGGAGACATTTATTTTAGTAATGAAGAAACAAACTACGCG
AGCTGGGCGAAAGGCCGATTTACCATCTCCAAAACCTCGACCACGGTGGATCTGAATGTC
ATCAGTCCGACAACCGAGGACACGGCCACCTATTTCTGTGCCAGAGGTTCTCCTGATGTT
GATATTGGTATAGATATGTGGGGCCCGGGCACCCTCGTCACCGTCTCGAGCGCCTCCACC
AAGGGCCCATCGGTCTTCCCCCTGGCACCCTCCTCCAAGAGCACCTCTGGGGGCACAGCG
GCCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTAC
TCCCTCAGCAGCGTGGTGACCGTGCCCTCCAGCAGCTTGGGCACCCAGACCTACATCTGC
AACGTGAATCACAAGCCCAGCAACACCAAGGTGGACAAGAGAGTTGAGCCCAAATCTTGT
GACAAAACTCACACATGCCCACCGTGCCCAGCACCTGAACTCCTGGGGGGACCGTCAGTC
TTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGAC

FIG. 13B

GGCGTGGAGGTGCATAATGCCAAGACAAAGCCGCGGGAGGAGCAGTACGCCAGCACGTAC
CGTGTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAGGAGATGACCAAG
AACCAGGTCAGCCTGACCTGCCTGGTCAAAGGCTTCTATCCCAGCGACATCGCCGTGGAG
TGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGG
AACGTCTTCTCATGCTCCGTGATGCATGAGGCTCTGCACAACCACTACACGCAGAAGAGC
CTCTCCCTGTCTCCGGGTAAATGA (SEQ ID NO: 324)

Light_chain Full length protein sequence.

AAVLTQTPSPVSAAVGGTVSISCQSSQNVYKNNYLSWYQQKPGQPPKLLIYKASTLASGV
PSRFKGGGSGTDFTLTISDVQCDAAATYYCAGGYTSSSDNAFGGGTEVVVKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 122)

Variable_region_light_chain protein sequence.

AAVLTQTPSPVSAAVGGTVSISCQSSQNVYKNNYLSWYQQKPGQPPKLLIYKASTLASGV
PSRFKGGGSGTDFTLTISDVQCDAAATYYCAGGYTSSSDNAFGGGTEVVVKR (SEQ ID
NO: 121)

Variable_region_light_chain protein sequence. CDR1:Bold; CDR2: Underline; CDR3:Italics.

AAVLTQTPSPVSAAVGGTVSISCQSSQNVYKNNYLSWYQQKPGQPPKLLIYKASTLASGV
PSRFKGGGSGTDFTLTISDVQCDAAATYYC*AGGYTSSSDNA*FGGGTEVVVKR (SEQ ID
NOS: 125, 126, 127, respectively)

Variable_region_light_chain DNA sequence. CDR1:Bold; CDR2: Underline; CDR3:Italics.

GCCGCCGTGCTGACCCAGACTCCATCTCCCGTGTCTGCAGCTGTGGGAGGCACAGTCAGC
ATCAGTTGCCAGTCCAGTCAGAATGTTTATAAGAACAACTACTTATCCTGGTATCAGCAG
AAACCAGGGCAGCCTCCCAAGCTCCTGATCTACAAGGCATCCACTCTGGCATCTGGGGTC
CCATCGCGGTTCAAAGGCGGTGGATCTGGGACAGATTTCACTCTCACCATCAGCGACGTG
CAGTGTGACGCTGCTGCCACTTACTACTGT*GCAGGCGGTTATACCAGTAGTAGTGATAAT*
*GCT*TTCGGCGGAGGGACCGAGGTGGTGGTCAAACGT (SEQ ID NO: 321)

Light_chain Full length DNA sequence.

GCCGCCGTGCTGACCCAGACTCCATCTCCCGTGTCTGCAGCTGTGGGAGGCACAGTCAGC
ATCAGTTGCCAGTCCAGTCAGAATGTTTATAAGAACAACTACTTATCCTGGTATCAGCAG
AAACCAGGGCAGCCTCCCAAGCTCCTGATCTACAAGGCATCCACTCTGGCATCTGGGGTC
CCATCGCGGTTCAAAGGCGGTGGATCTGGGACAGATTTCACTCTCACCATCAGCGACGTG
CAGTGTGACGCTGCTGCCACTTACTACTGTGCAGGCGGTTATACCAGTAGTAGTGATAAT
GCTTTCGGCGGAGGGACCGAGGTGGTGGTCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 322)

Ab14

Heavy chain Full length protein sequence.
EVQLVESGGGLVQPGGSLRLSCAASGFTVSTYWMSWVRQAPGKGLEWVGDIYFSNEETNY
ASSAKGRFTISRDNSKNTLYLQMNSLRAEDTAVYYCARGSPDVDIGIDMWGPGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 134)

Variable region heavy chain protein sequence.
EVQLVESGGGLVQPGGSLRLSCAASGFTVSTYWMSWVRQAPGKGLEWVGDIYFSNEETNY
ASSAKGRFTISRDNSKNTLYLQMNSLRAEDTAVYYCARGSPDVDIGIDMWGPGTLVTVSS
(SEQ ID NO: 133)

Variable region heavy chain protein sequence. CDR1:Bold; CDR2: Underline; CDR3:Italics.
EVQLVESGGGLVQPGGSLRLSCAASGFTVSTYWMSWVRQAPGKGLEWVGDIYFSNEETNY
ASSAKGRFTISRDNSKNTLYLQMNSLRAEDTAVYYCAR*GSPDVDIGIDM*WGPGTLVTVSS
(SEQ ID NOS: 138, 139, 140, respectively)

Variable region heavy chain DNA sequence. CDR1:Bold; CDR2: Underline; CDR3:Italics.
GAGGTGCAGCTGGTGGAGTCTGGGGGAGGCTTGGTCCAGCCTGGGGGGTCCCTGAGACTC
TCCTGTGCAGCCTCTGGATTCACCGTCAGTACCTACTGGATGAGCTGGGTCCGTCAGGCT
CCAGGGAAGGGGCTGGAGTGGGTCGGAGACATTTACTTTAGTAATGAAGAAACAAACTAC
GCGAGCAGCGCGAAAGGCCGATTCACCATCTCCAGAGACAATTCCAAGAACACCCTGTAT
CTTCAAATGAACAGCCTGAGAGCTGAGGACACTGCTGTGTATTACTGTGCTAGA*GGTTCT
CCTGATGTTGATATTGGTATAGATATGT*GGGGCCCAGGGACCCTCGTCACCGTCTCGAGC
(SEQ ID NO: 333)

Heavy chain Full length DNA sequence.
GAGGTGCAGCTGGTGGAGTCTGGGGGAGGCTTGGTCCAGCCTGGGGGGTCCCTGAGACTC
TCCTGTGCAGCCTCTGGATTCACCGTCAGTACCTACTGGATGAGCTGGGTCCGTCAGGCT
CCAGGGAAGGGGCTGGAGTGGGTCGGAGACATTTACTTTAGTAATGAAGAAACAAACTAC
GCGAGCAGCGCGAAAGGCCGATTCACCATCTCCAGAGACAATTCCAAGAACACCCTGTAT
CTTCAAATGAACAGCCTGAGAGCTGAGGACACTGCTGTGTATTACTGTGCTAGAGGTTCT
CCTGATGTTGATATTGGTATAGATATGTGGGGCCCAGGGACCCTCGTCACCGTCTCGAGC
GCCTCCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGG

FIG. 14B

TACGTGGACGGCGTGGAGGTGCATAATGCCAAGACAAAGCCGCGGGAGGAGCAGTACGCC
AGCACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATCTCC
AAAGCCAAAGGGCAGCCCCGAGAACCACAGGTGTACACCCTGCCCCCATCCCGGGAGGAG
ATGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACG
CAGAAGAGCCTCTCCCTGTCTCCGGGTAAATGA (SEQ ID NO: 334)

Light_chain Full length protein sequence.

DIQMTQSPSSLSASVGDRVTITCQSSQNVYKNNYLSWYQQKPGKVPKLLIYKASTLASGV
PSRFSGSGSGTDFTLTISSLQPEDVATYYCAGGYTSSSDNAFGGGTKVEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 132)

Variable_region Light_chain protein sequence.

DIQMTQSPSSLSASVGDRVTITCQSSQNVYKNNYLSWYQQKPGKVPKLLIYKASTLASGV
PSRFSGSGSGTDFTLTISSLQPEDVATYYCAGGYTSSSDNAFGGGTKVEIKR (SEQ ID
NO: 131)

Variable_region Light_chain protein sequence. CDR1:Bold; CDR2: Underline; CDR3:Italics.

DIQMTQSPSSLSASVGDRVTITCQSSQNVYKNNYLSWYQQKPGKVPKLLIYKASTLASGV
PSRFSGSGSGTDFTLTISSLQPEDVATYYC*AGGYTSSSDNA*FGGGTKVEIKR (SEQ ID
NOS: 135, 136, 137, respectively)

Variable_region Light_chain DNA sequence. CDR1:Bold; CDR2: Underline; CDR3:Italics.

GACATCCAGATGACCCAGTCTCCATCCTCCCTGTCTGCATCTGTAGGAGACAGAGTCACC
ATCACTTGCCAGTCCAGTCAGAATGTTTATAAGAACAACTACTTATCCTGGTATCAGCAG
AAACCAGGGAAAGTCCCTAAGCTCCTGATCTATAAGGCATCCACTCTGGCATCTGGGGTC
CCATCTCGTTTCAGTGGCAGTGGATCTGGGACAGATTTCACTCTCACCATCAGCAGCCTG
CAGCCTGAAGATGTTGCAACTTATTACTGT*GCAGGCGGTTATACCAGTAGTAGTGATAAT*
*GCT*TTCGGCGGAGGAACCAAGGTGGAAATCAAACGT (SEQ ID NO: 331)

Light_chain Full length DNA sequence.

GACATCCAGATGACCCAGTCTCCATCCTCCCTGTCTGCATCTGTAGGAGACAGAGTCACC
ATCACTTGCCAGTCCAGTCAGAATGTTTATAAGAACAACTACTTATCCTGGTATCAGCAG
AAACCAGGGAAAGTCCCTAAGCTCCTGATCTATAAGGCATCCACTCTGGCATCTGGGGTC
CCATCTCGTTTCAGTGGCAGTGGATCTGGGACAGATTTCACTCTCACCATCAGCAGCCTG
CAGCCTGAAGATGTTGCAACTTATTACTGTGCAGGCGGTTATACCAGTAGTAGTGATAAT
GCTTTCGGCGGAGGAACCAAGGTGGAAATCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 332)

Heavy_chain Full length protein sequence.

QSVEESGGRLVTPGTPLTLTCTVSGIDLSSYAMIWVRQAPGKGLEYIGIIWSGGTYYATW
AKGRFTISKTSTTVDLQITSPTTEDAATYFCAAGGGSIYDVWGPGTLVTVSSASTKGPSV
FPLAPSSKSTSGGTAALGCLVKDYFPEPVTVSWNSGALTSGVHTFPAVLQSSGLYSLSSV
VTVPSSSLGTQTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREEQYASTYRVVSV
LTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSC
SVMHEALHNHYTQKSLSLSPGK (SEQ ID NO: 144)

Variable_region_heavy_chain protein sequence.

QSVEESGGRLVTPGTPLTLTCTVSGIDLSSYAMIWVRQAPGKGLEYIGIIWSGGTYYATW
AKGRFTISKTSTTVDLQITSPTTEDAATYFCAAGGGSIYDVWGPGTLVTVSS (SEQ ID
NO: 143)

Variable_region_heavy_chain protein sequence. CDR1:Bold; CDR2: Underline; CDR3:Italics.

QSVEESGGRLVTPGTPLTLTCTVSGIDLSSYAMIWVRQAPGKGLEYIGIIWSGGTYYATW
AKGRFTISKTSTTVDLQITSPTTEDAATYFCAA*GGGSIYDV*WGPGTLVTVSS (SEQ ID
NOS: 148, 149, 150, respectively)

Variable_region_heavy_chain DNA sequence. CDR1:Bold; CDR2: Underline; CDR3:Italics.

CAGTCGGTGGAGGAGTCCGGGGGTCGCCTGGTCACGCCTGGGACACCCCTGACACTCACC
TGCACAGTCTCTGGAATCGACCTCAGTAGCTATGCAATGATCTGGGTCCGCCAGGCTCCA
GGGAAGGGGCTGGAATACATCGGAATCATTTGGAGTGGTGGCACCTACTACGCGACCTGG
GCGAAAGGCCGATTCACCATCTCCAAAACCTCGACCACGGTGGATCTGCAAATCACCAGT
CCGACAACCGAGGACGCGGCCACCTATTTCTGTGCCGCA*GGTGGTGGTAGTATTTATGAT*
*GTT*TGGGGCCCGGGCACCCTGGTCACCGTCTCGAGC (SEQ ID NO: 343)

Heavy_chain Full length DNA sequence.

CAGTCGGTGGAGGAGTCCGGGGGTCGCCTGGTCACGCCTGGGACACCCCTGACACTCACC
TGCACAGTCTCTGGAATCGACCTCAGTAGCTATGCAATGATCTGGGTCCGCCAGGCTCCA
GGGAAGGGGCTGGAATACATCGGAATCATTTGGAGTGGTGGCACCTACTACGCGACCTGG
GCGAAAGGCCGATTCACCATCTCCAAAACCTCGACCACGGTGGATCTGCAAATCACCAGT
CCGACAACCGAGGACGCGGCCACCTATTTCTGTGCCGCAGGTGGTGGTAGTATTTATGAT
GTTTGGGGCCCGGGCACCCTGGTCACCGTCTCGAGCGCCTCCACCAAGGGCCCATCGGTC
TTCCCCCTGGCACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCACAAG
CCCAGCAACACCAAGGTGGACAAGAGAGTTGAGCCCAAATCTTGTGACAAAACTCACACA
TGCCCACCGTGCCCAGCACCTGAACTCCTGGGGGGACCGTCAGTCTTCCTCTTCCCCCCA
AAACCCAAGGACACCCTCATGATCTCCCGGACCCCTGAGGTCACATGCGTGGTGGTGGAC
GTGAGCCACGAAGACCCTGAGGTCAAGTTCAACTGGTACGTGGACGGCGTGGAGGTGCAT
AATGCCAAGACAAAGCCGCGGGAGGAGCAGTACGCCAGCACGTACCGTGTGGTCAGCGTC

FIG. 15B

CTCACCGTCCTGCACCAGGACTGGCTGAATGGCAAGGAGTACAAGTGCAAGGTCTCCAAC
AAAGCCCTCCCAGCCCCCATCGAGAAAACCATCTCCAAAGCCAAAGGGCAGCCCCGAGAA
CCACAGGTGTACACCCTGCCCCCATCCCGGGAGGAGATGACCAAGAACCAGGTCAGCCTG
ACCTGCCTGGTCAAAGGCTTCTATCCCAGCGACATCGCCGTGGAGTGGGAGAGCAATGGG
CAGCCGGAGAACAACTACAAGACCACGCCTCCCGTGCTGGACTCCGACGGCTCCTTCTTC
CTCTACAGCAAGCTCACCGTGGACAAGAGCAGGTGGCAGCAGGGGAACGTCTTCTCATGC
TCCGTGATGCATGAGGCTCTGCACAACCACTACACGCAGAAGAGCCTCTCCCTGTCTCCG
GGTAAATGA (SEQ ID NO: 344)

Light_chain Full length protein sequence.

AAVLTQTPSPVSAAVGDTVTIKCQSSQSVYKNNYLSWYQQKPGQPPKLLIYDASNLPSGV
PSRFSGSGSGTQFTLTISGVQCDDAATYYCLGDYDDDTDNGFGGGTEVVVKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 142)

Variable_region_light_chain protein sequence.

AAVLTQTPSPVSAAVGDTVTIKCQSSQSVYKNNYLSWYQQKPGQPPKLLIYDASNLPSGV
PSRFSGSGSGTQFTLTISGVQCDDAATYYCLGDYDDDTDNGFGGGTEVVVKR (SEQ ID
NO: 141)

Variable_region_light_chain protein sequence. CDR1:Bold; CDR2: Underline; CDR3:Italics.

AAVLTQTPSPVSAAVGDTVTIKCQSSQSVYKNNYLSWYQQKPGQPPKLLIYDASNLPSGV
PSRFSGSGSGTQFTLTISGVQCDDAATYYC*LGDYDDDTDNGF*GGGTEVVVKR (SEQ ID
NOS: 145, 146, 147, respectively)

Variable_region_light_chain DNA sequence. CDR1:Bold; CDR2: Underline; CDR3:Italics.

GCAGCCGTGCTGACCCAGACACCATCGCCCGTGTCTGCAGCTGTGGGAGACACAGTCACC
ATCAAGTGCCAGTCCAGTCAGAGTGTTTATAAGAACAACTACTTATCCTGGTATCAGCAG
AAACCAGGGCAGCCTCCCAAGCTCCTGATCTATGATGCATCCAATCTGCCATCTGGGGTC
CCATCACGGTTCAGCGGCAGTGGATCTGGGACACAGTTCACTCTCACCATCAGCGGCGTG
CAGTGTGACGATGCTGCCACTTACTACTGT*CTAGGCGATTATGATGATGATACTGATAAT*
*GG*TTTCGGCGGAGGGACCGAGGTGGTGGTCAAACGT (SEQ ID NO: 341)

Light_chain Full length DNA sequence.

GCAGCCGTGCTGACCCAGACACCATCGCCCGTGTCTGCAGCTGTGGGAGACACAGTCACC
ATCAAGTGCCAGTCCAGTCAGAGTGTTTATAAGAACAACTACTTATCCTGGTATCAGCAG
AAACCAGGGCAGCCTCCCAAGCTCCTGATCTATGATGCATCCAATCTGCCATCTGGGGTC
CCATCACGGTTCAGCGGCAGTGGATCTGGGACACAGTTCACTCTCACCATCAGCGGCGTG
CAGTGTGACGATGCTGCCACTTACTACTGTCTAGGCGATTATGATGATGATACTGATAAT
GGTTTCGGCGGAGGGACCGAGGTGGTGGTCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 342)

Heavy_chain Full length protein sequence.

QSVEEFGGRLVTPGTPLTLTCTVSGFSLNNYAMTWVRQAPGKGLEWIGIIGSIGTTYYAS
WAKGRFFISKTSTTVDLKIISPTTEDTATYFCARDAGVTVDGYGYYFNIWGPGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 154)

Variable_region_heavy_chain protein sequence.

QSVEEFGGRLVTPGTPLTLTCTVSGFSLNNYAMTWVRQAPGKGLEWIGIIGSIGTTYYAS
WAKGRFFISKTSTTVDLKIISPTTEDTATYFCARDAGVTVDGYGYYFNIWGPGTLVTVSS
(SEQ ID NO: 153)

Variable_region_heavy_chain protein sequence. CDR1:Bold; CDR2: Underline; CDR3:Italics.

QSVEEFGGRLVTPGTPLTLTCTVSGFSLNNYAMTWVRQAPGKGLEWIG<u>IIGSIGTTYYAS</u>
<u>WAKG</u>RFFISKTSTTVDLKIISPTTEDTATYFCAR*DAGVTVDGYGYYFNI*WGPGTLVTVSS
(SEQ ID NOS: 158, 159, 160, respectively)

Variable_region_heavy_chain DNA sequence. CDR1:Bold; CDR2: Underline; CDR3:Italics.

CAGTCGGTGGAGGAGTTCGGGGGTCGCCTGGTCACGCCTGGGACACCCCTGACACTCACC
TGCACCGTCTCTGGATTCTCCCTCAATAACTATGCAATGACCTGGGTCCGCCAGGCTCCA
GGGAAGGGGCTGGAGTGGATCGGG<u>ATCATTGGTAGTATTGGTACCACATACTACGCGAGC</u>
<u>TGGGCGAAAGGC</u>CGATTCTTCATCTCCAAAACCTCGACCACTGTGGATCTGAAAATCATT
AGTCCGACAACCGAGGACACGGCCACCTATTTCTGTGCCAGA*GATGCTGGCGTTACTGTT*
*GATGGTTATGGCTACTACTTTAACATC*TGGGGCCCAGGCACCCTCGTCACCGTCTCGAGC
(SEQ ID NO: 353)

Heavy_chain Full length DNA sequence.

CAGTCGGTGGAGGAGTTCGGGGGTCGCCTGGTCACGCCTGGGACACCCCTGACACTCACC
TGCACCGTCTCTGGATTCTCCCTCAATAACTATGCAATGACCTGGGTCCGCCAGGCTCCA
GGGAAGGGGCTGGAGTGGATCGGGATCATTGGTAGTATTGGTACCACATACTACGCGAGC
TGGGCGAAAGGCCGATTCTTCATCTCCAAAACCTCGACCACTGTGGATCTGAAAATCATT
AGTCCGACAACCGAGGACACGGCCACCTATTTCTGTGCCAGAGATGCTGGCGTTACTGTT
GATGGTTATGGCTACTACTTTAACATCTGGGGCCCAGGCACCCTCGTCACCGTCTCGAGC
GCCTCCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGG

FIG. 16B

TACGTGGACGGCGTGGAGGTGCATAATGCCAAGACAAAGCCGCGGGAGGAGCAGTACGCC
AGCACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATCTCC
AAAGCCAAAGGGCAGCCCCGAGAACCACAGGTGTACACCCTGCCCCCATCCCGGGAGGAG
ATGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACG
CAGAAGAGCCTCTCCCTGTCTCCGGGTAAATGA (SEQ ID NO: 354)

Light_chain Full length protein sequence.

ALVMTQTPSSTSEPVGGTVTINCQASQNIGNDLSWYQQKPGQPPELLIYSTSKLATGVPK
RFSGSRSGTQFTLTISDLECDDAATYYCLGVYSYISDDGNAFGGGTEVVVKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 152)

Variable_region_light_chain protein sequence.

ALVMTQTPSSTSEPVGGTVTINCQASQNIGNDLSWYQQKPGQPPELLIYSTSKLATGVPK
RFSGSRSGTQFTLTISDLECDDAATYYCLGVYSYISDDGNAFGGGTEVVVKR (SEQ ID NO: 151)

Variable_region_light_chain protein sequence. CDR1:Bold; CDR2: Underline; CDR3:Italics.

ALVMTQTPSSTSEPVGGTVTINCQASQNIGNDLSWYQQKPGQPPELLIY<u>STSKLAT</u>GVPK
RFSGSRSGTQFTLTISDLECDDAATYYC*LGVYSYISDDGNA*FGGGTEVVVKR (SEQ ID NOS: 155, 156, 157, respectively)

Variable_region_light_chain DNA sequence. CDR1:Bold; CDR2: Underline; CDR3:Italics.

GCCCTGGTGATGACCCAGACTCCATCCTCCACGTCTGAACCAGTGGGAGGCACAGTCACC
ATCAATTGCCAGGCTAGTCAGAATATTGGTAACGACCTATCCTGGTATCAGCAGAAACCA
GGGCAGCCTCCCGAGCTCCTAATCTAT<u>TCTACATCCAAACTGGCAACT</u>GGGGTCCCAAAG
CGGTTCAGTGGCAGCAGATCTGGGACACAGTTCACTCTCACCATCAGCGACCTGGAGTGT
GACGATGCTGCCACTTACTACTGT*CTAGGTGTTTATAGTTATATTAGTGATGATGGTAAT*
*GCT*TTCGGCGGAGGGACCGAGGTGGTGGTCAAACGT (SEQ ID NO: 351)

Light_chain Full length DNA sequence.

GCCCTGGTGATGACCCAGACTCCATCCTCCACGTCTGAACCAGTGGGAGGCACAGTCACC
ATCAATTGCCAGGCTAGTCAGAATATTGGTAACGACCTATCCTGGTATCAGCAGAAACCA
GGGCAGCCTCCCGAGCTCCTAATCTATTCTACATCCAAACTGGCAACTGGGGTCCCAAAG
CGGTTCAGTGGCAGCAGATCTGGGACACAGTTCACTCTCACCATCAGCGACCTGGAGTGT
GACGATGCTGCCACTTACTACTGTCTAGGTGTTTATAGTTATATTAGTGATGATGGTAAT
GCTTTCGGCGGAGGGACCGAGGTGGTGGTCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 352)

Heavy_chain Full length protein sequence.

QSLEESGGRLVTPGGSLTLTCAASGFSLTGYNLVWVRQAPGKGLEWIGFISYGDTTYYAS
WAKGRFTISKTSTTVTLTITDLQPSDTGTYFCARETANTYDYGIWGPGTLVTVSSASTKG
PSVFPLAPSSKSTSGGTAALGCLVKDYFPEPVTVSWNSGALTSGVHTFPAVLQSSGLYSL
SSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYASTYRV
VSVLTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQGNV
FSCSVMHEALHNHYTQKSLSLSPGK (SEQ ID NO: 164)

Variable_region_heavy_chain protein sequence.

QSLEESGGRLVTPGGSLTLTCAASGFSLTGYNLVWVRQAPGKGLEWIGFISYGDTTYYAS
WAKGRFTISKTSTTVTLTITDLQPSDTGTYFCARETANTYDYGIWGPGTLVTVSS (SEQ
ID NO: 163)

Variable_region_heavy_chain protein sequence. CDR1:Bold; CDR2: Underline; CDR3:Italics.

QSLEESGGRLVTPGGSLTLTCAASGFSLTGYNLVWVRQAPGKGLEWIGFISYGDTTYYAS
WAKGRFTISKTSTTVTLTITDLQPSDTGTYFCAR*ETANTYDYGI*WGPGTLVTVSS (SEQ
ID NOS: 168, 169, 170, respectively)

Variable_region_heavy_chain DNA sequence. CDR1:Bold; CDR2: Underline; CDR3:Italics.

CAGTCGCTGGAGGAGTCCGGGGGTCGCCTGGTCACGCCTGGGGGATCCCTGACACTCACC
TGCGCAGCCTCTGGATTCTCCCTCACTGGCTACAACTTGGTCTGGGTCCGCCAGGCTCCA
GGGAAGGGGCTGGAGTGGATCGGATTCATTAGTTATGGTGATACCACATACTACGCGAGC
TGGGCGAAAGGCCGATTCACCATCTCCAAAACCTCGACCACGGTGACTCTGACGATCACC
GATCTGCAACCTTCAGACACGGGCACCTATTTCTGTGCCAGA*GAGACTGCTAATACTTAT*
*GATTATGGCATC*TGGGGCCCAGGCACCCTCGTCACCGTCTCGAGC (SEQ ID NO:
363)

Heavy_chain Full length DNA sequence.

CAGTCGCTGGAGGAGTCCGGGGGTCGCCTGGTCACGCCTGGGGGATCCCTGACACTCACC
TGCGCAGCCTCTGGATTCTCCCTCACTGGCTACAACTTGGTCTGGGTCCGCCAGGCTCCA
GGGAAGGGGCTGGAGTGGATCGGATTCATTAGTTATGGTGATACCACATACTACGCGAGC
TGGGCGAAAGGCCGATTCACCATCTCCAAAACCTCGACCACGGTGACTCTGACGATCACC
GATCTGCAACCTTCAGACACGGGCACCTATTTCTGTGCCAGAGAGACTGCTAATACTTAT
GATTATGGCATCTGGGGCCCAGGCACCCTCGTCACCGTCTCGAGCGCCTCCACCAAGGGC
CCATCGGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACTCAGGCGCC
CTGACCAGCGGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACATCTGCAACGTG
AATCACAAGCCCAGCAACACCAAGGTGGACAAGAGAGTTGAGCCCAAATCTTGTGACAAA
ACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTG
GTGGTGGACGTGAGCCACGAAGACCCTGAGGTCAAGTTCAACTGGTACGTGGACGGCGTG

FIG. 17B

GAGGTGCATAATGCCAAGACAAAGCCGCGGGAGGAGCAGTACGCCAGCACGTACCGTGTG
GTCAGCGTCCTCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGCCAAAGGGCAG
CCCCGAGAACCACAGGTGTACACCCTGCCCCCATCCCGGGAGGAGATGACCAAGAACCAG
GTCAGCCTGACCTGCCTGGTCAAAGGCTTCTATCCCAGCGACATCGCCGTGGAGTGGGAG
AGCAATGGGCAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAGGGGAACGTC
TTCTCATGCTCCGTGATGCATGAGGCTCTGCACAACCACTACACGCAGAAGAGCCTCTCC
CTGTCTCCGGGTAAATGA (SEQ ID NO: 364)

Light_chain Full length protein sequence.

AIEMTQTPFSVSAAVGGTVTIKCQASQTISNYLAWYQQKPGQPPKLLIYGASNLESGVPS
RFKGSGSGTQFTLTISDLECDDAATYYCQQGYTISNVDNNVFGGGTEVVVKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 162)

Variable_region_light_chain protein sequence.

AIEMTQTPFSVSAAVGGTVTIKCQASQTISNYLAWYQQKPGQPPKLLIYGASNLESGVPS
RFKGSGSGTQFTLTISDLECDDAATYYCQQGYTISNVDNNVFGGGTEVVVKR (SEQ ID
NO: 161)

Variable_region_light_chain protein sequence. CDR1:Bold; CDR2: Underline; CDR3:Italics.

AIEMTQTPFSVSAAVGGTVTIKCQASQTISNYLAWYQQKPGQPPKLLIYGASNLESGVPS
RFKGSGSGTQFTLTISDLECDDAATYYC*QQGYTISNVDNNV*FGGGTEVVVKR (SEQ ID
NOS: 165, 166, 167, respectively)

Variable_region_light_chain DNA sequence. CDR1:Bold; CDR2: Underline; CDR3:Italics.

GCCATCGAAATGACCCAGACTCCATTCTCCGTGTCTGCAGCTGTGGGAGGCACAGTCACC
ATCAAGTGCCAGGCCAGTCAGACCATTAGCAACTACTTAGCCTGGTATCAGCAGAAACCA
GGGCAGCCTCCCAAGCTCCTGATCTATGGTGCATCCAATCTGGAATCTGGGGTCCCATCG
CGGTTCAAAGGCAGTGGATCTGGGACACAGTTCACTCTCACCATCAGCGACCTGGAGTGT
GACGATGCTGCCACTTACTACTGT*CAACAGGGTTATACTATCAGTAATGTTGATAACAAT*
*GTT*TTCGGCGGAGGGACCGAGGTGGTGGTCAAACGT (SEQ ID NO: 361)

Light_chain Full length DNA sequence.

GCCATCGAAATGACCCAGACTCCATTCTCCGTGTCTGCAGCTGTGGGAGGCACAGTCACC
ATCAAGTGCCAGGCCAGTCAGACCATTAGCAACTACTTAGCCTGGTATCAGCAGAAACCA
GGGCAGCCTCCCAAGCTCCTGATCTATGGTGCATCCAATCTGGAATCTGGGGTCCCATCG
CGGTTCAAAGGCAGTGGATCTGGGACACAGTTCACTCTCACCATCAGCGACCTGGAGTGT
GACGATGCTGCCACTTACTACTGTCAACAGGGTTATACTATCAGTAATGTTGATAACAAT
GTTTTCGGCGGAGGGACCGAGGTGGTGGTCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 362)

Heavy_chain Full length protein sequence.

EVQLVESGGGLVQPGGSLRLSCAASGFTVSGYNLVWVRQAPGKGLEWVGFISYGDTTYYA
SSAKGRFTISRDNSKNTLYLQMNSLRAEDTAVYYCARETANTYDYGIWGQGTLVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYAST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 174)

Variable_region_heavy_chain protein sequence.

EVQLVESGGGLVQPGGSLRLSCAASGFTVSGYNLVWVRQAPGKGLEWVGFISYGDTTYYA
SSAKGRFTISRDNSKNTLYLQMNSLRAEDTAVYYCARETANTYDYGIWGQGTLVTVSS
(SEQ ID NO: 173)

Variable_region_heavy_chain protein sequence. CDR1:Bold; CDR2: Underline; CDR3:Italics.

EVQLVESGGGLVQPGGSLRLSCAASGFTVSGYNLVWVRQAPGKGLEWVG<u>FISYGDTTYYA</u>
<u>SSAKG</u>RFTISRDNSKNTLYLQMNSLRAEDTAVYYCAR*ETANTYDYGI*WGQGTLVTVSS
(SEQ ID NOS: 178, 179, 180, respectively)

Variable_region_heavy_chain DNA sequence. CDR1:Bold; CDR2: Underline; CDR3:Italics.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTGGCTACAACTTGGTCTGGGTCCGTCAGGCT
CCAGGGAAGGGGCTGGAGTGGGTCGGA<u>TTCATTAGTTATGGTGATACCACATACTACGCT</u>
<u>AGCTCTGCTAAAGGC</u>CGATTCACCATCTCCAGAGACAATTCCAAGAACACCCTGTATCTT
CAAATGAACAGCCTGAGAGCTGAGGACACTGCTGTGTATTACTGTGCTAGA*GAGACTGCT*
*AATACTTATGATTATGGCATC*TGGGGCCAAGGGACCCTCGTCACCGTCTCGAGC (SEQ
ID NO: 373)

Heavy_chain Full length DNA sequence.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTGGCTACAACTTGGTCTGGGTCCGTCAGGCT
CCAGGGAAGGGGCTGGAGTGGGTCGGATTCATTAGTTATGGTGATACCACATACTACGCT
AGCTCTGCTAAAGGCCGATTCACCATCTCCAGAGACAATTCCAAGAACACCCTGTATCTT
CAAATGAACAGCCTGAGAGCTGAGGACACTGCTGTGTATTACTGTGCTAGAGAGACTGCT
AATACTTATGATTATGGCATCTGGGGCCAAGGGACCCTCGTCACCGTCTCGAGCGCCTCC
ACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAAATCT
TGTGACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGAGGTC
ACATGCGTGGTGGTGGACGTGAGCCACGAAGACCCTGAGGTCAAGTTCAACTGGTACGTG

FIG. 18B

GACGGCGTGGAGGTGCATAATGCCAAGACAAAGCCGCGGGAGGAGCAGTACGCCAGCACG
TACCGTGTGGTCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGAGGAGATGACC
AAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACGCAGAAG
AGCCTCTCCCTGTCTCCGGGTAAATGA (SEQ ID NO: 374)

Light_chain Full length protein sequence.

DIQMTQSPSTLSASVGDRVTITCQASQTISNYLAWYQQKPGKAPKLLIYGASNLESGVPS
RFSGSGSGTEFTLTISSLQPDDFATYYCQQGYTISNVDNNVFGGGTKVEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 172)

Variable_region_Light_chain protein sequence.

DIQMTQSPSTLSASVGDRVTITCQASQTISNYLAWYQQKPGKAPKLLIYGASNLESGVPS
RFSGSGSGTEFTLTISSLQPDDFATYYCQQGYTISNVDNNVFGGGTKVEIKR (SEQ ID NO: 171)

Variable_region_Light_chain protein sequence. CDR1:Bold; CDR2: Underline; CDR3:Italics.

DIQMTQSPSTLSASVGDRVTITCQASQTISNYLAWYQQKPGKAPKLLIY<u>GASNLES</u>GVPS
RFSGSGSGTEFTLTISSLQPDDFATYYC*QQGYTISNVDNNV*FGGGTKVEIKR (SEQ ID NOS: 175, 176, 177, respectively)

Variable_region_Light_chain DNA sequence. CDR1:Bold; CDR2: Underline; CDR3:Italics.

GACATCCAGATGACCCAGTCTCCTTCCACCCTGTCTGCATCTGTAGGAGACAGAGTCACC
ATCACTTGTCAGGCTAGTCAGACCATTAGCAACTACTTAGCCTGGTATCAGCAGAAACCA
GGAAAAGCCCCTAAGCTCCTGATCTAT<u>GGTGCATCCAATCTGGAATCT</u>GGAGTCCCATCA
AGGTTCAGCGGCAGTGGATCTGGAACAGAATTCACTCTCACCATCAGCAGCCTGCAGCCT
GATGATTTTGCAACTTACTACTGT*CAACAGGGTTATACTATCAGTAATGTTGATAACAAT*
*GTT*TTCGGCGGAGGAACCAAGGTGGAAATCAAACGT (SEQ ID NO: 371)

Light_chain Full length DNA sequence.

GACATCCAGATGACCCAGTCTCCTTCCACCCTGTCTGCATCTGTAGGAGACAGAGTCACC
ATCACTTGTCAGGCTAGTCAGACCATTAGCAACTACTTAGCCTGGTATCAGCAGAAACCA
GGAAAAGCCCCTAAGCTCCTGATCTATGGTGCATCCAATCTGGAATCTGGAGTCCCATCA
AGGTTCAGCGGCAGTGGATCTGGAACAGAATTCACTCTCACCATCAGCAGCCTGCAGCCT
GATGATTTTGCAACTTACTACTGTCAACAGGGTTATACTATCAGTAATGTTGATAACAAT
GTTTTCGGCGGAGGAACCAAGGTGGAAATCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 372)

Heavy_chain Full length protein sequence.

QSVEASGGRLVMPGGSLTLTCTASGFSLSTYWMSWVRQAPGKGLEWIGDIYFSNEETNYA
TWAKGRFTISKTSTTVDLNVISPTTEDTATYFCARGSPDVEIAIDMWGQGTLVTVSSAST
KGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSV
FLFPPKPKDTLMISRTPEVTCVVVDVSHEDPEVKFNWYVDGVEVHNAKTKPREEQYASTY
RVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQG
NVFSCSVMHEALHNHYTQKSLSLSPGK (SEQ ID NO: 184)

Variable_region_heavy_chain protein sequence.

QSVEASGGRLVMPGGSLTLTCTASGFSLSTYWMSWVRQAPGKGLEWIGDIYFSNEETNYA
TWAKGRFTISKTSTTVDLNVISPTTEDTATYFCARGSPDVEIAIDMWGQGTLVTVSS
(SEQ ID NO: 183)

Variable_region_heavy_chain protein sequence. CDR1:Bold; CDR2: Underline; CDR3:Italics.

QSVEASGGRLVMPGGSLTLTCTASGFSLSTYWMSWVRQAPGKGLEWIG<u>DIYFSNEETNYA</u>
<u>TWAKG</u>RFTISKTSTTVDLNVISPTTEDTATYFCAR*GSPDVEIAIDMWG*QGTLVTVSS
(SEQ ID NOS: 188, 189, 190, respectively)

Variable_region_heavy_chain DNA sequence. CDR1:Bold; CDR2: Underline; CDR3:Italics.

CAGTCGGTGGAGGCGTCCGGGGGTCGTCTGGTCATGCCTGGAGGATCCCTGACACTCACC
TGCACAGCCTCTGGATTCTCCCTCAGTACCTACTGGATGTCCTGGGTCCGCCAGGCTCCA
GGGAAGGGGCTGGAATGGATCGGA<u>GACATTTATTTTAGTAATGAGGAAACAAACTACGCG</u>
<u>ACCTGGGCGAAAGGC</u>CGATTTACCATCTCCAAAACCTCGACCACGGTGGATCTGAATGTC
ATCAGTCCGACAACCGAGGACACGGCCACCTATTTCTGTGCAAGA*GGTTCTCCTGATGTT*
*GAGATTGCTATAGATATG*TGGGGCCAGGGCACCCTCGTCACCGTCTCGAGC (SEQ ID
NO: 383)

Heavy_chain Full length DNA sequence.

CAGTCGGTGGAGGCGTCCGGGGGTCGTCTGGTCATGCCTGGAGGATCCCTGACACTCACC
TGCACAGCCTCTGGATTCTCCCTCAGTACCTACTGGATGTCCTGGGTCCGCCAGGCTCCA
GGGAAGGGGCTGGAATGGATCGGAGACATTTATTTTAGTAATGAGGAAACAAACTACGCG
ACCTGGGCGAAAGGCCGATTTACCATCTCCAAAACCTCGACCACGGTGGATCTGAATGTC
ATCAGTCCGACAACCGAGGACACGGCCACCTATTTCTGTGCAAGAGGTTCTCCTGATGTT
GAGATTGCTATAGATATGTGGGGCCAGGGCACCCTCGTCACCGTCTCGAGCGCCTCCACC
AAGGGCCCATCGGTCTTCCCCCTGGCACCCTCCTCCAAGAGCACCTCTGGGGGCACAGCG
GCCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTAC
TCCCTCAGCAGCGTGGTGACCGTGCCCTCCAGCAGCTTGGGCACCCAGACCTACATCTGC
AACGTGAATCACAAGCCCAGCAACACCAAGGTGGACAAGAGAGTTGAGCCCAAATCTTGT
GACAAAACTCACACATGCCCACCGTGCCCAGCACCTGAACTCCTGGGGGGACCGTCAGTC
TTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGAC

FIG. 19B

GGCGTGGAGGTGCATAATGCCAAGACAAAGCCGCGGGAGGAGCAGTACGCCAGCACGTAC
CGTGTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAGGAGATGACCAAG
AACCAGGTCAGCCTGACCTGCCTGGTCAAAGGCTTCTATCCCAGCGACATCGCCGTGGAG
TGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGG
AACGTCTTCTCATGCTCCGTGATGCATGAGGCTCTGCACAACCACTACACGCAGAAGAGC
CTCTCCCTGTCTCCGGGTAAATGA (SEQ ID NO: 384)

Light_chain Full length protein sequence.

AAVLTQTPSPVSAAVGGTVSISCQSSQNVYKNNYLSWYQQKPGQPPKLLIYKASTLASGV
PSRFKGSGSGTDFTLTISDVQCDAAATYYCAGGYSSSSDNAFGGGTEVVVKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 182)

Variable_region_light_chain protein sequence.

AAVLTQTPSPVSAAVGGTVSISCQSSQNVYKNNYLSWYQQKPGQPPKLLIYKASTLASGV
PSRFKGSGSGTDFTLTISDVQCDAAATYYCAGGYSSSSDNAFGGGTEVVVKR (SEQ ID NO: 181)

Variable_region_light_chain protein sequence. CDR1:Bold; CDR2: Underline; CDR3:Italics.

AAVLTQTPSPVSAAVGGTVSISCQSSQNVYKNNYLSWYQQKPGQPPKLLIY<u>KASTLAS</u>GV
PSRFKGSGSGTDFTLTISDVQCDAAATYYC*AGGYSSSSDNA*FGGGTEVVVKR (SEQ ID NOS: 185, 186, 187, respectively)

Variable_region_light_chain DNA sequence. CDR1:Bold; CDR2: Underline; CDR3:Italics.

GCCGCCGTGCTGACCCAGACTCCATCTCCCGTGTCTGCAGCTGTGGGAGGCACAGTCAGC
ATCAGTTGCCAGTCCAGTCAGAATGTTTATAAGAACAACTATTTATCCTGGTATCAGCAG
AAACCAGGGCAGCCTCCCAAGCTCCTGATCTAC<u>AAGGCTTCCACTCTGGCATCT</u>GGGGTC
CCATCGCGGTTCAAAGGCAGTGGATCTGGGACAGATTTCACTCTCACCATCAGCGACGTG
CAGTGTGACGCTGCTGCCACTTACTACTGT*GCAGGCGGTTATAGTAGTAGTAGTGATAAT*
*GCT*TTCGGCGGAGGGACCGAGGTGGTGGTCAAACGT (SEQ ID NO: 381)

Light_chain Full length DNA sequence.

GCCGCCGTGCTGACCCAGACTCCATCTCCCGTGTCTGCAGCTGTGGGAGGCACAGTCAGC
ATCAGTTGCCAGTCCAGTCAGAATGTTTATAAGAACAACTATTTATCCTGGTATCAGCAG
AAACCAGGGCAGCCTCCCAAGCTCCTGATCTACAAGGCTTCCACTCTGGCATCTGGGGTC
CCATCGCGGTTCAAAGGCAGTGGATCTGGGACAGATTTCACTCTCACCATCAGCGACGTG
CAGTGTGACGCTGCTGCCACTTACTACTGTGCAGGCGGTTATAGTAGTAGTAGTGATAAT
GCTTTCGGCGGAGGGACCGAGGTGGTGGTCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 382)

Heavy_chain Full length protein sequence.

EVQLVESGGGLVQPGGSLRLSCAASGFTVSTYWMSWVRQAPGKGLEWVGDIYFSNEETNY
ATSAKGRFTISRDNSKNTLYLQMNSLRAEDTAVYYCARGSPDVEIAIDMWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 194)

Variable_region_heavy_chain protein sequence.

EVQLVESGGGLVQPGGSLRLSCAASGFTVSTYWMSWVRQAPGKGLEWVGDIYFSNEETNY
ATSAKGRFTISRDNSKNTLYLQMNSLRAEDTAVYYCARGSPDVEIAIDMWGQGTLVTVSS
(SEQ ID NO: 193)

Variable_region_heavy_chain protein sequence. CDR1:Bold; CDR2: Underline; CDR3:Italics.

EVQLVESGGGLVQPGGSLRLSCAASGFTVSTYWMSWVRQAPGKGLEWVG<u>DIYFSNEETNY</u>
<u>ATSAKG</u>RFTISRDNSKNTLYLQMNSLRAEDTAVYYCAR*GSPDVEIAIDM*WGQGTLVTVSS
(SEQ ID NOS: 198, 199, 200, respectively)

Variable_region_heavy_chain DNA sequence. CDR1:Bold; CDR2: Underline; CDR3:Italics.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTACCTACTGGATGAGCTGGGTCCGTCAGGCT
CCAGGGAAGGGGCTGGAGTGGGTCGGA<u>GACATTTACTTTAGTAATGAAGAAACAAACTAC</u>
<u>GCGACCAGCGCGAAAGGC</u>CGATTCACCATCTCCAGAGACAATTCCAAGAACACCCTGTAT
CTTCAAATGAACAGCCTGAGAGCTGAGGACACTGCTGTGTATTACTGTGCTAGA*GGTTCT*
*CCTGATGTTGAGATTGCTATAGATATG*TGGGGCCAAGGGACCCTCGTCACCGTCTCGAGC
(SEQ ID NO: 393)

Heavy_chain Full length DNA sequence.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTACCTACTGGATGAGCTGGGTCCGTCAGGCT
CCAGGGAAGGGGCTGGAGTGGGTCGGAGACATTTACTTTAGTAATGAAGAAACAAACTAC
GCGACCAGCGCGAAAGGCCGATTCACCATCTCCAGAGACAATTCCAAGAACACCCTGTAT
CTTCAAATGAACAGCCTGAGAGCTGAGGACACTGCTGTGTATTACTGTGCTAGAGGTTCT
CCTGATGTTGAGATTGCTATAGATATGTGGGGCCAAGGGACCCTCGTCACCGTCTCGAGC
GCCTCCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGG

FIG. 20B

TACGTGGACGGCGTGGAGGTGCATAATGCCAAGACAAAGCCGCGGGAGGAGCAGTACGCC
AGCACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATCTCC
AAAGCCAAAGGGCAGCCCCGAGAACCACAGGTGTACACCCTGCCCCCATCCCGGGAGGAG
ATGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACG
CAGAAGAGCCTCTCCCTGTCTCCGGGTAAATGA (SEQ ID NO: 394)

Light_chain Full length protein sequence.

DIQMTQSPSSLSASVGDRVTITCQSSQNVYKNNYLSWYQQKPGKVPKLLIYKASTLASGV
PSRFSGSGSGTDFTLTISSLQPEDVATYYCAGGYTSSSDNAFGGGTKVEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 192)

Variable_region_Light_chain protein sequence.

DIQMTQSPSSLSASVGDRVTITCQSSQNVYKNNYLSWYQQKPGKVPKLLIYKASTLASGV
PSRFSGSGSGTDFTLTISSLQPEDVATYYCAGGYTSSSDNAFGGGTKVEIKR (SEQ ID
NO: 191)

Variable_region_Light_chain protein sequence. CDR1:Bold; CDR2: Underline; CDR3:Italics.

DIQMTQSPSSLSASVGDRVTITCQSSQNVYKNNYLSWYQQKPGKVPKLLIYKASTLASGV
PSRFSGSGSGTDFTLTISSLQPEDVATYYC*AGGYTSSSDNA*FGGGTKVEIKR (SEQ ID
NOS: 195, 196, 197, respectively)

Variable_region_Light_chain DNA sequence. CDR1:Bold; CDR2: Underline; CDR3:Italics.

GACATCCAGATGACCCAGTCTCCATCCTCCCTGTCTGCATCTGTAGGAGACAGAGTCACC
ATCACTTGCCAGTCCAGTCAGAATGTTTATAAGAACAACTACTTATCCTGGTATCAGCAG
AAACCAGGGAAAGTCCCTAAGCTCCTGATCTATAAGGCATCCACTCTGGCATCTGGGGTC
CCATCTCGTTTCAGTGGCAGTGGATCTGGGACAGATTTCACTCTCACCATCAGCAGCCTG
CAGCCTGAAGATGTTGCAACTTATTACTGT*GCAGGCGGTTATACCAGTAGTAGTGATAAT*
*GCT*TTCGGCGGAGGAACCAAGGTGGAAATCAAACGT (SEQ ID NO: 391)

Light_chain Full length DNA sequence.

GACATCCAGATGACCCAGTCTCCATCCTCCCTGTCTGCATCTGTAGGAGACAGAGTCACC
ATCACTTGCCAGTCCAGTCAGAATGTTTATAAGAACAACTACTTATCCTGGTATCAGCAG
AAACCAGGGAAAGTCCCTAAGCTCCTGATCTATAAGGCATCCACTCTGGCATCTGGGGTC
CCATCTCGTTTCAGTGGCAGTGGATCTGGGACAGATTTCACTCTCACCATCAGCAGCCTG
CAGCCTGAAGATGTTGCAACTTATTACTGTGCAGGCGGTTATACCAGTAGTAGTGATAAT
GCTTTCGGCGGAGGAACCAAGGTGGAAATCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 392)

Heavy_chain Full length protein sequence.

EVQLVESGGGLVQPGGSLRLSCAASGFTVSNYAVGWVRQAPGKGLEWVGIIGRNGNTWYA
SSARGRFTISRDNSKNTLYLQMNSLRAEDTAVYYCARGYGRSVAYYVFNIWGPGTLVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDARVEPKSCDKTHTCPPCPAPELLG
GPSVFLFPPKPKDTLMISRTPEVTCVVVDVSHEDPEVKFNWYVDGVEVHNAKTKPREEQY
ASTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 402)

Heavy_chain Full length DNA sequence.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTAACTATGCAGTGGGCTGGGTCCGTCAGGCT
CCAGGGAAGGGGCTGGAGTGGGTCGGAATCATTGGTCGTAATGGTAACACATGGTACGCG
AGCTCTGCAAGAGGCCGATTCACCATCTCCAGAGACAATTCCAAGAACACCCTGTATCTT
CAAATGAACAGCCTGAGAGCTGAGGACACTGCTGTGTATTACTGTGCTAGAGGATATGGC
CGTAGTGTTGCTTACTACGTCTTTAACATCTGGGGCCCAGGGACCCTCGTCACCGTCTCG
AGCGCCTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACGCGAGAGTTGAG
CCCAAATCTTGTGACAAAACTCACACATGCCCACCGTGCCCAGCACCTGAACTCCTGGGG
GGACCGTCAGTCTTCCTCTTCCCCCCAAAACCCAAGGACACCCTCATGATCTCCCGGACC
CCTGAGGTCACATGCGTGGTGGTGGACGTGAGCCACGAAGACCCTGAGGTCAAGTTCAAC
TGGTACGTGGACGGCGTGGAGGTGCATAATGCCAAGACAAAGCCGCGGGAGGAGCAGTAC
GCCAGCACGTACCGTGTGGTCAGCGTCCTCACCGTCCTGCACCAGGACTGGCTGAATGGC
AAGGAGTACAAGTGCAAGGTCTCCAACAAAGCCCTCCCAGCCCCCATCGAGAAAACCATC
TCCAAAGCCAAAGGGCAGCCCCGAGAACCACAGGTGTACACCCTGCCCCCATCCCGGGAG
GAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTAC
ACGCAGAAGAGCCTCTCCCTGTCTCCGGGTAAATGA (SEQ ID NO: 404)

Light_chain Full length protein sequence.

DIQMTQSPSTLSASVGDRVTITCQASQSIYSNLAWYQQKPGKAPKLLIYDASTLESGVPS
RFSGSGSGTEYTLTISSLQPDDFATYYCQQGFTVSDIDNAFGGGTKVEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO: 401)

Light_chain Full length DNA sequence.

GACATCCAGATGACCCAGTCTCCTTCCACCCTGTCTGCATCTGTAGGAGACAGAGTCACC
ATCACTTGCCAGGCCAGTCAGAGCATTTACAGCAATCTTGCCTGGTATCAGCAGAAACCA
GGAAAAGCCCCTAAGCTCCTGATCTATGATGCATCCACTCTGGAATCTGGAGTCCCATCA

FIG. 21B

AGGTTCAGCGGCAGTGGATCTGGGACAGAGTACACTCTCACCATCAGCAGCCTGCAGCCT
GATGATTTTGCAACTTACTACTGCCAACAGGGTTTTACTGTTAGTGATATTGATAATGCT
TTCGGCGGAGGAACCAAGGTGGAAATCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ
ID NO: 403)

Figure 22

Fab1 Sequences

Heavy_chain Fab protein sequence.

EVQLVESGGGLVQPGGSLRLSCAASGFTVSNYAVGWVRQAPGKGLEWVGIIGRNGNTWYA
SSARGRFTISRDNSKNTLYLQMNSLRAEDTAVYYCARGYGRSVAYYVFNIWGPGTLVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDARVEPKSCDKTH (SEQ ID NO:
406)

Light_chain Fab protein sequence.

DIQMTQSPSTLSASVGDRVTITCQASQSIYSNLAWYQQKPGKAPKLLIYDASTLESGVPS
RFSGSGSGTEYTLTISSLQPDDFATYYCQQGFTVSDIDNAFGGGTKVEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO: 405)

Figure 23

Fab2 Sequences

Heavy_chain Fab protein sequence.

EVQLVESGGGLVQPGGSLRLSCAASGFTVSNYAVGWVRQAPGKGLEWVGIIGRNGNTWYA
SSARGRFTISRDNSKNTLYLQMNSLRAEDTAVYYCARGYGRSVAYYVFNIWGPGTLVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDARVEPKSCDKTH (SEQ ID NO:
408)

Heavy_chain Fab DNA sequence.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTAACTATGCAGTGGGCTGGGTCCGTCAGGCT
CCAGGGAAGGGGCTGGAGTGGGTCGGAATCATTGGTCGTAATGGTAACACATGGTACGCG
AGCTCTGCAAGAGGCCGATTCACCATCTCCAGAGACAATTCCAAGAACACCCTGTATCTT
CAAATGAACAGCCTGAGAGCTGAGGACACTGCTGTGTATTACTGTGCTAGAGGATATGGC
CGTAGTGTTGCTTACTACGTCTTTAACATCTGGGGCCCAGGGACCCTCGTCACCGTCTCG
AGCGCCTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACGCGAGAGTTGAG
CCCAAATCTTGTGACAAAACTCACTAG (SEQ ID NO: 410)

Light_chain Fab protein sequence.

DIQMTQSPSTLSASVGDRVTITCQASQSIYSNLAWYQQKPGKAPKLLIYDASTLESGVPS
RFSGSGSGTEYTLTISSLQPDDFATYYCQQGFTVSDIDNAFGGGTKVEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO: 407)

Light_chain Fab DNA sequence.

GACATCCAGATGACCCAGTCTCCTTCCACCCTGTCTGCATCTGTAGGAGACAGAGTCACC
ATCACTTGCCAGGCCAGTCAGAGCATTTACAGCAATCTTGCCTGGTATCAGCAGAAACCA
GGAAAAGCCCCTAAGCTCCTGATCTATGATGCATCCACTCTGGAATCTGGAGTCCCATCA
AGGTTCAGCGGCAGTGGATCTGGGACAGAGTACACTCTCACCATCAGCAGCCTGCAGCCT
GATGATTTTGCAACTTACTACTGCCAACAGGGTTTTACTGTTAGTGATATTGATAATGCT
TTCGGCGGAGGAACCAAGGTGGAAATCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ
ID NO: 409)

Antigen Binding ELISA

| | Ab1 | Ab2 |
|---|---|---|
| EC50(pM) | 571 | 692 |

Antigen Binding ELISA

| | Ab3 |
|---|---|
| EC50(pM) | 257 |

| | Ab4 |
|---|---|
| EC50(pM) | 535 |

Antigen Binding ELISA

| | Ab5 | Ab6 |
|---|---|---|
| EC50(pM) | 253 | 256 |

Antigen Binding ELISA

| | Fab1 |
|---|---|
| **EC50(pM)** | **400** |

Antigen Binding ELISA

| | Fab2 |
|---|---|
| **EC50(pM)** | **800** |

Antigen Binding ELISA

| | Ab7 | Ab8 |
|---|---|---|
| EC50(pM) | 203 | 207 |

| | Ab9 | Ab10 |
|---|---|---|
| EC50(pM) | 221 | 306 |

| | Ab11 |
|---|---|
| EC50(pM) | 379 |

Antigen Binding ELISA

| | Ab12 |
|---|---|
| EC50(pM) | 780 |

| | Ab13 |
|---|---|
| EC50(pM) | 339 |

Antigen Binding ELISA

| | Ab14 |
|---|---|
| EC50(pM) | 646 |

| | Ab15 |
|---|---|
| EC50(pM) | 239 |

Antigen Binding ELISA

| | Ab16 |
| --- | --- |
| EC50(pM) | 358 |

Antigen Binding ELISA

| | Ab17 | Ab18 |
|---|---|---|
| EC50(pM) | 700 | 561 |

Antigen Binding ELISA

| | Ab19 |
|---|---|
| EC50(pM) | 441 |

Antigen Binding ELISA

| | Ab20 |
|---|---|
| EC50(pM) | 667 |

Inhibition of NGF induced TF1 cells proliferation

| | Ab1 | Ab2 |
|---|---|---|
| IC50(pM) | 36 | 33 |

Inhibition of NGF induced TF1 cells proliferation

| | Ab3 | Ab4 |
|---|---|---|
| IC50(pM) | 36 | 72 |

Inhibition of NGF induced TF1 cells proliferation

| | Ab5 | Ab6 |
|---|---|---|
| IC50(pM) | 39 | 54 |

Inhibition of NGF induced TF1 cells proliferation

| | Fab 1 | Fab 2 |
|---|---|---|
| IC50(pM) | 95 | 157 |

Inhibition of NGF induced TF1 cells proliferation

| | Ab7 | Ab8 |
|---|---|---|
| IC50(pM) | 36 | 55 |

Inhibition of NGF induced TF1 cells proliferation

| | Ab9 | Ab10 |
|---|---|---|
| IC50(pM) | 48 | 70 |

Inhibition of NGF induced TF1 cells proliferation

| | Ab11 | Ab12 |
|---|---|---|
| IC50(pM) | 53 | 53 |

Inhibition of NGF induced TF1 cells proliferation

| | Ab13 | Ab14 |
|---|---|---|
| IC50(pM) | 29 | 57 |

Inhibition of NGF induced TF1 cells proliferation

| | Ab15 |
|---|---|
| IC50(pM) | 34 |

Inhibition of NGF induced TF1 cells proliferation

| | Ab16 |
|---|---|
| IC50(pM) | 32 |

Inhibition of NGF induced TF1 cells proliferation

| | Ab17 | Ab18 |
|---|---|---|
| IC50(pM) | 51 | 66 |

Inhibition of NGF induced TF1 cells proliferation

| | Ab19 | Ab20 |
|---|---|---|
| IC50(pM) | 45 | 74 |

Figure 53
Inhibition of NGF-P75 interactions
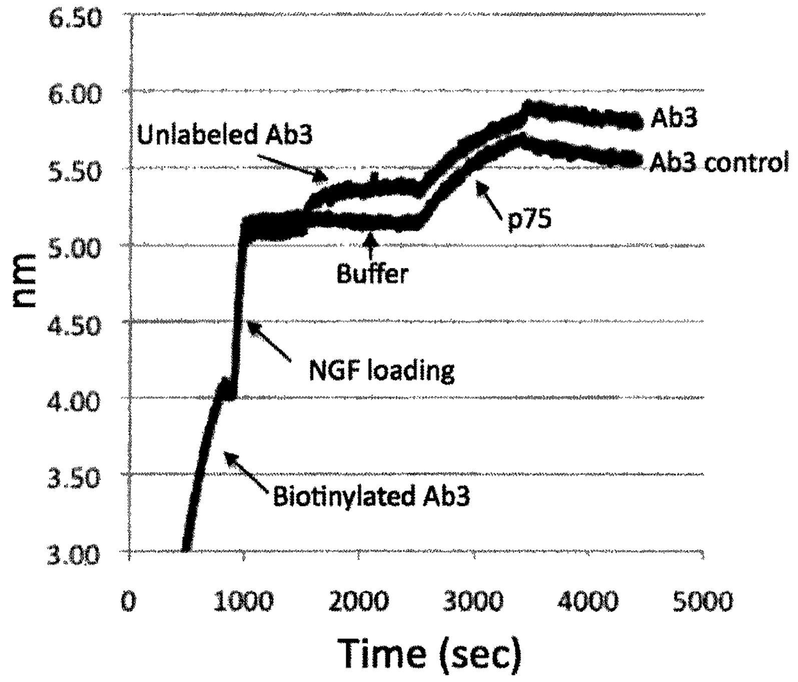
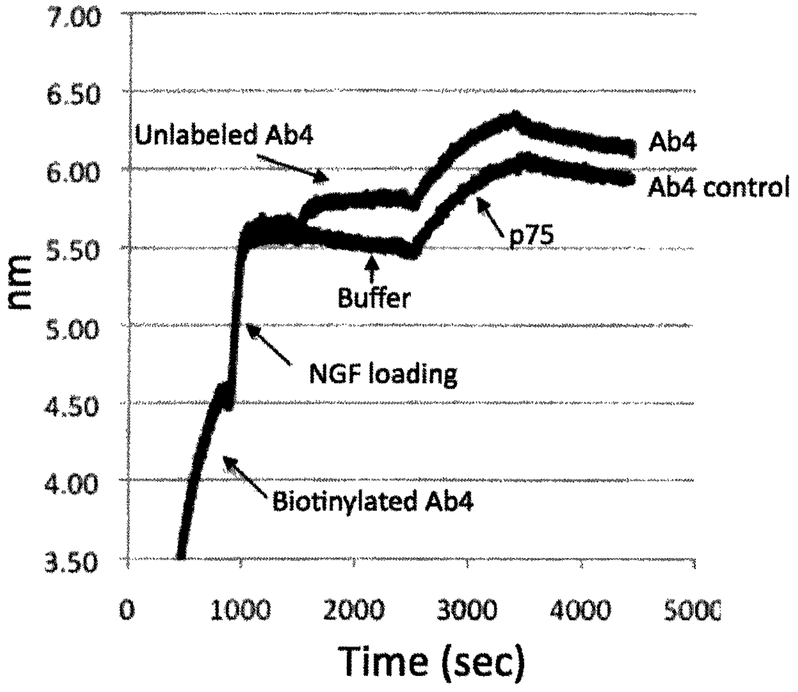

PC-12 Neurite Outgrowth

Ab1

PC-12 Neurite Outgrowth

Ab2

PC-12 Neurite Outgrowth

Ab3

PC-12 Neurite Outgrowth

Ab5

PC-12 Neurite Outgrowth

Ab6

PC-12 Neurite Outgrowth

Ab7

PC-12 Neurite Outgrowth

Ab8

PC-12 Neurite Outgrowth

Ab9

Figure 64
PC-12 Neurite Outgrowth
Ab10
Control-NGF only
0.1X Ab10
0.3X Ab10
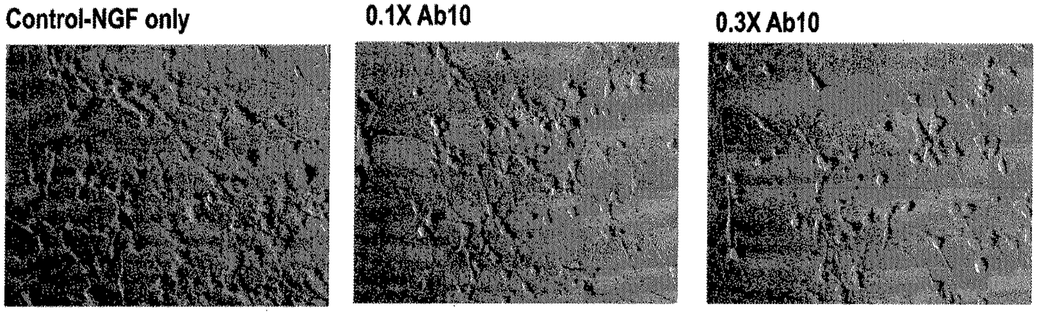
1X Ab10
3X Ab10
10X Ab10
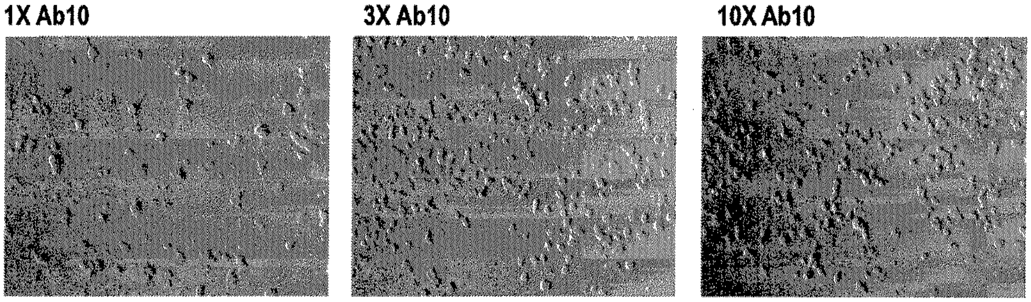

PC-12 Neurite Outgrowth

Ab11

PC-12 Neurite Outgrowth

Ab13

PC-12 Neurite Outgrowth

Ab18

PC-12 Neurite Outgrowth

Ab19

PC-12 Neurite Outgrowth

Ab16

PC-12 Neurite Outgrowth

Ab15

METHODS OF PREVENTING INFLAMMATION AND TREATING PAIN USING ANTI-NGF COMPOSITIONS

CROSS-REFERENCE TO RELATED APPLICATIONS

This application claims the benefit of priority to U.S. provisional patent application No. 61/418,832, filed Dec. 1, 2010, the contents of which are incorporated herein by reference in its entirety. In addition this application relates to U.S. application Ser. No. 13/308,831, entitled "METHODS OF PREVENTING INFLAMMATION AND TREATING PAIN USING ANTI-NGF COMPOSITIONS"; U.S. application Ser. No. 13/309,153, now U.S. Pat. No. 8,728,473 entitled "METHODS OF PREVENTING OR TREATING PAIN USING ANTI-NGF ANTIBODIES", and U.S. application Ser. No. 13/309,295 entitled "ANTI-NGF COMPOSITIONS AND USE THEREOF", all assigned to Alder Biopharmaceuticals, and all filed on Dec. 1, 2011, the contents of which are all incorporated by reference in their entireties.

BACKGROUND OF THE INVENTION

Field of the Invention

This invention pertains to monovalent agents (including Fab fragments and other monovalent NGF binding agents identified infra) having binding specificity to human Nerve Growth Factor (hereinafter "NGF"), and methods of using one or more of said monovalent agents in methods of treating pain in an individual wherein there is no substantial increase in the inflammatory response of the individual following administration of the one or more monovalent agents. These monovalent agents optionally may be modified to extend their circulation half-life such as by the addition of polyethylenes glycol (PEG), or other water soluble polymers and the like)

Description of Related Art

Nerve Growth Factor (NGF) (also known as beta nerve growth factor (Beta-NGF)) is produced as a mature protein of 222 amino acids in length, following cleavage of a 18 amino acid signal peptide. The gene encoding NGF is located on chromosome 1p13.1. A biologically active form of NGF is a secreted protein which homodimerizes and is incorporated into a larger complex. NGF is a member of the neurotrophins (NTs), which are a group of structurally-related proteins further including brain-derived neurotrophic factor (BDNF), NT-3, and NT-4/5. (Wyman et al., Gene Therapy (1999), 6:1648-1660). NTs support the survival of specific types of neurons and neurotransmitter systems, being produced by cells that are targeted by innervating neurons. Id. Basal forebrain, substantia nigra, brain stem, cortex, and spinal cord are nervous system regions having demonstrated responsiveness to NGF. Id.

All NTs bind to a low-affinity receptor identified as p75. (Sarchielli et al., Expert Rev. Neurotherapeutics (2004), 4(1):115-127). NGF selectively binds to, and displays a high affinity for, the high affinity neurotrophin receptor TrkA. Id. It has recently been demonstrated that NGF acts through its low-affinity receptor p75 in a developmentally-regulated signaling pathway necessary for myogenic differentiation and muscle repair in vivo. (Deponti et al., Mol. Biol. Cell (2009), 20:3620-3627).

NGF has also been demonstrated to interact with pain-signalling systems in adult animals, and is responsible for hyperalgesia when administered either locally or systemically in many species. (Sarchielli et al., Expert Rev. Neurotherapeutics (2004), 4(1):115-127). NGF has been shown to induce a pain-like response when infused into the CSF in rats, and has been demonstrated to maintain chronic pain. Furthermore, NGF has been demonstrated to contribute to the development of mechanical allodynia occurring 8-12 hours later, and to the secondary pain response. Id.

Pain may often be addressed through the administration of certain narcotics or non-steroidal anti-inflammatory drugs (NSAIDs). However, the administration of these treatments may occur at the cost of certain negative consequences. NSAIDs have the potential to cause kidney failure, intestinal bleeding, and liver dysfunction. Narcotics have the potential to cause nausea, vomiting, impaired mental functioning, and addiction. Therefore, it is desirable to identify alternative treatments for pain in order to avoid certain of these negative consequences.

NGF is believed to play a role in a multitude of diseases and disorders, including but not limited to pain associated with a broad range of diseases and disorders, such as pain associated with cancers, neuropathic pain, and neurogenic pain. Due to the perceived involvement of NGF in a wide range of pain-related diseases and disorders, there remains a need in the art for compositions and methods useful for preventing or treating diseases and disorders associated with NGF, and particularly those associated with pain. Particularly preferred anti-NGF compositions are those having minimal or minimizing adverse reactions, such as inflammation when administered to the patient. Compositions or methods that reduce or inhibit diseases or disorders associated with NGF, such as pain, are beneficial to the patient in need thereof.

BRIEF SUMMARY OF THE INVENTION

The present invention is directed to methods of treating pain without substantially increasing the inflammatory response of an individual. Another embodiment of the invention contemplates anti-human NGF monovalent agents derived from specific antibodies and fragments thereof and having binding specificity for NGF, in particular monovalent agents having desired epitopic specificity, high affinity or avidity and/or functional properties. Another embodiment of this invention relates to anti-human NGF monovalent agents derived from antibodies described herein and having binding specificity for NGF, comprising the sequences of the VH, VL and CDR polypeptides described herein, and the polynucleotides encoding them. Such monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof that bind NGF.

In some embodiments these monovalent agents will block or inhibit the interaction of NGF with TrkA and/or p75. In other embodiments these monovalent agents may be chemically modified to modify circulation half-life such as by PEGylation or by attachment to other water soluble polymers.

In a preferred embodiment of the invention, anti-human NGF monovalent agents such as Fab fragments of antibodies described herein are capable of significantly reducing pain in vivo in murine models, as measured by Gait analysis (as described in the examples herein). A particularly preferred embodiment of the invention is directed to the use of anti-human NGF monovalent Fab, Fab', Fv, scFv fragments, SMIPs (small molecule immunopharmaceuticals), camelbodies, nanobodies, IgNAR, a monovalent antibody molecule analogous to MetMab, or one or more combinations thereof in methods of alleviating or treating pain. In another preferred embodiment of the invention, monovalent agents having binding specificity for NGF (such as the Fab fragments of the full length antibodies described herein or alternatively Fab', Fv, scFv fragments, SMIPs (small molecule immunopharmaceuticals), camelbodies, nanobodies, IgNAR, a monovalent antibody molecule analogous to MetMab, or one or more combinations thereof, which have binding specificity for NGF, are useful for alleviating or treating pain in an individual, while not substantially increasing inflammation compared to full length antibodies dosed at the same concentration, as demonstrated in vivo in murine models following the Gait analysis.

In another embodiment of the invention these monovalent agents may be derived from parent antibodies and humanized versions which are themselves derived from rabbit immune cells (B lymphocytes) and optionally selected based on their homology (sequence identity) to human germ line sequences. These parent antibodies may require minimal or no sequence modifications, thereby facilitating retention of functional properties after humanization, prior to their use as a source of monovalent agents. A further embodiment of the invention is directed to anti-human NGF monovalent agents derived from anti-human NGF antibodies encompassing $V_H$, $V_L$ and CDR polypeptides, e.g., derived from rabbit immune cells and the polynucleotides encoding the same, as well as the use of these antibody and fragments thereof and the polynucleotides encoding them in the creation of novel monovalent agents and compositions comprising said monovalent agents capable of binding to NGF and reducing pain in an individual, while not substantially increasing the inflammatory response of said individual. As noted, in some embodiments these monovalent agents will block or inhibit the interaction of NGF with TrkA and/or p75. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof, having binding specificity for NGF, preferably those containing the CDRs of the antibodies exemplified herein and/or having the same epitopic specificity.

The invention also contemplates conjugates of monovalent agents conjugated to one or more functional or detectable moieties, e.g., moieties that affect half-life or agents that affect other therapeutic properties of the monovalent agent. The invention also contemplates methods of making said chimeric or humanized anti-NGF monovalent agents. In one embodiment, monovalent agents include, but are not limited to, Fab, Fab', Fv, scFv fragments, SMIPs (small molecule immunopharmaceuticals), camelbodies, nanobodies, and IgNAR. Embodiments of the invention pertain to the use of anti-NGF monovalent agents for the diagnosis, assessment and treatment of diseases and disorders associated with NGF or aberrant expression thereof. As noted, in some embodiments these monovalent agents will block or inhibit the interaction of NGF with TrkA and/or p75.

The invention also contemplates the use of monovalent agents for the diagnosis, assessment and treatment of diseases and disorders associated with NGF or aberrant expression thereof. Other embodiments of the invention relate to the production of anti-human NGF monovalent agents in recombinant host cells, for example mammalian cells such as CHO, NSO or HEK 293 cells, or yeast cells (for example diploid yeast such as diploid *Pichia*) and other yeast strains.

BRIEF DESCRIPTION OF THE SEVERAL VIEWS OF THE DRAWINGS

FIG. 1 provides polynucleotide and polypeptide sequences corresponding to the full-length Antibody Ab1.

FIG. 2 provides polynucleotide and polypeptide sequences corresponding to the full-length Antibody Ab2.

FIG. 3 provides polynucleotide and polypeptide sequences corresponding to the full-length Antibody Ab3.

FIG. 4 provides polynucleotide and polypeptide sequences corresponding to the full-length Antibody Ab4.

FIG. 5 provides polynucleotide and polypeptide sequences corresponding to the full-length Antibody Ab5.

FIG. 6 provides polynucleotide and polypeptide sequences corresponding to the full-length Antibody Ab6.

FIG. 7 provides polynucleotide and polypeptide sequences corresponding to the full-length Antibody Ab7.

FIG. 8 provides polynucleotide and polypeptide sequences corresponding to the full-length Antibody Ab8.

FIG. 9 provides polynucleotide and polypeptide sequences corresponding to the full-length Antibody Ab9.

FIG. 10 provides polynucleotide and polypeptide sequences corresponding to the full-length Antibody Ab10.

FIG. 11 provides polynucleotide and polypeptide sequences corresponding to the full-length Antibody Ab11.

FIG. 12 provides polynucleotide and polypeptide sequences corresponding to the full-length Antibody Ab12.

FIG. 13 provides polynucleotide and polypeptide sequences corresponding to the full-length Antibody Ab13.

FIG. 14 provides polynucleotide and polypeptide sequences corresponding to the full-length Antibody Ab14.

FIG. 15 provides polynucleotide and polypeptide sequences corresponding to the full-length Antibody Ab15.

FIG. 16 provides polynucleotide and polypeptide sequences corresponding to the full-length Antibody Ab16.

FIG. 17 provides polynucleotide and polypeptide sequences corresponding to the full-length Antibody Ab17.

FIG. 18 provides polynucleotide and polypeptide sequences corresponding to the full-length Antibody Ab18.

FIG. 19 provides polynucleotide and polypeptide sequences corresponding to the full-length Antibody Ab19.

FIG. 20 provides polynucleotide and polypeptide sequences corresponding to the full-length Antibody Ab20.

FIG. 21 provides polynucleotide and polypeptide sequences corresponding to the full-length Antibody Ab21, produced by expression in *Pichia pastoris*.

FIG. 22 provides the heavy and light chain polypeptide sequences of Fab1.

FIG. 23 provides the heavy and light chain polypeptide sequences of Fab2.

FIG. 53 provides the inhibition of NGF-p75 interaction data obtained following example 5 for antibodies Ah3 and Ab4. Antibodies Ab3 and Ab4 do not demonstrate the ability to inhibit the interaction of NGF and p75.

FIG. 64 demonstrates the inhibition of PC-12 neurite outgrowth in the presence of increasing concentrations of antibody Ab10 obtained following example 6.

DETAILED DESCRIPTION OF PREFERRED EMBODIMENTS

Definitions

Figure 24:
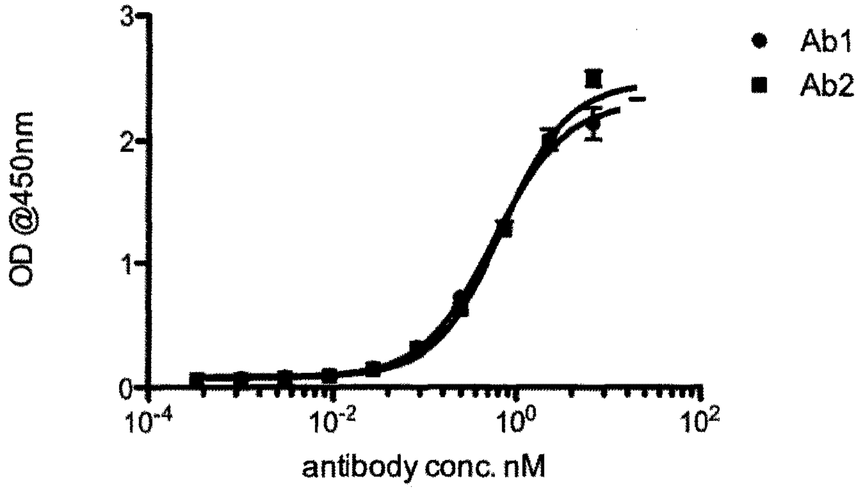
FIG. 24 provides the NGF ELISA binding data obtained following the protocol described infra for antibodies Ab1 and Ab2.
Figure 25:
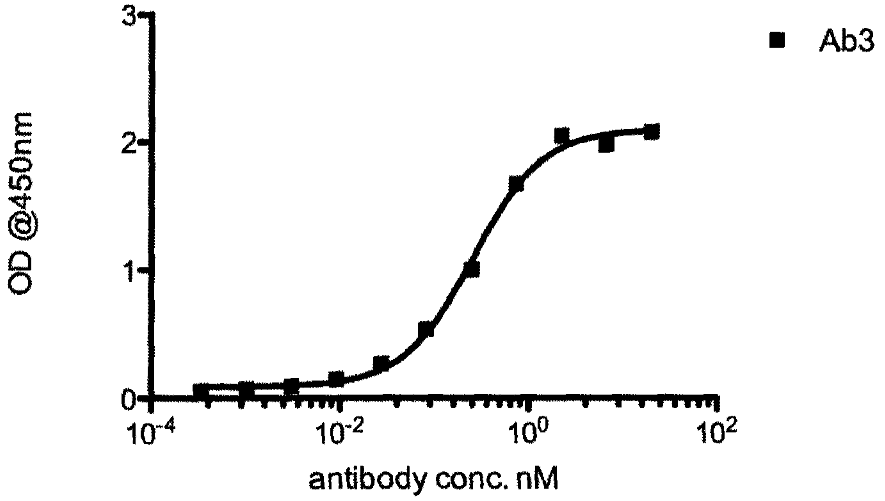
FIG. 25 provides the NGF ELISA binding data obtained following the protocol described infra for antibody Ab3.
Figure 26:
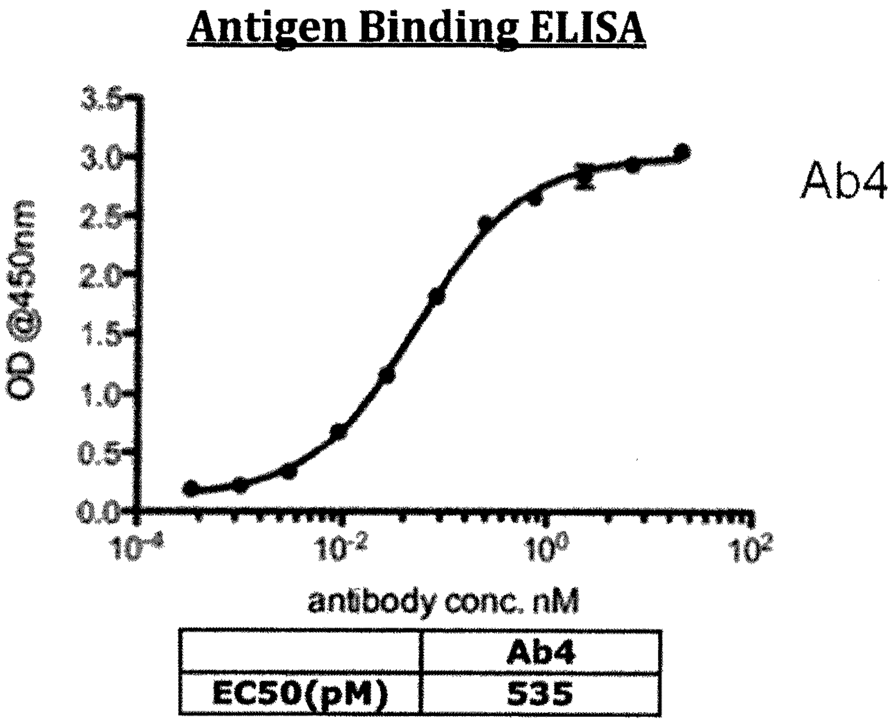
FIG. 26 provides the NGF ELISA binding data obtained following the protocol described infra for antibody Ab4.
Figure 27:
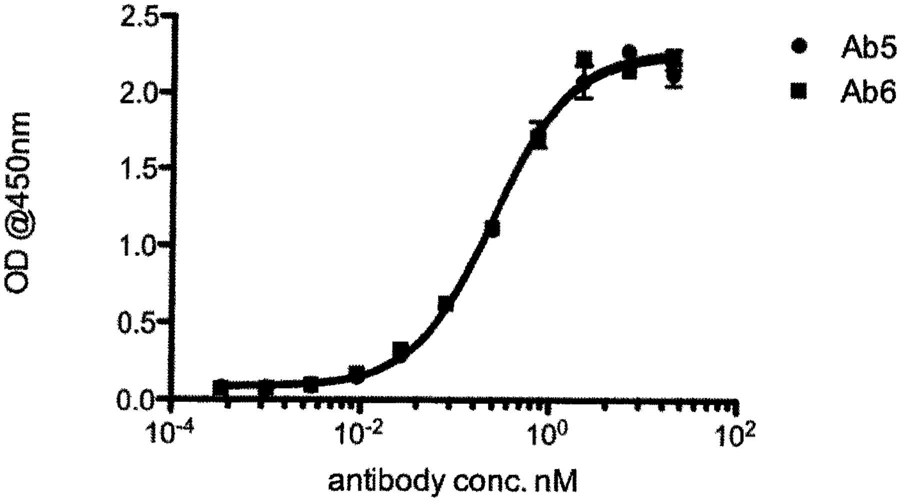
FIG. 27 provides the NGF ELISA binding data obtained following the protocol described infra for antibodies Ab5 and Ab6.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims. As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Nerve Growth Factor (NGF): As used herein, NGF (also referred to as Beta-NGF; HSAN5; and NGFB) encompasses not only the following mature amino acid sequence available from R&D Systems (Minneapolis, Minn.) as *Homo sapiens* Beta-Nerve Growth Factor (3-NGF): SSSHPIFHRGEFSVCDSVSVWVGDKTTATDIKGKEV-MVLGEVNINNSVFKQYFFET KCRDPNPVDS-GCRGIDSKHWNSYCTTTHTFVKALTMDGKQAAW-RFIRIDTACVC VLSRKAVRRA (SEQ ID NO: 411), but also any pro-, mature, soluble, and/or membrane-bound forms of this NGF amino acid sequence, as well as mutants (mutiens), splice variants, isoforms, orthologues, homologues and variants of this sequence.

Host Cell: In the present invention this is generally intended to include any cell that provides for the expression of antibodies or antibody fragments according to the invention. This includes by way of example bacterial, plant, yeast, fungi, avian, mammalian, and insect cell expression systems. Typically antibodies or antibody fragments are expressed in mammalian, bacterial and yeast cells. In a preferred embodiment the subject antibodies or antibody fragments are expressed in a proprietary secretory expression system that uses diploid *Pichia* yeast cultures for antibody expression. This expression system is disclosed in U.S. Pat. No. 7,927,863, by Cregg, issued Apr. 19, 2011, the contents of which are incorporated by reference herein.

Transgenic Animal or Plant: In the present invention this refers to any animal (non-human) or plant that has been genetically modified, e.g., by mutation of an endogenous gene, gene knock-in, gene knock-out, and the like. As is well known in the art transgenic animals, e.g., rodents, bovines, et al. and plants such as tobacco and other species can be engineered with human immunoglobulin genes and thereby express human antibodies. Accordingly transgenic animals and plants herein includes non-human animals and plants that are engineered to express anti-NGF antibodies or other NGF antagonists.

Mating competent yeast species: In the present invention this is intended to broadly encompass any diploid or tetraploid yeast which can be grown in culture. Such species of yeast may exist in a haploid, diploid, or other polyploid form. The cells of a given ploidy may, under appropriate conditions, proliferate for an indefinite number of generations in that form. Diploid cells can also sporulate to form haploid cells. Sequential mating can result in tetraploid strains through further mating or fusion of diploid strains. The present invention contemplates the use of haploid yeast, as well as diploid or other polyploid yeast cells produced, for example, by mating or spheroplast fusion.

In one embodiment of the invention, the mating competent yeast is a member of the Saccharomycetaceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis*; and *Zygosaccharomyces*. Other types of yeast potentially useful in the invention include *Yarrowia; Rhodosporidium; Candida; Hansenula; Filobasium; Sporidiobolus; Bullera; Leucosporidium* and *Filobasidella*.

In a preferred embodiment of the invention, the mating competent yeast is a member of the genus *Pichia*. In a further preferred embodiment of the invention, the mating competent yeast of the genus *Pichia* is one of the following species: *Pichia pastoris, Pichia methanolica*, and *Hansenula polymorpha* (*Pichia angusta*). In a particularly preferred embodiment of the invention, the mating competent yeast of the genus *Pichia* used for antibody expression is the species *Pichia pastoris* and is diploid.

Selectable Marker: A selectable marker is a gene or gene fragment that confers a growth phenotype (physical growth characteristic) on a cell receiving that gene as, for example through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature when two ts mutants are crossed or a ts mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers include but are not limited to: ZEO; G418; LYS3; MET1; MET3a; ADE1; ADE3; URA3; and the like.

Expression Vector: These DNA vectors contain elements that facilitate manipulation for the expression of a foreign protein within the target host cell. Usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Stearns, T. (2000). Methods in yeast genetics: a Cold Spring Harbor Laboratory course manual. Plainview, N.Y.: Cold Spring Harbor Laboratory Press.

Expression vectors for use in the methods of the invention will further include host cell specific sequences, including a selectable auxotrophic or drug marker for identifying transformed host cells. A drug marker may further be used to amplify copy number of the vector in a host cell.

The polypeptide coding sequence of interest is operably linked to transcriptional and translational regulatory sequences that provide for expression of the polypeptide in host cells. These vector components may include, but are not limited to, one or more of the following: an enhancer element, a promoter, and a transcription termination sequence. Sequences for the secretion of the polypeptide may also be included, e.g. a signal sequence, and the like. If yeast cells are used for expression, a yeast origin of replication is optional, as expression vectors are often integrated into the yeast genome. In one embodiment of the invention, the antibody polypeptide of interest is operably linked, or fused, to sequences providing for optimized secretion of the polypeptide from yeast diploid cells.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (Gateway® Technology; Invitrogen, Carlsbad Calif.). If such sites do not exist, the synthetic oligonucleotide adapters or linkers are used in accordance with conventional practice.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature.

The antibody or antibody polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell. The *S. cerevisiae* alpha factor pre-pro signal has proven effective in the secretion of a variety of recombinant proteins from *P. pastoris*. Other secretion signals of interest also include mammalian and bacterial signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 preprotoxin sequence, PHA-E, FACE, human MCP-1, human serum albumin signal sequences, human Ig heavy chain, human Ig light chain, and the like. For example, see Hashimoto et. al. Protein Eng 11(2) 75 (1998); and Kobayashi et. al. Therapeutic Apheresis 2(4) 257 (1998).

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion and/or sequenced.

As an alternative to restriction and ligation of fragments, recombination methods based on att sites and recombination enzymes may be used to insert DNA sequences into a vector. Such methods are described, for example, by Landy (1989) Ann. Rev. Biochem. 58:913-949; and are known to those of skill in the art. Such methods utilize intermolecular DNA recombination that is mediated by a mixture of lambda and *E. coli*-encoded recombination proteins. Recombination occurs between specific attachment (Ott) sites on the interacting DNA molecules. For a description of att sites see Weisberg and Landy (1983) Site-Specific Recombination in Phage Lambda, in *Lambda II*, Weisberg, ed. (Cold Spring Harbor, N.Y.: Cold Spring Harbor Press), pp. 211-250. The DNA segments flanking the recombination sites are switched, such that after recombination, the att sites are hybrid sequences comprised of sequences donated by each parental vector. The recombination can occur between DNAs of any topology.

Att sites may be introduced into a sequence of interest by ligating the sequence of interest into an appropriate vector; generating a PCR product containing att B sites through the use of specific primers; generating a cDNA library cloned into an appropriate vector containing att sites; and the like.

Folding, as used herein, refers to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

The expression host may be further modified by the introduction of sequences encoding one or more enzymes that enhance folding and disulfide bond formation, i.e. foldases, chaperonins, etc. Such sequences may be constitutively or inducibly expressed in the yeast host cell, using vectors, markers, etc. as known in the art.

The terms “desired protein” or “desired antibody” are used interchangeably and refer generally to a parent antibody specific to a target, i.e., NGF or a chimeric or humanized antibody or a binding portion thereof derived therefrom as described herein. The term “antibody” is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be “antibodies.” A preferred source for producing antibodies useful as starting material according to the invention is rabbits. Numerous antibody coding sequences have been described; and others may be raised by methods well-known in the art. Examples thereof include chimeric antibodies, human antibodies and other non-human mammalian antibodies, humanized antibodies, single chain antibodies (such as scFvs), camelbodies, nanobodies, IgNAR (single-chain antibodies derived from sharks), small-modular immunopharmaceuticals (SMIPs), and antibody fragments such as Fabs, Fab', $F(ab')_2$ and the like. See Streltsov V A, et al., Structure of a shark IgNAR antibody variable domain and modeling of an early-developmental isotype, Protein Sci. 2005 November; 14(11):2901-9. Epub 2005 Sep. 30; Greenberg A S, et al., A new antigen receptor gene family that undergoes rearrangement and extensive somatic diversification in sharks, Nature. 1995 Mar. 9; 374(6518):168-73; Nuttall S D, et al., Isolation of the new antigen receptor from wobbegong sharks, and use as a scaffold for the display of protein loop libraries, Mol. Immunol. 2001 August; 38(4):313-26; Hamers-Casterman C, et al., Naturally occurring antibodies devoid of light chains, Nature. 1993 Jun. 3; 363(6428):446-8; Gill D S, et al., Biopharmaceutical drug discovery using novel protein scaffolds, Curr Opin Biotechnol. 2006 December; 17(6): 653-8. Epub 2006 Oct. 19.

As noted above, antibodies or monovalent agents such as antigen binding fragments may be produced by different well known methods of making antibodies and antibody fragments, typically hybridoma technology or genetic engineering methods. For high level production of antibodies, such as antibodies which are to be used for human therapy as herein, genetic engineering methods are preferably used as these methods facilitate the production of high amounts of a desired antibody or antibody polypeptide. In these genetic engineering techniques, immune cells are obtained by in vitro immunization or in vivo immunization of desired hosts or host cells with a desired antigen, resulting in the production of immune cells that produce antibodies against a desired antigen or immunogen. The messenger RNA is isolated from these antibody producing immune cells and is used as a template to make cDNA using PCR amplification. The resultant cDNA’s expressing the antibody heavy and light chains are then isolated and incorporated in suitable expression vectors, the particulars of which depend on the specific host cell wherein antibody expression occurs, and the vectors are the incorporated in host cells which then express, and preferably secrete the desired antibodies or antibody fragments.

In some methods, a library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies or antibody fragments that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies herein include any antibody or antibody fragment which comprises residues of at least 2 different antibodies of the same or different species. Humanized antibodies as described herein, are a species of chimeric antibodies. Therefore, these terms are sometimes used interchangeably herein. Typically chimeric antibodies are made by recombinant means, e.g., by combining the variable light and heavy chain regions $V_L$ and $V_H$), obtained from antibody producing cells of one species with the constant light and heavy chain regions from another. Often chimeric antibodies combine rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the chimeric antibodies of the invention may comprise human constant regions selected from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions or other constant regions, e.g., that of other primates.

Humanized antibodies are antibodies containing human and non-human sequences which are engineered to retain the binding properties of a parent, non-human antibody, and therefore contain human and non-human residues. Typically, humanized antibodies are engineered to contain human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

In addition to entire immunoglobulins (or their recombinant counterparts), monovalent agents and other antibody fragments such as immunoglobulin fragments comprising the epitope binding site (e.g., Fab, Fab', Fv or scFv fragments, SMIPs (small molecule immunopharmaceuticals), camelbodies, nanobodies, IgNAR, monovalent antibody molecules analogous to MetMab, $F(ab')_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. In another embodiment of the invention, SMIPs (small molecule immunopharmaceuticals), camelbodies, nanobodies, and IgNAR are encompassed by immunoglobulin fragments.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties and the like, or specific binding moieties, such as streptavidin, avidin, or biotin, and the like may be utilized in the methods and compositions of the present invention. Examples of additional effector molecules are provided infra.

Also, the antibodies may be modified to affect half-life or circulation time such as by PEGylation. Antibodies or fragments thereof may also be chemically modified to provide additional advantages such as increased solubility, stability and circulating time (in viva half-life) of the polypeptide, or decreased immunogenicity (See U.S. Pat. No. 4,179,337). The chemical moieties for derivatization may be selected from water soluble polymers such as polyethylene glycol, ethylene glycol/propylene glycol copolymers, carboxymethylcellulose, dextran, polyvinyl alcohol and the like. The antibodies and fragments thereof may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

There are a number of attachment methods available to those skilled in the art, See e.g., EP 0 401 384, herein incorporated by reference (coupling PEG to G-CSF), See also Malik et al., Exp. Hematol. 20:1028-1035 (1992) (reporting PEGylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to polypeptides via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) or to more than one type of amino acid residue (e.g., lysine, histidine, aspartic acid, glutamic acid, cysteine and combinations thereof).

Alternatively, antibodies or fragments thereof may have increased in vivo half lives via fusion with albumin (including but not limited to recombinant human serum albumin or fragments or variants thereof (see, e.g., U.S. Pat. No. 5,876,969, issued Mar. 2, 1999, EP Patent 0 413 622, and U.S. Pat.

No. 5,766,883, issued Jun. 16, 1998, herein incorporated by reference in their entirety)) or other circulating blood proteins such as transferrin or ferritin. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. Polynucleotides encoding fusion proteins of the invention are also encompassed by the invention.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A "coding sequence" is an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. Promoter sequences typically contain additional sites for binding of regulatory molecules (e.g., transcription factors) which affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

Vectors are used to introduce a foreign substance, such as DNA, RNA or protein, into an organism or host cell. Typical vectors include recombinant viruses (for polynucleotides) and liposomes (for polypeptides). A "DNA vector" is a replicon, such as plasmid, phage or cosmid, to which another polynucleotide segment may be attached so as to bring about the replication of the attached segment. An "expression vector" is a DNA vector which contains regulatory sequences which will direct polypeptide synthesis by an appropriate host cell. This usually means a promoter to bind RNA polymerase and initiate transcription of mRNA, as well as ribosome binding sites and initiation signals to direct translation of the mRNA into a polypeptide(s). Incorporation of a polynucleotide sequence into an expression vector at the proper site and in correct reading frame, followed by transformation of an appropriate host cell by the vector, enables the production of a polypeptide encoded by said polynucleotide sequence.

"Amplification" of polynucleotide sequences is the in vitro production of multiple copies of a particular nucleic acid sequence. The amplified sequence is usually in the form of DNA. A variety of techniques for carrying out such amplification are described in a review article by Van Brunt (1990, Bio/Technol., 8(4):291-294). Polymerase chain reaction or PCR is a prototype of nucleic acid amplification, and use of PCR herein should be considered exemplary of other suitable amplification techniques.

The general structure of antibodies in vertebrates now is well understood (Edelman, G. M., Ann. N.Y. Acad. Sci., 190: 5 (1971)). Antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the $F_C$ region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to $\gamma$, $\mu$, $\alpha$, $\delta$, and $\epsilon$ (gamma, mu, alpha, delta, or epsilon) heavy chain constant regions). The constant region or class determines subsequent effector function of the antibody, including activation of complement (Kabat, E. A., Structural Concepts in Immunology and Immunochemistry, 2nd Ed., p. 413-436, Holt, Rinehart, Winston (1976)), and other cellular responses (Andrews, D. W., et al., Clinical Immunobiology, pp 1-18, W. B. Sanders (1980); Kohl, S., et al., Immunology, 48: 187 (1983)); while the variable region determines the antigen with which it will react. Light chains are classified as either $\kappa$ (kappa) or $\lambda$ (lambda). Each heavy chain class can be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

The expression "variable region" or "VR" refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions (CDRs) found in the variable regions of light or heavy chains of an antibody (See Kabat, E. A. et al., Sequences of Proteins of Immunological Interest, National Institutes of Health, Bethesda, Md., (1987)). These expressions include the hypervariable regions as defined by Kabat et al. ("Sequences of Proteins of Immunological Interest," Kabat E., et al., US Dept. of Health and Human Services, 1983) or the hypervariable loops in 3-dimensional structures of antibodies (Chothia and Lesk, J. Mol. Biol. 196 901-917 (1987)). The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction (Kashmiri, S., Methods, 36:25-34 (2005)).

The expressions "framework region" or "FR" refer to one or more of the framework regions within the variable regions of the light and heavy chains of an antibody (See Kabat, E. A. et al., Sequences of Proteins of Immunological Interest, National Institutes of Health, Bethesda, Md., (1987)). These expressions include those amino acid sequence regions interposed between the CDRs within the variable regions of the light and heavy chains of an antibody.

Anti-NGF Antibodies and Binding Fragments Thereof Having Binding Activity for NGF Antibody Ab1

Methods of the invention include methods of preventing inflammation and treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab1 polypeptides set forth below. Ab1 antibodies inhibit the interaction of NGF with TrkA and also the interaction of NGF with p75. In one embodiment, the invention includes chimeric antibodies having binding specificity to NGF and possessing a variable light chain sequence comprising the sequence set forth below:

```
                                          (SEQ ID NO: 1)
ALVMTQTPSSVSAAVGGTVTINCQASQNIYSNLAWYQQRPGQRPKLLIYG

ASNLDAGVPSRFRGSGSGTEYTLTISDLECDDVGTYYCQSAFDSDSTENT

FGGGTEVVVKR.
```

The invention also includes chimeric antibodies having binding specificity to NGF and possessing a light chain sequence comprising the sequence set forth below:

```
                                          (SEQ ID NO: 2)
ALVMTQTPSSVSAAVGGTVTINCQASQNIYSNLAWYQQRPGQRPKLLIYG

ASNLDAGVPSRFRGSGSGTEYTLTISDLECDDVGTYYCQSAFDSDSTENT

FGGGTEVVVKRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC.
```

The invention further includes chimeric antibodies having binding specificity to NGF and possessing a variable heavy chain sequence comprising the sequence set forth below:

```
                                          (SEQ ID NO: 3)
QSLEESGGRLVTPGTPLTLTCTVSGFSLSSYAMSWVRQAPGKGLEWIGVI

TSIGSTVYASWAKGRFTISKTSTTVDLKITSPTTEDTATYFCARGYDDYD

EMTYFNIWGQGTLVTVSS.
```

The invention also includes chimeric antibodies having binding specificity to NGF and possessing a heavy chain sequence comprising the sequence set forth below:

```
                                          (SEQ ID NO: 4)
QSLEESGGRLVTPGTPLTLTCTVSGFSLSSYAMSWVRQAPGKGLEWIGVI

TSIGSTVYASWAKGRFTISKTSTTVDLKITSPTTEDTATYFCARGYDDYD

EMTYFNIWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK.
```

The invention further contemplates antibodies comprising one or more of the polypeptide sequences of SEQ ID NO: 5; SEQ ID NO: 6; and SEQ ID NO: 7 which correspond to the complementarity-determining regions (CDRs, or hypervariable regions) of the variable light chain sequence of SEQ ID NO: 1 or the light chain sequence of SEQ ID NO: 2, and/or one or more of the polypeptide sequences of SEQ ID NO: 8; SEQ ID NO: 9; and SEQ ID NO: 10 which correspond to the complementarity-determining regions (CDRs, or hypervariable regions) of the variable heavy chain sequence of SEQ ID NO: 3 or the heavy chain sequence of SEQ ID NO: 4, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 1 or SEQ ID NO: 2. In another embodiment of the invention, antibody fragments of the invention comprise, or alternatively consist of, the polypeptide sequence of SEQ ID NO: 3 or SEQ ID NO: 4.

In a further embodiment of the invention, fragments of the antibody having binding specificity to NGF comprise, or alternatively consist of, one or more of the polypeptide sequences of SEQ ID NO: 5; SEQ ID NO: 6; and SEQ ID NO: 7 which correspond to the complementarity-determining regions (CDRs, or hypervariable regions) of the variable light chain sequence of SEQ ID NO: 1 or the light chain sequence of SEQ ID NO: 2.

In a further embodiment of the invention, fragments of the antibody having binding specificity to NGF comprise, or alternatively consist of, one or more of the polypeptide sequences of SEQ ID NO: 8; SEQ ID NO: 9; and SEQ ID NO: 10 which correspond to the complementarity-determining regions (CDRs, or hypervariable regions) of the variable heavy chain sequence of SEQ ID NO: 3 or the heavy chain sequence of SEQ ID NO: 4.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 1; the variable heavy chain region of SEQ ID NO: 3; the complementarity-determining regions (SEQ ID NO: 5; SEQ ID NO: 6; and SEQ ID NO: 7) of the variable light chain region of SEQ ID NO: 1; and the complementarity-determining regions (SEQ ID NO: 8; SEQ ID NO: 9; and SEQ ID NO: 10) of the variable heavy chain region of SEQ ID NO: 3.

In a particularly preferred embodiment of the invention, the chimeric anti-NGF antibody is Ab1, comprising, or alternatively consisting of, SEQ ID NO: 2 and SEQ ID NO: 4, and having at least one of the biological activities set forth herein.

In a further particularly preferred embodiment of the invention, antibody fragments comprise, or alternatively consist of, Fab (fragment antigen binding) fragments having binding specificity for NGF and MetMab like monovalent agents. With respect to antibody Ab1, the Fab fragment includes the variable light chain sequence of SEQ ID NO: 1 and the variable heavy chain sequence of SEQ ID NO: 3. This embodiment of the invention further contemplates additions, deletions, and variants of SEQ ID NO: 1 and/or SEQ ID NO: 3 in said Fab while retaining binding specificity for NGF.

In one embodiment of the invention described herein (infra), Fab fragments may be produced by enzymatic digestion (e.g., papain) of Ab1. In another embodiment of the invention, anti-NGF antibodies such as Ab1 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab2

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab2 polypeptides set forth below. Ab2 antibodies inhibit the interaction of NGF with TrkA and also the interaction of NGF with p75. In one embodiment, the invention includes chimeric or humanized antibodies having binding specificity to NGF and possessing a variable light chain sequence comprising the sequence set forth below:

(SEQ ID NO: 11)

DIQMTQSPSTLSASVGDRVTITCQASQNIYSNLAWYQQKPGKAPKLLIYG

ASNLDAGVPSRFSGSGSGTEYTLTISSLQPDDFATYYCQSAFDSDSTENT

FGGGTKVEIKR.

The invention also includes chimeric or humanized antibodies having binding specificity to NGF and possessing a light chain sequence comprising the sequence set forth below:

(SEQ ID NO: 12)

DIQMTQSPSTLSASVGDRVTITCQASQNIYSNLAWYQQKPGKAPKLLIYG

ASNLDAGVPSRFSGSGSGTEYTLTISSLQPDDFATYYCQSAFDSDSTENT

FGGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC.

The invention further includes chimeric or humanized antibodies having binding specificity to NGF and possessing a variable heavy chain sequence comprising the sequence set forth below:

(SEQ ID NO: 13)

EVQLVESGGGLVQPGGSLRLSCAASGFTVSSYAMSWVRQAPGKGLEWVGV

ITSIGSTVYASSAKGRFTISRDNSKNTLYLQMNSLRAEDTAVYYCARGYD

DYDEMTYFNIWGQGTLVTVSS.

The invention also includes chimeric or humanized antibodies having binding specificity to NGF and possessing a heavy chain sequence comprising the sequence set forth below:

(SEQ ID NO: 14)

EVQLVESGGGLVQPGGSLRLSCAASGFTVSSYAMSWVRQAPGKGLEWVGV

ITSIGSTVYASSAKGRFTISRDNSKNTLYLQMNSLRAEDTAVYYCARGYD

DYDEMTYFNIWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

ASTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K.

The invention further contemplates antibodies comprising one or more of the polypeptide sequences of SEQ ID NO: 15; SEQ ID NO: 16; and SEQ ID NO: 17 which correspond to the complementarity-determining regions (CDRs, or hypervariable regions) of the variable light chain sequence of SEQ ID NO: 11 or the light chain sequence of SEQ ID NO: 12, and/or one or more of the polypeptide sequences of SEQ ID NO: 18; SEQ ID NO: 19; and SEQ ID NO: 20 which correspond to the complementarity-determining regions (CDRs, or hypervariable regions) of the variable heavy chain sequence of SEQ ID NO: 13 or the heavy chain sequence of SEQ ID NO: 14, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 11 or SEQ ID NO: 12. In another embodiment of the invention, antibody fragments of the invention comprise, or alternatively consist of, the polypeptide sequence of SEQ ID NO: 13 or SEQ ID NO: 14.

In a further embodiment of the invention, fragments of the antibody having binding specificity to NGF comprise, or alternatively consist of, one or more of the polypeptide sequences of SEQ ID NO: 15; SEQ ID NO: 16; and SEQ ID NO: 17 which correspond to the complementarity-determining regions (CDRs, or hypervariable regions) of the variable light chain sequence of SEQ ID NO: 11 or the light chain sequence of SEQ ID NO: 12.

In a further embodiment of the invention, fragments of the antibody having binding specificity to NGF comprise, or alternatively consist of, one or more of the polypeptide sequences of SEQ ID NO: 18; SEQ ID NO: 19; and SEQ ID NO: 20 which correspond to the complementarity-determining regions (CDRs, or hypervariable regions) of the variable heavy chain sequence of SEQ ID NO: 13 or the heavy chain sequence of SEQ ID NO: 14.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 11; the variable heavy chain region of SEQ ID NO: 13; the complementarity-determining regions (SEQ ID NO: 15; SEQ ID NO: 16; and SEQ ID NO: 17) of the variable light chain region of SEQ ID NO: 11; and the complementarity-determining regions (SEQ ID NO: 18; SEQ ID NO: 19; and SEQ ID NO: 20) of the variable heavy chain region of SEQ ID NO: 13.

In a particularly preferred embodiment of the invention, the chimeric or humanized anti-NGF antibody is Ab2, comprising, or alternatively consisting of, SEQ ID NO: 12 and SEQ ID NO: 14, and having at least one of the biological activities set forth herein.

In a further particularly preferred embodiment of the invention, antibody fragments comprise, or alternatively consist of, Fab (fragment antigen binding) fragments having binding specificity for NGF and MetMab like monovalent agents. With respect to antibody Ab2, the Fab fragment includes the variable light chain sequence of SEQ ID NO: 11 and the variable heavy chain sequence of SEQ ID NO: 13. This embodiment of the invention further contemplates additions, deletions, and variants of SEQ ID NO: 11 and/or SEQ ID NO: 13 in said Fab while retaining binding specificity for NGF.

In one embodiment of the invention described herein (infra), Fab fragments may be produced by enzymatic digestion (e.g., papain) of Ab2. In another embodiment of the invention, anti-NGF antibodies such as Ab2 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris.*

Antibody Ab3

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab3 polypeptides set forth below. Ab3 antibodies inhibit the interaction of NGF with TrkA and do not appreciably affect the interaction of NGF with p75 In one embodiment, the invention includes chimeric antibodies having binding specificity to NGF and possessing a variable light chain sequence comprising the sequence set forth below:

```
                                          (SEQ ID NO: 21)
AVLTQTPSPVSAAMGDTVTIKCQSSQSVYKNNYLSWYQQKPGQPPRLLIY

DASNLPSGVPSRFSGSGSGTQFTLTISGVQCDDAATYYCLGDYDDDADNA

FGGGTEVVVKR.
```

The invention also includes chimeric antibodies having binding specificity to NGF and possessing a light chain sequence comprising the sequence set forth below:

```
                                          (SEQ ID NO: 22)
AVLTQTPSPVSAAMGDTVTIKCQSSQSVYKNNYLSWYQQKPGQPPRLLIY

DASNLPSGVPSRFSGSGSGTQFTLTISGVQCDDAATYYCLGDYDDDADNA

FGGGTEVVVKRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC.
```

The invention further includes chimeric antibodies having binding specificity to NGF and possessing a variable heavy chain sequence comprising the sequence set forth below:

(SEQ ID NO: 23)
QSVEESGGRLVTPGTPLTLTCTVSGFSLSSYVMIWVRQAPGKGLEYIGIT

WSAGTYYASWAKGRFTISKTSSTTVDLKITSPTTEDTATYFCAGGGGSIY

DIWGPGTLVTVSS.

The invention also includes chimeric antibodies having binding specificity to NGF and possessing a heavy chain sequence comprising the sequence set forth below:

(SEQ ID NO: 24)
QSVEESGGRLVTPGTPLTLTCTVSGFSLSSYVMIWVRQAPGKGLEYIGI

TWSAGTYYASWAKGRFTISKTSSTTVDLKITSPTTEDTATYFCAGGGGS

IYDIWGPGTLVTVSSASTKGPSVFPLAPSSKSTSGGTAALGCLVKDYFP

EPVTVSWNSGALTSGVHTFPAVLQSSGLYSLSSVVTVPSSSLGTQTYIC

NVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYAS

TYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSP

GK.

The invention further contemplates antibodies comprising one or more of the polypeptide sequences of SEQ ID NO: 25; SEQ ID NO: 26; and SEQ ID NO: 27 which correspond to the complementarity-determining regions (CDRs, or hypervariable regions) of the variable light chain sequence of SEQ ID NO: 21 or the light chain sequence of SEQ ID NO: 22, and/or one or more of the polypeptide sequences of SEQ ID NO: 28; SEQ ID NO: 29; and SEQ ID NO: 30 which correspond to the complementarity-determining regions (CDRs, or hypervariable regions) of the variable heavy chain sequence of SEQ ID NO: 23 or the heavy chain sequence of SEQ ID NO: 24, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 21 or SEQ ID NO: 22. In another embodiment of the invention, antibody fragments of the invention comprise, or alternatively consist of, the polypeptide sequence of SEQ ID NO: 23 or SEQ ID NO: 24.

In a further embodiment of the invention, fragments of the antibody having binding specificity to NGF comprise, or alternatively consist of, one or more of the polypeptide sequences of SEQ ID NO: 25; SEQ ID NO: 26; and SEQ ID NO: 27 which correspond to the complementarity-determining regions (CDRs, or hypervariable regions) of the variable light chain sequence of SEQ ID NO: 21 or the light chain sequence of SEQ ID NO: 22.

In a further embodiment of the invention, fragments of the antibody having binding specificity to NGF comprise, or alternatively consist of, one or more of the polypeptide sequences of SEQ ID NO: 28; SEQ ID NO: 29; and SEQ ID NO: 30 which correspond to the complementarity-determining regions (CDRs, or hypervariable regions) of the variable heavy chain sequence of SEQ ID NO: 23 or the heavy chain sequence of SEQ ID NO: 24.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 21; the variable heavy chain region of SEQ ID NO: 23; the complementarity-determining regions (SEQ ID NO: 25; SEQ ID NO: 26; and SEQ ID NO: 27) of the variable light chain region of SEQ ID NO: 21; and the complementarity-determining regions (SEQ ID NO: 28; SEQ ID NO: 29; and SEQ ID NO: 30) of the variable heavy chain region of SEQ ID NO: 23.

In a particularly preferred embodiment of the invention, the chimeric anti-NGF antibody is Ab3, comprising, or alternatively consisting of, SEQ ID NO: 22 and SEQ ID NO: 24, and having at least one of the biological activities set forth herein.

In a further particularly preferred embodiment of the invention, antibody fragments comprise, or alternatively consist of, Fab (fragment antigen binding) fragments having binding specificity for NGF and MetMab like monovalent agents. With respect to antibody Ab3, the Fab fragment includes the variable light chain sequence of SEQ ID NO: 21 and the variable heavy chain sequence of SEQ ID NO: 23. This embodiment of the invention further contemplates additions, deletions, and variants of SEQ ID NO: 21 and/or SEQ ID NO: 23 in said Fab while retaining binding specificity for NGF.

In one embodiment of the invention described herein (infra), Fab fragments may be produced by enzymatic digestion (e.g., papain) of Ab3. In another embodiment of the invention, anti-NGF antibodies such as Ab3 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab4

Methods of the invention include methods of treating pain by administering one or more anti-human NGF monovalent agents to an individual in a therapeutically effective amount, wherein there is no substantial increase in the inflammatory response of the individual following administration of the one or more monovalent agents. Anti-human NGF monovalent agents used in the methods of the invention may be derived from one or more of the antibody Ab4 polypeptides set forth below. Ab4 antibodies inhibit the interaction of NGF with TrkA and do not appreciably affect the interaction of NGF with p75. In one embodiment, the invention includes chimeric or humanized antibodies having binding specificity to NGF and possessing a variable light chain sequence comprising the sequence set forth below: DIQMTQSPSTLSASVGDRVTITCQSSQSVYKN-NYLSWYQQKPGKAPKLLIYDASNL PSGVPSRF-SGSGSGTEFTLTISSLQPDDFATYYCLGDYDDDAD-NAFGGGTKVEIKR (SEQ ID NO: 31). As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

The invention also includes chimeric or humanized antibodies having binding specificity to NGF and possessing a light chain sequence comprising the sequence set forth below:

(SEQ ID NO: 32)
DIQMTQSPSTLSASVGDRVTITCQSSQSVYKNNYLSWYQQKPGKAPKLL

IYDASNLPSGVPSRFSGSGSGTEFTLTISSLQPDDFATYYCLGDYDDDA

DNAFGGGTKVEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC.

The invention further includes chimeric or humanized antibodies having binding specificity to NGF and possessing a variable heavy chain sequence comprising the sequence set forth below:

(SEQ ID NO: 33)
EVQLVESGGGLVQPGGSLRLSCAASGFTVSSYVMIWVRQAPGKGLEYIG

ITWSAGTYYASSAKGRFTISRDNSKNTLYLQMNSLRAEDTAVYYCAGGG

GSIYDIWGQGTLVTVSS.

The invention also includes chimeric or humanized antibodies having binding specificity to NGF and possessing a heavy chain sequence comprising the sequence set forth below:

(SEQ ID NO: 34)
EVQLVESGGGLVQPGGSLRLSCAASGFTVSSYVMIWVRQAPGKGLEYIG

ITWSAGTYYASSAKGRFTISRDNSKNTLYLQMNSLRAEDTAVYYCAGGG

GSIYDIWGQGTLVTVSSASTKGPSVFPLAPSSKSTSGGTAALGCLVKDY

FPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKP

KDTLMISRTPEVTCVVVDVSHEDPEVKFNWYVDGVEVHNAKTKPREEQY

ASTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSL

SPGK.

The invention further contemplates antibodies comprising one or more of the polypeptide sequences of SEQ ID NO: 35; SEQ ID NO: 36; and SEQ ID NO: 37 which correspond to the complementarity-determining regions (CDRs, or hypervariable regions) of the variable light chain sequence of SEQ ID NO: 31 or the light chain sequence of SEQ ID NO: 32, and/or one or more of the polypeptide sequences of SEQ ID NO: 38; SEQ ID NO: 39; and SEQ ID NO: 40 which correspond to the complementarity-determining regions (CDRs, or hypervariable regions) of the variable heavy chain sequence of SEQ ID NO: 33 or the heavy chain sequence of SEQ ID NO: 34, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 31 or SEQ ID NO: 32. In another embodiment of the invention, antibody fragments of the invention comprise, or alternatively consist of, the polypeptide sequence of SEQ ID NO: 33 or SEQ ID NO: 34.

In a further embodiment of the invention, fragments of the antibody having binding specificity to NGF comprise, or alternatively consist of, one or more of the polypeptide sequences of SEQ ID NO: 35; SEQ ID NO: 36; and SEQ ID NO: 37 which correspond to the complementarity-determining regions (CDRs, or hypervariable regions) of the variable light chain sequence of SEQ ID NO: 31 or the light chain sequence of SEQ ID NO: 32.

In a further embodiment of the invention, fragments of the antibody having binding specificity to NGF comprise, or alternatively consist of, one or more of the polypeptide sequences of SEQ ID NO: 38; SEQ ID NO: 39; and SEQ ID NO: 40 which correspond to the complementarity-determining regions (CDRs, or hypervariable regions) of the variable heavy chain sequence of SEQ ID NO: 33 or the heavy chain sequence of SEQ ID NO: 34.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 31; the variable heavy chain region of SEQ ID NO: 33; the complementarity-determining regions (SEQ ID NO: 35; SEQ ID NO: 36; and SEQ ID NO: 37) of the variable light chain region of SEQ ID NO: 31; and the complementarity-determining regions (SEQ ID NO: 38; SEQ ID NO: 39; and SEQ ID NO: 40) of the variable heavy chain region of SEQ ID NO: 33.

In a particularly preferred embodiment of the invention, the chimeric or humanized anti-NGF antibody is Ab4, comprising, or alternatively consisting of, SEQ ID NO: 32 and SEQ ID NO: 34, and having at least one of the biological activities set forth herein.

In a further particularly preferred embodiment of the invention, antibody fragments comprise, or alternatively consist of, Fab (fragment antigen binding) fragments having binding specificity for NGF or MetMab like monvalent agents. With respect to antibody Ab4, the Fab fragment includes the variable light chain sequence of SEQ ID NO: 31 and the variable heavy chain sequence of SEQ ID NO: 33. This embodiment of the invention further contemplates additions, deletions, and variants of SEQ ID NO: 31 and/or SEQ ID NO: 33 in said Fab while retaining binding specificity for NGF.

In one embodiment of the invention described herein (infra), Fab fragments may be produced by enzymatic digestion (e.g., papain) of Ab4. In another embodiment of the invention, anti-NGF antibodies such as Ab4 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab5

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof. Anti-human NGF monovalent agents used in the methods of the invention may be derived from one or more of the antibody Ab5 polypeptides set forth below. Ab5 antibodies inhibit the interaction of NGF with TrkA and also the interaction of NGF with p75.

In one embodiment, the invention includes chimeric antibodies having binding specificity to NGF and possessing a variable light chain sequence comprising the sequence set forth below:

(SEQ ID NO: 41)
AYDMTQTPASVEVAVGGTVTIKCQASQSIYSNLAWYQQRPGQPPKLLIY

DASTLESGVPSRFKGSGSGTEYTLTISGVECADAASYYCQQGFTVSDID

NAFGGGTEVVVKR.

The invention also includes chimeric antibodies having binding specificity to NGF and possessing a light chain sequence comprising the sequence set forth below:

(SEQ ID NO: 42)
AYDMTQTPASVEVAVGGTVTIKCQASQSIYSNLAWYQQRPGQPPKLLIY

DASTLESGVPSRFKGSGSGTEYTLTISGVECADAASYYCQQGFTVSDID

NAFGGGTEVVVKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC.

The invention further includes chimeric antibodies having binding specificity to NGF and possessing a variable heavy chain sequence comprising the sequence set forth below:

(SEQ ID NO: 43)
QSVEESGGRLVTPGTPLTLTCTVSGFSLSNYAVGWVRQAPGKGLEWIGI

IGRNGNTWYASWARGRFTISKTSTTVDLKITSPTSEDTATYFCARGYGR

SVAYYVFNIWGPGTLVTVSS.

The invention also includes chimeric antibodies having binding specificity to NGF and possessing a heavy chain sequence comprising the sequence set forth below:

(SEQ ID NO: 44)
QSVEESGGRLVTPGTPLTLTCTVSGFSLSNYAVGWVRQAPGKGLEWIGI

IGRNGNTWYASWARGRFTISKTSTTVDLKITSPTSEDTATYFCARGYGR

-continued

SVAYYVFNIWGPGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKTKPRE

EQYASTYRVVSVLTVLHQDWLNGKEYKCKVSNKALPAPIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPGK.

The invention further contemplates antibodies comprising one or more of the polypeptide sequences of SEQ ID NO: 45; SEQ ID NO: 46; and SEQ ID NO: 47 which correspond to the complementarity-determining regions (CDRs, or hypervariable regions) of the variable light chain sequence of SEQ ID NO: 41 or the light chain sequence of SEQ ID NO: 42, and/or one or more of the polypeptide sequences of SEQ ID NO: 48; SEQ ID NO: 49; and SEQ ID NO: 50 which correspond to the complementarity-determining regions (CDRs, or hypervariable regions) of the variable heavy chain sequence of SEQ ID NO: 43 or the heavy chain sequence of SEQ ID NO: 44, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 41 or SEQ ID NO: 42. In another embodiment of the invention, antibody fragments of the invention comprise, or alternatively consist of, the polypeptide sequence of SEQ ID NO: 43 or SEQ ID NO: 44.

In a further embodiment of the invention, fragments of the antibody having binding specificity to NGF comprise, or alternatively consist of, one or more of the polypeptide sequences of SEQ ID NO: 45; SEQ ID NO: 46; and SEQ ID NO: 47 which correspond to the complementarity-determining regions (CDRs, or hypervariable regions) of the variable light chain sequence of SEQ ID NO: 41 or the light chain sequence of SEQ ID NO: 42.

In a further embodiment of the invention, fragments of the antibody having binding specificity to NGF comprise, or alternatively consist of, one or more of the polypeptide sequences of SEQ ID NO: 48; SEQ ID NO: 49; and SEQ ID NO: 50 which correspond to the complementarity-determining regions (CDRs, or hypervariable regions) of the variable heavy chain sequence of SEQ ID NO: 43 or the heavy chain sequence of SEQ ID NO: 44.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 41; the variable heavy chain region of SEQ ID NO: 43; the complementarity-determining regions (SEQ ID NO: 45; SEQ ID NO: 46; and SEQ ID NO: 47) of the variable light chain region of SEQ ID NO: 41; and the complementarity-determining regions (SEQ ID NO: 48; SEQ ID NO: 49; and SEQ ID NO: 50) of the variable heavy chain region of SEQ ID NO: 43.

In a particularly preferred embodiment of the invention, the chimeric anti-NGF antibody is Ab5, comprising, or alternatively consisting of, SEQ ID NO: 42 and SEQ ID NO: 44, and having at least one of the biological activities set forth herein.

In a further particularly preferred embodiment of the invention, antibody fragments comprise, or alternatively consist of, Fab (fragment antigen binding) fragments having binding specificity for NGF or MetMab like monovalent agents. With respect to antibody Ab5, the Fab fragment includes the variable light chain sequence of SEQ ID NO: 41 and the variable heavy chain sequence of SEQ ID NO: 43. This embodiment of the invention further contemplates additions, deletions, and variants of SEQ ID NO: 41 and/or SEQ ID NO: 43 in said Fab while retaining binding specificity for NGF.

In one embodiment of the invention described herein (infra), Fab fragments may be produced by enzymatic digestion (e.g., papain) of Ab5. In another embodiment of the invention, anti-NGF antibodies such as Ab5 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab6

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab6 polypeptides set forth below. Ab6 antibodies inhibit the interaction of NGF with TrkA and also the interaction of NGF with p75. In one embodiment, the invention includes chimeric or humanized antibodies having binding specificity to NGF and possessing a variable light chain sequence comprising the sequence set forth below:

```
                                          (SEQ ID NO: 51)
DIQMTQSPSTLSASVGDRVTITCQASQSIYSNLAWYQQKPGKAPKLLIY

DASTLESGVPSRFSGSGSGTEYTLTISSLQPDDFATYYCQQGFTVSDID

NAFGGGTKVEIKR.
```

The invention also includes chimeric or humanized antibodies having binding specificity to NGF and possessing a light chain sequence comprising the sequence set forth below:

```
                                          (SEQ ID NO: 52)
DIQMTQSPSTLSASVGDRVTITCQASQSIYSNLAWYQQKPGKAPKLLIY

DASTLESGVPSRFSGSGSGTEYTLTISSLQPDDFATYYCQQGFTVSDID

NAFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC.
```

The invention further includes humanized antibodies having binding specificity to NGF and possessing a variable heavy chain sequence comprising the sequence set forth below:

```
                                          (SEQ ID NO: 53)
EVQLVESGGGLVQPGGSLRLSCAASGFTVSNYAVGWVRQAPGKGLEWVG

IIGRNGNTWYASSARGRFTISRDNSKNTLYLQMNSLRAEDTAVYYCARG

YGRSVAYYVFNIWGPGTLVTVSS.
```

The invention also includes chimeric or humanized antibodies having binding specificity to NGF and possessing a heavy chain sequence comprising the sequence set forth below:

```
                                          (SEQ ID NO: 54)
EVQLVESGGGLVQPGGSLRLSCAASGFTVSNYAVGWVRQAPGKGLEWVG

IIGRNGNTWYASSARGRFTISRDNSKNTLYLQMNSLRAEDTAVYYCARG

YGRSVAYYVFNIWGPGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKRVEPKSCDKTHTCPPCPAPELLGGPSVF

LFPPKPKDTLMISRTPEVTCVVVDVSHEDPEVKFNWYVDGVEVHNAKTK

PREEQYASTYRVVSVLTVLHQDWLNGKEYKCKVSNKALPAPIEKTISKA

KGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYT

QKSLSLSPGK.
```

The invention further contemplates antibodies comprising one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 52, and/or one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 54, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 51 or SEQ ID NO: 52. In another embodiment of the invention, antibody fragments of the invention comprise, or alternatively consist of, the polypeptide sequence of SEQ ID NO: 53 or SEQ ID NO: 54.

In a further embodiment of the invention, fragments of the antibody having binding specificity to NGF comprise, or alternatively consist of, one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 52.

In a further embodiment of the invention, fragments of the antibody having binding specificity to NGF comprise, or alternatively consist of, one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 54.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 51; the variable heavy chain region of SEQ ID NO: 53; the complementarity-determining regions (SEQ ID NO: 55; SEQ ID NO: 56; and SEQ ID NO: 57) of the variable light chain region of SEQ ID NO: 51; and the complementarity-determining regions (SEQ ID NO: 58; SEQ ID NO: 59; and SEQ ID NO: 60) of the variable heavy chain region of SEQ ID NO: 53.

In a particularly preferred embodiment of the invention, the chimeric or humanized anti-NGF antibody is Ab6, comprising, or alternatively consisting of, SEQ ID NO: 52 and SEQ ID NO: 54, and having at least one of the biological activities set forth herein.

In a further particularly preferred embodiment of the invention, antibody fragments comprise, or alternatively consist of, Fab (fragment antigen binding) fragments having binding specificity for NGF and MetMab like monovalent agents. With respect to antibody Ab6, the Fab fragment includes the variable light chain sequence of SEQ ID NO: 51 and the variable heavy chain sequence of SEQ ID NO: 53. This embodiment of the invention further contemplates additions, deletions, and variants of SEQ ID NO: 51 and/or SEQ ID NO: 53 in said Fab while retaining binding specificity for NGF.

In one embodiment of the invention described herein (infra), Fab fragments may be produced by enzymatic digestion (e.g., papain) of Ab6. In another embodiment of the invention, anti-NGF antibodies such as Ab6 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab7

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab7 polypeptides set forth below. Ab7 antibodies inhibit the interaction of NGF with TrkA and also the interaction of NGF with p75. In one embodiment, the invention includes chimeric antibodies having binding specificity to NGF and possessing a variable light chain sequence comprising the sequence set forth below:

(SEQ ID NO: 61)

ADVVMTQTPASVSQPVGGTVTIKCQASEDIYNLLAWYQQKPGQPPKLLI

YSASTLASGVPSRFKGSGSGTEYTLTISGLECADAATYYCQNNYLVTTY

GVAFGGGTEVVVKR.

The invention also includes chimeric antibodies having binding specificity to NGF and possessing a light chain sequence comprising the sequence set forth below:

(SEQ ID NO: 62)

ADVVMTQTPASVSQPVGGTVTIKCQASEDIYNLLAWYQQKPGQPPKLLI

YSASTLASGVPSRFKGSGSGTEYTLTISGLECADAATYYCQNNYLVTTY

GVAFGGGTEVVVKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC.

The invention further includes chimeric antibodies having binding specificity to NGF and possessing a variable heavy chain sequence comprising the sequence set forth below:

(SEQ ID NO: 63)

QEQLKESGGRLVTPGTPLTLTCTVSGFSLSSYAMIWVRQAPGKGLEYIG

YIDTDTSAYYASWVKGRFTISRTSTTVDLKITSPTTEDTATYFCARSYA

AYGGYPATFDPWGPGTLVTVSS.

The invention also includes chimeric antibodies having binding specificity to NGF and possessing a heavy chain sequence comprising the sequence set forth below:

(SEQ ID NO: 64)

QEQLKESGGRLVTPGTPLTLTCTVSGFSLSSYAMIWVRQAPGKGLEYIGY

IDTDTSAYYASWVKGRFTISRTSTTVDLKITSPTTEDTATYFCARSYAAY

GGYPATFDPWGPGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKSCDKTHTCPPCPAPELLGGPSVFLFPPKP

KDTLMISRTPEVTCVVVDVSHEDPEVKFNWYVDGVEVHNAKTKPREEQYA

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

-continued

LDSDGSFFLYSKLTVDKSRWQQGNVFSCSVMHEALHNHYTQKSLSLSPG

K.

The invention further contemplates antibodies comprising one or more of the polypeptide sequences of SEQ ID NO: 65; SEQ ID NO: 66; and SEQ ID NO: 67 which correspond to the complementarity-determining regions (CDRs, or hypervariable regions) of the variable light chain sequence of SEQ ID NO: 61 or the light chain sequence of SEQ ID NO: 62, and/or one or more of the polypeptide sequences of SEQ ID NO: 68; SEQ ID NO: 69; and SEQ ID NO: 70 which correspond to the complementarity-determining regions (CDRs, or hypervariable regions) of the variable heavy chain sequence of SEQ ID NO: 63 or the heavy chain sequence of SEQ ID NO: 64, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 61 or SEQ ID NO: 62. In another embodiment of the invention, antibody fragments of the invention comprise, or alternatively consist of, the polypeptide sequence of SEQ ID NO: 63 or SEQ ID NO: 64.

In a further embodiment of the invention, fragments of the antibody having binding specificity to NGF comprise, or alternatively consist of, one or more of the polypeptide sequences of SEQ ID NO: 65; SEQ ID NO: 66; and SEQ ID NO: 67 which correspond to the complementarity-determining regions (CDRs, or hypervariable regions) of the variable light chain sequence of SEQ ID NO: 61 or the light chain sequence of SEQ ID NO: 62.

In a further embodiment of the invention, fragments of the antibody having binding specificity to NGF comprise, or alternatively consist of, one or more of the polypeptide sequences of SEQ ID NO: 68; SEQ ID NO: 69; and SEQ ID NO: 70 which correspond to the complementarity-determining regions (CDRs, or hypervariable regions) of the variable heavy chain sequence of SEQ ID NO: 63 or the heavy chain sequence of SEQ ID NO: 64.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 61; the variable heavy chain region of SEQ ID NO: 63; the complementarity-determining regions (SEQ ID NO: 65; SEQ ID NO: 66; and SEQ ID NO: 67) of the variable light chain region of SEQ ID NO: 61; and the complementarity-determining regions (SEQ ID NO: 68; SEQ ID NO: 69; and SEQ ID NO: 70) of the variable heavy chain region of SEQ ID NO: 63.

In a particularly preferred embodiment of the invention, the chimeric anti-NGF antibody is Ab7, comprising, or alternatively consisting of, SEQ ID NO: 62 and SEQ ID NO: 64, and having at least one of the biological activities set forth herein.

In a further particularly preferred embodiment of the invention, antibody fragments comprise, or alternatively consist of, Fab (fragment antigen binding) fragments having binding specificity for NGF and MetMab-like monovalent agents. With respect to antibody Ab7, the Fab fragment includes the variable light chain sequence of SEQ ID NO: 61 and the variable heavy chain sequence of SEQ ID NO: 63. This embodiment of the invention further contemplates additions, deletions, and variants of SEQ ID NO: 61 and/or SEQ ID NO: 63 in said Fab while retaining binding specificity for NGF.

In one embodiment of the invention described herein (infra), Fab fragments may be produced by enzymatic digestion (e.g., papain) of Ab7. In another embodiment of the invention, anti-NGF antibodies such as Ab7 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab8

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab8 polypeptides set forth below. Ab8 antibodies inhibit the interaction of NGF with TrkA and also the interaction of NGF with p75. In one embodiment, the invention includes chimeric or humanized antibodies having binding specificity to NGF and possessing a variable light chain sequence comprising the sequence set forth below:

(SEQ ID NO: 71)
DIQMTQSPSSLSASVGDRVTITCQASEDIYNLLAWYQQKPGKVPKLLIYS

ASTLASGVPSRFSGSGSGTDYTLTISSLQPEDVATYYCQNNYLVTTYGVA

FGGGTKVEIKR.

The invention also includes chimeric or humanized antibodies having binding specificity to NGF and possessing a light chain sequence comprising the sequence set forth below:

(SEQ ID NO: 72)
DIQMTQSPSSLSASVGDRVTITCQASEDIYNLLAWYQQKPGKVPKLLIYS

ASTLASGVPSRFSGSGSGTDYTLTISSLQPEDVATYYCQNNYLVTTYGVA

FGGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC.

The invention further includes humanized antibodies having binding specificity to NGF and possessing a variable heavy chain sequence comprising the sequence set forth below:

(SEQ ID NO: 73)
QVQLVESGGGVVQPGRSLRLSCAASGFTFSSYAMIWVRQAPGKGLEYIGY

IDTDTSAYYASSVKGRFTISRDNSKNTLYLQMSSLRAEDTAVYYCARSYA

AYGGYPATFDPWGQGTLVTVSS.

The invention also includes chimeric or humanized antibodies having binding specificity to NGF and possessing a heavy chain sequence comprising the sequence set forth below:

(SEQ ID NO: 74)
QVQLVESGGGVVQPGRSLRLSCAASGFTFSSYAMIWVRQAPGKGLEYIGY

IDTDTSAYYASSVKGRFTISRDNSKNTLYLQMSSLRAEDTAVYYCARSYA

AYGGYPATFDPWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFPP

KPKDTLMISRTPEVTCVVVDVSHEDPEVKFNWYVDGVEVHNAKTKPREEQ

YASTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK.

The invention further contemplates antibodies comprising one or more of the polypeptide sequences of SEQ ID NO: 75; SEQ ID NO: 76; and SEQ JD NO: 77 which correspond to the complementarity-determining regions (CDRs, or hypervariable regions) of the variable light chain sequence of SEQ ID NO: 71 or the light chain sequence of SEQ ID NO: 72, and/or one or more of the polypeptide sequences of SEQ ID NO: 78; SEQ ID NO: 79; and SEQ ID NO: 80 which correspond to the complementarity-determining regions (CDRs, or hypervariable regions) of the variable heavy chain sequence of SEQ ID NO: 73 or the heavy chain sequence of SEQ ID NO: 74, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 71 or SEQ ID NO: 72. In another embodiment of the invention, antibody fragments of the invention comprise, or alternatively consist of, the polypeptide sequence of SEQ ID NO: 73 or SEQ ID NO: 74.

In a further embodiment of the invention, fragments of the antibody having binding specificity to NGF comprise, or alternatively consist of, one or more of the polypeptide sequences of SEQ ID NO: 75; SEQ ID NO: 76; and SEQ ID NO: 77 which correspond to the complementarity-determining regions (CDRs, or hypervariable regions) of the variable light chain sequence of SEQ ID NO: 71 or the light chain sequence of SEQ ID NO: 72.

In a further embodiment of the invention, fragments of the antibody having binding specificity to NGF comprise, or alternatively consist of, one or more of the polypeptide sequences of SEQ ID NO: 78; SEQ ID NO: 79; and SEQ ID NO: 80 which correspond to the complementarity-determining regions (CDRs, or hypervariable regions) of the variable heavy chain sequence of SEQ ID NO: 73 or the heavy chain sequence of SEQ ID NO: 74.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 71; the variable heavy chain region of SEQ ID NO: 73; the complementarity-determining regions (SEQ ID NO: 75; SEQ ID NO: 76; and SEQ ID NO: 77) of the variable light chain region of SEQ ID NO: 71; and the complementarity-determining regions (SEQ ID NO: 78; SEQ ID NO: 79; and SEQ ID NO: 80) of the variable heavy chain region of SEQ ID NO: 73.

In a particularly preferred embodiment of the invention, the chimeric or humanized anti-NGF antibody is Ab8, comprising, or alternatively consisting of, SEQ ID NO: 72 and SEQ ID NO: 74, and having at least one of the biological activities set forth herein.

In a further particularly preferred embodiment of the invention, antibody fragments comprise, or alternatively consist of, Fab (fragment antigen binding) fragments having binding specificity for NGF and MetMab-like monovalent agents. With respect to antibody Ab8, the Fab fragment includes the variable light chain sequence of SEQ ID NO: 71 and the variable heavy chain sequence of SEQ ID NO: 73. This embodiment of the invention further contemplates additions, deletions, and variants of SEQ ID NO: 71 and/or SEQ ID NO: 73 in said Fab while retaining binding specificity for NGF.

In one embodiment of the invention described herein (infra), Fab fragments may be produced by enzymatic digestion (e.g., papain) of Ab8. In another embodiment of the invention, anti-NGF antibodies such as Ab8 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab9

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab9 polypeptides set forth below. Ab9 antibodies inhibit the interaction of NGF with TrkA and also the interaction of NGF with p75. In one embodiment, the invention includes chimeric antibodies having binding specificity to NGF and possessing a variable light chain sequence comprising the sequence set forth below:

(SEQ ID NO: 81)

AYDMTQTPASVSAAVGGTVTIKCQASENIGSYLAWYQQKPGQPPELLIYR

ASTLASGVPSRFKGSGSGTQFTLTISGVECADAATYYCQQGYNSENLDNA

FGGGTEVVVKR.

The invention also includes chimeric antibodies having binding specificity to NGF and possessing a light chain sequence comprising the sequence set forth below:

(SEQ ID NO: 82)

AYDMTQTPASVSAAVGGTVTIKCQASENIGSYLAWYQQKPGQPPELLIYR

ASTLASGVPSRFKGSGSGTQFTLTISGVECADAATYYCQQGYNSENLDNA

FGGGTEVVVKRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC.

The invention further includes chimeric antibodies having binding specificity to NGF and possessing a variable heavy chain sequence comprising the sequence set forth below:

(SEQ ID NO: 83)

QSVEESGGRLVTPGTPLTLTCTVSGIDLSMYSMGWVRQAPGKGLEYIGWI

SYGGTAYYASWAKGRFTISKTSTTVELKITSPTIEDTATYFCARETPVNY

YLDIWGQGTLVTVSS.

The invention also includes chimeric antibodies having binding specificity to NGF and possessing a heavy chain sequence comprising the sequence set forth below:

(SEQ ID NO: 84)

QSVEESGGRLVTPGTPLTLTCTVSGIDLSMYSMGWVRQAPGKGLEYIGWI

SYGGTAYYASWAKGRFTISKTSTTVELKITSPTIEDTATYFCARETPVNY

YLDIWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKRVEPKSCDKTHTCPPCPAPELLGGPSVFLFPPKPKDTLM

ISRTPEVTCVVVDVSHEDPEVKFNWYVDGVEVHNAKTKPREEQYASTYRV

VSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDG

SFFLYSKLTVDKSRWQQGNVFSCSVMHEALHNHYTQKSLSLSPGK.

The invention further contemplates antibodies comprising one or more of the polypeptide sequences of SEQ ID NO: 85; SEQ ID NO: 86; and SEQ ID NO: 87 which correspond to the complementarity-determining regions (CDRs, or hypervariable regions) of the variable light chain sequence of SEQ ID NO: 81 or the light chain sequence of SEQ ID NO: 82, and/or one or more of the polypeptide sequences of SEQ ID NO: 88; SEQ ID NO: 89; and SEQ ID NO: 90 which correspond to the complementarity-determining regions (CDRs, or hypervariable regions) of the variable heavy chain sequence of SEQ ID NO: 83 or the heavy chain sequence of SEQ ID NO: 84, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 81 or SEQ ID NO: 82. In another embodiment of the invention, antibody fragments of the invention comprise, or alternatively consist of, the polypeptide sequence of SEQ ID NO: 83 or SEQ ID NO: 84.

In a further embodiment of the invention, fragments of the antibody having binding specificity to NGF comprise, or alternatively consist of, one or more of the polypeptide sequences of SEQ ID NO: 85; SEQ ID NO: 86; and SEQ ID NO: 87 which correspond to the complementarity-determining regions (CDRs, or hypervariable regions) of the variable light chain sequence of SEQ ID NO: 81 or the light chain sequence of SEQ ID NO: 82.

In a further embodiment of the invention, fragments of the antibody having binding specificity to NGF comprise, or alternatively consist of, one or more of the polypeptide sequences of SEQ ID NO: 88; SEQ ID NO: 89; and SEQ ID NO: 90 which correspond to the complementarity-determining regions (CDRs, or hypervariable regions) of the variable heavy chain sequence of SEQ ID NO: 83 or the heavy chain sequence of SEQ ID NO: 84.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 81; the variable heavy chain region of SEQ ID NO: 83; the complementarity-determining regions (SEQ ID NO: 85; SEQ ID NO: 86; and SEQ ID NO: 87) of the variable light chain region of SEQ ID NO: 81; and the complementarity-determining regions (SEQ ID NO: 88; SEQ ID NO: 89; and SEQ ID NO: 90) of the variable heavy chain region of SEQ ID NO: 83.

In a particularly preferred embodiment of the invention, the chimeric anti-NGF antibody is Ab9, comprising, or alternatively consisting of, SEQ ID NO: 82 and SEQ ID NO: 84, and having at least one of the biological activities set forth herein.

In a further particularly preferred embodiment of the invention, antibody fragments comprise, or alternatively consist of, Fab (fragment antigen binding) fragments having binding specificity for NGF and MetMab-like monovalent agents. With respect to antibody Ab9, the Fab fragment includes the variable light chain sequence of SEQ ID NO: 81 and the variable heavy chain sequence of SEQ ID NO: 83. This embodiment of the invention further contemplates additions, deletions, and variants of SEQ ID NO: 81 and/or SEQ ID NO: 83 in said Fab while retaining binding specificity for NGF.

In one embodiment of the invention described herein (infra), Fab fragments may be produced by enzymatic digestion (e.g., papain) of Ab9. In another embodiment of the invention, anti-NGF antibodies such as Ab9 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab10

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab10 polypeptides set forth below. Ab10 antibodies inhibit the interaction of NGF with TrkA and also the interaction of NGF with p75. In one embodiment, the invention includes chimeric or humanized antibodies having binding specificity to NGF and possessing a variable light chain sequence comprising the sequence set forth below:

(SEQ ID NO: 91)
AYDMTQSPSSLSASVGDRVTITCQASENIGSYLAWYQQKPGKVPKLLIYR

ASTLASGVPSRFSGSGSGTDFTLTISSLQPEDVATYYCQQGYNSENLDNA

FGGGTKVEIKR.

The invention also includes chimeric or humanized antibodies having binding specificity to NGF and possessing a light chain sequence comprising the sequence set forth below:

(SEQ ID NO: 92)
AYDMTQSPSSLSASVGDRVTITCQASENIGSYLAWYQQKPGKVPKLLIYR

ASTLASGVPSRFSGSGSGTDFTLTISSLQPEDVATYYCQQGYNSENLDNA

FGGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC.

The invention further includes chimeric or humanized antibodies having binding specificity to NGF and possessing a variable heavy chain sequence comprising the sequence set forth below:

(SEQ ID NO: 93)
QVQLVESGGGVVQPGRSLRLSCAASGFTFSMYSMGWVRQAPGKGLEYIGW

ISYGGTAYYASSAKGRFTISRDNSKNTLYLQMSSLRAEDTAVYYCARETP

VNYYLDIWGQGTLVTVSS.

The invention also includes chimeric or humanized antibodies having binding specificity to NGF and possessing a heavy chain sequence comprising the sequence set forth below:

(SEQ ID NO: 94)
QVQLVESGGGVVQPGRSLRLSCAASGFTFSMYSMGWVRQAPGKGLEYIGW

ISYGGTAYYASSAKGRFTISRDNSKNTLYLQMSSLRAEDTAVYYCARETP

VNYYLDIWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK.

The invention further contemplates antibodies comprising one or more of the polypeptide sequences of SEQ ID NO: 95; SEQ ID NO: 96; and SEQ ID NO: 97 which correspond to the complementarity-determining regions (CDRs, or hypervariable regions) of the variable light chain sequence of SEQ ID NO: 91 or the light chain sequence of SEQ ID NO: 92, and/or one or more of the polypeptide sequences of SEQ ID NO: 98; SEQ ID NO: 99; and SEQ ID NO: 100 which correspond to the complementarity-determining regions (CDRs, or hypervariable regions) of the variable heavy chain sequence of SEQ ID NO: 93 or the heavy chain sequence of SEQ ID NO: 94, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 91 or SEQ ID NO: 92. In another embodiment of the invention, antibody fragments of the invention comprise, or alternatively consist of, the polypeptide sequence of SEQ ID NO: 93 or SEQ ID NO: 94.

In a further embodiment of the invention, fragments of the antibody having binding specificity to NGF comprise, or alternatively consist of, one or more of the polypeptide sequences of SEQ ID NO: 95; SEQ ID NO: 96; and SEQ ID NO: 97 which correspond to the complementarity-determining regions (CDRs, or hypervariable regions) of the variable light chain sequence of SEQ ID NO: 91 or the light chain sequence of SEQ ID NO: 92.

In a further embodiment of the invention, fragments of the antibody having binding specificity to NGF comprise, or alternatively consist of, one or more of the polypeptide sequences of SEQ ID NO: 98; SEQ ID NO: 99; and SEQ ID NO: 100 which correspond to the complementarity-determining regions (CDRs, or hypervariable regions) of the variable heavy chain sequence of SEQ ID NO: 93 or the heavy chain sequence of SEQ ID NO: 94.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 91; the variable heavy chain region of SEQ ID NO: 93; the complementarity-determining regions (SEQ ID NO: 95; SEQ ID NO: 96; and SEQ ID NO: 97) of the variable light chain region of SEQ ID NO: 91; and the complementarity-determining regions (SEQ ID NO: 98; SEQ ID NO: 99; and SEQ ID NO: 100) of the variable heavy chain region of SEQ ID NO: 93.

In a particularly preferred embodiment of the invention, the chimeric or humanized anti-NGF antibody is Ab10, comprising, or alternatively consisting of, SEQ ID NO: 92 and SEQ ID NO: 94, and having at least one of the biological activities set forth herein.

In a further particularly preferred embodiment of the invention, antibody fragments comprise, or alternatively consist of, Fab (fragment antigen binding) fragments having binding specificity for NGF or MetMab like monovalent agents. With respect to antibody Ab10, the Fab fragment includes the variable light chain sequence of SEQ ID NO: 91 and the variable heavy chain sequence of SEQ ID NO: 93. This embodiment of the invention further contemplates additions, deletions, and variants of SEQ ID NO: 91 and/or SEQ ID NO: 93 in said Fab while retaining binding specificity for NGF.

In one embodiment of the invention described herein (infra), Fab fragments may be produced by enzymatic digestion (e.g., papain) of Ab10. In another embodiment of the invention, anti-NGF antibodies such as Ab10 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab11

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab11 polypeptides set forth below. Ab11 antibodies inhibit the interaction of NGF with TrkA and also the interaction of NGF with p75. In one embodiment, the invention includes chimeric antibodies having binding specificity to NGF and possessing a variable light chain sequence comprising the sequence set forth below:

(SEQ ID NO: 101)
AFELTQTPSSVEAAVGGTVTIKCQASQNIVTNLAWYQQKPGQPPKLLIYG
ASTLASGVSSRFKGSGSGTQFTLTISDLECADAATYFCQSYDGFNSAGFG
GGTEVVVKR.

The invention also includes chimeric antibodies having binding specificity to NGF and possessing a light chain sequence comprising the sequence set forth below:

(SEQ ID NO: 102)
AFELTQTPSSVEAAVGGTVTIKCQASQNIVTNLAWYQQKPGQPPKLLIYG
ASTLASGVSSRFKGSGSGTQFTLTISDLECADAATYFCQSYDGFNSAGFG
GGTEVVVKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC.

The invention further includes chimeric antibodies having binding specificity to NGF and possessing a variable heavy chain sequence comprising the sequence set forth below:

(SEQ ID NO: 103)
QSLEESGGRLVTPGTPLTLTCTASGFSLSGYDMSWVRQAPGKGLEYIGLI
SYDGNTYYATWAKGRFTISKTSTTVDLKITSPTTEDTATYFCARSLYAGP
NAGIGPFNIWGQGTLVTVSS.

The invention also includes chimeric antibodies having binding specificity to NGF and possessing a heavy chain sequence comprising the sequence set forth below:

(SEQ ID NO: 104)
QSLEESGGRLVTPGTPLTLTCTASGFSLSGYDMSWVRQAPGKGLEYIGLI
SYDGNTYYATWAKGRFTISKTSTTVDLKITSPTTEDTATYFCARSLYAGP
NAGIGPFNIWGQGTLVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKRVEPKSCDKTHTCPPCPAPELLGGPSVFLFPPKP
KDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLS
PGK.

The invention further contemplates antibodies comprising one or more of the polypeptide sequences of SEQ ID NO: 105; SEQ ID NO: 106; and SEQ ID NO: 107 which correspond to the complementarity-determining regions (CDRs, or hypervariable regions) of the variable light chain sequence of SEQ ID NO: 101 or the light chain sequence of SEQ ID NO: 102, and/or one or more of the polypeptide sequences of SEQ ID NO: 108; SEQ ID NO: 109; and SEQ ID NO: 110 which correspond to the complementarity-determining regions (CDRs, or hypervariable regions) of the variable heavy chain sequence of SEQ ID NO: 103 or the heavy chain sequence of SEQ ID NO: 104, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 101 or SEQ ID NO: 102. In another embodiment of the invention, antibody fragments of the invention comprise, or alternatively consist of, the polypeptide sequence of SEQ ID NO: 103 or SEQ ID NO: 104.

In a further embodiment of the invention, fragments of the antibody having binding specificity to NGF comprise, or alternatively consist of, one or more of the polypeptide sequences of SEQ ID NO: 105; SEQ ID NO: 106; and SEQ ID NO: 107 which correspond to the complementarity-determining regions (CDRs, or hypervariable regions) of the variable light chain sequence of SEQ ID NO: 101 or the light chain sequence of SEQ ID NO: 102.

In a further embodiment of the invention, fragments of the antibody having binding specificity to NGF comprise, or alternatively consist of, one or more of the polypeptide sequences of SEQ ID NO: 108; SEQ ID NO: 109; and SEQ ID NO: 110 which correspond to the complementarity-determining regions (CDRs, or hypervariable regions) of the variable heavy chain sequence of SEQ ID NO: 103 or the heavy chain sequence of SEQ ID NO: 104.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 101; the variable heavy chain region of SEQ ID NO: 103; the complementarity-determining regions (SEQ ID NO: 105; SEQ ID NO: 106; and SEQ ID NO: 107) of the variable light chain region of SEQ ID NO: 101; and the complementarity-determining regions (SEQ ID NO: 108; SEQ ID NO: 109; and SEQ ID NO: 110) of the variable heavy chain region of SEQ ID NO: 103.

In a particularly preferred embodiment of the invention, the chimeric anti-NGF antibody is Ab11, comprising, or alternatively consisting of, SEQ ID NO: 102 and SEQ ID NO: 104, and having at least one of the biological activities set forth herein.

In a further particularly preferred embodiment of the invention, antibody fragments comprise, or alternatively consist of, Fab (fragment antigen binding) fragments having binding specificity for NGF or MetMab like monovalent agents. With respect to antibody Ab11, the Fab fragment includes the variable light chain sequence of SEQ ID NO: 101 and the variable heavy chain sequence of SEQ ID NO: 103. This embodiment of the invention further contemplates additions, deletions, and variants of SEQ ID NO: 101 and/or SEQ ID NO: 103 in said Fab while retaining binding specificity for NGF.

In one embodiment of the invention described herein (infra), Fab fragments may be produced by enzymatic digestion (e.g., papain) of Ab11. In another embodiment of the invention, anti-NGF antibodies such as Ab11 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab12

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab12 polypeptides set forth below. Ab12 antibodies inhibit the interaction of NGF with TrkA and also the interaction of NGF with p75. In one embodiment, the invention includes chimeric or humanized antibodies having binding specificity to NGF and possessing a variable light chain sequence comprising the sequence set forth below:

(SEQ ID NO: 111)
AFQMTQSPSSLSASVGDRVTITCQASQNIVTNLAWYQQKPGKVPKLLIYG
ASTLASGVPSRFSGSGSGTDFTLTISSLQPEDVATYYCQSYDGFNSAGFG
GGTKVEIKR.

The invention also includes chimeric or humanized antibodies having binding specificity to NGF and possessing a light chain sequence comprising the sequence set forth below:

(SEQ ID NO: 112)
AFQMTQSPSSLSASVGDRVTITCQASQNIVTNLAWYQQKPGKVPKLLIYG
ASTLASGVPSRFSGSGSGTDFTLTISSLQPEDVATYYCQSYDGFNSAGFG
GGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC.

The invention further includes chimeric or humanized antibodies having binding specificity to NGF and possessing a variable heavy chain sequence comprising the sequence set forth below:

(SEQ ID NO: 113)
QVQLVESGGGVVQPGRSLRLSCAASGFSLSGYDMSWVRQAPGKGLEWVGL
ISYDGNTYYATSAKGRFTISRDNSKNTLYLQMSSLRAEDTAVYYCARSLY
AGPNAGIGPFNIWGQGTLVTVSS.

The invention also includes chimeric or humanized antibodies having binding specificity to NGF and possessing a heavy chain sequence comprising the sequence set forth below:

(SEQ ID NO: 114)
QVQLVESGGGVVQPGRSLRLSCAASGFSLSGYDMSWVRQAPGKGLEWVGL
ISYDGNTYYATSAKGRFTISRDNSKNTLYLQMSSLRAEDTAVYYCARSLY
AGPNAGIGPFNIWGQGTLVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREE
QYASTYRVVSVLTVLHQDWLNGKEYKCKVSNKALPAPIEKTISKAKGQPR

-continued

```
EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PGK.
```

The invention further contemplates antibodies comprising one or more of the polypeptide sequences of SEQ ID NO: 115; SEQ ID NO: 116; and SEQ ID NO: 117 which correspond to the complementarity-determining regions (CDRs, or hypervariable regions) of the variable light chain sequence of SEQ ID NO: 111 or the light chain sequence of SEQ ID NO: 112, and/or one or more of the polypeptide sequences of SEQ ID NO: 118; SEQ ID NO: 119; and SEQ ID NO: 120 which correspond to the complementarity-determining regions (CDRs, or hypervariable regions) of the variable heavy chain sequence of SEQ ID NO: 113 or the heavy chain sequence of SEQ ID NO: 114, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 111 or SEQ ID NO: 112. In another embodiment of the invention, antibody fragments of the invention comprise, or alternatively consist of, the polypeptide sequence of SEQ ID NO: 113 or SEQ ID NO: 114.

In a further embodiment of the invention, fragments of the antibody having binding specificity to NGF comprise, or alternatively consist of, one or more of the polypeptide sequences of SEQ ID NO: 115; SEQ ID NO: 116; and SEQ ID NO: 117 which correspond to the complementarity-determining regions (CDRs, or hypervariable regions) of the variable light chain sequence of SEQ ID NO: 111 or the light chain sequence of SEQ ID NO: 112.

In a further embodiment of the invention, fragments of the antibody having binding specificity to NGF comprise, or alternatively consist of, one or more of the polypeptide sequences of SEQ ID NO: 118; SEQ ID NO: 119; and SEQ ID NO: 120 which correspond to the complementarity-determining regions (CDRs, or hypervariable regions) of the variable heavy chain sequence of SEQ ID NO: 113 or the heavy chain sequence of SEQ ID NO: 114.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 111; the variable heavy chain region of SEQ ID NO: 113; the complementarity-determining regions (SEQ ID NO: 115; SEQ ID NO: 116; and SEQ ID NO: 117) of the variable light chain region of SEQ ID NO: 111; and the complementarity-determining regions (SEQ ID NO: 118; SEQ ID NO: 119; and SEQ ID NO: 120) of the variable heavy chain region of SEQ ID NO: 113.

In a particularly preferred embodiment of the invention, the chimeric or humanized anti-NGF antibody is Ab12, comprising, or alternatively consisting of, SEQ ID NO: 112 and SEQ ID NO: 114, and having at least one of the biological activities set forth herein.

In a further particularly preferred embodiment of the invention, antibody fragments comprise, or alternatively consist of, Fab (fragment antigen binding) fragments having binding specificity for NGF and MetMab like monovalent agents. With respect to antibody Ab12, the Fab fragment includes the variable light chain sequence of SEQ ID NO: 111 and the variable heavy chain sequence of SEQ ID NO: 113. This embodiment of the invention further contemplates additions, deletions, and variants of SEQ ID NO: 111 and/or SEQ ID NO: 113 in said Fab while retaining binding specificity for NGF.

In one embodiment of the invention described herein (infra), Fab fragments may be produced by enzymatic digestion (e.g., papain) of Ab12. In another embodiment of the invention, anti-NGF antibodies such as Ab12 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab13

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab13 polypeptides set forth below. Ab13 antibodies inhibit the interaction of NGF with TrkA and also the interaction of NGF with p75. In one embodiment, the invention includes chimeric antibodies having binding specificity to NGF and possessing a variable light chain sequence comprising the sequence set forth below:

```
                                           (SEQ ID NO: 121)
AAVLTQTPSPVSAAVGGTVSISCQSSQNVYKNNYLSWYQQKPGQPPKLLI

YKASTLASGVPSRFKGGGSGTDFTLTISDVQCDAAATYYCAGGYTSSSDN

AFGGGTEVVVKR.
```

The invention also includes chimeric antibodies having binding specificity to NGF and possessing a light chain sequence comprising the sequence set forth below:

```
                                           (SEQ ID NO: 122)
AAVLTQTPSPVSAAVGGTVSISCQSSQNVYKNNYLSWYQQKPGQPPKLLI

YKASTLASGVPSRFKGGGSGTDFTLTISDVQCDAAATYYCAGGYTSSSDN

AFGGGTEVVVKRTVAAPSVFIFPPSDEQLKSGTASVVCLLNNFYPREAKV
```

-continued

QWKVDNALQSGNSQESVTEQDSKDSTYSLSSTLTLSKADYEKHKVYACEV

THQGLSSPVTKSFNRGEC.

The invention further includes chimeric antibodies having binding specificity to NGF and possessing a variable heavy chain sequence comprising the sequence set forth below:

(SEQ ID NO: 123)
QSVEASGGRLVTPGTPLTLTCTASGFSLSTYWMSWVRQAPGKGLEWIGDI

YFSNEETNYASWAKGRFTISKTSTTVDLNVISPTTEDTATYFCARGSPDV

DIGIDMWGPGTLVTVSS.

The invention also includes chimeric antibodies having binding specificity to NGF and possessing a heavy chain sequence comprising the sequence set forth below:

(SEQ ID NO: 124)
QSVEASGGRLVTPGTPLTLTCTASGFSLSTYWMSWVRQAPGKGLEWIGDI

YFSNEETNYASWAKGRFTISKTSTTVDLNVISPTTEDTATYFCARGSPDV

DIGIDMWGPGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKRVEPKSCDKTHTCPPCPAPELLGGPSVFLFPPKPKDT

LMISRTPEVTCVVVDVSHEDPEVKFNWYVDGVEVHNAKTKPREEQYASTY

RVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK.

The invention further contemplates antibodies comprising one or more of the polypeptide sequences of SEQ ID NO: 125; SEQ ID NO: 126; and SEQ ID NO: 127 which correspond to the complementarity-determining regions (CDRs, or hypervariable regions) of the variable light chain sequence of SEQ ID NO: 121 or the light chain sequence of SEQ ID NO: 122, and/or one or more of the polypeptide sequences of SEQ ID NO: 128; SEQ ID NO: 129; and SEQ ID NO: 130 which correspond to the complementarity-determining regions (CDRs, or hypervariable regions) of the variable heavy chain sequence of SEQ ID NO: 123 or the heavy chain sequence of SEQ ID NO: 124, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 121 or SEQ ID NO: 122. In another embodiment of the invention, antibody fragments of the invention comprise, or alternatively consist of, the polypeptide sequence of SEQ ID NO: 123 or SEQ ID NO: 124.

In a further embodiment of the invention, fragments of the antibody having binding specificity to NGF comprise, or alternatively consist of, one or more of the polypeptide sequences of SEQ ID NO: 125; SEQ ID NO: 126; and SEQ ID NO: 127 which correspond to the complementarity-determining regions (CDRs, or hypervariable regions) of the variable light chain sequence of SEQ ID NO: 121 or the light chain sequence of SEQ ID NO: 122.

In a further embodiment of the invention, fragments of the antibody having binding specificity to NGF comprise, or alternatively consist of, one or more of the polypeptide sequences of SEQ ID NO: 128; SEQ ID NO: 129; and SEQ ID NO: 130 which correspond to the complementarity-determining regions (CDRs, or hypervariable regions) of the variable heavy chain sequence of SEQ ID NO: 123 or the heavy chain sequence of SEQ ID NO: 124.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 121; the variable heavy chain region of SEQ ID NO: 123; the complementarity-determining regions (SEQ ID NO: 125; SEQ ID NO: 126; and SEQ ID NO: 127) of the variable light chain region of SEQ ID NO: 121; and the complementarity-determining regions (SEQ ID NO: 128; SEQ ID NO: 129; and SEQ ID NO: 130) of the variable heavy chain region of SEQ ID NO: 123.

In a particularly preferred embodiment of the invention, the chimeric anti-NGF antibody is Ab13, comprising, or alternatively consisting of, SEQ ID NO: 122 and SEQ ID NO: 124, and having at least one of the biological activities set forth herein.

In a further particularly preferred embodiment of the invention, antibody fragments comprise, or alternatively consist of, Fab (fragment antigen binding) fragments having binding specificity for NGF or MetMab-like monovalent agents. With respect to antibody Ab13, the Fab fragment includes the variable light chain sequence of SEQ ID NO: 121 and the variable heavy chain sequence of SEQ ID NO: 123. This embodiment of the invention further contemplates additions, deletions, and variants of SEQ ID NO: 121 and/or SEQ ID NO: 123 in said Fab while retaining binding specificity for NGF.

In one embodiment of the invention described herein (infra), Fab fragments may be produced by enzymatic digestion (e.g., papain) of Ab13. In another embodiment of the invention, anti-NGF antibodies such as Ab13 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab14

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab14 polypeptides set forth below. Ab14 antibodies inhibit the interaction of NGF with TrkA and also the interaction of NGF with p75. In one embodiment, the invention includes humanized antibodies having binding specificity to NGF and possessing a variable light chain sequence comprising the sequence set forth below:

```
                                            (SEQ ID NO: 131)
DIQMTQSPSSLSASVGDRVTITCQSSQNVYKNNYLSWYQQKPGKVPKLLI

YKASTLASGVPSRFSGSGSGTDFTLTISSLQPEDVATYYCAGGYTSSSDN

AFGGGTKVEIKR.
```

The invention also includes chimeric or humanized antibodies having binding specificity to NGF and possessing a light chain sequence comprising the sequence set forth below:

```
                                            (SEQ ID NO: 132)
DIQMTQSPSSLSASVGDRVTITCQSSQNVYKNNYLSWYQQKPGKVPKLLI

YKASTLASGVPSRFSGSGSGTDFTLTISSLQPEDVATYYCAGGYTSSSDN

AFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

The invention further includes chimeric or humanized antibodies having binding specificity to NGF and possessing a variable heavy chain sequence comprising the sequence set forth below:

```
                                            (SEQ ID NO: 133)
EVQLVESGGGLVQPGGSLRLSCAASGFTVSTYWMSWVRQAPGKGLEWVGD

IYFSNEETNYASSAKGRFTISRDNSKNTLYLQMNSLRAEDTAVYYCARGS

PDVDIGIDMWGPGTLVTVSS.
```

The invention also includes chimeric or humanized antibodies having binding specificity to NGF and possessing a heavy chain sequence comprising the sequence set forth below:

```
                                            (SEQ ID NO: 134)
EVQLVESGGGLVQPGGSLRLSCAASGFTVSTYWMSWVRQAPGKGLEWVGD

IYFSNEETNYASSAKGRFTISRDNSKNTLYLQMNSLRAEDTAVYYCARGS

PDVDIGIDMWGPGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKSCDKTHTCPPCPAPELLGGPSVFLFPPKP

KDTLMISRTPEVTCVVVDVSHEDPEVKFNWYVDGVEVHNAKTKPREEQYA

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLS

PGK.
```

The invention further contemplates antibodies comprising one or more of the polypeptide sequences of SEQ ID NO: 135; SEQ ID NO: 136; and SEQ ID NO: 137 which correspond to the complementarity-determining regions (CDRs, or hypervariable regions) of the variable light chain sequence of SEQ ID NO: 131 or the light chain sequence of SEQ ID NO: 132, and/or one or more of the polypeptide sequences of SEQ ID NO: 138; SEQ ID NO: 139; and SEQ ID NO: 140 which correspond to the complementarity-determining regions (CDRs, or hypervariable regions) of the variable heavy chain sequence of SEQ ID NO: 133 or the heavy chain sequence of SEQ ID NO: 134, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 131 or SEQ ID NO: 132. In another embodiment of the invention, antibody fragments of the invention comprise, or alternatively consist of, the polypeptide sequence of SEQ ID NO: 133 or SEQ ID NO: 134.

In a further embodiment of the invention, fragments of the antibody having binding specificity to NGF comprise, or alternatively consist of, one or more of the polypeptide sequences of SEQ ID NO: 135; SEQ ID NO: 136; and SEQ ID NO: 137 which correspond to the complementarity-determining regions (CDRs, or hypervariable regions) of the variable light chain sequence of SEQ ID NO: 131 or the light chain sequence of SEQ ID NO: 132.

In a further embodiment of the invention, fragments of the antibody having binding specificity to NGF comprise, or alternatively consist of, one or more of the polypeptide sequences of SEQ ID NO: 138; SEQ ID NO: 139; and SEQ ID NO: 140 which correspond to the complementarity-determining regions (CDRs, or hypervariable regions) of the variable heavy chain sequence of SEQ ID NO: 133 or the heavy chain sequence of SEQ ID NO: 134.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 131; the variable heavy chain region of SEQ ID NO: 133; the complementarity-determining regions (SEQ ID NO: 135; SEQ ID NO: 136; and SEQ ID NO: 137) of the variable light chain region of SEQ ID NO: 131; and the complementarity-determining regions (SEQ ID NO: 138; SEQ ID NO: 139; and SEQ ID NO: 140) of the variable heavy chain region of SEQ ID NO: 133.

In a particularly preferred embodiment of the invention, the chimeric or humanized anti-NGF antibody is Ab14, comprising, or alternatively consisting of, SEQ ID NO: 132 and SEQ ID NO: 134, and having at least one of the biological activities set forth herein.

In a further particularly preferred embodiment of the invention, antibody fragments comprise, or alternatively consist of, Fab (fragment antigen binding) fragments having binding specificity for NGF and MetMab-like monovalent agents. With respect to antibody Ab14, the Fab fragment includes the variable light chain sequence of SEQ ID NO: 131 and the variable heavy chain sequence of SEQ ID NO: 133. This embodiment of the invention further contemplates additions, deletions, and variants of SEQ ID NO: 131 and/or SEQ ID NO: 133 in said Fab while retaining binding specificity for NGF.

In one embodiment of the invention described herein (infra), Fab fragments may be produced by enzymatic digestion (e.g., papain) of Ab14. In another embodiment of the invention, anti-NGF antibodies such as Ab14 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab15

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab15 polypeptides set forth below. Ab15 antibodies inhibit the interaction of NGF with TrkA and do not appreciably affect the interaction of NGF with p75. In one embodiment, the invention includes chimeric antibodies having binding specificity to NGF and possessing a variable light chain sequence comprising the sequence set forth below:

(SEQ ID NO: 141)
AAVLTQTPSPVSAAVGDTVTIKCQSSQSVYKNNYLSWYQQKPGQPPKLLI

YDASNLPSGVPSRFSGSGSGTQFTLTISGVQCDDAATYYCLGDYDDDTDN

GFGGGTEVVVKR.

The invention also includes chimeric antibodies having binding specificity to NGF and possessing a light chain sequence comprising the sequence set forth below:

(SEQ ID NO: 142)
AAVLTQTPSPVSAAVGDTVTIKCQSSQSVYKNNYLSWYQQKPGQPPKLLI

YDASNLPSGVPSRFSGSGSGTQFTLTISGVQCDDAATYYCLGDYDDDTDN

GFGGGTEVVVKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.

The invention further includes chimeric antibodies having binding specificity to NGF and possessing a variable heavy chain sequence comprising the sequence set forth below:

(SEQ ID NO: 143)
QSVEESGGRLVTPGTPLTLTCTVSGIDLSSYAMIWVRQAPGKGLEYIGII

WSGGTYYATWAKGRFTISKTSTTVDLQITSPTTEDAATYFCAAGGGSIYD

VWGPGTLVTVSS.

The invention also includes chimeric antibodies having binding specificity to NGF and possessing a heavy chain sequence comprising the sequence set forth below:

(SEQ ID NO: 144)
QSVEESGGRLVTPGTPLTLTCTVSGIDLSSYAMIWVRQAPGKGLEYIGII

WSGGTYYATWAKGRFTISKTSTTVDLQITSPTTEDAATYFCAAGGGSIYD

VWGPGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHK

PSNTKVDKRVEPKSCDKTHTCPPCPAPELLGGPSVFLFPPKPKDTLMISR

TPEVTCVVVDVSHEDPEVKFNWYVDGVEVHNAKTKPREEQYASTYRVVSV

LTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFF

LYSKLTVDKSRWQQGNVFSCSVMHEALHNHYTQKSLSLSPGK.

The invention further contemplates antibodies comprising one or more of the polypeptide sequences of SEQ ID NO: 145; SEQ ID NO: 146; and SEQ ID NO: 147 which correspond to the complementarity-determining regions (CDRs, or hypervariable regions) of the variable light chain sequence of SEQ ID NO: 141 or the light chain sequence of SEQ ID NO: 142, and/or one or more of the polypeptide sequences of SEQ ID NO: 148; SEQ ID NO: 149; and SEQ ID NO: 150 which correspond to the complementarity-determining regions (CDRs, or hypervariable regions) of the variable heavy chain sequence of SEQ ID NO: 143 or the heavy chain sequence of SEQ ID NO: 144, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 141 or SEQ ID NO: 142. In another embodiment of the invention, antibody fragments of the invention comprise, or alternatively consist of, the polypeptide sequence of SEQ ID NO: 143 or SEQ ID NO: 144.

In a further embodiment of the invention, fragments of the antibody having binding specificity to NGF comprise, or alternatively consist of, one or more of the polypeptide sequences of SEQ ID NO: 145; SEQ ID NO: 146; and SEQ ID NO: 147 which correspond to the complementarity-determining regions (CDRs, or hypervariable regions) of the variable light chain sequence of SEQ ID NO: 141 or the light chain sequence of SEQ ID NO: 142.

In a further embodiment of the invention, fragments of the antibody having binding specificity to NGF comprise, or alternatively consist of, one or more of the polypeptide sequences of SEQ ID NO: 148; SEQ ID NO: 149; and SEQ ID NO: 150 which correspond to the complementarity-determining regions (CDRs, or hypervariable regions) of the variable heavy chain sequence of SEQ ID NO: 143 or the heavy chain sequence of SEQ ID NO: 144.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 141; the variable heavy chain region of SEQ ID NO: 143; the complementarity-determining regions (SEQ ID NO: 145; SEQ ID NO: 146; and SEQ ID NO: 147) of the variable light chain region of SEQ ID NO: 141; and the complementarity-determining regions (SEQ ID NO: 148; SEQ ID NO: 149; and SEQ ID NO: 150) of the variable heavy chain region of SEQ ID NO: 143.

In a particularly preferred embodiment of the invention, the chimeric anti-NGF antibody is Ab15, comprising, or alternatively consisting of, SEQ ID NO: 142 and SEQ ID NO: 144, and having at least one of the biological activities set forth herein.

In a further particularly preferred embodiment of the invention, antibody fragments comprise, or alternatively consist of, Fab (fragment antigen binding) fragments having binding specificity for NGF and MetMab-like monovalent agents. With respect to antibody Ab15, the Fab fragment includes the variable light chain sequence of SEQ ID NO: 141 and the variable heavy chain sequence of SEQ ID NO: 143. This embodiment of the invention further contemplates additions, deletions, and variants of SEQ ID NO: 141 and/or SEQ ID NO: 143 in said Fab while retaining binding specificity for NGF.

In one embodiment of the invention described herein (infra), Fab fragments may be produced by enzymatic digestion (e.g., papain) of Ab15. In another embodiment of the invention, anti-NGF antibodies such as Ab15 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab16

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab16 polypeptides set forth below. Ab16 antibodies inhibit the interaction of NGF with TrkA and do not appreciably affect the interaction of NGF with p75. In one embodiment, the invention includes chimeric or humanized antibodies having binding specificity to NGF and possessing a variable light chain sequence comprising the sequence set forth below:

(SEQ ID NO: 151)
ALVMTQTPSSTSEPVGGTVTINCQASQNIGNDLSWYQQKPGQPPELLIYS
TSKLATGVPKRFSGSRSGTQFTLTISDLECDDAATYYCLGVYSYISDDGN
AFGGGTEVVVKR.

The invention also includes chimeric or humanized antibodies having binding specificity to NGF and possessing a light chain sequence comprising the sequence set forth below:

(SEQ ID NO: 152)
ALVMTQTPSSTSEPVGGTVTINCQASQNIGNDLSWYQQKPGQPPELLIYS
TSKLATGVPKRFSGSRSGTQFTLTISDLECDDAATYYCLGVYSYISDDGN
AFGGGTEVVVKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC.

The invention further includes chimeric or humanized antibodies having binding specificity to NGF and possessing a variable heavy chain sequence comprising the sequence set forth below:

(SEQ ID NO: 153)
QSVEEFGGRLVTPGTPLTLTCTVSGFSLNNYAMTWVRQAPGKGLEWIGII
GSIGTTYYASWAKGRFFISKTSTTVDLKIISPTTEDTATYFCARDAGVTV
DGYGYYFNIWGPGTLVTVSS.

The invention also includes chimeric or humanized antibodies having binding specificity to NGF and possessing a heavy chain sequence comprising the sequence set forth below:

(SEQ ID NO: 154)
QSVEEFGGRLVTPGTPLTLTCTVSGFSLNNYAMTWVRQAPGKGLEWIGII
GSIGTTYYASWAKGRFFISKTSTTVDLKIISPTTEDTATYFCARDAGVTV
DGYGYYFNIWGPGTLVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKRVEPKSCDKTHTCPPCPAPELLGGPSVFLFPPKP
KDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPG
K.

The invention further contemplates antibodies comprising one or more of the polypeptide sequences of SEQ ID NO: 155; SEQ ID NO: 156; and SEQ ID NO: 157 which correspond to the complementarity-determining regions (CDRs, or hypervariable regions) of the variable light chain sequence of SEQ ID NO: 151 or the light chain sequence of SEQ ID NO: 152, and/or one or more of the polypeptide sequences of SEQ ID NO: 158; SEQ ID NO: 159; and SEQ ID NO: 160 which correspond to the complementarity-determining regions (CDRs, or hypervariable regions) of the variable heavy chain sequence of SEQ ID NO: 153 or the heavy chain sequence of SEQ ID NO: 154, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 151 or SEQ ID NO: 152. In another embodiment of the invention, antibody fragments of the invention comprise, or alternatively consist of, the polypeptide sequence of SEQ ID NO: 153 or SEQ ID NO: 154.

In a further embodiment of the invention, fragments of the antibody having binding specificity to NGF comprise, or alternatively consist of, one or more of the polypeptide sequences of SEQ ID NO: 155; SEQ ID NO: 156; and SEQ ID NO: 157 which correspond to the complementarity-determining regions (CDRs, or hypervariable regions) of the variable light chain sequence of SEQ ID NO: 151 or the light chain sequence of SEQ ID NO: 152.

In a further embodiment of the invention, fragments of the antibody having binding specificity to NGF comprise, or alternatively consist of, one or more of the polypeptide sequences of SEQ ID NO: 158; SEQ ID NO: 159; and SEQ ID NO: 160 which correspond to the complementarity-determining regions (CDRs, or hypervariable regions) of the variable heavy chain sequence of SEQ ID NO: 153 or the heavy chain sequence of SEQ ID NO: 154.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 151; the variable heavy chain region of SEQ ID NO: 153; the complementarity-determining regions (SEQ ID NO: 155; SEQ ID NO: 156; and SEQ ID NO: 157) of the variable light chain region of SEQ ID NO: 151; and the complementarity-determining regions (SEQ ID NO: 158; SEQ ID NO: 159; and SEQ ID NO: 160) of the variable heavy chain region of SEQ ID NO: 153.

In a particularly preferred embodiment of the invention, the chimeric or humanized anti-NGF antibody is Ab16, comprising, or alternatively consisting of, SEQ ID NO: 152 and SEQ ID NO: 154, and having at least one of the biological activities set forth herein.

In a further particularly preferred embodiment of the invention, antibody fragments comprise, or alternatively consist of, Fab (fragment antigen binding) fragments having binding specificity for NGF and MetMab like monovalent agents. With respect to antibody Ab16, the Fab fragment includes the variable light chain sequence of SEQ ID NO: 151 and the variable heavy chain sequence of SEQ ID NO: 153. This embodiment of the invention further contemplates additions, deletions, and variants of SEQ ID NO: 151 and/or SEQ ID NO: 153 in said Fab while retaining binding specificity for NGF.

In one embodiment of the invention described herein (infra), Fab fragments may be produced by enzymatic digestion (e.g., papain) of Ab16. In another embodiment of the invention, anti-NGF antibodies such as Ab16 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris.*

Antibody Ab17

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab17 polypeptides set forth below. Ab17 antibodies inhibit the interaction of NGF with TrkA and also the interaction of NGF with p75. In one embodiment, the invention includes chimeric antibodies having binding specificity to NGF and possessing a variable light chain sequence comprising the sequence set forth below:

(SEQ ID NO: 161)
AIEMTQTPFSVSAAVGGTVTIKCQASQTISNYLAWYQQKPGQPPKLLIYG

ASNLESGVPSRFKGSGSGTQFTLTISDLECDDAATYYCQQGYTISNVDNN

VFGGGTEVVVKR.

The invention also includes chimeric antibodies having binding specificity to NGF and possessing a light chain sequence comprising the sequence set forth below:

(SEQ ID NO: 162)
AIEMTQTPFSVSAAVGGTVTIKCQASQTISNYLAWYQQKPGQPPKLLIYG

ASNLESGVPSRFKGSGSGTQFTLTISDLECDDAATYYCQQGYTISNVDNN

VFGGGTEVVVKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.

The invention further includes chimeric antibodies having binding specificity to NGF and possessing a variable heavy chain sequence comprising the sequence set forth below:

(SEQ ID NO: 163)
QSLEESGGRLVTPGGSLTLTCAASGFSLTGYNLVWVRQAPGKGLEWIGFI

SYGDTTYYASWAKGRFTISKTSTTVTLTITDLQPSDTGTYFCARETANTY

DYGIWGPGTLVTVSS.

The invention also includes chimeric antibodies having binding specificity to NGF and possessing a heavy chain sequence comprising the sequence set forth below:

(SEQ ID NO: 164)
QSLEESGGRLVTPGGSLTLTCAASGFSLTGYNLVWVRQAPGKGLEWIGFI

SYGDTTYYASWAKGRFTISKTSTTVTLTITDLQPSDTGTYFCARETANTY

DYGIWGPGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKRVEPKSCDKTHTCPPCPAPELLGGPSVFLFPPKPKDTLM

ISRTPEVTCVVVDVSHEDPEVKFNWYVDGVEVHNAKTKPREEQYASTYRV

VSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDG

SFFLYSKLTVDKSRWQQGNVFSCSVMHEALHNHYTQKSLSLSPGK.

The invention further contemplates antibodies comprising one or more of the polypeptide sequences of SEQ ID NO: 165; SEQ ID NO: 166; and SEQ ID NO: 167 which correspond to the complementarity-determining regions (CDRs, or hypervariable regions) of the variable light chain sequence of SEQ ID NO: 161 or the light chain sequence of SEQ ID NO: 162, and/or one or more of the polypeptide sequences of SEQ ID NO: 168; SEQ ID NO: 169; and SEQ ID NO: 170 which correspond to the complementarity-determining regions (CDRs, or hypervariable regions) of the variable heavy chain sequence of SEQ ID NO: 163 or the heavy chain sequence of SEQ ID NO: 164, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 161 or SEQ ID NO: 162. In another embodiment of the invention, antibody fragments of the invention comprise, or alternatively consist of, the polypeptide sequence of SEQ ID NO: 163 or SEQ ID NO: 164.

In a further embodiment of the invention, fragments of the antibody having binding specificity to NGF comprise, or alternatively consist of, one or more of the polypeptide sequences of SEQ ID NO: 165; SEQ ID NO: 166; and SEQ ID NO: 167 which correspond to the complementarity-determining regions (CDRs, or hypervariable regions) of the variable light chain sequence of SEQ ID NO: 161 or the light chain sequence of SEQ ID NO: 162.

In a further embodiment of the invention, fragments of the antibody having binding specificity to NGF comprise, or alternatively consist of, one or more of the polypeptide sequences of SEQ ID NO: 168; SEQ ID NO: 169; and SEQ ID NO: 170 which correspond to the complementarity-determining regions (CDRs, or hypervariable regions) of the variable heavy chain sequence of SEQ ID NO: 163 or the heavy chain sequence of SEQ ID NO: 164.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 161; the variable heavy chain region of SEQ ID NO: 163; the complementarity-determining regions (SEQ ID NO: 165; SEQ ID NO: 166; and SEQ ID NO: 167) of the variable light chain region of SEQ ID NO: 161; and the complementarity-determining regions (SEQ ID NO: 168; SEQ ID NO: 169; and SEQ ID NO: 170) of the variable heavy chain region of SEQ ID NO: 163.

In a particularly preferred embodiment of the invention, the chimeric anti-NGF antibody is Ab17, comprising, or alternatively consisting of, SEQ ID NO: 162 and SEQ ID NO: 164, and having at least one of the biological activities set forth herein.

In a further particularly preferred embodiment of the invention, antibody fragments comprise, or alternatively consist of, Fab (fragment antigen binding) fragments having binding specificity for NGF and MetMab like monovalent agents. With respect to antibody Ab17, the Fab fragment includes the variable light chain sequence of SEQ ID NO: 161 and the variable heavy chain sequence of SEQ ID NO: 163. This embodiment of the invention further contemplates additions, deletions, and variants of SEQ ID NO: 161 and/or SEQ ID NO: 163 in said Fab while retaining binding specificity for NGF.

In one embodiment of the invention described herein (infra), Fab fragments may be produced by enzymatic digestion (e.g., papain) of Ab17. In another embodiment of the invention, anti-NGF antibodies such as Ab17 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab18

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab18 polypeptides set forth below. Ab18 antibodies inhibit the interaction of NGF with TrkA and also the interaction of NGF with p75. In one embodiment, the invention includes chimeric or humanized antibodies having binding specificity to NGF and possessing a variable light chain sequence comprising the sequence set forth below:

(SEQ ID NO: 171)
DIQMTQSPSTLSASVGDRVTITCQASQTISNYLAWYQQKPGKAPKLLIYG

ASNLESGVPSRFSGSGSGTEFTLTISSLQPDDFATYYCQQGYTISNVDNN

VFGGGTKVEIKR.

The invention also includes chimeric or humanized antibodies having binding specificity to NGF and possessing a light chain sequence comprising the sequence set forth below:

(SEQ ID NO: 172)

DIQMTQSPSTLSASVGDRVTITCQASQTISNYLAWYQQKPGKAPKLLIYG

ASNLESGVPSRFSGSGSGTEFTLTISSLQPDDFATYYCQQGYTISNVDNN

VFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.

The invention further includes chimeric or humanized antibodies having binding specificity to NGF and possessing a variable heavy chain sequence comprising the sequence set forth below:

(SEQ ID NO: 173)

EVQLVESGGGLVQPGGSLRLSCAASGFTVSGYNLVWVRQAPGKGLEWVGF

ISYGDTTYYASSAKGRFTISRDNSKNTLYLQMNSLRAEDTAVYYCARETA

NTYDYGIWGQGTLVTVSS.

The invention also includes chimeric or humanized antibodies having binding specificity to NGF and possessing a heavy chain sequence comprising the sequence set forth below:

(SEQ ID NO: 174)

EVQLVESGGGLVQPGGSLRLSCAASGFTVSGYNLVWVRQAPGKGLEWVG

FISYGDTTYYASSAKGRFTISRDNSKNTLYLQMNSLRAEDTAVYYCARE

TANTYDYGIWGQGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKTKPRE

EQYASTYRVVSVLTVLHQDWLNGKEYKCKVSNKALPAPIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPGK.

The invention further contemplates antibodies comprising one or more of the polypeptide sequences of SEQ ID NO: 175; SEQ ID NO: 176; and SEQ ID NO: 177 which correspond to the complementarity-determining regions (CDRs, or hypervariable regions) of the variable light chain sequence of SEQ ID NO: 171 or the light chain sequence of SEQ ID NO: 172, and/or one or more of the polypeptide sequences of SEQ ID NO: 178; SEQ ID NO: 179; and SEQ ID NO: 180 which correspond to the complementarity-determining regions (CDRs, or hypervariable regions) of the variable heavy chain sequence of SEQ ID NO: 173 or the heavy chain sequence of SEQ ID NO: 174, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 171 or SEQ ID NO: 172. In another embodiment of the invention, antibody fragments of the invention comprise, or alternatively consist of, the polypeptide sequence of SEQ ID NO: 173 or SEQ ID NO: 174.

In a further embodiment of the invention, fragments of the antibody having binding specificity to NGF comprise, or alternatively consist of, one or more of the polypeptide sequences of SEQ ID NO: 175; SEQ ID NO: 176; and SEQ ID NO: 177 which correspond to the complementarity-determining regions (CDRs, or hypervariable regions) of the variable light chain sequence of SEQ ID NO: 171 or the light chain sequence of SEQ ID NO: 172.

In a further embodiment of the invention, fragments of the antibody having binding specificity to NGF comprise, or alternatively consist of, one or more of the polypeptide sequences of SEQ ID NO: 178; SEQ ID NO: 179; and SEQ ID NO: 180 which correspond to the complementarity-determining regions (CDRs, or hypervariable regions) of the variable heavy chain sequence of SEQ ID NO: 173 or the heavy chain sequence of SEQ ID NO: 174.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 171; the variable heavy chain region of SEQ ID NO: 173; the complementarity-determining regions (SEQ ID NO: 175; SEQ ID NO: 176; and SEQ ID NO: 177) of the variable light chain region of SEQ ID NO: 171; and the complementarity-determining regions (SEQ ID NO: 178; SEQ ID NO: 179; and SEQ ID NO: 180) of the variable heavy chain region of SEQ ID NO: 173.

In a particularly preferred embodiment of the invention, the chimeric or humanized anti-NGF antibody is Ab18, comprising, or alternatively consisting of, SEQ ID NO: 172 and SEQ ID NO: 174, and having at least one of the biological activities set forth herein.

In a further particularly preferred embodiment of the invention, antibody fragments comprise, or alternatively consist of, Fab (fragment antigen binding) fragments having binding specificity for NGF or MetMab like monovalent agents. With respect to antibody Ab18, the Fab fragment includes the variable light chain sequence of SEQ ID NO: 171 and the variable heavy chain sequence of SEQ ID NO: 173. This embodiment of the invention further contemplates additions, deletions, and variants of SEQ ID NO: 171 and/or SEQ ID NO: 173 in said Fab while retaining binding specificity for NGF.

In one embodiment of the invention described herein (infra), Fab fragments may be produced by enzymatic digestion (e.g., papain) of Ab18. In another embodiment of the invention, anti-NGF antibodies such as Ab18 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab19

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab19 polypeptides set forth below. Ab19 antibodies inhibit the interaction of NGF with TrkA and also the interaction of NGF with p75. In one embodiment, the invention includes chimeric antibodies having binding specificity to NGF and possessing a variable light chain sequence comprising the sequence set forth below:

(SEQ ID NO: 181)
AAVLTQTPSPVSAAVGGTVSISCQSSQNVYKNNYLSWYQQKPGQPPKLL

IYKASTLASGVPSRFKGSGSGTDFTLTISDVQCDAAATYYCAGGYSSSS

DNAFGGGTEVVVKR.

The invention also includes chimeric antibodies having binding specificity to NGF and possessing a light chain sequence comprising the sequence set forth below:

(SEQ ID NO: 182)
AAVLTQTPSPVSAAVGGTVSISCQSSQNVYKNNYLSWYQQKPGQPPKLL

IYKASTLASGVPSRFKGSGSGTDFTLTISDVQCDAAATYYCAGGYSSSS

DNAFGGGTEVVVKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC.

The invention further includes chimeric antibodies having binding specificity to NGF and possessing a variable heavy chain sequence comprising the sequence set forth below:

(SEQ ID NO: 183)
QSVEASGGRLVMPGGSLTLTCTASGFSLSTYWMSWVRQAPGKGLEWIGD

IYFSNEETNYATWAKGRFTISKTSTTVDLNVISPTTEDTATYFCARGSP

DVEIAIDMWGQGTLVTVSS.

The invention also includes chimeric antibodies having binding specificity to NGF and possessing a heavy chain sequence comprising the sequence set forth below:

(SEQ ID NO: 184)
QSVEASGGRLVMPGGSLTLTCTASGFSLSTYWMSWVRQAPGKGLEWIGD

IYFSNEETNYATWAKGRFTISKTSTTVDLNVISPTTEDTATYFCARGSP

DVEIAIDMWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPP

KPKDTLMISRTPEVTCVVVDVSHEDPEVKFNWYVDGVEVHNAKTKPREE

QYASTYRVVSVLTVLHQDWLNGKEYKCKVSNKALPAPIEKTISKAKGQP

REPQVYTLPPSREEMTKNQVSLTCLVKGFYPSDIAVEWESNGQPENNYK

-continued

TTPPVLDSDGSFFLYSKLTVDKSRWQQGNVFSCSVMHEALHNHYTQKSL

SLSPGK.

The invention further contemplates antibodies comprising one or more of the polypeptide sequences of SEQ ID NO: 185; SEQ ID NO: 186; and SEQ ID NO: 187 which correspond to the complementarity-determining regions (CDRs, or hypervariable regions) of the variable light chain sequence of SEQ ID NO: 181 or the light chain sequence of SEQ ID NO: 182, and/or one or more of the polypeptide sequences of SEQ ID NO: 188; SEQ ID NO: 189; and SEQ ID NO: 190 which correspond to the complementarity-determining regions (CDRs, or hypervariable regions) of the variable heavy chain sequence of SEQ ID NO: 183 or the heavy chain sequence of SEQ ID NO: 184, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 181 or SEQ ID NO: 182. In another embodiment of the invention, antibody fragments of the invention comprise, or alternatively consist of, the polypeptide sequence of SEQ ID NO: 183 or SEQ ID NO: 184.

In a further embodiment of the invention, fragments of the antibody having binding specificity to NGF comprise, or alternatively consist of, one or more of the polypeptide sequences of SEQ ID NO: 185; SEQ ID NO: 186; and SEQ ID NO: 187 which correspond to the complementarity-determining regions (CDRs, or hypervariable regions) of the variable light chain sequence of SEQ ID NO: 181 or the light chain sequence of SEQ ID NO: 182.

In a further embodiment of the invention, fragments of the antibody having binding specificity to NGF comprise, or alternatively consist of, one or more of the polypeptide sequences of SEQ ID NO: 188; SEQ ID NO: 189; and SEQ ID NO: 190 which correspond to the complementarity-determining regions (CDRs, or hypervariable regions) of the variable heavy chain sequence of SEQ ID NO: 183 or the heavy chain sequence of SEQ ID NO: 184.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 181; the variable heavy chain region of SEQ ID NO: 183; the complementarity-determining regions (SEQ ID NO: 185; SEQ ID NO: 186; and SEQ ID NO: 187) of the variable light chain region of SEQ ID NO: 181; and the complementarity-determining regions (SEQ ID NO: 188; SEQ ID NO: 189; and SEQ ID NO: 190) of the variable heavy chain region of SEQ ID NO: 183.

In a particularly preferred embodiment of the invention, the chimeric anti-NGF antibody is Ab19, comprising, or alternatively consisting of, SEQ ID NO: 182 and SEQ ID NO: 184, and having at least one of the biological activities set forth herein.

In a further particularly preferred embodiment of the invention, antibody fragments comprise, or alternatively consist of, Fab (fragment antigen binding) fragments having binding specificity for NGF and MetMab-like monovalent agents. With respect to antibody Ab19, the Fab fragment includes the variable light chain sequence of SEQ ID NO: 181 and the variable heavy chain sequence of SEQ ID NO: 183. This embodiment of the invention further contemplates additions, deletions, and variants of SEQ ID NO: 181 and/or SEQ ID NO: 183 in said Fab while retaining binding specificity for NGF.

In one embodiment of the invention described herein (infra), Fab fragments may be produced by enzymatic digestion (e.g., papain) of Ab19. In another embodiment of the invention, anti-NGF antibodies such as Ab19 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab20

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab20 polypeptides set forth below. Ab20 antibodies inhibit the interaction of NGF with TrkA and also the interaction of NGF with p75. In one embodiment, the invention includes chimeric or humanized antibodies having binding specificity to NGF and possessing a variable light chain sequence comprising the sequence set forth below:

```
                                         (SEQ ID NO: 191)
DIQMTQSPSSLSASVGDRVTITCQSSQNVYKNNYLSWYQQKPGKVPKLL

IYKASTLASGVPSRFSGSGSGTDFTLTISSLQPEDVATYYCAGGYTSSS

DNAFGGGTKVEIKR.
```

The invention also includes chimeric or humanized antibodies having binding specificity to NGF and possessing a light chain sequence comprising the sequence set forth below:

```
                                         (SEQ ID NO: 192)
DIQMTQSPSSLSASVGDRVTITCQSSQNVYKNNYLSWYQQKPGKVPKLL

IYKASTLASGVPSRFSGSGSGTDFTLTISSLQPEDVATYYCAGGYTSSS

DNAFGGGTKVEIKRTVAAPSVFIFPPSDEQLKSGTASVVCLLNNFYPRE
```

-continued

```
AKVQWKVDNALQSGNSQESVTEQDSKDSTYSLSSTLTLSKADYEKHKVY

ACEVTHQGLSSPVTKSFNRGEC.
```

The invention further includes chimeric or humanized antibodies having binding specificity to NGF and possessing a variable heavy chain sequence comprising the sequence set forth below:

```
                                         (SEQ ID NO: 193)
EVQLVESGGGLVQPGGSLRLSCAASGFTVSTYWMSWVRQAPGKGLEWVG

DIYFSNEETNYATSAKGRFTISRDNSKNTLYLQMNSLRAEDTAVYYCAR

GSPDVEIAIDMWGQGTLVTVSS.
```

The invention also includes chimeric or humanized antibodies having binding specificity to NGF and possessing a heavy chain sequence comprising the sequence set forth below:

```
                                         (SEQ ID NO: 194)
EVQLVESGGGLVQPGGSLRLSCAASGFTVSTYWMSWVRQAPGKGLEWVG

DIYFSNEETNYATSAKGRFTISRDNSKNTLYLQMNSLRAEDTAVYYCAR

GSPDVEIAIDMWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFL

FPPKPKDTLMISRTPEVTCVVVDVSHEDPEVKFNWYVDGVEVHNAKTKP

REEQYASTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK.
```

The invention further contemplates antibodies comprising one or more of the polypeptide sequences of SEQ ID NO: 195; SEQ ID NO: 196; and SEQ ID NO: 197 which correspond to the complementarity-determining regions (CDRs, or hypervariable regions) of the variable light chain sequence of SEQ ID NO: 191 or the light chain sequence of SEQ ID NO: 192, and/or one or more of the polypeptide sequences of SEQ ID NO: 198; SEQ ID NO: 199; and SEQ ID NO: 200 which correspond to the complementarity-determining regions (CDRs, or hypervariable regions) of the variable heavy chain sequence of SEQ ID NO: 193 or the heavy chain sequence of SEQ ID NO: 194, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 191 or SEQ ID NO: 192. In another embodiment of the invention, antibody fragments of the invention comprise, or alternatively consist of, the polypeptide sequence of SEQ ID NO: 193 or SEQ ID NO: 194.

In a further embodiment of the invention, fragments of the antibody having binding specificity to NGF comprise, or alternatively consist of, one or more of the polypeptide sequences of SEQ ID NO: 195; SEQ ID NO: 196; and SEQ ID NO: 197 which correspond to the complementarity-determining regions (CDRs, or hypervariable regions) of the variable light chain sequence of SEQ ID NO: 191 or the light chain sequence of SEQ ID NO: 192.

In a further embodiment of the invention, fragments of the antibody having binding specificity to NGF comprise, or alternatively consist of, one or more of the polypeptide sequences of SEQ ID NO: 198; SEQ ID NO: 199; and SEQ ID NO: 200 which correspond to the complementarity-determining regions (CDRs, or hypervariable regions) of the variable heavy chain sequence of SEQ ID NO: 193 or the heavy chain sequence of SEQ ID NO: 194.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 191; the variable heavy chain region of SEQ ID NO: 193; the complementarity-determining regions (SEQ ID NO: 195; SEQ ID NO: 196; and SEQ ID NO: 197) of the variable light chain region of SEQ ID NO: 191; and the complementarity-determining regions (SEQ ID NO: 198; SEQ ID NO: 199; and SEQ ID NO: 200) of the variable heavy chain region of SEQ ID NO: 193.

In a particularly preferred embodiment of the invention, the chimeric or humanized anti-NGF antibody is Ab20, comprising, or alternatively consisting of, SEQ ID NO: 192 and SEQ ID NO: 194, and having at least one of the biological activities set forth herein.

In a further particularly preferred embodiment of the invention, antibody fragments comprise, or alternatively consist of, Fab (fragment antigen binding) fragments having binding specificity for NGF or MetMab like monovalent agents. With respect to antibody Ab20, the Fab fragment includes the variable light chain sequence of SEQ ID NO: 191 and the variable heavy chain sequence of SEQ ID NO: 193. This embodiment of the invention further contemplates additions, deletions, and variants of SEQ ID NO: 191 and/or SEQ ID NO: 193 in said Fab while retaining binding specificity for NGF.

In one embodiment of the invention described herein (infra), Fab fragments may be produced by enzymatic digestion (e.g., papain) of Ab20. In another embodiment of the invention, anti-NGF antibodies such as Ab20 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab21

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be derived from one or more of the antibody Ab21 polypeptides set forth below. Ab21 antibodies inhibit the interaction of NGF with TrkA and also the interaction of NGF with p75. In one embodiment, the invention includes chimeric or humanized antibodies having binding specificity to NGF and possessing a variable light chain sequence comprising the sequence set forth below:

(SEQ ID NO: 51)
DIQMTQSPSTLSASVGDRVTITCQASQSIYSNLAWYQQKPGKAPKLLIY

DASTLESGVPSRFSGSGSGTEYTLTISSLQPDDFATYYCQQGFTVSDID

NAFGGGTKVEIKR.

The invention also includes chimeric or humanized antibodies having binding specificity to NGF and possessing a light chain sequence comprising the sequence set forth below:

(SEQ ID NO: 401)
DIQMTQSPSTLSASVGDRVTITCQASQSIYSNLAWYQQKPGKAPKLLIY

DASTLESGVPSRFSGSGSGTEYTLTISSLQPDDFATYYCQQGFTVSDID

NAFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC.

The invention further includes chimeric or humanized antibodies having binding specificity to NGF and possessing a variable heavy chain sequence comprising the sequence set forth below:

(SEQ ID NO: 53)
EVQLVESGGGLVQPGGSLRLSCAASGFTVSNYAVGWVRQAPGKGLEWVG

IIGRNGNTWYASSARGRFTISRDNSKNTLYLQMNSLRAEDTAVYYCARG

YGRSVAYYVFNIWGPGTLVTVSS.

The invention also includes chimeric or humanized antibodies having binding specificity to NGF and possessing a heavy chain sequence comprising the sequence set forth below:

(SEQ ID NO: 402)
EVQLVESGGGLVQPGGSLRLSCAASGFTVSNYAVGWVRQAPGKGLEWVG

IIGRNGNTWYASSARGRFTISRDNSKNTLYLQMNSLRAEDTAVYYCARG

YGRSVAYYVFNIWGPGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDARVEPKSCDKTHTCPPCPAPELLGGPSVF

LFPPKPKDTLMISRTPEVTCVVVDVSHEDPEVKFNWYVDGVEVHNAKTK

PREEQYASTYRVVSVLTVLHQDWLNGKEYKCKVSNKALPAPIEKTISKA

KGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYT

-continued

QKSLSLSPGK.

The invention further contemplates antibodies comprising one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 401, and/or one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 402, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 51 or SEQ ID NO: 401. In another embodiment of the invention, antibody fragments of the invention comprise, or alternatively consist of, the polypeptide sequence of SEQ ID NO: 53 or SEQ ID NO: 402. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

In a further embodiment of the invention, fragments of the antibody having binding specificity to NGF comprise, or alternatively consist of, one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 401.

In a further embodiment of the invention, fragments of the antibody having binding specificity to NGF comprise, or alternatively consist of, one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 402.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 51; the variable heavy chain region of SEQ ID NO: 53; the complementarity-determining regions (SEQ ID NO: 55; SEQ ID NO: 56; and SEQ ID NO: 57) of the variable light chain region of SEQ ID NO: 51; and the complementarity-determining regions (SEQ ID NO: 58; SEQ ID NO: 59; and SEQ ID NO: 60) of the variable heavy chain region of SEQ ID NO: 53.

In a particularly preferred embodiment of the invention, the chimeric or humanized anti-NGF antibody is Ab21, comprising, or alternatively consisting of, SEQ ID NO: 401 and SEQ ID NO: 402, and having at least one of the biological activities set forth herein.

In a further particularly preferred embodiment of the invention, antibody fragments comprise, or alternatively consist of, Fab (fragment antigen binding) fragments having binding specificity for NGF or MetMab-like monovalent agents. With respect to antibody Ab21, the Fab fragment includes the variable light chain sequence of SEQ ID NO: 51 and the variable heavy chain sequence of SEQ ID NO: 53. This embodiment of the invention further contemplates additions, deletions, and variants of SEQ ID NO: 51 and/or SEQ ID NO: 53 in said Fab while retaining binding specificity for NGF.

In one embodiment of the invention described herein (infra), Fab fragments may be produced by enzymatic digestion (e.g., papain) of Ab21. In another embodiment of the invention, anti-NGF antibodies such as Ab21 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris.*

Antibody fragment Fab1

Methods of the invention include methods of treating pain by administering one or more anti-human NGF monovalent agents to an individual in a therapeutically effective amount, wherein there is no substantial increase in the inflammatory response of the individual following administration of the one or more monovalent agents. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

Anti-human NGF monovalent agents used in the methods of the invention may be the antibody fragment Fab1 polypeptides set forth below, or may be derived from one or more of the antibody fragment Fab1 polypeptides set forth below. Fab1 polypeptides inhibit the interaction of NGF with TrkA and also the interaction of NGF with p75. In one embodiment, the invention includes Fab antibody fragments having binding specificity to NGF and possessing a light chain sequence comprising the sequence set forth below:

(SEQ ID NO: 405)
DIQMTQSPSTLSASVGDRVTITCQASQSIYSNLAWYQQKPGKAPKLLIY

DASTLESGVPSRFSGSGSGTEYTLTISSLQPDDFATYYCQQGFTVSDID

NAFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC.

The invention further includes Fab antibody fragments having binding specificity to NGF and possessing a heavy chain sequence comprising the sequence set forth below:

(SEQ ID NO: 406)
EVQLVESGGGLVQPGGSLRLSCAASGFTVSNYAVGWVRQAPGKGLEWVG

IIGRNGNTWYASSARGRFTISRDNSKNTLYLQMNSLRAEDTAVYYCARG

YGRSVAYYVFNIWGPGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDARVEPKSCDKTH.

The invention further contemplates antibody fragments comprising one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 405, and/or one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 406, or combinations of these polypeptide sequences. In another embodiment of the invention, antibody fragments of the invention comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF. In one embodiment of the invention, antibody fragments of the invention comprise, or alternatively consist of, the polypeptide sequence of SEQ ID NO: 51 or SEQ ID NO: 405. In another embodiment of the invention, antibody fragments of the invention comprise, or alternatively consist of, the polypeptide sequence of SEQ ID NO: 53 or SEQ ID NO: 406.

In a further embodiment of the invention, antibody fragments having binding specificity to NGF comprise, or alternatively consist of, one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 405.

In a further embodiment of the invention, antibody fragments having binding specificity to NGF comprise, or alternatively consist of, one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 406.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 51; the variable heavy chain region of SEQ ID NO: 53; the complementarity-determining regions (SEQ ID NO: 55; SEQ ID NO: 56; and SEQ ID NO: 57) of the variable light chain region of SEQ ID NO: 51; and the complementarity-determining regions (SEQ ID NO: 58; SEQ ID NO: 59; and SEQ ID NO: 60) of the variable heavy chain region of SEQ ID NO: 53.

In a particularly preferred embodiment of the invention, the anti-NGF antibody fragment is Fab1, comprising SEQ ID NO: 405 and SEQ ID NO: 406, and having at least one of the biological activities set forth herein. In one embodiment of the invention, antibody fragment Fab1 may be produced by enzymatic digestion (e.g., papain) of Ab21.

Antibody fragment Fab2

Methods of the invention include methods of treating pain by administering one or more anti-human NGF monovalent agents to an individual in a therapeutically effective amount, wherein there is no substantial increase in the inflammatory response of the individual following administration of the one or more monovalent agents. Anti-human NGF monovalent agents used in the methods of the invention may be the antibody fragment Fab2 polypeptides set forth below, or may be derived from one or more of the antibody fragment Fab2 polypeptides set forth below. Fab2 polypeptides inhibit the interaction of NGF with TrkA and also the interaction of NGF with p75. In one embodiment, the invention includes Fab antibody fragments having binding specificity to NGF and possessing a light chain sequence comprising the sequence set forth below:

(SEQ ID NO: 407)
DIQMTQSPSTLSASVGDRVTITCQASQSIYSNLAWYQQKPGKAPKLLIY

DASTLESGVPSRFSGSGSGTEYTLTISSLQPDDFATYYCQQGFTVSDI

DNAFGGGTKVEIKRTVAAPSVFIFPPSDEQLKSGTASVVCLLNNFYPR

EAKVQWKVDNALQSGNSQESVTEQDSKDSTYSLSSTLTLSKADYEK

HKVYACEVTHQGLSSPVTKSFNRGEC.

The invention further includes Fab antibody fragments having binding specificity to NGF and possessing a heavy chain sequence comprising the sequence set forth below:

(SEQ ID NO: 408)
EVQLVESGGGLVQPGGSLRLSCAASGFTVSNYAVGWVRQAPGKGLEW

VGIIGRNGNTWYASSARGRFTISRDNSKNTLYLQMNSLRAEDTAVYYCAR

GYGRSVAYYVFNIWGPGTLVTVSSASTKGPSVFPLAPSSKSTSGGTAA

LGCLVKDYFPEPVTVSWNSGALTSGVHTFPAVLQSSGLYSLSSVVTVP

SSSLGTQTYICNVNHKPSNTKVDARVEPKSCDKTH.

The invention further contemplates antibody fragments comprising one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 407, and/or one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 408, or combinations of these polypeptide sequences. In another embodiment of the invention, antibody fragments of the invention comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF and MetMab-like monovalent agents. In one embodiment of the invention, antibody fragments of the invention comprise, or alternatively consist of, the polypeptide sequence of SEQ ID NO: 51 or SEQ ID NO: 407. In another embodiment of the invention, antibody fragments of the invention comprise, or alternatively consist of, the polypeptide sequence of SEQ ID NO: 53 or SEQ ID NO: 408. As noted, in some embodiments these monovalent agents or other antibody fragments will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

In a further embodiment of the invention, antibody fragments having binding specificity to NGF comprise, or alternatively consist of, one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 407.

In a further embodiment of the invention, antibody fragments having binding specificity to NGF comprise, or alternatively consist of, one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 408.

The invention also contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 51; the variable heavy chain region of SEQ ID NO: 53; the complementarity-determining regions (SEQ ID NO: 55; SEQ ID NO: 56; and SEQ ID NO: 57) of the variable light chain region of SEQ ID NO: 51; and the complementarity-determining regions (SEQ ID NO: 58; SEQ ID NO: 59; and SEQ ID NO: 60) of the variable heavy chain region of SEQ ID NO: 53. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

In a particularly preferred embodiment of the invention, the anti-NGF antibody fragment is Fab1, comprising SEQ ID NO: 407 and SEQ ID NO: 408, and having at least one of the biological activities set forth herein.

In another embodiment of the invention described herein (infra), Fab fragments may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*. In one embodiment of the invention, antibody fragment Fab2 may be produced by expression in *Pichia pastoris* using protocols set forth herein in the examples.

In another embodiment, monovalent agents such as antibody fragments may be present in one or more of the following non-limiting forms: Fab, Fab', $F(ab')_2$, Fv and single chain Fv antibody forms. These monovalent agents optionally may be modified such as the attachment of functional or detectable moieties and more specifically the attachment of moieties such as water soluble polymers that affect in vivo half-life. In a preferred embodiment, the anti-NGF antibodies described herein further comprises the kappa constant light chain sequence comprising the sequence set forth below:

```
                                      (SEQ ID NO: 412)
VAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTK

SFNRGEC.
```

In another preferred embodiment, the anti-NGF antibodies described herein further comprises the gamma-1 constant heavy chain polypeptide sequence comprising the sequence set forth below:

```
                                      (SEQ ID NO: 413)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

In another embodiment, the invention contemplates an isolated anti-NGF antibody comprising a $V_H$ polypeptide sequence selected from: SEQ ID NO: 3, 13, 23, 33, 43, 53, 63, 73, 83, 93, 103, 113, 123, 133, 143, 153, 163, 173, 183, 193, or 402, or a variant thereof; and further comprising a $V_L$ polypeptide sequence selected from: SEQ ID NO: 1, 11, 21, 31, 41, 51, 61, 71, 81, 91, 101, 111, 121, 131, 141, 151, 161, 171, 181, 191, or 401, or a variant thereof, wherein one or more of the framework residues (FR residues) in said $V_H$ or $V_L$ polypeptide has been substituted with another amino acid residue resulting in an anti-NGF antibody that specifically binds NGF. The invention contemplates humanized and chimeric forms of these antibodies. The chimeric antibodies may include an Fc derived from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions. Such antibodies may suitably act as the source of monovalent agents, using techniques set forth herein.

In one embodiment of the invention, the antibodies or $V_H$ or $V_L$ polypeptides originate or are selected from one or more rabbit B cell populations prior to initiation of the humanization process referenced herein.

In the exemplary embodiments set forth in the working examples infra, the antibodies were raised against human NGF. All of the antibodies which are disclosed herein blocked or inhibited the interaction of NGF with TrkA and/or p'75. The observed antibody specificity of some of the obtained antibodies to selectively block or inhibit the NGF interactions with TrkA and not with p75 was unexpected. However, as disclosed herein, in other embodiments of the invention, the anti-human NGF monovalent agents of the present invention may not possess binding specificity for p75 or TrkA.

In some preferred embodiments of the invention, the subject antibodies and fragments thereof (including Fab fragments and other monovalent antibody molecules such as camelbodies, SMIPs, monovalent antibody molecules analogous to MetMab and the like disclosed herein) having binding specificity for NGF, will inhibit biological activities mediated by the binding of NGF to the p75 and/or TrkA receptors. In other preferred embodiments of the invention, the anti-NGF antibodies are selected from Ab1, Ab2, Ab5-Ab14, or Ab17-Ab21 and derivatives and fragments thereof that inhibit biological activities mediated by the binding of NGF to both of the p75 and TrkA receptors.

Other preferred embodiments of the invention are directed to antibodies and fragments thereof capable of binding to NGF and selectively inhibiting biological activities mediated by the binding of NGF to the TrkA receptor, while not inhibiting biological activities mediated by the binding of NGF to the p75 receptor. In a particularly preferred embodiment of the invention, the anti-NGF antibodies are selected from Ab3, Ab4, Ab15, or Ab16 and derivatives and fragments thereof, especially chimeric and humanized antibodies and fragments thereof, that inhibit biological activities mediated by the binding of NGF to the TrkA receptor while not appreciably inhibiting biological activities mediated by the binding of NGF to the p75 receptor.

As stated herein, anti-human NGF monovalent agents may be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Regarding detectable moieties, further exemplary enzymes include, but are not limited to, horseradish peroxidase, acetylcholinesterase, alkaline phosphatase, beta-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent moieties include, but are not limited to, luminol. Further exemplary bioluminescent materials include, but are not limited to, luciferin and aequorin. Further exemplary radioactive materials include, but are not limited to, Iodine 125 ($^{125}I$), Carbon 14 ($^{14}C$), Sulfur 35 ($^{35}S$), Tritium ($^{3}H$) and Phosphorus 32 ($^{32}P$).

Regarding functional moieties, exemplary cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, canninomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (taxol), ricin, pseudomonas exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine and bleomycin. Toxic enzymes from plants and bacteria such as ricin, diphtheria toxin and *Pseudomonas* toxin may be conjugated to the humanized or chimeric antibodies, or binding fragments thereof, to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the antibody, or binding fragments thereof, with or without the use of a complex-forming agent. Such radionuclides include beta-emitters such as Phosphorus-32 ($^{32}P$), Scandium-47 ($^{47}Sc$), Copper-67 ($^{67}Cu$), Gallium-67 ($^{67}Ga$), Yttrium-88 ($^{88}Y$), Yttrium-90 ($^{90}Y$), Iodine-125 ($^{125}I$), Iodine-131 ($^{131}I$), Samarium-153 ($^{153}Sm$), Lutetium-177 ($^{177}Lu$), Rhenium-186 ($^{186}Re$) or Rhenium-188 ($^{188}Re$), and alpha-emitters such as Astatine-211 ($^{211}At$), Lead-212 ($^{212}Pb$), Bismuth-212 ($^{212}Bi$) or -213 ($^{213}Bi$) or Actinium-225 ($^{225}Ac$).

Methods are known in the art for conjugating an antibody or binding fragment thereof to a detectable moiety and the like, such as for example those methods described by Hunter et al, Nature 144:945 (1962); David et al, Biochemistry 13:1014 (1974); Pain et al, J. Immunol. Meth. 40:219 (1981); and Nygren, J., Histochem. and Cytochem. 30:407 (1982).

Embodiments described herein further include variants and equivalents that are substantially homologous to the antibodies, antibody fragments, diabodies, SMIPs, MetMab like monovalent agents, camelbodies, nanobodies, IgNAR, polypeptides, variable regions and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

In another embodiment, the invention contemplates polypeptide sequences having at least 90% or greater sequence homology to any one or more of the polypeptide sequences of antibody fragments, variable regions and CDRs set forth herein. More preferably, the invention contemplates polypeptide sequences having at least 95% or greater sequence homology, even more preferably at least 96, 97 or 98% or greater than 98% sequence homology, and still more preferably at least 99% or greater sequence homology to any one or more of the polypeptide sequences of antibody fragments, variable regions and CDRs set forth herein. Methods for determining homology between nucleic acid and amino acid sequences are well known to those of ordinary skill in the art.

In another embodiment, the invention further contemplates the above-recited polypeptide homologs of the anti-human NGF monovalent agents, variable regions and CDRs set forth herein further having anti-NGF activity. Non-limiting examples of anti-NGF activity are set forth herein.

In another embodiment, the invention further contemplates the generation and use of anti-idiotypic antibodies that bind any of the foregoing sequences. In an exemplary embodiment, such an anti-idiotypic antibody could be administered to a subject who has received an anti-NGF monovalent agent to modulate, reduce, or neutralize, the effect of the anti-NGF monovalent agent. Such anti-idiotypic antibodies could also be useful for treatment of an autoimmune disease characterized by the presence of anti-NGF antibodies. A further exemplary use of such anti-idiotypic antibodies is for detection of the anti-NGF antibodies of the present invention, for example to monitor the levels of the anti-NGF antibodies present in a subject's blood or other bodily fluids.

The present invention also contemplates anti-NGF antibodies comprising any of the polypeptide or polynucleotide sequences described herein substituted for any of the other polynucleotide sequences described herein. For example, without limitation thereto, the present invention contemplates antibodies comprising the combination of any of the variable light chain and variable heavy chain sequences described herein, and further contemplates antibodies resulting from substitution of any of the CDR sequences described herein for any of the other CDR sequences described herein.

Additional Exemplary Embodiments of the Invention

In another embodiment, the invention contemplates one or more anti-human NGF monovalent agents which specifically bind to the same or overlapping linear or conformational epitope(s) and/or competes for binding to the same or overlapping linear or conformational epitope(s) on an intact human NGF polypeptide or fragment thereof as an anti-human NGF antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, or Ab21. In a preferred embodiment, the anti-human NGF monovalent agents specifically bind to the same or overlapping linear or conformational epitope(s) and/or competes for binding to the same or overlapping linear or conformational epitope(s) on an intact human NGF polypeptide or a fragment thereof as Ab3, Ab4, Ab5, Ab6, Ab15, or Ab16.

A preferred embodiment of the invention is directed to methods of treating pain in an individual without substantially increasing the inflammatory response in the individual, said method comprising administering one or more anti-human NGF monovalent agents to said individual. Exemplary monovalent agents include, but are not limited to, Fab, Fab', Fv, scFv fragments, SMIPs (small molecule immunopharmaceuticals), camelbodies, nanobodies, IgNAR, monovalent antibodies analagous to MetMab described herein, or one or more combinations thereof.

In another preferred embodiment of the invention, the anti-human NGF monovalent agents are capable of significantly reducing pain in vivo in murine models as assessed by using Gait analysis (as described in Example 5 herein), compared to results obtained with controls.

A particularly preferred embodiment of the invention contemplates the use of Fab or MetMab type monovalent antibody polypeptide sequences in methods for the treatment of pain in a patient without substantially increasing the inflammatory response in the individual following administration of the Fab polypeptides. Non-limiting types of pain that may be treated using Fab polypeptide sequences are provided elsewhere in this disclosure.

In another preferred embodiment, the invention contemplates Fab fragments of the full length antibodies described herein that do not substantially increase inflammation in a patient compared to full length antibodies. The invention also contemplates a method of treating a patient suffering from pain by administering an Fab fragment of the full length antibodies described herein that do not substantially raise inflammation in a patient compared to full length antibodies dosed at the same concentration. In a particularly preferred embodiment of the invention, the Fab fragment(s) comprise a light chain polypeptide sequence of SEQ ID NO: 405 or SEQ ID NO:407, and a heavy chain polypeptide sequence of SEQ ID NO:406 or SEQ ID NO:408.

In another embodiment of the invention, the anti-human NGF antibody is an antibody which specifically binds to the same or overlapping linear or conformational epitopes on an intact NGF polypeptide or fragment thereof that is (are) specifically bound by Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20 or Ab21 as ascertained by epitopic mapping using overlapping linear peptide fragments which span the full length of the native human NGF polypeptide.

In a particularly preferred embodiment of the invention, monovalent agents are utilized in methods of treating pain in a patient without substantially increasing inflammation in said patient. These monovalent agents at the administered dosage amount, such as from 0.01 mg/kg to 100 mg/kg effectively alleviate pain, while unexpectedly not increasing inflammation in the patient. Exemplary monovalent agents include, but are not limited to, Fab, Fab', Fv, scFv fragments, SMIPs (small molecule immunopharmaceuticals), camelbodies, nanobodies, IgNAR, MetFab like monovalent antibody molecules, or one or more combinations thereof. These monovalent agents are well suited in treating conditions associated with a pain response wherein inflammation is a significant problem or side effect, e.g., inflammatory diseases such as psoriasis, rheumatoid arthritis and conditions such as are disclosed in this application.

The present invention includes in particular monovalent antibody molecules that bind NGF, which are analogous to MetMab molecules. MetMab is a monovalent antibody specific to Met. (Met is a protein encoded by the nucleotide sequence set forth in Park et al., Proc. Natl. Acad. Sci. 84, 7479-(1987), or fragments thereof, as well as related polypeptides, which include, but are not limited to, allelic variants, splice variants, derivative variants, substitution variants, deletion variants, and/or insertion variants, fusion polypeptides, and interspecies homologs). The MetMab antibody, is a monovalent antibody known by different names including OA-5d5 (Genentech) and is also called One Armed 5d5, 5d5, MetMab, PRO143966, among others). Antibody OA-5d5, including its structure and properties, and methods for making and using it, are described in U.S. Publication No. 2007/0092520. In one embodiment, an anti-NGF antibody according to the invention may comprise a single Fab region linked to an Fc region. In such embodiment, an antibody of the invention may comprise light and heavy chain variable domains as described herein. In such an embodiment, the antibody is monovalent and may comprise an intact Fc region. In another such embodiment, the Fc region may comprise at least one protuberance (knob) and at least one cavity (hole), wherein the presence of the protuberance and cavity enhances formation of a complex between an Fc polypeptide comprising the protuberance and an Fc polypeptide comprising the cavity, for example as described in WO 2005/063816. In one embodiment, the Fc region of an antibody of the invention may comprise a first and a second Fc polypeptide, wherein the first and second polypeptide each comprises one or more mutations with respect to wild type human Fc. In one embodiment, a cavity mutation is T366S, L368A and/or Y407V. In another embodiment, a protuberance mutation is T366W. In a specific embodiment, a monovalent antibody according to the subject invention may comprise a one-armed antibody synthesized as described in WO2005/063816. In such embodiment, the one-armed antibody may comprise Fc mutations constituting "knobs" and "holes" as described in WO2005/063816. For example, a hole mutation can be one or more of T366A, L368A and/or Y407V in an Fc polypeptide, and a cavity mutation can be T366W.

The invention is also directed to an anti-human NGF monovalent agent that binds with the same or overlapping NGF epitope and/or competes with an anti-NGF antibody for binding to NGF as an antibody or antibody fragment disclosed herein, including but not limited to an anti-NGF antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20 or Ab21.

In another embodiment, the invention is also directed to an isolated anti-human NGF monovalent agents comprising one or more of the CDRs contained in the $V_H$ polypeptide sequences selected from: 3, 13, 23, 33, 43, 53, 63, 73, 83, 93, 103, 113, 123, 133, 143, 153, 163, 173, 183, 193, or 402, or a variant thereof, and/or one or more of the CDRs contained in the $V_L$ polypeptide sequences selected from: 1, 11, 21, 31, 41, 51, 61, 71, 81, 91, 101, 111, 121, 131, 141, 151, 161, 171, 181, 191, or 401, or a variant thereof.

In one embodiment of the invention, the anti-human NGF monovalent agents discussed above and comprise at least 2 complementarity determining regions (CDRs) in each the variable light and the variable heavy regions which are identical to those contained in an anti-human NGF antibody selected from the group consisting of Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20 or Ab21.

In a preferred embodiment, the anti-human NGF monovalent agents discussed above comprises at least 2 complementarity determining regions (CDRs) in each the variable light and the variable heavy regions which are identical to those contained in Ab3, Ab4, Ab5, or Ab6. In another embodiment, all of the CDRs of the anti-human NGF monovalent agents discussed above are identical to the CDRs contained in an anti-human NGF antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20 or Ab21. In a preferred embodiment of the invention, all of the CDRs of the anti-human NGF monovalent agents discussed above are identical to the CDRs contained in an anti-human NGF antibody selected from Ab3, Ab4, Ab5, or Abb.

The invention further contemplates that the one or more anti-human NGF monovalent agents discussed above are aglycosylated; are derived from human, humanized, single chain or chimeric antibodies; or are derived from a humanized antibody itself derived from a rabbit (parent) anti-human NGF antibody.

The invention further contemplates one or more anti-human NGF monovalent agents wherein the framework regions (FRs) in the variable light region and the variable heavy regions of said antibody respectively are human FRs which are unmodified or which have been modified by the substitution of at most 2 or 3 human FR residues in the variable light or heavy chain region with the corresponding FR residues of the parent rabbit antibody, and wherein said human FRs have been derived from human variable heavy and light chain antibody sequences which have been selected from a library of human germline antibody sequences based on their high level of homology to the corresponding rabbit variable heavy or light chain regions relative to other human germline antibody sequences contained in the library.

In one embodiment of the invention, the anti-human NGF monovalent agents specifically bind to NGF expressing human cells and/or to circulating soluble NGF molecules in vivo, including NGF expressed on or by human cells in a patient with a disease associated with cells that express NGF.

In another embodiment, the disease is selected from inflammatory pain, post-operative incision pain, complex regional pain syndrome, cancer pain, primary or metastatic bone cancer pain, fracture pain, osteoporotic fracture pain, pain resulting from burn, osteoporosis, gout joint pain, pain associated with sickle cell crises, and other nociceptic pain, as well as hepatocellular carcinoma, breast cancer, liver cirrhosis, neurogenic pain, neuropathic pain, nociceptic pain, trigeminal neuralgia, post-herpetic neuralgia, phantom limb pain, fibromyalgia, menstrual pain, ovarialgia, reflex sympathetic dystrophy, neurogenic pain, osteoarthritis or rheumatoid arthritis pain, lower back pain, diabetic neuropathy, sciatica, or migraine.

The invention further contemplates anti-human anti-NGF monovalent agents directly or indirectly attached to a detectable label or therapeutic agent.

The invention also contemplates one or more nucleic acid sequences which result in the expression of an anti-human NGF monovalent agent as set forth above, including those comprising, or alternatively consisting of, yeast or human preferred codons. The invention also contemplates vectors (including plasmids or recombinant viral vectors) comprising said nucleic acid sequence(s). The invention also contemplates host cells or recombinant host cells and tansgenic animals or plants expressing at least one of the antibodies set forth above, including a mammalian, yeast, bacterial, plant and insect cells. In a preferred embodiment, the host cell is a yeast cell. In a further preferred embodiment, the yeast cell is a diploidal yeast cell. In a more preferred embodiment, the yeast cell is a *Pichia* yeast.

The invention also contemplates a method of treatment comprising administering to a patient with a disease or condition associated with NGF expressing cells a therapeutically effective amount of at least one anti-human NGF monovalent agent described herein. The invention also contemplates that the treatment method may involve the administration of two or more anti-NGF monovalent agents disclosed herein. If more than one monovalent agent is administered to the patient, the multiple monovalent agents may be administered simultaneously or concurrently, or may be staggered in their administration. The diseases that may be treated are presented in the non-limiting list set forth above and elsewhere herein. In a preferred embodiment, the disease is selected from cancer pain or neuropathic pain. In a particularly preferred embodiment, the disease is cancer pain. In another embodiment the treatment further includes the administration of another therapeutic agent or regimen selected from chemotherapy, radiotherapy, cytokine administration or gene therapy.

In a non-limiting embodiment of the invention, another therapeutic agent or regimen includes Taxol (paclitaxel) or its derivatives, platinum compounds such as carboplatin or cisplatin, anthrocyclines such as doxorubicin, alkylating agents such as cyclophosphamide, anti-metabolites such as 5-fluorouracil, or etoposide.

The invention further contemplates a method of in vivo imaging which detects the presence of cells which express NGF comprising administering a diagnostically effective amount of at least one anti-human NGF monovalent agent. In one embodiment, said administration further includes the administration of a radionuclide or fluorophore that facilitates detection of the monovalent agent at NGF expressing disease sites. In another embodiment of the invention, the method of in vivo imaging is used to detect NGF expressing tumors or metastases, or tumors or metastases expressing TrkA and/or p75 capable of binding to NGF. In a further embodiment, the results of said in vivo imaging method are used to facilitate the design of an appropriate therapeutic regimen, including therapeutic regimens including radiotherapy, chemotherapy or a combination thereof.

Polynucleotides Encoding Anti-NGF Antibody Polypeptides

Antibody Ab1

The invention is further directed to the use of polynucleotides encoding Ab1 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab1 antibody polypeptides having binding specificity to NGF. As noted above, Ab1 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 1:

(SEQ ID NO: 201)
GCCCTTGTGATGACCCAGACTCCATCCTCCGTGTCTGCAGCTGTGGGAG
GCACAGTCACCATCAATTGCCAGGCCAGTCAGAACATTTACAGCAATTT
AGCCTGGTATCAACAGAGACCAGGGCAGCGTCCCAAGCTCCTGATCTAT
GGTGCATCCAATCTGGATGCTGGGGTCCCATCGCGGTTCAGAGGCAGTG
GATCTGGGACAGAGTACACTCTCACCATCAGCGACCTGGAGTGTGACGA
TGTTGGCACTTACTACTGTCAAAGTGCTTTTGATAGTGATAGTACTGAAA
ATACTTTCGGCGGAGGGACCGAGGTGGTGGTCAAACGT.

In one embodiment of the invention, polynucleotides of the invention comprise, or alternatively consist of, the following polynucleotide sequence encoding the light chain polypeptide sequence of SEQ ID NO: 2:

(SEQ ID NO: 202)
GCCCTTGTGATGACCCAGACTCCATCCTCCGTGTCTGCAGCTGTGGGAG
GCACAGTCACCATCAATTGCCAGGCCAGTCAGAACATTTACAGCAATTT
AGCCTGGTATCAACAGAGACCAGGGCAGCGTCCCAAGCTCCTGATCTAT
GGTGCATCCAATCTGGATGCTGGGGTCCCATCGCGGTTCAGAGGCAGTG
GATCTGGGACAGAGTACACTCTCACCATCAGCGACCTGGAGTGTGACGAT
GTTGGCACTTACTACTGTCAAAGTGCTTTTGATAGTGATAGTACTGAAAA
TACTTTCGGCGGAGGGACCGAGGTGGTGGTCAAACGTACGGTAGCGGCCC
CATCTGTCTTCATCTTCCCGCCATCTGATGAGCAGTTGAAATCTGGAACT
GCCTCTGTTGTGTGCCTGCTGAATAACTTCTATCCCAGAGAGGCCAAAGT
ACAGTGGAAGGTGGATAACGCCCTCCAATCGGGTAACTCCCAGGAGAGT
GTCACAGAGCAGGACAGCAAGGACAGCACCTACAGCCTCAGCAGCACCCT
GACGCTGAGCAAAGCAGACTACGAGAAACACAAAGTCTACGCCTGCGAAG
TCACCCATCAGGGCCTGAGCTCGCCCGTCACAAAGAGCTTCAACAGGGGA
GAGTGTTAG.

In another embodiment of the invention, polynucleotides of the invention comprise, or alternatively consist of, the following polynucleotide sequence encoding the variable heavy chain polypeptide sequence of SEQ ID NO: 3:

(SEQ ID NO: 203)
CAGTCGCTGGAGGAGTCCGGGGGTCGCCTGGTCACGCCTGGGACACCCCT
GACACTCACCTGCACAGTCTCTGGCTTCTCCCTCAGTAGCTATGCAATGA
GCTGGGTCCGCCAGGCTCCAGGGAAGGGGCTGGAATGGATCGGAGTCA
TTACTAGTATTGGTAGCACAGTCTACGCGAGCTGGGCGAAAGGCCGATT
CACCATCTCCAAAACCTCGACCACGGTGGATCTGAAAATCACCAGTCCGA
CAACCGAGGACACGGCCACCTATTTCTGTGCCAGAGGCTACGATGACTAT
GATGAGATGACCTACTTTAACATCTGGGGCCAGGGGACCCTCGTCACCGT
CTCGAGC.

In one embodiment of the invention, polynucleotides of the invention comprise, or alternatively consist of, the following polynucleotide sequence encoding the heavy chain polypeptide sequence of SEQ ID NO: 4:

(SEQ ID NO: 204)
CAGTCGCTGGAGGAGTCCGGGGGTCGCCTGGTCACGCCTGGGACACCCCT
GACACTCACCTGCACAGTCTCTGGCTTCTCCCTCAGTAGCTATGCAATGA
GCTGGGTCCGCCAGGCTCCAGGGAAGGGGCTGGAATGGATCGGAGTCA
TTACTAGTATTGGTAGCACAGTCTACGCGAGCTGGGCGAAAGGCCGATT
CACCATCTCCAAAACCTCGACCACGGTGGATCTGAAAATCACCAGTCC
GACAACCGAGGACACGGCCACCTATTTCTGTGCCAGAGGCTACGATGA
CTATGATGAGATGACCTACTTTAACATCTGGGGCCAGGGGACCCTCGTC
ACCGTCTCGAGCGCCTCCACCAAGGGCCCATCGGTCTTCCCCCTGGCA
CCCTCCTCCAAGAGCACCTCTGGGGGCACAGCGGCCCTGGGCTGCCTG
GTCAAGGACTACTTCCCCGAACCGGTGACGGTGTCGTGGAACTCAGGCG

-continued

```
CCCTGACCAGCGGCGTGCACACCTTCCCGGCTGTCCTACAGTCCTCAGG

ACTCTACTCCCTCAGCAGCGTGGTGACCGTGCCCTCCAGCAGCTTGGGC

ACCCAGACCTACATCTGCAACGTGAATCACAAGCCCAGCAACACCAAGG

TGGACAAGAGAGTTGAGCCCAAATCTTGTGACAAAACTCACACATGCCCA

CCGTGCCCAGCACCTGAACTCCTGGGGGGACCGTCAGTCTTCCTCTTCC

CCCCAAAACCCAAGGACACCCTCATGATCTCCCGGACCCCTGAGGTCA

CATGCGTGGTGGTGGACGTGAGCCACGAAGACCCTGAGGTCAAGTTCAA

CTGGTACGTGGACGGCGTGGAGGTGCATAATGCCAAGACAAAGCCGCG

GGAGGAGCAGTACGCCAGCACGTACCGTGTGGTCAGCGTCCTCACCGT

CCTGCACCAGGACTGGCTGAATGGCAAGGAGTACAAGTGCAAGGTCTC

CAACAAAGCCCTCCCAGCCCCCATCGAGAAAACCATCTCCAAAGCCA

AAGGGCAGCCCCGAGAACCACAGGTGTACACCCTGCCCCCATCCCG

GGAGGAGATGACCAAGAACCAGGTCAGCCTGACCTGCCTGGTCAAAG

GCTTCTATCCCAGCGACATCGCCGTGGAGTGGGAGAGCAATGGGCAG

CCGGAGAACAACTACAAGACCACGCCTCCCGTGCTGGACTCCGACG

GCTCCTTCTTCCTCTACAGCAAGCTCACCGTGGACAAGAGCAGGTGG

CAGCAGGGGAACGTCTTCTCATGCTCCGTGATGCATGAGGCTCTGCA

CAACCACTACACGCAGAAGAGCCTCTCCCTGTCTCCGGGTAAATGA.
```

In a further embodiment of the invention, polynucleotides encoding antibody fragments having binding specificity to NGF comprise, or alternatively consist of, one or more of the polynucleotide sequences of SEQ ID NO: 205; SEQ ID NO: 206; and SEQ ID NO: 207 which correspond to polynucleotides encoding the complementarity-determining regions (CDRs, or hypervariable regions) of the light chain variable sequence of SEQ ID NO: 1 or the light chain sequence of SEQ ID NO: 2.

In a further embodiment of the invention, polynucleotides encoding antibody fragments having binding specificity to NGF comprise, or alternatively consist of, one or more of the polynucleotide sequences of SEQ ID NO: 208; SEQ ID NO: 209; and SEQ ID NO: 210 which correspond to polynucleotides encoding the complementarity-determining regions (CDRs, or hypervariable regions) of the heavy chain variable sequence of SEQ ID NO: 3 or the heavy chain sequence of SEQ ID NO: 4.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 201 encoding the light chain variable sequence of SEQ ID NO: 1; the polynucleotide SEQ ID NO: 202 encoding the light chain sequence of SEQ ID NO: 2; the polynucleotide SEQ ID NO: 203 encoding the heavy chain variable sequence of SEQ ID NO: 3; the polynucleotide SEQ ID NO: 204 encoding the heavy chain sequence of SEQ ID NO: 4; polynucleotides encoding the complementarity-determining regions (SEQ ID NO: 205; SEQ ID NO: 206; and SEQ ID NO: 207) of the light chain variable sequence of SEQ ID NO: 1 or the light chain sequence of SEQ ID NO: 2; and polynucleotides encoding the complementarity-determining regions (SEQ ID NO: 208; SEQ ID NO: 209; and SEQ ID NO: 210) of the heavy chain variable sequence of SEQ ID NO: 3 or the heavy chain sequence of SEQ ID NO: 4.

In a preferred embodiment of the invention, polynucleotides of the invention comprise, or alternatively consist of, polynucleotides encoding Fab (fragment antigen binding) fragments having binding specificity for NGF. With respect to antibody Ab1, the polynucleotides encoding the full length Ab1 antibody comprise, or alternatively consist of, the polynucleotide SEQ ID NO: 202 encoding the light chain sequence of SEQ ID NO: 2 and the polynucleotide SEQ ID NO: 204 encoding the heavy chain sequence of SEQ ID NO: 4.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab1 following expression of the full-length polynucleotides in a suitable host. In another embodiment of the invention, anti-NGF antibodies such as Ab1 or Fab fragments or MetMab like monovalent agents thereof may be produced via expression of Ab1 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris.*

Antibody Ab2

The invention is further directed to the use of polynucleotides encoding Ab2 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab2 antibody polypeptides having binding specificity to NGF. As noted above, Ab2 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 11:

```
                                     (SEQ ID NO: 211)
GACATCCAGATGACCCAGTCTCCTTCCACCCTGTCTGCATCTGTAGGAG

ACAGAGTCACCATCACTTGCCAGGCCAGTCAGAACATTTACAGCAACTT

AGCCTGGTATCAGCAGAAACCAGGAAAAGCCCCTAAGCTCCTGATCTAT

GGTGCATCCAATCTGGATGCTGGAGTCCCATCAAGGTTCTCTGGCAGTG

GATCTGGGACAGAGTACACTCTCACCATCAGCAGCCTGCAGCCTGATG
```

-continued

ATTTTGCAACTTACTACTGCCAAAGTGCTTTTGATAGTGATAGTACTGAA

AACACTTTCGGCGGAGGAACCAAGGTGGAAATCAAACGT.

In one embodiment of the invention, polynucleotides of the invention comprise, or alternatively consist of, the following polynucleotide sequence encoding the light chain polypeptide sequence of SEQ ID NO: 12:

(SEQ ID NO: 212)
GACATCCAGATGACCCAGTCTCCTTCCACCCTGTCTGCATCTGTAGGA

GACAGAGTCACCATCACTTGCCAGGCCAGTCAGAACATTTACAGCAA

CTTAGCCTGGTATCAGCAGAAACCAGGAAAAGCCCCTAAGCTCCTGAT

CTATGGTGCATCCAATCTGGATGCTGGAGTCCCATCAAGGTTCTCTGGC

AGTGGATCTGGGACAGAGTACACTCTCACCATCAGCAGCCTGCAGCCTG

ATGATTTTGCAACTTACTACTGCCAAAGTGCTTTTGATAGTGATAGTACT

GAAAACACTTTCGGCGGAGGAACCAAGGTGGAAATCAAACGTACGGTA

GCGGCCCCATCTGTCTTCATCTTCCCGCCATCTGATGAGCAGTTGAAAT

CTGGAACTGCCTCTGTTGTGTGCCTGCTGAATAACTTCTATCCCAGAGA

GGCCAAAGTACAGTGGAAGGTGGATAACGCCCTCCAATCGGGTAACTC

CCAGGAGAGTGTCACAGAGCAGGACAGCAAGGACAGCACCTACAGCC

TCAGCAGCACCCTGACGCTGAGCAAAGCAGACTACGAGAAACACAAA

GTCTACGCCTGCGAAGTCACCCATCAGGGCCTGAGCTCGCCCGTCAC

AAAGAGCTTCAACAGGGGAGAGTGTTAG.

In another embodiment of the invention, polynucleotides of the invention comprise, or alternatively consist of, the following polynucleotide sequence encoding the variable heavy chain polypeptide sequence of SEQ ID NO: 13:

(SEQ ID NO: 213)
GAGGTGCAGCTGGTGGAGTCTGGGGGAGGCTTGGTCCAGCCTGGGGGGT

CCCTGAGACTCTCCTGTGCAGCCTCTGGATTCACCGTCAGTAGCTATGCA

ATGAGCTGGGTCCGTCAGGCTCCAGGGAAGGGGCTGGAGTGGGTCGGAG

TCATTACTAGTATTGGTAGCACAGTCTACGCGAGCAGCGCGAAAGGCCGA

TTCACCATCTCCAGAGACAATTCCAAGAACACCCTGTATCTTCAAATGAA

CAGCCTGAGAGCTGAGGACACTGCTGTGTATTACTGTGCTAGAGGCTACG

ATGACTATGATGAGATGACCTACTTTAACATCTGGGGCCAAGGGACCCTC

GTCACCGTCTCGAGC.

In one embodiment of the invention, polynucleotides of the invention comprise, or alternatively consist of, the following polynucleotide sequence encoding the heavy chain polypeptide sequence of SEQ ID NO: 14:

(SEQ ID NO: 214)
GAGGTGCAGCTGGTGGAGTCTGGGGGAGGCTTGGTCCAGCCTGGGGGG

TCCCTGAGACTCTCCTGTGCAGCCTCTGGATTCACCGTCAGTAGCTATG

CAATGAGCTGGGTCCGTCAGGCTCCAGGGAAGGGGCTGGAGTGGGTC

GGAGTCATTACTAGTATTGGTAGCACAGTCTACGCGAGCAGCGCGAAA

-continued

GGCCGATTCACCATCTCCAGAGACAATTCCAAGAACACCCTGTATCTT

CAAATGAACAGCCTGAGAGCTGAGGACACTGCTGTGTATTACTGTGCT

AGAGGCTACGATGACTATGATGAGATGACCTACTTTAACATCTGGGGC

CAAGGGACCCTCGTCACCGTCTCGAGCGCCTCCACCAAGGGCCCAT

CGGTCTTCCCCCTGGCACCCTCCTCCAAGAGCACCTCTGGGGGCAC

AGCGGCCCTGGGCTGCCTGGTCAAGGACTACTTCCCCGAACCGGTG

ACGGTGTCGTGGAACTCAGGCGCCCTGACCAGCGGCGTGCACACCT

TCCCGGCTGTCCTACAGTCCTCAGGACTCTACTCCCTCAGCAGCGTG

GTGACCGTGCCCTCCAGCAGCTTGGGCACCCAGACCTACATCTGCA

ACGTGAATCACAAGCCCAGCAACACCAAGGTGGACAAGAGAGTTGA

GCCCAAATCTTGTGACAAAACTCACACATGCCCACCGTGCCCAGCA

CCTGAACTCCTGGGGGGACCGTCAGTCTTCCTCTTCCCCCCAAAAC

CCAAGGACACCCTCATGATCTCCCGGACCCCTGAGGTCACATGCGT

GGTGGTGGACGTGAGCCACGAAGACCCTGAGGTCAAGTTCAACTGG

TACGTGGACGGCGTGGAGGTGCATAATGCCAAGACAAAGCCGCGGG

AGGAGCAGTACGCCAGCACGTACCGTGTGGTCAGCGTCCTCACCGT

CCTGCACCAGGACTGGCTGAATGGCAAGGAGTACAAGTGCAAGGTC

TCCAACAAAGCCCTCCCAGCCCCCATCGAGAAAACCATCTCCAAAG

CCAAAGGGCAGCCCCGAGAACCACAGGTGTACACCCTGCCCCCAT

CCCGGGAGGAGATGACCAAGAACCAGGTCAGCCTGACCTGCCTGG

TCAAAGGCTTCTATCCCAGCGACATCGCCGTGGAGTGGGAGAGCAA

TGGGCAGCCGGAGAACAACTACAAGACCACGCCTCCCGTGCTGGA

CTCCGACGGCTCCTTCTTCCTCTACAGCAAGCTCACCGTGGACAAG

AGCAGGTGGCAGCAGGGGAACGTCTTCTCATGCTCCGTGATGCATG

AGGCTCTGCACAACCACTACACGCAGAAGAGCCTCTCCCTGTCTCC

GGGTAAATGA.

In a further embodiment of the invention, polynucleotides encoding antibody fragments having binding specificity to NGF comprise, or alternatively consist of, one or more of the polynucleotide sequences of SEQ ID NO: 215; SEQ ID NO: 216; and SEQ ID NO: 217 which correspond to polynucleotides encoding the complementarity-determining regions (CDRs, or hypervariable regions) of the light chain variable sequence of SEQ ID NO: 11 or the light chain sequence of SEQ ID NO: 12.

In a further embodiment of the invention, polynucleotides encoding antibody fragments having binding specificity to NGF comprise, or alternatively consist of, one or more of the polynucleotide sequences of SEQ ID NO: 218; SEQ ID NO: 219; and SEQ ID NO: 220 which correspond to polynucleotides encoding the complementarity-determining regions (CDRs, or hypervariable regions) of the heavy chain variable sequence of SEQ ID NO: 13 or the heavy chain sequence of SEQ ID NO: 14.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 211 encoding the light chain variable sequence of SEQ ID NO: 11; the polynucleotide SEQ ID NO: 212 encoding the light chain sequence of SEQ ID NO: 12; the polynucleotide SEQ ID NO: 213 encoding the heavy chain variable sequence of SEQ ID NO: 13; the polynucleotide SEQ ID NO: 214 encoding the heavy chain sequence of SEQ ID NO: 14; polynucleotides encoding the complementarity-determining regions (SEQ ID NO: 215; SEQ ID NO: 216; and SEQ ID NO: 217) of the light chain variable sequence of SEQ ID NO: 11 or the light chain sequence of SEQ ID NO: 12; and polynucleotides encoding the complementarity-determining regions (SEQ ID NO: 218; SEQ ID NO: 219; and SEQ ID NO: 220) of the heavy chain variable sequence of SEQ ID NO: 13 or the heavy chain sequence of SEQ ID NO: 14.

In a preferred embodiment of the invention, polynucleotides of the invention comprise, or alternatively consist of, polynucleotides encoding Fab (fragment antigen binding) fragments having binding specificity for NGF. With respect to antibody Ab2, the polynucleotides encoding the full length Ab2 antibody comprise, or alternatively consist of, the polynucleotide SEQ ID NO: 212 encoding the light chain sequence of SEQ ID NO: 12 and the polynucleotide SEQ ID NO: 214 encoding the heavy chain sequence of SEQ ID NO: 14.

Another embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab2 following expression of the full-length polynucleotides in a suitable host. In another embodiment of the invention, anti-NGF antibodies such as Ab2 or Fab fragments thereof may be produced via expression of Ab2 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab3

The invention is further directed to the use of polynucleotides encoding Ab3 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab3 antibody polypeptides having binding specificity to NGF. As noted above, Ab3 antibodies inhibit the interaction of NGF with TrkA and do not appreciably inhibit the interaction of NGF with p75. In one embodiment of the invention, polynucleotides of the invention comprise, or alternatively consist of, the following polynucleotide sequence encoding the variable light chain polypeptide sequence of SEQ ID NO: 21:

```
                                        (SEQ ID NO: 221)
GCAGCCGTGCTGACCCAGACACCATCGCCCGTGTCTGCAGCTATGGGAG

ACACAGTCACCATCAAGTGCCAGTCCAGTCAGAGTGTTTATAAGAACAA

CTACTTATCCTGGTATCAGCAGAAACCAGGGCAGCCTCCCAGGCTCCTGA

TCTATGATGCATCCAATCTGCCATCTGGGGTCCCATCACGGTTCAGCGGC

AGTGGATCTGGGACACAGTTCACTCTCACCATCAGCGGCGTGCAGTGTGA

CGATGCTGCCACTTACTACTGTCTAGGCGATTATGATGATGATGCTGATA

ATGCTTTCGGCGGAGGGACCGAGGTGGTGGTCAAACGT.
```

In one embodiment of the invention, polynucleotides of the invention comprise, or alternatively consist of, the following polynucleotide sequence encoding the light chain polypeptide sequence of SEQ ID NO: 22:

```
                                        (SEQ ID NO: 222)
GCAGCCGTGCTGACCCAGACACCATCGCCCGTGTCTGCAGCTATGGGAG

ACACAGTCACCATCAAGTGCCAGTCCAGTCAGAGTGTTTATAAGAACAA

CTACTTATCCTGGTATCAGCAGAAACCAGGGCAGCCTCCCAGGCTCCT

GATCTATGATGCATCCAATCTGCCATCTGGGGTCCCATCACGGTTCAGC

GGCAGTGGATCTGGGACACAGTTCACTCTCACCATCAGCGGCGTGCAG

TGTGACGATGCTGCCACTTACTACTGTCTAGGCGATTATGATGATGATGC

TGATAATGCTTTCGGCGGAGGGACCGAGGTGGTGGTCAAACGTACGGTA

GCGGCCCCATCTGTCTTCATCTTCCCGCCATCTGATGAGCAGTTGAAATC

TGGAACTGCCTCTGTTGTGTGCCTGCTGAATAACTTCTATCCCAGAGAGG

CCAAAGTACAGTGGAAGGTGGATAACGCCCTCCAATCGGGTAACTCCCA

GGAGAGTGTCACAGAGCAGGACAGCAAGGACAGCACCTACAGCCTCAG

CAGCACCCTGACGCTGAGCAAAGCAGACTACGAGAAACACAAAGTCTA

CGCCTGCGAAGTCACCCATCAGGGCCTGAGCTCGCCCGTCACAAAGAG

CTTCAACAGGGGAGAGTGTTAG.
```

In another embodiment of the invention, polynucleotides of the invention comprise, or alternatively consist of, the following polynucleotide sequence encoding the variable heavy chain polypeptide sequence of SEQ ID NO: 23:

```
                                        (SEQ ID NO: 223)
CAGTCGGTGGAGGAGTCCGGGGGTCGCCTGGTCACGCCTGGGACACCCC

TGACACTCACCTGCACAGTCTCTGGATTCTCCCTCAGTAGCTATGTAATG

ATCTGGGTCCGCCAGGCTCCAGGGAAGGGGCTGGAATACATCGGAATCA

CTTGGAGTGCTGGTACATACTACGCGAGCTGGGCGAAAGGCCGATTCACC

ATCTCCAAAACCTCGTCGACCACGGTGGATCTGAAAATCACCAGTCCGA

CAACCGAGGACACGGCCACCTATTTCTGTGCCGGAGGTGGTGGTAGTAT

TTATGATATTTGGGGCCCGGGCACCCTGGTCACCGTCTCGAGC.
```

In one embodiment of the invention, polynucleotides of the invention comprise, or alternatively consist of, the following polynucleotide sequence encoding the heavy chain polypeptide sequence of SEQ ID NO: 24:

(SEQ ID NO: 224)

CAGTCGGTGGAGGAGTCCGGGGGTCGCCTGGTCACGCCTGGGACACCCC

TGACACTCACCTGCACAGTCTCTGGATTCTCCCTCAGTAGCTATGTAAT

GATCTGGGTCCGCCAGGCTCCAGGGAAGGGGCTGGAATACATCGGAATC

ACTTGGAGTGCTGGTACATACTACGCGAGCTGGGCGAAAGGCCGATTCA

CCATCTCCAAAACCTCGTCGACCACGGTGGATCTGAAAATCACCAGTCC

GACAACCGAGGACACGGCCACCTATTTCTGTGCCGGAGGTGGTGGTAGT

ATTTATGATATTTGGGGCCCGGGCACCCTGGTCACCGTCTCGAGCGCCT

CCACCAAGGGCCCATCGGTCTTCCCCCTGGCACCCTCCTCCAAGAGCAC

CTCTGGGGGCACAGCGGCCCTGGGCTGCCTGGTCAAGGACTACTTCCCC

GAACCGGTGACGGTGTCGTGGAACTCAGGCGCCCTGACCAGCGGCGTGC

ACACCTTCCCGGCTGTCCTACAGTCCTCAGGACTCTACTCCCTCAGCAG

CGTGGTGACCGTGCCCTCCAGCAGCTTGGGCACCCAGACCTACATCTGC

AACGTGAATCACAAGCCCAGCAACACCAAGGTGGACAAGAGAGTTGAGC

CCAAATCTTGTGACAAAACTCACACATGCCCACCGTGCCCAGCACCTGA

ACTCCTGGGGGGACCGTCAGTCTTCCTCTTCCCCCCAAAACCCAAGGAC

ACCCTCATGATCTCCCGGACCCCTGAGGTCACATGCGTGGTGGTGGACG

TGAGCCACGAAGACCCTGAGGTCAAGTTCAACTGGTACGTGGACGGCGT

GGAGGTGCATAATGCCAAGACAAAGCCGCGGGAGGAGCAGTACGCCAGC

ACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCC

CATCGAGAAAACCATCTCCAAAGCCAAAGGGCAGCCCCGAGAACCACAG

GTGTACACCCTGCCCCCATCCCGGGAGGAGATGACCAAGAACCAGGTCA

GCCTGACCTGCCTGGTCAAAGGCTTCTATCCCAGCGACATCGCCGTGGA

GTGGGAGAGCAATGGGCAGCCGGAGAACAACTACAAGACCACGCCTCCC

GTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCA

TGAGGCTCTGCACAACCACTACACGCAGAAGAGCCTCTCCCTGTCTCCG

GGTAAATGA.

In a further embodiment of the invention, polynucleotides encoding antibody fragments having binding specificity to NGF comprise, or alternatively consist of, one or more of the polynucleotide sequences of SEQ ID NO: 225; SEQ ID NO: 226; and SEQ ID NO: 227 which correspond to polynucleotides encoding the complementarity-determining regions (CDRs, or hypervariable regions) of the light chain variable sequence of SEQ ID NO: 21 or the light chain sequence of SEQ ID NO: 22.

In a further embodiment of the invention, polynucleotides encoding antibody fragments having binding specificity to NGF comprise, or alternatively consist of, one or more of the polynucleotide sequences of SEQ ID NO: 228; SEQ ID NO: 229; and SEQ ID NO: 230 which correspond to polynucleotides encoding the complementarity-determining regions (CDRs, or hypervariable regions) of the heavy chain variable sequence of SEQ ID NO: 23 or the heavy chain sequence of SEQ ID NO: 24.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 221 encoding the light chain variable sequence of SEQ ID NO: 21; the polynucleotide SEQ ID NO: 222 encoding the light chain sequence of SEQ ID NO: 22; the polynucleotide SEQ ID NO: 223 encoding the heavy chain variable sequence of SEQ ID NO: 23; the polynucleotide SEQ ID NO: 224 encoding the heavy chain sequence of SEQ ID NO: 24; polynucleotides encoding the complementarity-determining regions (SEQ ID NO: 225; SEQ ID NO: 226; and SEQ ID NO: 227) of the light chain variable sequence of SEQ ID NO: 21 or the light chain sequence of SEQ ID NO: 22; and polynucleotides encoding the complementarity-determining regions (SEQ ID NO: 228; SEQ ID NO: 229; and SEQ ID NO: 230) of the heavy chain variable sequence of SEQ ID NO: 23 or the heavy chain sequence of SEQ ID NO: 24.

In a preferred embodiment of the invention, polynucleotides of the invention comprise, or alternatively consist of, polynucleotides encoding Fab (fragment antigen binding) fragments having binding specificity for NGF. With respect to antibody Ab3, the polynucleotides encoding the full length Ab3 antibody comprise, or alternatively consist of, the polynucleotide SEQ ID NO: 222 encoding the light chain sequence of SEQ ID NO: 22 and the polynucleotide SEQ ID NO: 224 encoding the heavy chain sequence of SEQ ID NO: 24.

Another embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab3 following expression of the full-length polynucleotides in a suitable host. In another embodiment of the invention, anti-NGF antibodies such as Ab3 or Fab fragments thereof or MetMab like monovalent agents may be produced via expression of Ab3 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab4

The invention is further directed to the use of polynucleotides encoding Ab4 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nobodies, IgNAR, a monovalent antibody molecule analagous to MetMab, or one or more combinations thereof. Described below are polynucleotides encoding Ab4 antibody polypeptides having binding specificity to NGF. As noted above, Ab4 antibodies inhibit the interaction of NGF with TrkA and do not appreciably inhibit the interaction of NGF with p75. In one embodiment of the invention, polynucleotides of the invention comprise, or alternatively consist of, the following polynucleotide sequence encoding the variable light chain polypeptide sequence of SEQ ID NO: 31:

(SEQ ID NO: 231)
GACATCCAGATGACCCAGTCTCCTTCCACCCTGTCTGCATCTGTAGGAG
ACAGAGTCACCATCACTTGCCAGTCCAGTCAGAGTGTCTATAAGAACAA
CTACTTATCCTGGTATCAGCAGAAACCAGGAAAAGCCCCTAAGCTCCTG
ATCTATGATGCATCCAATCTGCCATCTGGAGTCCCATCAAGGTTCAGCG
GCAGTGGATCTGGAACAGAATTCACTCTCACCATCAGCAGCCTGCAGCC
TGATGATTTTGCAACTTATTACTGCCTAGGCGATTATGATGATGATGCT
GATAATGCTTTCGGCGGAGGAACCAAGGTGGAAATCAAACGT.

In one embodiment of the invention, polynucleotides of the invention comprise, or alternatively consist of, the following polynucleotide sequence encoding the light chain polypeptide sequence of SEQ ID NO: 32:

(SEQ ID NO: 232)
GACATCCAGATGACCCAGTCTCCTTCCACCCTGTCTGCATCTGTAGGAG
ACAGAGTCACCATCACTTGCCAGTCCAGTCAGAGTGTCTATAAGAACAA
CTACTTATCCTGGTATCAGCAGAAACCAGGAAAAGCCCCTAAGCTCCTG
ATCTATGATGCATCCAATCTGCCATCTGGAGTCCCATCAAGGTTCAGCG
GCAGTGGATCTGGAACAGAATTCACTCTCACCATCAGCAGCCTGCAGCC
TGATGATTTTGCAACTTATTACTGCCTAGGCGATTATGATGATGATGCT
GATAATGCTTTCGGCGGAGGAACCAAGGTGGAAATCAAACGTACGGTAG
CGGCCCCATCTGTCTTCATCTTCCCGCCATCTGATGAGCAGTTGAAATC
TGGAACTGCCTCTGTTGTGTGCCTGCTGAATAACTTCTATCCCAGAGAG
GCCAAAGTACAGTGGAAGGTGGATAACGCCCTCCAATCGGGTAACTCCC
AGGAGAGTGTCACAGAGCAGGACAGCAAGGACAGCACCTACAGCCTCAG
CAGCACCCTGACGCTGAGCAAAGCAGACTACGAGAAACACAAAGTCTAC
GCCTGCGAAGTCACCCATCAGGGCCTGAGCTCGCCCGTCACAAAGAGCT
TCAACAGGGGAGAGTGTTAG.

In another embodiment of the invention, polynucleotides of the invention comprise, or alternatively consist of, the following polynucleotide sequence encoding the variable heavy chain polypeptide sequence of SEQ ID NO: 33:

(SEQ ID NO: 233)
GAGGTGCAGCTGGTGGAGTCTGGGGGAGGCTTGGTCCAGCCTGGGGGGT
CCCTGAGACTCTCCTGTGCAGCCTCTGGATTCACCGTCAGTAGCTATGT
AATGATCTGGGTCCGTCAGGCTCCAGGGAAGGGGCTGGAGTACATCGGA
ATCACTTGGAGTGCTGGTACATACTACGCGAGCAGTGCGAAAGGCCGAT
TCACCATCTCCAGAGACAATTCCAAGAACACCCTGTATCTTCAAATGAA
CAGCCTGAGAGCTGAGGACACTGCTGTGTATTACTGTGCTGGAGGTGGT
GGTAGTATCTATGATATTTGGGGCCAAGGGACCCTCGTCACCGTCTCGA
GC.

In one embodiment of the invention, polynucleotides of the invention comprise, or alternatively consist of, the following polynucleotide sequence encoding the heavy chain polypeptide sequence of SEQ ID NO: 34:

(SEQ ID NO: 234)
GAGGTGCAGCTGGTGGAGTCTGGGGGAGGCTTGGTCCAGCCTGGGGGGT
CCCTGAGACTCTCCTGTGCAGCCTCTGGATTCACCGTCAGTAGCTATGT
AATGATCTGGGTCCGTCAGGCTCCAGGGAAGGGGCTGGAGTACATCGGA
ATCACTTGGAGTGCTGGTACATACTACGCGAGCAGTGCGAAAGGCCGAT
TCACCATCTCCAGAGACAATTCCAAGAACACCCTGTATCTTCAAATGAA
CAGCCTGAGAGCTGAGGACACTGCTGTGTATTACTGTGCTGGAGGTGGT
GGTAGTATCTATGATATTTGGGGCCAAGGGACCCTCGTCACCGTCTCGA
GCGCCTCCACCAAGGGCCCATCGGTCTTCCCCCTGGCACCCTCCTCCAA
GAGCACCTCTGGGGGCACAGCGGCCCTGGGCTGCCTGGTCAAGGACTAC
TTCCCCGAACCGGTGACGGTGTCGTGGAACTCAGGCGCCCTGACCAGCG
GCGTGCACACCTTCCCGGCTGTCCTACAGTCCTCAGGACTCTACTCCCT
CAGCAGCGTGGTGACCGTGCCCTCCAGCAGCTTGGGCACCCAGACCTAC
ATCTGCAACGTGAATCACAAGCCCAGCAACACCAAGGTGGACAAGAGAG
TTGAGCCCAAATCTTGTGACAAAACTCACACATGCCCACCGTGCCCAGC
AACCTGACTCCTGGGGGGACCGTCAGTCTTCCTCTTCCCCCCAAAACCC
AAGGACACCCTCATGATCTCCCGGACCCCTGAGGTCACATGCGTGGTGG
TGGACGTGAGCCACGAAGACCCTGAGGTCAAGTTCAACTGGTACGTGGA
CGGCGTGGAGGTGCATAATGCCAAGACAAAGCCGCGGGAGGAGCAGTAC
GCCAGCACGTACCGTGTGGTCAGCGTCCTCACCGTCCTGCACCAGGACT
GGCTGAATGGCAAGGAGTACAAGTGCAAGGTCTCCAACAAAGCCCTCCC
AGCCCCCATCGAGAAAACCATCTCCAAAGCCAAAGGGCAGCCCCGAGAA
CCACAGGTGTACACCCTGCCCCCATCCCGGGAGGAGATGACCAAGAACC
AGGTCAGCCTGACCTGCCTGGTCAAAGGCTTCTATCCCAGCGACATCGC
CGTGGAGTGGGAGAGCAATGGGCAGCCGGAGAACAACTACAAGACCACG
CCTCCCGTGCTGGACTCCGACGGCTCCTTCTTCCTCTACAGCAAGCTCA
CCGTGGACAAGAGCAGGTGGCAGCAGGGGAACGTCTTCTCATGCTCCGT
GATGCATGAGGCTCTGCACAACCACTACACGCAGAAGAGCCTCTCCCTG
TCTCCGGGTAAATGA.

In a further embodiment of the invention, polynucleotides encoding antibody fragments having binding specificity to NGF comprise, or alternatively consist of, one or more of the polynucleotide sequences of SEQ ID NO: 235; SEQ ID NO: 236; and SEQ ID NO: 237 which correspond to polynucleotides encoding the complementarity-determining regions (CDRs, or hypervariable regions) of the light chain variable sequence of SEQ ID NO: 31 or the light chain sequence of SEQ ID NO: 32.

In a further embodiment of the invention, polynucleotides encoding antibody fragments having binding specificity to NGF comprise, or alternatively consist of, one or more of the polynucleotide sequences of SEQ ID NO: 238; SEQ ID NO: 239; and SEQ ID NO: 240 which correspond to polynucleotides encoding the complementarity-determining regions (CDRs, or hypervariable regions) of the heavy chain variable sequence of SEQ ID NO: 33 or the heavy chain sequence of SEQ ID NO: 34.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 231 encoding the light chain variable sequence of SEQ ID NO: 31; the polynucleotide SEQ ID NO: 232 encoding the light chain sequence of SEQ ID NO: 32; the polynucleotide SEQ ID NO: 233 encoding the heavy chain variable sequence of SEQ ID NO: 33; the polynucleotide SEQ ID NO: 234 encoding the heavy chain sequence of SEQ ID NO: 34; polynucleotides encoding the complementarity-determining regions (SEQ ID NO: 235; SEQ ID NO: 236; and SEQ ID NO: 237) of the light chain variable sequence of SEQ ID NO: 31 or the light chain sequence of SEQ ID NO: 32; and polynucleotides encoding the complementarity-determining regions (SEQ ID NO: 238; SEQ ID NO: 239; and SEQ ID NO: 240) of the heavy chain variable sequence of SEQ ID NO: 33 or the heavy chain sequence of SEQ ID NO: 34.

In a preferred embodiment of the invention, polynucleotides of the invention comprise, or alternatively consist of, polynucleotides encoding Fab (fragment antigen binding) fragments having binding specificity for NGF. With respect to antibody Ab4, the polynucleotides encoding the full length Ab4 antibody comprise, or alternatively consist of, the polynucleotide SEQ ID NO: 232 encoding the light chain sequence of SEQ ID NO: 32 and the polynucleotide SEQ ID NO: 234 encoding the heavy chain sequence of SEQ ID NO: 34.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab4 following expression of the full-length polynucleotides in a suitable host. In another embodiment of the invention, anti-NGF antibodies such as Ab4 or Fab fragments thereof or MetMab like monovalent agents may be produced via expression of Ab4 polynucleotides in mammalian cells such as CHO, NSO or HEK 293 cells, fungal, insect, plant cells or transgenic plants, transgenic animal or microbial systems such as yeast cells (for example diploid yeast such as diploid *Pichia*) and other yeast strains. Suitable *Pichia* species include, but are not limited to, *Pichia pastoris*.

Antibody Ab5

The invention is further directed to the use of polynucleotides encoding Ab5 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab5 antibody polypeptides having binding specificity to NGF. As noted above, Ab5 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 41:

```
                                        (SEQ ID NO: 241)
GCCTATGATATGACCCAGACTCCAGCCTCTGTGGAGGTAGCTGTGGGAG
GCACAGTCACCATCAAGTGCCAGGCCAGTCAGAGCATTTACAGCAATTT
AGCCTGGTATCAGCAGAGACCAGGGCAGCCTCCCAAGCTCCTGATCTAT
GATGCATCCACTCTGGAATCTGGGGTCCCATCGCGGTTCAAAGGCAGTG
GATCTGGGACAGAGTACACTCTCACCATCAGCGGCGTGGAGTGTGCCGA
TGCTGCCTCTTACTACTGTCAACAGGGTTTTACTGTTAGTGATATTGAT
AATGCTTTCGGCGGAGGGACCGAGGTGGTGGTCAAACGT.
```

In one embodiment of the invention, polynucleotides of the invention comprise, or alternatively consist of, the following polynucleotide sequence encoding the light chain polypeptide sequence of SEQ ID NO: 42:

```
                                        (SEQ ID NO: 242)
GCCTATGATATGACCCAGACTCCAGCCTCTGTGGAGGTAGCTGTGGGAG
GCACAGTCACCATCAAGTGCCAGGCCAGTCAGAGCATTTACAGCAATTT
AGCCTGGTATCAGCAGAGACCAGGGCAGCCTCCCAAGCTCCTGATCTAT
GATGCATCCACTCTGGAATCTGGGGTCCCATCGCGGTTCAAAGGCAGTG
GATCTGGGACAGAGTACACTCTCACCATCAGCGGCGTGGAGTGTGCCGA
TGCTGCCTCTTACTACTGTCAACAGGGTTTTACTGTTAGTGATATTGAT
AATGCTTTCGGCGGAGGGACCGAGGTGGTGGTCAAACGTACGGTAGCGG
CCCCATCTGTCTTCATCTTCCCGCCATCTGATGAGCAGTTGAAATCTGG
AACTGCCTCTGTTGTGTGCCTGCTGAATAACTTCTATCCCAGAGAGGCC
AAAGTACAGTGGAAGGTGGATAACGCCCTCCAATCGGGTAACTCCCAGG
AGAGTGTCACAGAGCAGGACAGCAAGGACAGCACCTACAGCCTCAGCAG
CACCCTGACGCTGAGCAAAGCAGACTACGAGAAACACAAAGTCTACGCC
TGCGAAGTCACCCATCAGGGCCTGAGCTCGCCCGTCACAAAGAGCTTCA
ACAGGGGAGAGTGTTAG.
```

In another embodiment of the invention, polynucleotides of the invention comprise, or alternatively consist of, the following polynucleotide sequence encoding the variable heavy chain polypeptide sequence of SEQ ID NO: 43:

```
                                        (SEQ ID NO: 243)
CAGTCGGTGGAGGAGTCCGGGGGTCGCCTGGTCACGCCTGGGACACCCC
TGACACTCACCTGCACAGTCTCTGGATTCTCCCTCAGTAACTATGCAGT
GGGCTGGGTCCGCCAGGCTCCAGGGAAGGGGCTGGAATGGATCGGAATC
ATTGGTCGTAATGGTAACACATGGTACGCGAGCTGGGCAAGAGGCCGAT
TCACCATCTCCAAAACCTCGACCACGGTGGATCTGAAAATCACCAGTCC
GACAAGCGAGGACACGGCCACATATTTCTGTGCCAGAGGATATGGCCGT
```

-continued

AGTGTTGCTTATTACGTCTTTAACATCTGGGGCCCAGGCACCCTCGTCA

CCGTCTCGAGC.

In one embodiment of the invention, polynucleotides of the invention comprise, or alternatively consist of, the following polynucleotide sequence encoding the heavy chain polypeptide sequence of SEQ ID NO: 44:

(SEQ ID NO: 244)

CAGTCGGTGGAGGAGTCCGGGGGTCGCCTGGTCACGCCTGGGACACCCC

TGACACTCACCTGCACAGTCTCTGGATTCTCCCTCAGTAACTATGCAGT

GGGCTGGGTCCGCCAGGCTCCAGGGAAGGGGCTGGAATGGATCGGAATC

ATTGGTCGTAATGGTAACACATGGTACGCGAGCTGGGCAAGAGGCCGAT

TCACCATCTCCAAAACCTCGACCACGGTGGATCTGAAAATCACCAGTCC

GACAAGCGAGGACACGGCCACATATTTCTGTGCCAGAGGATATGGCCGT

AGTGTTGCTTATTACGTCTTTAACATCTGGGGCCCAGGCACCCTCGTCA

CCGTCTCGAGCGCCTCCACCAAGGGCCCATCGGTCTTCCCCCTGGCACC

CTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCC

TGACCAGCGGCGTGCACACCTTCCCGGCTGTCCTACAGTCCTCAGGACT

CTACTCCCTCAGCAGCGTGGTGACCGTGCCCTCCAGCAGCTTGGGCACC

CAGACCTACATCTGCAACGTGAATCACAAGCCCAGCAACACCAAGGTGG

ACAAGAGAGTTGAGCCCAAATCTTGTGACAAAACTCACACATGCCCACC

GTGCCCAGCACCTGAACTCCTGGGGGGACCGTCAGTCTTCCTCTTCCCC

CCAAAACCCAAGGACACCCTCATGATCTCCCGGACCCCTGAGGTCACAT

GCGTGGTGGTGGACGTGAGCCACGAAGACCCTGAGGTCAAGTTCAACTG

GTACGTGGACGGCGTGGAGGTGCATAATGCCAAGACAAAGCCGCGGGAG

GAGCAGTACGCCAGCACGTACCGTGTGGTCAGCGTCCTCACCGTCCTGC

ACCAGGACTGGCTGAATGGCAAGGAGTACAAGTGCAAGGTCTCCAACAA

AGCCCTCCCAGCCCCCATCGAGAAAACCATCTCCAAAGCCAAAGGGCAG

CCCCGAGAACCACAGGTGTACACCCTGCCCCCATCCCGGGAGGAGATGA

CCAAGAACCAGGTCAGCCTGACCTGCCTGGTCAAAGGCTTCTATCCCAG

CGACATCGCCGTGGAGTGGGAGAGCAATGGGCAGCCGGAGAACAACTAC

AAGACCACGCCTCCCGTGCTGGACTCCGACGGCTCCTTCTTCCTCTACA

GCAAGCTCACCGTGGACAAGAGCAGGTGGCAGCAGGGGAACGTCTTCTC

ATGCTCCGTGATGCATGAGGCTCTGCACAACCACTACACGCAGAAGAGC

CTCTCCCTGTCTCCGGGTAAATGA.

In a further embodiment of the invention, polynucleotides encoding antibody fragments having binding specificity to NGF comprise, or alternatively consist of, one or more of the polynucleotide sequences of SEQ ID NO: 245; SEQ ID NO: 246; and SEQ ID NO: 247 which correspond to polynucleotides encoding the complementarity-determining regions (CDRs, or hypervariable regions) of the light chain variable sequence of SEQ ID NO: 41 or the light chain sequence of SEQ ID NO: 42.

In a further embodiment of the invention, polynucleotides encoding antibody fragments having binding specificity to NGF comprise, or alternatively consist of, one or more of the polynucleotide sequences of SEQ ID NO: 248; SEQ ID NO: 249; and SEQ ID NO: 250 which correspond to polynucleotides encoding the complementarity-determining regions (CDRs, or hypervariable regions) of the heavy chain variable sequence of SEQ ID NO: 43 or the heavy chain sequence of SEQ ID NO: 44.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 241 encoding the light chain variable sequence of SEQ ID NO: 41; the polynucleotide SEQ ID NO: 242 encoding the light chain sequence of SEQ ID NO: 42; the polynucleotide SEQ ID NO: 243 encoding the heavy chain variable sequence of SEQ ID NO: 43; the polynucleotide SEQ ID NO: 244 encoding the heavy chain sequence of SEQ ID NO: 44; polynucleotides encoding the complementarity-determining regions (SEQ ID NO: 245; SEQ ID NO: 246; and SEQ ID NO: 247) of the light chain variable sequence of SEQ ID NO: 41 or the light chain sequence of SEQ ID NO: 42; and polynucleotides encoding the complementarity-determining regions (SEQ ID NO: 248; SEQ ID NO: 249; and SEQ ID NO: 250) of the heavy chain variable sequence of SEQ ID NO: 43 or the heavy chain sequence of SEQ ID NO: 44.

In a preferred embodiment of the invention, polynucleotides of the invention comprise, or alternatively consist of, polynucleotides encoding Fab (fragment antigen binding) fragments having binding specificity for NGF and MetMab like monovalent agents. With respect to antibody Ab5, the polynucleotides encoding the full length Ab5 antibody comprise, or alternatively consist of, the polynucleotide SEQ ID NO: 242 encoding the light chain sequence of SEQ ID NO: 42 and the polynucleotide SEQ ID NO: 244 encoding the heavy chain sequence of SEQ ID NO: 44.

Another embodiment of the invention contemplates these polynucleotides incorporated into an expression vector for expression in mammalian cells such as CHO, NSO, HEK-293, or in fungal, insect, transgenic plant or animals, plant cells, or microbial systems such as bacterial or yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab5 following expression of the full-length polynucleotides in a suitable host. In another embodiment of the invention, anti-NGF antibodies such as Ab5 or Fab fragments thereof may be produced via expression of Ab5 polynucleotides in mammalian cells such as CHO, NSO or HEK 293 cells, fungal, insect, plant, or microbial systems such as yeast cells (for example diploid yeast such as diploid *Pichia*) and other yeast strains. Suitable *Pichia* species include, but are not limited to, *Pichia pastoris*.

Antibody Ab6

The invention is further directed to the use of polynucleotides encoding Ab6 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab6 antibody polypeptides having binding specificity to NGF. As noted above, Ab6 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 51:

(SEQ ID NO: 251)
GACATCCAGATGACCCAGTCTCCTTCCACCCTGTCTGCATCTGTAGGAG

ACAGAGTCACCATCACTTGCCAGGCCAGTCAGAGCATTTACAGCAATCT

TGCCTGGTATCAGCAGAAACCAGGAAAAGCCCCTAAGCTCCTGATCTAT

GATGCATCCACTCTGGAATCTGGAGTCCCATCAAGGTTCAGCGGCAGTG

GATCTGGGACAGAGTACACTCTCACCATCAGCAGCCTGCAGCCTGATGA

TTTTGCAACTTACTACTGCCAACAGGGTTTTACTGTTAGTGATATTGAT

AATGCTTTCGGCGGAGGAACCAAGGTGGAAATCAAACGT.

In one embodiment of the invention, polynucleotides of the invention comprise, or alternatively consist of, the following polynucleotide sequence encoding the light chain polypeptide sequence of SEQ ID NO: 52:

(SEQ ID NO: 252)
GACATCCAGATGACCCAGTCTCCTTCCACCCTGTCTGCATCTGTAGGAG

ACAGAGTCACCATCACTTGCCAGGCCAGTCAGAGCATTTACAGCAATCT

TGCCTGGTATCAGCAGAAACCAGGAAAAGCCCCTAAGCTCCTGATCTAT

GATGCATCCACTCTGGAATCTGGAGTCCCATCAAGGTTCAGCGGCAGTG

GATCTGGGACAGAGTACACTCTCACCATCAGCAGCCTGCAGCCTGATGA

TTTTGCAACTTACTACTGCCAACAGGGTTTTACTGTTAGTGATATTGAT

AATGCTTTCGGCGGAGGAACCAAGGTGGAAATCAAACGTACGGTAGCGG

CCCCATCTGTCTTCATCTTCCCGCCATCTGATGAGCAGTTGAAATCTGG

AACTGCCTCTGTTGTGTGCCTGCTGAATAACTTCTATCCCAGAGAGGCC

AAAGTACAGTGGAAGGTGGATAACGCCCTCCAATCGGGTAACTCCCAGG

AGAGTGTCACAGAGCAGGACAGCAAGGACAGCACCTACAGCCTCAGCAG

CACCCTGACGCTGAGCAAAGCAGACTACGAGAAACACAAAGTCTACGCC

TGCGAAGTCACCCATCAGGGCCTGAGCTCGCCCGTCACAAAGAGCTTCA

ACAGGGGAGAGTGTTAG.

In another embodiment of the invention, polynucleotides of the invention comprise, or alternatively consist of, the following polynucleotide sequence encoding the variable heavy chain polypeptide sequence of SEQ ID NO: 53:

(SEQ ID NO: 253)
GAGGTGCAGCTGGTGGAGTCTGGGGGAGGCTTGGTCCAGCCTGGGGGGT

CCCTGAGACTCTCCTGTGCAGCCTCTGGATTCACCGTCAGTAACTATGC

AGTGGGCTGGGTCCGTCAGGCTCCAGGGAAGGGGCTGGAGTGGGTCGGA

-continued

ATCATTGGTCGTAATGGTAACACATGGTACGCGAGCTCTGCAAGAGGCC

GATTCACCATCTCCAGAGACAATTCCAAGAACACCCTGTATCTTCAAAT

GAACAGCCTGAGAGCTGAGGACACTGCTGTGTATTACTGTGCTAGAGGA

TATGGCCGTAGTGTTGCTTATTACGTCTTTAACATCTGGGGCCCAGGGA

CCCTCGTCACCGTCTCGAGC.

In one embodiment of the invention, polynucleotides of the invention comprise, or alternatively consist of, the following polynucleotide sequence encoding the heavy chain polypeptide sequence of SEQ ID NO: 54:

(SEQ ID NO: 254)
GAGGTGCAGCTGGTGGAGTCTGGGGGAGGCTTGGTCCAGCCTGGGGGGT

CCCTGAGACTCTCCTGTGCAGCCTCTGGATTCACCGTCAGTAACTATGC

AGTGGGCTGGGTCCGTCAGGCTCCAGGGAAGGGGCTGGAGTGGGTCGGA

ATCATTGGTCGTAATGGTAACACATGGTACGCGAGCTCTGCAAGAGGCC

GATTCACCATCTCCAGAGACAATTCCAAGAACACCCTGTATCTTCAAAT

GAACAGCCTGAGAGCTGAGGACACTGCTGTGTATTACTGTGCTAGAGGA

TATGGCCGTAGTGTTGCTTATTACGTCTTTAACATCTGGGGCCCAGGGA

CCCTCGTCACCGTCTCGAGCGCCTCCACCAAGGGCCCATCGGTCTTCCC

CCTGGCACCCTCCTCCAAGAGCACCTCTGGGGGCACAGCGGCCCTGGGC

TGCCTGGTCAAGGACTACTTCCCCGAACCGGTGACGGTGTCGTGGAACT

CAGGCGCCCTGACCAGCGGCGTGCACACCTTCCCGGCTGTCCTACAGTC

CTCAGGACTCTACTCCCTCAGCAGCGTGGTGACCGTGCCCTCCAGCAGC

TTGGGCACCCAGACCTACATCTGCAACGTGAATCACAAGCCCAGCAACA

CCAAGGTGGACAAGAGAGTTGAGCCCAAATCTTGTGACAAAACTCACAC

ATGCCCACCGTGCCCAGCACCTGAACTCCTGGGGGGACCGTCAGTCTTC

CTCTTCCCCCCAAAACCCAAGGACACCCTCATGATCTCCCGGACCCCTG

AGGTCACATGCGTGGTGGTGGACGTGAGCCACGAAGACCCTGAGGTCAA

GTTCAACTGGTACGTGGACGGCGTGGAGGTGCATAATGCCAAGACAAAG

CCGCGGGAGGAGCAGTACGCCAGCACGTACCGTGTGGTCAGCGTCCTCA

CCGTCCTGCACCAGGACTGGCTGAATGGCAAGGAGTACAAGTGCAAGGT

CTCCAACAAAGCCCTCCCAGCCCCCATCGAGAAAACCATCTCCAAAGCC

AAAGGGCAGCCCCGAGAACCACAGGTGTACACCCTGCCCCCATCCCGGG

AGGAGATGACCAAGAACCAGGTCAGCCTGACCTGCCTGGTCAAAGGCTT

CTATCCCAGCGACATCGCCGTGGAGTGGGAGAGCAATGGGCAGCCGGAG

AACAACTACAAGACCACGCCTCCCGTGCTGGACTCCGACGGCTCCTTCT

TCCTCTACAGCAAGCTCACCGTGGACAAGAGCAGGTGGCAGCAGGGGAA

CGTCTTCTCATGCTCCGTGATGCATGAGGCTCTGCACAACCACTACACG

CAGAAGAGCCTCTCCCTGTCTCCGGGTAAATGA.

In a further embodiment of the invention, polynucleotides encoding antibody fragments having binding specificity to NGF comprise, or alternatively consist of, one or more of the polynucleotide sequences of SEQ ID NO: 255; SEQ ID NO: 256; and SEQ ID NO: 257 which correspond to polynucleotides encoding the complementarity-determining regions (CDRs, or hypervariable regions) of the light chain variable sequence of SEQ ID NO: 51 or the light chain sequence of SEQ ID NO: 52.

In a further embodiment of the invention, polynucleotides encoding antibody fragments having binding specificity to NGF comprise, or alternatively consist of, one or more of the polynucleotide sequences of SEQ ID NO: 258; SEQ ID NO: 259; and SEQ ID NO: 260 which correspond to polynucleotides encoding the complementarity-determining regions (CDRs, or hypervariable regions) of the heavy chain variable sequence of SEQ ID NO: 53 or the heavy chain sequence of SEQ ID NO: 54.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 251 encoding the light chain variable sequence of SEQ ID NO: 51; the polynucleotide SEQ ID NO: 252 encoding the light chain sequence of SEQ ID NO: 52; the polynucleotide SEQ ID NO: 253 encoding the heavy chain variable sequence of SEQ ID NO: 53; the polynucleotide SEQ ID NO: 254 encoding the heavy chain sequence of SEQ ID NO: 54; polynucleotides encoding the complementarity-determining regions (SEQ ID NO: 255; SEQ ID NO: 256; and SEQ ID NO: 257) of the light chain variable sequence of SEQ ID NO: 51 or the light chain sequence of SEQ ID NO: 52; and polynucleotides encoding the complementarity-determining regions (SEQ ID NO: 258; SEQ ID NO: 259; and SEQ ID NO: 260) of the heavy chain variable sequence of SEQ ID NO: 53 or the heavy chain sequence of SEQ ID NO: 54.

In a preferred embodiment of the invention, polynucleotides of the invention comprise, or alternatively consist of, polynucleotides encoding Fab (fragment antigen binding) fragments having binding specificity for NGF. With respect to antibody Ab6, the polynucleotides encoding the full length Ab6 antibody comprise, or alternatively consist of, the polynucleotide SEQ ID NO: 252 encoding the light chain sequence of SEQ ID NO: 52 and the polynucleotide SEQ ID NO: 254 encoding the heavy chain sequence of SEQ ID NO: 54.

Another embodiment of the invention contemplates these polynucleotides incorporated into an expression vector for expression in mammalian cells such as CHO, NSO, HEK-293, or in fungal, insect, plant cells, transgenic plants and animals, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab6 following expression of the full-length polynucleotides in a suitable host. In another embodiment of the invention, anti-NGF antibodies such as Ab6 or Fab fragments thereof may be produced via expression of Ab6 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris.*

Antibody Ab7

The invention is further directed to the use of polynucleotides encoding Ab7 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab7 antibody polypeptides having binding specificity to NGF. In one embodiment of the invention, polynucleotides of the invention comprise, or alternatively consist of, the following polynucleotide sequence encoding the variable light chain polypeptide sequence of SEQ ID NO: 61:

```
                                        (SEQ ID NO: 261)
GCCGATGTTGTGATGACCCAGACTCCAGCCTCCGTGTCTCAACCTGTGG

GAGGCACAGTCACCATCAAGTGCCAGGCCAGTGAGGACATTTATAACTT

ATTGGCCTGGTATCAGCAGAAACCAGGGCAGCCTCCCAAGCTCCTGATC

TATTCTGCATCCACTCTGGCATCTGGGGTCCCATCGCGGTTCAAAGGCA

GTGGATCTGGGACAGAGTACACTCTCACCATCAGCGGCCTGGAGTGTGC

CGATGCTGCCACTTACTACTGTCAAAACAATTATCTTGTTACTACTTAT

GGTGTTGCTTTCGGCGGAGGGACCGAGGTGGTGGTCAAACGT.
```

In one embodiment of the invention, polynucleotides of the invention comprise, or alternatively consist of, the following polynucleotide sequence encoding the light chain polypeptide sequence of SEQ ID NO: 62:

```
                                        (SEQ ID NO: 262)
GCCGATGTTGTGATGACCCAGACTCCAGCCTCCGTGTCTCAACCTGTGG

GAGGCACAGTCACCATCAAGTGCCAGGCCAGTGAGGACATTTATAACTT

ATTGGCCTGGTATCAGCAGAAACCAGGGCAGCCTCCCAAGCTCCTGATC

TATTCTGCATCCACTCTGGCATCTGGGGTCCCATCGCGGTTCAAAGGCA

GTGGATCTGGGACAGAGTACACTCTCACCATCAGCGGCCTGGAGTGTGC

CGATGCTGCCACTTACTACTGTCAAAACAATTATCTTGTTACTACTTAT

GGTGTTGCTTTCGGCGGAGGGACCGAGGTGGTGGTCAAACGTACGGTAG

CGGCCCCATCTGTCTTCATCTTCCCGCCATCTGATGAGCAGTTGAAATC

TGGAACTGCCTCTGTTGTGTGCCTGCTGAATAACTTCTATCCCAGAGAG

GCCAAAGTACAGTGGAAGGTGGATAACGCCCTCCAATCGGGTAACTCCC

AGGAGAGTGTCACAGAGCAGGACAGCAAGGACAGCACCTACAGCCTCAG

CAGCACCCTGACGCTGAGCAAAGCAGACTACGAGAAACACAAAGTCTAC

GCCTGCGAAGTCACCCATCAGGGCCTGAGCTCGCCCGTCACAAAGAGCT

TCAACAGGGGAGAGTGTTAG.
```

In another embodiment of the invention, polynucleotides of the invention comprise, or alternatively consist of, the following polynucleotide sequence encoding the variable heavy chain polypeptide sequence of SEQ ID NO: 63:

(SEQ ID NO: 263)
CAGGAGCAGCTGAAGGAGTCCGGGGGTCGCCTGGTCACGCCTGGGACAC
CCCTGACACTCACCTGTACAGTCTCTGGATTCTCCCTCAGTAGCTATGC
AATGATCTGGGTCCGCCAGGCTCCAGGGAAGGGGCTGGAATACATCGGA
TACATTGATACTGATACTAGCGCATACTACGCGAGCTGGGTGAAAGGCC
GATTCACCATCTCCAGAACCTCGACCACGGTGGATCTCAAAATCACTAG
TCCGACAACCGAGGACACGGCCACCTATTTCTGTGCCAGATCTTATGCT
GCTTATGGTGGTTATCCTGCTACTTTTGATCCCTGGGGCCCAGGCACCC
TGGTCACCGTCTCGAGC.

In one embodiment of the invention, polynucleotides of the invention comprise, or alternatively consist of, the following polynucleotide sequence encoding the heavy chain polypeptide sequence of SEQ ID NO: 64:

(SEQ ID NO: 264)
CAGGAGCAGCTGAAGGAGTCCGGGGGTCGCCTGGTCACGCCTGGGACAC
CCCTGACACTCACCTGTACAGTCTCTGGATTCTCCCTCAGTAGCTATGC
AATGATCTGGGTCCGCCAGGCTCCAGGGAAGGGGCTGGAATACATCGGA
TACATTGATACTGATACTAGCGCATACTACGCGAGCTGGGTGAAAGGCC
GATTCACCATCTCCAGAACCTCGACCACGGTGGATCTCAAAATCACTAG
TCCGACAACCGAGGACACGGCCACCTATTTCTGTGCCAGATCTTATGCT
GCTTATGGTGGTTATCCTGCTACTTTTGATCCCTGGGGCCCAGGCACCC
TGGTCACCGTCTCGAGCGCCTCCACCAAGGGCCCATCGGTCTTCCCCCT
GGCACCCTCCTCCAAGAGCACCTCTGGGGGCACAGCGGCCCTGGGCTGC
CTGGTCAAGGACTACTTCCCCGAACCGGTGACGGTGTCGTGGAACTCAG
GCGCCCTGACCAGCGGCGTGCACACCTTCCCGGCTGTCCTACAGTCCTC
AGGACTCTACTCCCTCAGCAGCGTGGTGACCGTGCCCTCCAGCAGCTTG
GGCACCCAGACCTACATCTGCAACGTGAATCACAAGCCCAGCAACACCA
AGGTGGACAAGAGAGTTGAGCCCAAATCTTGTGACAAAACTCACACATG
CCCACCGTGCCCAGCACCTGAACTCCTGGGGGGACCGTCAGTCTTCCTC
TTCCCCCCAAAACCCAAGGACACCCTCATGATCTCCCGGACCCCTGAGG
TCACATGCGTGGTGGTGGACGTGAGCCACGAAGACCCTGAGGTCAAGTT
CAACTGGTACGTGGACGGCGTGGAGGTGCATAATGCCAAGACAAAGCCG
CGGGAGGAGCAGTACGCCAGCACGTACCGTGTGGTCAGCGTCCTCACCG
TCCTGCACCAGGACTGGCTGAATGGCAAGGAGTACAAGTGCAAGGTCTC
CAACAAAGCCCTCCCAGCCCCCATCGAGAAAACCATCTCCAAAGCCAAA
GGGCAGCCCCGAGAACCACAGGTGTACACCCTGCCCCCATCCCGGGAGG
AGATGACCAAGAACCAGGTCAGCCTGACCTGCCTGGTCAAAGGCTTCTA
TCCCAGCGACATCGCCGTGGAGTGGGAGAGCAATGGGCAGCCGGAGAAC
AACTACAAGACCACGCCTCCCGTGCTGGACTCCGACGGCTCCTTCTTCC
TCTACAGCAAGCTCACCGTGGACAAGAGCAGGTGGCAGCAGGGGAACGT
CTTCTCATGCTCCGTGATGCATGAGGCTCTGCACAACCACTACACGCAG
AAGAGCCTCTCCCTGTCTCCGGGTAAATGA.

In a further embodiment of the invention, polynucleotides encoding antibody fragments having binding specificity to NGF comprise, or alternatively consist of, one or more of the polynucleotide sequences of SEQ ID NO: 265; SEQ ID NO: 266; and SEQ ID NO: 267 which correspond to polynucleotides encoding the complementarity-determining regions (CDRs, or hypervariable regions) of the light chain variable sequence of SEQ ID NO: 61 or the light chain sequence of SEQ ID NO: 62.

In a further embodiment of the invention, polynucleotides encoding antibody fragments having binding specificity to NGF comprise, or alternatively consist of, one or more of the polynucleotide sequences of SEQ ID NO: 268; SEQ ID NO: 269; and SEQ ID NO: 270 which correspond to polynucleotides encoding the complementarity-determining regions (CDRs, or hypervariable regions) of the heavy chain variable sequence of SEQ ID NO: 63 or the heavy chain sequence of SEQ ID NO: 64.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 261 encoding the light chain variable sequence of SEQ ID NO: 61; the polynucleotide SEQ ID NO: 262 encoding the light chain sequence of SEQ ID NO: 62; the polynucleotide SEQ ID NO: 263 encoding the heavy chain variable sequence of SEQ ID NO: 63; the polynucleotide SEQ ID NO: 264 encoding the heavy chain sequence of SEQ ID NO: 64; polynucleotides encoding the complementarity-determining regions (SEQ ID NO: 265; SEQ ID NO: 266; and SEQ ID NO: 267) of the light chain variable sequence of SEQ ID NO: 61 or the light chain sequence of SEQ ID NO: 62; and polynucleotides encoding the complementarity-determining regions (SEQ ID NO: 268; SEQ ID NO: 269; and SEQ ID NO: 270) of the heavy chain variable sequence of SEQ ID NO: 63 or the heavy chain sequence of SEQ ID NO: 64.

In a preferred embodiment of the invention, polynucleotides of the invention comprise, or alternatively consist of, polynucleotides encoding Fab (fragment antigen binding) fragments having binding specificity for NGF and MetMab like monovalent agents. With respect to antibody Ab7, the polynucleotides encoding the full length Ab7 antibody comprise, or alternatively consist of, the polynucleotide SEQ ID NO: 262 encoding the light chain sequence of SEQ ID NO: 62 and the polynucleotide SEQ ID NO: 264 encoding the heavy chain sequence of SEQ ID NO: 64.

Another embodiment of the invention contemplates these polynucleotides incorporated into an expression vector for expression in mammalian cells such as CHO, NSO, HEK-293, or in fungal, insect, plant cells, transgenic plants or animals, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab7 following expression of the full-length polynucleotides in a suitable host. In another embodiment of the invention, anti-NGF antibodies such as Ab7 or Fab fragments thereof may be produced via expression of Ab7 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris.*

Antibody Ab8

The invention is further directed to the use of polynucleotides encoding Ab8 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab8 antibody polypeptides having binding specificity to NGF. As noted above, Ab8 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 71:

(SEQ ID NO: 271)
GACATCCAGATGACCCAGTCTCCATCCTCCCTGTCTGCATCTGTAGGAG
ACAGAGTCACCATCACTTGCCAGGCCAGTGAGGACATTTACAACTTATT
GGCCTGGTATCAGCAGAAACCAGGGAAAGTCCCTAAGCTCCTGATCTAT
TCTGCATCCACTCTGGCATCTGGGGTCCCATCTCGTTTCAGTGGCAGTG
GATCTGGGACAGATTACACTCTCACCATCAGCAGCCTGCAGCCTGAAGA
TGTTGCAACTTATTACTGTCAAAACAACTATCTTGTTACTACTTATGGT
GTTGCTTTCGGCGGAGGAACCAAGGTGGAAATCAAACGT.

In one embodiment of the invention, polynucleotides of the invention comprise, or alternatively consist of, the following polynucleotide sequence encoding the light chain polypeptide sequence of SEQ ID NO: 72:

(SEQ ID NO: 272)
GACATCCAGATGACCCAGTCTCCATCCTCCCTGTCTGCATCTGTAGGAG
ACAGAGTCACCATCACTTGCCAGGCCAGTGAGGACATTTACAACTTATT
GGCCTGGTATCAGCAGAAACCAGGGAAAGTCCCTAAGCTCCTGATCTAT
TCTGCATCCACTCTGGCATCTGGGGTCCCATCTCGTTTCAGTGGCAGTG
GATCTGGGACAGATTACACTCTCACCATCAGCAGCCTGCAGCCTGAAGA
TGTTGCAACTTATTACTGTCAAAACAACTATCTTGTTACTACTTATGGT
GTTGCTTTCGGCGGAGGAACCAAGGTGGAAATCAAACGTACGGTAGCGG
CCCCATCTGTCTTCATCTTCCCGCCATCTGATGAGCAGTTGAAATCTGG
AACTGCCTCTGTTGTGTGCCTGCTGAATAACTTCTATCCCAGAGAGGCC
AAAGTACAGTGGAAGGTGGATAACGCCCTCCAATCGGGTAACTCCCAGG
AGAGTGTCACAGAGCAGGACAGCAAGGACAGCACCTACAGCCTCAGCAG
CACCCTGACGCTGAGCAAAGCAGACTACGAGAAACACAAAGTCTACGCC

-continued

TGCGAAGTCACCCATCAGGGCCTGAGCTCGCCCGTCACAAAGAGCTTCA
ACAGGGGAGAGTGTTAG.

In another embodiment of the invention, polynucleotides of the invention comprise, or alternatively consist of, the following polynucleotide sequence encoding the variable heavy chain polypeptide sequence of SEQ ID NO: 73:

(SEQ ID NO: 273)
CAGGTACAGCTGGTGGAGTCTGGTGGAGGCGTGGTCCAGCCTGGGAGGT
CCCTGAGACTCTCCTGTGCAGCTTCTGGATTCACCTTCAGTAGCTATGC
AATGATCTGGGTCCGCCAGGCTCCAGGGAAGGGGCTGGAATACATCGGA
TACATTGATACTGATACTAGCGCATACTACGCAAGCAGTGTGAAAGGCC
GATTCACCATCTCCAGAGACAATTCCAAGAACACGCTGTACCTGCAAAT
GTCTAGCCTGAGAGCCGAGGACACGGCTGTGTATTACTGTGCTAGATCT
TATGCTGCTTATGGTGGTTATCCTGCTACTTTTGATCCCTGGGGCCAAG
GTACCCTCGTCACCGTCTCGAGC.

In one embodiment of the invention, polynucleotides of the invention comprise, or alternatively consist of, the following polynucleotide sequence encoding the heavy chain polypeptide sequence of SEQ ID NO: 74:

(SEQ ID NO: 274)
CAGGTACAGCTGGTGGAGTCTGGTGGAGGCGTGGTCCAGCCTGGGAGGT
CCCTGAGACTCTCCTGTGCAGCTTCTGGATTCACCTTCAGTAGCTATGC
AATGATCTGGGTCCGCCAGGCTCCAGGGAAGGGGCTGGAATACATCGGA
TACATTGATACTGATACTAGCGCATACTACGCAAGCAGTGTGAAAGGCC
GATTCACCATCTCCAGAGACAATTCCAAGAACACGCTGTACCTGCAAAT
GTCTAGCCTGAGAGCCGAGGACACGGCTGTGTATTACTGTGCTAGATCT
TATGCTGCTTATGGTGGTTATCCTGCTACTTTTGATCCCTGGGGCCAAG
GTACCCTCGTCACCGTCTCGAGCGCCTCCACCAAGGGCCCATCGGTCTT
CCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGA
ACTCAGGCGCCCTGACCAGCGGCGTGCACACCTTCCCGGCTGTCCTACA
GTCCTCAGGACTCTACTCCCTCAGCAGCGTGGTGACCGTGCCCTCCAGC
AGCTTGGGCACCCAGACCTACATCTGCAACGTGAATCACAAGCCCAGCA
ACACCAAGGTGGACAAGAGAGTTGAGCCCAAATCTTGTGACAAAACTCA
CACATGCCCACCGTGCCCAGCACCTGAACTCCTGGGGGGACCGTCAGTC
TTCCTCTTCCCCCCAAAACCCAAGGACACCCTCATGATCTCCCGGACCC
CTGAGGTCACATGCGTGGTGGTGGACGTGAGCCACGAAGACCCTGAGGT
CAAGTTCAACTGGTACGTGGACGGCGTGGAGGTGCATAATGCCAAGACA
AAGCCGCGGGAGGAGCAGTACGCCAGCACGTACCGTGTGGTCAGCGTCC
TCACCGTCCTGCACCAGGACTGGCTGAATGGCAAGGAGTACAAGTGCAA
GGTCTCCAACAAAGCCCTCCCAGCCCCCATCGAGAAAACCATCTCCAAA
GCCAAAGGGCAGCCCCGAGAACCACAGGTGTACACCCTGCCCCCATCCC
GGGAGGAGATGACCAAGAACCAGGTCAGCCTGACCTGCCTGGTCAAAGG

-continued

CTTCTATCCCAGCGACATCGCCGTGGAGTGGGAGAGCAATGGGCAGCCG

GAGAACAACTACAAGACCACGCCTCCCGTGCTGGACTCCGACGGCTCCT

TCTTCCTCTACAGCAAGCTCACCGTGGACAAGAGCAGGTGGCAGCAGGG

GAACGTCTTCTCATGCTCCGTGATGCATGAGGCTCTGCACAACCACTAC

ACGCAGAAGAGCCTCTCCCTGTCTCCGGGTAAATGA.

In a further embodiment of the invention, polynucleotides encoding antibody fragments having binding specificity to NGF comprise, or alternatively consist of, one or more of the polynucleotide sequences of SEQ ID NO: 275; SEQ ID NO: 276; and SEQ ID NO: 277 which correspond to polynucleotides encoding the complementarity-determining regions (CDRs, or hypervariable regions) of the light chain variable sequence of SEQ ID NO: 71 or the light chain sequence of SEQ ID NO: 72.

In a further embodiment of the invention, polynucleotides encoding antibody fragments having binding specificity to NGF comprise, or alternatively consist of, one or more of the polynucleotide sequences of SEQ ID NO: 278; SEQ ID NO: 279; and SEQ ID NO: 280 which correspond to polynucleotides encoding the complementarity-determining regions (CDRs, or hypervariable regions) of the heavy chain variable sequence of SEQ ID NO: 73 or the heavy chain sequence of SEQ ID NO: 74.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 271 encoding the light chain variable sequence of SEQ ID NO: 71; the polynucleotide SEQ ID NO: 272 encoding the light chain sequence of SEQ ID NO: 72; the polynucleotide SEQ ID NO: 273 encoding the heavy chain variable sequence of SEQ ID NO: 73; the polynucleotide SEQ ID NO: 274 encoding the heavy chain sequence of SEQ ID NO: 74; polynucleotides encoding the complementarity-determining regions (SEQ ID NO: 275; SEQ ID NO: 276; and SEQ ID NO: 277) of the light chain variable sequence of SEQ ID NO: 71 or the light chain sequence of SEQ ID NO: 72; and polynucleotides encoding the complementarity-determining regions (SEQ ID NO: 278; SEQ ID NO: 279; and SEQ ID NO: 280) of the heavy chain variable sequence of SEQ ID NO: 73 or the heavy chain sequence of SEQ ID NO: 74.

In a preferred embodiment of the invention, polynucleotides of the invention comprise, or alternatively consist of, polynucleotides encoding Fab (fragment antigen binding) fragments having binding specificity for NGF and MetMab like monovalent agents. With respect to antibody Ab8, the polynucleotides encoding the full length Ab8 antibody comprise, or alternatively consist of, the polynucleotide SEQ ID NO: 272 encoding the light chain sequence of SEQ ID NO: 72 and the polynucleotide SEQ ID NO: 274 encoding the heavy chain sequence of SEQ ID NO: 74.

Another embodiment of the invention contemplates these polynucleotides incorporated into an expression vector for expression in mammalian cells such as CHO, NSO, HEK-293, or in fungal, insect, plant cells, transgenic plants and animals, or microbial systems such as bacterial or yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab8 following expression of the full-length polynucleotides in a suitable host. In another embodiment of the invention, anti-NGF antibodies such as Ab8 or Fab fragments thereof may be produced via expression of Ab8 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris.*

Antibody Ab9

The invention is further directed to the use of polynucleotides encoding Ab9 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab9 antibody polypeptides having binding specificity to NGF. As noted above, Ab9 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 81:

(SEQ ID NO: 281)

GCCTATGATATGACCCAGACTCCAGCCTCCGTGTCTGCAGCTGTGGGAG

GCACAGTCACCATCAAGTGCCAGGCCAGTGAGAACATTGGTAGCTACTT

AGCCTGGTATCAGCAGAAACCAGGGCAGCCTCCCGAACTCCTGATCTAC

AGGGCGTCCACTCTGGCATCTGGGGTCCCATCGCGGTTCAAAGGCAGTG

GATCTGGGACACAGTTCACTCTCACCATCAGCGGCGTGGAGTGTGCCGA

TGCTGCCACTTACTACTGTCAACAGGGTTATAATAGTGAGAATCTTGAT

AATGCTTTCGGCGGAGGGACCGAGGTGGTGGTCAAACGT.

In one embodiment of the invention, polynucleotides of the invention comprise, or alternatively consist of, the following polynucleotide sequence encoding the light chain polypeptide sequence of SEQ ID NO: 82:

(SEQ ID NO: 282)

GCCTATGATATGACCCAGACTCCAGCCTCCGTGTCTGCAGCTGTGGGAG

GCACAGTCACCATCAAGTGCCAGGCCAGTGAGAACATTGGTAGCTACTT

AGCCTGGTATCAGCAGAAACCAGGGCAGCCTCCCGAACTCCTGATCTAC

AGGGCGTCCACTCTGGCATCTGGGGTCCCATCGCGGTTCAAAGGCAGTG

GATCTGGGACACAGTTCACTCTCACCATCAGCGGCGTGGAGTGTGCCGA

TGCTGCCACTTACTACTGTCAACAGGGTTATAATAGTGAGAATCTTGAT

AATGCTTTCGGCGGAGGGACCGAGGTGGTGGTCAAACGTACGGTAGCGG

CCCCATCTGTCTTCATCTTCCCGCCATCTGATGAGCAGTTGAAATCTGG

-continued

```
AACTGCCTCTGTTGTGTGCCTGCTGAATAACTTCTATCCCAGAGAGGCC
AAAGTACAGTGGAAGGTGGATAACGCCCTCCAATCGGGTAACTCCCAGG
AGAGTGTCACAGAGCAGGACAGCAAGGACAGCACCTACAGCCTCAGCAG
CACCCTGACGCTGAGCAAAGCAGACTACGAGAAACACAAAGTCTACGCC
TGCGAAGTCACCCATCAGGGCCTGAGCTCGCCCGTCACAAAGAGCTTCA
ACAGGGGAGAGTGTTAG.
```

In another embodiment of the invention, polynucleotides of the invention comprise, or alternatively consist of, the following polynucleotide sequence encoding the variable heavy chain polypeptide sequence of SEQ ID NO: 83:

```
                                      (SEQ ID NO: 283)
CAGTCGGTGGAGGAGTCCGGGGGTCGCCTGGTCACGCCTGGGACACCCC
TGACACTCACCTGCACAGTCTCTGGAATCGACCTCAGTATGTATTCAAT
GGGCTGGGTCCGCCAGGCTCCAGGGAAGGGGCTGGAATACATCGGATGG
ATTAGTTATGGTGGTACTGCATATTACGCGAGCTGGGCGAAGGGCCGAT
TCACCATCTCCAAAACCTCGACCACGGTGGAGCTGAAGATCACCAGTCC
GACAATCGAGGACACGGCCACCTATTTCTGTGCCAGAGAGACTCCTGTT
AATTATTATTTGGACATTTGGGGCCAGGGGACCCTCGTCACCGTCTCGA
GC.
```

In one embodiment of the invention, polynucleotides of the invention comprise, or alternatively consist of, the following polynucleotide sequence encoding the heavy chain polypeptide sequence of SEQ ID NO: 84:

```
                                      (SEQ ID NO: 284)
CAGTCGGTGGAGGAGTCCGGGGGTCGCCTGGTCACGCCTGGGACACCCC
TGACACTCACCTGCACAGTCTCTGGAATCGACCTCAGTATGTATTCAAT
GGGCTGGGTCCGCCAGGCTCCAGGGAAGGGGCTGGAATACATCGGATGG
ATTAGTTATGGTGGTACTGCATATTACGCGAGCTGGGCGAAGGGCCGAT
TCACCATCTCCAAAACCTCGACCACGGTGGAGCTGAAGATCACCAGTCC
GACAATCGAGGACACGGCCACCTATTTCTGTGCCAGAGAGACTCCTGTT
AATTATTATTTGGACATTTGGGGCCAGGGGACCCTCGTCACCGTCTCGA
GCGCCTCCACCAAGGGCCCATCGGTCTTCCCCCTGGCACCCTCCTCCAA
GAGCACCTCTGGGGGCACAGCGGCCCTGGGCTGCCTGGTCAAGGACTAC
TTCCCCGAACCGGTGACGGTGTCGTGGAACTCAGGCGCCCTGACCAGCG
GCGTGCACACCTTCCCGGCTGTCCTACAGTCCTCAGGACTCTACTCCCT
CAGCAGCGTGGTGACCGTGCCCTCCAGCAGCTTGGGCACCCAGACCTAC
ATCTGCAACGTGAATCACAAGCCCAGCAACACCAAGGTGGACAAGAGAG
TTGAGCCCAAATCTTGTGACAAAACTCACACATGCCCACCGTGCCCAGC
ACCTGAACTCCTGGGGGGACCGTCAGTCTTCCTCTTCCCCCCAAAACCC
AAGGACACCCTCATGATCTCCCGGACCCCTGAGGTCACATGCGTGGTGG
TGGACGTGAGCCACGAAGACCCTGAGGTCAAGTTCAACTGGTACGTGGA
CGGCGTGGAGGTGCATAATGCCAAGACAAAGCCGCGGGAGGAGCAGTAC
```

-continued

```
GCCAGCACGTACCGTGTGGTCAGCGTCCTCACCGTCCTGCACCAGGACT
GGCTGAATGGCAAGGAGTACAAGTGCAAGGTCTCCAACAAAGCCCTCCC
AGCCCCCATCGAGAAAACCATCTCCAAAGCCAAAGGGCAGCCCCGAGAA
CCACAGGTGTACACCCTGCCCCCATCCCGGGAGGAGATGACCAAGAACC
AGGTCAGCCTGACCTGCCTGGTCAAAGGCTTCTATCCCAGCGACATCGC
CGTGGAGTGGGAGAGCAATGGGCAGCCGGAGAACAACTACAAGACCACG
CCTCCCGTGCTGGACTCCGACGGCTCCTTCTTCCTCTACAGCAAGCTCA
CCGTGGACAAGAGCAGGTGGCAGCAGGGGAACGTCTTCTCATGCTCCGT
GATGCATGAGGCTCTGCACAACCACTACACGCAGAAGAGCCTCTCCCTG
TCTCCGGGTAAATGA.
```

In a further embodiment of the invention, polynucleotides encoding antibody fragments having binding specificity to NGF comprise, or alternatively consist of, one or more of the polynucleotide sequences of SEQ ID NO: 285; SEQ ID NO: 286; and SEQ ID NO: 287 which correspond to polynucleotides encoding the complementarity-determining regions (CDRs, or hypervariable regions) of the light chain variable sequence of SEQ ID NO: 81 or the light chain sequence of SEQ ID NO: 82.

In a further embodiment of the invention, polynucleotides encoding antibody fragments having binding specificity to NGF comprise, or alternatively consist of, one or more of the polynucleotide sequences of SEQ ID NO: 288; SEQ ID NO: 289; and SEQ ID NO: 290 which correspond to polynucleotides encoding the complementarity-determining regions (CDRs, or hypervariable regions) of the heavy chain variable sequence of SEQ ID NO: 83 or the heavy chain sequence of SEQ ID NO: 84.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 281 encoding the light chain variable sequence of SEQ ID NO: 81; the polynucleotide SEQ ID NO: 282 encoding the light chain sequence of SEQ ID NO: 82; the polynucleotide SEQ ID NO: 283 encoding the heavy chain variable sequence of SEQ ID NO: 83; the polynucleotide SEQ ID NO: 284 encoding the heavy chain sequence of SEQ ID NO: 84; polynucleotides encoding the complementarity-determining regions (SEQ ID NO: 285; SEQ ID NO: 286; and SEQ ID NO: 287) of the light chain variable sequence of SEQ ID NO: 81 or the light chain sequence of SEQ ID NO: 82; and polynucleotides encoding the complementarity-determining regions (SEQ ID NO: 288; SEQ ID NO: 289; and SEQ ID NO: 290) of the heavy chain variable sequence of SEQ ID NO: 83 or the heavy chain sequence of SEQ ID NO: 84.

In a preferred embodiment of the invention, polynucleotides of the invention comprise, or alternatively consist of, polynucleotides encoding Fab (fragment antigen binding) fragments having binding specificity for NGF. With respect to antibody Ab9, the polynucleotides encoding the full length Ab9 antibody comprise, or alternatively consist of, the polynucleotide SEQ ID NO: 282 encoding the light chain sequence of SEQ ID NO: 82 and the polynucleotide SEQ ID NO: 284 encoding the heavy chain sequence of SEQ ID NO: 84.

Another embodiment of the invention contemplates these polynucleotides incorporated into an expression vector for expression in mammalian cells such as CHO, NSO, HEK-293, or in fungal, insect, plant, transgenic plants or animals, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab9 following expression of the full-length polynucleotides in a suitable host. In another embodiment of the invention, anti-NGF antibodies such as Ab9 or Fab fragments thereof or MetMab like monovalent agents may be produced via expression of Ab9 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab10

The invention is further directed to the use of polynucleotides encoding Ab10 polypeptides set forth below to produce anti-human NGF monovalent agents used in the pain treatment methods described herein. Described below are polynucleotides encoding Ab10 antibody polypeptides having binding specificity to NGF. As noted above, Ab10 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 91:

```
                                          (SEQ ID NO: 291)
GCCTATGATATGACCCAGTCTCCATCCTCCCTGTCTGCATCTGTAGGAG
ACAGAGTCACCATCACTTGCCAGGCCAGTGAGAACATTGGTAGCTACTT
AGCCTGGTATCAGCAGAAACCAGGGAAAGTCCCTAAGCTCCTGATCTAT
AGGGCTTCCACTCTGGCATCTGGGGTCCCATCTCGTTTCAGTGGCAGTG
GATCTGGGACAGATTTCACTCTCACCATCAGCAGCCTGCAGCCTGAAGA
TGTTGCAACTTATTACTGTCAACAGGGTTACAATAGTGAGAATCTTGAT
AATGCTTTCGGCGGAGGAACCAAGGTGGAAATCAAACGT.
```

In one embodiment of the invention, polynucleotides of the invention comprise, or alternatively consist of, the following polynucleotide sequence encoding the light chain polypeptide sequence of SEQ JD NO: 92:

```
                                          (SEQ ID NO: 292)
GCCTATGATATGACCCAGTCTCCATCCTCCCTGTCTGCATCTGTAGGAG
ACAGAGTCACCATCACTTGCCAGGCCAGTGAGAACATTGGTAGCTACTT
AGCCTGGTATCAGCAGAAACCAGGGAAAGTCCCTAAGCTCCTGATCTAT
AGGGCTTCCACTCTGGCATCTGGGGTCCCATCTCGTTTCAGTGGCAGTG
GATCTGGGACAGATTTCACTCTCACCATCAGCAGCCTGCAGCCTGAAGA
TGTTGCAACTTATTACTGTCAACAGGGTTACAATAGTGAGAATCTTGAT
AATGCTTTCGGCGGAGGAACCAAGGTGGAAATCAAACGTACGGTAGCGG
CCCCATCTGTCTTCATCTTCCCGCCATCTGATGAGCAGTTGAAATCTGG
AACTGCCTCTGTTGTGTGCCTGCTGAATAACTTCTATCCCAGAGAGGCC
```

-continued

```
AAAGTACAGTGGAAGGTGGATAACGCCCTCCAATCGGGTAACTCCCAGG
AGAGTGTCACAGAGCAGGACAGCAAGGACAGCACCTACAGCCTCAGCAG
CACCCTGACGCTGAGCAAAGCAGACTACGAGAAACACAAAGTCTACGCC
TGCGAAGTCACCCATCAGGGCCTGAGCTCGCCCGTCACAAAGAGCTTCA
ACAGGGGAGAGTGTTAG.
```

In another embodiment of the invention, polynucleotides of the invention comprise, or alternatively consist of, the following polynucleotide sequence encoding the variable heavy chain polypeptide sequence of SEQ ID NO: 93:

```
                                          (SEQ ID NO: 293)
CAGGTACAGCTGGTGGAGTCTGGTGGAGGCGTGGTCCAGCCTGGGAGGT
CCCTGAGACTCTCCTGTGCAGCTTCTGGATTCACCTTCAGTATGTATTC
AATGGGCTGGGTCCGCCAGGCTCCAGGGAAGGGGCTGGAATACATCGGA
TGGATTAGTTATGGTGGTACTGCATACTACGCTAGCAGCGCTAAGGGCC
GATTCACCATCTCCAGAGACAATTCCAAGAACACGCTGTACCTGCAAAT
GTCTAGCCTGAGAGCCGAGGACACGGCTGTGTATTACTGTGCTAGAGAG
ACTCCTGTTAATTACTACTTGGACATTTGGGGCCAAGGTACCCTCGTCA
CCGTCTCGAGC.
```

In one embodiment of the invention, polynucleotides of the invention comprise, or alternatively consist of, the following polynucleotide sequence encoding the heavy chain polypeptide sequence of SEQ ID NO: 94:

```
                                          (SEQ ID NO: 294)
CAGGTACAGCTGGTGGAGTCTGGTGGAGGCGTGGTCCAGCCTGGGAGGT
CCCTGAGACTCTCCTGTGCAGCTTCTGGATTCACCTTCAGTATGTATTC
AATGGGCTGGGTCCGCCAGGCTCCAGGGAAGGGGCTGGAATACATCGGA
TGGATTAGTTATGGTGGTACTGCATACTACGCTAGCAGCGCTAAGGGCC
GATTCACCATCTCCAGAGACAATTCCAAGAACACGCTGTACCTGCAAAT
GTCTAGCCTGAGAGCCGAGGACACGGCTGTGTATTACTGTGCTAGAGAG
ACTCCTGTTAATTACTACTTGGACATTTGGGGCCAAGGTACCCTCGTCA
CCGTCTCGAGCGCCTCCACCAAGGGCCCATCGGTCTTCCCCCTGGCACC
CTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCC
TGACCAGCGGCGTGCACACCTTCCCGGCTGTCCTACAGTCCTCAGGACT
CTACTCCCTCAGCAGCGTGGTGACCGTGCCCTCCAGCAGCTTGGGCACC
CAGACCTACATCTGCAACGTGAATCACAAGCCCAGCAACACCAAGGTGG
ACAAGAGAGTTGAGCCCAAATCTTGTGACAAAACTCACACATGCCCACC
GTGCCCAGCACCTGAACTCCTGGGGGGACCGTCAGTCTTCCTCTTCCCC
CCAAAACCCAAGGACACCCTCATGATCTCCCGGACCCCTGAGGTCACAT
GCGTGGTGGTGGACGTGAGCCACGAAGACCCTGAGGTCAAGTTCAACTG
GTACGTGGACGGCGTGGAGGTGCATAATGCCAAGACAAAGCCGCGGGAG
GAGCAGTACGCCAGCACGTACCGTGTGGTCAGCGTCCTCACCGTCCTGC
ACCAGGACTGGCTGAATGGCAAGGAGTACAAGTGCAAGGTCTCCAACAA
```

-continued

AGCCCTCCCAGCCCCCATCGAGAAAACCATCTCCAAAGCCAAAGGGCAG

CCCCGAGAACCACAGGTGTACACCCTGCCCCCATCCCGGGAGGAGATGA

CCAAGAACCAGGTCAGCCTGACCTGCCTGGTCAAAGGCTTCTATCCCAG

CGACATCGCCGTGGAGTGGGAGAGCAATGGGCAGCCGGAGAACAACTAC

AAGACCACGCCTCCCGTGCTGGACTCCGACGGCTCCTTCTTCCTCTACA

GCAAGCTCACCGTGGACAAGAGCAGGTGGCAGCAGGGGAACGTCTTCTC

ATGCTCCGTGATGCATGAGGCTCTGCACAACCACTACACGCAGAAGAGC

CTCTCCCTGTCTCCGGGTAAATGA.

In a further embodiment of the invention, polynucleotides encoding antibody fragments having binding specificity to NGF comprise, or alternatively consist of, one or more of the polynucleotide sequences of SEQ ID NO: 295; SEQ ID NO: 296; and SEQ ID NO: 297 which correspond to polynucleotides encoding the complementarity-determining regions (CDRs, or hypervariable regions) of the light chain variable sequence of SEQ ID NO: 91 or the light chain sequence of SEQ ID NO: 92.

In a further embodiment of the invention, polynucleotides encoding antibody fragments having binding specificity to NGF comprise, or alternatively consist of, one or more of the polynucleotide sequences of SEQ ID NO: 298; SEQ ID NO: 299; and SEQ ID NO: 300 which correspond to polynucleotides encoding the complementarity-determining regions (CDRs, or hypervariable regions) of the heavy chain variable sequence of SEQ ID NO: 93 or the heavy chain sequence of SEQ ID NO: 94.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 291 encoding the light chain variable sequence of SEQ ID NO: 91; the polynucleotide SEQ ID NO: 292 encoding the light chain sequence of SEQ ID NO: 92; the polynucleotide SEQ ID NO: 293 encoding the heavy chain variable sequence of SEQ ID NO: 93; the polynucleotide SEQ ID NO: 294 encoding the heavy chain sequence of SEQ ID NO: 94; polynucleotides encoding the complementarity-determining regions (SEQ ID NO: 295; SEQ ID NO: 296; and SEQ ID NO: 297) of the light chain variable sequence of SEQ ID NO: 91 or the light chain sequence of SEQ ID NO: 92; and polynucleotides encoding the complementarity-determining regions (SEQ ID NO: 298; SEQ ID NO: 299; and SEQ ID NO: 300) of the heavy chain variable sequence of SEQ ID NO: 93 or the heavy chain sequence of SEQ ID NO: 94.

In a preferred embodiment of the invention, polynucleotides of the invention comprise, or alternatively consist of, polynucleotides encoding Fab (fragment antigen binding) fragments having binding specificity for NGF and MetMab like monovalent agents. With respect to antibody Ab10, the polynucleotides encoding the full length Ab10 antibody comprise, or alternatively consist of, the polynucleotide SEQ ID NO: 292 encoding the light chain sequence of SEQ ID NO: 92 and the polynucleotide SEQ ID NO: 294 encoding the heavy chain sequence of SEQ ID NO: 94.

Another embodiment of the invention contemplates these polynucleotides incorporated into an expression vector for expression in mammalian cells such as CHO, NSO, HEK-293, or in fungal, insect, plant cells, transgenic plants and animals, or microbial systems such as bacterial or yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab10 following expression of the full-length polynucleotides in a suitable host. In another embodiment of the invention, anti-NGF antibodies such as Ab10 or Fab fragments thereof may be produced via expression of Ab10 polynucleotides in mammalian cells such as CHO, NSO or HEK 293 cells, fungal, insect, plant, or microbial systems such as yeast cells (for example diploid yeast such as diploid *Pichia*) and other yeast strains. Suitable *Pichia* species include, but are not limited to, *Pichia pastoris*.

Antibody Ab11

The invention is further directed to the use of polynucleotides encoding Ab11 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab11 antibody polypeptides having binding specificity to NGF. As noted above, Ab11 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 101:

(SEQ ID NO: 301)

GCATTCGAATTGACCCAGACTCCATCCTCCGTGGAGGCAGCTGTGGGAG

GCACAGTCACCATCAAGTGCCAGGCCAGTCAGAACATTGTTACCAATTT

AGCCTGGTATCAACAGAAACCAGGGCAGCCTCCCAAGCTCCTGATCTAT

GGTGCATCCACTCTGGCATCTGGGGTCTCATCGCGGTTCAAAGGCAGTG

GATCTGGGACACAGTTCACTCTCACCATCAGCGACCTGGAGTGTGCCGA

TGCTGCCACTTATTTCTGTCAGAGCTATGATGGTTTTAATAGTGCTGGG

TTCGGCGGAGGGACCGAGGTGGTGGTCAAACGT.

In one embodiment of the invention, polynucleotides of the invention comprise, or alternatively consist of, the following polynucleotide sequence encoding the light chain polypeptide sequence of SEQ ID NO: 102:

(SEQ ID NO: 302)

GCATTCGAATTGACCCAGACTCCATCCTCCGTGGAGGCAGCTGTGGGAGG

CACAGTCACCATCAAGTGCCAGGCCAGTCAGAACATTGTTACCAATTTAG

CCTGGTATCAACAGAAACCAGGGCAGCCTCCCAAGCTCCTGATCTATGGT

GCATCCACTCTGGCATCTGGGGTCTCATCGCGGTTCAAAGGCAGTGGATC

TGGGACACAGTTCACTCTCACCATCAGCGACCTGGAGTGTGCCGATGCTG

-continued

CCACTTATTTCTGTCAGAGCTATGATGGTTTTAATAGTGCTGGGTTCGGC

GGAGGGACCGAGGTGGTGGTCAAACGTACGGTAGCGGCCCCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAG.

In another embodiment of the invention, polynucleotides of the invention comprise, or alternatively consist of, the following polynucleotide sequence encoding the variable heavy chain polypeptide sequence of SEQ ID NO: 103:

(SEQ ID NO: 303)

CAGTCGCTGGAGGAGTCCGGGGGTCGCCTGGTCACGCCTGGGACACCCCT

GACACTCACCTGCACAGCCTCTGGATTCTCCCTCAGTGGCTACGACATGA

GCTGGGTCCGCCAGGCTCCAGGAAAGGGGCTGGAATACATCGGACTCATT

AGTTATGATGGTAACACATACTACGCGACCTGGGCGAAAGGCCGATTCAC

CATCTCCAAAACCTCGACCACGGTGGATCTGAAAATCACCAGTCCGACAA

CCGAGGACACGGCCACCTATTTCTGTGCCAGAAGTCTTTATGCTGGTCCT

AATGCTGGTATCGGACCGTTTAACATCTGGGGCCAGGGGACCCTCGTCAC

CGTCTCGAGC.

In one embodiment of the invention, polynucleotides of the invention comprise, or alternatively consist of, the following polynucleotide sequence encoding the heavy chain polypeptide sequence of SEQ ID NO: 104:

(SEQ ID NO: 304)

CAGTCGCTGGAGGAGTCCGGGGGTCGCCTGGTCACGCCTGGGACACCCCT

GACACTCACCTGCACAGCCTCTGGATTCTCCCTCAGTGGCTACGACATGA

GCTGGGTCCGCCAGGCTCCAGGAAAGGGGCTGGAATACATCGGACTCATT

AGTTATGATGGTAACACATACTACGCGACCTGGGCGAAAGGCCGATTCAC

CATCTCCAAAACCTCGACCACGGTGGATCTGAAAATCACCAGTCCGACAA

CCGAGGACACGGCCACCTATTTCTGTGCCAGAAGTCTTTATGCTGGTCCT

AATGCTGGTATCGGACCGTTTAACATCTGGGGCCAGGGGACCCTCGTCAC

CGTCTCGAGCGCCTCCACCAAGGGCCCATCGGTCTTCCCCCTGGCACCCT

CCTCCAAGAGCACCTCTGGGGGCACAGCGGCCCTGGGCTGCCTGGTCAAG

GACTACTTCCCCGAACCGGTGACGGTGTCGTGGAACTCAGGCGCCCTGAC

CAGCGGCGTGCACACCTTCCCGGCTGTCCTACAGTCCTCAGGACTCTACT

CCCTCAGCAGCGTGGTGACCGTGCCCTCCAGCAGCTTGGGCACCCAGACC

TACATCTGCAACGTGAATCACAAGCCCAGCAACACCAAGGTGGACAAGAG

AGTTGAGCCCAAATCTTGTGACAAAACTCACACATGCCCACCGTGCCCAG

CACCTGAACTCCTGGGGGGACCGTCAGTCTTCCTCTTCCCCCCAAAACCC

AAGGACACCCTCATGATCTCCCGGACCCCTGAGGTCACATGCGTGGTGGT

-continued

GGACGTGAGCCACGAAGACCCTGAGGTCAAGTTCAACTGGTACGTGGACG

GCGTGGAGGTGCATAATGCCAAGACAAAGCCGCGGGAGGAGCAGTACGCC

AGCACGTACCGTGTGGTCAGCGTCCTCACCGTCCTGCACCAGGACTGGCT

GAATGGCAAGGAGTACAAGTGCAAGGTCTCCAACAAAGCCCTCCCAGCCC

CCATCGAGAAAACCATCTCCAAAGCCAAAGGGCAGCCCCGAGAACCACAG

GTGTACACCCTGCCCCCATCCCGGGAGGAGATGACCAAGAACCAGGTCAG

CCTGACCTGCCTGGTCAAAGGCTTCTATCCCAGCGACATCGCCGTGGAGT

GGGAGAGCAATGGGCAGCCGGAGAACAACTACAAGACCACGCCTCCCGTG

CTGGACTCCGACGGCTCCTTCTTCCTCTACAGCAAGCTCACCGTGGACAA

GAGCAGGTGGCAGCAGGGGAACGTCTTCTCATGCTCCGTGATGCATGAGG

CTCTGCACAACCACTACACGCAGAAGAGCCTCTCCCTGTCTCCGGGTAAA

TGA.

In a further embodiment of the invention, polynucleotides encoding antibody fragments having binding specificity to NGF comprise, or alternatively consist of, one or more of the polynucleotide sequences of SEQ ID NO: 305; SEQ ID NO: 306; and SEQ ID NO: 307 which correspond to polynucleotides encoding the complementarity-determining regions (CDRs, or hypervariable regions) of the light chain variable sequence of SEQ ID NO: 101 or the light chain sequence of SEQ ID NO: 102.

In a further embodiment of the invention, polynucleotides encoding antibody fragments having binding specificity to NGF comprise, or alternatively consist of, one or more of the polynucleotide sequences of SEQ ID NO: 308; SEQ ID NO: 309; and SEQ ID NO: 310 which correspond to polynucleotides encoding the complementarity-determining regions (CDRs, or hypervariable regions) of the heavy chain variable sequence of SEQ ID NO: 103 or the heavy chain sequence of SEQ ID NO: 104.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 301 encoding the light chain variable sequence of SEQ ID NO: 101; the polynucleotide SEQ ID NO: 302 encoding the light chain sequence of SEQ ID NO: 102; the polynucleotide SEQ ID NO: 303 encoding the heavy chain variable sequence of SEQ ID NO: 103; the polynucleotide SEQ ID NO: 304 encoding the heavy chain sequence of SEQ ID NO: 104; polynucleotides encoding the complementarity-determining regions (SEQ ID NO: 305; SEQ ID NO: 306; and SEQ ID NO: 307) of the light chain variable sequence of SEQ ID NO: 101 or the light chain sequence of SEQ ID NO: 102; and polynucleotides encoding the complementarity-determining regions (SEQ ID NO: 308; SEQ ID NO: 309; and SEQ ID NO: 310) of the heavy chain variable sequence of SEQ ID NO: 103 or the heavy chain sequence of SEQ ID NO: 104.

In a preferred embodiment of the invention, polynucleotides of the invention comprise, or alternatively consist of, polynucleotides encoding Fab (fragment antigen binding) fragments having binding specificity for NGF. With respect to antibody Ab11, the polynucleotides encoding the full length Ab11 antibody comprise, or alternatively consist of, the polynucleotide SEQ ID NO: 302 encoding the light chain sequence of SEQ ID NO: 102 and the polynucleotide SEQ ID NO: 304 encoding the heavy chain sequence of SEQ ID NO: 104.

Another embodiment of the invention contemplates these polynucleotides incorporated into an expression vector for expression in mammalian cells such as CHO, NSO, HEK-293, or in fungal, insect, plant cell, transgenic plants or animals, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab11 following expression of the full-length polynucleotides in a suitable host. In another embodiment of the invention, anti-NGF antibodies such as Ab11 or Fab fragments thereof and MetMab like monovalent agents may be produced via expression of Ab11 polynucleotides in mammalian cells such as CHO, NSO or HEK 293 cells, fungal, insect, plant, or microbial systems such as yeast cells (for example diploid yeast such as diploid *Pichia*) and other yeast strains. Suitable *Pichia* species include, but are not limited to, *Pichia pastoris.*

Antibody Ab12

The invention is further directed to the use of polynucleotides encoding Ab12 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab12 antibody polypeptides having binding specificity to NGF. As noted above, Ab12 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 111:

```
                                        (SEQ ID NO: 311)
GCATTCCAGATGACCCAGTCTCCATCCTCCCTGTCTGCATCTGTAGGAGA
CAGAGTCACCATCACTTGCCAGGCCAGTCAGAACATTGTTACCAACTTAG
CCTGGTATCAGCAGAAACCAGGGAAAGTCCCTAAGCTCCTGATCTATGGT
GCATCCACTCTGGCATCTGGGGTCCCATCTCGTTTCAGTGGCAGTGGATC
TGGGACAGATTTCACTCTCACCATCAGCAGCCTGCAGCCTGAAGATGTTG
CAACTTATTACTGTCAGAGCTATGATGGTTTCAATAGTGCTGGTTTCGGC
GGAGGAACCAAGGTGGAAATCAAACGT.
```

In one embodiment of the invention, polynucleotides of the invention comprise, or alternatively consist of, the following polynucleotide sequence encoding the light chain polypeptide sequence of SEQ ID NO: 112:

```
                                        (SEQ ID NO: 312)
GCATTCCAGATGACCCAGTCTCCATCCTCCCTGTCTGCATCTGTAGGAGA
CAGAGTCACCATCACTTGCCAGGCCAGTCAGAACATTGTTACCAACTTAG
CCTGGTATCAGCAGAAACCAGGGAAAGTCCCTAAGCTCCTGATCTATGGT
GCATCCACTCTGGCATCTGGGGTCCCATCTCGTTTCAGTGGCAGTGGATC
TGGGACAGATTTCACTCTCACCATCAGCAGCCTGCAGCCTGAAGATGTTG
CAACTTATTACTGTCAGAGCTATGATGGTTTCAATAGTGCTGGTTTCGGC
GGAGGAACCAAGGTGGAAATCAAACGTACGGTAGCGGCCCCATCTGTCTT
CATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCA
GGACAGCAAGGACAGCACCTACAGCCTCAGCAGCACCCTGACGCTGAGCA
AAGCAGACTACGAGAAACACAAAGTCTACGCCTGCGAAGTCACCCATCAG
GGCCTGAGCTCGCCCGTCACAAAGAGCTTCAACAGGGGAGAGTGTTAG.
```

In another embodiment of the invention, polynucleotides of the invention comprise, or alternatively consist of, the following polynucleotide sequence encoding the variable heavy chain polypeptide sequence of SEQ ID NO: 113:

```
                                        (SEQ ID NO: 313)
CAGGTACAGCTGGTGGAGTCTGGTGGAGGCGTGGTCCAGCCTGGGAGGTC
CCTGAGACTCTCCTGTGCAGCTTCTGGATTCTCCCTCAGTGGCTACGACA
TGAGCTGGGTCCGTCAGGCTCCAGGCAAGGGACTGGAGTGGGTGGGACTC
ATTAGTTATGATGGTAACACATACTACGCGACCTCCGCGAAAGGCCGATT
CACCATCTCCAGAGACAATTCCAAGAACACGCTGTACCTGCAAATGTCTA
GCCTGAGAGCCGAGGACACGGCTGTGTATTACTGTGCTAGAAGTCTTTAT
GCTGGTCCTAATGCTGGTATCGGACCGTTTAACATCTGGGGCCAAGGTAC
CCTCGTCACCGTCTCGAGC.
```

In one embodiment of the invention, polynucleotides of the invention comprise, or alternatively consist of, the following polynucleotide sequence encoding the heavy chain polypeptide sequence of SEQ ID NO: 114:

```
                                        (SEQ ID NO: 314)
CAGGTACAGCTGGTGGAGTCTGGTGGAGGCGTGGTCCAGCCTGGGAGGTC
CCTGAGACTCTCCTGTGCAGCTTCTGGATTCTCCCTCAGTGGCTACGACA
TGAGCTGGGTCCGTCAGGCTCCAGGCAAGGGACTGGAGTGGGTGGGACTC
ATTAGTTATGATGGTAACACATACTACGCGACCTCCGCGAAAGGCCGATT
CACCATCTCCAGAGACAATTCCAAGAACACGCTGTACCTGCAAATGTCTA
GCCTGAGAGCCGAGGACACGGCTGTGTATTACTGTGCTAGAAGTCTTTAT
GCTGGTCCTAATGCTGGTATCGGACCGTTTAACATCTGGGGCCAAGGTAC
CCTCGTCACCGTCTCGAGCGCCTCCACCAAGGGCCCATCGGTCTTCCCCC
TGGCACCCTCCTCCAAGAGCACCTCTGGGGGCACAGCGGCCCTGGGCTGC
CTGGTCAAGGACTACTTCCCCGAACCGGTGACGGTGTCGTGGAACTCAGG
CGCCCTGACCAGCGGCGTGCACACCTTCCCGGCTGTCCTACAGTCCTCAG
```

-continued

GACTCTACTCCCTCAGCAGCGTGGTGACCGTGCCCTCCAGCAGCTTGGGC

ACCCAGACCTACATCTGCAACGTGAATCACAAGCCCAGCAACACCAAGGT

GGACAAGAGAGTTGAGCCCAAATCTTGTGACAAAACTCACACATGCCCAC

CGTGCCCAGCACCTGAACTCCTGGGGGGACCGTCAGTCTTCCTCTTCCCC

CCAAAACCCAAGGACACCCTCATGATCTCCCGGACCCCTGAGGTCACATG

CGTGGTGGTGGACGTGAGCCACGAAGACCCTGAGGTCAAGTTCAACTGGT

ACGTGGACGGCGTGGAGGTGCATAATGCCAAGACAAAGCCGCGGGAGGAG

CAGTACGCCAGCACGTACCGTGTGGTCAGCGTCCTCACCGTCCTGCACCA

GGACTGGCTGAATGGCAAGGAGTACAAGTGCAAGGTCTCCAACAAAGCCC

TCCCAGCCCCCATCGAGAAAACCATCTCCAAAGCCAAAGGGCAGCCCCGA

GAACCACAGGTGTACACCCTGCCCCCATCCCGGGAGGAGATGACCAAGAA

CCAGGTCAGCCTGACCTGCCTGGTCAAAGGCTTCTATCCCAGCGACATCG

CCGTGGAGTGGGAGAGCAATGGGCAGCCGGAGAACAACTACAAGACCACG

CCTCCCGTGCTGGACTCCGACGGCTCCTTCTTCCTCTACAGCAAGCTCAC

CGTGGACAAGAGCAGGTGGCAGCAGGGGAACGTCTTCTCATGCTCCGTGA

TGCATGAGGCTCTGCACAACCACTACACGCAGAAGAGCCTCTCCCTGTCT

CCGGGTAAATGA.

In a further embodiment of the invention, polynucleotides encoding antibody fragments having binding specificity to NGF comprise, or alternatively consist of, one or more of the polynucleotide sequences of SEQ ID NO: 315; SEQ ID NO: 316; and SEQ ID NO: 317 which correspond to polynucleotides encoding the complementarity-determining regions (CDRs, or hypervariable regions) of the light chain variable sequence of SEQ ID NO: 111 or the light chain sequence of SEQ ID NO: 112.

In a further embodiment of the invention, polynucleotides encoding antibody fragments having binding specificity to NGF comprise, or alternatively consist of, one or more of the polynucleotide sequences of SEQ ID NO: 318; SEQ ID NO: 319; and SEQ ID NO: 320 which correspond to polynucleotides encoding the complementarity-determining regions (CDRs, or hypervariable regions) of the heavy chain variable sequence of SEQ ID NO: 113 or the heavy chain sequence of SEQ ID NO: 114.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 311 encoding the light chain variable sequence of SEQ ID NO: 111; the polynucleotide SEQ ID NO: 312 encoding the light chain sequence of SEQ ID NO: 112; the polynucleotide SEQ ID NO: 313 encoding the heavy chain variable sequence of SEQ ID NO: 113; the polynucleotide SEQ ID NO: 314 encoding the heavy chain sequence of SEQ ID NO: 114; polynucleotides encoding the complementarity-determining regions (SEQ ID NO: 315; SEQ ID NO: 316; and SEQ ID NO: 317) of the light chain variable sequence of SEQ ID NO: 111 or the light chain sequence of SEQ ID NO: 112; and polynucleotides encoding the complementarity-determining regions (SEQ ID NO: 318; SEQ ID NO: 319; and SEQ ID NO: 320) of the heavy chain variable sequence of SEQ ID NO: 113 or the heavy chain sequence of SEQ ID NO: 114.

In a preferred embodiment of the invention, polynucleotides of the invention comprise, or alternatively consist of, polynucleotides encoding Fab (fragment antigen binding) fragments having binding specificity for NGF. With respect to antibody Ab12, the polynucleotides encoding the full length Ab12 antibody comprise, or alternatively consist of, the polynucleotide SEQ ID NO: 312 encoding the light chain sequence of SEQ ID NO: 112 and the polynucleotide SEQ ID NO: 314 encoding the heavy chain sequence of SEQ ID NO: 114.

Another embodiment of the invention contemplates these polynucleotides incorporated into an expression vector for expression in mammalian cells such as CHO, NSO, HEK-293, or in fungal, insect, plant cells, transgenic plants or animals, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab12 following expression of the full-length polynucleotides in a suitable host. In another embodiment of the invention, anti-NGF antibodies such as Ab12 or Fab fragments thereof or MetMab like monovalent agents may be produced via expression of Ab12 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab13

The invention is further directed to the use of polynucleotides encoding Ab13 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab13 antibody polypeptides having binding specificity to NGF. As noted above, Ab13 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 121:

(SEQ ID NO: 321)

GCCGCCGTGCTGACCCAGACTCCATCTCCCGTGTCTGCAGCTGTGGGAGG

CACAGTCAGCATCAGTTGCCAGTCCAGTCAGAATGTTTATAAGAACAACT

ACTTATCCTGGTATCAGCAGAAACCAGGGCAGCCTCCCAAGCTCCTGATC

TACAAGGCATCCACTCTGGCATCTGGGGTCCCATCGCGGTTCAAAGGCGG

TGGATCTGGGACAGATTTCACTCTCACCATCAGCGACGTGCAGTGTGACG

CTGCTGCCACTTACTACTGTGCAGGCGGTTATACCAGTAGTAGTGATAAT

-continued

GCTTTCGGCGGAGGGACCGAGGTGGTGGTCAAACGT.

In one embodiment of the invention, polynucleotides of the invention comprise, or alternatively consist of, the following polynucleotide sequence encoding the light chain polypeptide sequence of SEQ ID NO: 122:

(SEQ ID NO: 322)
GCCGCCGTGCTGACCCAGACTCCATCTCCCGTGTCTGCAGCTGTGGGAGG
CACAGTCAGCATCAGTTGCCAGTCCAGTCAGAATGTTTATAAGAACAACT
ACTTATCCTGGTATCAGCAGAAACCAGGGCAGCCTCCCAAGCTCCTGATC
TACAAGGCATCCACTCTGGCATCTGGGGTCCCATCGCGGTTCAAAGGCGG
TGGATCTGGGACAGATTTCACTCTCACCATCAGCGACGTGCAGTGTGACG
CTGCTGCCACTTACTACTGTGCAGGCGGTTATACCAGTAGTAGTGATAAT
GCTTTCGGCGGAGGGACCGAGGTGGTGGTCAAACGTACGGTAGCGGCCCC
ATCTGTCTTCATCTTCCCGCCATCTGATGAGCAGTTGAAATCTGGAACTG
CCTCTGTTGTGTGCCTGCTGAATAACTTCTATCCCAGAGAGGCCAAAGTA
CAGTGGAAGGTGGATAACGCCCTCCAATCGGGTAACTCCCAGGAGAGTGT
CACAGAGCAGGACAGCAAGGACAGCACCTACAGCCTCAGCAGCACCCTGA
CGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGA
GTGTTA.

In another embodiment of the invention, polynucleotides of the invention comprise, or alternatively consist of, the following polynucleotide sequence encoding the variable heavy chain polypeptide sequence of SEQ ID NO: 123:

(SEQ ID NO: 323)
CAGTCGGTGGAGGCGTCCGGGGGTCGCCTGGTCACGCCTGGGACACCCC
TGACACTCACCTGCACAGCCTCTGGATTCTCCCTCAGTACCTACTGGAT
GAGCTGGGTCCGCCAGGCTCCAGGGAAGGGGCTGGAATGGATCGGAGAC
ATTTATTTTAGTAATGAAGAAACAAACTACGCGAGCTGGGCGAAAGGCC
GATTTACCATCTCCAAAACCTCGACCACGGTGGATCTGAATGTCATCAG
TCCGACAACCGAGGACACGGCCACCTATTTCTGTGCCAGAGGTTCTCCT
GATGTTGATATTGGTATAGATATGTGGGGCCCGGGCACCCTCGTCACCG
TCTCGAGC.

In one embodiment of the invention, polynucleotides of the invention comprise, or alternatively consist of, the following polynucleotide sequence encoding the heavy chain polypeptide sequence of SEQ ID NO: 124:

(SEQ ID NO: 324)
CAGTCGGTGGAGGCGTCCGGGGGTCGCCTGGTCACGCCTGGGACACCCCT
GACACTCACCTGCACAGCCTCTGGATTCTCCCTCAGTACCTACTGGATGA
GCTGGGTCCGCCAGGCTCCAGGGAAGGGGCTGGAATGGATCGGAGACATT
TATTTTAGTAATGAAGAAACAAACTACGCGAGCTGGGCGAAAGGCCGATT
TACCATCTCCAAAACCTCGACCACGGTGGATCTGAATGTCATCAGTCCGA

-continued

CAACCGAGGACACGGCCACCTATTTCTGTGCCAGAGGTTCTCCTGATGTT
GATATTGGTATAGATATGTGGGGCCCGGGCACCCTCGTCACCGTCTCGAG
CGCCTCCACCAAGGGCCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAGAGTTGAGCC
CAAATCTTGTGACAAAACTCACACATGCCCACCGTGCCCAGCACCTGAAC
TCCTGGGGGGACCGTCAGTCTTCCTCTTCCCCCCAAAACCCAAGGACACC
CTCATGATCTCCCGGACCCCTGAGGTCACATGCGTGGTGGTGGACGTGAG
CCACGAAGACCCTGAGGTCAAGTTCAACTGGTACGTGGACGGCGTGGAGG
TGCATAATGCCAAGACAAAGCCGCGGGAGGAGCAGTACGCCAGCACGTAC
CGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGA
AAACCATCTCCAAAGCCAAAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGTAAATGA.

In a further embodiment of the invention, polynucleotides encoding antibody fragments having binding specificity to NGF comprise, or alternatively consist of, one or more of the polynucleotide sequences of SEQ ID NO: 325; SEQ ID NO: 326; and SEQ ID NO: 327 which correspond to polynucleotides encoding the complementarity-determining regions (CDRs, or hypervariable regions) of the light chain variable sequence of SEQ ID NO: 121 or the light chain sequence of SEQ ID NO: 122.

In a further embodiment of the invention, polynucleotides encoding antibody fragments having binding specificity to NGF comprise, or alternatively consist of, one or more of the polynucleotide sequences of SEQ ID NO: 328; SEQ ID NO: 329; and SEQ ID NO: 330 which correspond to polynucleotides encoding the complementarity-determining regions (CDRs, or hypervariable regions) of the heavy chain variable sequence of SEQ ID NO: 123 or the heavy chain sequence of SEQ ID NO: 124.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 321 encoding the light chain variable sequence of SEQ ID NO: 121; the polynucleotide SEQ ID NO: 322 encoding the light chain sequence of SEQ ID NO: 122; the polynucleotide SEQ ID NO: 323 encoding the heavy chain variable sequence of SEQ ID NO: 123; the polynucleotide SEQ ID NO: 324 encoding the heavy chain sequence of SEQ ID NO: 124; polynucleotides encoding the complementarity-determining regions (SEQ ID NO: 325; SEQ ID NO: 326; and SEQ ID NO: 327) of the light chain variable sequence of SEQ ID NO: 121 or the light chain sequence of SEQ ID NO: 122; and polynucleotides encoding the complementarity-determining regions (SEQ ID NO: 328; SEQ ID NO: 329; and SEQ ID NO: 330) of the heavy chain variable sequence of SEQ ID NO: 123 or the heavy chain sequence of SEQ ID NO: 124.

In a preferred embodiment of the invention, polynucleotides of the invention comprise, or alternatively consist of, polynucleotides encoding Fab (fragment antigen binding) fragments having binding specificity for NGF and MetMab like monovalent agents. With respect to antibody Ab13, the polynucleotides encoding the full length Ab13 antibody comprise, or alternatively consist of, the polynucleotide SEQ ID NO: 322 encoding the light chain sequence of SEQ ID NO: 122 and the polynucleotide SEQ ID NO: 324 encoding the heavy chain sequence of SEQ ID NO: 124.

Another embodiment of the invention contemplates these polynucleotides incorporated into an expression vector for expression in mammalian cells such as CHO, NSO, HEK-293, or in fungal, insect, plant cell, transgenic plants or animals, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab13 following expression of the full-length polynucleotides in a suitable host. In another embodiment of the invention, anti-NGF antibodies such as Ab13 or Fab fragments thereof may be produced via expression of Ab13 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab14

The invention is further directed to the use of polynucleotides encoding Ab14 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab14 antibody polypeptides having binding specificity to NGF. As noted above, Ab14 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 131:

(SEQ ID NO: 331)
GACATCCAGATGACCCAGTCTCCATCCTCCCTGTCTGCATCTGTAGGAGA
CAGAGTCACCATCACTTGCCAGTCCAGTCAGAATGTTTATAAGAACAACT
ACTTATCCTGGTATCAGCAGAAACCAGGGAAAGTCCCTAAGCTCCTGATC
TATAAGGCATCCACTCTGGCATCTGGGGTCCCATCTCGTTTCAGTGGCAG
TGGATCTGGGACAGATTTCACTCTCACCATCAGCAGCCTGCAGCCTGAAG
ATGTTGCAACTTATTACTGTGCAGGCGGTTATACCAGTAGTAGTGATAAT
GCTTTCGGCGGAGGAACCAAGGTGGAAATCAAACGT.

In one embodiment of the invention, polynucleotides of the invention comprise, or alternatively consist of, the following polynucleotide sequence encoding the light chain polypeptide sequence of SEQ ID NO: 132:

(SEQ ID NO: 332)
GACATCCAGATGACCCAGTCTCCATCCTCCCTGTCTGCATCTGTAGGAG
ACAGAGTCACCATCACTTGCCAGTCCAGTCAGAATGTTTATAAGAACAA
CTACTTATCCTGGTATCAGCAGAAACCAGGGAAAGTCCCTAAGCTCCTG
ATCTATAAGGCATCCACTCTGGCATCTGGGGTCCCATCTCGTTTCAGTG
GCAGTGGATCTGGGACAGATTTCACTCTCACCATCAGCAGCCTGCAGCC
TGAAGATGTTGCAACTTATTACTGTGCAGGCGGTTATACCAGTAGTAGT
GATAATGCTTTCGGCGGAGGAACCAAGGTGGAAATCAAACGTACGGTAG
CGGCCCCATCTGTCTTCATCTTCCCGCCATCTGATGAGCAGTTGAAATC
TGGAACTGCCTCTGTTGTGTGCCTGCTGAATAACTTCTATCCCAGAGAG
GCCAAAGTACAGTGGAAGGTGGATAACGCCCTCCAATCGGGTAACTCCC
AGGAGAGTGTCACAGAGCAGGACAGCAAGGACAGCACCTACAGCCTCAG
CAGCACCCTGACGCTGAGCAAAGCAGACTACGAGAAACACAAAGTCTAC
GCCTGCGAAGTCACCCATCAGGGCCTGAGCTCGCCCGTCACAAAGAGCT
TCAACAGGGGAGAGTGTTAG.

In another embodiment of the invention, polynucleotides of the invention comprise, or alternatively consist of, the following polynucleotide sequence encoding the variable heavy chain polypeptide sequence of SEQ ID NO: 133:

(SEQ ID NO: 333)
GAGGTGCAGCTGGTGGAGTCTGGGGGAGGCTTGGTCCAGCCTGGGGGGTC
CCTGAGACTCTCCTGTGCAGCCTCTGGATTCACCGTCAGTACCTACTGGA
TGAGCTGGGTCCGTCAGGCTCCAGGGAAGGGGCTGGAGTGGGTCGGAGAC
ATTTACTTTAGTAATGAAGAAACAAACTACGCGAGCAGCGCGAAAGGCCG
ATTCACCATCTCCAGAGACAATTCCAAGAACACCCTGTATCTTCAAATGA
ACAGCCTGAGAGCTGAGGACACTGCTGTGTATTACTGTGCTAGAGGTTCT
CCTGATGTTGATATTGGTATAGATATGTGGGGCCCAGGGACCCTCGTCAC
CGTCTCGAGC.

In one embodiment of the invention, polynucleotides of the invention comprise, or alternatively consist of, the following polynucleotide sequence encoding the heavy chain polypeptide sequence of SEQ ID NO: 134:

(SEQ ID NO: 334)

GAGGTGCAGCTGGTGGAGTCTGGGGGAGGCTTGGTCCAGCCTGGGGGGTC

CCTGAGACTCTCCTGTGCAGCCTCTGGATTCACCGTCAGTACCTACTGGA

TGAGCTGGGTCCGTCAGGCTCCAGGGAAGGGGCTGGAGTGGGTCGGAGAC

ATTTACTTTAGTAATGAAGAAACAAACTACGCGAGCAGCGCGAAAGGCCG

ATTCACCATCTCCAGAGACAATTCCAAGAACACCCTGTATCTTCAAATGA

ACAGCCTGAGAGCTGAGGACACTGCTGTGTATTACTGTGCTAGAGGTTCT

CCTGATGTTGATATTGGTATAGATATGTGGGGCCCAGGGACCCTCGTCAC

CGTCTCGAGCGCCTCCACCAAGGGCCCATCGGTCTTCCCCCTGGCACCCT

CCTCCAAGAGCACCTCTGGGGGCACAGCGGCCCTGGGCTGCCTGGTCAAG

GACTACTTCCCCGAACCGGTGACGGTGTCGTGGAACTCAGGCGCCCTGAC

CAGCGGCGTGCACACCTTCCCGGCTGTCCTACAGTCCTCAGGACTCTACT

CCCTCAGCAGCGTGGTGACCGTGCCCTCCAGCAGCTTGGGCACCCAGACC

TACATCTGCAACGTGAATCACAAGCCCAGCAACACCAAGGTGGACAAGAG

AGTTGAGCCCAAATCTTGTGACAAAACTCACACATGCCCACCGTGCCCAG

CACCTGAACTCCTGGGGGGACCGTCAGTCTTCCTCTTCCCCCCAAAACCC

AAGGACACCCTCATGATCTCCCGGACCCCTGAGGTCACATGCGTGGTGGT

GGACGTGAGCCACGAAGACCCTGAGGTCAAGTTCAACTGGTACGTGGACG

GCGTGGAGGTGCATAATGCCAAGACAAAGCCGCGGGAGGAGCAGTACGCC

AGCACGTACCGTGTGGTCAGCGTCCTCACCGTCCTGCACCAGGACTGGCT

GAATGGCAAGGAGTACAAGTGCAAGGTCTCCAACAAAGCCCTCCCAGCCC

CCATCGAGAAAACCATCTCCAAAGCCAAAGGGCAGCCCCGAGAACCACAG

GTGTACACCCTGCCCCCATCCCGGGAGGAGATGACCAAGAACCAGGTCAG

CCTGACCTGCCTGGTCAAAGGCTTCTATCCCAGCGACATCGCCGTGGAGT

GGGAGAGCAATGGGCAGCCGGAGAACAACTACAAGACCACGCCTCCCGTG

CTGGACTCCGACGGCTCCTTCTTCCTCTACAGCAAGCTCACCGTGGACAA

GAGCAGGTGGCAGCAGGGGAACGTCTTCTCATGCTCCGTGATGCATGAGG

CTCTGCACAACCACTACACGCAGAAGAGCCTCTCCCTGTCTCCGGGTAAA

TGA.

In a further embodiment of the invention, polynucleotides encoding antibody fragments having binding specificity to NGF comprise, or alternatively consist of, one or more of the polynucleotide sequences of SEQ ID NO: 335; SEQ ID NO: 336; and SEQ ID NO: 337 which correspond to polynucleotides encoding the complementarity-determining regions (CDRs, or hypervariable regions) of the light chain variable sequence of SEQ ID NO: 131 or the light chain sequence of SEQ ID NO: 132.

In a further embodiment of the invention, polynucleotides encoding antibody fragments having binding specificity to NGF comprise, or alternatively consist of, one or more of the polynucleotide sequences of SEQ ID NO: 338; SEQ ID NO: 339; and SEQ ID NO: 340 which correspond to polynucleotides encoding the complementarity-determining regions (CDRs, or hypervariable regions) of the heavy chain variable sequence of SEQ ID NO: 133 or the heavy chain sequence of SEQ ID NO: 134.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 331 encoding the light chain variable sequence of SEQ ID NO: 131; the polynucleotide SEQ ID NO: 332 encoding the light chain sequence of SEQ ID NO: 132; the polynucleotide SEQ ID NO: 333 encoding the heavy chain variable sequence of SEQ ID NO: 133; the polynucleotide SEQ ID NO: 334 encoding the heavy chain sequence of SEQ ID NO: 134; polynucleotides encoding the complementarity-determining regions (SEQ ID NO: 335; SEQ ID NO: 336; and SEQ ID NO: 337) of the light chain variable sequence of SEQ ID NO: 131 or the light chain sequence of SEQ ID NO: 132; and polynucleotides encoding the complementarity-determining regions (SEQ ID NO: 338; SEQ ID NO: 339; and SEQ ID NO: 340) of the heavy chain variable sequence of SEQ ID NO: 133 or the heavy chain sequence of SEQ ID NO: 134.

In a preferred embodiment of the invention, polynucleotides of the invention comprise, or alternatively consist of, polynucleotides encoding Fab (fragment antigen binding) fragments having binding specificity for NGF. With respect to antibody Ab14, the polynucleotides encoding the full length Ab14 antibody comprise, or alternatively consist of, the polynucleotide SEQ ID NO: 332 encoding the light chain sequence of SEQ ID NO: 132 and the polynucleotide SEQ ID NO: 334 encoding the heavy chain sequence of SEQ ID NO: 134.

Another embodiment of the invention contemplates these polynucleotides incorporated into an expression vector for expression in mammalian cells such as CHO, NSO, HEK-293, or in fungal, insect, plant cells, transgenic plants or animals, or microbial systems such as bacterial or yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab14 following expression of the full-length polynucleotides in a suitable host. In another embodiment of the invention, anti-NGF antibodies such as Ab14 or Fab fragments or MetMab like monovalent agents thereof may be produced via expression of Ab14 polynucleotides in mammalian cells such as CHO, NSO or HEK 293 cells, fungal, insect, plant, animal, or microbial systems such as yeast cells (for example diploid yeast such as diploid *Pichia*) and other yeast strains. Suitable *Pichia* species include, but are not limited to, *Pichia pastoris*.

Antibody Ab15

The invention is further directed to the use of polynucleotides encoding Ab15 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab15 antibody polypeptides having binding specificity to NGF. As noted above, Ab15 antibodies inhibit the interaction of NGF with TrkA and do not appreciably inhibit the interaction of NGF with p75. In one embodiment of the invention, polynucleotides of the invention comprise, or alternatively consist of, the following polynucleotide sequence encoding the variable light chain polypeptide sequence of SEQ ID NO: 141:

(SEQ ID NO: 341)

GCAGCCGTGCTGACCCAGACACCATCGCCCGTGTCTGCAGCTGTGGG

AGACACAGTCACCATCAAGTGCCAGTCCAGTCAGAGTGTTTATAAGAA

CAACTACTTATCCTGGTATCAGCAGAAACCAGGGCAGCCTCCCAAGCT

CCTGATCTATGATGCATCCAATCTGCCATCTGGGGTCCCATCACGGTT

CAGCGGCAGTGGATCTGGGACACAGTTCACTCTCACCATCAGCGGCGT

GCAGTGTGACGATGCTGCCACTTACTACTGTCTAGGCGATTATGATGA

TGATACTGATAATGGTTTCGGCGGAGGGACCGAGGTGGTGGTCAAACGT.

In one embodiment of the invention, polynucleotides of the invention comprise, or alternatively consist of, the following polynucleotide sequence encoding the light chain polypeptide sequence of SEQ ID NO: 142:

(SEQ ID NO: 342)

GCAGCCGTGCTGACCCAGACACCATCGCCCGTGTCTGCAGCTGTGGG

AGACACAGTCACCATCAAGTGCCAGTCCAGTCAGAGTGTTTATAAGAA

CAACTACTTATCCTGGTATCAGCAGAAACCAGGGCAGCCTCCCAAGCT

CCTGATCTATGATGCATCCAATCTGCCATCTGGGGTCCCATCACGGTT

CAGCGGCAGTGGATCTGGGACACAGTTCACTCTCACCATCAGCGGCGT

GCAGTGTGACGATGCTGCCACTTACTACTGTCTAGGCGATTATGATGA

TGATACTGATAATGGTTTCGGCGGAGGGACCGAGGTGGTGGTCAAACG

TACGGTAGCGGCCCCATCTGTCTTCATCTTCCCGCCATCTGATGAGCA

GTTGAAATCTGGAACTGCCTCTGTTGTGTGCCTGCTGAATAACTTCTA

TCCCAGAGAGGCCAAAGTACAGTGGAAGGTGGATAACGCCCTCCAATC

GGGTAACTCCCAGGAGAGTGTCACAGAGCAGGACAGCAAGGACAGCAC

CTACAGCCTCAGCAGCACCCTGACGCTGAGCAAAGCAGACTACGAGAA

ACACAAAGTCTACGCCTGCGAAGTCACCCATCAGGGCCTGAGCTCGCC

CGTCACAAAGAGCTTCAACAGGGGAGAGTGTTAG.

In another embodiment of the invention, polynucleotides of the invention comprise, or alternatively consist of, the following polynucleotide sequence encoding the variable heavy chain polypeptide sequence of SEQ ID NO: 143:

(SEQ ID NO: 343)

CAGTCGGTGGAGGAGTCCGGGGGTCGCCTGGTCACGCCTGGGACACC

CCTGACACTCACCTGCACAGTCTCTGGAATCGACCTCAGTAGCTATGC

AATGATCTGGGTCCGCCAGGCTCCAGGGAAGGGGCTGGAATACATCGG

AATCATTTGGAGTGGTGGCACCTACTACGCGACCTGGGCGAAAGGCCG

ATTCACCATCTCCAAAACCTCGACCACGGTGGATCTGCAAATCACCAG

TCCGACAACCGAGGACGCGGCCACCTATTTCTGTGCCGCAGGTGGTGG

TAGTATTTATGATGTTTGGGGCCCGGGCACCCTGGTCACCGTCTCGAGC.

In one embodiment of the invention, polynucleotides of the invention comprise, or alternatively consist of, the following polynucleotide sequence encoding the heavy chain polypeptide sequence of SEQ ID NO: 144:

(SEQ ID NO: 344)

CAGTCGGTGGAGGAGTCCGGGGGTCGCCTGGTCACGCCTGGGACACCC

CTGACACTCACCTGCACAGTCTCTGGAATCGACCTCAGTAGCTATGCA

ATGATCTGGGTCCGCCAGGCTCCAGGGAAGGGGCTGGAATACATCGGA

ATCATTTGGAGTGGTGGCACCTACTACGCGACCTGGGCGAAAGGCCGA

TTCACCATCTCCAAAACCTCGACCACGGTGGATCTGCAAATCACCAGT

CCGACAACCGAGGACGCGGCCACCTATTTCTGTGCCGCAGGTGGTGGT

AGTATTTATGATGTTTGGGGCCCGGGCACCCTGGTCACCGTCTCGAGC

GCCTCCACCAAGGGCCCATCGGTCTTCCCCCTGGCACCCTCCTCCAAG

AGCACCTCTGGGGGCACAGCGGCCCTGGGCTGCCTGGTCAAGGACTAC

TTCCCCGAACCGGTGACGGTGTCGTGGAACTCAGGCGCCCTGACCAGC

GGCGTGCACACCTTCCCGGCTGTCCTACAGTCCTCAGGACTCTACTCC

CTCAGCAGCGTGGTGACCGTGCCCTCCAGCAGCTTGGGCACCCAGACC

TACATCTGCAACGTGAATCACAAGCCCAGCAACACCAAGGTGGACAAG

AGAGTTGAGCCCAAATCTTGTGACAAAACTCACACATGCCCACCGTGC

CCAGCACCTGAACTCCTGGGGGGACCGTCAGTCTTCCTCTTCCCCCCA

AAACCCAAGGACACCCTCATGATCTCCCGGACCCCTGAGGTCACATGC

GTGGTGGTGGACGTGAGCCACGAAGACCCTGAGGTCAAGTTCAACTGG

TACGTGGACGGCGTGGAGGTGCATAATGCCAAGACAAAGCCGCGGGAG

GAGCAGTACGCCAGCACGTACCGTGTGGTCAGCGTCCTCACCGTCCTG

CACCAGGACTGGCTGAATGGCAAGGAGTACAAGTGCAAGGTCTCCAAC

AAAGCCCTCCCAGCCCCCATCGAGAAAACCATCTCCAAAGCCAAAGGG

CAGCCCCGAGAACCACAGGTGTACACCCTGCCCCCATCCCGGGAGGAG

ATGACCAAGAACCAGGTCAGCCTGACCTGCCTGGTCAAAGGCTTCTAT

CCCAGCGACATCGCCGTGGAGTGGGAGAGCAATGGGCAGCCGGAGAAC

AACTACAAGACCACGCCTCCCGTGCTGGACTCCGACGGCTCCTTCTTC

CTCTACAGCAAGCTCACCGTGGACAAGAGCAGGTGGCAGCAGGGGAAC

GTCTTCTCATGCTCCGTGATGCATGAGGCTCTGCACAACCACTACACG

CAGAAGAGCCTCTCCCTGTCTCCGGGTAAATGA.

In a further embodiment of the invention, polynucleotides encoding antibody fragments having binding specificity to NGF comprise, or alternatively consist of, one or more of the polynucleotide sequences of SEQ ID NO: 345; SEQ ID NO: 346; and SEQ ID NO: 347 which correspond to polynucleotides encoding the complementarity-determining regions (CDRs, or hypervariable regions) of the light chain variable sequence of SEQ ID NO: 141 or the light chain sequence of SEQ ID NO: 142.

In a further embodiment of the invention, polynucleotides encoding antibody fragments having binding specificity to NGF comprise, or alternatively consist of, one or more of the polynucleotide sequences of SEQ ID NO: 348; SEQ ID NO: 349; and SEQ ID NO: 350 which correspond to polynucleotides encoding the complementarity-determining regions (CDRs, or hypervariable regions) of the heavy chain variable sequence of SEQ ID NO: 143 or the heavy chain sequence of SEQ ID NO: 144.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 341 encoding the light chain variable sequence of SEQ ID NO: 141; the polynucleotide SEQ ID NO: 342 encoding the light chain sequence of SEQ ID NO: 142; the polynucleotide SEQ ID NO: 343 encoding the heavy chain variable sequence of SEQ ID NO: 143; the polynucleotide SEQ ID NO: 344 encoding the heavy chain sequence of SEQ ID NO: 144; polynucleotides encoding the complementarity-determining regions (SEQ ID NO: 345; SEQ ID NO: 346; and SEQ ID NO: 347) of the light chain variable sequence of SEQ ID NO: 141 or the light chain sequence of SEQ ID NO: 142; and polynucleotides encoding the complementarity-determining regions (SEQ ID NO: 348; SEQ ID NO: 349; and SEQ ID NO: 350) of the heavy chain variable sequence of SEQ ID NO: 143 or the heavy chain sequence of SEQ ID NO: 144.

In a preferred embodiment of the invention, polynucleotides of the invention comprise, or alternatively consist of, polynucleotides encoding Fab (fragment antigen binding) fragments having binding specificity for NGF or MetMab like monovalent agents. With respect to antibody Ab15, the polynucleotides encoding the full length Ab15 antibody comprise, or alternatively consist of, the polynucleotide SEQ ID NO: 342 encoding the light chain sequence of SEQ ID NO: 142 and the polynucleotide SEQ ID NO: 344 encoding the heavy chain sequence of SEQ ID NO: 144.

Another embodiment of the invention contemplates these polynucleotides incorporated into an expression vector for expression in mammalian cells such as CHO, NSO, HEK-293, or in fungal, insect, plant cells, transgenic plants or animals, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab15 following expression of the full-length polynucleotides in a suitable host. In another embodiment of the invention, anti-NGF antibodies such as Ab15 or Fab fragments thereof may be produced via expression of Ab15 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris.*

Antibody Ab16

The invention is further directed to the use of polynucleotides encoding Ab16 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof. Described below are polynucleotides encoding Ab16 antibody polypeptides having binding specificity to NGF. As noted above, Ab16 antibodies inhibit the interaction of NGF with TrkA and do not appreciably inhibit the interaction of NGF with p75. In one embodiment of the invention, polynucleotides of the invention comprise, or alternatively consist of, the following polynucleotide sequence encoding the variable light chain polypeptide sequence of SEQ ID NO: 151:

(SEQ ID NO: 351)
GCCCTGGTGATGACCCAGACTCCATCCTCCACGTCTGAACCAGTGGG
AGGCACAGTCACCATCAATTGCCAGGCTAGTCAGAATATTGGTAACGA
CCTATCCTGGTATCAGCAGAAACCAGGGCAGCCTCCCGAGCTCCTAAT
CTATTCTACATCCAAACTGGCAACTGGGGTCCCAAAGCGGTTCAGTGG
CAGCAGATCTGGGACACAGTTCACTCTCACCATCAGCGACCTGGAGTG
TGACGATGCTGCCACTTACTACTGTCTAGGTGTTTATAGTTATATTAG
TGATGATGGTAATGCTTTCGGCGGAGGGACCGAGGTGGTGGTCAAACGT.

In one embodiment of the invention, polynucleotides of the invention comprise, or alternatively consist of, the following polynucleotide sequence encoding the light chain polypeptide sequence of SEQ ID NO: 152:

(SEQ ID NO: 352)
GCCCTGGTGATGACCCAGACTCCATCCTCCACGTCTGAACCAGTGGG
AGGCACAGTCACCATCAATTGCCAGGCTAGTCAGAATATTGGTAACGA
CCTATCCTGGTATCAGCAGAAACCAGGGCAGCCTCCCGAGCTCCTAAT
CTATTCTACATCCAAACTGGCAACTGGGGTCCCAAAGCGGTTCAGTGG
CAGCAGATCTGGGACACAGTTCACTCTCACCATCAGCGACCTGGAGTG
TGACGATGCTGCCACTTACTACTGTCTAGGTGTTTATAGTTATATTAG
TGATGATGGTAATGCTTTCGGCGGAGGGACCGAGGTGGTGGTCAAACG
TACGGTAGCGGCCCCATCTGTCTTCATCTTCCCGCCATCTGATGAGCA
GTTGAAATCTGGAACTGCCTCTGTTGTGTGCCTGCTGAATAACTTCTA
TCCCAGAGAGGCCAAAGTACAGTGGAAGGTGGATAACGCCCTCCAATC
GGGTAACTCCCAGGAGAGTGTCACAGAGCAGGACAGCAAGGACAGCAC
CTACAGCCTCAGCAGCACCCTGACGCTGAGCAAAGCAGACTACGAGAA
ACACAAAGTCTACGCCTGCGAAGTCACCCATCAGGGCCTGAGCTCGCC
CGTCACAAAGAGCTTCAACAGGGGAGAGTGTTAG.

In another embodiment of the invention, polynucleotides of the invention comprise, or alternatively consist of, the following polynucleotide sequence encoding the variable heavy chain polypeptide sequence of SEQ ID NO: 153:

(SEQ ID NO: 353)
CAGTCGGTGGAGGAGTTCGGGGGTCGCCTGGTCACGCCTGGGACACC
CCTGACACTCACCTGCACCGTCTCTGGATTCTCCCTCAATAACTATGCA
ATGACCTGGGTCCGCCAGGCTCCAGGGAAGGGGCTGGAGTGGATCGGGA
TCATTGGTAGTATTGGTACCACATACTACGCGAGCTGGGCGAAAGGCCG
ATTCTTCATCTCCAAAACCTCGACCACTGTGGATCTGAAAATCATTAGT
CCGACAACCGAGGACACGGCCACCTATTTCTGTGCCAGAGATGCTGGCG

-continued

TTACTGTTGATGGTTATGGCTACTACTTTAACATCTGGGGCCCAGGCAC

CCTCGTCACCGTCTCGAGC.

In one embodiment of the invention, polynucleotides of the invention comprise, or alternatively consist of, the following polynucleotide sequence encoding the heavy chain polypeptide sequence of SEQ ID NO: 154:

(SEQ ID NO: 354)

CAGTCGGTGGAGGAGTTCGGGGGTCGCCTGGTCACGCCTGGGACACC

CCTGACACTCACCTGCACCGTCTCTGGATTCTCCCTCAATAACTATGCA

ATGACCTGGGTCCGCCAGGCTCCAGGGAAGGGGCTGGAGTGGATCGGGA

TCATTGGTAGTATTGGTACCACATACTACGCGAGCTGGGCGAAAGGCCG

ATTCTTCATCTCCAAAACCTCGACCACTGTGGATCTGAAAATCATTAGT

CCGACAACCGAGGACACGGCCACCTATTTCTGTGCCAGAGATGCTGGCG

TTACTGTTGATGGTTATGGCTACTACTTTAACATCTGGGGCCCAGGCAC

CCTCGTCACCGTCTCGAGCGCCTCCACCAAGGGCCCATCGGTCTTCCCC

CTGGCACCCTCCTCCAAGAGCACCTCTGGGGGCACAGCGGCCCTGGGCT

GCCTGGTCAAGGACTACTTCCCCGAACCGGTGACGGTGTCGTGGAACTC

AGGCGCCCTGACCAGCGGCGTGCACACCTTCCCGGCTGTCCTACAGTCC

TCAGGACTCTACTCCCTCAGCAGCGTGGTGACCGTGCCCTCCAGCAGCT

TGGGCACCCAGACCTACATCTGCAACGTGAATCACAAGCCCAGCAACAC

CAAGGTGGACAAGAGAGTTGAGCCCAAATCTTGTGACAAAACTCACACA

TGCCCACCGTGCCCAGCACCTGAACTCCTGGGGGGACCGTCAGTCTTCC

TCTTCCCCCCAAAACCCAAGGACACCCTCATGATCTCCCGGACCCCTGA

GGTCACATGCGTGGTGGTGGACGTGAGCCACGAAGACCCTGAGGTCAAG

TTCAACTGGTACGTGGACGGCGTGGAGGTGCATAATGCCAAGACAAAGC

CGCGGGAGGAGCAGTACGCCAGCACGTACCGTGTGGTCAGCGTCCTCAC

CGTCCTGCACCAGGACTGGCTGAATGGCAAGGAGTACAAGTGCAAGGTC

TCCAACAAAGCCCTCCCAGCCCCCATCGAGAAAACCATCTCCAAAGCCA

AAGGGCAGCCCCGAGAACCACAGGTGTACACCCTGCCCCCATCCCGGGA

GGAGATGACCAAGAACCAGGTCAGCCTGACCTGCCTGGTCAAAGGCTTC

TATCCCAGCGACATCGCCGTGGAGTGGGAGAGCAATGGGCAGCCGGAGA

ACAACTACAAGACCACGCCTCCCGTGCTGGACTCCGACGGCTCCTTCTT

CCTCTACAGCAAGCTCACCGTGGACAAGAGCAGGTGGCAGCAGGGGAAC

GTCTTCTCATGCTCCGTGATGCATGAGGCTCTGCACAACCACTACACGC

AGAAGAGCCTCTCCCTGTCTCCGGGTAAATGA.

In a further embodiment of the invention, polynucleotides encoding antibody fragments having binding specificity to NGF comprise, or alternatively consist of, one or more of the polynucleotide sequences of SEQ ID NO: 355; SEQ ID NO: 356; and SEQ ID NO: 357 which correspond to polynucleotides encoding the complementarity-determining regions (CDRs, or hypervariable regions) of the light chain variable sequence of SEQ ID NO: 151 or the light chain sequence of SEQ ID NO: 152.

In a further embodiment of the invention, polynucleotides encoding antibody fragments having binding specificity to NGF comprise, or alternatively consist of, one or more of the polynucleotide sequences of SEQ ID NO: 358; SEQ ID NO: 359; and SEQ ID NO: 360 which correspond to polynucleotides encoding the complementarity-determining regions (CDRs, or hypervariable regions) of the heavy chain variable sequence of SEQ ID NO: 153 or the heavy chain sequence of SEQ ID NO: 154.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 351 encoding the light chain variable sequence of SEQ ID NO: 151; the polynucleotide SEQ ID NO: 352 encoding the light chain sequence of SEQ ID NO: 152; the polynucleotide SEQ ID NO: 353 encoding the heavy chain variable sequence of SEQ ID NO: 153; the polynucleotide SEQ ID NO: 354 encoding the heavy chain sequence of SEQ ID NO: 154; polynucleotides encoding the complementarity-determining regions (SEQ ID NO: 355; SEQ ID NO: 356; and SEQ ID NO: 357) of the light chain variable sequence of SEQ ID NO: 151 or the light chain sequence of SEQ ID NO: 152; and polynucleotides encoding the complementarity-determining regions (SEQ ID NO: 358; SEQ ID NO: 359; and SEQ ID NO: 360) of the heavy chain variable sequence of SEQ ID NO: 153 or the heavy chain sequence of SEQ ID NO: 154.

In a preferred embodiment of the invention, polynucleotides of the invention comprise, or alternatively consist of, polynucleotides encoding Fab (fragment antigen binding) fragments having binding specificity for NGF. With respect to antibody Ab16, the polynucleotides encoding the full length Ab16 antibody comprise, or alternatively consist of, the polynucleotide SEQ ID NO: 352 encoding the light chain sequence of SEQ ID NO: 152 and the polynucleotide SEQ ID NO: 354 encoding the heavy chain sequence of SEQ ID NO: 154.

Another embodiment of the invention contemplates these polynucleotides incorporated into an expression vector for expression in mammalian cells such as CHO, NSO, HEK-293, or in fungal, insect, plant cells, transgenic plants or animals, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab16 following expression of the full-length polynucleotides in a suitable host. In another embodiment of the invention, anti-NGF antibodies such as Ab16 or Fab fragments thereof or MetMab like monovalent agents may be produced via expression of Ab16 polynucleotides in mammalian cells such as CHO, NSO or HEK 293 cells, fungal, insect, plant, animal, or microbial systems such as yeast cells (for example diploid yeast such as diploid *Pichia*) and other yeast strains. Suitable *Pichia* species include, but are not limited to, *Pichia pastoris*.

Antibody Ab17

The invention is further directed to the use of polynucleotides encoding Ab17 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab17 antibody polypeptides having binding specificity to NGF. As noted above, Ab17 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 161:

(SEQ ID NO: 361)
GCCATCGAAATGACCCAGACTCCATTCTCCGTGTCTGCAGCTGTGGG

AGGCACAGTCACCATCAAGTGCCAGGCCAGTCAGACCATTAGCAACTAC

TTAGCCTGGTATCAGCAGAAACCAGGGCAGCCTCCCAAGCTCCTGATCT

ATGGTGCATCCAATCTGGAATCTGGGGTCCCATCGCGGTTCAAAGGCAG

TGGATCTGGGACACAGTTCACTCTCACCATCAGCGACCTGGAGTGTGAC

GATGCTGCCACTTACTACTGTCAACAGGGTTATACTATCAGTAATGTTG

ATAACAATGTTTTCGGCGGAGGGACCGAGGTGGTGGTCAAACGT.

In one embodiment of the invention, polynucleotides of the invention comprise, or alternatively consist of, the following polynucleotide sequence encoding the light chain polypeptide sequence of SEQ ID NO: 162:

(SEQ ID NO: 362)
GCCATCGAAATGACCCAGACTCCATTCTCCGTGTCTGCAGCTGTGGG

AGGCACAGTCACCATCAAGTGCCAGGCCAGTCAGACCATTAGCAACTAC

TTAGCCTGGTATCAGCAGAAACCAGGGCAGCCTCCCAAGCTCCTGATCT

ATGGTGCATCCAATCTGGAATCTGGGGTCCCATCGCGGTTCAAAGGCAG

TGGATCTGGGACACAGTTCACTCTCACCATCAGCGACCTGGAGTGTGAC

GATGCTGCCACTTACTACTGTCAACAGGGTTATACTATCAGTAATGTTG

ATAACAATGTTTTCGGCGGAGGGACCGAGGTGGTGGTCAAACGTACGGT

AGCGGCCCCATCTGTCTTCATCTTCCCGCCATCTGATGAGCAGTTGAAA

TCTGGAACTGCCTCTGTTGTGTGCCTGCTGAATAACTTCTATCCCAGAG

AGGCCAAAGTACAGTGGAAGGTGGATAACGCCCTCCAATCGGGTAACTC

CCAGGAGAGTGTCACAGAGCAGGACAGCAAGGACAGCACCTACAGCCTC

AGCAGCACCCTGACGCTGAGCAAAGCAGACTACGAGAAACACAAAGTCT

ACGCCTGCGAAGTCACCCATCAGGGCCTGAGCTCGCCCGTCACAAAGAG

CTTCAACAGGGGAGAGTGTTAG.

In another embodiment of the invention, polynucleotides of the invention comprise, or alternatively consist of, the following polynucleotide sequence encoding the variable heavy chain polypeptide sequence of SEQ ID NO: 163:

(SEQ ID NO: 363)
CAGTCGCTGGAGGAGTCCGGGGGTCGCCTGGTCACGCCTGGGGGATC

CCTGACACTCACCTGCGCAGCCTCTGGATTCTCCCTCACTGGCTACAACT

-continued

TGGTCTGGGTCCGCCAGGCTCCAGGGAAGGGGCTGGAGTGGATCGGATTC

ATTAGTTATGGTGATACCACATACTACGCGAGCTGGGCGAAAGGCCGATT

CACCATCTCCAAAACCTCGACCACGGTGACTCTGACGATCACCGATCTGC

AACCTTCAGACACGGGCACCTATTTCTGTGCCAGAGAGACTGCTAATACT

TATGATTATGGCATCTGGGGCCCAGGCACCCTCGTCACCGTCTCGAGC.

In one embodiment of the invention, polynucleotides of the invention comprise, or alternatively consist of, the following polynucleotide sequence encoding the heavy chain polypeptide sequence of SEQ ID NO: 164:

(SEQ ID NO: 364)
CAGTCGCTGGAGGAGTCCGGGGGTCGCCTGGTCACGCCTGGGGGATCCCT

GACACTCACCTGCGCAGCCTCTGGATTCTCCCTCACTGGCTACAACTTGG

TCTGGGTCCGCCAGGCTCCAGGGAAGGGGCTGGAGTGGATCGGATTCATT

AGTTATGGTGATACCACATACTACGCGAGCTGGGCGAAAGGCCGATTCAC

CATCTCCAAAACCTCGACCACGGTGACTCTGACGATCACCGATCTGCAAC

CTTCAGACACGGGCACCTATTTCTGTGCCAGAGAGACTGCTAATACTTAT

GATTATGGCATCTGGGGCCCAGGCACCCTCGTCACCGTCTCGAGCGCCTC

CACCAAGGGCCCATCGGTCTTCCCCCTGGCACCCTCCTCCAAGAGCACCT

CTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACAC

CTTCCCGGCTGTCCTACAGTCCTCAGGACTCTACTCCCTCAGCAGCGTGG

TGACCGTGCCCTCCAGCAGCTTGGGCACCCAGACCTACATCTGCAACGTG

AATCACAAGCCCAGCAACACCAAGGTGGACAAGAGAGTTGAGCCCAAATC

TTGTGACAAAACTCACACATGCCCACCGTGCCCAGCACCTGAACTCCTGG

GGGGACCGTCAGTCTTCCTCTTCCCCCCAAAACCCAAGGACACCCTCATG

ATCTCCCGGACCCCTGAGGTCACATGCGTGGTGGTGGACGTGAGCCACGA

AGACCCTGAGGTCAAGTTCAACTGGTACGTGGACGGCGTGGAGGTGCATA

ATGCCAAGACAAAGCCGCGGGAGGAGCAGTACGCCAGCACGTACCGTGTG

GTCAGCGTCCTCACCGTCCTGCACCAGGACTGGCTGAATGGCAAGGAGTA

CAAGTGCAAGGTCTCCAACAAAGCCCTCCCAGCCCCCATCGAGAAAACCA

TCTCCAAAGCCAAAGGGCAGCCCCGAGAACCACAGGTGTACACCCTGCCC

CCATCCCGGGAGGAGATGACCAAGAACCAGGTCAGCCTGACCTGCCTGGT

CAAAGGCTTCTATCCCAGCGACATCGCCGTGGAGTGGGAGAGCAATGGGC

AGCCGGAGAACAACTACAAGACCACGCCTCCCGTGCTGGACTCCGACGGC

TCCTTCTTCCTCTACAGCAAGCTCACCGTGGACAAGAGCAGGTGGCAGCA

GGGGAACGTCTTCTCATGCTCCGTGATGCATGAGGCTCTGCACAACCACT

ACACGCAGAAGAGCCTCTCCCTGTCTCCGGGTAAATGA.

In a further embodiment of the invention, polynucleotides encoding antibody fragments having binding specificity to NGF comprise, or alternatively consist of, one or more of the polynucleotide sequences of SEQ ID NO: 365; SEQ ID NO: 366; and SEQ ID NO: 367 which correspond to polynucleotides encoding the complementarity-determining regions (CDRs, or hypervariable regions) of the light chain variable sequence of SEQ ID NO: 161 or the light chain sequence of SEQ ID NO: 162.

In a further embodiment of the invention, polynucleotides encoding antibody fragments having binding specificity to NGF comprise, or alternatively consist of, one or more of the polynucleotide sequences of SEQ ID NO: 368; SEQ ID NO: 369; and SEQ ID NO: 370 which correspond to polynucleotides encoding the complementarity-determining regions (CDRs, or hypervariable regions) of the heavy chain variable sequence of SEQ ID NO: 163 or the heavy chain sequence of SEQ ID NO: 164.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 361 encoding the light chain variable sequence of SEQ ID NO: 161; the polynucleotide SEQ ID NO: 362 encoding the light chain sequence of SEQ ID NO: 162; the polynucleotide SEQ ID NO: 363 encoding the heavy chain variable sequence of SEQ ID NO: 163; the polynucleotide SEQ ID NO: 364 encoding the heavy chain sequence of SEQ ID NO: 164; polynucleotides encoding the complementarity-determining regions (SEQ ID NO: 365; SEQ ID NO: 366; and SEQ ID NO: 367) of the light chain variable sequence of SEQ ID NO: 161 or the light chain sequence of SEQ ID NO: 162; and polynucleotides encoding the complementarity-determining regions (SEQ ID NO: 368; SEQ ID NO: 369; and SEQ ID NO: 370) of the heavy chain variable sequence of SEQ ID NO: 163 or the heavy chain sequence of SEQ ID NO: 164.

In a preferred embodiment of the invention, polynucleotides of the invention comprise, or alternatively consist of, polynucleotides encoding Fab (fragment antigen binding) fragments having binding specificity for NGF and MetMab like monovalent agents. With respect to antibody Ab17, the polynucleotides encoding the full length Ab17 antibody comprise, or alternatively consist of, the polynucleotide SEQ ID NO: 362 encoding the light chain sequence of SEQ ID NO: 162 and the polynucleotide SEQ ID NO: 364 encoding the heavy chain sequence of SEQ ID NO: 164.

Another embodiment of the invention contemplates these polynucleotides incorporated into an expression vector for expression in mammalian cells such as CHO, NSO, HEK-293, or in fungal, insect, plant cells, transsgenic plants or animals, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab17 following expression of the full-length polynucleotides in a suitable host. In another embodiment of the invention, anti-NGF antibodies such as Ab17 or Fab fragments thereof may be produced via expression of Ab17 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris.*

Antibody Ab18

The invention is further directed to the use of polynucleotides encoding Ab18 polypeptides set forth below to produce anti-human NGF monovalent agents used in the pain treatment methods described herein. Described below are polynucleotides encoding Ab18 antibody polypeptides having binding specificity to NGF. As noted above, Ab18 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 171:

```
(SEQ ID NO: 371)
GACATCCAGATGACCCAGTCTCCTTCCACCCTGTCTGCATCTGTAGGA

GACAGAGTCACCATCACTTGTCAGGCTAGTCAGACCATTAGCAACTACT

TAGCCTGGTATCAGCAGAAACCAGGAAAAGCCCCTAAGCTCCTGATCTA

TGGTGCATCCAATCTGGAATCTGGAGTCCCATCAAGGTTCAGCGGCAGT

GGATCTGGAACAGAATTCACTCTCACCATCAGCAGCCTGCAGCCTGATG

ATTTTGCAACTTACTACTGTCAACAGGGTTATACTATCAGTAATGTTGA

TAACAATGTTTTCGGCGGAGGAACCAAGGTGGAAATCAAACGT.
```

In one embodiment of the invention, polynucleotides of the invention comprise, or alternatively consist of, the following polynucleotide sequence encoding the light chain polypeptide sequence of SEQ ID NO: 172:

```
(SEQ ID NO: 372)
GACATCCAGATGACCCAGTCTCCTTCCACCCTGTCTGCATCTGTAGGA

GACAGAGTCACCATCACTTGTCAGGCTAGTCAGACCATTAGCAACTACT

TAGCCTGGTATCAGCAGAAACCAGGAAAAGCCCCTAAGCTCCTGATCTA

TGGTGCATCCAATCTGGAATCTGGAGTCCCATCAAGGTTCAGCGGCAGT

GGATCTGGAACAGAATTCACTCTCACCATCAGCAGCCTGCAGCCTGATG

ATTTTGCAACTTACTACTGTCAACAGGGTTATACTATCAGTAATGTTGA

TAACAATGTTTTCGGCGGAGGAACCAAGGTGGAAATCAAACGTACGGTA

GCGGCCCCATCTGTCTTCATCTTCCCGCCATCTGATGAGCAGTTGAAAT

CTGGAACTGCCTCTGTTGTGTGCCTGCTGAATAACTTCTATCCCAGAGA

GGCCAAAGTACAGTGGAAGGTGGATAACGCCCTCCAATCGGGTAACTCC

CAGGAGAGTGTCACAGAGCAGGACAGCAAGGACAGCACCTACAGCCTCA

GCAGCACCCTGACGCTGAGCAAAGCAGACTACGAGAAACACAAAGTCTA

CGCCTGCGAAGTCACCCATCAGGGCCTGAGCTCGCCCGTCACAAAGAGC

TTCAACAGGGGAGAGTGTTAG.
```

In another embodiment of the invention, polynucleotides of the invention comprise, or alternatively consist of, the following polynucleotide sequence encoding the variable heavy chain polypeptide sequence of SEQ ID NO: 173:

```
(SEQ ID NO: 373)
GAGGTGCAGCTGGTGGAGTCTGGGGGAGGCTTGGTCCAGCCTGGGGG

GTCCCTGAGACTCTCCTGTGCAGCCTCTGGATTCACCGTCAGTGGCTACA

ACTTGGTCTGGGTCCGTCAGGCTCCAGGGAAGGGGCTGGAGTGGGTCGGA

TTCATTAGTTATGGTGATACCACATACTACGCTAGCTCTGCTAAAGGCCG

ATTCACCATCTCCAGAGACAATTCCAAGAACACCCTGTATCTTCAAATGA
```

-continued

ACAGCCTGAGAGCTGAGGACACTGCTGTGTATTACTGTGCTAGAGAGACT

GGCTAATACTTATGATTATGCATCTGGGGCCAAGGGACCCTCGTCACCGT

CTCGAGC.

In one embodiment of the invention, polynucleotides of the invention comprise, or alternatively consist of, the following polynucleotide sequence encoding the heavy chain polypeptide sequence of SEQ ID NO: 174:

(SEQ ID NO: 374)

GAGGTGCAGCTGGTGGAGTCTGGGGGAGGCTTGGTCCAGCCTGGGGGGTC

CCTGAGACTCTCCTGTGCAGCCTCTGGATTCACCGTCAGTGGCTACAACT

TGGTCTGGGTCCGTCAGGCTCCAGGGAAGGGGCTGGAGTGGGTCGGATTC

ATTAGTTATGGTGATACCACATACTACGCTAGCTCTGCTAAAGGCCGATT

CACCATCTCCAGAGACAATTCCAAGAACACCCTGTATCTTCAAATGAACA

GCCTGAGAGCTGAGGACACTGCTGTGTATTACTGTGCTAGAGAGACTGCT

AATACTTATGATTATGGCATCTGGGGCCAAGGGACCCTCGTCACCGTCTC

GAGCGCCTCCACCAAGGGCCCATCGGTCTTCCCCCTGGCACCCTCCTCCA

AGAGCACCTCTGGGGGCACAGCGGCCCTGGGCTGCCTGGTCAAGGACTAC

TTCCCCGAACCGGTGACGGTGTCGTGGAACTCAGGCGCCCTGACCAGCGG

CGTGCACACCTTCCCGGCTGTCCTACAGTCCTCAGGACTCTACTCCCTCA

GCAGCGTGGTGACCGTGCCCTCCAGCAGCTTGGGCACCCAGACCTACATC

TGCAACGTGAATCACAAGCCCAGCAACACCAAGGTGGACAAGAGAGTTGA

GCCCAAATCTTGTGACAAAACTCACACATGCCCACCGTGCCCAGCACCTG

AACTCCTGGGGGGACCGTCAGTCTTCCTCTTCCCCCCAAAACCCAAGGAC

ACCCTCATGATCTCCCGGACCCCTGAGGTCACATGCGTGGTGGTGGACGT

GAGCCACGAAGACCCTGAGGTCAAGTTCAACTGGTACGTGGACGGCGTGG

AGGTGCATAATGCCAAGACAAAGCCGCGGGAGGAGCAGTACGCCAGCACG

TACCGTGTGGTCAGCGTCCTCACCGTCCTGCACCAGGACTGGCTGAATGG

CAAGGAGTACAAGTGCAAGGTCTCCAACAAAGCCCTCCCAGCCCCCATCG

AGAAAACCATCTCCAAAGCCAAAGGGCAGCCCCGAGAACCACAGGTGTAC

ACCCTGCCCCCATCCCGGGAGGAGATGACCAAGAACCAGGTCAGCCTGAC

CTGCCTGGTCAAAGGCTTCTATCCCAGCGACATCGCCGTGGAGTGGGAGA

GCAATGGGCAGCCGGAGAACAACTACAAGACCACGCCTCCCGTGCTGGAC

TCCGACGGCTCCTTCTTCCTCTACAGCAAGCTCACCGTGGACAAGAGCAG

GTGGCAGCAGGGGAACGTCTTCTCATGCTCCGTGATGCATGAGGCTCTGC

ACAACCACTACACGCAGAAGAGCCTCTCCCTGTCTCCGGGTAAATGA.

In a further embodiment of the invention, polynucleotides encoding antibody fragments having binding specificity to NGF comprise, or alternatively consist of, one or more of the polynucleotide sequences of SEQ ID NO: 375; SEQ ID NO: 376; and SEQ ID NO: 377 which correspond to polynucleotides encoding the complementarity-determining regions (CDRs, or hypervariable regions) of the light chain variable sequence of SEQ ID NO: 171 or the light chain sequence of SEQ ID NO: 172.

In a further embodiment of the invention, polynucleotides encoding antibody fragments having binding specificity to NGF comprise, or alternatively consist of, one or more of the polynucleotide sequences of SEQ ID NO: 378; SEQ ID NO: 379; and SEQ ID NO: 380 which correspond to polynucleotides encoding the complementarity-determining regions (CDRs, or hypervariable regions) of the heavy chain variable sequence of SEQ ID NO: 173 or the heavy chain sequence of SEQ ID NO: 174.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 371 encoding the light chain variable sequence of SEQ ID NO: 171; the polynucleotide SEQ ID NO: 372 encoding the light chain sequence of SEQ ID NO: 172; the polynucleotide SEQ ID NO: 373 encoding the heavy chain variable sequence of SEQ ID NO: 173; the polynucleotide SEQ ID NO: 374 encoding the heavy chain sequence of SEQ ID NO: 174; polynucleotides encoding the complementarity-determining regions (SEQ ID NO: 375; SEQ ID NO: 376; and SEQ ID NO: 377) of the light chain variable sequence of SEQ ID NO: 171 or the light chain sequence of SEQ ID NO: 172; and polynucleotides encoding the complementarity-determining regions (SEQ ID NO: 378; SEQ ID NO: 379; and SEQ ID NO: 380) of the heavy chain variable sequence of SEQ ID NO: 173 or the heavy chain sequence of SEQ ID NO: 174.

In a preferred embodiment of the invention, polynucleotides of the invention comprise, or alternatively consist of, polynucleotides encoding Fab (fragment antigen binding) fragments having binding specificity for NGF. With respect to antibody Ab18, the polynucleotides encoding the full length Ab18 antibody comprise, or alternatively consist of, the polynucleotide SEQ ID NO: 372 encoding the light chain sequence of SEQ ID NO: 172 and the polynucleotide SEQ ID NO: 374 encoding the heavy chain sequence of SEQ ID NO: 174.

Another embodiment of the invention contemplates these polynucleotides incorporated into an expression vector for expression in mammalian cells such as CHO, NSO, HEK-293, or in fungal, insect, plant cells, transgenic plants or animals, or microbial systems such as bacterial or yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab18 following expression of the full-length polynucleotides in a suitable host. In another embodiment of the invention, anti-NGF antibodies such as Ab18 or Fab fragments thereof may be produced via expression of Ab18 polynucleotides in mammalian cells such as CHO, NSO or HEK 293 cells, fungal, insect, plant or animal, or microbial systems such as yeast cells (for example diploid yeast such as diploid *Pichia*) and other yeast strains. Suitable *Pichia* species include, but are not limited to, *Pichia pastoris*.

Antibody Ab19

The invention is further directed to the use of polynucleotides encoding Ab19 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof. Described below are polynucleotides encoding Ab19 antibody polypeptides having binding specificity to NGF. As noted above, Ab19 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 181:

(SEQ ID NO: 381)
GCCGCCGTGCTGACCCAGACTCCATCTCCCGTGTCTGCAGCTGTGGGAGG
CACAGTCAGCATCAGTTGCCAGTCCAGTCAGAATGTTTATAAGAACAACT
ATTTATCCTGGTATCAGCAGAAACCAGGGCAGCCTCCCAAGCTCCTGATC
TACAAGGCTTCCACTCTGGCATCTGGGGTCCCATCGCGGTTCAAAGGCAG
TGGATCTGGGACAGATTTCACTCTCACCATCAGCGACGTGCAGTGTGACG
CTGCTGCCACTTACTACTGTGCAGGCGGTTATAGTAGTAGTAGTGATAAT
GCTTTCGGCGGAGGGACCGAGGTGGTGGTCAAACGT.

In one embodiment of the invention, polynucleotides of the invention comprise, or alternatively consist of, the following polynucleotide sequence encoding the light chain polypeptide sequence of SEQ ID NO: 182:

(SEQ ID NO: 382)
GCCGCCGTGCTGACCCAGACTCCATCTCCCGTGTCTGCAGCTGTGGGAGG
CACAGTCAGCATCAGTTGCCAGTCCAGTCAGAATGTTTATAAGAACAACT
ATTTATCCTGGTATCAGCAGAAACCAGGGCAGCCTCCCAAGCTCCTGATC
TACAAGGCTTCCACTCTGGCATCTGGGGTCCCATCGCGGTTCAAAGGCAG
TGGATCTGGGACAGATTTCACTCTCACCATCAGCGACGTGCAGTGTGACG
CTGCTGCCACTTACTACTGTGCAGGCGGTTATAGTAGTAGTAGTGATAAT
GCTTTCGGCGGAGGGACCGAGGTGGTGGTCAAACGTACGGTAGCGGCCCC
ATCTGTCTTCATCTTCCCGCCATCTGATGAGCAGTTGAAATCTGGAACTG
CCTCTGTTGTGTGCCTGCTGAATAACTTCTATCCCAGAGAGGCCAAAGTA
CAGTGGAAGGTGGATAACGCCCTCCAATCGGGTAACTCCCAGGAGAGTGT
CACAGAGCAGGACAGCAAGGACAGCACCTACAGCCTCAGCAGCACCCTGA
CGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGA
GTGTTAG.

In another embodiment of the invention, polynucleotides of the invention comprise, or alternatively consist of, the following polynucleotide sequence encoding the variable heavy chain polypeptide sequence of SEQ ID NO: 183:

(SEQ ID NO: 383)
CAGTCGGTGGAGGCGTCCGGGGGTCGTCTGGTCATGCCTGGAGGATCCCT
GACACTCACCTGCACAGCCTCTGGATTCTCCCTCAGTACCTACTGGATGT

-continued

CCTGGGTCCGCCAGGCTCCAGGGAAGGGGCTGGAATGGATCGGAGACATT
TATTTTAGTAATGAGGAAACAAACTACGCGACCTGGGCGAAAGGCCGATT
TACCATCTCCAAAACCTCGACCACGGTGGATCTGAATGTCATCAGTCCGA
CAACCGAGGACACGGCCACCTATTTCTGTGCAAGAGGTTCTCCTGATGTT
GAGATTGCTATAGATATGTGGGGCCAGGGCACCCTCGTCACCGTCTCGAG
C.

In one embodiment of the invention, polynucleotides of the invention comprise, or alternatively consist of, the following polynucleotide sequence encoding the heavy chain polypeptide sequence of SEQ ID NO: 184:

(SEQ ID NO: 384)
CAGTCGGTGGAGGCGTCCGGGGGTCGTCTGGTCATGCCTGGAGGATCCCT
GACACTCACCTGCACAGCCTCTGGATTCTCCCTCAGTACCTACTGGATGT
CCTGGGTCCGCCAGGCTCCAGGGAAGGGGCTGGAATGGATCGGAGACATT
TATTTTAGTAATGAGGAAACAAACTACGCGACCTGGGCGAAAGGCCGATT
TACCATCTCCAAAACCTCGACCACGGTGGATCTGAATGTCATCAGTCCGA
CAACCGAGGACACGGCCACCTATTTCTGTGCAAGAGGTTCTCCTGATGTT
GAGATTGCTATAGATATGTGGGGCCAGGGCACCCTCGTCACCGTCTCGAG
CGCCTCCACCAAGGGCCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAGAGTTGAGCC
CAAATCTTGTGACAAAACTCACACATGCCCACCGTGCCCAGCACCTGAAC
TCCTGGGGGGACCGTCAGTCTTCCTCTTCCCCCCAAAACCCAAGGACACC
CTCATGATCTCCCGGACCCCTGAGGTCACATGCGTGGTGGTGGACGTGAG
CCACGAAGACCCTGAGGTCAAGTTCAACTGGTACGTGGACGGCGTGGAGG
TGCATAATGCCAAGACAAAGCCGCGGGAGGAGCAGTACGCCAGCACGTAC
CGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGA
AAACCATCTCCAAAGCCAAAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGTAAATGA.

In a further embodiment of the invention, polynucleotides encoding antibody fragments having binding specificity to NGF comprise, or alternatively consist of, one or more of the polynucleotide sequences of SEQ ID NO: 385; SEQ ID NO: 386; and SEQ ID NO: 387 which correspond to polynucleotides encoding the complementarity-determining regions (CDRs, or hypervariable regions) of the light chain variable sequence of SEQ ID NO: 181 or the light chain sequence of SEQ ID NO: 182.

In a further embodiment of the invention, polynucleotides encoding antibody fragments having binding specificity to NGF comprise, or alternatively consist of, one or more of the polynucleotide sequences of SEQ ID NO: 388; SEQ ID NO: 389; and SEQ ID NO: 390 which correspond to polynucleotides encoding the complementarity-determining regions (CDRs, or hypervariable regions) of the heavy chain variable sequence of SEQ ID NO: 183 or the heavy chain sequence of SEQ ID NO: 184.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 381 encoding the light chain variable sequence of SEQ ID NO: 181; the polynucleotide SEQ ID NO: 382 encoding the light chain sequence of SEQ ID NO: 182; the polynucleotide SEQ ID NO: 383 encoding the heavy chain variable sequence of SEQ ID NO: 183; the polynucleotide SEQ ID NO: 384 encoding the heavy chain sequence of SEQ ID NO: 184; polynucleotides encoding the complementarity-determining regions (SEQ ID NO: 385; SEQ ID NO: 386; and SEQ ID NO: 387) of the light chain variable sequence of SEQ ID NO: 181 or the light chain sequence of SEQ ID NO: 182; and polynucleotides encoding the complementarity-determining regions (SEQ ID NO: 388; SEQ ID NO: 389; and SEQ ID NO: 390) of the heavy chain variable sequence of SEQ ID NO: 183 or the heavy chain sequence of SEQ ID NO: 184.

In a preferred embodiment of the invention, polynucleotides of the invention comprise, or alternatively consist of, polynucleotides encoding Fab (fragment antigen binding) fragments having binding specificity for NGF. With respect to antibody Ab19, the polynucleotides encoding the full length Ab19 antibody comprise, or alternatively consist of, the polynucleotide SEQ ID NO: 382 encoding the light chain sequence of SEQ ID NO: 182 and the polynucleotide SEQ ID NO: 384 encoding the heavy chain sequence of SEQ ID NO: 184.

Another embodiment of the invention contemplates these polynucleotides incorporated into an expression vector for expression in mammalian cells such as CHO, NSO, HEK-293, or in fungal, insect, plant cells, transgenic plant or animal, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab19 following expression of the full-length polynucleotides in a suitable host. In another embodiment of the invention, anti-NGF antibodies such as Ab19 or Fab fragments thereof or MetMab like monovalent agents may be produced via expression of Ab19 polynucleotides in mammalian cells such as CHO, NSO or HEK 293 cells, fungal, insect, plant, animal, or microbial systems such as bacterial or yeast cells (for example diploid yeast such as diploid *Pichia*) and other yeast strains. Suitable *Pichia* species include, but are not limited to, *Pichia pastoris.*

Antibody Ab20

The invention is further directed to the use of polynucleotides encoding Ab20 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nobodies, IgNAR, a monovalent antibody molecule analagous to MetMab, or one or more combinations thereof. Described below are polynucleotides encoding Ab20 antibody polypeptides having binding specificity to NGF. As noted above, Ab20 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 191:

(SEQ ID NO: 391)

GACATCCAGATGACCCAGTCTCCATCCTCCCTGTCTGCATCTGTAGGAGA
CAGAGTCACCATCACTTGCCAGTCCAGTCAGAATGTTTATAAGAACAACT
ACTTATCCTGGTATCAGCAGAAACCAGGGAAAGTCCCTAAGCTCCTGATC
TATAAGGCATCCACTCTGGCATCTGGGGTCCCATCTCGTTTCAGTGGCAG
TGGATCTGGGACAGATTTCACTCTCACCATCAGCAGCCTGCAGCCTGAAG
ATGTTGCAACTTATTACTGTGCAGGCGGTTATACCAGTAGTAGTGATAAT
GCTTTCGGCGGAGGAACCAAGGTGGAAATCAAACGT.

In one embodiment of the invention, polynucleotides of the invention comprise, or alternatively consist of, the following polynucleotide sequence encoding the light chain polypeptide sequence of SEQ ID NO: 192:

(SEQ ID NO: 392)

GACATCCAGATGACCCAGTCTCCATCCTCCCTGTCTGCATCTGTAGGAGA
CAGAGTCACCATCACTTGCCAGTCCAGTCAGAATGTTTATAAGAACAACT
ACTTATCCTGGTATCAGCAGAAACCAGGGAAAGTCCCTAAGCTCCTGATC
TATAAGGCATCCACTCTGGCATCTGGGGTCCCATCTCGTTTCAGTGGCAG
TGGATCTGGGACAGATTTCACTCTCACCATCAGCAGCCTGCAGCCTGAAG
ATGTTGCAACTTATTACTGTGCAGGCGGTTATACCAGTAGTAGTGATAAT
GCTTTCGGCGGAGGAACCAAGGTGGAAATCAAACGTACGGTAGCGGCCCC
ATCTGTCTTCATCTTCCCGCCATCTGATGAGCAGTTGAAATCTGGAACTG
CCTCTGTTGTGTGCCTGCTGAATAACTTCTATCCCAGAGAGGCCAAAGTA
CAGTGGAAGGTGGATAACGCCCTCCAATCGGGTAACTCCCAGGAGAGTGT
CACAGAGCAGGACAGCAAGGACAGCACCTACAGCCTCAGCAGCACCCTGA
CGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGA
GTGTTAG.

In another embodiment of the invention, polynucleotides of the invention comprise, or alternatively consist of, the following polynucleotide sequence encoding the variable heavy chain polypeptide sequence of SEQ ID NO: 193:

(SEQ ID NO: 393)

```
GAGGTGCAGCTGGTGGAGTCTGGGGGAGGCTTGGTCCAGCCTGGGGGGTC
CCTGAGACTCTCCTGTGCAGCCTCTGGATTCACCGTCAGTACCTACTGGA
TGAGCTGGGTCCGTCAGGCTCCAGGGAAGGGGCTGGAGTGGGTCGGAGAC
ATTTACTTTAGTAATGAAGAAACAAACTACGCGACCAGCGCGAAAGGCCG
ATTCACCATCTCCAGAGACAATTCCAAGAACACCCTGTATCTTCAAATGA
ACAGCCTGAGAGCTGAGGACACTGCTGTGTATTACTGTGCTAGAGGTTCT
CCTGATGTTGAGATTGCTATAGATATGTGGGGCCAAGGGACCCTCGTCAC
CGTCTCGAGC.
```

In one embodiment of the invention, polynucleotides of the invention comprise, or alternatively consist of, the following polynucleotide sequence encoding the heavy chain polypeptide sequence of SEQ ID NO: 194:

(SEQ ID NO: 394)

```
GAGGTGCAGCTGGTGGAGTCTGGGGGAGGCTTGGTCCAGCCTGGGGGGTC
CCTGAGACTCTCCTGTGCAGCCTCTGGATTCACCGTCAGTACCTACTGGA
TGAGCTGGGTCCGTCAGGCTCCAGGGAAGGGGCTGGAGTGGGTCGGAGAC
ATTTACTTTAGTAATGAAGAAACAAACTACGCGACCAGCGCGAAAGGCCG
ATTCACCATCTCCAGAGACAATTCCAAGAACACCCTGTATCTTCAAATGA
ACAGCCTGAGAGCTGAGGACACTGCTGTGTATTACTGTGCTAGAGGTTCT
CCTGATGTTGAGATTGCTATAGATATGTGGGGCCAAGGGACCCTCGTCAC
CGTCTCGAGCGCCTCCACCAAGGGCCCATCGGTCTTCCCCCTGGCACCCT
CCTCCAAGAGCACCTCTGGGGGCACAGCGGCCCTGGGCTGCCTGGTCAAG
GACTACTTCCCCGAACCGGTGACGGTGTCGTGGAACTCAGGCGCCCTGAC
CAGCGGCGTGCACACCTTCCCGGCTGTCCTACAGTCCTCAGGACTCTACT
CCCTCAGCAGCGTGGTGACCGTGCCCTCCAGCAGCTTGGGCACCCAGACC
TACATCTGCAACGTGAATCACAAGCCCAGCAACACCAAGGTGGACAAGAG
AGTTGAGCCCAAATCTTGTGACAAAACTCACACATGCCCACCGTGCCCAG
CACCTGAACTCCTGGGGGGACCGTCAGTCTTCCTCTTCCCCCCAAAACCC
AAGGACACCCTCATGATCTCCCGGACCCCTGAGGTCACATGCGTGGTGGT
GGACGTGAGCCACGAAGACCCTGAGGTCAAGTTCAACTGGTACGTGGACG
GCGTGGAGGTGCATAATGCCAAGACAAAGCCGCGGGAGGAGCAGTACGCC
AGCACGTACCGTGTGGTCAGCGTCCTCACCGTCCTGCACCAGGACTGGCT
GAATGGCAAGGAGTACAAGTGCAAGGTCTCCAACAAAGCCCTCCCAGCCC
CCATCGAGAAAACCATCTCCAAAGCCAAAGGGCAGCCCCGAGAACCACAG
GTGTACACCCTGCCCCCATCCCGGGAGGAGATGACCAAGAACCAGGTCAG
CCTGACCTGCCTGGTCAAAGGCTTCTATCCCAGCGACATCGCCGTGGAGT
GGGAGAGCAATGGGCAGCCGGAGAACAACTACAAGACCACGCCTCCCGTG
CTGGACTCCGACGGCTCCTTCTTCCTCTACAGCAAGCTCACCGTGGACAA
GAGCAGGTGGCAGCAGGGGAACGTCTTCTCATGCTCCGTGATGCATGAGG
CTCTGCACAACCACTACACGCAGAAGAGCCTCTCCCTGTCTCCGGGTAAA
TGA.
```

In a further embodiment of the invention, polynucleotides encoding antibody fragments having binding specificity to NGF comprise, or alternatively consist of, one or more of the polynucleotide sequences of SEQ ID NO: 395; SEQ ID NO: 396; and SEQ ID NO: 397 which correspond to polynucleotides encoding the complementarity-determining regions (CDRs, or hypervariable regions) of the light chain variable sequence of SEQ ID NO: 191 or the light chain sequence of SEQ ID NO: 192.

In a further embodiment of the invention, polynucleotides encoding antibody fragments having binding specificity to NGF comprise, or alternatively consist of, one or more of the polynucleotide sequences of SEQ ID NO: 398; SEQ ID NO: 399; and SEQ ID NO: 400 which correspond to polynucleotides encoding the complementarity-determining regions (CDRs, or hypervariable regions) of the heavy chain variable sequence of SEQ ID NO: 193 or the heavy chain sequence of SEQ ID NO: 194.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 391 encoding the light chain variable sequence of SEQ ID NO: 191; the polynucleotide SEQ ID NO: 392 encoding the light chain sequence of SEQ ID NO: 192; the polynucleotide SEQ ID NO: 393 encoding the heavy chain variable sequence of SEQ ID NO: 193; the polynucleotide SEQ ID NO: 394 encoding the heavy chain sequence of SEQ ID NO: 194; polynucleotides encoding the complementarity-determining regions (SEQ ID NO: 395; SEQ ID NO: 396; and SEQ ID NO: 397) of the light chain variable sequence of SEQ ID NO: 191 or the light chain sequence of SEQ ID NO: 192; and polynucleotides encoding the complementarity-determining regions (SEQ ID NO: 398; SEQ ID NO: 399; and SEQ ID NO: 400) of the heavy chain variable sequence of SEQ ID NO: 193 or the heavy chain sequence of SEQ ID NO: 194.

In a preferred embodiment of the invention, polynucleotides of the invention comprise, or alternatively consist of, polynucleotides encoding Fab (fragment antigen binding) fragments or MetMab like monovalent agents having binding specificity for NGF. With respect to antibody Ab20, the polynucleotides encoding the full length Ab20 antibody comprise, or alternatively consist of, the polynucleotide SEQ ID NO: 392 encoding the light chain sequence of SEQ ID NO: 192 and the polynucleotide SEQ ID NO: 394 encoding the heavy chain sequence of SEQ ID NO: 194.

Another embodiment of the invention contemplates these polynucleotides incorporated into an expression vector for expression in mammalian cells such as CHO, NSO, HEK-293, or in fungal, insect, plant cells, transgenic plants and animals, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab20 following expression of the full-length polynucleotides in a suitable host. In another embodiment of the invention, anti-NGF antibodies such as Ab20 or Fab fragments thereof may be produced via expression of Ab20 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab21

The invention is further directed to the use of polynucleotides encoding Ab21 polypeptides set forth below to produce anti-human NGF monovalent agents used in the pain treatment methods described herein. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. Described below are polynucleotides encoding Ab21 antibody polypeptides having binding specificity to NGF. As noted above, Ab21 antibodies inhibit the interaction of NGF with TrkA and inhibit the interaction of NGF with p75. In one embodiment of the invention, polynucleotides of the invention comprise, or alternatively consist of, the following polynucleotide sequence encoding the variable light chain polypeptide sequence of SEQ ID NO: 51:

(SEQ ID NO: 251)
GACATCCAGATGACCCAGTCTCCTTCCACCCTGTCTGCATCTGTAGGAGA
CAGAGTCACCATCACTTGCCAGGCCAGTCAGAGCATTTACAGCAATCTTG
CCTGGTATCAGCAGAAACCAGGAAAAGCCCCTAAGCTCCTGATCTATGAT
GCATCCACTCTGGAATCTGGAGTCCCATCAAGGTTCAGCGGCAGTGGATC
TGGGACAGAGTACACTCTCACCATCAGCAGCCTGCAGCCTGATGATTTTG
CAACTTACTACTGCCAACAGGGTTTTACTGTTAGTGATATTGATAATGCT
TTCGGCGGAGGAACCAAGGTGGAAATCAAACGT.

In one embodiment of the invention, polynucleotides of the invention comprise, or alternatively consist of, the following polynucleotide sequence encoding the light chain polypeptide sequence of SEQ ID NO: 401:

(SEQ ID NO: 403)
GACATCCAGATGACCCAGTCTCCTTCCACCCTGTCTGCATCTGTAGGAGA
CAGAGTCACCATCACTTGCCAGGCCAGTCAGAGCATTTACAGCAATCTTG
CCTGGTATCAGCAGAAACCAGGAAAAGCCCCTAAGCTCCTGATCTATGAT
GCATCCACTCTGGAATCTGGAGTCCCATCAAGGTTCAGCGGCAGTGGATC
TGGGACAGAGTACACTCTCACCATCAGCAGCCTGCAGCCTGATGATTTTG
CAACTTACTACTGCCAACAGGGTTTTACTGTTAGTGATATTGATAATGCT
TTCGGCGGAGGAACCAAGGTGGAAATCAAACGTACGGTAGCGGCCCCATC
TGTCTTCATCTTCCCGCCATCTGATGAGCAGTTGAAATCTGGAACTGCCT
CTGTTGTGTGCCTGCTGAATAACTTCTATCCCAGAGAGGCCAAAGTACAG
TGGAAGGTGGATAACGCCCTCCAATCGGGTAACTCCCAGGAGAGTGTCAC
AGAGCAGGACAGCAAGGACAGCACCTACAGCCTCAGCAGCACCCTGACGC
TGAGCAAAGCAGACTACGAGAAACACAAAGTCTACGCCTGCGAAGTCACC

-continued

CATCAGGGCCTGAGCTCGCCCGTCACAAAGAGCTTCAACAGGGGAGAGTG
TTAG.

In another embodiment of the invention, polynucleotides of the invention comprise, or alternatively consist of, the following polynucleotide sequence encoding the variable heavy chain polypeptide sequence of SEQ ID NO: 53:

(SEQ ID NO: 253)
GAGGTGCAGCTGGTGGAGTCTGGGGGAGGCTTGGTCCAGCCTGGGGGGTC
CCTGAGACTCTCCTGTGCAGCCTCTGGATTCACCGTCAGTAACTATGCAG
TGGGCTGGGTCCGTCAGGCTCCAGGGAAGGGGCTGGAGTGGGTCGGAATC
ATTGGTCGTAATGGTAACACATGGTACGCGAGCTCTGCAAGAGGCCGATT
CACCATCTCCAGAGACAATTCCAAGAACACCCTGTATCTTCAAATGAACA
GCCTGAGAGCTGAGGACACTGCTGTGTATTACTGTGCTAGAGGATATGGC
CGTAGTGTTGCTTATTACGTCTTTAACATCTGGGGCCCAGGGACCCTCGT
CACCGTCTCGAGC.

In one embodiment of the invention, polynucleotides of the invention comprise, or alternatively consist of, the following polynucleotide sequence encoding the heavy chain polypeptide sequence of SEQ ID NO: 402:

(SEQ ID NO: 404)
GAGGTGCAGCTGGTGGAGTCTGGGGGAGGCTTGGTCCAGCCTGGGGGGTC
CCTGAGACTCTCCTGTGCAGCCTCTGGATTCACCGTCAGTAACTATGCAG
TGGGCTGGGTCCGTCAGGCTCCAGGGAAGGGGCTGGAGTGGGTCGGAATC
ATTGGTCGTAATGGTAACACATGGTACGCGAGCTCTGCAAGAGGCCGATT
CACCATCTCCAGAGACAATTCCAAGAACACCCTGTATCTTCAAATGAACA
GCCTGAGAGCTGAGGACACTGCTGTGTATTACTGTGCTAGAGGATATGGC
CGTAGTGTTGCTTACTACGTCTTTAACATCTGGGGCCCAGGGACCCTCGT
CACCGTCTCGAGCGCCTCCACCAAGGGCCCATCGGTCTTCCCCCTGGCAC
CCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCT
GACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAG
ACCTACATCTGCAACGTGAATCACAAGCCCAGCAACACCAAGGTGGACGC
GAGAGTTGAGCCCAAATCTTGTGACAAAACTCACACATGCCCACCGTGCC
CAGCACCTGAACTCCTGGGGGGACCGTCAGTCTTCCTCTTCCCCCCAAAA
CCCAAGGACACCCTCATGATCTCCCGGACCCCTGAGGTCACATGCGTGGT
GGTGGACGTGAGCCACGAAGACCCTGAGGTCAAGTTCAACTGGTACGTGG
ACGGCGTGGAGGTGCATAATGCCAAGACAAAGCCGCGGGAGGAGCAGTAC
GCCAGCACGTACCGTGTGGTCAGCGTCCTCACCGTCCTGCACCAGGACTG
GCTGAATGGCAAGGAGTACAAGTGCAAGGTCTCCAACAAAGCCCTCCCAG
CCCCCATCGAGAAAACCATCTCCAAAGCCAAAGGGCAGCCCCGAGAACCA
CAGGTGTACACCCTGCCCCCATCCCGGGAGGAGATGACCAAGAACCAGGT

-continued

CAGCCTGACCTGCCTGGTCAAAGGCTTCTATCCCAGCGACATCGCCGTGG

AGTGGGAGAGCAATGGGCAGCCGGAGAACAACTACAAGACCACGCCTCCC

GTGCTGGACTCCGACGGCTCCTTCTTCCTCTACAGCAAGCTCACCGTGGA

CAAGAGCAGGTGGCAGCAGGGGAACGTCTTCTCATGCTCCGTGATGCATG

AGGCTCTGCACAACCACTACACGCAGAAGAGCCTCTCCCTGTCTCCGGGT

AAATGA.

In a further embodiment of the invention, polynucleotides encoding antibody fragments having binding specificity to NGF comprise, or alternatively consist of, one or more of the polynucleotide sequences of SEQ ID NO: 255; SEQ ID NO: 256; and SEQ ID NO: 257 which correspond to polynucleotides encoding the complementarity-determining regions (CDRs, or hypervariable regions) of the light chain variable sequence of SEQ ID NO: 51 or the light chain sequence of SEQ ID NO: 401.

In a further embodiment of the invention, polynucleotides encoding antibody fragments having binding specificity to NGF comprise, or alternatively consist of, one or more of the polynucleotide sequences of SEQ ID NO: 258; SEQ ID NO: 259; and SEQ ID NO: 260 which correspond to polynucleotides encoding the complementarity-determining regions (CDRs, or hypervariable regions) of the heavy chain variable sequence of SEQ ID NO: 53 or the heavy chain sequence of SEQ ID NO: 402.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 251 encoding the light chain variable sequence of SEQ ID NO: 51; the polynucleotide SEQ ID NO: 403 encoding the light chain sequence of SEQ ID NO: 401; the polynucleotide SEQ ID NO: 253 encoding the heavy chain variable sequence of SEQ ID NO: 53; the polynucleotide SEQ ID NO: 404 encoding the heavy chain sequence of SEQ ID NO: 402; polynucleotides encoding the complementarity-determining regions (SEQ ID NO: 255; SEQ ID NO: 256; and SEQ ID NO: 257) of the light chain variable sequence of SEQ ID NO: 51 or the light chain sequence of SEQ ID NO: 401; and polynucleotides encoding the complementarity-determining regions (SEQ ID NO: 258; SEQ ID NO: 259; and SEQ ID NO: 260) of the heavy chain variable sequence of SEQ ID NO: 53 or the heavy chain sequence of SEQ ID NO: 402.

In a preferred embodiment of the invention, polynucleotides of the invention comprise, or alternatively consist of, polynucleotides encoding Fab (fragment antigen binding) fragments and MetMab like monovalent agents having binding specificity for NGF. With respect to antibody Ab21, the polynucleotides encoding the full length Ab21 antibody comprise, or alternatively consist of, the polynucleotide SEQ ID NO: 403 encoding the light chain sequence of SEQ ID NO: 401 and the polynucleotide SEQ ID NO: 404 encoding the heavy chain sequence of SEQ ID NO: 402.

Another embodiment of the invention contemplates these polynucleotides incorporated into an expression vector for expression in mammalian cells such as CHO, NSO, HEK-293, or in fungal, insect, plant cells, transgenic plants or animals, or microbial systems such as bacterial or yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab21 following expression of the full-length polynucleotides in a suitable host. In another embodiment of the invention, anti-NGF antibodies such as Ab21 or Fab fragments thereof may be produced via expression of Ab21 polynucleotides in mammalian cells such as CHO, NSO or HEK 293 cells, fungal, insect, plant, animal, or microbial systems such as bacterial or yeast cells (for example diploid yeast such as diploid *Pichia*) and other yeast strains. Suitable *Pichia* species include, but are not limited to, *Pichia pastoris*.

Antibody Fragment Fab2

The invention is further directed to the use of polynucleotides encoding antibody fragment Fab2 polypeptides set forth below to produce anti-human NGF monovalent agents used in the pain treatment methods described herein. Described below are polynucleotides encoding antibody fragment Fab2 polypeptides having binding specificity to NGF. As noted, in some embodiments these monovalent agents will block or inhibit the interaction of NGF with TrkA and/or p75. Also, in some instances these monovalent agents may be modified to affect circulation half-life, such as via the attachment of PEG or other polymers. These monovalent agents include by way of example Fab, Fab', Fv, scFv fragments, SMIPs (small molecule immunopharmaceuticals), camelbodies, nanobodies, IgNAR, a monovalent antibody molecule analagous to MetMab, or one or more combinations thereof. As noted above, the Fab1 and Fab2 antibodies described herein inhibit the interaction of NGF with TrkA and inhibit the interaction of NGF with p75.

In one embodiment of the invention, Fab polynucleotides of the invention comprise, or alternatively consist of, the following polynucleotide sequence encoding the light chain polypeptide sequence of SEQ ID NO: 407:

(SEQ ID NO: 409)

GACATCCAGATGACCCAGTCTCCTTCCACCCTGTCTGCATCTGTAGGAGA

CAGAGTCACCATCACTTGCCAGGCCAGTCAGAGCATTTACAGCAATCTTG

CCTGGTATCAGCAGAAACCAGGAAAAGCCCCTAAGCTCCTGATCTATGAT

GCATCCACTCTGGAATCTGGAGTCCCATCAAGGTTCAGCGGCAGTGGATC

TGGGACAGAGTACACTCTCACCATCAGCAGCCTGCAGCCTGATGATTTTG

CAACTTACTACTGCCAACAGGGTTTTACTGTTAGTGATATTGATAATGCT

TTCGGCGGAGGAACCAAGGTGGAAATCAAACGTACGGTAGCGGCCCCATC

TGTCTTCATCTTCCCGCCATCTGATGAGCAGTTGAAATCTGGAACTGCCT

CTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCAC

AGAGCAGGACAGCAAGGACAGCACCTACAGCCTCAGCAGCACCCTGACGC

TGAGCAAAGCAGACTACGAGAAACACAAAGTCTACGCCTGCGAAGTCACC

CATCAGGGCCTGAGCTCGCCCGTCACAAAGAGCTTCAACAGGGGAGAGTG

TTAG.

In another embodiment of the invention, polynucleotides of the invention comprise, or alternatively consist of, the following polynucleotide sequence encoding the heavy chain polypeptide sequence of SEQ ID NO: 408:

(SEQ ID NO: 410)

```
GAGGTGCAGCTGGTGGAGTCTGGGGGAGGCTTGGTCCAGCCTGGGGGGTC

CCTGAGACTCTCCTGTGCAGCCTCTGGATTCACCGTCAGTAACTATGCAG

TGGGCTGGGTCCGTCAGGCTCCAGGGAAGGGGCTGGAGTGGGTCGGAATC

ATTGGTCGTAATGGTAACACATGGTACGCGAGCTCTGCAAGAGGCCGATT

CACCATCTCCAGAGACAATTCCAAGAACACCCTGTATCTTCAAATGAACA

GCCTGAGAGCTGAGGACACTGCTGTGTATTACTGTGCTAGAGGATATGGC

CGTAGTGTTGCTTACTACGTCTTTAACATCTGGGGCCCAGGGACCCTCGT

CACCGTCTCGAGCGCCTCCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCTTGGGCACCCAG

ACCTACATCTGCAACGTGAATCACAAGCCCAGCAACACCAAGGTGGACGC

GAGAGTTGAGCCCAAATCTTGTGACAAAACTCACTAG.
```

In a further embodiment of the invention, polynucleotides encoding Fab antibody fragments having binding specificity to NGF comprise one or more of the polynucleotide sequences of SEQ ID NO: 255; SEQ ID NO: 256; and SEQ ID NO: 257 which correspond to polynucleotides encoding the complementarity-determining regions (CDRs, or hypervariable regions) of the light chain variable sequence of SEQ ID NO: 51 or the light chain sequence of SEQ ID NO: 409.

In a further embodiment of the invention, polynucleotides encoding Fab antibody fragments having binding specificity to NGF comprise one or more of the polynucleotide sequences of SEQ ID NO: 258; SEQ ID NO: 259; and SEQ ID NO: 260 which correspond to polynucleotides encoding the complementarity-determining regions (CDRs, or hypervariable regions) of the heavy chain variable sequence of SEQ ID NO: 53 or the heavy chain sequence of SEQ ID NO: 410.

The invention also contemplates polynucleotide sequences including one or more of the polynucleotide sequences encoding antibody fragments described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 251 encoding the light chain variable sequence of SEQ ID NO: 51; the polynucleotide SEQ ID NO: 409 encoding the light chain sequence of SEQ ID NO: 407; the polynucleotide SEQ ID NO: 253 encoding the heavy chain variable sequence of SEQ ID NO: 53; the polynucleotide SEQ ID NO: 410 encoding the heavy chain sequence of SEQ ID NO: 408; polynucleotides encoding the complementarity-determining regions (SEQ ID NO: 255; SEQ ID NO: 256; and SEQ ID NO: 257) of the light chain variable sequence of SEQ ID NO: 51 or the light chain sequence of SEQ ID NO: 407; and polynucleotides encoding the complementarity-determining regions (SEQ ID NO: 258; SEQ ID NO: 259; and SEQ ID NO: 260) of the heavy chain variable sequence of SEQ ID NO: 53 or the heavy chain sequence of SEQ ID NO: 408.

In a preferred embodiment of the invention, polynucleotides of the invention comprise, or alternatively consist of, polynucleotides encoding Fab (fragment antigen binding) fragments having binding specificity for NGF. With respect to antibody fragment Fab2, the polynucleotides encoding the Fab fragment include the polynucleotide SEQ ID NO: 409 encoding the light chain sequence of SEQ ID NO: 407 and the polynucleotide SEQ ID NO: 410 encoding the heavy chain sequence of SEQ ID NO: 408.

Another embodiment of the invention contemplates these polynucleotides incorporated into an expression vector for expression in mammalian cells such as CHO, NSO, HEK-293, or in fungal, insect, plant cells, transgenic plants or animals, or microbial systems such as bacterial or yeast cells such as the yeast *Pichia*. Suitable *Pichia* species include, but are not limited to, *Pichia pastoris*. In one embodiment of the invention described herein (infra), Fab fragments may be produced via expression of Fab2 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

In one embodiment, the invention is directed to an isolated polynucleotide comprising a polynucleotide encoding an anti-NGF $V_H$ antibody amino acid sequence selected from SEQ ID NO: 3, 13, 23, 33, 43, 53, 63, 73, 83, 93, 103, 113, 123, 133, 143, 153, 163, 173, 183, 193, or 402, or encoding a variant thereof wherein at least one framework residue (FR residue) has been substituted with an amino acid present at the corresponding position in a rabbit anti-NGF antibody $V_H$ polypeptide or a conservative amino acid substitution.

In another embodiment, the invention is directed to an isolated polynucleotide comprising the polynucleotide sequence encoding an anti-NGF $V_L$ antibody amino acid sequence of 1, 11, 21, 31, 41, 51, 61, 71, 81, 91, 101, 111, 121, 131, 141, 151, 161, 171, 181, 191, or 401, or encoding a variant thereof wherein at least one framework residue (FR residue) has been substituted with an amino acid present at the corresponding position in a rabbit anti-NGF antibody $V_L$ polypeptide or a conservative amino acid substitution.

In yet another embodiment, the invention is directed to one or more heterologous polynucleotides comprising a sequence encoding the polypeptides contained in SEQ ID NO:1 and SEQ ID NO:3; SEQ ID NO:11 and SEQ ID NO:13; SEQ ID NO:21 and SEQ ID NO:23; SEQ ID NO:31 and SEQ ID NO:33; SEQ ID NO:41 and SEQ ID NO:43; SEQ ID NO:51 and SEQ ID NO:53, SEQ ID NO:61 and SEQ ID NO:63; SEQ ID NO:71 and SEQ ID NO:73; SEQ ID NO:81 and SEQ ID NO:83; SEQ ID NO:91 and SEQ ID NO:93; SEQ ID NO:101 and SEQ ID NO:103; SEQ ID NO:111 and SEQ ID NO:113; SEQ ID NO:121 and SEQ ID NO:123; SEQ ID NO:131 and SEQ ID NO:133; SEQ ID NO:141 and SEQ ID NO:143; SEQ ID NO:151 and SEQ ID NO:153; SEQ ID NO:161 and SEQ ID NO:163; SEQ ID NO:171 and SEQ ID NO:173; SEQ ID NO:181 and SEQ ID NO:183; SEQ ID NO:191 and SEQ ID NO:193; or SEQ ID NO:401 and SEQ ID NO:403.

In another embodiment, the invention is directed to an isolated polynucleotide that expresses a polypeptide containing at least one CDR polypeptide derived from an anti-NGF antibody wherein said expressed polypeptide alone specifically binds NGF or specifically binds NGF when expressed in association with another polynucleotide sequence that expresses a polypeptide containing at least one CDR polypeptide derived from an anti-NGF antibody wherein said at least one CDR is selected from those contained in the $V_L$ or $V_H$ polypeptides of SEQ ID NO: 1, 3, 11, 13, 21, 23, 31, 33, 41, 43, 51, 53, 61, 63, 71, 73, 81, 83, 91, 93, 101, 103, 111, 113, 121, 123, 131, 133, 141, 143, 151, 153, 161, 163, 171, 173, 181, 183, 191, 193, 401 or SEQ ID NO:403.

Host cells and vectors comprising said polynucleotides are also contemplated.

The invention further contemplates vectors comprising the polynucleotide sequences encoding the variable heavy and light chain polypeptide sequences, as well as the individual complementarity-determining regions (CDRs, or hypervariable regions), as set forth herein, as well as host cells comprising said vector sequences. In one embodiment of the invention, the host cell is a yeast cell. In another embodiment of the invention, the yeast host cell belongs to the genus *Pichia*. However, as disclosed herein, any in vitro or in vivo expression system suitable for antibody or antibody fragment expression may be utilized.

Anti-NGF Activity

The anti-NGF activity of the anti-NGF monovalent agents of the present invention having binding specificity to NGF may also be described by their strength of binding or their affinity for NGF. In one embodiment of the invention, the anti-NGF monovalent agents of the present invention bind to NGF with a dissociation constant ($K_D$) of less than or equal to $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, or $10^{-13}$ M. Preferably, the anti-NGF monovalent agents bind NGF with a dissociation constant of less than or equal to $5\times10^{-10}$ M. In another embodiment of the invention, the anti-NGF monovalent agents bind to a linear or conformational NGF epitope.

In another embodiment of the invention, the anti-NGF activity of the anti-NGF monovalent agents bind to NGF with an off-rate of less than or equal to $10^{-4}$ $S^{-1}$, $5\times10^{-5}$ $S^{-1}$, $10^{-5}$ $S^{-1}$, $5\times10^{-6}$ $S^{-1}$, $10^{-6}$ $S^{-1}$, $5\times10^{-7}$ $S^{-1}$, or $10^{-7}$ $S^{-1}$.

In a further embodiment of the invention, the anti-NGF activity of the anti-NGF monovalent agents exhibit anti-NGF activity by preventing, ameliorating or reducing the symptoms of, or alternatively treating, diseases and disorders associated with NGF. Non-limiting examples of diseases and disorders associated with NGF are set forth infra.

B-cell Screening and Isolation

In one embodiment, the present invention contemplates the preparation and isolation of a clonal population of antigen-specific B cells that may be used for isolating at least one NGF antigen-specific cell, which can be used to produce a monoclonal antibody against NGF, which is specific to a desired NGF antigen, or a nucleic acid sequence corresponding to such an antibody. Methods of preparing and isolating said clonal population of antigen-specific B cells are taught, for example, in U.S. patent publication no. US 2007/0269868 to Carvalho-Jensen et al., the disclosure of which is herein incorporated by reference in its entirety. Methods of preparing and isolating said clonal population of antigen-specific B cells are also taught herein in the examples. Methods of "enriching" a cell population by size or density are known in the art. See, e.g., U.S. Pat. No. 5,627,052. These steps can be used in addition to enriching the cell population by antigen-specificity.

Methods of Humanizing Antibodies

In another embodiment, the present invention contemplates methods for humanizing antibody heavy and light chains. Methods for humanizing antibody heavy and light chains which may be applied to anti-NGF antibodies are taught, for example, in U.S. patent application publication no. US 2009/0022659 to Olson et al., and in U.S. patent application publication no. US 2009/0028784 to Garcia-Martinez et al., the disclosures of each of which are herein incorporated by reference in their entireties.

Methods of Producing Antibodies and Fragments Thereof

In another embodiment, the present invention contemplates methods for producing anti-NGF antibodies and fragments thereof. Methods for producing anti-NGF antibodies and fragments thereof secreted from polyploidal, preferably diploid or tetraploid strains of mating competent yeast are taught, for example, in U.S. patent application publication no. US 2009/0022659 to Olson et al., and in U.S. patent application publication no. US 2009/0028784 to Garcia-Martinez et al., the disclosures of each of which are herein incorporated by reference in their entireties.

Other methods of producing antibodies are well known to those of ordinary skill in the art. For example, methods of producing chimeric antibodies are now well known in the art (See, for example, U.S. Pat. No. 4,816,567 to Cabilly et al.; Morrison et al., P.N.A.S. USA, 81:8651-55 (1984); Neuberger, M. S. et al., Nature, 314:268-270 (1985); Boulianne, G. L. et al., Nature, 312:643-46 (1984), the disclosures of each of which are herein incorporated by reference in their entireties).

Likewise, other methods of producing humanized antibodies are now well known in the art (See, for example, U.S. Pat. Nos. 5,530,101, 5,585,089, 5,693,762, and 6,180,370 to Queen et al; U.S. Pat. Nos. 5,225,539 and 6,548,640 to Winter; U.S. Pat. Nos. 6,054,297, 6,407,213 and 6,639,055 to Carter et al; U.S. Pat. No. 6,632,927 to Adair; Jones, P. T. et al, Nature, 321:522-525 (1986); Reichmann, L., et al, Nature, 332:323-327 (1988); Verhoeyen, M, et al, Science, 239:1534-36 (1988), the disclosures of each of which are herein incorporated by reference in their entireties). The definition of humanized antibodies herein includes such humanization methods.

Antibody polypeptides of the invention having NGF binding specificity may also be produced by constructing, using conventional techniques well known to those of ordinary skill in the art, an expression vector containing an operon and a DNA sequence encoding an antibody heavy chain in which the DNA sequence encoding the CDRs required for antibody specificity is derived from a non-human cell source, preferably a rabbit B-cell source, while the DNA sequence encoding the remaining parts of the antibody chain is derived from a human cell source.

A second expression vector is produced using the same conventional means well known to those of ordinary skill in the art, said expression vector containing an operon and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding an operon and a light chain-derived polypeptide and the second vector containing DNA encoding an operon and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA, genomic DNA, or both.

The host cells used to express the antibody polypeptides may be a bacterial cell such as *E. coli*, or a eukaryotic cell. In a particularly preferred embodiment of the invention, a mammalian cell of a well-defined type for this purpose, such as a myeloma cell, a Chinese hamster ovary (CHO) cell line, a NSO cell line, or a HEK293 cell line may be used. Alternatively, antibodies and monovalent agents specific to NGF may be expressed in transgenic animals.

The general methods by which the vectors may be constructed, transfection methods required to produce the host cell and culturing methods required to produce the antibody polypeptides from said host cells all include conventional techniques. Although preferably the cell line used to produce the antibody is a mammalian cell line, any other suitable cell line, such as a bacterial cell line such as an *E. coli*-derived bacterial strain, or a yeast cell line, may alternatively be used.

Similarly, once produced the antibody polypeptides may be purified according to standard procedures in the art, such as for example cross-flow filtration, ammonium sulphate precipitation, affinity column chromatography and the like.

The antibody polypeptides described herein may also be used for the design and synthesis of either peptide or non-peptide mimetics that would be useful for the same therapeutic applications as the antibody polypeptides of the invention. See, for example, Saragobi et al, Science, 253: 792-795 (1991), the contents of which is herein incorporated by reference in its entirety.

Screening Assays

The invention also includes screening assays designed to assist in the identification of diseases and disorders associated with NGF in patients exhibiting symptoms of an NGF associated disease or disorder.

In one embodiment of the invention, the anti-NGF monovalent agents are used to detect the presence of NGF in a biological sample obtained from a patient exhibiting symptoms of a disease or disorder associated with NGF. The presence of NGF, or elevated levels thereof when compared to pre-disease levels of NGF in a comparable biological sample, may be beneficial in diagnosing a disease or disorder associated with NGF.

Another embodiment of the invention provides a diagnostic or screening assay to assist in diagnosis of diseases or disorders associated with NGF in patients exhibiting symptoms of an NGF associated disease or disorder identified herein, comprising assaying the level of NGF expression in a biological sample from said patient using a post-translationally modified anti-NGF monovalent agent. The anti-NGF monovalent agent may be post-translationally modified to include a detectable moiety such as set forth previously in the disclosure.

The NGF level in the biological sample is determined using a modified anti-NGF monovalent agent as set forth herein, and comparing the level of NGF in the biological sample against a standard level of NGF (e.g., the level in normal biological samples). The skilled clinician would understand that some variability may exist between normal biological samples, and would take that into consideration when evaluating results. In one embodiment of the invention, the anti-NGF antibodies of the invention may be used to correlate NGF expression levels with a particular stage of cancerous development. One skilled in the art would be able to measure NGF in numerous subjects in order to establish ranges of NGF expression that correspond to clinically defined stages of cancerous development. These ranges will allow the skilled practitioner to measure NGF in a subject diagnosed with a cancer and correlate the levels in each subject with a range that corresponds to a stage of said cancer. One skilled in the art would understand that by measuring NGF in the patient at different intervals, the progression of the cancer can be determined.

The above-recited assay may also be useful in monitoring a disease or disorder, where the level of NGF obtained in a biological sample from a patient believed to have a NGF associated disease or disorder is compared with the level of NGF in prior biological samples from the same patient, in order to ascertain whether the NGF level in said patient has changed with, for example, a treatment regimen.

The invention is also directed to a method of in vivo imaging which detects the presence of cells which express NGF comprising administering a diagnostically effective amount of a diagnostic composition. Said in vivo imaging is useful for the detection or imaging of NGF expressing tumors or metastases, for example, and can be useful as part of a planning regimen for the design of an effective cancer treatment protocol. The treatment protocol may include, for example, one or more of radiation, chemotherapy, cytokine therapy, gene therapy, and antibody therapy, as well as an anti-NGF monovalent agent.

The present invention further provides for a kit for detecting binding of an anti-NGF monovalent agent of the invention to NGF. In particular, the kit may be used to detect the presence of a NGF specifically reactive with an anti-NGF monovalent agent of the invention or an immunoreactive fragment thereof. The kit may also include an antibody bound to a substrate, a secondary antibody reactive with the antigen and a reagent for detecting a reaction of the secondary antibody with the antigen. Such a kit may be an ELISA kit and can comprise the substrate, primary and secondary antibodies when appropriate, and any other necessary reagents such as detectable moieties, enzyme substrates, and color reagents, for example as described herein. The diagnostic kit may also be in the form of an immunoblot kit.

A skilled clinician would understand that a biological sample includes, but is not limited to, sera, plasma, urine, saliva, mucous, pleural fluid, synovial fluid and spinal fluid.

Methods of Ameliorating or Reducing Symptoms of, or Treating, or Preventing, Diseases and Disorders Associated with, NGF In another embodiment of the invention, anti-NGF monovalent agents described herein are useful for ameliorating or reducing the symptoms of, or treating, or preventing, diseases and disorders associated with NGF. Anti-NGF monovalent agents as well as combinations can also be administered in a therapeutically effective amount to patients in need of treatment of diseases and disorders associated with NGF in the form of a pharmaceutical composition as described in greater detail below.

In a preferred embodiment of the invention, Fab fragments are utilized for the treatment of pain in a patient.

In another embodiment of the invention, one or more anti-NGF monovalent agents are useful in methods of ameliorating or reducing the symptoms of, or treating, or preventing, pain in an individual without substantially raising inflammation in said individual. Exemplary pain is set forth below.

In one embodiment of the invention, anti-NGF monovalent agents and/or with a second agent, are useful for ameliorating or reducing the symptoms of, or treating, or preventing, the following non-limiting listing of diseases and disorders: inflammatory pain, post-operative incision pain, complex regional pain syndrome, cancer pain (particularly primary or metastatic bone cancer pain), fracture pain, osteoporotic fracture pain, pain resulting from burn, osteoporosis, gout joint pain, pain associated with sickle cell crises, and other nociceptic pain, as well as hepatocellular carcinoma, breast cancer, liver cirrhosis.

In another embodiment of the invention, anti-NGF monovalent agents and/or with a second agent, are useful for ameliorating or reducing the symptoms of, or treating, or preventing, the following non-limiting listing of diseases and disorders: neurogenic, neuropathic or nociceptic pain. Neuropathic pain may include, but is not limited to, trigeminal neuralgia, post-herpetic neuralgia, phantom limb pain, fibromyalgia, menstrual pain, ovarialgia, reflex sympathetic dystrophy and neurogenic pain. In other preferred embodiments, osteoarthritis or rheumatoid arthritis pain, lower back pain, diabetic neuropathy, sciatica, migraine, and other neuropathic pain.

In general the anti-NGF monovalent agents and/or with a second agent, are useful for ameliorating or reducing the symptoms of, or treating, or preventing, the following non-limiting listing of NGF-associated diseases and disorders wherein the condition is acute pain, dental pain, pain from trauma, surgical pain, pain resulting from amputation or abscess, causalgia, demyelinating diseases, trigeminal neuralgia, cancer, chronic alcoholism, stroke, thalamic pain syndrome, diabetes, acquired immune deficiency syndrome ("AIDS"), toxins, chemotherapy, general headache, migraine, cluster headache, mixed-vascular or non-vascular syndromes, tension headache, general inflammation, arthritis, rheumatic diseases, lupus, osteoarthritis, fibromyalgia, inflammatory bowel disorders, irritable bowel syndrome, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia or allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, colitis, gastric ulceration, duodenal ulcers, vasomotor or allergic rhinitis, or bronchial disorders, dysmenorrhea, dyspepsia, gastroesophageal reflux, pancreatitis, or visceralgia.

The terms "NGF-mediated disease" and "NGF-mediated condition" treatable or preventable with the anti-NGF monovalent agents of the invention alone and/or with a second agent, broadly encompass any medical condition or disorder associated with increased levels of NGF or increased sensitivity to NGF including, but not limited to, acute pain, dental pain, pain from trauma, surgical pain, pain resulting from amputation or abscess, causalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, irritable bowel syndrome, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, colitis, gastric ulceration, duodenal ulcers, vasomotor or allergic rhinitis, or bronchial disorders, dysmenorrhea, dyspepsia, gastroesophageal reflux, pancreatitis, and visceralgia.

Administration

In one embodiment of the invention, the anti-NGF monovalent agents as well as combinations thereof are administered to a subject at a concentration of between about 0.01 mg/kg and 100.0 mg/kg of body weight of recipient subject. (Relating to these dosage ranges, other anti-NGF antibody polypeptides have been tested in the clinic at concentrations as low as 0.025 mg/kg) (http//www.clinicaltrials.gov/ct2/show/NCT00809783?term=tanezumab&rank=5) In a preferred embodiment of the invention, the anti-NGF monovalent agents as well as combinations thereof are administered to a subject at a concentration of about 0.4 mg/kg of body weight of recipient subject. In a preferred embodiment of the invention, the anti-NGF monovalent agents as well as combinations thereof are administered to a recipient subject with a frequency of once every twenty-six weeks or less, such as once every sixteen weeks or less, once every eight weeks or less, once every four weeks or less, once every two weeks or less, once every week or less, or once daily or less.

Fab fragments may be administered every two weeks or less, every week or less, once daily or less, multiple times per day, and/or every few hours. In one embodiment of the invention, a patient receives Fab fragments of 0.01 mg/kg to 40 mg/kg per day given in divided doses of 1 to 6 times a day, or in a sustained release form, effective to obtain desired results.

It is to be understood that the concentration of the monovalent agent or Fab administered to a given patient may be greater or lower than the exemplary administration concentrations set forth above.

A person of skill in the art would be able to determine an effective dosage and frequency of administration through routine experimentation, for example guided by the disclosure herein and the teachings in Goodman, L. S., Gilman, A., Brunton, L. L., Lazo, J. S., & Parker, K. L. (2006). Goodman & Gilman's the pharmacological basis of therapeutics. New York: McGraw-Hill; Howland, R. D., Mycek, M. J., Harvey, R. A., Champe, P. C., & Mycek, M. J. (2006). Pharmacology. Lippincott's illustrated reviews. Philadelphia: Lippincott Williams & Wilkins; and Golan, D. E. (2008). Principles of pharmacology: the pathophysiological basis of drug therapy. Philadelphia, Pa., [etc.]: Lippincott Williams & Wilkins.

In another embodiment of the invention, the anti-NGF monovalent agents as well as combinations thereof are administered to a subject in a pharmaceutical formulation.

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, powder, liquid, gel, drops, or other means of administration. Preferred pharmaceutical compositions for use herein are suited for intravenous, subcutaneous, intranasal or transcutaneous administration.

In one embodiment of the invention, the anti-NGF monovalent agents as well as combinations thereof may be optionally administered in combination with one or more active agents. Such active agents include analgesic, anti-histamine, antipyretic, anti-inflammatory, antibiotic, antiviral, and anti-cytokine agents. Active agents include agonists, antagonists, and modulators of TNF-α, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors. Active agents also include but are not limited to 2-Arylpropionic acids, Aceclofenac, Acemetacin, Acetylsalicylic acid (Aspirin), Alclofenac, Alminoprofen, Amoxiprin, Ampyrone, Arylalkanoic acids, Azapropazone, Benorylate/Benorilate, Benoxaprofen, Bromfenac, Carprofen, Celecoxib, Choline magnesium salicylate, Clofezone, COX-2 inhibitors, Dexibuprofen, Dexketoprofen, Diclofenac, Diflunisal, Droxicam, Ethenzamide, Etodolac, Etoricoxib, Faislamine, fenamic acids, Fenbufen, Fenoprofen, Flufenamic acid, Flunoxaprofen, Flurbiprofen, Ibuprofen, Ibuproxam, Indometacin, Indoprofen, Kebuzone, Ketoprofen, Ketorolac, Lomoxicam, Loxoprofen, Lumiracoxib, Magnesium salicylate, Meclofenamic acid, Mefenamic acid, Meloxicam, Metamizole, Methyl salicylate, Mofebutazone, Nabumetone, Naproxen, N-Arylanthranilic acids, Nerve Growth Factor (NGF), Oxametacin, Oxaprozin, Oxicams, Oxyphenbutazone, Parecoxib, Phenazone, Phenylbutazone, Phenylbutazone, Piroxicam, Pirprofen, profens, Proglumetacin, Pyrazolidine derivatives, Rofecoxib, Salicyl salicylate, Salicylamide, Salicylates, Sulfinpyrazone, Sulindac, Suprofen, Tenoxicam, Tiaprofenic acid, Tolfenamic acid, Tolmetin, and Valdecoxib.

An anti-histamine can be any compound that opposes the action of histamine or its release from cells (e.g., mast cells). Anti-histamines include but are not limited to acrivastine, astemizole, azatadine, azelastine, betatastine, brompheniramine, buclizine, cetirizine, cetirizine analogues, chlorpheniramine, clemastine, CS 560, cyproheptadine, desloratadine, dexchlorpheniramine, ebastine, epinastine, fexofenadine, HSR 609, hydroxyzine, levocabastine, loratidine, methscopolamine, mizolastine, norastemizole, phenindamine, promethazine, pyrilamine, terfenadine, and tranilast.

Antibiotics include but are not limited to Amikacin, Aminoglycosides, Amoxicillin, Ampicillin, Ansamycins, Arsphenamine, Azithromycin, Azlocillin, Aztreonam, Bacitracin, Carbacephem, Carbapenems, Carbenicillin, Cefaclor, Cefadroxil, Cefalexin, Cefalothin, Cefalotin, Cefamandole, Cefazolin, Cefdinir, Cefditoren, Cefepime, Cefixime, Cefoperazone, Cefotaxime, Cefoxitin, Cefpodoxime, Cefprozil, Ceftazidime, Ceftibuten, Ceftizoxime, Ceftobiprole, Ceftriaxone, Cefuroxime, Cephalosporins, Chloramphenicol, Cilastatin, Ciprofloxacin, Clarithromycin, Clindamycin, Cloxacillin, Colistin, Co-trimoxazole, Dalfopristin, Demeclocycline, Dicloxacillin, Dirithromycin, Doripenem, Doxycycline, Enoxacin, Ertapenem, Erythromycin, Ethambutol, Flucloxacillin, Fosfomycin, Furazolidone, Fusidic acid, Gatifloxacin, Geldanamycin, Gentamicin, Glycopeptides, Herbimycin, Imipenem, Isoniazid, Kanamycin, Levofloxacin, Lincomycin, Linezolid, Lomefloxacin, Loracarbef, Macrolides, Mafenide, Meropenem, Meticillin, Metronidazole, Mezlocillin, Minocycline, Monobactams, Moxifloxacin, Mupirocin, Nafcillin, Neomycin, Netilmicin, Nitrofurantoin, Norfloxacin, Ofloxacin, Oxacillin, Oxytetracycline, Paromomycin, Penicillin, Penicillins, Piperacillin, Platensimycin, Polymyxin B, Polypeptides, Prontosil, Pyrazinamide, Quinolones, Quinupristin, Rifampicin, Rifampin, Roxithromycin, Spectinomycin, Streptomycin, Sulfacetamide, Sulfamethizole, Sulfanilimide, Sulfasalazine, Sulfisoxazole, Sulfonamides, Teicoplanin, Telithromycin, Tetracycline, Tetracyclines, Ticarcillin, Tinidazole, Tobramycin, Trimethoprim, Trimethoprim-Sulfamethoxazole, Troleandomycin, Trovafloxacin, and Vancomycin.

Active agents also include Aldosterone, Beclometasone, Betamethasone, Corticosteroids, Cortisol, Cortisone acetate, Deoxycorticosterone acetate, Dexamethasone, Fludrocortisone acetate, Glucocorticoids, Hydrocortisone, Methylprednisolone, Prednisolone, Prednisone, Steroids, and Triamcinolone. Any suitable combination of these active agents is also contemplated.

A "pharmaceutical excipient" or a "pharmaceutically acceptable excipient" is a carrier, usually a liquid, in which an active therapeutic agent is formulated. In one embodiment of the invention, the active therapeutic agent is a monovalent agent described herein. The excipient generally does not provide any pharmacological activity to the formulation, though it may provide chemical and/or biological stability, and release characteristics. Exemplary formulations can be found, for example, in Remington's Pharmaceutical Sciences, $19^{th}$ Ed., Grennaro, A., Ed., 1995 which is incorporated by reference.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions and sterile powders for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The invention contemplates that the pharmaceutical composition is present in lyophilized form. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the alkaline polypeptide can be formulated in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

For each of the recited embodiments, the compounds can be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

Certain teachings related to methods for obtaining a clonal population of antigen-specific B cells were disclosed in U.S. Provisional patent application No. 60/801,412, filed May 19, 2006, the disclosure of which is herein incorporated by reference in its entirety.

Certain teachings related to humanization of rabbit-derived monoclonal antibodies and preferred sequence modifications to maintain antigen binding affinity were disclosed in International Application No. PCT/US2008/064421, corresponding to International Publication No. WO/2008/144757, entitled "Novel Rabbit Antibody Humanization Methods and Humanized Rabbit Antibodies", filed May 21, 2008, the disclosure of which is herein incorporated by reference in its entirety.

Certain teachings related to producing antibodies or fragments thereof using mating competent yeast and corresponding methods were disclosed in U.S. patent application Ser. No. 11/429,053, filed May 8, 2006, (U.S. Patent Application Publication No. US 2006/0270045), the disclosure of which is herein incorporated by reference in its entirety.

Certain teachings related to anti-NGF compositions and uses thereof were disclosed in U.S. provisional patent application No. 61/418,832, filed Dec. 1, 2010, the disclosure of which is herein incorporated by reference in its entirety.

Certain NGF antibody polynucleotides and polypeptides are disclosed in the sequence listing accompanying this patent application filing, and the disclosure of said sequence listing is herein incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1 Preparation of Antibodies that Bind NGF

By using the antibody selection protocol described herein, one can generate an extensive panel of antibodies.

Immunization Strategy

Rabbits were immunized with huNGF (R&D Systems, Minneapolis, Minn.). Immunization consisted of a first subcutaneous (sc) injection of 100 μg in complete Freund's adjuvant (CFA) (Sigma) followed by two boosts, two weeks apart, of 50 μg each in incomplete Freund's adjuvant (IFA) (Sigma). Animals were bled on day 55, and serum titers were determined by ELISA (antigen recognition) and by non-radioactive proliferation assay (Promega) using the T1165 cell line.

Antibody Selection Titer Assessment

To identify and characterize antibodies that bind to human NGF, antibody containing solutions were tested by ELISA. Briefly, neutravidin coated plates (Thermo Scientific), were blocked with ELISA buffer (0.1 mg/mL BSA, 1×PBS pH 7.4, 0.002% Tween 20 and 0.005% sodium azide) for 1 hr at room temperature. The plates were then coated with a 1 μg/mL biotinylated B-NGF solution in ELISA buffer for 1 hour at room temperature. This was followed by a wash step (3× using PBS plus 0.05% Tween 20) and a second block with ELISA buffer. The recombinant antibodies were then added onto the plates and incubated for 1 hour at room temperature and then washed 3× with PBS/Tween solution. For development, an anti-rabbit Fc-HRP (1:5000 dilution in ELISA buffer) was added onto the wells and incubated for 45 min at RT. After a 3× wash step with PBS/Tween solution, the plate was developed using TMB substrate for 3 minutes, stopped using 0.5M HCl and read at 450 nm.

Functional Titer Assessment

To test for the ability of NGF antibodies to block or inhibit NGF-dependent cell proliferation, we used TF-1 cells (Chevalier et al. Expression and functionality of the TrkA proto-oncogene product/NGF receptor in undifferentiated hematopoietic cells. Blood (1994) vol. 83 (6) pp. 1479-85).

Briefly, TF-1 cells were maintained in 10% FBS cRPMI media ("complete media") supplemented with rhuGM-CSF. On the day of the assay, the antibodies were serially diluted in complete media in a round bottom 96 well plate. B-NGF (R&D systems) was concomitantly added and the resultant antibody/B-NGF mixture was incubated at 37° C. for 1 hr. While the Ab and B-NGF mixture was incubating, TF-1 cells were washed 3× with complete media, counted and plated in a flat bottom 96 well plate using 25,000 cells per well in a 50 μL volume. After 1 hour incubation the NGF-Antibody mixtures were added onto the cells and the plates were incubated for 48 hrs at 37° C. in a humidified 5% $CO_2$ incubator. Cell proliferation was measured using the "CellTiter" aqueous one solution cell proliferation assay (Promega) according to the manufacturer's instructions. The dependency of the signals on the concentration of antibody was analyzed, and IC50 values were calculated using the GraphPad Prism program.

Tissue Harvesting

Once acceptable titers were established, the rabbit(s) were sacrificed. Spleen, lymph nodes, and whole blood were harvested and processed as follows:

Spleen and lymph nodes were processed into a single cell suspension by disassociating the tissue and pushing through sterile wire mesh at 70 μm (Fisher) with a plunger of a 20 cc syringe. Cells were collected in PBS. Cells were washed twice by centrifugation. After the last wash, cell density was determined by trypan blue. Cells were centrifuged at 1500 rpm for 10 minutes; the supernatant was discarded. Cells were resuspended in the appropriate volume of 10% dimethyl sulfoxide (DMSO, Sigma) in FBS (Hyclone) and dispensed at 1 ml/vial. Vials were stored at −70° C. in a slow freezing chamber for 24 hours and stored in liquid nitrogen.

Peripheral blood mononuclear cells (PBMCs) were isolated by mixing whole blood with equal parts of the low glucose medium described above without FBS. 35 ml of the whole blood mixture was carefully layered onto 8 ml of Lympholyte Rabbit (Cedarlane) into a 45 ml conical tube (Corning) and centrifuged 30 minutes at 2500 rpm at room temperature without brakes. After centrifugation, the PBMC layers were carefully removed using a glass Pasteur pipette (VWR), combined, and placed into a clean 50 ml vial. Cells were washed twice with the modified medium described above by centrifugation at 1500 rpm for 10 minutes at room temperature, and cell density was determined by trypan blue staining. After the last wash, cells were resuspended in an appropriate volume of 10% DMSO/FBS medium and frozen as described above.

B Cell Culture

On the day of setting up B cell culture, PBMC, splenocyte, or lymph node vials were thawed for use. Vials were removed from LN2 tank and placed in a 37° C. water bath until thawed. Contents of vials were transferred into 15 ml conical centrifuge tube (Corning) and 10 ml of modified RPMI described above was slowly added to the tube. Cells were centrifuged for 5 minutes at 1.5K rpm, and the supernatant was discarded. Cells were resuspended in 10 ml of fresh media. Cell density and viability was determined by trypan blue. Cells were washed again and resuspended at 1E07 cells/80 μL medium. Biotinylated huNGF (B huNGF) was added to the cell suspension at the final concentration of 3 μg/mL and incubated for 30 minutes at 4° C. Unbound B huNGF was removed with two 10 ml washes of phosphate-buffered (PBF):Ca/Mg free PBS (Hyclone), 2 mM ethylenediamine tetraacetic acid (EDTA), 0.5% bovine serum albumin (BSA) (Sigma-biotin free). After the second wash, cells were resuspended at 1E07 cells/80 μl PBF. 20 of MACS® streptavidin beads (Milteni)/10E7 cells were added to the cell suspension. Cells were incubated at 4° C. for 15 minutes. Cells were washed once with 2 ml of PBF/10E7 cells. After washing, the cells were resuspended at 1E08 cells/500 μA of PBF and set aside. A MACS® MS column (Milteni) was pre-rinsed with 500 ml of PBF on a magnetic stand (Milteni). Cell suspension was applied to the column through a pre-filter, and unbound fraction was collected. The column was washed with 1.5 ml of PBF buffer. The column was removed from the magnet stand and placed onto a clean, sterile 5 ml Polypropylene Falcon tube. 1 ml of PBF buffer was added to the top of the column, and positive selected cells were collected. The yield and viability of positive and negative cell fraction was determined by trypan blue staining. Positive selection yielded an average of 1% of the starting cell concentration.

A pilot cell screen was established to provide information on seeding levels for the culture. Plates were seeded at 10, 25, 50, 100, or 200 enriched B cells/well. In addition, each well contained 50K cells/well of irradiated EL-4.B5 cells (5,000 Rads) and an appropriate level of activated rabbit T cell supernatant (See U.S. Patent Application Publication No. 20070269868) (ranging from 1-5% depending on preparation) in high glucose modified RPMI medium at a final volume of 250 μl/well. Cultures were incubated for 5 to 7 days at 37° C. in 4% $CO_2$.

Identification of Selective Antibody Secreting B Cells

Cultures were tested for antigen recognition and functional activity between days 5 and 7.

Antigen Recognition Screening

The ELISA format used is as described above except 50 μl of supernatant from the B cell cultures (BCC) wells was used as the source of the antibody. The conditioned medium was transferred to antigen-coated plates. After positive wells were identified, the supernatant was removed and transferred to a 96-well master plate(s). The original culture plates were then frozen by removing all the supernatant except 40 μl/well and adding 60 μl/well of 16% DMSO in FBS. Plates were wrapped in paper towels to slow freezing and frozen after the addition of 10% DMSO at −70° C.

Functional Activity Screening

To test for the ability of NGF antibodies to block or inhibit NGF-dependent cell proliferation, we used TF-1 cells (Chevalier et al. Expression and functionality of the trkA proto-oncogene product/NGF receptor in undifferentiated hematopoietic cells. Blood (1994) vol. 83 (6) pp. 1479-85). Briefly, TF-1 cells were maintained in 10% FBS cRPMI media ("complete media") supplemented with rhuGM-CSF. On the day of the assay, the antibodies were serially diluted in complete media in a round bottom 96 well plate. B-NGF (R&D systems) was concomitantly added and the resultant antibody/B-NGF mixture was incubated at 37° C. for 1 hr. While the Ab and B-NGF mixture was incubating, TF-1 cells were washed 3× with complete media, counted and plated in a flat bottom 96 well plate using 25,000 cells per well in a 50 μL volume. After 1 hour incubation the NGF-Antibody mixtures were added onto the cells and the plates were incubated for 48 hrs at 37° C. in a humidified 5% $CO_2$ incubator. Cell proliferation was measured using the "CellTiter" aqueous one solution cell proliferation assay (Promega) according to the manufacturer's instructions. The dependency of the signals on the concentration of antibody was analyzed, and IC50 values were calculated using the GraphPad Prism program.

B Cell Recovery

Plates containing wells of interest were removed from −70° C., and the cells from each well were recovered with 5-200 μl washes of medium/well. The washes were pooled in a 1.5 ml sterile centrifuge tube, and cells were pelleted for 2 minutes at 1500 rpm.

The tube was inverted, the spin repeated, and the supernatant carefully removed. Cells were resuspended in 100 μl/tube of medium. 100 μl biotinylated NGF coated streptavidin M280 dynabeads (Invitrogen) and 16 μl of goat anti-rabbit H&L IgG-FITC diluted 1:100 in medium was added to the cell suspension.

20 μl of cell/beads/FITC suspension was removed, and 5 μl droplets were prepared on a glass slide (Corning) previously treated with Sigmacote (Sigma), 35 to 40 droplets/slide. An impermeable barrier of paraffin oil (JT Baker) was added to submerge the droplets, and the slide was incubated for 90 minutes at 37° C., 4% $CO_2$ in the dark.

Specific B cells that produce antibody can be identified by the fluorescent ring around them due to antibody secretion, recognition of the bead-associated biotinylated antigen, and subsequent detection by the fluorescent-IgG detection reagent. Once a cell of interest was identified, the cell in the center of the fluorescent ring was recovered via a micromanipulator (Eppendorf). The single cell synthesizing and exporting the antibody was transferred into a 250 μl microcentrifuge tube and placed in dry ice. After recovering all cells of interest, these were transferred to −70° C. for long-term storage.

Isolation of Antibody Sequences From Antigen-Specific B Cell

Antibody sequences were recovered using a combined RT-PCR based method from a single isolated B-cell or an antigenic specific B cell isolated from the clonal B cell population. Primers are designed to anneal in conserved and constant regions of the target immunoglobulin genes (heavy and light), such as rabbit immunoglobulin sequences, and a two-step nested PCR recovery step is used to obtain the antibody sequence. Amplicons from each well are analyzed for recovery and size integrity. The resulting fragments are then digested with AluI to fingerprint the sequence clonality. Identical sequences display a common fragmentation pattern in their electrophoretic analysis. The original heavy and light chain amplicon fragments are then restriction enzyme digested with HindIII and XhoI or HindIII and BsiwI to prepare the respective pieces of DNA for cloning. The resulting digestions are then ligated into an expression vector and transformed into bacteria for plasmid propagation and production. Colonies are selected for sequence characterization.

Recombinant Production of Monoclonal Antibody of Desired Antigen Specificity and/or Functional Properties Correct full-length antibody sequences for each well containing a single monoclonal antibody are established and miniprep DNA is prepared using Qiagen solid-phase methodology. This DNA is then used to transfect mammalian cells to produce recombinant full-length antibody. Either antibody containing supernatants or protein-A affinity purified antibodies are tested for antigen recognition and functional properties to confirm the original characteristics are found in the recombinant antibody protein.

Antigen Specific ELISA

To identify and characterize antibodies and Fab fragments that bind to human NGF, antibody- and Fab-containing solutions were tested by ELISA. Briefly, neutravidin coated plates (Thermo Scientific), were blocked with ELISA buffer (0.1 mg/mL BSA, 1×PBS pH 7.4, 0.002% Tween 20 and 0.005% sodium azide) for 1 hr at room temperature. The plates were then coated with a 1 μg/mL biotinylated B-NGF solution in ELISA buffer for 1 hour at room temperature. This was followed by a wash step (3× using PBS plus 0.05% Tween 20) and a second block with ELISA buffer. The recombinant antibodies or Fabs were then added onto the plates and incubated for 1 hour at room temperature and then washed 3× with PBS/Tween solution. For development, an anti-human Fc-HRP or an anti-human Fab-fragment HRP (1:5000 dilution in ELISA buffer) was added onto the wells and incubated for 45 min at RT. After a 3× wash step with PBS/Tween solution, the plate was developed using TMB substrate for 3 minutes, stopped using 0.5M HCl, and read at 450 nm.

Figure 28:
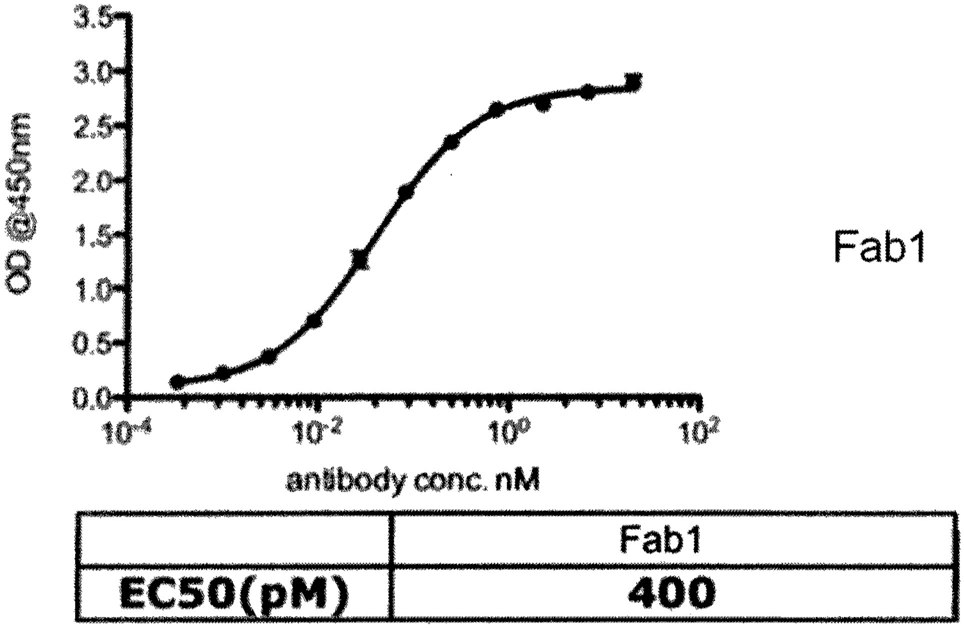
FIG. 28 provides the NGF ELISA binding data obtained following the protocol described infra for Fab1.
Figure 29:
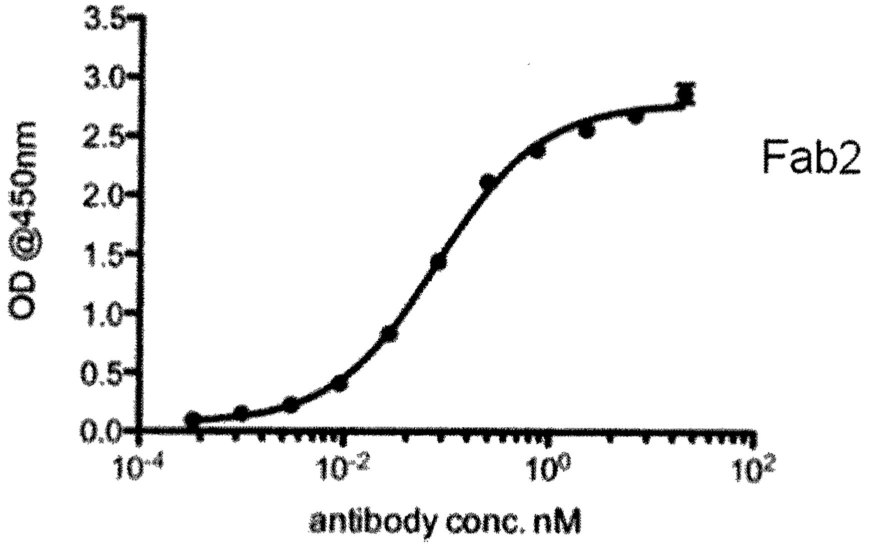
FIG. 29 provides the NGF ELISA binding data obtained following the protocol described infra for Fab2.
Figure 30:
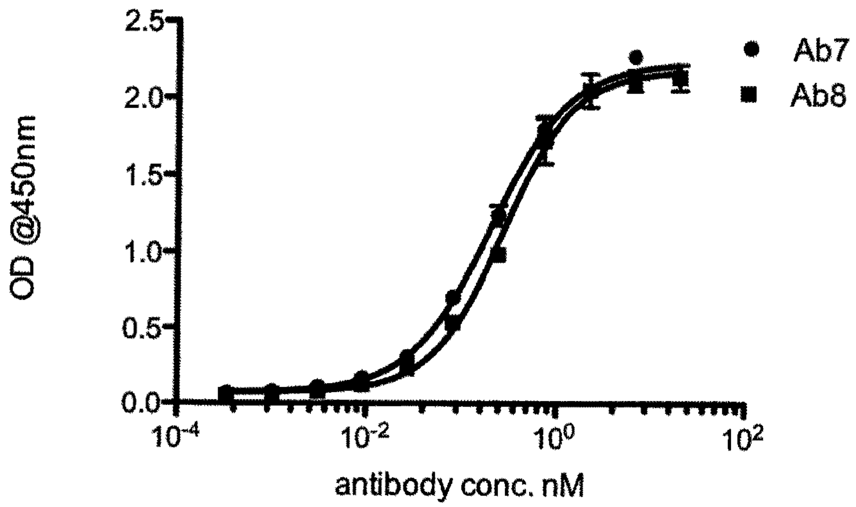
FIG. 30 provides the NGF ELISA binding data obtained following the protocol described infra for antibodies Ab7 and Ab8.
Figure 31:
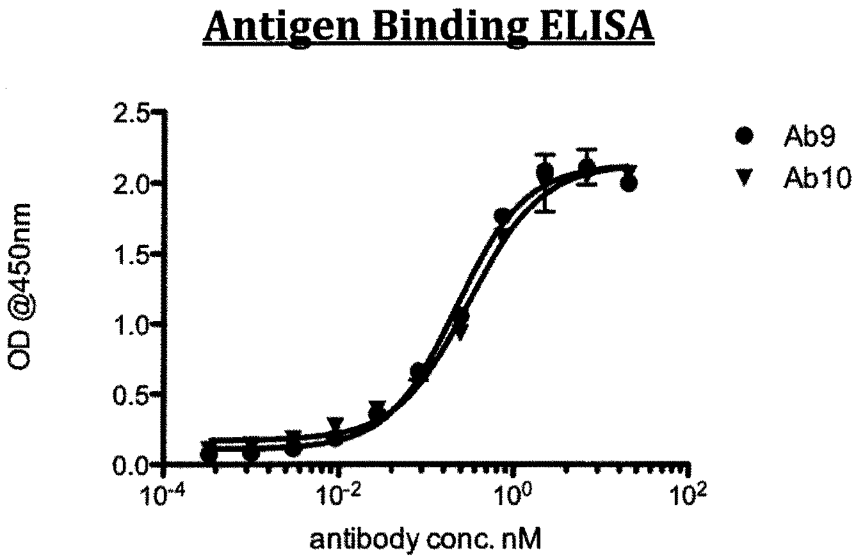
FIG. 31 provides the NGF ELISA binding data obtained following the protocol described infra for antibodies Ab9 and Ab10.
Figure 32:
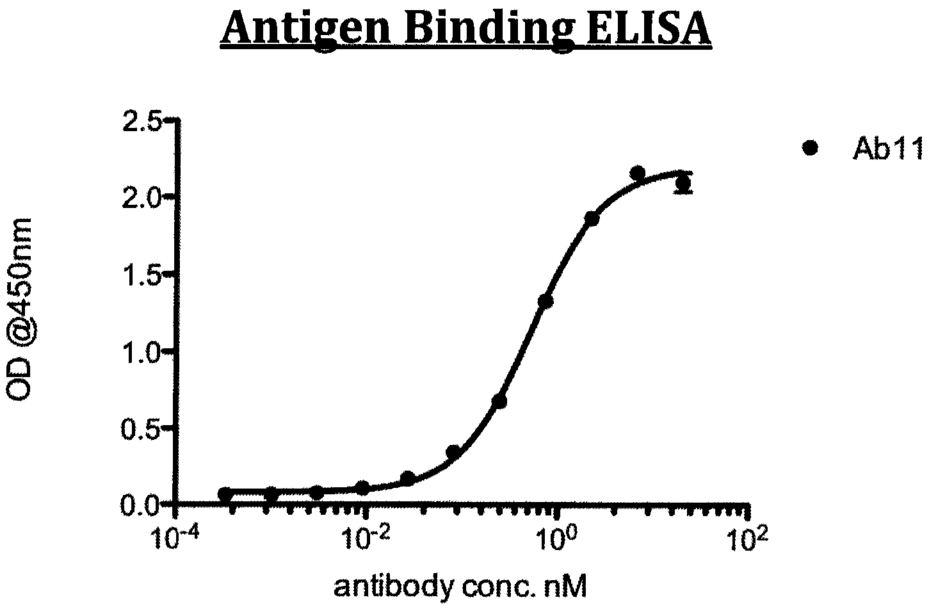
FIG. 32 provides the NGF ELISA binding data obtained following the protocol described infra for antibody Ab11.
Figure 33:
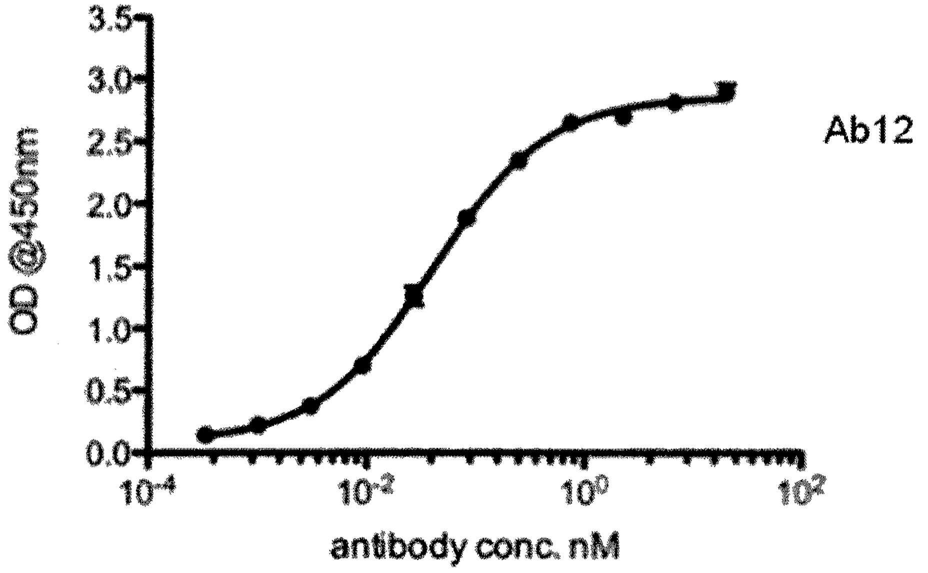
FIG. 33 provides the NGF ELISA binding data obtained following the protocol described infra for antibody Ab12.
Figure 34:
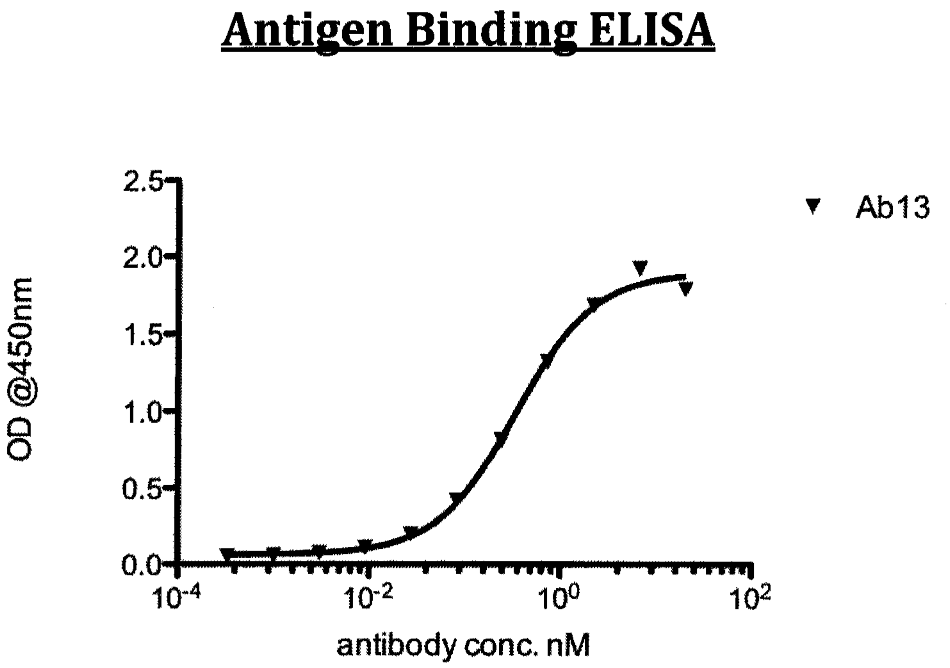
FIG. 34 provides the NGF ELISA binding data obtained following the protocol described infra for antibody Ab13.
Figure 35:
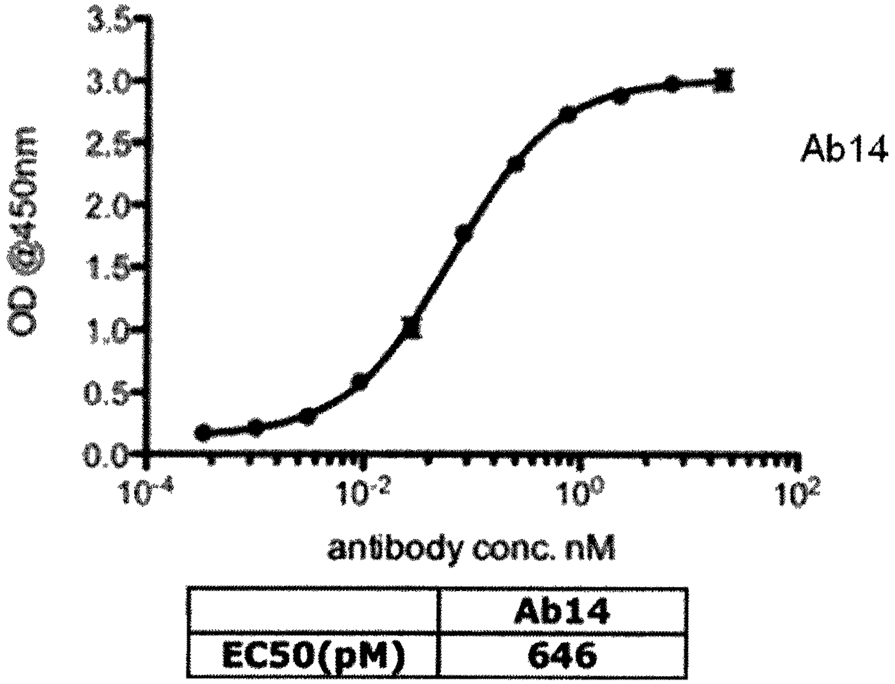
FIG. 35 provides the NGF ELISA binding data obtained following the protocol described infra for antibody Ab14.
Figure 36:
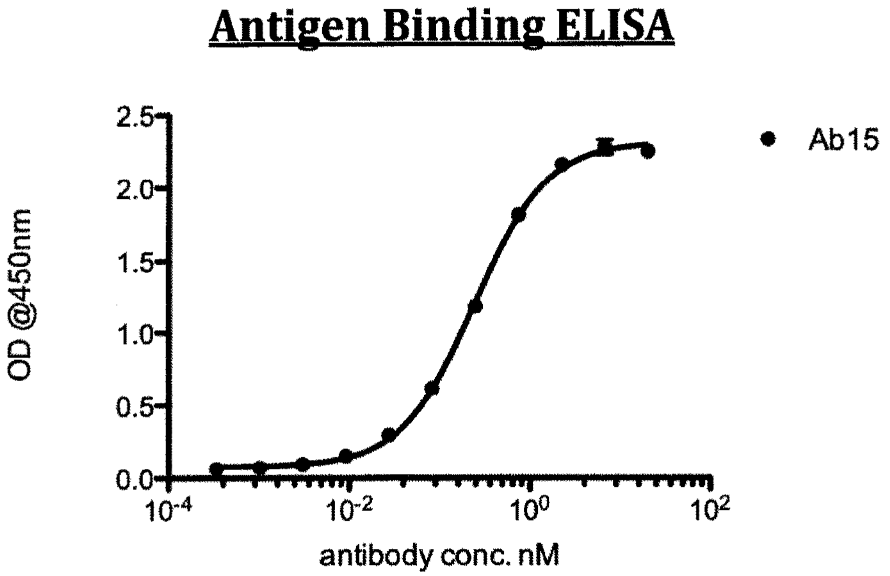
FIG. 36 provides the NGF ELISA binding data obtained following the protocol described infra for antibody Ab15.
Figure 37:
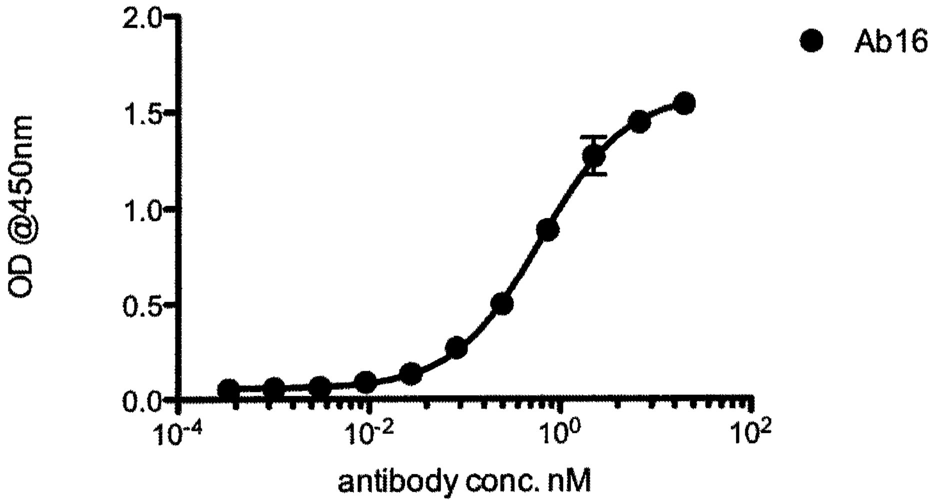
FIG. 37 provides the NGF ELISA binding data obtained following the protocol described infra for antibody Ab16.
Figure 38:
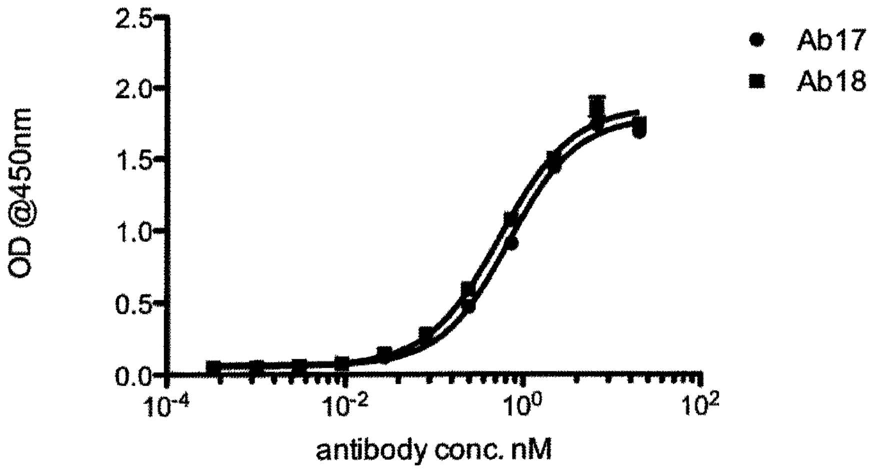
FIG. 38 provides the NGF ELBA binding data obtained following the protocol described infra for antibodies Ab17 and Ab18.
Figure 39:
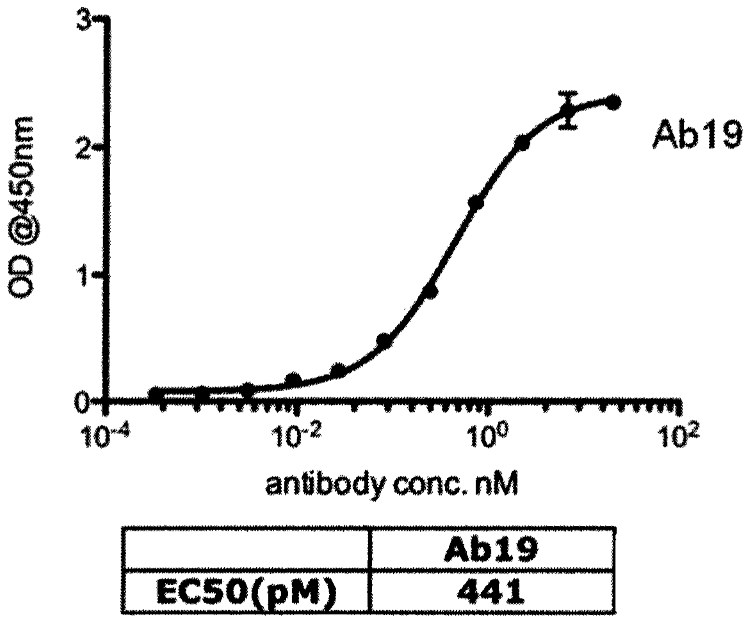
FIG. 39 provides the NGF ELISA binding data obtained following the protocol described infra for antibody Ab19.
Figure 40:
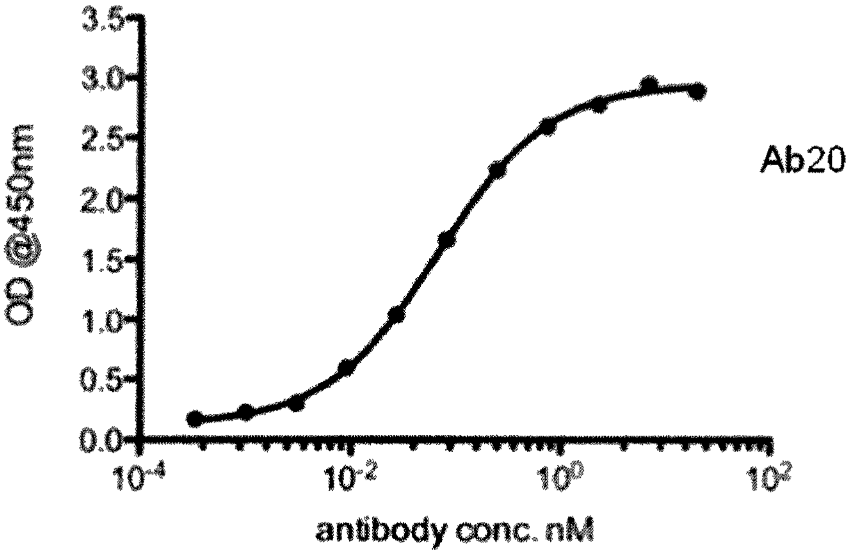
FIG. 40 provides the NGF ELISA binding data obtained following the protocol described infra for antibody Ab20.
Figure 41:
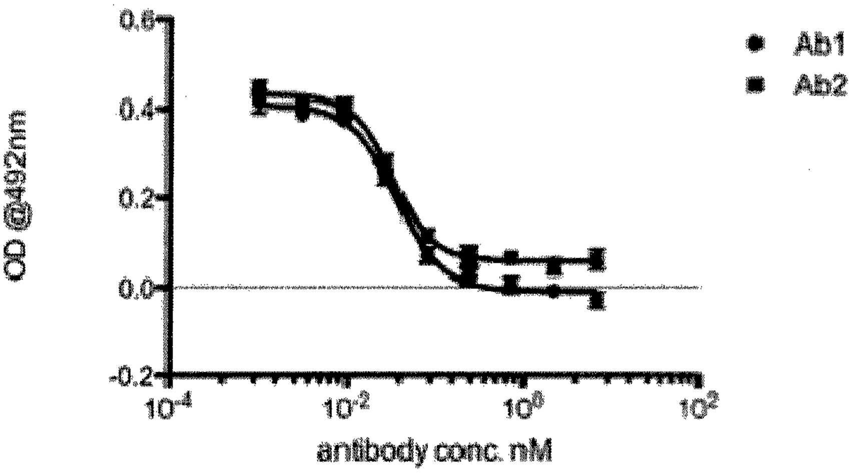
FIG. 41 provides the TF1 cell proliferation data obtained following example 1 for antibodies Ab1 and Ab2.
Figure 42:
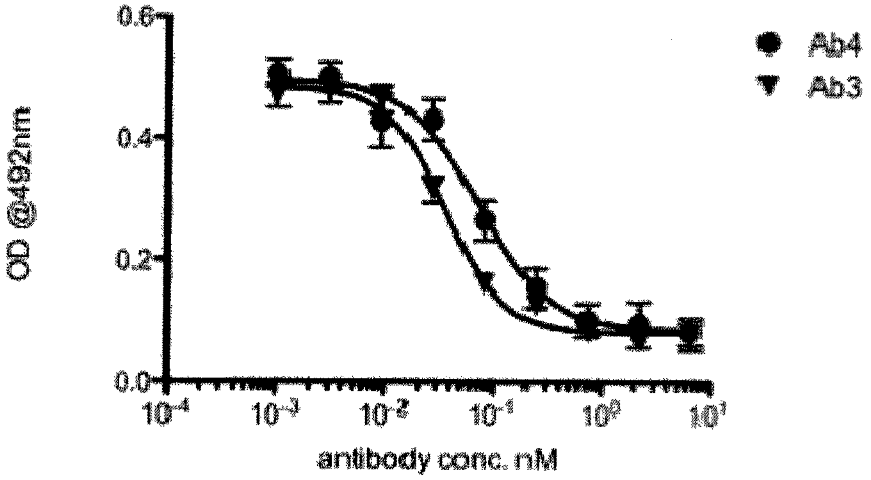
FIG. 42 provides the TF1 cell proliferation data obtained following example 1 for antibodies Ab3 and Ab4.
Figure 43:
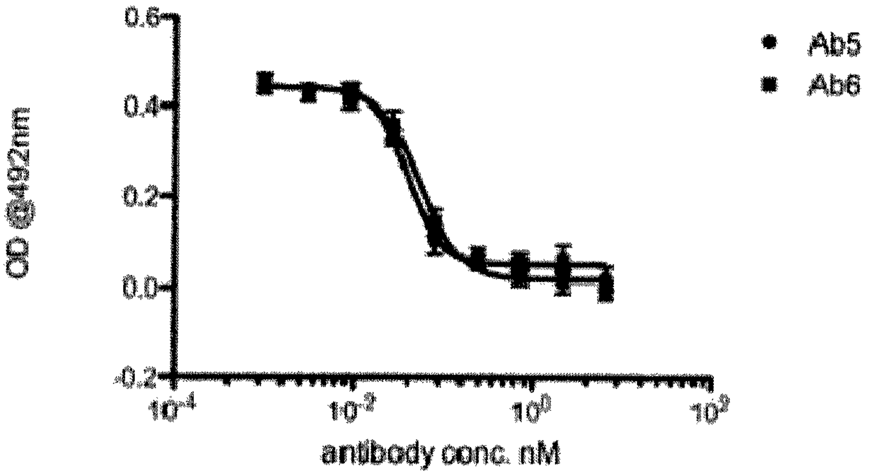
FIG. 43 provides the TF1 cell proliferation data obtained following example 1 for antibodies Ab5 and Ab6.
Figure 44:
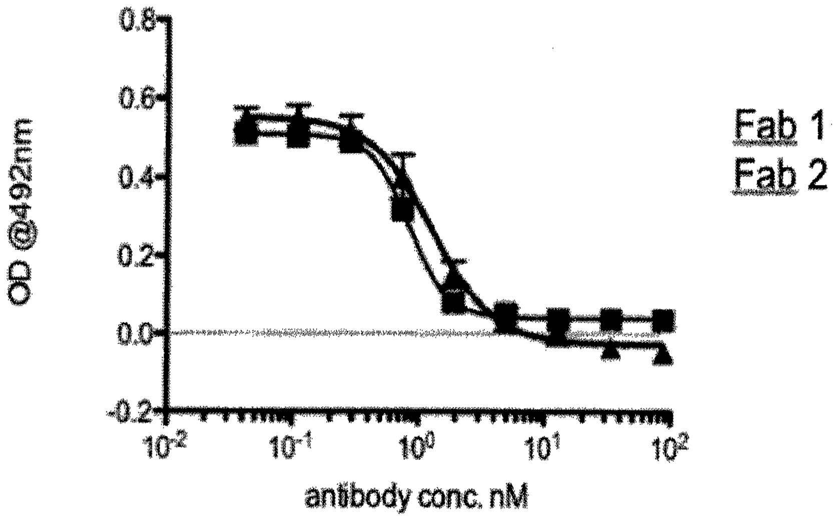
FIG. 44 provides the TF1 cell proliferation data obtained following example 1 for the Fab1 and Fab2 antibody fragments.
Figure 45:
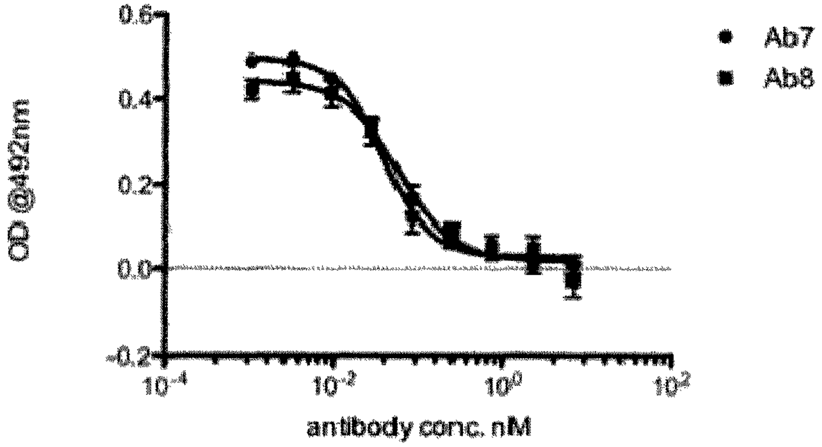
FIG. 45 provides the TF1 cell proliferation data obtained following example 1 for antibodies Ab7 and Ab8.
Figure 46:
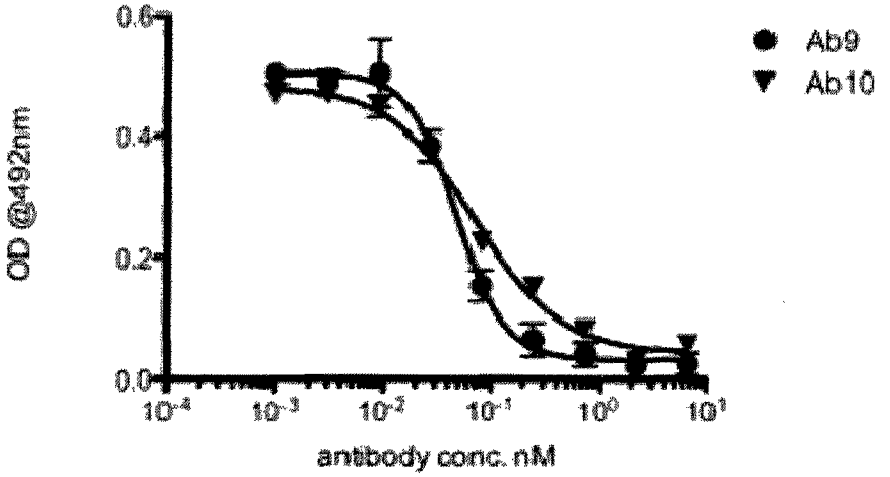
FIG. 46 provides the TF1 cell proliferation data obtained following example 1 for antibodies Ab9 and Ab10.
Figure 47:
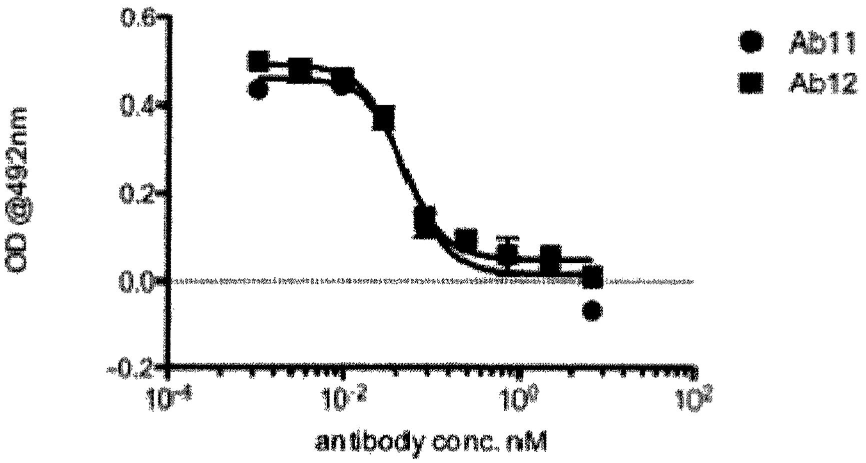
FIG. 47 provides the TF1 cell proliferation data obtained following example 1 for antibodies Ab11 and Ab12.
Figure 48:
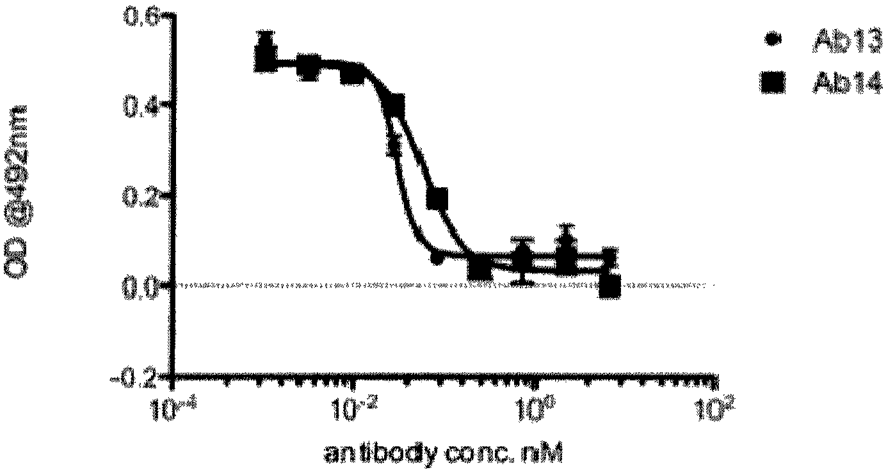
FIG. 48 provides the TF1 cell proliferation data obtained following example 1 for antibodies Ab13 and Ab14.
Figure 49:
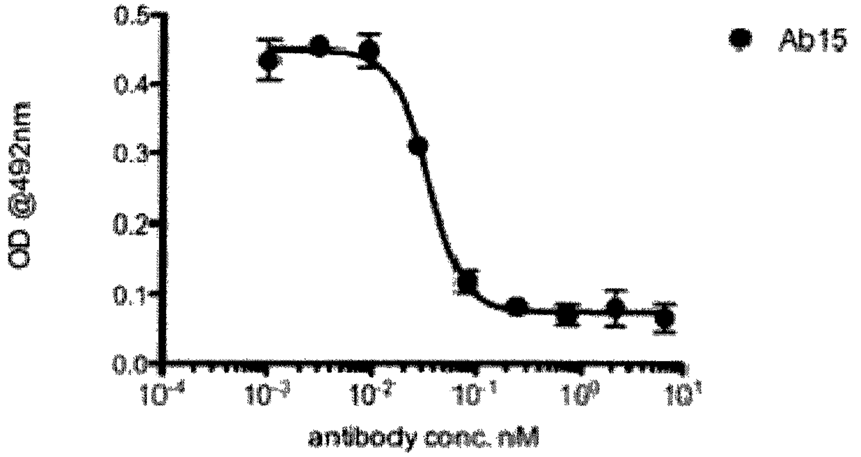
FIG. 49 provides the TF1 cell proliferation data obtained following example 1 for antibody Ab15.
Figure 50:
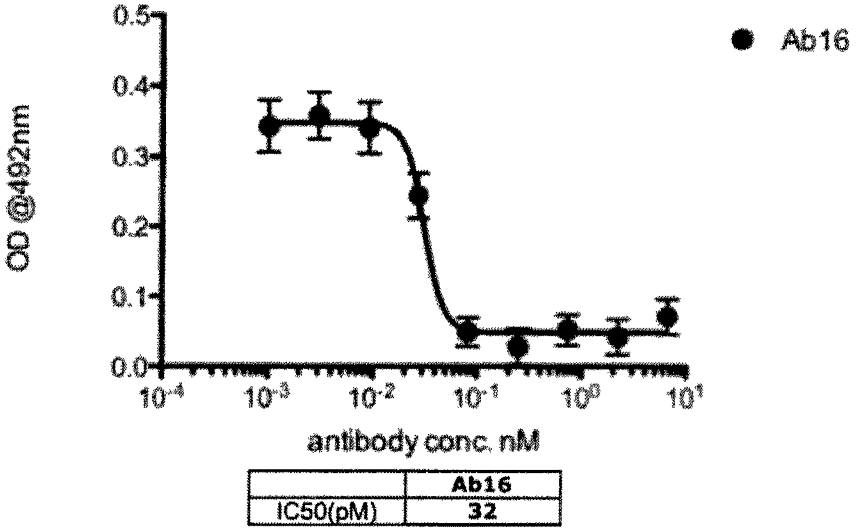
FIG. 50 provides the TF1 cell proliferation data obtained following example 1 for antibody Ab16.
Figure 51:
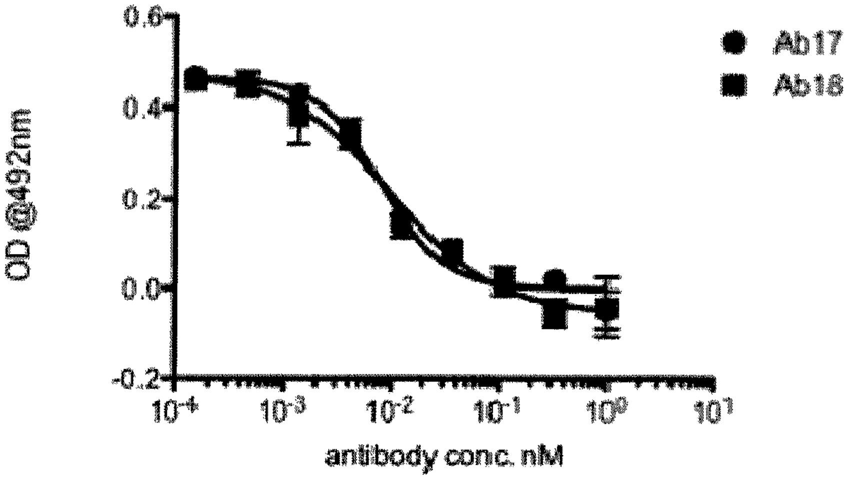
FIG. 51 provides the TF1 cell proliferation data obtained following example 1 for antibodies Ab17 and Ab18.
Figure 52:
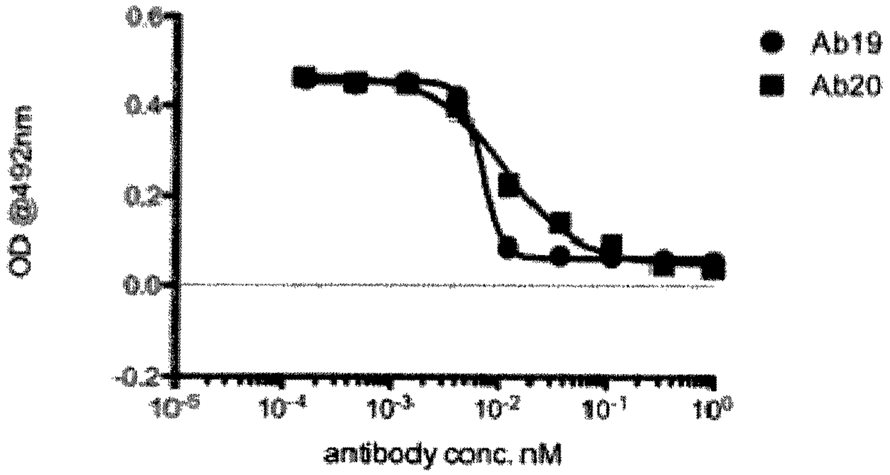
FIG. 52 provides the TF1 cell proliferation data obtained following example 1 for antibodies Ab19 and Ab20.

Results: FIGS. 24-40 demonstrate that anti-NGF antibodies Ab1-Ab21 bind to NGF. Furthermore, FIGS. 28 and 29 demonstrate that Fab antibody fragments Fab1 and Fab2 bind to NGF.

Functional Activity Screening

To test for the ability of NGF antibodies to block or inhibit NGF-dependent and TrkA receptor-mediated cell proliferation activity, we used TF-1 cells (Chevalier et al. Expression and functionality of the trkA proto-oncogene product/NGF receptor in undifferentiated hematopoietic cells. Blood (1994) vol. 83 (6) pp. 1479-85). Briefly, TF-1 cells were maintained in 10% FBS cRPMI media ("complete media") supplemented with rhuGM-CSF. On the day of the assay, the antibodies were serially diluted in complete media in a round bottom 96 well plate. B-NGF (R&D systems) was concomitantly added and the resultant antibody/B-NGF mixture was incubated at 37° C. for 1 hr. While the Ab and B-NGF mixture was incubating, TF-1 cells were washed 3× with complete media, counted and plated in a flat bottom 96 well plate using 25,000 cells per well in a 50 μL volume. After 1 hour incubation the NGF-Antibody mixtures were added onto the cells and the plates were incubated for 48 hrs at 37° C. in a humidified 5% $CO_2$ incubator. Cell proliferation was measured using the "CellTiter" aqueous one solution cell proliferation assay (Promega) according to the manufacturer's instructions. The dependency of the signals on the concentration of antibody was analyzed, and IC50 values were calculated using the GraphPad Prism program.

Results: FIGS. 41-52 demonstrate that anti-NGF antibodies Ab1-Ab20 inhibit the proliferation of TF-1 cells. Furthermore, FIG. 44 demonstrates that Fab antibody fragments also inhibit the proliferation of TF-1 cells. These Fab antibody fragments were produced by: 1.) *Pichia pastoris* expression of Fab2; and 2.) enzymatic digestion of Ab21 produced in *Pichia pastoris* (Fab1).

Example 2 Enzymatic Production of Fab Fragments

Papain digestions were conducted using immobilized papain (Thermo/Pierce) as per manufacturer's instructions. Briefly, purified antibodies were incubated in a cystein/HCl-containing buffer with immobilized papain at 37° C. with gentle rocking. The digestion was monitored by taking an aliquot and analyzing using SDS-PAGE for cleavage of the heavy chain. To stop the reaction, the immobilized papain was spun out and washed using 50 mM Tris pH 7.5 and filtered. Undigested full length antibody and Fc fragments were removed by using a MabSelectSure (GE) column.

Example 3 Yeast Cell Expression

Antibody genes: Genes were cloned and constructed that directed the synthesis of a chimeric humanized rabbit monoclonal antibody.

Methods

Construction of *Pichia pastoris* Expression Vectors for Heavy and Light Chain Antibodies.

The light and heavy chain fragments (chimera or humanized) were commercially synthesized and subcloned into a pGAP expression vector. The pGAP expression vector uses the GAP promoter to drive expression of the immunoglobulin chain and the human serum albumin (HAS) leader sequence for export. In addition, this vector contains common elements such as a bacterial origin of replication, and a copy of the Sh ble gene which confers resistance to the antibiotic Zeocin™ (phleomycin). Zeocin™ provides a means of selection for strains that contain the desired expression vector integrated into their genome.

Transformation of Expression Vectors into Haploid Met1 and Lys3 Host Strains of *Pichia pastoris*

All methods used for transformation of haploid *P. pastoris* strains and manipulation of the *P. pastoris* sexual cycle were done as described in *Pichia* Protocols (Methods in Molecular Biology Riggings, D R, and Cregg, J M, Eds. 1998. Humana Press, Totowa, N.J.). Prior to transformation each vector was linearized within the GAP promoter sequences to direct the integration of the vector into the GAP promoter locus of the *P. pastoris* genome. Haploid strains were transfected using electroporation and successful transformants were selected on YPD Zeocin™ plates and then cultured in 96-well plates for two days. Haploid strains were mated and selected for their ability to grow in the absence of the auxotroph markers (i.e., Lys and Met). Diploid strains were then selected for their ability to express either full length or Fab antibody fragments using a ForteBio Octet system fitted with Protein A biosensors to monitor expression.

Example 4 Expression of Ab21 and Fab2 in *Pichia pastoris*

Two *Pichia* strains for expression of either full length Ab21 or Fab2 antibody fragment were made. For both the full length or the Fab expressing strains, haploids strains were created and subsequently mated. One haploid strain expressed full length light sequences for Ab21 and another haploid strain expressed either the full length Ab21 or a truncated form of heavy chain to express an Fab fragment (e.g., Fab2). Each diploid strain was used to generate a research cell bank and used for expression in a bioreactor.

First an inoculum was expanded using the research cell bank using medium comprised of the following nutrients (% w/v): yeast extract 3%, anhydrous dextrose 4%, YNB 1.34%, 0.004% Biotin with 100 mM potassium phosphate. The culture was expanded for approximately 24 hours in a shaking incubator at 30° C. and 300 rpm to generate the inoculum for the fermenters. A 10% inoculum was then added to Labfors 2.5 L working volume vessels containing sterile growth medium. The growth medium for the full length Ab21 was comprised of the following nutrients: potassium sulfate 18.2 g/L, ammonium phosphate monobasic 36.4 g/L, potassium phosphate dibasic 12.8 g/L, magnesium sulfate heptahydrate 3.72 g/L, sodium citrate dihydrate 10 g/L, glycerol 40 g/L, yeast extract 30 g/L, PTM1 trace metals 4.35 mL/L, and antifoam 204 1.67 mL/L. The PTM1 trace metal solution was comprised of the following components: cupric sulfate pentahydrate 6 g/L, sodium iodide 0.08 g/L, manganese sulfate hydrate 3 g/L, sodium molybdate dihyrate 0.2 g/L, boric acid 0.02 g/L, cobalt chloride 0.5 g/L, zinc chloride 20 g/L, ferrous sulfate heptahydrate 65 g/L, biotin 0.2 g/L, and sulfuric acid 5 mL/L.

The growth medium for the Fab2 fragment was comprised of the following nutrients: potassium sulfate 10.92 g/L, ammonium phosphate monobasic 21.84 g/L, potassium phosphate dibasic 7.68 g/L, magnesium sulfate heptahydrate 3.72 g/L, sodium citrate dihydrate 10 g/L, glycerol 40 g/L, yeast extract 30 g/L, PTM1 trace metal solution 2.61 mL/L, and antifoam 204 1.67 mL/L. The PTM1 trace metal solution was comprised of the following components: cupric sulfate pentahydrate 6 g/L, sodium iodide 0.08 g/L, manganese sulfate hydrate 3 g/L, sodium molybdate dihyrate 0.2 g/L, boric acid 0.02 g/L, cobalt chloride 0.5 g/L, zinc chloride 20 g/L, ferrous sulfate heptahydrate 65 g/L, biotin 0.2 g/L, and sulfuric acid 5 mL/L. Both proteins were expressed under similar conditions. Briefly, the bioreactor process control parameters were set as follows: Agitation 1000 rpm, airflow 1.35 standard liter per minute, temperature 28° C. and pH was controlled at six using ammonium hydroxide. No oxygen supplementation was provided.

The fermentation cultures were grown for approximately 12 to 16 hours until the initial glycerol was consumed as denoted by a dissolved oxygen spike. The cultures were starved for approximately three hours after the dissolved oxygen spike. After this starvation period, a bolus addition of ethanol was added to the reactor to reach 1% ethanol (w/v). The fermentation cultures were allowed to equilibrate for 15 to 30 minutes. Feed addition was initiated 30 minutes post-ethanol bolus and set at a constant rate of 1 mL/min for 40 minutes, then the feed pump was controlled by an ethanol sensor keeping the concentration of ethanol at 1% for the remainder of the run. The feed was comprised of the following components: yeast extract 50 g/L, dextrose 500 g/L, magnesium sulfate heptahydrate 3 g/L, and PTM1 trace metals 12 mL/L. For fermentation of the full length Ab21, sodium citrate dihydrate (0.5 g/L) was also added to the feed. The total fermentation time was approximately 90 hours.

Example 5 Inhibition of NGF-p75 Interactions

NGF is reported to interact with two receptors on the cell surface: TrkA and p75. A biolayer interferometry assay via the "Octet" was used to characterize the ability of anti-NGF antibodies to inhibit NGF-p75 interactions. Briefly, streptavidin (SA) sensors were pre-wetted in 1× kinetics buffer (1×PBS ph 7.4, 0.002% Tween 20, 0.005% sodium azide and 0.1 mg/mL BSA). A baseline was obtained using again 1× kinetics buffer, followed by binding of the biotinylated antibody being tested and another short baseline in 1× kinetics buffer. NGF (1 μg/mL) was loaded next and the sensor was then transferred onto 1× kinetics buffer. After loading of NGF onto the antibody, on one sensor, all possible sites of NGF were blocked using an un-labeled solution of the biotinylated antibody at 5 μg/mL. As control, a parallel sensor was submerged into 1× kinetics buffer during this second blocking step. Both sensors were then exposed to a solution containing p75 (1.2 μg/mL). The ability of an antibody to block or inhibit NGF-p75 interactions was then characterized by monitoring the increase in signal when antibody-immobilized NGF was exposed to soluble p75.

Figure 54:
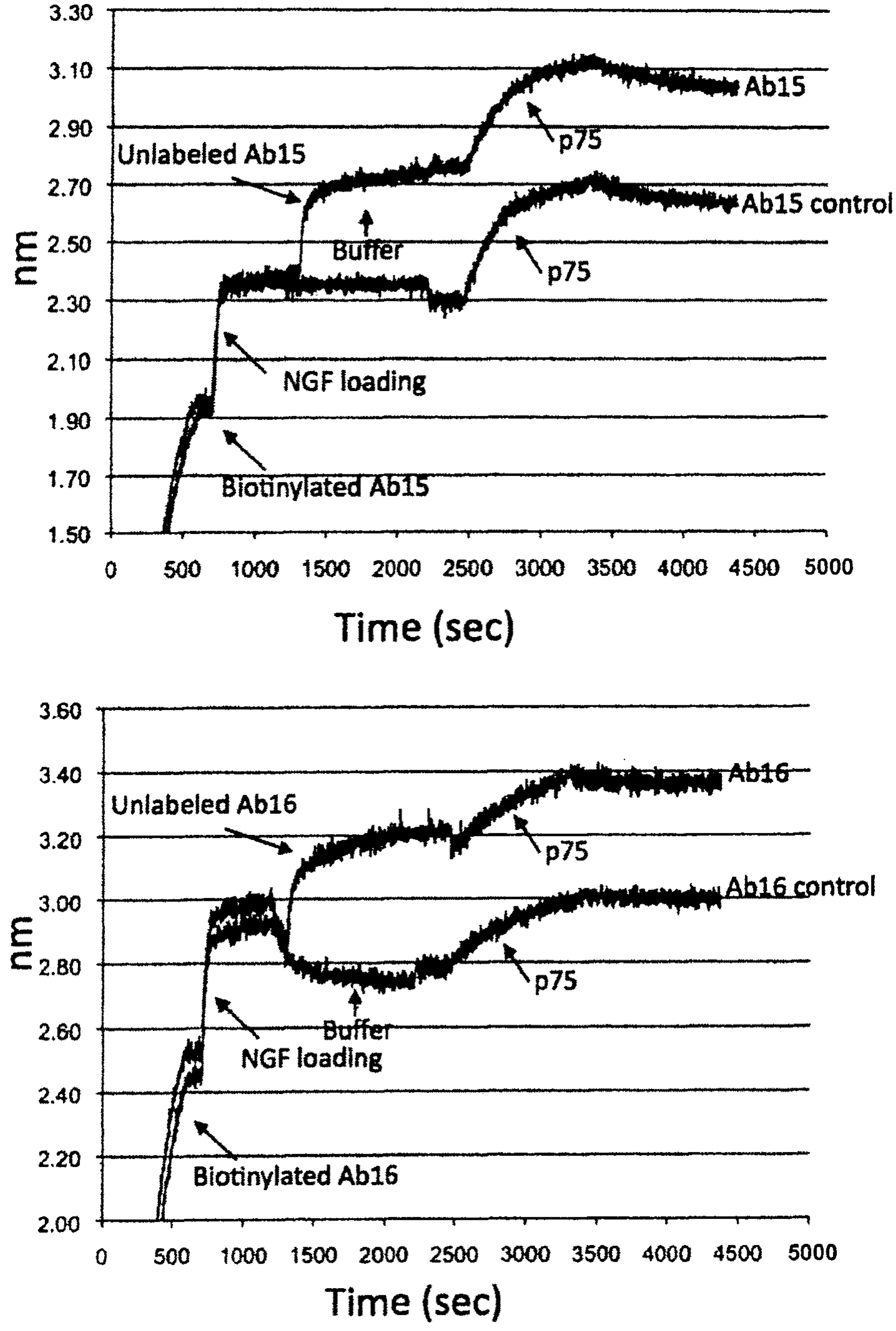
FIG. 54 provides the inhibition of NGF-p75 interaction data obtained following example 5 for antibodies Ab15 and Ab16. Antibodies Ab15 and Ab16 do not demonstrate the ability to inhibit the interaction of NGF and p75.
Figure 55:
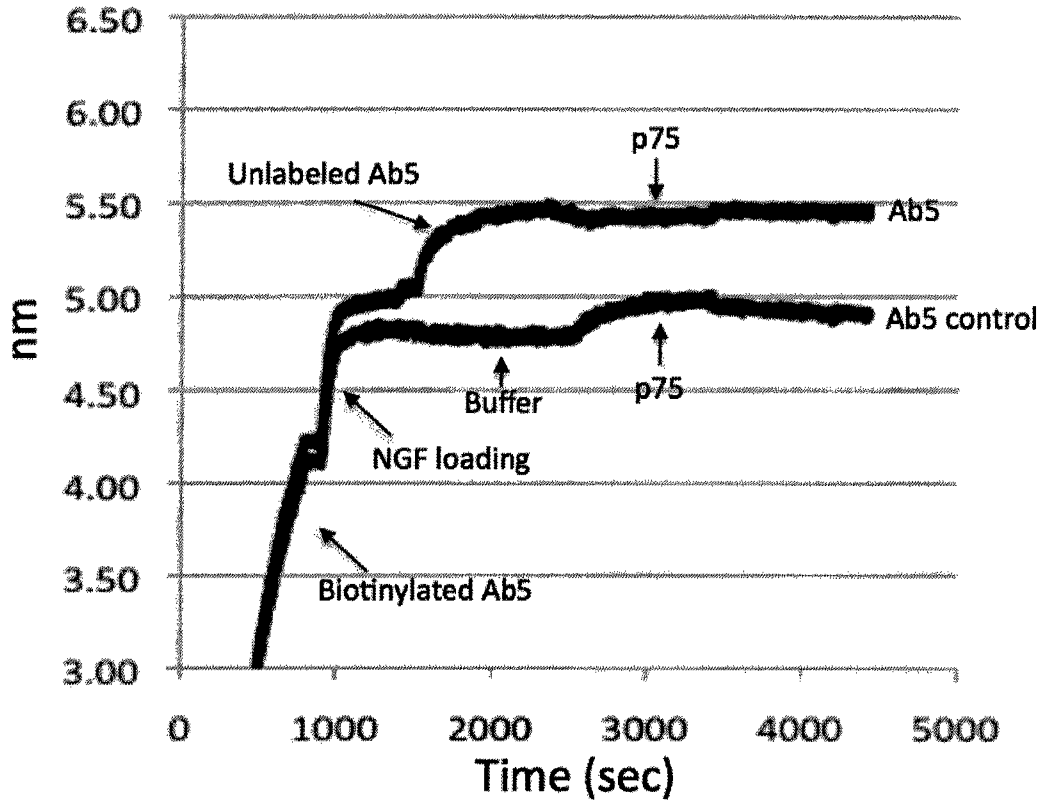
FIG. 55 provides the inhibition of NGF-p75 interaction data obtained following example 5 for antibody Ab5. Antibody Ab5 demonstrates the ability to inhibit the interaction of NGF and p75.
Figure 56:
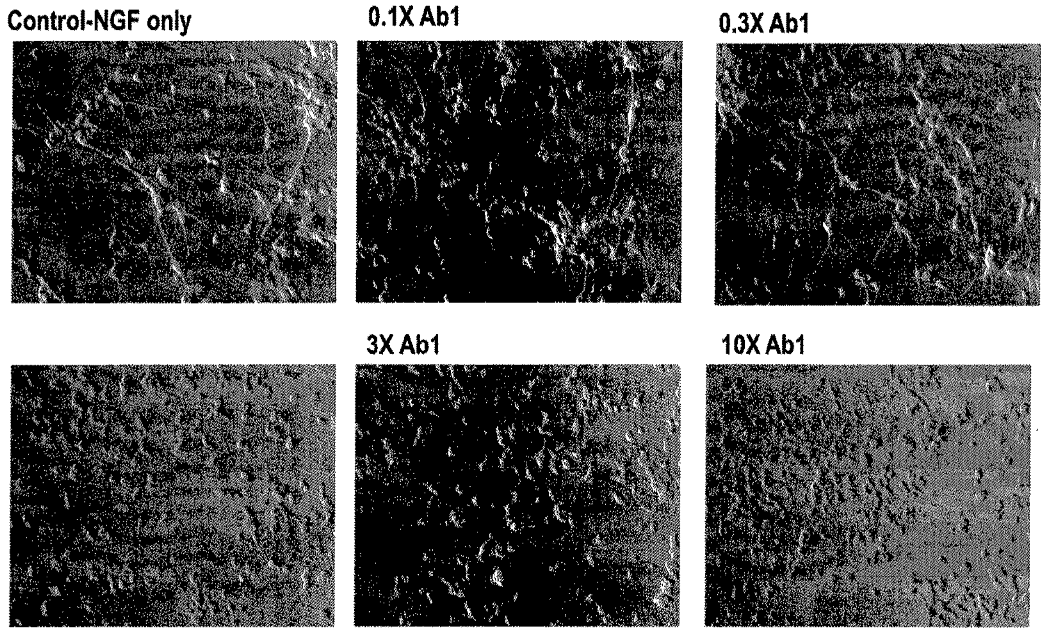
FIG. 56 demonstrates the inhibition of PC-12 neurite outgrowth in the presence of increasing concentrations of antibody Ab1 obtained following example 6.
Figure 57:
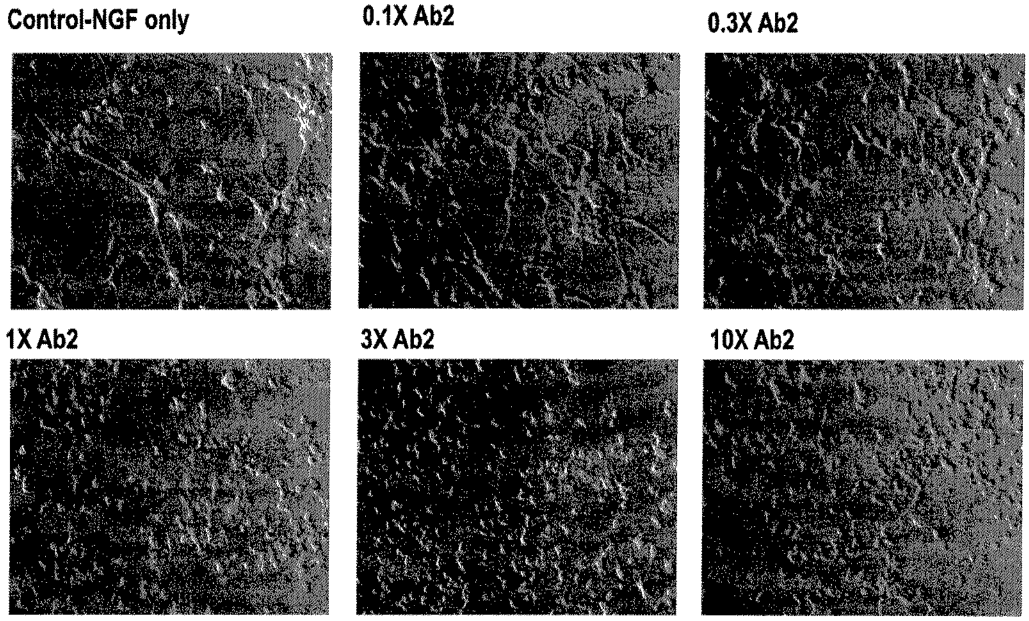
FIG. 57 demonstrates the inhibition of PC-12 neurite outgrowth in the presence of increasing concentrations of antibody Ab2 obtained following example 6.
Figure 58:
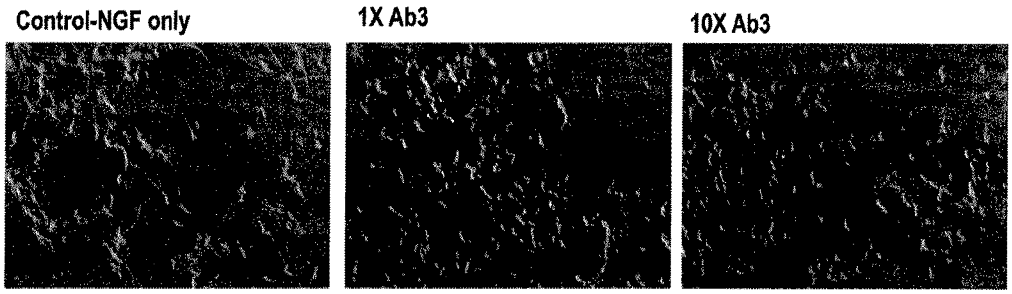
FIG. 58 demonstrates the inhibition of PC-12 neurite outgrowth in the presence of increasing concentrations of antibody Ab3 obtained following example 6. The results also demonstrate that the inhibition of PC-12 neurite outgrowth at the same concentrations of antibody is less than that seen with anti-NGF antibodies which exhibit different NGF binding selectivity.
Figure 59:
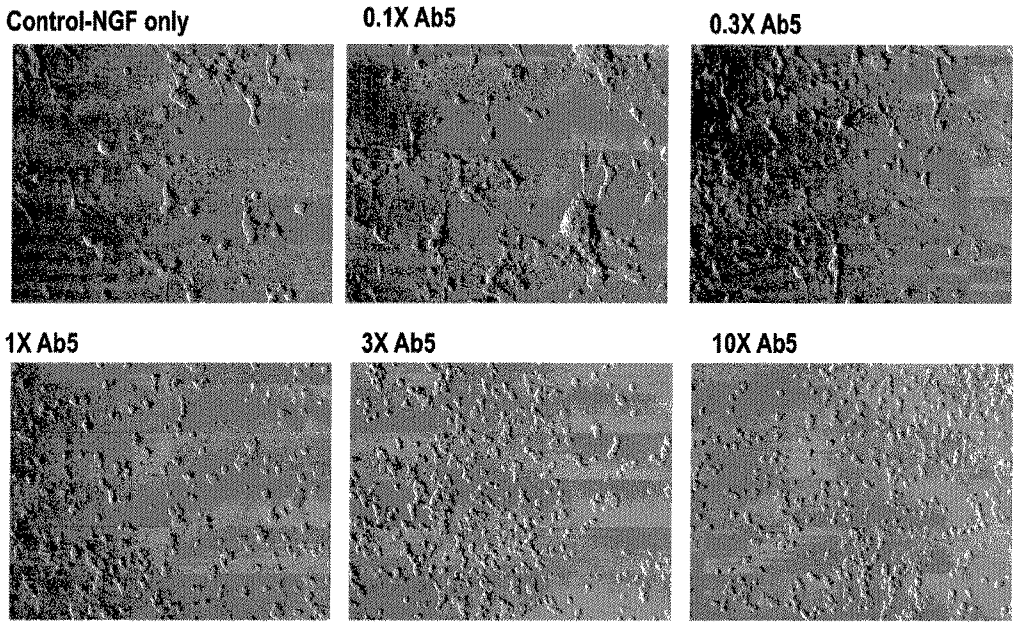
FIG. 59 demonstrates the inhibition of PC-12 neurite outgrowth in the presence of increasing concentrations of antibody Ab5 obtained following example 6.
Figure 60:
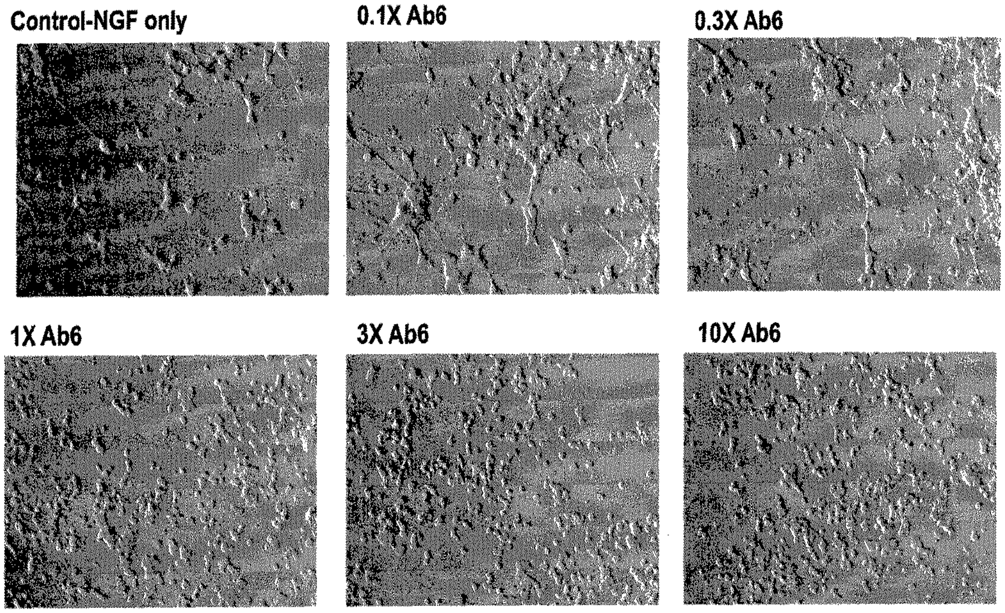
FIG. 60 demonstrates the inhibition of PC-12 neurite outgrowth in the presence of increasing concentrations of antibody Ab6 obtained following example 6.
Figure 61:
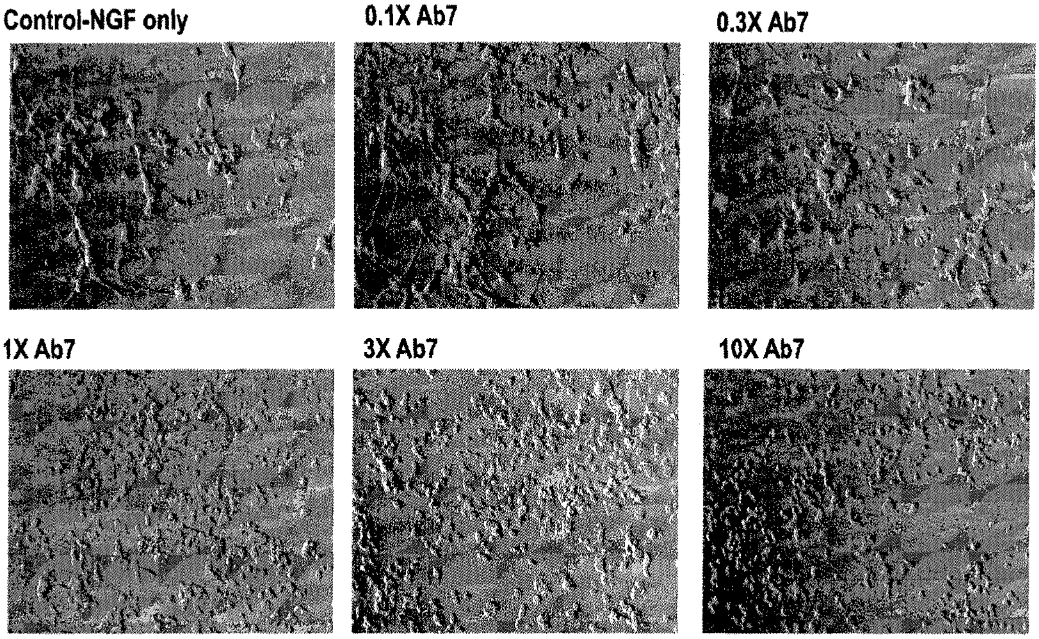
FIG. 61 demonstrates the inhibition of PC-12 neurite outgrowth in the presence of increasing concentrations of antibody Ab7 obtained following example 6.
Figure 62:
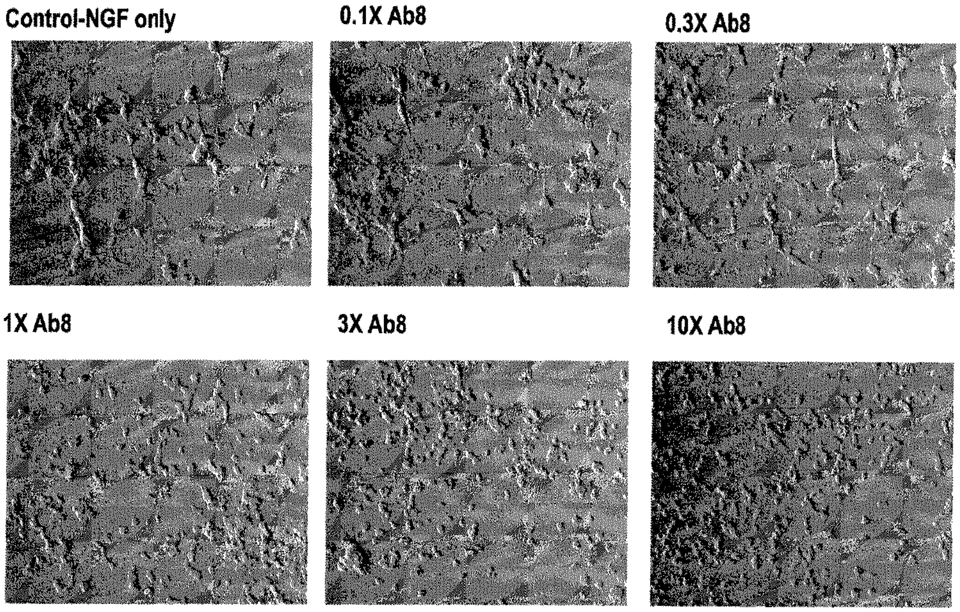
FIG. 62 demonstrates the inhibition of PC-12 neurite outgrowth in the presence of increasing concentrations of antibody Ab8 obtained following example 6.
Figure 63:
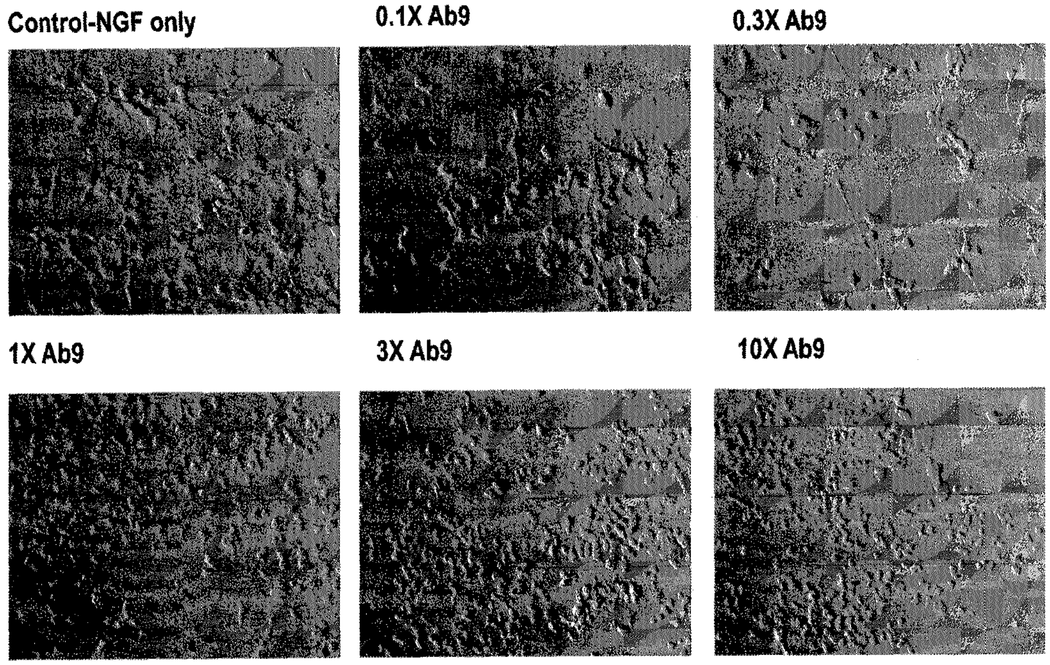
FIG. 63 demonstrates the inhibition of PC-12 neurite outgrowth in the presence of increasing concentrations of antibody Ab9 obtained following example 6.
Figure 65:
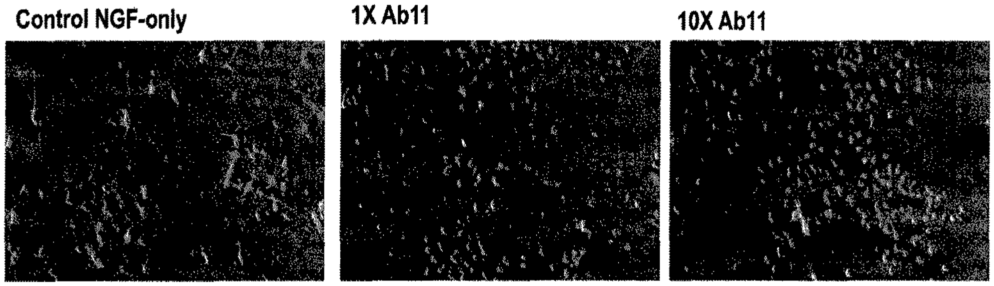
FIG. 65 demonstrates the inhibition of PC-12 neurite outgrowth in the presence of increasing concentrations of antibody Ab11 obtained following example 6.
Figure 66:
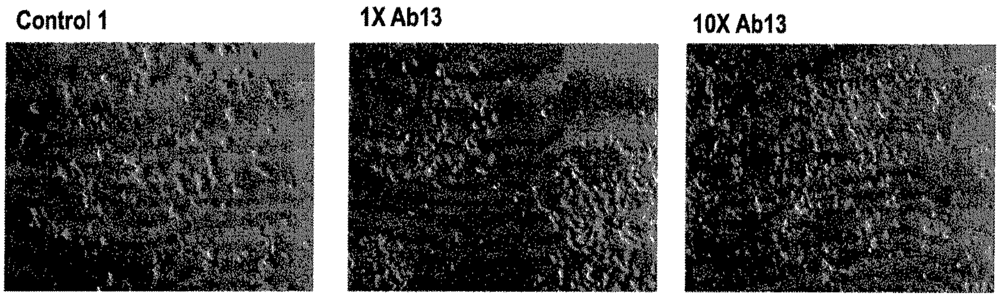
FIG. 66 demonstrates the inhibition of PC-12 neurite outgrowth in the presence of increasing concentrations of antibody Ab13 obtained following example 6.
Figure 67:
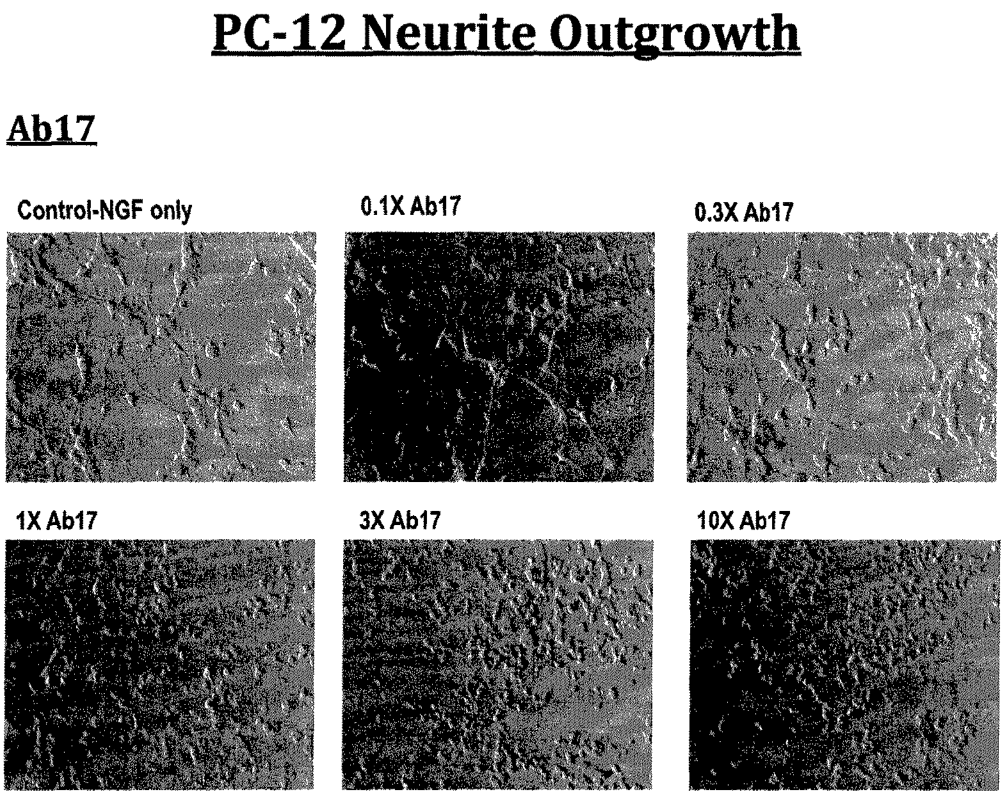
FIG. 67 demonstrates the inhibition of PC-12 neurite outgrowth in the presence of increasing concentrations of antibody Ab17 obtained following example 6.
Figure 68:
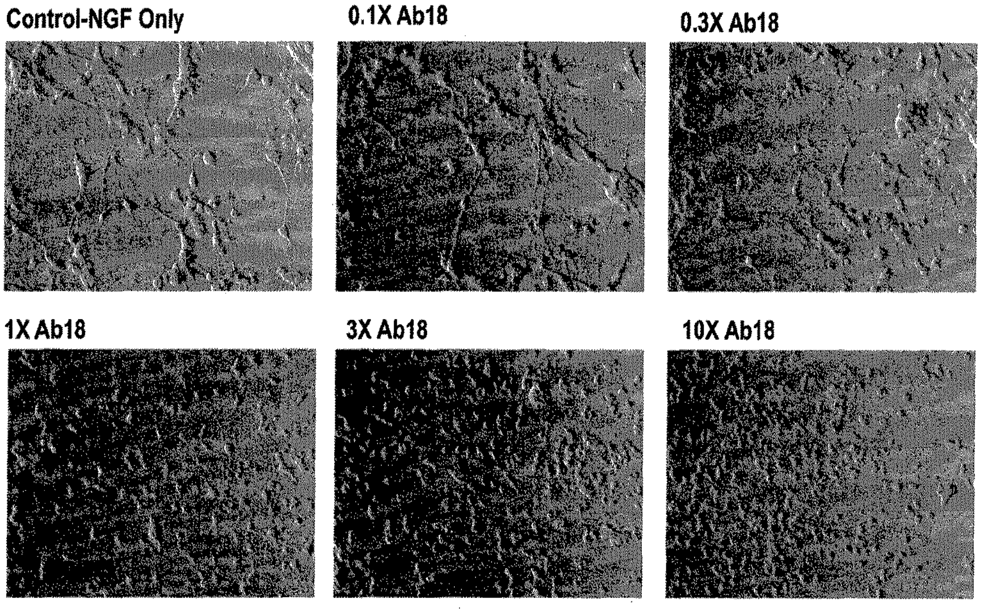
FIG. 68 demonstrates the inhibition of PC-12 neurite outgrowth in the presence of increasing concentrations of antibody Ab18 obtained following example 6.
Figure 69:
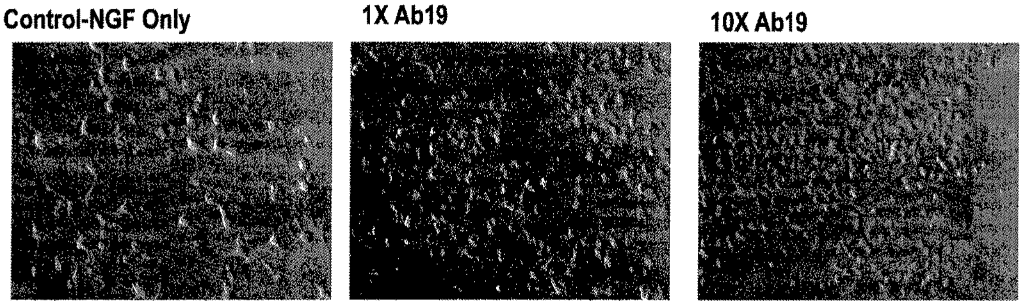
FIG. 69 demonstrates the inhibition of PC-12 neurite outgrowth in the presence of increasing concentrations of antibody Ab19 obtained following example 6.

Results: FIGS. 53 and 54 demonstrates that anti-NGF antibodies Ab3, Ab4, Ab15, and Ab16 do not inhibit binding of NGF to p75, while FIG. 55 demonstrates that antibody Ab5 inhibits binding of NGF to p75.

Example 6 Neurite PC12 Assay

The ability of anti-NGF antibodies to block or inhibit NGF signaling mediated through the p75 and TrkA receptors was measured in vitro using a rat adrenal medulla cell line, PC12. PC12 cells express both p75 and TrkA receptors on their cell surface (Urdiales et al. Cell cycle phase-specific surface expression of nerve growth factor receptors TrkA and p75(NTR). J Neurosci (1998) vol. 18 (17) pp. 6767-75); (Greene and Tischler. Establishment of a noradrenergic clonal line of rat adrenal pheochromocytoma cells which respond to nerve growth factor. Proc Natl Acad Sci USA (1976) vol. 73 (7) pp. 2424-8). Briefly, PC12 cells were maintained in culture using 15% FBS RPMI and grown on a collagen I-coated flask for 48 hours before priming. The cells were then 'primed' for 72 hours by exposing them to 100 ng/mL NGF in differentiation media (1% horse serum RPMI). On the day of the assay, the cells were harvested with a cell scraper, resuspended, rinsed in differentiation media (without NGF) and plated onto a collagen I-coated 24-well plate. The final concentration of NGF in the assay was 100 ng/mL. The antibodies being tested were pre-incubated with the NGF at different molar ratios (from 10× to 0.1×) for 1 hour in differentiation media prior to adding them onto the PC-12 cells. On day 3, the media was gently removed and antibody-NGF mixtures were replaced. On day 10, the wells were observed under a microscope and representative fields were digitized using a 10× magnification lens.

Results: FIGS. 56-69 and FIGS. 78 and 79 demonstrate that anti-NGF antibodies Ab1-Ab3, Ab5-Ab11, Ab13, Ab15, Ab16, and Ab17-Ab19 inhibit the outgrowth of PC-12 neurite cells at increasing concentrations. It can be seen that antibodies Ab3, Ab15 and Ab16, when assayed at the same antibody concentrations as the other tested anti-NGF antibodies, showed significantly less inhibition of the outgrowth of PC-12 neurite cells. This difference is believed to be attributable to the fact that Ab3, Ab15 and Ab16, all inhibit TrkA/NGF interactions and not NGF/p75 interactions, whereas the remaining tested antibodies inhibit the interaction of NGF with both TrkA and p75.

Example 7 Modulation of Pain Assessed by Gait Analysis

To assess the effect of anti-NGF agents (full length and Fab fragments) in their ability to modulate pain, a PGPS (peptidoglycan polysaccharide)-induced arthritis model was used. Briefly, male Lewis rats were injected with a solution of PGPS into their right ankle on day (−)17. One day later, ankles were evaluated for an inflammatory response to the PGPS injection and non-responders were eliminated. Responders were allowed to recover for seventeen days before an IV tail vein reactivation with PGPS.

Full-length antibodies were dosed once, either 2 hours or the night before reactivation. Fab fragments were administered once a day with the first dose administered two hours prior to reactivation. Gait analysis was performed by applying ink to the ventral surface of the foot and documenting weight bearing during movement (footprints) across paper. The rear feet of the rats were placed in blue colored ink, and black ink was applied to the dorsal side of the foot on the suspected painful leg. Rats were placed on paper and allowed to walk. Gaits were scored as follows: 0=normal, equal ink staining on both feet; 1=slight limp, toe staining evident and some heel staining; 2=limping, toes only staining; 3=dragging/carrying leg, black drag marks from dorsal side of foot present; 4=carrying leg, no staining from painful leg.

Figure 70:
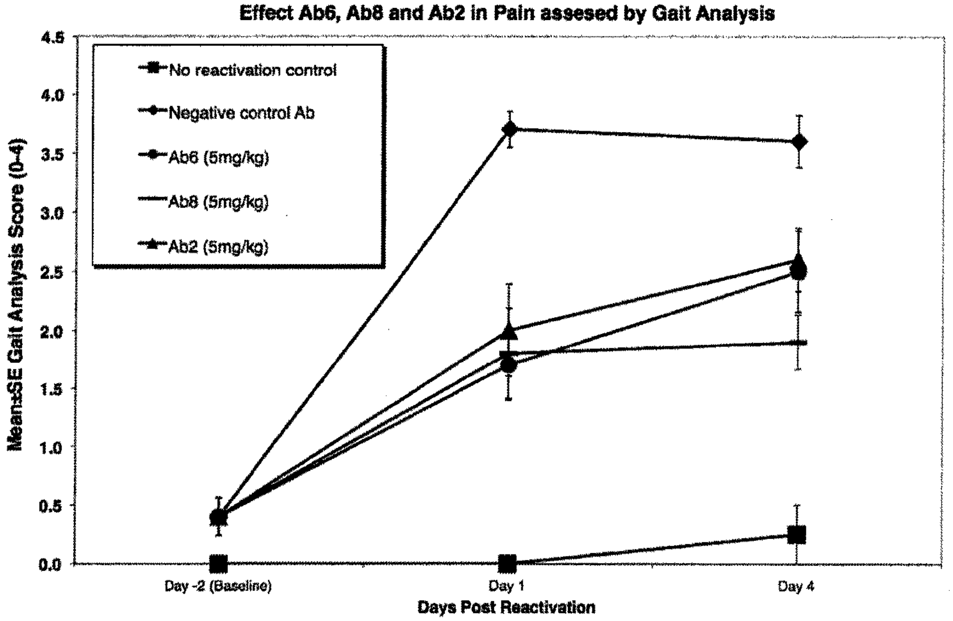
FIG. 70 demonstrates a statistically significant reduction in pain as assessed by Gait analysis following administration of antibodies Ab2, Ab6, and Ab8, when compared with results obtained with the controls following example 7.

Results: FIG. 70 demonstrates a statistically significant reduction in pain as assessed by Gait analysis following administration of antibodies Ab2, Ab6, and Ab8, when compared with results obtained with the controls.

Figure 71:
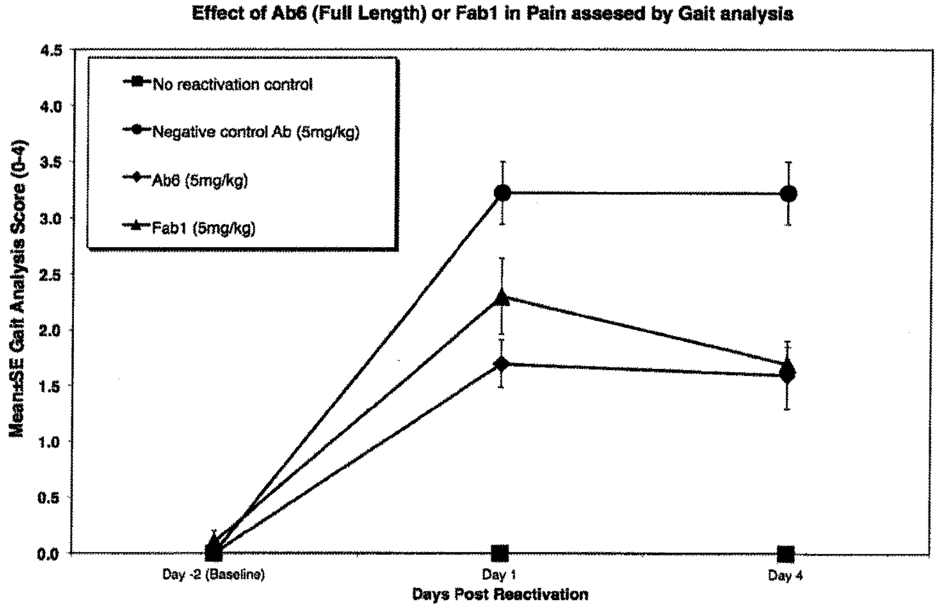
FIG. 71 demonstrates a statistically significant reduction in pain as assessed by Gait analysis following administration of antibody Ab6 and Fab1, when compared with results obtained with the controls following example 7.

FIG. 71 demonstrates a statistically significant reduction in pain as assessed by Gait analysis following administration of antibody Ab6 and Fab1, when compared with results obtained with the controls.

Figure 72:
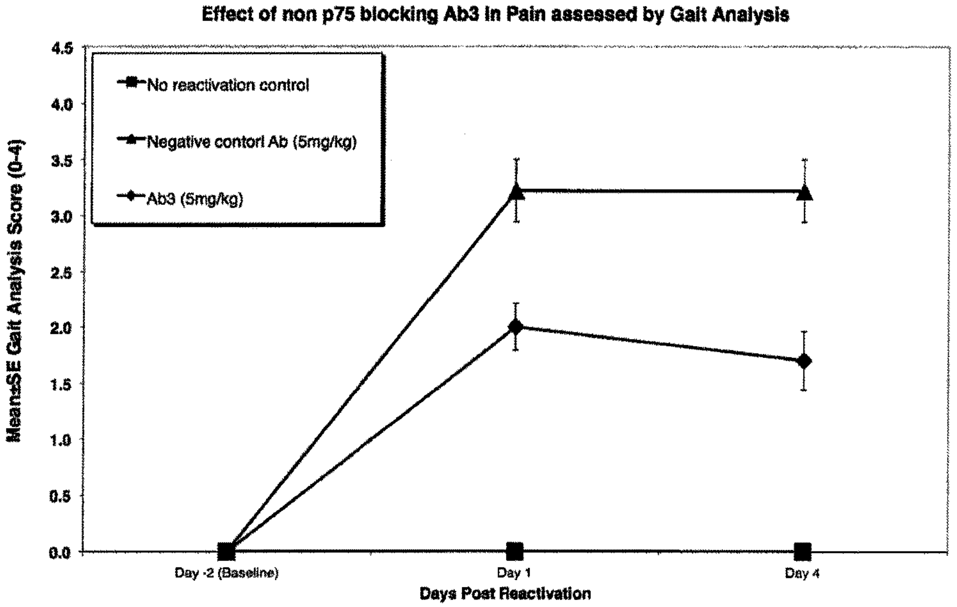
FIG. 72 demonstrates a statistically significant reduction in pain as assessed by Gait analysis following administration of antibody Ab3, when compared with results obtained with the controls following example 7.

FIG. 72 demonstrates a statistically significant reduction in pain as assessed by Gait analysis following administration of antibody Ab3, when compared with results obtained with the controls.

Figure 73:
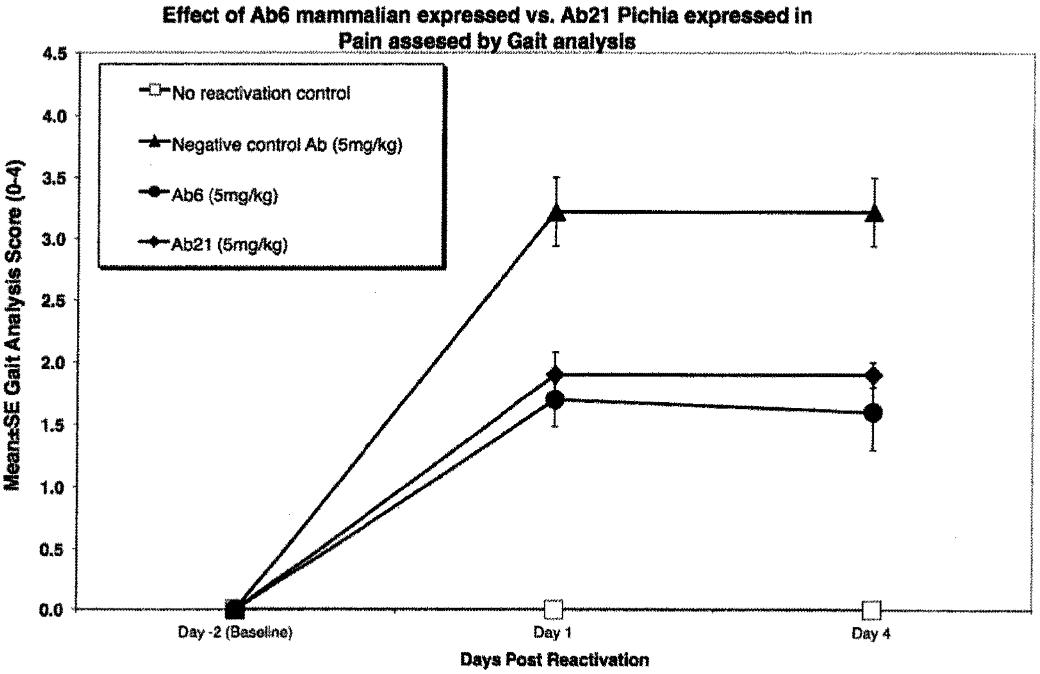
FIG. 73 demonstrates a statistically significant reduction in pain as assessed by Gait analysis following administration of antibody Ab6 and antibody Ab21, when compared with results obtained with the controls following example 7.

FIG. 73 demonstrates a statistically significant reduction in pain as assessed by Gait analysis following administration of antibody Ab6 and antibody Ab21, when compared with results obtained with the controls.

Example 8 Inflammation in PGPS-Induced Arthritis

The PGPS (peptidoglycan polysaccharide) induced arthritis model used to assess pain (Example 7) also has an associated inflammation response. To assess inflammation, all animals had caliper measurements taken of their ankles prior to reactivation on day 0, and then on days 1, 2, 3 and 4 to determine any anti-inflammatory or pro-inflammatory effects present in treated rats.

Figure 74:
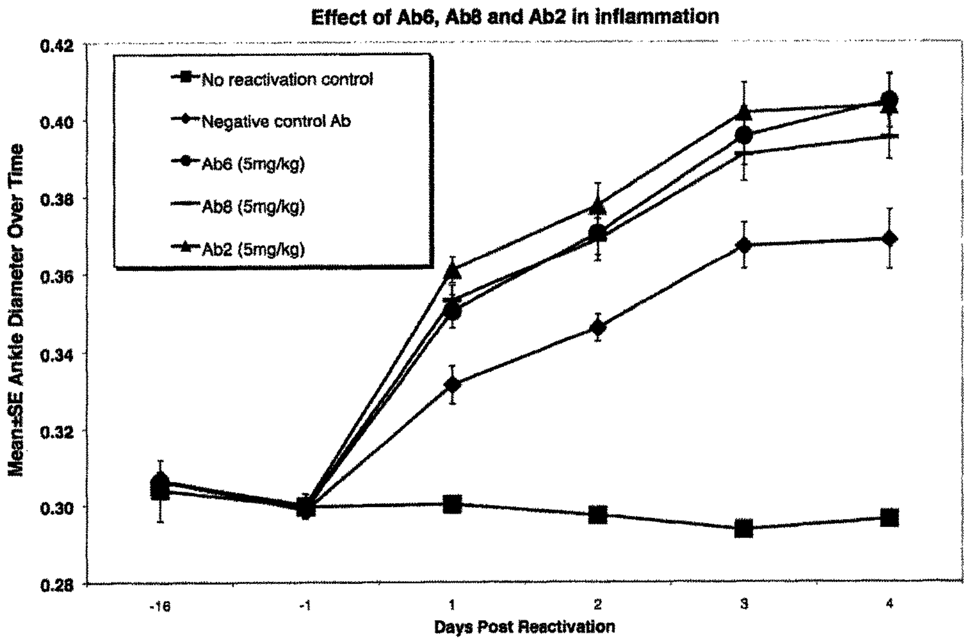
FIG. 74 demonstrates an increase in inflammation following administration of each of antibodies Ab2, Ab6, and Ab8, when compared with inflammation results for the controls following example 8.

Results: FIG. 74 demonstrates an increase in inflammation following administration of each of antibodies Ab2, Ab6, and Ab8, when compared with inflammation results for the controls.

Figure 75:
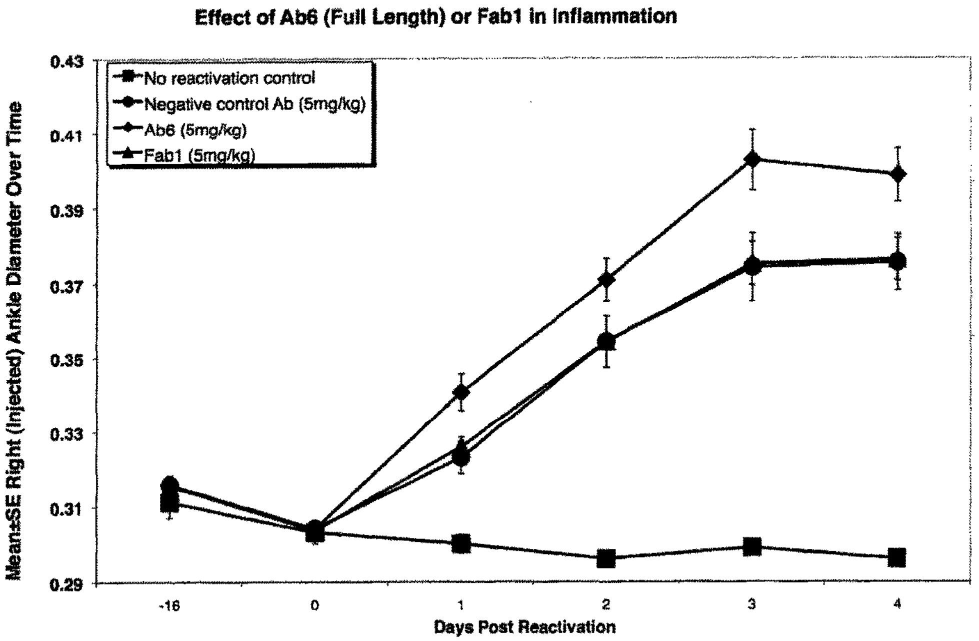
FIG. 75 demonstrates no significant increase in inflammation following administration of the Fab1 antibody fragment, when compared with inflammation results for the control. In contrast, administration of antibody Ab6 resulted in increased inflammation, when compared with inflammation results for the controls following example 8.

FIG. 75 demonstrates no significant increase in inflammation following administration of the Fab1 antibody fragment, when compared with inflammation results for the control. In contrast, administration of antibody Ab6 resulted in increased inflammation, when compared with inflammation results for the controls.

Figure 76:
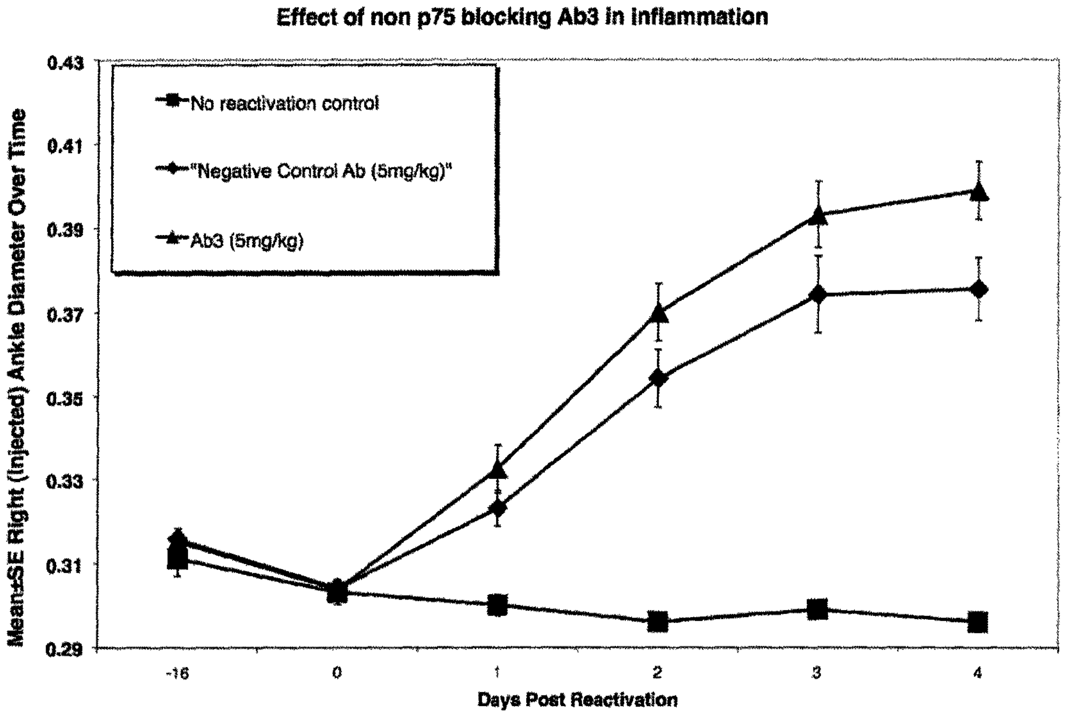
FIG. 76 demonstrates an increase in inflammation following administration of antibody Ab3, when compared with inflammation results for the controls following example 8.

FIG. 76 demonstrates an increase in inflammation following administration of antibody Ab3, when compared with inflammation results for the controls.

Figure 77:
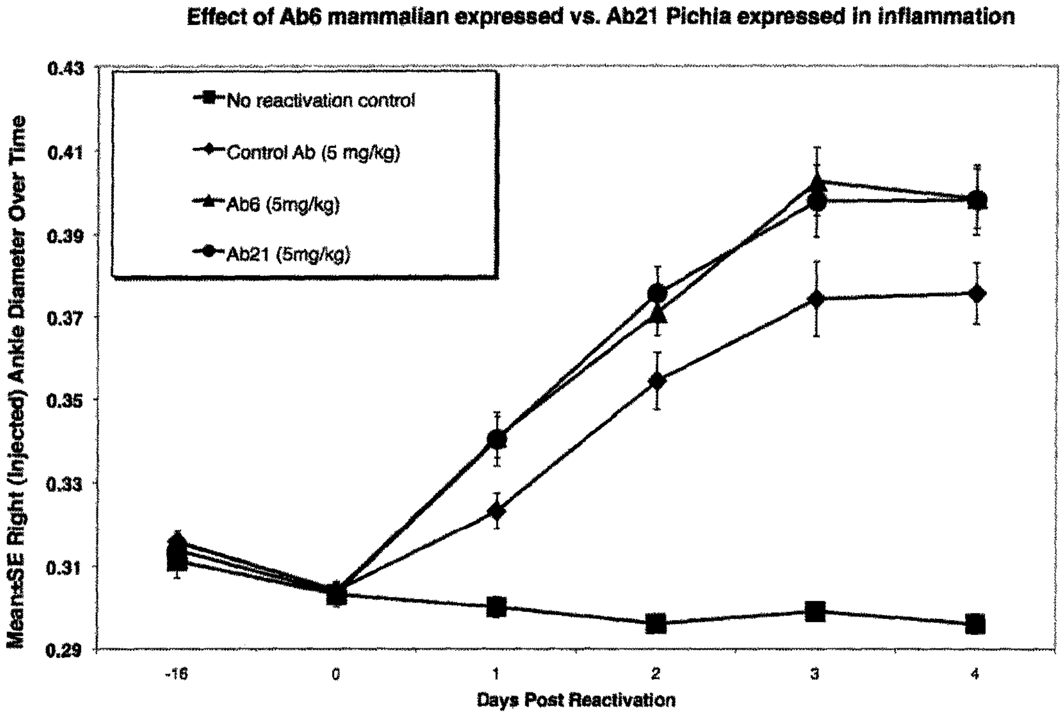
FIG. 77 also demonstrates an increase in inflammation following administration of antibody Ab6 and antibody Ab21, when compared with inflammation results for the controls following example 8.
Figure 78:
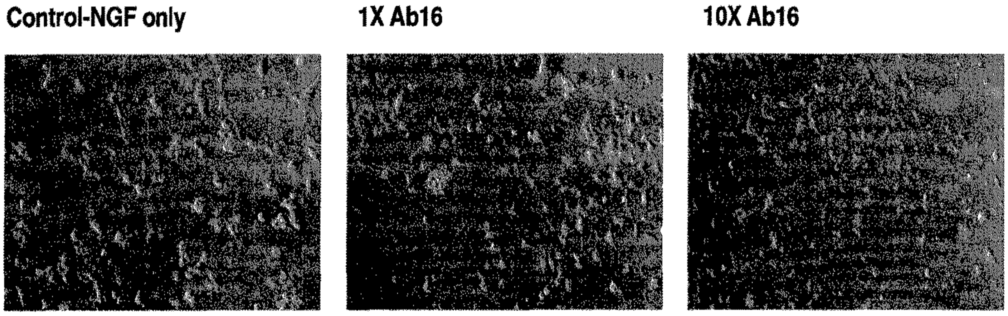
FIG. 78 demonstrates the inhibition of PC-12 neurite outgrowth in the presence of increasing concentrations of antibody Ab16 obtained following example 6. The results also demonstrate that the inhibition of PC-12 neurite outgrowth at the same concentrations of antibody is less than that seen with anti-NGF antibodies which exhibit different NGF binding selectivity.
Figure 79:
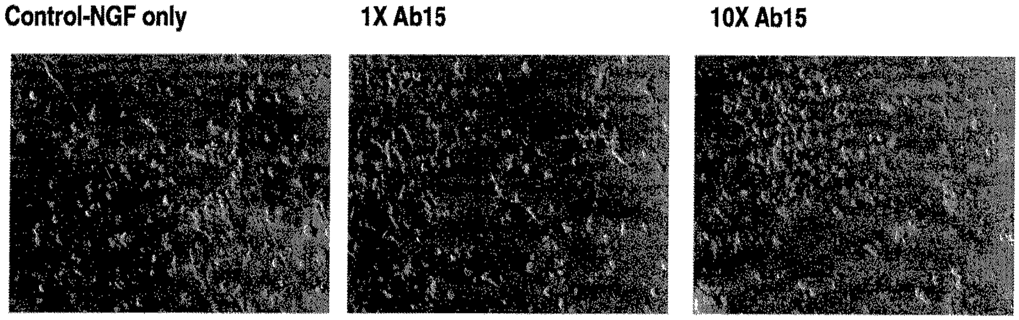
FIG. 79 demonstrates the inhibition of PC-12 neurite outgrowth in the presence of increasing concentrations of antibody Ab15 obtained following example 6. The results also demonstrate that the inhibition of PC-12 neurite outgrowth at the same concentrations of antibody is less than that seen with anti-NGF antibodies which exhibit different NGF binding selectivity.

FIG. 77 also demonstrates an increase in inflammation following administration of antibody Ab6 and antibody Ab21, when compared with inflammation results for the controls.

What is claimed is:

1. A method of treating pain in an individual, comprising administering a therapeutically effective amount of a humanized anti-human NGF monovalent antibody or antigen-binding fragment thereof comprising the CDR1 sequence of SEQ ID NO:55, the CDR2 sequence of SEQ ID NO:56, and the CDR3 sequence of SEQ ID NO:57, and a variable heavy chain comprising the CDR1 sequence of SEQ ID NO:58, the CDR2 sequence of SEQ ID NO:59, and the CDR3 sequence of SEQ ID NO:60.

2. The method of claim 1, wherein said monovalent antibody or antigen-binding fragment thereof is a Fab antibody fragment.

3. The method of claim 2, wherein the Fab antibody fragment is obtained by papain digestion of Ab21.

4. The method of claim 1, wherein said anti-human NGF antibody or antigen-binding fragment thereof comprises a $V_L$ polypeptide comprising the amino acid sequence of SEQ ID NO: 405 and a $V_H$ polypeptide comprising the amino acid sequence of SEQ ID NO:406.

5. The method of claim 1, wherein said anti-human NGF monovalent antibody or antigen-binding fragment thereof specifically binds to NGF expressing human cells and/or to circulating soluble NGF molecules in vivo.

6. The method of claim 1, wherein said anti-human NGF monovalent antibody or antigen-binding fragment thereof is directly or indirectly attached to a detectable label or therapeutic agent.

7. The method of claim 1, wherein said anti-human NGF monovalent antibody or antigen-binding fragment thereof further comprises an effector moiety.

8. The method of claim 7, wherein said effector moiety is a detectable moiety or a functional moiety.

9. The method of claim 8, wherein said detectable moiety is a fluorescent dye, an enzyme, a substrate, a bioluminescent material, a radioactive material, or a chemiluminescent material.

10. The method of claim 8, wherein said functional moiety is streptavidin, avidin, biotin, a cytotoxin, a cytotoxic agent, or a radioactive material.

11. The method of claim 1, further comprising the administration of another therapeutic agent or regimen selected from analgesic agents, anti-histamines, antiinflammatory agents or antibiotics.

12. The method of claim 1, wherein said anti-human NGF monovalent antibody or antigen-binding fragment thereof is contained in a pharmaceutical or diagnostic composition comprising a pharmaceutically acceptable carrier.

13. The method of claim 12, wherein said pharmaceutical or diagnostic composition further comprises at least one stabilizer.

14. The method of claim 12, wherein said pharmaceutical or diagnostic composition is lyophilized.

15. The method of claim 1, wherein the administration is effected via craniofacial mucosal administration, intranasal administration, buccal administration, sublingual administration or conjunctival administration.

16. The method of claim 1, wherein the anti-human NGF monovalent antibody or antigen-binding fragment thereof is modified in order to enhance in vivo half-life.

17. The method of claim 16, wherein said modification comprises the addition of at least one water-soluble polymer or alteration of glycosylation.

18. The method of claim 16, wherein the modification comprises the addition of at least one polyethylene glycol to the anti-human NGF monovalent antibody or antigen-binding fragment thereof.

19. The method of claim 1, wherein the anti-human NGF monovalent antibody or antigen-binding fragment thereof is administered subcutaneously, intravenously, intranasally, or transcutaneously.

* * * * *

SEQUENCE LISTING

<160> NUMBER OF SEQ ID NOS: 413

<210> SEQ ID NO 1
<211> LENGTH: 111
<212> TYPE: PRT

<213> ORGANISM: Oryctolagus cuniculus

<400> SEQUENCE: 1

```
Ala Leu Val Met Thr Gln Thr Pro Ser Ser Val Ser Ala Ala Val Gly
1               5                   10                  15

Gly Thr Val Thr Ile Asn Cys Gln Ala Ser Gln Asn Ile Tyr Ser Asn
            20                  25                  30

Leu Ala Trp Tyr Gln Gln Arg Pro Gly Gln Arg Pro Lys Leu Leu Ile
        35                  40                  45

Tyr Gly Ala Ser Asn Leu Asp Ala Gly Val Pro Ser Arg Phe Arg Gly
    50                  55                  60

Ser Gly Ser Gly Thr Glu Tyr Thr Leu Thr Ile Ser Asp Leu Glu Cys
65                  70                  75                  80

Asp Asp Val Gly Thr Tyr Tyr Cys Gln Ser Ala Phe Asp Ser Asp Ser
                85                  90                  95

Thr Glu Asn Thr Phe Gly Gly Gly Thr Glu Val Val Val Lys Arg
            100                 105                 110
```

<210> SEQ ID NO 2
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 2

```
Ala Leu Val Met Thr Gln Thr Pro Ser Ser Val Ser Ala Ala Val Gly
1               5                   10                  15

Gly Thr Val Thr Ile Asn Cys Gln Ala Ser Gln Asn Ile Tyr Ser Asn
            20                  25                  30

Leu Ala Trp Tyr Gln Gln Arg Pro Gly Gln Arg Pro Lys Leu Leu Ile
        35                  40                  45

Tyr Gly Ala Ser Asn Leu Asp Ala Gly Val Pro Ser Arg Phe Arg Gly
    50                  55                  60

Ser Gly Ser Gly Thr Glu Tyr Thr Leu Thr Ile Ser Asp Leu Glu Cys
65                  70                  75                  80

Asp Asp Val Gly Thr Tyr Tyr Cys Gln Ser Ala Phe Asp Ser Asp Ser
                85                  90                  95

Thr Glu Asn Thr Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 3

<211> LENGTH: 118
<212> TYPE: PRT
<213> ORGANISM: Oryctolagus cuniculus

<400> SEQUENCE: 3

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Val Ile Thr Ser Ile Gly Ser Thr Val Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Tyr
                85                  90                  95

Asp Asp Tyr Asp Glu Met Thr Tyr Phe Asn Ile Trp Gly Gln Gly Thr
            100                 105                 110

Leu Val Thr Val Ser Ser
        115
```

<210> SEQ ID NO 4
<211> LENGTH: 448
<212> TYPE: PRT
<213> ORGANISM: Artificial Sequence
<220> FEATURE:
<223> OTHER INFORMATION: Chemically Synthesized

<400> SEQUENCE: 4

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Val Ile Thr Ser Ile Gly Ser Thr Val Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Tyr
                85                  90                  95

Asp Asp Tyr Asp Glu Met Thr Tyr Phe Asn Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

-continued

```
Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 5
<211> LENGTH: 11
<212> TYPE: PRT
<213> ORGANISM: Oryctolagus cuniculus

<400> SEQUENCE: 5

Gln Ala Ser Gln Asn Ile Tyr Ser Asn Leu Ala
1               5                   10


<210> SEQ ID NO 6
<211> LENGTH: 7
<212> TYPE: PRT
<213> ORGANISM: Oryctolagus cuniculus

<400> SEQUENCE: 6

Gly Ala Ser Asn Leu Asp Ala
1               5


<210> SEQ ID NO 7
<211> LENGTH: 12
<212> TYPE: PRT
<213> ORGANISM: Oryctolagus cuniculus

<400> SEQUENCE: 7

Gln Ser Ala Phe Asp Ser Asp Ser Thr Glu Asn Thr
1               5                   10
```

<210> SEQ ID NO 8
<211> LENGTH: 5
<212> TYPE: PRT
<213> ORGANISM: Oryctolagus cuniculus

<400> SEQUENCE: 8

Ser Tyr Ala Met Ser
1               5

<210> SEQ ID NO 9
<211> LENGTH: 16
<212> TYPE: PRT
<213> ORGANISM: Oryctolagus cuniculus

<400> SEQUENCE: 9

Val Ile Thr Ser Ile Gly Ser Thr Val Tyr Ala Ser Trp Ala Lys Gly
1               5                   10                  15

<210> SEQ ID NO 10
<211> LENGTH: 13
<212> TYPE: PRT
<213> ORGANISM: Oryctolagus cuniculus

<400> SEQUENCE: 10

Gly Tyr Asp Asp Tyr Asp Glu Met Thr Tyr Phe Asn Ile
1               5                   10

<210> SEQ ID NO 11
<211> LENGTH: 111
<212> TYPE: PRT
<213> ORGANISM: Artificial Sequence
<220> FEATURE:
<223> OTHER INFORMATION: Chemically Synthesized

<400> SEQUENCE: 11

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Gly Ala Ser Asn Leu Asp Ala Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Ser Ala Phe Asp Ser Asp Ser
                85                  90                  95

Thr Glu Asn Thr Phe Gly Gly Gly Thr Lys Val Glu Ile Lys Arg
            100                 105                 110

<210> SEQ ID NO 12
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 12

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Asn Ile Tyr Ser Asn
            20                  25                  30

-continued

```
Leu Ala Trp Tyr Gln Gln Lys Pro Gly Lys Ala Pro Lys Leu Leu Ile
        35                  40                  45

Tyr Gly Ala Ser Asn Leu Asp Ala Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Ser Ala Phe Asp Ser Asp Ser
                85                  90                  95

Thr Glu Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 13
<211> LENGTH: 121
<212> TYPE: PRT
<213> ORGANISM: Artificial Sequence
<220> FEATURE:
<223> OTHER INFORMATION: Chemically Synthesized

<400> SEQUENCE: 13

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Ala Met Ser Trp Val Arg Gln Ala Pro Gly Lys Gly Leu Glu Trp Val
        35                  40                  45

Gly Val Ile Thr Ser Ile Gly Ser Thr Val Tyr Ala Ser Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Asp Asp Tyr Asp Glu Met Thr Tyr Phe Asn Ile Trp Gly
            100                 105                 110

Gln Gly Thr Leu Val Thr Val Ser Ser
        115                 120
```

<210> SEQ ID NO 14
<211> LENGTH: 451
<212> TYPE: PRT
<213> ORGANISM: Artificial Sequence
<220> FEATURE:
<223> OTHER INFORMATION: Chemically Synthesized

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Ala Met Ser Trp Val Arg Gln Ala Pro Gly Lys Gly Leu Glu Trp Val
        35                  40                  45

Gly Val Ile Thr Ser Ile Gly Ser Thr Val Tyr Ala Ser Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Asp Asp Tyr Asp Glu Met Thr Tyr Phe Asn Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

-continued

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 15
<211> LENGTH: 11
<212> TYPE: PRT
<213> ORGANISM: Oryctolagus cuniculus

<400> SEQUENCE: 15

Gln Ala Ser Gln Asn Ile Tyr Ser Asn Leu Ala
1               5                   10


<210> SEQ ID NO 16
<211> LENGTH: 7
<212> TYPE: PRT
<213> ORGANISM: Oryctolagus cuniculus

<400> SEQUENCE: 16

Gly Ala Ser Asn Leu Asp Ala
1               5


<210> SEQ ID NO 17
<211> LENGTH: 12
<212> TYPE: PRT
<213> ORGANISM: Oryctolagus cuniculus

<400> SEQUENCE: 17

Gln Ser Ala Phe Asp Ser Asp Ser Thr Glu Asn Thr
1               5                   10


<210> SEQ ID NO 18
<211> LENGTH: 5
<212> TYPE: PRT
<213> ORGANISM: Oryctolagus cuniculus

<400> SEQUENCE: 18

Ser Tyr Ala Met Ser
1               5


<210> SEQ ID NO 19
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 19

Val Ile Thr Ser Ile Gly Ser Thr Val Tyr Ala Ser Ser Ala Lys Gly
1               5                   10                  15


<210> SEQ ID NO 20
<211> LENGTH: 13
<212> TYPE: PRT
<213> ORGANISM: Oryctolagus cuniculus

<400> SEQUENCE: 20

Gly Tyr Asp Asp Tyr Asp Glu Met Thr Tyr Phe Asn Ile
1               5                   10


<210> SEQ ID NO 21
```

```
<211> LENGTH: 111
<212> TYPE: PRT
<213> ORGANISM: Oryctolagus cuniculus

<400> SEQUENCE: 21

Ala Val Leu Thr Gln Thr Pro Ser Pro Val Ser Ala Ala Met Gly Asp
1               5                   10                  15

Thr Val Thr Ile Lys Cys Gln Ser Ser Gln Ser Val Tyr Lys Asn Asn
            20                  25                  30

Tyr Leu Ser Trp Tyr Gln Gln Lys Pro Gly Gln Pro Pro Arg Leu Leu
        35                  40                  45

Ile Tyr Asp Ala Ser Asn Leu Pro Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Leu Gly Asp Tyr Asp Asp Asp
                85                  90                  95

Ala Asp Asn Ala Phe Gly Gly Gly Thr Glu Val Val Val Lys Arg
            100                 105                 110


<210> SEQ ID NO 22
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 22

Ala Val Leu Thr Gln Thr Pro Ser Pro Val Ser Ala Ala Met Gly Asp
1               5                   10                  15

Thr Val Thr Ile Lys Cys Gln Ser Ser Gln Ser Val Tyr Lys Asn Asn
            20                  25                  30

Tyr Leu Ser Trp Tyr Gln Gln Lys Pro Gly Gln Pro Pro Arg Leu Leu
        35                  40                  45

Ile Tyr Asp Ala Ser Asn Leu Pro Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Leu Gly Asp Tyr Asp Asp Asp
                85                  90                  95

Ala Asp Asn Ala Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 23
<211> LENGTH: 113
<212> TYPE: PRT
<213> ORGANISM: Oryctolagus cuniculus

<400> SEQUENCE: 23

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Val
            20                  25                  30

Met Ile Trp Val Arg Gln Ala Pro Gly Lys Gly Leu Glu Tyr Ile Gly
        35                  40                  45

Ile Thr Trp Ser Ala Gly Thr Tyr Tyr Ala Ser Trp Ala Lys Gly Arg
    50                  55                  60

Phe Thr Ile Ser Lys Thr Ser Ser Thr Thr Val Asp Leu Lys Ile Thr
65                  70                  75                  80

Ser Pro Thr Thr Glu Asp Thr Ala Thr Tyr Phe Cys Ala Gly Gly Gly
                85                  90                  95

Gly Ser Ile Tyr Asp Ile Trp Gly Pro Gly Thr Leu Val Thr Val Ser
            100                 105                 110

Ser
```

<210> SEQ ID NO 24
<211> LENGTH: 443
<212> TYPE: PRT
<213> ORGANISM: Artificial Sequence
<220> FEATURE:
<223> OTHER INFORMATION: Chemically Synthesized

<400> SEQUENCE: 24

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Val
            20                  25                  30

Met Ile Trp Val Arg Gln Ala Pro Gly Lys Gly Leu Glu Tyr Ile Gly
        35                  40                  45

Ile Thr Trp Ser Ala Gly Thr Tyr Tyr Ala Ser Trp Ala Lys Gly Arg
    50                  55                  60

Phe Thr Ile Ser Lys Thr Ser Ser Thr Thr Val Asp Leu Lys Ile Thr
65                  70                  75                  80

Ser Pro Thr Thr Glu Asp Thr Ala Thr Tyr Phe Cys Ala Gly Gly Gly
                85                  90                  95

Gly Ser Ile Tyr Asp Ile Trp Gly Pro Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205
```

Lys Arg Val Glu Pro Lys Ser Cys Asp Lys Thr His Thr Cys Pro Pro
210 215 220

Cys Pro Ala Pro Glu Leu Leu Gly Gly Pro Ser Val Phe Leu Phe Pro
225 230 235 240

Pro Lys Pro Lys Asp Thr Leu Met Ile Ser Arg Thr Pro Glu Val Thr
245 250 255

Cys Val Val Val Asp Val Ser His Glu Asp Pro Glu Val Lys Phe Asn
260 265 270

Trp Tyr Val Asp Gly Val Glu Val His Asn Ala Lys Thr Lys Pro Arg
275 280 285

Glu Glu Gln Tyr Ala Ser Thr Tyr Arg Val Val Ser Val Leu Thr Val
290 295 300

Leu His Gln Asp Trp Leu Asn Gly Lys Glu Tyr Lys Cys Lys Val Ser
305 310 315 320

Asn Lys Ala Leu Pro Ala Pro Ile Glu Lys Thr Ile Ser Lys Ala Lys
325 330 335

Gly Gln Pro Arg Glu Pro Gln Val Tyr Thr Leu Pro Pro Ser Arg Glu
340 345 350

Glu Met Thr Lys Asn Gln Val Ser Leu Thr Cys Leu Val Lys Gly Phe
355 360 365

Tyr Pro Ser Asp Ile Ala Val Glu Trp Glu Ser Asn Gly Gln Pro Glu
370 375 380

Asn Asn Tyr Lys Thr Thr Pro Pro Val Leu Asp Ser Asp Gly Ser Phe
385 390 395 400

Phe Leu Tyr Ser Lys Leu Thr Val Asp Lys Ser Arg Trp Gln Gln Gly
405 410 415

Asn Val Phe Ser Cys Ser Val Met His Glu Ala Leu His Asn His Tyr
420 425 430

Thr Gln Lys Ser Leu Ser Leu Ser Pro Gly Lys
435 440

<210> SEQ ID NO 25
<211> LENGTH: 13
<212> TYPE: PRT
<213> ORGANISM: Oryctolagus cuniculus

<400> SEQUENCE: 25

Gln Ser Ser Gln Ser Val Tyr Lys Asn Asn Tyr Leu Ser
1 5 10

<210> SEQ ID NO 26
<211> LENGTH: 7
<212> TYPE: PRT
<213> ORGANISM: Oryctolagus cuniculus

<400> SEQUENCE: 26

Asp Ala Ser Asn Leu Pro Ser
1 5

<210> SEQ ID NO 27
<211> LENGTH: 11
<212> TYPE: PRT
<213> ORGANISM: Oryctolagus cuniculus

<400> SEQUENCE: 27

Leu Gly Asp Tyr Asp Asp Asp Ala Asp Asn Ala
1 5 10

<210> SEQ ID NO 28
<211> LENGTH: 5
<212> TYPE: PRT
<213> ORGANISM: Oryctolagus cuniculus

<400> SEQUENCE: 28

Ser Tyr Val Met Ile
1 5

<210> SEQ ID NO 29
<211> LENGTH: 15
<212> TYPE: PRT
<213> ORGANISM: Oryctolagus cuniculus

<400> SEQUENCE: 29

Ile Thr Trp Ser Ala Gly Thr Tyr Tyr Ala Ser Trp Ala Lys Gly
1 5 10 15

<210> SEQ ID NO 30
<211> LENGTH: 8
<212> TYPE: PRT
<213> ORGANISM: Oryctolagus cuniculus

<400> SEQUENCE: 30

Gly Gly Gly Ser Ile Tyr Asp Ile
1 5

<210> SEQ ID NO 31
<211> LENGTH: 112
<212> TYPE: PRT
<213> ORGANISM: Artificial Sequence
<220> FEATURE:
<223> OTHER INFORMATION: Chemically Synthesized

<400> SEQUENCE: 31

Asp Ile Gln Met Thr Gln Ser Pro Ser Thr Leu Ser Ala Ser Val Gly
1 5 10 15

Asp Arg Val Thr Ile Thr Cys Gln Ser Ser Gln Ser Val Tyr Lys Asn
20 25 30

Asn Tyr Leu Ser Trp Tyr Gln Gln Lys Pro Gly Lys Ala Pro Lys Leu
35 40 45

Leu Ile Tyr Asp Ala Ser Asn Leu Pro Ser Gly Val Pro Ser Arg Phe
50 55 60

Ser Gly Ser Gly Ser Gly Thr Glu Phe Thr Leu Thr Ile Ser Ser Leu
65 70 75 80

Gln Pro Asp Asp Phe Ala Thr Tyr Tyr Cys Leu Gly Asp Tyr Asp Asp
85 90 95

Asp Ala Asp Asn Ala Phe Gly Gly Gly Thr Lys Val Glu Ile Lys Arg
100 105 110

<210> SEQ ID NO 32
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 32

Asp Ile Gln Met Thr Gln Ser Pro Ser Thr Leu Ser Ala Ser Val Gly
1 5 10 15

Asp Arg Val Thr Ile Thr Cys Gln Ser Ser Gln Ser Val Tyr Lys Asn
20 25 30

```
Asn Tyr Leu Ser Trp Tyr Gln Gln Lys Pro Gly Lys Ala Pro Lys Leu
        35                  40                  45

Leu Ile Tyr Asp Ala Ser Asn Leu Pro Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Leu Gly Asp Tyr Asp Asp
                85                  90                  95

Asp Ala Asp Asn Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 33
<211> LENGTH: 115
<212> TYPE: PRT
<213> ORGANISM: Artificial Sequence
<220> FEATURE:
<223> OTHER INFORMATION: Chemically Synthesized

<400> SEQUENCE: 33

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Val Met Ile Trp Val Arg Gln Ala Pro Gly Lys Gly Leu Glu Tyr Ile
        35                  40                  45

Gly Ile Thr Trp Ser Ala Gly Thr Tyr Tyr Ala Ser Ser Ala Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Gly
                85                  90                  95

Gly Gly Gly Ser Ile Tyr Asp Ile Trp Gly Gln Gly Thr Leu Val Thr
            100                 105                 110

Val Ser Ser
        115
```

<210> SEQ ID NO 34
<211> LENGTH: 445
<212> TYPE: PRT
<213> ORGANISM: Artificial Sequence
<220> FEATURE:
<223> OTHER INFORMATION: Chemically Synthesized

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Val Met Ile Trp Val Arg Gln Ala Pro Gly Lys Gly Leu Glu Tyr Ile
        35                  40                  45

Gly Ile Thr Trp Ser Ala Gly Thr Tyr Tyr Ala Ser Ser Ala Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Gly
                85                  90                  95

Gly Gly Gly Ser Ile Tyr Asp Ile Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Ala Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415
```

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 35
<211> LENGTH: 13
<212> TYPE: PRT
<213> ORGANISM: Oryctolagus cuniculus

<400> SEQUENCE: 35

Gln Ser Ser Gln Ser Val Tyr Lys Asn Asn Tyr Leu Ser
1 5 10

<210> SEQ ID NO 36
<211> LENGTH: 7
<212> TYPE: PRT
<213> ORGANISM: Oryctolagus cuniculus

<400> SEQUENCE: 36

Asp Ala Ser Asn Leu Pro Ser
1 5

<210> SEQ ID NO 37
<211> LENGTH: 11
<212> TYPE: PRT
<213> ORGANISM: Oryctolagus cuniculus

<400> SEQUENCE: 37

Leu Gly Asp Tyr Asp Asp Asp Ala Asp Asn Ala
1 5 10

<210> SEQ ID NO 38
<211> LENGTH: 5
<212> TYPE: PRT
<213> ORGANISM: Oryctolagus cuniculus

<400> SEQUENCE: 38

Ser Tyr Val Met Ile
1 5

<210> SEQ ID NO 39
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 39

Ile Thr Trp Ser Ala Gly Thr Tyr Tyr Ala Ser Ser Ala Lys Gly
1 5 10 15

<210> SEQ ID NO 40
<211> LENGTH: 8
<212> TYPE: PRT
<213> ORGANISM: Oryctolagus cuniculus

<400> SEQUENCE: 40

Gly Gly Gly Ser Ile Tyr Asp Ile
1 5

<210> SEQ ID NO 41
<211> LENGTH: 111
<212> TYPE: PRT

-continued

<213> ORGANISM: Oryctolagus cuniculus

<400> SEQUENCE: 41

```
Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Tyr Ser Asn
            20                  25                  30

Leu Ala Trp Tyr Gln Gln Arg Pro Gly Gln Pro Pro Lys Leu Leu Ile
        35                  40                  45

Tyr Asp Ala Ser Thr Leu Glu Ser Gly Val Pro Ser Arg Phe Lys Gly
    50                  55                  60

Ser Gly Ser Gly Thr Glu Tyr Thr Leu Thr Ile Ser Gly Val Glu Cys
65                  70                  75                  80

Ala Asp Ala Ala Ser Tyr Tyr Cys Gln Gln Gly Phe Thr Val Ser Asp
                85                  90                  95

Ile Asp Asn Ala Phe Gly Gly Gly Thr Glu Val Val Val Lys Arg
            100                 105                 110
```

<210> SEQ ID NO 42
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 42

```
Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Tyr Ser Asn
            20                  25                  30

Leu Ala Trp Tyr Gln Gln Arg Pro Gly Gln Pro Pro Lys Leu Leu Ile
        35                  40                  45

Tyr Asp Ala Ser Thr Leu Glu Ser Gly Val Pro Ser Arg Phe Lys Gly
    50                  55                  60

Ser Gly Ser Gly Thr Glu Tyr Thr Leu Thr Ile Ser Gly Val Glu Cys
65                  70                  75                  80

Ala Asp Ala Ala Ser Tyr Tyr Cys Gln Gln Gly Phe Thr Val Ser Asp
                85                  90                  95

Ile Asp Asn Ala Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 43

-continued

```
<211> LENGTH: 118
<212> TYPE: PRT
<213> ORGANISM: Oryctolagus cuniculus

<400> SEQUENCE: 43

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30

Val Gly Trp Val Arg Gln Ala Pro Gly Lys Gly Leu Glu Trp Ile Gly
        35                  40                  45

Ile Ile Gly Arg Asn Gly Asn Thr Trp Tyr Ala Ser Trp Ala Arg Gly
    50                  55                  60

Arg Phe Thr Ile Ser Lys Thr Ser Thr Thr Val Asp Leu Lys Ile Thr
65                  70                  75                  80

Ser Pro Thr Ser Glu Asp Thr Ala Thr Tyr Phe Cys Ala Arg Gly Tyr
                85                  90                  95

Gly Arg Ser Val Ala Tyr Tyr Val Phe Asn Ile Trp Gly Pro Gly Thr
            100                 105                 110

Leu Val Thr Val Ser Ser
        115


<210> SEQ ID NO 44
<211> LENGTH: 448
<212> TYPE: PRT
<213> ORGANISM: Artificial Sequence
<220> FEATURE:
<223> OTHER INFORMATION: Chemically Synthesized

<400> SEQUENCE: 44

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30

Val Gly Trp Val Arg Gln Ala Pro Gly Lys Gly Leu Glu Trp Ile Gly
        35                  40                  45

Ile Ile Gly Arg Asn Gly Asn Thr Trp Tyr Ala Ser Trp Ala Arg Gly
    50                  55                  60

Arg Phe Thr Ile Ser Lys Thr Ser Thr Thr Val Asp Leu Lys Ile Thr
65                  70                  75                  80

Ser Pro Thr Ser Glu Asp Thr Ala Thr Tyr Phe Cys Ala Arg Gly Tyr
                85                  90                  95

Gly Arg Ser Val Ala Tyr Tyr Val Phe Asn Ile Trp Gly Pro Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

-continued

```
Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 45
<211> LENGTH: 11
<212> TYPE: PRT
<213> ORGANISM: Oryctolagus cuniculus

<400> SEQUENCE: 45

Gln Ala Ser Gln Ser Ile Tyr Ser Asn Leu Ala
1               5                   10


<210> SEQ ID NO 46
<211> LENGTH: 7
<212> TYPE: PRT
<213> ORGANISM: Oryctolagus cuniculus

<400> SEQUENCE: 46

Asp Ala Ser Thr Leu Glu Ser
1               5


<210> SEQ ID NO 47
<211> LENGTH: 12
<212> TYPE: PRT
<213> ORGANISM: Oryctolagus cuniculus

<400> SEQUENCE: 47

Gln Gln Gly Phe Thr Val Ser Asp Ile Asp Asn Ala
1               5                   10
```

<210> SEQ ID NO 48
<211> LENGTH: 5
<212> TYPE: PRT
<213> ORGANISM: Oryctolagus cuniculus

<400> SEQUENCE: 48

```
Asn Tyr Ala Val Gly
1               5
```

<210> SEQ ID NO 49
<211> LENGTH: 16
<212> TYPE: PRT
<213> ORGANISM: Oryctolagus cuniculus

<400> SEQUENCE: 49

```
Ile Ile Gly Arg Asn Gly Asn Thr Trp Tyr Ala Ser Trp Ala Arg Gly
1               5                   10                  15
```

<210> SEQ ID NO 50
<211> LENGTH: 13
<212> TYPE: PRT
<213> ORGANISM: Oryctolagus cuniculus

<400> SEQUENCE: 50

```
Gly Tyr Gly Arg Ser Val Ala Tyr Tyr Val Phe Asn Ile
1               5                   10
```

<210> SEQ ID NO 51
<211> LENGTH: 111
<212> TYPE: PRT
<213> ORGANISM: Artificial Sequence
<220> FEATURE:
<223> OTHER INFORMATION: Chemically Synthesized

<400> SEQUENCE: 51

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Gly Phe Thr Val Ser Asp
                85                  90                  95

Ile Asp Asn Ala Phe Gly Gly Gly Thr Lys Val Glu Ile Lys Arg
            100                 105                 110
```

<210> SEQ ID NO 52
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 52

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Tyr Ser Asn
            20                  25                  30
```

```
Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Gly Phe Thr Val Ser Asp
                85                  90                  95

Ile Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 53
<211> LENGTH: 121
<212> TYPE: PRT
<213> ORGANISM: Artificial Sequence
<220> FEATURE:
<223> OTHER INFORMATION: Chemically Synthesized

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Ala Val Gly Trp Val Arg Gln Ala Pro Gly Lys Gly Leu Glu Trp Val
        35                  40                  45

Gly Ile Ile Gly Arg Asn Gly Asn Thr Trp Tyr Ala Ser Ser Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Gly Arg Ser Val Ala Tyr Tyr Val Phe Asn Ile Trp Gly
            100                 105                 110

Pro Gly Thr Leu Val Thr Val Ser Ser
        115                 120


<210> SEQ ID NO 54
<211> LENGTH: 451
<212> TYPE: PRT
<213> ORGANISM: Artificial Sequence
<220> FEATURE:
<223> OTHER INFORMATION: Chemically Synthesized

<400> SEQUENCE: 54
```

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Ala Val Gly Trp Val Arg Gln Ala Pro Gly Lys Gly Leu Glu Trp Val
        35                  40                  45

Gly Ile Ile Gly Arg Asn Gly Asn Thr Trp Tyr Ala Ser Ser Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Gly Arg Ser Val Ala Tyr Tyr Val Phe Asn Ile Trp Gly
            100                 105                 110

Pro Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 55
<211> LENGTH: 11
<212> TYPE: PRT
<213> ORGANISM: Oryctolagus cuniculus

<400> SEQUENCE: 55

Gln Ala Ser Gln Ser Ile Tyr Ser Asn Leu Ala
1               5                   10


<210> SEQ ID NO 56
<211> LENGTH: 7
<212> TYPE: PRT
<213> ORGANISM: Oryctolagus cuniculus

<400> SEQUENCE: 56

Asp Ala Ser Thr Leu Glu Ser
1               5


<210> SEQ ID NO 57
<211> LENGTH: 12
<212> TYPE: PRT
<213> ORGANISM: Oryctolagus cuniculus

<400> SEQUENCE: 57

Gln Gln Gly Phe Thr Val Ser Asp Ile Asp Asn Ala
1               5                   10


<210> SEQ ID NO 58
<211> LENGTH: 5
<212> TYPE: PRT
<213> ORGANISM: Oryctolagus cuniculus

<400> SEQUENCE: 58

Asn Tyr Ala Val Gly
1               5


<210> SEQ ID NO 59
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 59

Ile Ile Gly Arg Asn Gly Asn Thr Trp Tyr Ala Ser Ser Ala Arg Gly
1               5                   10                  15


<210> SEQ ID NO 60
<211> LENGTH: 13
<212> TYPE: PRT
<213> ORGANISM: Oryctolagus cuniculus

<400> SEQUENCE: 60

Gly Tyr Gly Arg Ser Val Ala Tyr Tyr Val Phe Asn Ile
1               5                   10


<210> SEQ ID NO 61
```

<211> LENGTH: 112
<212> TYPE: PRT
<213> ORGANISM: Oryctolagus cuniculus

<400> SEQUENCE: 61

Ala Asp Val Val Met Thr Gln Thr Pro Ala Ser Val Ser Gln Pro Val
1               5                   10                  15

Gly Gly Thr Val Thr Ile Lys Cys Gln Ala Ser Glu Asp Ile Tyr Asn
            20                  25                  30

Leu Leu Ala Trp Tyr Gln Gln Lys Pro Gly Gln Pro Pro Lys Leu Leu
        35                  40                  45

Ile Tyr Ser Ala Ser Thr Leu Ala Ser Gly Val Pro Ser Arg Phe Lys
    50                  55                  60

Gly Ser Gly Ser Gly Thr Glu Tyr Thr Leu Thr Ile Ser Gly Leu Glu
65                  70                  75                  80

Cys Ala Asp Ala Ala Thr Tyr Tyr Cys Gln Asn Asn Tyr Leu Val Thr
                85                  90                  95

Thr Tyr Gly Val Ala Phe Gly Gly Gly Thr Glu Val Val Val Lys Arg
            100                 105                 110

<210> SEQ ID NO 62
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 62

Ala Asp Val Val Met Thr Gln Thr Pro Ala Ser Val Ser Gln Pro Val
1               5                   10                  15

Gly Gly Thr Val Thr Ile Lys Cys Gln Ala Ser Glu Asp Ile Tyr Asn
            20                  25                  30

Leu Leu Ala Trp Tyr Gln Gln Lys Pro Gly Gln Pro Pro Lys Leu Leu
        35                  40                  45

Ile Tyr Ser Ala Ser Thr Leu Ala Ser Gly Val Pro Ser Arg Phe Lys
    50                  55                  60

Gly Ser Gly Ser Gly Thr Glu Tyr Thr Leu Thr Ile Ser Gly Leu Glu
65                  70                  75                  80

Cys Ala Asp Ala Ala Thr Tyr Tyr Cys Gln Asn Asn Tyr Leu Val Thr
                85                  90                  95

Thr Tyr Gly Val Ala Phe Gly Gly Gly Thr Glu Val Val Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 63
<211> LENGTH: 120
<212> TYPE: PRT
<213> ORGANISM: Oryctolagus cuniculus

<400> SEQUENCE: 63

```
Gln Glu Gln Leu Lys Glu Ser Gly Gly Arg Leu Val Thr Pro Gly Thr
1               5                   10                  15

Pro Leu Thr Leu Thr Cys Thr Val Ser Gly Phe Ser Leu Ser Ser Tyr
            20                  25                  30

Ala Met Ile Trp Val Arg Gln Ala Pro Gly Lys Gly Leu Glu Tyr Ile
        35                  40                  45

Gly Tyr Ile Asp Thr Asp Thr Ser Ala Tyr Tyr Ala Ser Trp Val Lys
    50                  55                  60

Gly Arg Phe Thr Ile Ser Arg Thr Ser Thr Thr Val Asp Leu Lys Ile
65                  70                  75                  80

Thr Ser Pro Thr Thr Glu Asp Thr Ala Thr Tyr Phe Cys Ala Arg Ser
                85                  90                  95

Tyr Ala Ala Tyr Gly Gly Tyr Pro Ala Thr Phe Asp Pro Trp Gly Pro
            100                 105                 110

Gly Thr Leu Val Thr Val Ser Ser
        115                 120
```

<210> SEQ ID NO 64
<211> LENGTH: 450
<212> TYPE: PRT
<213> ORGANISM: Artificial Sequence
<220> FEATURE:
<223> OTHER INFORMATION: Chemically Synthesized

<400> SEQUENCE: 64

```
Gln Glu Gln Leu Lys Glu Ser Gly Gly Arg Leu Val Thr Pro Gly Thr
1               5                   10                  15

Pro Leu Thr Leu Thr Cys Thr Val Ser Gly Phe Ser Leu Ser Ser Tyr
            20                  25                  30

Ala Met Ile Trp Val Arg Gln Ala Pro Gly Lys Gly Leu Glu Tyr Ile
        35                  40                  45

Gly Tyr Ile Asp Thr Asp Thr Ser Ala Tyr Tyr Ala Ser Trp Val Lys
    50                  55                  60

Gly Arg Phe Thr Ile Ser Arg Thr Ser Thr Thr Val Asp Leu Lys Ile
65                  70                  75                  80

Thr Ser Pro Thr Thr Glu Asp Thr Ala Thr Tyr Phe Cys Ala Arg Ser
                85                  90                  95

Tyr Ala Ala Tyr Gly Gly Tyr Pro Ala Thr Phe Asp Pro Trp Gly Pro
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

```
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 65
<211> LENGTH: 11
<212> TYPE: PRT
<213> ORGANISM: Oryctolagus cuniculus

<400> SEQUENCE: 65

Gln Ala Ser Glu Asp Ile Tyr Asn Leu Leu Ala
1               5                   10


<210> SEQ ID NO 66
<211> LENGTH: 7
<212> TYPE: PRT
<213> ORGANISM: Oryctolagus cuniculus

<400> SEQUENCE: 66

Ser Ala Ser Thr Leu Ala Ser
1               5


<210> SEQ ID NO 67
<211> LENGTH: 12
<212> TYPE: PRT
<213> ORGANISM: Oryctolagus cuniculus

<400> SEQUENCE: 67
```

Gln Asn Asn Tyr Leu Val Thr Thr Tyr Gly Val Ala
1 5 10

<210> SEQ ID NO 68
<211> LENGTH: 5
<212> TYPE: PRT
<213> ORGANISM: Oryctolagus cuniculus

<400> SEQUENCE: 68

Ser Tyr Ala Met Ile
1 5

<210> SEQ ID NO 69
<211> LENGTH: 16
<212> TYPE: PRT
<213> ORGANISM: Oryctolagus cuniculus

<400> SEQUENCE: 69

Tyr Ile Asp Thr Asp Thr Ser Ala Tyr Tyr Ala Ser Trp Val Lys Gly
1 5 10 15

<210> SEQ ID NO 70
<211> LENGTH: 14
<212> TYPE: PRT
<213> ORGANISM: Oryctolagus cuniculus

<400> SEQUENCE: 70

Ser Tyr Ala Ala Tyr Gly Gly Tyr Pro Ala Thr Phe Asp Pro
1 5 10

<210> SEQ ID NO 71
<211> LENGTH: 111
<212> TYPE: PRT
<213> ORGANISM: Artificial Sequence
<220> FEATURE:
<223> OTHER INFORMATION: Chemically Synthesized

<400> SEQUENCE: 71

Asp Ile Gln Met Thr Gln Ser Pro Ser Ser Leu Ser Ala Ser Val Gly
1 5 10 15

Asp Arg Val Thr Ile Thr Cys Gln Ala Ser Glu Asp Ile Tyr Asn Leu
20 25 30

Leu Ala Trp Tyr Gln Gln Lys Pro Gly Lys Val Pro Lys Leu Leu Ile
35 40 45

Tyr Ser Ala Ser Thr Leu Ala Ser Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Val Ala Thr Tyr Tyr Cys Gln Asn Asn Tyr Leu Val Thr Thr
85 90 95

Tyr Gly Val Ala Phe Gly Gly Gly Thr Lys Val Glu Ile Lys Arg
100 105 110

<210> SEQ ID NO 72
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 72

Asp Ile Gln Met Thr Gln Ser Pro Ser Ser Leu Ser Ala Ser Val Gly

```
1               5                   10                  15

Asp Arg Val Thr Ile Thr Cys Gln Ala Ser Glu Asp Ile Tyr Asn Leu
            20                  25                  30

Leu Ala Trp Tyr Gln Gln Lys Pro Gly Lys Val Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Asn Asn Tyr Leu Val Thr Thr
                85                  90                  95

Tyr Gly Val Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 73
<211> LENGTH: 122
<212> TYPE: PRT
<213> ORGANISM: Artificial Sequence
<220> FEATURE:
<223> OTHER INFORMATION: Chemically Synthesized

<400> SEQUENCE: 73

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ile Trp Val Arg Gln Ala Pro Gly Lys Gly Leu Glu Tyr Ile
        35                  40                  45

Gly Tyr Ile Asp Thr Asp Thr Ser Ala Tyr Tyr Ala Ser Ser Val Lys
    50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

Arg Ser Tyr Ala Ala Tyr Gly Gly Tyr Pro Ala Thr Phe Asp Pro Trp
            100                 105                 110

Gly Gln Gly Thr Leu Val Thr Val Ser Ser
        115                 120


<210> SEQ ID NO 74
<211> LENGTH: 452
<212> TYPE: PRT
```

<213> ORGANISM: Artificial Sequence
<220> FEATURE:
<223> OTHER INFORMATION: Chemically Synthesized

<400> SEQUENCE: 74

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ile Trp Val Arg Gln Ala Pro Gly Lys Gly Leu Glu Tyr Ile
        35                  40                  45

Gly Tyr Ile Asp Thr Asp Thr Ser Ala Tyr Tyr Ala Ser Ser Val Lys
    50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

Arg Ser Tyr Ala Ala Tyr Gly Gly Tyr Pro Ala Thr Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Ala Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
```

-continued

```
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 75
<211> LENGTH: 11
<212> TYPE: PRT
<213> ORGANISM: Oryctolagus cuniculus

<400> SEQUENCE: 75

Gln Ala Ser Glu Asp Ile Tyr Asn Leu Leu Ala
1               5                   10


<210> SEQ ID NO 76
<211> LENGTH: 7
<212> TYPE: PRT
<213> ORGANISM: Oryctolagus cuniculus

<400> SEQUENCE: 76

Ser Ala Ser Thr Leu Ala Ser
1               5


<210> SEQ ID NO 77
<211> LENGTH: 12
<212> TYPE: PRT
<213> ORGANISM: Oryctolagus cuniculus

<400> SEQUENCE: 77

Gln Asn Asn Tyr Leu Val Thr Thr Tyr Gly Val Ala
1               5                   10


<210> SEQ ID NO 78
<211> LENGTH: 5
<212> TYPE: PRT
<213> ORGANISM: Oryctolagus cuniculus

<400> SEQUENCE: 78

Ser Tyr Ala Met Ile
1               5


<210> SEQ ID NO 79
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 79

Tyr Ile Asp Thr Asp Thr Ser Ala Tyr Tyr Ala Ser Ser Val Lys Gly
1               5                   10                  15


<210> SEQ ID NO 80
<211> LENGTH: 14
<212> TYPE: PRT
<213> ORGANISM: Oryctolagus cuniculus

<400> SEQUENCE: 80
```

```
Ser Tyr Ala Ala Tyr Gly Gly Tyr Pro Ala Thr Phe Asp Pro
1               5                   10


<210> SEQ ID NO 81
<211> LENGTH: 111
<212> TYPE: PRT
<213> ORGANISM: Oryctolagus cuniculus

<400> SEQUENCE: 81

Ala Tyr Asp Met Thr Gln Thr Pro Ala Ser Val Ser Ala Ala Val Gly
1               5                   10                  15

Gly Thr Val Thr Ile Lys Cys Gln Ala Ser Glu Asn Ile Gly Ser Tyr
            20                  25                  30

Leu Ala Trp Tyr Gln Gln Lys Pro Gly Gln Pro Pro Glu Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Asn Ser Glu Asn
                85                  90                  95

Leu Asp Asn Ala Phe Gly Gly Gly Thr Glu Val Val Val Lys Arg
            100                 105                 110


<210> SEQ ID NO 82
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 82

Ala Tyr Asp Met Thr Gln Thr Pro Ala Ser Val Ser Ala Ala Val Gly
1               5                   10                  15

Gly Thr Val Thr Ile Lys Cys Gln Ala Ser Glu Asn Ile Gly Ser Tyr
            20                  25                  30

Leu Ala Trp Tyr Gln Gln Lys Pro Gly Gln Pro Pro Glu Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Asn Ser Glu Asn
                85                  90                  95

Leu Asp Asn Ala Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
```

```
        195                 200                 205

Thr Lys Ser Phe Asn Arg Gly Glu Cys
    210                 215


<210> SEQ ID NO 83
<211> LENGTH: 115
<212> TYPE: PRT
<213> ORGANISM: Oryctolagus cuniculus

<400> SEQUENCE: 83

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Met Tyr Ser
            20                  25                  30

Met Gly Trp Val Arg Gln Ala Pro Gly Lys Gly Leu Glu Tyr Ile Gly
        35                  40                  45

Trp Ile Ser Tyr Gly Gly Thr Ala Tyr Tyr Ala Ser Trp Ala Lys Gly
    50                  55                  60

Arg Phe Thr Ile Ser Lys Thr Ser Thr Thr Val Glu Leu Lys Ile Thr
65                  70                  75                  80

Ser Pro Thr Ile Glu Asp Thr Ala Thr Tyr Phe Cys Ala Arg Glu Thr
                85                  90                  95

Pro Val Asn Tyr Tyr Leu Asp Ile Trp Gly Gln Gly Thr Leu Val Thr
            100                 105                 110

Val Ser Ser
        115


<210> SEQ ID NO 84
<211> LENGTH: 445
<212> TYPE: PRT
<213> ORGANISM: Artificial Sequence
<220> FEATURE:
<223> OTHER INFORMATION: Chemically Synthesized

<400> SEQUENCE: 84

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Met Tyr Ser
            20                  25                  30

Met Gly Trp Val Arg Gln Ala Pro Gly Lys Gly Leu Glu Tyr Ile Gly
        35                  40                  45

Trp Ile Ser Tyr Gly Gly Thr Ala Tyr Tyr Ala Ser Trp Ala Lys Gly
    50                  55                  60

Arg Phe Thr Ile Ser Lys Thr Ser Thr Thr Val Glu Leu Lys Ile Thr
65                  70                  75                  80

Ser Pro Thr Ile Glu Asp Thr Ala Thr Tyr Phe Cys Ala Arg Glu Thr
                85                  90                  95

Pro Val Asn Tyr Tyr Leu Asp Ile Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

Leu Tyr Ser Leu Ser Ser Val Val Thr Val Pro Ser Ser Ser Leu Gly
180 185 190

Thr Gln Thr Tyr Ile Cys Asn Val Asn His Lys Pro Ser Asn Thr Lys
195 200 205

Val Asp Lys Arg Val Glu Pro Lys Ser Cys Asp Lys Thr His Thr Cys
210 215 220

Pro Pro Cys Pro Ala Pro Glu Leu Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser His Glu Asp Pro Glu Val Lys
260 265 270

Phe Asn Trp Tyr Val Asp Gly Val Glu Val His Asn Ala Lys Thr Lys
275 280 285

Pro Arg Glu Glu Gln Tyr Ala Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Ala Leu Pro Ala Pro Ile Glu Lys Thr Ile Ser Lys
325 330 335

Ala Lys Gly Gln Pro Arg Glu Pro Gln Val Tyr Thr Leu Pro Pro Ser
340 345 350

Arg Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 85
<211> LENGTH: 11
<212> TYPE: PRT
<213> ORGANISM: Oryctolagus cuniculus

<400> SEQUENCE: 85

Gln Ala Ser Glu Asn Ile Gly Ser Tyr Leu Ala
1 5 10

<210> SEQ ID NO 86
<211> LENGTH: 7
<212> TYPE: PRT
<213> ORGANISM: Oryctolagus cuniculus

<400> SEQUENCE: 86

Arg Ala Ser Thr Leu Ala Ser
1 5

<210> SEQ ID NO 87
<211> LENGTH: 12
<212> TYPE: PRT
<213> ORGANISM: Oryctolagus cuniculus

<400> SEQUENCE: 87

Gln Gln Gly Tyr Asn Ser Glu Asn Leu Asp Asn Ala
1 5 10

<210> SEQ ID NO 88
<211> LENGTH: 5
<212> TYPE: PRT
<213> ORGANISM: Oryctolagus cuniculus

<400> SEQUENCE: 88

Met Tyr Ser Met Gly
1 5

<210> SEQ ID NO 89
<211> LENGTH: 16
<212> TYPE: PRT
<213> ORGANISM: Oryctolagus cuniculus

<400> SEQUENCE: 89

Trp Ile Ser Tyr Gly Gly Thr Ala Tyr Tyr Ala Ser Trp Ala Lys Gly
1 5 10 15

<210> SEQ ID NO 90
<211> LENGTH: 10
<212> TYPE: PRT
<213> ORGANISM: Oryctolagus cuniculus

<400> SEQUENCE: 90

Glu Thr Pro Val Asn Tyr Tyr Leu Asp Ile
1 5 10

<210> SEQ ID NO 91
<211> LENGTH: 111
<212> TYPE: PRT
<213> ORGANISM: Artificial Sequence
<220> FEATURE:
<223> OTHER INFORMATION: Chemically Synthesized

<400> SEQUENCE: 91

Ala Tyr Asp Met Thr Gln Ser Pro Ser Ser Leu Ser Ala Ser Val Gly
1 5 10 15

Asp Arg Val Thr Ile Thr Cys Gln Ala Ser Glu Asn Ile Gly Ser Tyr
20 25 30

Leu Ala Trp Tyr Gln Gln Lys Pro Gly Lys Val Pro Lys Leu Leu Ile
35 40 45

Tyr Arg Ala Ser Thr Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Val Ala Thr Tyr Tyr Cys Gln Gln Gly Tyr Asn Ser Glu Asn
85 90 95

Leu Asp Asn Ala Phe Gly Gly Gly Thr Lys Val Glu Ile Lys Arg
100 105 110

<210> SEQ ID NO 92
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 92

```
Ala Tyr Asp Met Thr Gln Ser Pro Ser Ser Leu Ser Ala Ser Val Gly
1               5                   10                  15

Asp Arg Val Thr Ile Thr Cys Gln Ala Ser Glu Asn Ile Gly Ser Tyr
            20                  25                  30

Leu Ala Trp Tyr Gln Gln Lys Pro Gly Lys Val Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Tyr Asn Ser Glu Asn
                85                  90                  95

Leu Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 93
<211> LENGTH: 118
<212> TYPE: PRT
<213> ORGANISM: Artificial Sequence
<220> FEATURE:
<223> OTHER INFORMATION: Chemically Synthesized

<400> SEQUENCE: 93

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Met Tyr
            20                  25                  30

Ser Met Gly Trp Val Arg Gln Ala Pro Gly Lys Gly Leu Glu Tyr Ile
        35                  40                  45

Gly Trp Ile Ser Tyr Gly Gly Thr Ala Tyr Tyr Ala Ser Ser Ala Lys
    50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

Arg Glu Thr Pro Val Asn Tyr Tyr Leu Asp Ile Trp Gly Gln Gly Thr
            100                 105                 110

Leu Val Thr Val Ser Ser
        115
```

<210> SEQ ID NO 94

<211> LENGTH: 448
<212> TYPE: PRT
<213> ORGANISM: Artificial Sequence
<220> FEATURE:
<223> OTHER INFORMATION: Chemically Synthesized

<400> SEQUENCE: 94

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Met Tyr
20 25 30

Ser Met Gly Trp Val Arg Gln Ala Pro Gly Lys Gly Leu Glu Tyr Ile
35 40 45

Gly Trp Ile Ser Tyr Gly Gly Thr Ala Tyr Tyr Ala Ser Ser Ala Lys
50 55 60

Gly Arg Phe Thr Ile Ser Arg Asp Asn Ser Lys Asn Thr Leu Tyr Leu
65 70 75 80

Gln Met Ser Ser Leu Arg Ala Glu Asp Thr Ala Val Tyr Tyr Cys Ala
85 90 95

Arg Glu Thr Pro Val Asn Tyr Tyr Leu Asp Ile Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Arg Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Ala Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

-continued

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 95
<211> LENGTH: 11
<212> TYPE: PRT
<213> ORGANISM: Oryctolagus cuniculus

<400> SEQUENCE: 95

Gln Ala Ser Glu Asn Ile Gly Ser Tyr Leu Ala
1               5                   10

<210> SEQ ID NO 96
<211> LENGTH: 7
<212> TYPE: PRT
<213> ORGANISM: Oryctolagus cuniculus

<400> SEQUENCE: 96

Arg Ala Ser Thr Leu Ala Ser
1               5

<210> SEQ ID NO 97
<211> LENGTH: 12
<212> TYPE: PRT
<213> ORGANISM: Oryctolagus cuniculus

<400> SEQUENCE: 97

Gln Gln Gly Tyr Asn Ser Glu Asn Leu Asp Asn Ala
1               5                   10

<210> SEQ ID NO 98
<211> LENGTH: 5
<212> TYPE: PRT
<213> ORGANISM: Oryctolagus cuniculus

<400> SEQUENCE: 98

Met Tyr Ser Met Gly
1               5

<210> SEQ ID NO 99
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 99

Trp Ile Ser Tyr Gly Gly Thr Ala Tyr Tyr Ala Ser Ser Ala Lys Gly
1               5                   10                  15

<210> SEQ ID NO 100
<211> LENGTH: 10
<212> TYPE: PRT
<213> ORGANISM: Oryctolagus cuniculus

<400> SEQUENCE: 100

Glu Thr Pro Val Asn Tyr Tyr Leu Asp Ile

```
1               5                   10


<210> SEQ ID NO 101
<211> LENGTH: 109
<212> TYPE: PRT
<213> ORGANISM: Oryctolagus cuniculus

<400> SEQUENCE: 101

Ala Phe Glu Leu Thr Gln Thr Pro Ser Ser Val Glu Ala Ala Val Gly
1               5                   10                  15

Gly Thr Val Thr Ile Lys Cys Gln Ala Ser Gln Asn Ile Val Thr Asn
            20                  25                  30

Leu Ala Trp Tyr Gln Gln Lys Pro Gly Gln Pro Pro Lys Leu Leu Ile
        35                  40                  45

Tyr Gly Ala Ser Thr Leu Ala Ser Gly Val Ser Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Phe Cys Gln Ser Tyr Asp Gly Phe Asn Ser
                85                  90                  95

Ala Gly Phe Gly Gly Gly Thr Glu Val Val Val Lys Arg
            100                 105


<210> SEQ ID NO 102
<211> LENGTH: 215
<212> TYPE: PRT
<213> ORGANISM: Artificial Sequence
<220> FEATURE:
<223> OTHER INFORMATION: Chemically Synthesized

<400> SEQUENCE: 102

Ala Phe Glu Leu Thr Gln Thr Pro Ser Ser Val Glu Ala Ala Val Gly
1               5                   10                  15

Gly Thr Val Thr Ile Lys Cys Gln Ala Ser Gln Asn Ile Val Thr Asn
            20                  25                  30

Leu Ala Trp Tyr Gln Gln Lys Pro Gly Gln Pro Pro Lys Leu Leu Ile
        35                  40                  45

Tyr Gly Ala Ser Thr Leu Ala Ser Gly Val Ser Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Phe Cys Gln Ser Tyr Asp Gly Phe Asn Ser
                85                  90                  95

Ala Gly Phe Gly Gly Gly Thr Glu Val Val Val Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

Ser Phe Asn Arg Gly Glu Cys
    210                 215

<210> SEQ ID NO 103
<211> LENGTH: 120
<212> TYPE: PRT
<213> ORGANISM: Oryctolagus cuniculus

<400> SEQUENCE: 103

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Gly Tyr Asp
            20                  25                  30

Met Ser Trp Val Arg Gln Ala Pro Gly Lys Gly Leu Glu Tyr Ile Gly
        35                  40                  45

Leu Ile Ser Tyr Asp Gly Asn Thr Tyr Tyr Ala Thr Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Ser Leu
                85                  90                  95

Tyr Ala Gly Pro Asn Ala Gly Ile Gly Pro Phe Asn Ile Trp Gly Gln
            100                 105                 110

Gly Thr Leu Val Thr Val Ser Ser
        115                 120

<210> SEQ ID NO 104
<211> LENGTH: 450
<212> TYPE: PRT
<213> ORGANISM: Artificial Sequence
<220> FEATURE:
<223> OTHER INFORMATION: Chemically Synthesized

<400> SEQUENCE: 104

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Gly Tyr Asp
            20                  25                  30

Met Ser Trp Val Arg Gln Ala Pro Gly Lys Gly Leu Glu Tyr Ile Gly
        35                  40                  45

Leu Ile Ser Tyr Asp Gly Asn Thr Tyr Tyr Ala Thr Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Ser Leu
                85                  90                  95

Tyr Ala Gly Pro Asn Ala Gly Ile Gly Pro Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 105
<211> LENGTH: 11
<212> TYPE: PRT
<213> ORGANISM: Oryctolagus cuniculus

<400> SEQUENCE: 105

Gln Ala Ser Gln Asn Ile Val Thr Asn Leu Ala
1               5                   10


<210> SEQ ID NO 106
<211> LENGTH: 7
<212> TYPE: PRT
<213> ORGANISM: Oryctolagus cuniculus

<400> SEQUENCE: 106

Gly Ala Ser Thr Leu Ala Ser
1               5


<210> SEQ ID NO 107
<211> LENGTH: 10
```

```
<212> TYPE: PRT
<213> ORGANISM: Oryctolagus cuniculus

<400> SEQUENCE: 107

Gln Ser Tyr Asp Gly Phe Asn Ser Ala Gly
1               5                   10


<210> SEQ ID NO 108
<211> LENGTH: 5
<212> TYPE: PRT
<213> ORGANISM: Oryctolagus cuniculus

<400> SEQUENCE: 108

Gly Tyr Asp Met Ser
1               5


<210> SEQ ID NO 109
<211> LENGTH: 16
<212> TYPE: PRT
<213> ORGANISM: Oryctolagus cuniculus

<400> SEQUENCE: 109

Leu Ile Ser Tyr Asp Gly Asn Thr Tyr Tyr Ala Thr Trp Ala Lys Gly
1               5                   10                  15


<210> SEQ ID NO 110
<211> LENGTH: 15
<212> TYPE: PRT
<213> ORGANISM: Oryctolagus cuniculus

<400> SEQUENCE: 110

Ser Leu Tyr Ala Gly Pro Asn Ala Gly Ile Gly Pro Phe Asn Ile
1               5                   10                  15


<210> SEQ ID NO 111
<211> LENGTH: 109
<212> TYPE: PRT
<213> ORGANISM: Artificial Sequence
<220> FEATURE:
<223> OTHER INFORMATION: Chemically Synthesized

<400> SEQUENCE: 111

Ala Phe Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Val Thr Asn
            20                  25                  30

Leu Ala Trp Tyr Gln Gln Lys Pro Gly Lys Val Pro Lys Leu Leu Ile
        35                  40                  45

Tyr Gly Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Tyr Asp Gly Phe Asn Ser
                85                  90                  95

Ala Gly Phe Gly Gly Gly Thr Lys Val Glu Ile Lys Arg
            100                 105


<210> SEQ ID NO 112
<211> LENGTH: 215
<212> TYPE: PRT
<213> ORGANISM: Artificial Sequence
<220> FEATURE:
<223> OTHER INFORMATION: Chemically Synthesized
```

<400> SEQUENCE: 112

Ala Phe Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Val Thr Asn
            20                  25                  30

Leu Ala Trp Tyr Gln Gln Lys Pro Gly Lys Val Pro Lys Leu Leu Ile
        35                  40                  45

Tyr Gly Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Tyr Asp Gly Phe Asn Ser
                85                  90                  95

Ala Gly Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 113
<211> LENGTH: 123
<212> TYPE: PRT
<213> ORGANISM: Artificial Sequence
<220> FEATURE:
<223> OTHER INFORMATION: Chemically Synthesized

<400> SEQUENCE: 113

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Ser Gly Tyr
            20                  25                  30

Asp Met Ser Trp Val Arg Gln Ala Pro Gly Lys Gly Leu Glu Trp Val
        35                  40                  45

Gly Leu Ile Ser Tyr Asp Gly Asn Thr Tyr Tyr Ala Thr Ser Ala Lys
    50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

Arg Ser Leu Tyr Ala Gly Pro Asn Ala Gly Ile Gly Pro Phe Asn Ile
            100                 105                 110

Trp Gly Gln Gly Thr Leu Val Thr Val Ser Ser
        115                 120

<210> SEQ ID NO 114
<211> LENGTH: 453
<212> TYPE: PRT
<213> ORGANISM: Artificial Sequence
<220> FEATURE:
<223> OTHER INFORMATION: Chemically Synthesized

<400> SEQUENCE: 114

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Ser Gly Tyr
            20                  25                  30

Asp Met Ser Trp Val Arg Gln Ala Pro Gly Lys Gly Leu Glu Trp Val
        35                  40                  45

Gly Leu Ile Ser Tyr Asp Gly Asn Thr Tyr Tyr Ala Thr Ser Ala Lys
    50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

Arg Ser Leu Tyr Ala Gly Pro Asn Ala Gly Ile Gly Pro Phe Asn Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Ala Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365
```

-continued

```
Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 115
<211> LENGTH: 11
<212> TYPE: PRT
<213> ORGANISM: Oryctolagus cuniculus

<400> SEQUENCE: 115

Gln Ala Ser Gln Asn Ile Val Thr Asn Leu Ala
1               5                   10


<210> SEQ ID NO 116
<211> LENGTH: 7
<212> TYPE: PRT
<213> ORGANISM: Oryctolagus cuniculus

<400> SEQUENCE: 116

Gly Ala Ser Thr Leu Ala Ser
1               5


<210> SEQ ID NO 117
<211> LENGTH: 10
<212> TYPE: PRT
<213> ORGANISM: Oryctolagus cuniculus

<400> SEQUENCE: 117

Gln Ser Tyr Asp Gly Phe Asn Ser Ala Gly
1               5                   10


<210> SEQ ID NO 118
<211> LENGTH: 5
<212> TYPE: PRT
<213> ORGANISM: Oryctolagus cuniculus

<400> SEQUENCE: 118

Gly Tyr Asp Met Ser
1               5


<210> SEQ ID NO 119
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 119

Leu Ile Ser Tyr Asp Gly Asn Thr Tyr Tyr Ala Thr Ser Ala Lys Gly
1               5                   10                  15


<210> SEQ ID NO 120
<211> LENGTH: 15
<212> TYPE: PRT
```

<213> ORGANISM: Oryctolagus cuniculus

<400> SEQUENCE: 120

Ser Leu Tyr Ala Gly Pro Asn Ala Gly Ile Gly Pro Phe Asn Ile
1 5 10 15

<210> SEQ ID NO 121
<211> LENGTH: 112
<212> TYPE: PRT
<213> ORGANISM: Oryctolagus cuniculus

<400> SEQUENCE: 121

Ala Ala Val Leu Thr Gln Thr Pro Ser Pro Val Ser Ala Ala Val Gly
1 5 10 15

Gly Thr Val Ser Ile Ser Cys Gln Ser Ser Gln Asn Val Tyr Lys Asn
20 25 30

Asn Tyr Leu Ser Trp Tyr Gln Gln Lys Pro Gly Gln Pro Pro Lys Leu
35 40 45

Leu Ile Tyr Lys Ala Ser Thr Leu Ala Ser Gly Val Pro Ser Arg Phe
50 55 60

Lys Gly Gly Gly Ser Gly Thr Asp Phe Thr Leu Thr Ile Ser Asp Val
65 70 75 80

Gln Cys Asp Ala Ala Ala Thr Tyr Tyr Cys Ala Gly Gly Tyr Thr Ser
85 90 95

Ser Ser Asp Asn Ala Phe Gly Gly Gly Thr Glu Val Val Val Lys Arg
100 105 110

<210> SEQ ID NO 122
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 122

Ala Ala Val Leu Thr Gln Thr Pro Ser Pro Val Ser Ala Ala Val Gly
1 5 10 15

Gly Thr Val Ser Ile Ser Cys Gln Ser Ser Gln Asn Val Tyr Lys Asn
20 25 30

Asn Tyr Leu Ser Trp Tyr Gln Gln Lys Pro Gly Gln Pro Pro Lys Leu
35 40 45

Leu Ile Tyr Lys Ala Ser Thr Leu Ala Ser Gly Val Pro Ser Arg Phe
50 55 60

Lys Gly Gly Gly Ser Gly Thr Asp Phe Thr Leu Thr Ile Ser Asp Val
65 70 75 80

Gln Cys Asp Ala Ala Ala Thr Tyr Tyr Cys Ala Gly Gly Tyr Thr Ser
85 90 95

Ser Ser Asp Asn Ala Phe Gly Gly Gly Thr Glu Val Val Val Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 123
<211> LENGTH: 117
<212> TYPE: PRT
<213> ORGANISM: Oryctolagus cuniculus

<400> SEQUENCE: 123

Gln Ser Val Glu Ala Ser Gly Gly Arg Leu Val Thr Pro Gly Thr Pro
1               5                   10                  15

Leu Thr Leu Thr Cys Thr Ala Ser Gly Phe Ser Leu Ser Thr Tyr Trp
            20                  25                  30

Met Ser Trp Val Arg Gln Ala Pro Gly Lys Gly Leu Glu Trp Ile Gly
        35                  40                  45

Asp Ile Tyr Phe Ser Asn Glu Glu Thr Asn Tyr Ala Ser Trp Ala Lys
    50                  55                  60

Gly Arg Phe Thr Ile Ser Lys Thr Ser Thr Thr Val Asp Leu Asn Val
65                  70                  75                  80

Ile Ser Pro Thr Thr Glu Asp Thr Ala Thr Tyr Phe Cys Ala Arg Gly
                85                  90                  95

Ser Pro Asp Val Asp Ile Gly Ile Asp Met Trp Gly Pro Gly Thr Leu
            100                 105                 110

Val Thr Val Ser Ser
        115


<210> SEQ ID NO 124
<211> LENGTH: 447
<212> TYPE: PRT
<213> ORGANISM: Artificial Sequence
<220> FEATURE:
<223> OTHER INFORMATION: Chemically Synthesized

<400> SEQUENCE: 124

Gln Ser Val Glu Ala Ser Gly Gly Arg Leu Val Thr Pro Gly Thr Pro
1               5                   10                  15

Leu Thr Leu Thr Cys Thr Ala Ser Gly Phe Ser Leu Ser Thr Tyr Trp
            20                  25                  30

Met Ser Trp Val Arg Gln Ala Pro Gly Lys Gly Leu Glu Trp Ile Gly
        35                  40                  45

Asp Ile Tyr Phe Ser Asn Glu Glu Thr Asn Tyr Ala Ser Trp Ala Lys
    50                  55                  60

Gly Arg Phe Thr Ile Ser Lys Thr Ser Thr Thr Val Asp Leu Asn Val
65                  70                  75                  80

Ile Ser Pro Thr Thr Glu Asp Thr Ala Thr Tyr Phe Cys Ala Arg Gly
                85                  90                  95

Ser Pro Asp Val Asp Ile Gly Ile Asp Met Trp Gly Pro Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
```

```
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 125
<211> LENGTH: 13
<212> TYPE: PRT
<213> ORGANISM: Oryctolagus cuniculus

<400> SEQUENCE: 125

Gln Ser Ser Gln Asn Val Tyr Lys Asn Asn Tyr Leu Ser
1               5                   10


<210> SEQ ID NO 126
<211> LENGTH: 7
<212> TYPE: PRT
<213> ORGANISM: Oryctolagus cuniculus

<400> SEQUENCE: 126

Lys Ala Ser Thr Leu Ala Ser
1               5
```

<210> SEQ ID NO 127
<211> LENGTH: 11
<212> TYPE: PRT
<213> ORGANISM: Oryctolagus cuniculus

<400> SEQUENCE: 127

Ala Gly Gly Tyr Thr Ser Ser Ser Asp Asn Ala
1               5                   10

<210> SEQ ID NO 128
<211> LENGTH: 5
<212> TYPE: PRT
<213> ORGANISM: Oryctolagus cuniculus

<400> SEQUENCE: 128

Thr Tyr Trp Met Ser
1               5

<210> SEQ ID NO 129
<211> LENGTH: 17
<212> TYPE: PRT
<213> ORGANISM: Oryctolagus cuniculus

<400> SEQUENCE: 129

Asp Ile Tyr Phe Ser Asn Glu Glu Thr Asn Tyr Ala Ser Trp Ala Lys
1               5                   10                  15

Gly

<210> SEQ ID NO 130
<211> LENGTH: 11
<212> TYPE: PRT
<213> ORGANISM: Oryctolagus cuniculus

<400> SEQUENCE: 130

Gly Ser Pro Asp Val Asp Ile Gly Ile Asp Met
1               5                   10

<210> SEQ ID NO 131
<211> LENGTH: 112
<212> TYPE: PRT
<213> ORGANISM: Artificial Sequence
<220> FEATURE:
<223> OTHER INFORMATION: Chemically Synthesized

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Asn Val Tyr Lys Asn
            20                  25                  30

Asn Tyr Leu Ser Trp Tyr Gln Gln Lys Pro Gly Lys Val Pro Lys Leu
        35                  40                  45

Leu Ile Tyr Lys Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Gly Tyr Thr Ser
                85                  90                  95

Ser Ser Asp Asn Ala Phe Gly Gly Gly Thr Lys Val Glu Ile Lys Arg
            100                 105                 110

<210> SEQ ID NO 132
<211> LENGTH: 218

<212> TYPE: PRT
<213> ORGANISM: Artificial Sequence
<220> FEATURE:
<223> OTHER INFORMATION: Chemically Synthesized

<400> SEQUENCE: 132

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Asn Val Tyr Lys Asn
            20                  25                  30

Asn Tyr Leu Ser Trp Tyr Gln Gln Lys Pro Gly Lys Val Pro Lys Leu
        35                  40                  45

Leu Ile Tyr Lys Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Gly Tyr Thr Ser
                85                  90                  95

Ser Ser Asp Asn Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 133
<211> LENGTH: 120
<212> TYPE: PRT
<213> ORGANISM: Artificial Sequence
<220> FEATURE:
<223> OTHER INFORMATION: Chemically Synthesized

<400> SEQUENCE: 133

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Trp Met Ser Trp Val Arg Gln Ala Pro Gly Lys Gly Leu Glu Trp Val
        35                  40                  45

Gly Asp Ile Tyr Phe Ser Asn Glu Glu Thr Asn Tyr Ala Ser Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Pro Asp Val Asp Ile Gly Ile Asp Met Trp Gly Pro
            100                 105                 110
```

```
Gly Thr Leu Val Thr Val Ser Ser
        115                 120


<210> SEQ ID NO 134
<211> LENGTH: 450
<212> TYPE: PRT
<213> ORGANISM: Artificial Sequence
<220> FEATURE:
<223> OTHER INFORMATION: Chemically Synthesized

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Trp Met Ser Trp Val Arg Gln Ala Pro Gly Lys Gly Leu Glu Trp Val
        35                  40                  45

Gly Asp Ile Tyr Phe Ser Asn Glu Glu Thr Asn Tyr Ala Ser Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Pro Asp Val Asp Ile Gly Ile Asp Met Trp Gly Pro
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 135
<211> LENGTH: 13
<212> TYPE: PRT
<213> ORGANISM: Oryctolagus cuniculus

<400> SEQUENCE: 135

Gln Ser Ser Gln Asn Val Tyr Lys Asn Asn Tyr Leu Ser
1               5                   10


<210> SEQ ID NO 136
<211> LENGTH: 7
<212> TYPE: PRT
<213> ORGANISM: Oryctolagus cuniculus

<400> SEQUENCE: 136

Lys Ala Ser Thr Leu Ala Ser
1               5


<210> SEQ ID NO 137
<211> LENGTH: 11
<212> TYPE: PRT
<213> ORGANISM: Oryctolagus cuniculus

<400> SEQUENCE: 137

Ala Gly Gly Tyr Thr Ser Ser Ser Asp Asn Ala
1               5                   10


<210> SEQ ID NO 138
<211> LENGTH: 5
<212> TYPE: PRT
<213> ORGANISM: Oryctolagus cuniculus

<400> SEQUENCE: 138

Thr Tyr Trp Met Ser
1               5


<210> SEQ ID NO 139
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 139

Asp Ile Tyr Phe Ser Asn Glu Glu Thr Asn Tyr Ala Ser Ser Ala Lys
1               5                   10                  15
```

Gly

<210> SEQ ID NO 140
<211> LENGTH: 11
<212> TYPE: PRT
<213> ORGANISM: Oryctolagus cuniculus

<400> SEQUENCE: 140

Gly Ser Pro Asp Val Asp Ile Gly Ile Asp Met
1               5                   10

<210> SEQ ID NO 141
<211> LENGTH: 112
<212> TYPE: PRT
<213> ORGANISM: Oryctolagus cuniculus

<400> SEQUENCE: 141

Ala Ala Val Leu Thr Gln Thr Pro Ser Pro Val Ser Ala Ala Val Gly
1               5                   10                  15

Asp Thr Val Thr Ile Lys Cys Gln Ser Ser Gln Ser Val Tyr Lys Asn
            20                  25                  30

Asn Tyr Leu Ser Trp Tyr Gln Gln Lys Pro Gly Gln Pro Pro Lys Leu
        35                  40                  45

Leu Ile Tyr Asp Ala Ser Asn Leu Pro Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Asp Tyr Asp Asp
                85                  90                  95

Asp Thr Asp Asn Gly Phe Gly Gly Gly Thr Glu Val Val Val Lys Arg
            100                 105                 110

<210> SEQ ID NO 142
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 142

Ala Ala Val Leu Thr Gln Thr Pro Ser Pro Val Ser Ala Ala Val Gly
1               5                   10                  15

Asp Thr Val Thr Ile Lys Cys Gln Ser Ser Gln Ser Val Tyr Lys Asn
            20                  25                  30

Asn Tyr Leu Ser Trp Tyr Gln Gln Lys Pro Gly Gln Pro Pro Lys Leu
        35                  40                  45

Leu Ile Tyr Asp Ala Ser Asn Leu Pro Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Asp Tyr Asp Asp
                85                  90                  95

Asp Thr Asp Asn Gly Phe Gly Gly Gly Thr Glu Val Val Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 143
<211> LENGTH: 112
<212> TYPE: PRT
<213> ORGANISM: Oryctolagus cuniculus

<400> SEQUENCE: 143

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Ile Trp Val Arg Gln Ala Pro Gly Lys Gly Leu Glu Tyr Ile Gly
        35                  40                  45

Ile Ile Trp Ser Gly Gly Thr Tyr Tyr Ala Thr Trp Ala Lys Gly Arg
    50                  55                  60

Phe Thr Ile Ser Lys Thr Ser Thr Thr Val Asp Leu Gln Ile Thr Ser
65                  70                  75                  80

Pro Thr Thr Glu Asp Ala Ala Thr Tyr Phe Cys Ala Ala Gly Gly Gly
                85                  90                  95

Ser Ile Tyr Asp Val Trp Gly Pro Gly Thr Leu Val Thr Val Ser Ser
            100                 105                 110


<210> SEQ ID NO 144
<211> LENGTH: 442
<212> TYPE: PRT
<213> ORGANISM: Artificial Sequence
<220> FEATURE:
<223> OTHER INFORMATION: Chemically Synthesized

<400> SEQUENCE: 144

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Ile Trp Val Arg Gln Ala Pro Gly Lys Gly Leu Glu Tyr Ile Gly
        35                  40                  45

Ile Ile Trp Ser Gly Gly Thr Tyr Tyr Ala Thr Trp Ala Lys Gly Arg
    50                  55                  60

Phe Thr Ile Ser Lys Thr Ser Thr Thr Val Asp Leu Gln Ile Thr Ser
65                  70                  75                  80

Pro Thr Thr Glu Asp Ala Ala Thr Tyr Phe Cys Ala Ala Gly Gly Gly
                85                  90                  95

Ser Ile Tyr Asp Val Trp Gly Pro Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
```

-continued

```
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Arg Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Ala Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440


<210> SEQ ID NO 145
<211> LENGTH: 13
<212> TYPE: PRT
<213> ORGANISM: Oryctolagus cuniculus

<400> SEQUENCE: 145

Gln Ser Ser Gln Ser Val Tyr Lys Asn Asn Tyr Leu Ser
1               5                   10


<210> SEQ ID NO 146
<211> LENGTH: 7
<212> TYPE: PRT
<213> ORGANISM: Oryctolagus cuniculus

<400> SEQUENCE: 146

Asp Ala Ser Asn Leu Pro Ser
```

1 5

<210> SEQ ID NO 147
<211> LENGTH: 11
<212> TYPE: PRT
<213> ORGANISM: Oryctolagus cuniculus

<400> SEQUENCE: 147

Leu Gly Asp Tyr Asp Asp Asp Thr Asp Asn Gly
1 5 10

<210> SEQ ID NO 148
<211> LENGTH: 5
<212> TYPE: PRT
<213> ORGANISM: Oryctolagus cuniculus

<400> SEQUENCE: 148

Ser Tyr Ala Met Ile
1 5

<210> SEQ ID NO 149
<211> LENGTH: 15
<212> TYPE: PRT
<213> ORGANISM: Oryctolagus cuniculus

<400> SEQUENCE: 149

Ile Ile Trp Ser Gly Gly Thr Tyr Tyr Ala Thr Trp Ala Lys Gly
1 5 10 15

<210> SEQ ID NO 150
<211> LENGTH: 8
<212> TYPE: PRT
<213> ORGANISM: Oryctolagus cuniculus

<400> SEQUENCE: 150

Gly Gly Gly Ser Ile Tyr Asp Val
1 5

<210> SEQ ID NO 151
<211> LENGTH: 112
<212> TYPE: PRT
<213> ORGANISM: Oryctolagus cuniculus

<400> SEQUENCE: 151

Ala Leu Val Met Thr Gln Thr Pro Ser Ser Thr Ser Glu Pro Val Gly
1 5 10 15

Gly Thr Val Thr Ile Asn Cys Gln Ala Ser Gln Asn Ile Gly Asn Asp
20 25 30

Leu Ser Trp Tyr Gln Gln Lys Pro Gly Gln Pro Pro Glu Leu Leu Ile
35 40 45

Tyr Ser Thr Ser Lys Leu Ala Thr Gly Val Pro Lys Arg Phe Ser Gly
50 55 60

Ser Arg Ser Gly Thr Gln Phe Thr Leu Thr Ile Ser Asp Leu Glu Cys
65 70 75 80

Asp Asp Ala Ala Thr Tyr Tyr Cys Leu Gly Val Tyr Ser Tyr Ile Ser
85 90 95

Asp Asp Gly Asn Ala Phe Gly Gly Gly Thr Glu Val Val Val Lys Arg
100 105 110

<210> SEQ ID NO 152
<211> LENGTH: 218
<212> TYPE: PRT

<213> ORGANISM: Artificial Sequence
<220> FEATURE:
<223> OTHER INFORMATION: Chemically Synthesized

<400> SEQUENCE: 152

```
Ala Leu Val Met Thr Gln Thr Pro Ser Ser Thr Ser Glu Pro Val Gly
1               5                   10                  15

Gly Thr Val Thr Ile Asn Cys Gln Ala Ser Gln Asn Ile Gly Asn Asp
            20                  25                  30

Leu Ser Trp Tyr Gln Gln Lys Pro Gly Gln Pro Pro Glu Leu Leu Ile
        35                  40                  45

Tyr Ser Thr Ser Lys Leu Ala Thr Gly Val Pro Lys Arg Phe Ser Gly
    50                  55                  60

Ser Arg Ser Gly Thr Gln Phe Thr Leu Thr Ile Ser Asp Leu Glu Cys
65                  70                  75                  80

Asp Asp Ala Ala Thr Tyr Tyr Cys Leu Gly Val Tyr Ser Tyr Ile Ser
                85                  90                  95

Asp Asp Gly Asn Ala Phe Gly Gly Gly Thr Glu Val Val Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 153
<211> LENGTH: 120
<212> TYPE: PRT
<213> ORGANISM: Oryctolagus cuniculus

<400> SEQUENCE: 153

```
Gln Ser Val Glu Glu Phe Gly Gly Arg Leu Val Thr Pro Gly Thr Pro
1               5                   10                  15

Leu Thr Leu Thr Cys Thr Val Ser Gly Phe Ser Leu Asn Asn Tyr Ala
            20                  25                  30

Met Thr Trp Val Arg Gln Ala Pro Gly Lys Gly Leu Glu Trp Ile Gly
        35                  40                  45

Ile Ile Gly Ser Ile Gly Thr Thr Tyr Tyr Ala Ser Trp Ala Lys Gly
    50                  55                  60

Arg Phe Phe Ile Ser Lys Thr Ser Thr Thr Val Asp Leu Lys Ile Ile
65                  70                  75                  80

Ser Pro Thr Thr Glu Asp Thr Ala Thr Tyr Phe Cys Ala Arg Asp Ala
                85                  90                  95

Gly Val Thr Val Asp Gly Tyr Gly Tyr Tyr Phe Asn Ile Trp Gly Pro
            100                 105                 110

Gly Thr Leu Val Thr Val Ser Ser
        115                 120
```

<210> SEQ ID NO 154
<211> LENGTH: 450
<212> TYPE: PRT
<213> ORGANISM: Artificial Sequence
<220> FEATURE:
<223> OTHER INFORMATION: Chemically Synthesized

<400> SEQUENCE: 154

```
Gln Ser Val Glu Glu Phe Gly Gly Arg Leu Val Thr Pro Gly Thr Pro
1               5                   10                  15

Leu Thr Leu Thr Cys Thr Val Ser Gly Phe Ser Leu Asn Asn Tyr Ala
            20                  25                  30

Met Thr Trp Val Arg Gln Ala Pro Gly Lys Gly Leu Glu Trp Ile Gly
        35                  40                  45

Ile Ile Gly Ser Ile Gly Thr Thr Tyr Tyr Ala Ser Trp Ala Lys Gly
    50                  55                  60

Arg Phe Phe Ile Ser Lys Thr Ser Thr Thr Val Asp Leu Lys Ile Ile
65                  70                  75                  80

Ser Pro Thr Thr Glu Asp Thr Ala Thr Tyr Phe Cys Ala Arg Asp Ala
                85                  90                  95

Gly Val Thr Val Asp Gly Tyr Gly Tyr Tyr Phe Asn Ile Trp Gly Pro
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 155
<211> LENGTH: 11
<212> TYPE: PRT
<213> ORGANISM: Oryctolagus cuniculus

<400> SEQUENCE: 155

Gln Ala Ser Gln Asn Ile Gly Asn Asp Leu Ser
1               5                   10


<210> SEQ ID NO 156
<211> LENGTH: 7
<212> TYPE: PRT
<213> ORGANISM: Oryctolagus cuniculus

<400> SEQUENCE: 156

Ser Thr Ser Lys Leu Ala Thr
1               5


<210> SEQ ID NO 157
<211> LENGTH: 13
<212> TYPE: PRT
<213> ORGANISM: Oryctolagus cuniculus

<400> SEQUENCE: 157

Leu Gly Val Tyr Ser Tyr Ile Ser Asp Asp Gly Asn Ala
1               5                   10


<210> SEQ ID NO 158
<211> LENGTH: 5
<212> TYPE: PRT
<213> ORGANISM: Oryctolagus cuniculus

<400> SEQUENCE: 158

Asn Tyr Ala Met Thr
1               5


<210> SEQ ID NO 159
<211> LENGTH: 16
<212> TYPE: PRT
<213> ORGANISM: Oryctolagus cuniculus

<400> SEQUENCE: 159

Ile Ile Gly Ser Ile Gly Thr Thr Tyr Tyr Ala Ser Trp Ala Lys Gly
1               5                   10                  15


<210> SEQ ID NO 160
<211> LENGTH: 15
<212> TYPE: PRT
<213> ORGANISM: Oryctolagus cuniculus
```

<400> SEQUENCE: 160

Asp Ala Gly Val Thr Val Asp Gly Tyr Gly Tyr Tyr Phe Asn Ile
1 5 10 15

<210> SEQ ID NO 161
<211> LENGTH: 112
<212> TYPE: PRT
<213> ORGANISM: Oryctolagus cuniculus

<400> SEQUENCE: 161

Ala Ile Glu Met Thr Gln Thr Pro Phe Ser Val Ser Ala Ala Val Gly
1 5 10 15

Gly Thr Val Thr Ile Lys Cys Gln Ala Ser Gln Thr Ile Ser Asn Tyr
20 25 30

Leu Ala Trp Tyr Gln Gln Lys Pro Gly Gln Pro Pro Lys Leu Leu Ile
35 40 45

Tyr Gly Ala Ser Asn Leu Glu Ser Gly Val Pro Ser Arg Phe Lys Gly
50 55 60

Ser Gly Ser Gly Thr Gln Phe Thr Leu Thr Ile Ser Asp Leu Glu Cys
65 70 75 80

Asp Asp Ala Ala Thr Tyr Tyr Cys Gln Gln Gly Tyr Thr Ile Ser Asn
85 90 95

Val Asp Asn Asn Val Phe Gly Gly Gly Thr Glu Val Val Val Lys Arg
100 105 110

<210> SEQ ID NO 162
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 162

Ala Ile Glu Met Thr Gln Thr Pro Phe Ser Val Ser Ala Ala Val Gly
1 5 10 15

Gly Thr Val Thr Ile Lys Cys Gln Ala Ser Gln Thr Ile Ser Asn Tyr
20 25 30

Leu Ala Trp Tyr Gln Gln Lys Pro Gly Gln Pro Pro Lys Leu Leu Ile
35 40 45

Tyr Gly Ala Ser Asn Leu Glu Ser Gly Val Pro Ser Arg Phe Lys Gly
50 55 60

Ser Gly Ser Gly Thr Gln Phe Thr Leu Thr Ile Ser Asp Leu Glu Cys
65 70 75 80

Asp Asp Ala Ala Thr Tyr Tyr Cys Gln Gln Gly Tyr Thr Ile Ser Asn
85 90 95

Val Asp Asn Asn Val Phe Gly Gly Gly Thr Glu Val Val Val Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys

```
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215


<210> SEQ ID NO 163
<211> LENGTH: 115
<212> TYPE: PRT
<213> ORGANISM: Oryctolagus cuniculus

<400> SEQUENCE: 163

Gln Ser Leu Glu Glu Ser Gly Gly Arg Leu Val Thr Pro Gly Gly Ser
1               5                   10                  15

Leu Thr Leu Thr Cys Ala Ala Ser Gly Phe Ser Leu Thr Gly Tyr Asn
            20                  25                  30

Leu Val Trp Val Arg Gln Ala Pro Gly Lys Gly Leu Glu Trp Ile Gly
        35                  40                  45

Phe Ile Ser Tyr Gly Asp Thr Thr Tyr Tyr Ala Ser Trp Ala Lys Gly
    50                  55                  60

Arg Phe Thr Ile Ser Lys Thr Ser Thr Thr Val Thr Leu Thr Ile Thr
65                  70                  75                  80

Asp Leu Gln Pro Ser Asp Thr Gly Thr Tyr Phe Cys Ala Arg Glu Thr
                85                  90                  95

Ala Asn Thr Tyr Asp Tyr Gly Ile Trp Gly Pro Gly Thr Leu Val Thr
            100                 105                 110

Val Ser Ser
        115


<210> SEQ ID NO 164
<211> LENGTH: 445
<212> TYPE: PRT
<213> ORGANISM: Artificial Sequence
<220> FEATURE:
<223> OTHER INFORMATION: Chemically Synthesized

<400> SEQUENCE: 164

Gln Ser Leu Glu Glu Ser Gly Gly Arg Leu Val Thr Pro Gly Gly Ser
1               5                   10                  15

Leu Thr Leu Thr Cys Ala Ala Ser Gly Phe Ser Leu Thr Gly Tyr Asn
            20                  25                  30

Leu Val Trp Val Arg Gln Ala Pro Gly Lys Gly Leu Glu Trp Ile Gly
        35                  40                  45

Phe Ile Ser Tyr Gly Asp Thr Thr Tyr Tyr Ala Ser Trp Ala Lys Gly
    50                  55                  60

Arg Phe Thr Ile Ser Lys Thr Ser Thr Thr Val Thr Leu Thr Ile Thr
65                  70                  75                  80

Asp Leu Gln Pro Ser Asp Thr Gly Thr Tyr Phe Cys Ala Arg Glu Thr
                85                  90                  95

Ala Asn Thr Tyr Asp Tyr Gly Ile Trp Gly Pro Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160
```

Leu Thr Ser Gly Val His Thr Phe Pro Ala Val Leu Gln Ser Ser Gly
165 170 175

Leu Tyr Ser Leu Ser Ser Val Val Thr Val Pro Ser Ser Ser Leu Gly
180 185 190

Thr Gln Thr Tyr Ile Cys Asn Val Asn His Lys Pro Ser Asn Thr Lys
195 200 205

Val Asp Lys Arg Val Glu Pro Lys Ser Cys Asp Lys Thr His Thr Cys
210 215 220

Pro Pro Cys Pro Ala Pro Glu Leu Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser His Glu Asp Pro Glu Val Lys
260 265 270

Phe Asn Trp Tyr Val Asp Gly Val Glu Val His Asn Ala Lys Thr Lys
275 280 285

Pro Arg Glu Glu Gln Tyr Ala Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Ala Leu Pro Ala Pro Ile Glu Lys Thr Ile Ser Lys
325 330 335

Ala Lys Gly Gln Pro Arg Glu Pro Gln Val Tyr Thr Leu Pro Pro Ser
340 345 350

Arg Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 165
<211> LENGTH: 11
<212> TYPE: PRT
<213> ORGANISM: Oryctolagus cuniculus

<400> SEQUENCE: 165

Gln Ala Ser Gln Thr Ile Ser Asn Tyr Leu Ala
1 5 10

<210> SEQ ID NO 166
<211> LENGTH: 7
<212> TYPE: PRT
<213> ORGANISM: Oryctolagus cuniculus

<400> SEQUENCE: 166

Gly Ala Ser Asn Leu Glu Ser
1 5

<210> SEQ ID NO 167

<211> LENGTH: 13
<212> TYPE: PRT
<213> ORGANISM: Oryctolagus cuniculus

<400> SEQUENCE: 167

Gln Gln Gly Tyr Thr Ile Ser Asn Val Asp Asn Asn Val
1 5 10

<210> SEQ ID NO 168
<211> LENGTH: 5
<212> TYPE: PRT
<213> ORGANISM: Oryctolagus cuniculus

<400> SEQUENCE: 168

Gly Tyr Asn Leu Val
1 5

<210> SEQ ID NO 169
<211> LENGTH: 16
<212> TYPE: PRT
<213> ORGANISM: Oryctolagus cuniculus

<400> SEQUENCE: 169

Phe Ile Ser Tyr Gly Asp Thr Thr Tyr Tyr Ala Ser Trp Ala Lys Gly
1 5 10 15

<210> SEQ ID NO 170
<211> LENGTH: 10
<212> TYPE: PRT
<213> ORGANISM: Oryctolagus cuniculus

<400> SEQUENCE: 170

Glu Thr Ala Asn Thr Tyr Asp Tyr Gly Ile
1 5 10

<210> SEQ ID NO 171
<211> LENGTH: 112
<212> TYPE: PRT
<213> ORGANISM: Artificial Sequence
<220> FEATURE:
<223> OTHER INFORMATION: Chemically Synthesized

<400> SEQUENCE: 171

Asp Ile Gln Met Thr Gln Ser Pro Ser Thr Leu Ser Ala Ser Val Gly
1 5 10 15

Asp Arg Val Thr Ile Thr Cys Gln Ala Ser Gln Thr Ile Ser Asn Tyr
20 25 30

Leu Ala Trp Tyr Gln Gln Lys Pro Gly Lys Ala Pro Lys Leu Leu Ile
35 40 45

Tyr Gly Ala Ser Asn Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Gly Tyr Thr Ile Ser Asn
85 90 95

Val Asp Asn Asn Val Phe Gly Gly Gly Thr Lys Val Glu Ile Lys Arg
100 105 110

<210> SEQ ID NO 172
<211> LENGTH: 218
<212> TYPE: PRT
<213> ORGANISM: Artificial Sequence
<220> FEATURE:

<223> OTHER INFORMATION: Chemically Synthesized

<400> SEQUENCE: 172

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Thr Ile Ser Asn Tyr
            20                  25                  30

Leu Ala Trp Tyr Gln Gln Lys Pro Gly Lys Ala Pro Lys Leu Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Thr Ile Ser Asn
                85                  90                  95

Val Asp Asn Asn Val Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 173
<211> LENGTH: 118
<212> TYPE: PRT
<213> ORGANISM: Artificial Sequence
<220> FEATURE:
<223> OTHER INFORMATION: Chemically Synthesized

<400> SEQUENCE: 173

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Gly Tyr
            20                  25                  30

Asn Leu Val Trp Val Arg Gln Ala Pro Gly Lys Gly Leu Glu Trp Val
        35                  40                  45

Gly Phe Ile Ser Tyr Gly Asp Thr Thr Tyr Tyr Ala Ser Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Thr Ala Asn Thr Tyr Asp Tyr Gly Ile Trp Gly Gln Gly Thr
            100                 105                 110

Leu Val Thr Val Ser Ser
        115
```

<210> SEQ ID NO 174
<211> LENGTH: 448
<212> TYPE: PRT
<213> ORGANISM: Artificial Sequence
<220> FEATURE:
<223> OTHER INFORMATION: Chemically Synthesized

<400> SEQUENCE: 174

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Gly Tyr
            20                  25                  30

Asn Leu Val Trp Val Arg Gln Ala Pro Gly Lys Gly Leu Glu Trp Val
        35                  40                  45

Gly Phe Ile Ser Tyr Gly Asp Thr Thr Tyr Tyr Ala Ser Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Thr Ala Asn Thr Tyr Asp Tyr Gly Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365
```

```
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 175
<211> LENGTH: 11
<212> TYPE: PRT
<213> ORGANISM: Oryctolagus cuniculus

<400> SEQUENCE: 175

Gln Ala Ser Gln Thr Ile Ser Asn Tyr Leu Ala
1               5                   10


<210> SEQ ID NO 176
<211> LENGTH: 7
<212> TYPE: PRT
<213> ORGANISM: Oryctolagus cuniculus

<400> SEQUENCE: 176

Gly Ala Ser Asn Leu Glu Ser
1               5


<210> SEQ ID NO 177
<211> LENGTH: 13
<212> TYPE: PRT
<213> ORGANISM: Oryctolagus cuniculus

<400> SEQUENCE: 177

Gln Gln Gly Tyr Thr Ile Ser Asn Val Asp Asn Asn Val
1               5                   10


<210> SEQ ID NO 178
<211> LENGTH: 5
<212> TYPE: PRT
<213> ORGANISM: Oryctolagus cuniculus

<400> SEQUENCE: 178

Gly Tyr Asn Leu Val
1               5


<210> SEQ ID NO 179
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 179

Phe Ile Ser Tyr Gly Asp Thr Thr Tyr Tyr Ala Ser Ser Ala Lys Gly
1               5                   10                  15


<210> SEQ ID NO 180
<211> LENGTH: 10
<212> TYPE: PRT
<213> ORGANISM: Oryctolagus cuniculus
```

<400> SEQUENCE: 180

Glu Thr Ala Asn Thr Tyr Asp Tyr Gly Ile
1 5 10

<210> SEQ ID NO 181
<211> LENGTH: 112
<212> TYPE: PRT
<213> ORGANISM: Oryctolagus cuniculus

<400> SEQUENCE: 181

Ala Ala Val Leu Thr Gln Thr Pro Ser Pro Val Ser Ala Ala Val Gly
1 5 10 15

Gly Thr Val Ser Ile Ser Cys Gln Ser Ser Gln Asn Val Tyr Lys Asn
20 25 30

Asn Tyr Leu Ser Trp Tyr Gln Gln Lys Pro Gly Gln Pro Pro Lys Leu
35 40 45

Leu Ile Tyr Lys Ala Ser Thr Leu Ala Ser Gly Val Pro Ser Arg Phe
50 55 60

Lys Gly Ser Gly Ser Gly Thr Asp Phe Thr Leu Thr Ile Ser Asp Val
65 70 75 80

Gln Cys Asp Ala Ala Ala Thr Tyr Tyr Cys Ala Gly Gly Tyr Ser Ser
85 90 95

Ser Ser Asp Asn Ala Phe Gly Gly Gly Thr Glu Val Val Val Lys Arg
100 105 110

<210> SEQ ID NO 182
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 182

Ala Ala Val Leu Thr Gln Thr Pro Ser Pro Val Ser Ala Ala Val Gly
1 5 10 15

Gly Thr Val Ser Ile Ser Cys Gln Ser Ser Gln Asn Val Tyr Lys Asn
20 25 30

Asn Tyr Leu Ser Trp Tyr Gln Gln Lys Pro Gly Gln Pro Pro Lys Leu
35 40 45

Leu Ile Tyr Lys Ala Ser Thr Leu Ala Ser Gly Val Pro Ser Arg Phe
50 55 60

Lys Gly Ser Gly Ser Gly Thr Asp Phe Thr Leu Thr Ile Ser Asp Val
65 70 75 80

Gln Cys Asp Ala Ala Ala Thr Tyr Tyr Cys Ala Gly Gly Tyr Ser Ser
85 90 95

Ser Ser Asp Asn Ala Phe Gly Gly Gly Thr Glu Val Val Val Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

```
His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 183
<211> LENGTH: 117
<212> TYPE: PRT
<213> ORGANISM: Oryctolagus cuniculus

<400> SEQUENCE: 183

```
Gln Ser Val Glu Ala Ser Gly Gly Arg Leu Val Met Pro Gly Gly Ser
1               5                   10                  15

Leu Thr Leu Thr Cys Thr Ala Ser Gly Phe Ser Leu Ser Thr Tyr Trp
            20                  25                  30

Met Ser Trp Val Arg Gln Ala Pro Gly Lys Gly Leu Glu Trp Ile Gly
        35                  40                  45

Asp Ile Tyr Phe Ser Asn Glu Glu Thr Asn Tyr Ala Thr Trp Ala Lys
    50                  55                  60

Gly Arg Phe Thr Ile Ser Lys Thr Ser Thr Thr Val Asp Leu Asn Val
65                  70                  75                  80

Ile Ser Pro Thr Thr Glu Asp Thr Ala Thr Tyr Phe Cys Ala Arg Gly
                85                  90                  95

Ser Pro Asp Val Glu Ile Ala Ile Asp Met Trp Gly Gln Gly Thr Leu
            100                 105                 110

Val Thr Val Ser Ser
        115
```

<210> SEQ ID NO 184
<211> LENGTH: 447
<212> TYPE: PRT
<213> ORGANISM: Artificial Sequence
<220> FEATURE:
<223> OTHER INFORMATION: Chemically Synthesized

<400> SEQUENCE: 184

```
Gln Ser Val Glu Ala Ser Gly Gly Arg Leu Val Met Pro Gly Gly Ser
1               5                   10                  15

Leu Thr Leu Thr Cys Thr Ala Ser Gly Phe Ser Leu Ser Thr Tyr Trp
            20                  25                  30

Met Ser Trp Val Arg Gln Ala Pro Gly Lys Gly Leu Glu Trp Ile Gly
        35                  40                  45

Asp Ile Tyr Phe Ser Asn Glu Glu Thr Asn Tyr Ala Thr Trp Ala Lys
    50                  55                  60

Gly Arg Phe Thr Ile Ser Lys Thr Ser Thr Thr Val Asp Leu Asn Val
65                  70                  75                  80

Ile Ser Pro Thr Thr Glu Asp Thr Ala Thr Tyr Phe Cys Ala Arg Gly
                85                  90                  95

Ser Pro Asp Val Glu Ile Ala Ile Asp Met Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 185
<211> LENGTH: 13
<212> TYPE: PRT
<213> ORGANISM: Oryctolagus cuniculus

<400> SEQUENCE: 185

Gln Ser Ser Gln Asn Val Tyr Lys Asn Asn Tyr Leu Ser
1               5                   10


<210> SEQ ID NO 186
<211> LENGTH: 7
<212> TYPE: PRT
<213> ORGANISM: Oryctolagus cuniculus

<400> SEQUENCE: 186

Lys Ala Ser Thr Leu Ala Ser
1               5


<210> SEQ ID NO 187
<211> LENGTH: 11
```

<212> TYPE: PRT
<213> ORGANISM: Oryctolagus cuniculus

<400> SEQUENCE: 187

Ala Gly Gly Tyr Ser Ser Ser Ser Asp Asn Ala
1 5 10

<210> SEQ ID NO 188
<211> LENGTH: 5
<212> TYPE: PRT
<213> ORGANISM: Oryctolagus cuniculus

<400> SEQUENCE: 188

Thr Tyr Trp Met Ser
1 5

<210> SEQ ID NO 189
<211> LENGTH: 17
<212> TYPE: PRT
<213> ORGANISM: Oryctolagus cuniculus

<400> SEQUENCE: 189

Asp Ile Tyr Phe Ser Asn Glu Glu Thr Asn Tyr Ala Thr Trp Ala Lys
1 5 10 15

Gly

<210> SEQ ID NO 190
<211> LENGTH: 11
<212> TYPE: PRT
<213> ORGANISM: Oryctolagus cuniculus

<400> SEQUENCE: 190

Gly Ser Pro Asp Val Glu Ile Ala Ile Asp Met
1 5 10

<210> SEQ ID NO 191
<211> LENGTH: 112
<212> TYPE: PRT
<213> ORGANISM: Artificial Sequence
<220> FEATURE:
<223> OTHER INFORMATION: Chemically Synthesized

<400> SEQUENCE: 191

Asp Ile Gln Met Thr Gln Ser Pro Ser Ser Leu Ser Ala Ser Val Gly
1 5 10 15

Asp Arg Val Thr Ile Thr Cys Gln Ser Ser Gln Asn Val Tyr Lys Asn
20 25 30

Asn Tyr Leu Ser Trp Tyr Gln Gln Lys Pro Gly Lys Val Pro Lys Leu
35 40 45

Leu Ile Tyr Lys Ala Ser Thr Leu Ala Ser Gly Val Pro Ser Arg Phe
50 55 60

Ser Gly Ser Gly Ser Gly Thr Asp Phe Thr Leu Thr Ile Ser Ser Leu
65 70 75 80

Gln Pro Glu Asp Val Ala Thr Tyr Tyr Cys Ala Gly Gly Tyr Thr Ser
85 90 95

Ser Ser Asp Asn Ala Phe Gly Gly Gly Thr Lys Val Glu Ile Lys Arg
100 105 110

<210> SEQ ID NO 192
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 192

Asp Ile Gln Met Thr Gln Ser Pro Ser Ser Leu Ser Ala Ser Val Gly
1 5 10 15

Asp Arg Val Thr Ile Thr Cys Gln Ser Ser Gln Asn Val Tyr Lys Asn
20 25 30

Asn Tyr Leu Ser Trp Tyr Gln Gln Lys Pro Gly Lys Val Pro Lys Leu
35 40 45

Leu Ile Tyr Lys Ala Ser Thr Leu Ala Ser Gly Val Pro Ser Arg Phe
50 55 60

Ser Gly Ser Gly Ser Gly Thr Asp Phe Thr Leu Thr Ile Ser Ser Leu
65 70 75 80

Gln Pro Glu Asp Val Ala Thr Tyr Tyr Cys Ala Gly Gly Tyr Thr Ser
85 90 95

Ser Ser Asp Asn Ala Phe Gly Gly Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 193
<211> LENGTH: 120
<212> TYPE: PRT
<213> ORGANISM: Artificial Sequence
<220> FEATURE:
<223> OTHER INFORMATION: Chemically Synthesized

<400> SEQUENCE: 193

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Val Ser Thr Tyr
20 25 30

Trp Met Ser Trp Val Arg Gln Ala Pro Gly Lys Gly Leu Glu Trp Val
35 40 45

Gly Asp Ile Tyr Phe Ser Asn Glu Glu Thr Asn Tyr Ala Thr Ser Ala
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Ser Pro Asp Val Glu Ile Ala Ile Asp Met Trp Gly Gln
100 105 110

Gly Thr Leu Val Thr Val Ser Ser 115 120

<210> SEQ ID NO 194
<211> LENGTH: 450
<212> TYPE: PRT
<213> ORGANISM: Artificial Sequence
<220> FEATURE:
<223> OTHER INFORMATION: Chemically Synthesized

<400> SEQUENCE: 194

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Trp Met Ser Trp Val Arg Gln Ala Pro Gly Lys Gly Leu Glu Trp Val
        35                  40                  45

Gly Asp Ile Tyr Phe Ser Asn Glu Glu Thr Asn Tyr Ala Thr Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Pro Asp Val Glu Ile Ala Ile Asp Met Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

```
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 195
<211> LENGTH: 13
<212> TYPE: PRT
<213> ORGANISM: Oryctolagus cuniculus

<400> SEQUENCE: 195

Gln Ser Ser Gln Asn Val Tyr Lys Asn Asn Tyr Leu Ser
1               5                   10


<210> SEQ ID NO 196
<211> LENGTH: 7
<212> TYPE: PRT
<213> ORGANISM: Oryctolagus cuniculus

<400> SEQUENCE: 196

Lys Ala Ser Thr Leu Ala Ser
1               5


<210> SEQ ID NO 197
<211> LENGTH: 11
<212> TYPE: PRT
<213> ORGANISM: Oryctolagus cuniculus

<400> SEQUENCE: 197

Ala Gly Gly Tyr Thr Ser Ser Ser Asp Asn Ala
1               5                   10


<210> SEQ ID NO 198
<211> LENGTH: 5
<212> TYPE: PRT
<213> ORGANISM: Oryctolagus cuniculus

<400> SEQUENCE: 198

Thr Tyr Trp Met Ser
1               5


<210> SEQ ID NO 199
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 199

Asp Ile Tyr Phe Ser Asn Glu Glu Thr Asn Tyr Ala Thr Ser Ala Lys
1               5                   10                  15

Gly
```

<210> SEQ ID NO 200
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 200

Gly Ser Pro Asp Val Glu Ile Ala Ile Asp Met
1 5 10

<210> SEQ ID NO 201
<211> LENGTH: 333
<212> TYPE: DNA
<213> ORGANISM: Oryctolagus cuniculus

<400> SEQUENCE: 201
gcccttgtga tgacccagac tccatcctcc gtgtctgcag ctgtgggagg cacagtcacc 60
atcaattgcc aggccagtca gaacatttac agcaatttag cctggtatca acagagacca 120
gggcagcgtc ccaagctcct gatctatggt gcatccaatc tggatgctgg ggtcccatcg 180
cggttcagag gcagtggatc tgggacagag tacactctca ccatcagcga cctggagtgt 240
gacgatgttg gcacttacta ctgtcaaagt gcttttgata gtgatagtac tgaaaatact 300
ttcggcggag ggaccgaggt ggtggtcaaa cgt 333

<210> SEQ ID NO 202
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 202
gcccttgtga tgacccagac tccatcctcc gtgtctgcag ctgtgggagg cacagtcacc 60
atcaattgcc aggccagtca gaacatttac agcaatttag cctggtatca acagagacca 120
gggcagcgtc ccaagctcct gatctatggt gcatccaatc tggatgctgg ggtcccatcg 180
cggttcagag gcagtggatc tgggacagag tacactctca ccatcagcga cctggagtgt 240
gacgatgttg gcacttacta ctgtcaaagt gcttttgata gtgatagtac tgaaaatact 300
ttcggcggag ggaccgaggt ggtggtcaaa cgtacggtag cggccccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg ttag 654

<210> SEQ ID NO 203
<211> LENGTH: 354
<212> TYPE: DNA
<213> ORGANISM: Oryctolagus cuniculus

<400> SEQUENCE: 203
cagtcgctgg aggagtccgg gggtcgcctg gtcacgcctg ggacacccct gacactcacc 60
tgcacagtct ctggcttctc cctcagtagc tatgcaatga gctgggtccg ccaggctcca 120
gggaaggggc tggaatggat cggagtcatt actagtattg gtagcacagt ctacgcgagc 180

```
tgggcgaaag gccgattcac catctccaaa acctcgacca cggtggatct gaaaatcacc    240

agtccgacaa ccgaggacac ggccacctat ttctgtgcca gaggctacga tgactatgat    300

gagatgacct actttaacat ctggggccag gggaccctcg tcaccgtctc gagc          354
```

<210> SEQ ID NO 204
<211> LENGTH: 1347
<212> TYPE: DNA
<213> ORGANISM: Artificial Sequence
<220> FEATURE:
<223> OTHER INFORMATION: Chemically Synthesized

<400> SEQUENCE: 204

```
cagtcgctgg aggagtccgg gggtcgcctg gtcacgcctg ggacacccct gacactcacc     60

tgcacagtct ctggcttctc cctcagtagc tatgcaatga gctgggtccg ccaggctcca    120

gggaaggggc tggaatggat cggagtcatt actagtattg gtagcacagt ctacgcgagc    180

tgggcgaaag gccgattcac catctccaaa acctcgacca cggtggatct gaaaatcacc    240

agtccgacaa ccgaggacac ggccacctat ttctgtgcca gaggctacga tgactatgat    300

gagatgacct actttaacat ctggggccag gggaccctcg tcaccgtctc gagcgcctcc    360

accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcaccca gacctacatc    600

tgcaacgtga atcacaagcc cagcaacacc aaggtggaca agagagttga gcccaaatct    660

tgtgacaaaa ctcacacatg cccaccgtgc ccagcacctg aactcctggg gggaccgtca    720

gtcttcctct tccccccaaa acccaaggac accctcatga tctcccggac ccctgaggtc    780

acatgcgtgg tggtggacgt gagccacgaa gaccctgagg tcaagttcaa ctggtacgtg    840

gacggcgtgg aggtgcataa tgccaagaca aagccgcggg aggagcagta cgccagcacg    900

taccgtgtgg tcagcgtcct caccgtcctg caccaggact ggctgaatgg caaggagtac    960

aagtgcaagg tctccaacaa agccctccca gcccccatcg agaaaaccat ctccaaagcc   1020

aaagggcagc cccgagaacc acaggtgtac accctgcccc catcccggga ggagatgacc   1080

aagaaccagg tcagcctgac ctgcctggtc aaaggcttct atcccagcga catcgccgtg   1140

gagtgggaga gcaatgggca gccggagaac aactacaaga ccacgcctcc cgtgctggac   1200

tccgacggct ccttcttcct ctacagcaag ctcaccgtgg acaagagcag gtggcagcag   1260

gggaacgtct tctcatgctc cgtgatgcat gaggctctgc acaaccacta cacgcagaag   1320

agcctctccc tgtctccggg taaatga                                       1347
```

<210> SEQ ID NO 205
<211> LENGTH: 33
<212> TYPE: DNA
<213> ORGANISM: Oryctolagus cuniculus

<400> SEQUENCE: 205

```
caggccagtc agaacattta cagcaattta gcc                                  33
```

<210> SEQ ID NO 206
<211> LENGTH: 21
<212> TYPE: DNA
<213> ORGANISM: Oryctolagus cuniculus

<400> SEQUENCE: 206
ggtgcatcca atctggatgc t 21

<210> SEQ ID NO 207
<211> LENGTH: 36
<212> TYPE: DNA
<213> ORGANISM: Oryctolagus cuniculus

<400> SEQUENCE: 207
caaagtgctt ttgatagtga tagtactgaa aatact 36

<210> SEQ ID NO 208
<211> LENGTH: 15
<212> TYPE: DNA
<213> ORGANISM: Oryctolagus cuniculus

<400> SEQUENCE: 208
agctatgcaa tgagc 15

<210> SEQ ID NO 209
<211> LENGTH: 48
<212> TYPE: DNA
<213> ORGANISM: Oryctolagus cuniculus

<400> SEQUENCE: 209
gtcattacta gtattggtag cacagtctac gcgagctggg cgaaaggc 48

<210> SEQ ID NO 210
<211> LENGTH: 39
<212> TYPE: DNA
<213> ORGANISM: Oryctolagus cuniculus

<400> SEQUENCE: 210
ggctacgatg actatgatga gatgacctac tttaacatc 39

<210> SEQ ID NO 211
<211> LENGTH: 333
<212> TYPE: DNA
<213> ORGANISM: Artificial Sequence
<220> FEATURE:
<223> OTHER INFORMATION: Chemically Synthesized

<400> SEQUENCE: 211
gacatccaga tgacccagtc tccttccacc ctgtctgcat ctgtaggaga cagagtcacc 60
atcacttgcc aggccagtca gaacatttac agcaacttag cctggtatca gcagaaacca 120
ggaaaagccc ctaagctcct gatctatggt gcatccaatc tggatgctgg agtcccatca 180
aggttctctg gcagtggatc tgggacagag tacactctca ccatcagcag cctgcagcct 240
gatgattttg caacttacta ctgccaaagt gcttttgata gtgatagtac tgaaaacact 300
ttcggcggag gaaccaaggt ggaaatcaaa cgt 333

<210> SEQ ID NO 212
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 212
gacatccaga tgacccagtc tccttccacc ctgtctgcat ctgtaggaga cagagtcacc 60
atcacttgcc aggccagtca gaacatttac agcaacttag cctggtatca gcagaaacca 120

```
ggaaaagccc ctaagctcct gatctatggt gcatccaatc tggatgctgg agtcccatca    180

aggttctctg gcagtggatc tgggacagag tacactctca ccatcagcag cctgcagcct    240

gatgattttg caacttacta ctgccaaagt gcttttgata gtgatagtac tgaaaacact    300

ttcggcggag gaaccaaggt ggaaatcaaa cgtacggtag cggccccatc tgtcttcatc    360

ttcccgccat ctgatgagca gttgaaatct ggaactgcct ctgttgtgtg cctgctgaat    420

aacttctatc ccagagaggc caaagtacag tggaaggtgg ataacgccct ccaatcgggt    480

aactcccagg agagtgtcac agagcaggac agcaaggaca gcacctacag cctcagcagc    540

accctgacgc tgagcaaagc agactacgag aaacacaaag tctacgcctg cgaagtcacc    600

catcagggcc tgagctcgcc cgtcacaaag agcttcaaca ggggagagtg ttag          654
```

```
<210> SEQ ID NO 213
<211> LENGTH: 363
<212> TYPE: DNA
<213> ORGANISM: Artificial Sequence
<220> FEATURE:
<223> OTHER INFORMATION: Chemically Synthesized

<400> SEQUENCE: 213

gaggtgcagc tggtggagtc tgggggaggc ttggtccagc ctggggggtc cctgagactc     60

tcctgtgcag cctctggatt caccgtcagt agctatgcaa tgagctgggt ccgtcaggct    120

ccagggaagg ggctggagtg ggtcggagtc attactagta ttggtagcac agtctacgcg    180

agcagcgcga aaggccgatt caccatctcc agagacaatt ccaagaacac cctgtatctt    240

caaatgaaca gcctgagagc tgaggacact gctgtgtatt actgtgctag aggctacgat    300

gactatgatg agatgaccta ctttaacatc tggggccaag ggaccctcgt caccgtctcg    360

agc                                                                  363
```

```
<210> SEQ ID NO 214
<211> LENGTH: 1356
<212> TYPE: DNA
<213> ORGANISM: Artificial Sequence
<220> FEATURE:
<223> OTHER INFORMATION: Chemically Synthesized

<400> SEQUENCE: 214

gaggtgcagc tggtggagtc tgggggaggc ttggtccagc ctggggggtc cctgagactc     60

tcctgtgcag cctctggatt caccgtcagt agctatgcaa tgagctgggt ccgtcaggct    120

ccagggaagg ggctggagtg ggtcggagtc attactagta ttggtagcac agtctacgcg    180

agcagcgcga aaggccgatt caccatctcc agagacaatt ccaagaacac cctgtatctt    240

caaatgaaca gcctgagagc tgaggacact gctgtgtatt actgtgctag aggctacgat    300

gactatgatg agatgaccta ctttaacatc tggggccaag ggaccctcgt caccgtctcg    360

agcgcctcca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gagagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840
```

tggtacgtgg acggcgtgga ggtgcataat gccaagacaa agccgcggga ggagcagtac 900
gccagcacgt accgtgtggt cagcgtcctc accgtcctgc accaggactg gctgaatggc 960
aaggagtaca agtgcaaggt ctccaacaaa gccctcccag cccccatcga gaaaaccatc 1020
tccaaagcca aagggcagcc ccgagaacca caggtgtaca ccctgccccc atcccgggag 1080
gagatgacca agaaccaggt cagcctgacc tgcctggtca aaggcttcta tcccagcgac 1140
atcgccgtgg agtgggagag caatgggcag ccggagaaca actacaagac cacgcctccc 1200
gtgctggact ccgacggctc cttcttcctc tacagcaagc tcaccgtgga caagagcagg 1260
tggcagcagg ggaacgtctt ctcatgctcc gtgatgcatg aggctctgca caaccactac 1320
acgcagaaga gcctctccct gtctccgggt aaatga 1356

<210> SEQ ID NO 215
<211> LENGTH: 33
<212> TYPE: DNA
<213> ORGANISM: Oryctolagus cuniculus

<400> SEQUENCE: 215
caggccagtc agaacattta cagcaactta gcc 33

<210> SEQ ID NO 216
<211> LENGTH: 21
<212> TYPE: DNA
<213> ORGANISM: Oryctolagus cuniculus

<400> SEQUENCE: 216
ggtgcatcca atctggatgc t 21

<210> SEQ ID NO 217
<211> LENGTH: 36
<212> TYPE: DNA
<213> ORGANISM: Oryctolagus cuniculus

<400> SEQUENCE: 217
caaagtgctt ttgatagtga tagtactgaa aacact 36

<210> SEQ ID NO 218
<211> LENGTH: 15
<212> TYPE: DNA
<213> ORGANISM: Oryctolagus cuniculus

<400> SEQUENCE: 218
agctatgcaa tgagc 15

<210> SEQ ID NO 219
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 219
gtcattacta gtattggtag cacagtctac gcgagcagcg cgaaaggc 48

<210> SEQ ID NO 220
<211> LENGTH: 39
<212> TYPE: DNA
<213> ORGANISM: Oryctolagus cuniculus

<400> SEQUENCE: 220
ggctacgatg actatgatga gatgacctac tttaacatc 39

<210> SEQ ID NO 221
<211> LENGTH: 336
<212> TYPE: DNA
<213> ORGANISM: Oryctolagus cuniculus

<400> SEQUENCE: 221
gcagccgtgc tgacccagac accatcgccc gtgtctgcag ctatgggaga cacagtcacc 60
atcaagtgcc agtccagtca gagtgtttat aagaacaact acttatcctg gtatcagcag 120
aaaccagggc agcctcccag gctcctgatc tatgatgcat ccaatctgcc atctggggtc 180
ccatcacggt tcagcggcag tggatctggg acacagttca ctctcaccat cagcggcgtg 240
cagtgtgacg atgctgccac ttactactgt ctaggcgatt atgatgatga tgctgataat 300
gctttcggcg gagggaccga ggtggtggtc aaacgt 336

<210> SEQ ID NO 222
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 222
gcagccgtgc tgacccagac accatcgccc gtgtctgcag ctatgggaga cacagtcacc 60
atcaagtgcc agtccagtca gagtgtttat aagaacaact acttatcctg gtatcagcag 120
aaaccagggc agcctcccag gctcctgatc tatgatgcat ccaatctgcc atctggggtc 180
ccatcacggt tcagcggcag tggatctggg acacagttca ctctcaccat cagcggcgtg 240
cagtgtgacg atgctgccac ttactactgt ctaggcgatt atgatgatga tgctgataat 300
gctttcggcg gagggaccga ggtggtggtc aaacgtacgg tagcggcccc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgttag 657

<210> SEQ ID NO 223
<211> LENGTH: 339
<212> TYPE: DNA
<213> ORGANISM: Oryctolagus cuniculus

<400> SEQUENCE: 223
cagtcggtgg aggagtccgg gggtcgcctg gtcacgcctg ggacacccct gacactcacc 60
tgcacagtct ctggattctc cctcagtagc tatgtaatga tctgggtccg ccaggctcca 120
gggaaggggc tggaatacat cggaatcact tggagtgctg gtacatacta cgcgagctgg 180
gcgaaaggcc gattcaccat ctccaaaacc tcgtcgacca cggtggatct gaaaatcacc 240
agtccgacaa ccgaggacac ggccacctat ttctgtgccg gaggtggtgg tagtatttat 300
gatatttggg gcccgggcac cctggtcacc gtctcgagc 339

<210> SEQ ID NO 224
<211> LENGTH: 1332
<212> TYPE: DNA
<213> ORGANISM: Artificial Sequence
<220> FEATURE:
<223> OTHER INFORMATION: Chemically Synthesized

<400> SEQUENCE: 224
cagtcggtgg aggagtccgg gggtcgcctg gtcacgcctg ggacacccct gacactcacc 60
tgcacagtct ctggattctc cctcagtagc tatgtaatga tctgggtccg ccaggctcca 120
gggaaggggc tggaatacat cggaatcact tggagtgctg gtacatacta cgcgagctgg 180
gcgaaaggcc gattcaccat ctccaaaacc tcgtcgacca cggtggatct gaaaatcacc 240
agtccgacaa ccgaggacac ggccacctat ttctgtgccg gaggtggtgg tagtatttat 300
gatatttggg gcccgggcac cctggtcacc gtctcgagcg cctccaccaa gggcccatcg 360
gtcttccccc tggcaccctc ctccaagagc acctctgggg gcacagcggc cctgggctgc 420
ctggtcaagg actacttccc cgaaccggtg acggtgtcgt ggaactcagg cgccctgacc 480
agcggcgtgc acaccttccc ggctgtccta cagtcctcag gactctactc cctcagcagc 540
gtggtgaccg tgccctccag cagcttgggc acccagacct acatctgcaa cgtgaatcac 600
aagcccagca acaccaaggt ggacaagaga gttgagccca aatcttgtga caaaactcac 660
acatgcccac cgtgcccagc acctgaactc ctggggggac cgtcagtctt cctcttcccc 720
ccaaaaccca aggacaccct catgatctcc cggacccctg aggtcacatg cgtggtggtg 780
gacgtgagcc acgaagaccc tgaggtcaag ttcaactggt acgtggacgg cgtggaggtg 840
cataatgcca agacaaagcc gcgggaggag cagtacgcca gcacgtaccg tgtggtcagc 900
gtcctcaccg tcctgcacca ggactggctg aatggcaagg agtacaagtg caaggtctcc 960
aacaaagccc tcccagcccc catcgagaaa accatctcca aagccaaagg gcagccccga 1020
gaaccacagg tgtacaccct gcccccatcc cgggaggaga tgaccaagaa ccaggtcagc 1080
ctgacctgcc tggtcaaagg cttctatccc agcgacatcg ccgtggagtg ggagagcaat 1140
gggcagccgg agaacaacta caagaccacg cctcccgtgc tggactccga cggctccttc 1200
ttcctctaca gcaagctcac cgtggacaag agcaggtggc agcaggggaa cgtcttctca 1260
tgctccgtga tgcatgaggc tctgcacaac cactacacgc agaagagcct ctccctgtct 1320
ccgggtaaat ga 1332

<210> SEQ ID NO 225
<211> LENGTH: 39
<212> TYPE: DNA
<213> ORGANISM: Oryctolagus cuniculus

<400> SEQUENCE: 225
cagtccagtc agagtgttta taagaacaac tacttatcc 39

<210> SEQ ID NO 226
<211> LENGTH: 21
<212> TYPE: DNA
<213> ORGANISM: Oryctolagus cuniculus

<400> SEQUENCE: 226
gatgcatcca atctgccatc t 21

<210> SEQ ID NO 227
<211> LENGTH: 33
<212> TYPE: DNA
<213> ORGANISM: Oryctolagus cuniculus

<400> SEQUENCE: 227
ctaggcgatt atgatgatga tgctgataat gct 33

<210> SEQ ID NO 228
<211> LENGTH: 15
<212> TYPE: DNA
<213> ORGANISM: Oryctolagus cuniculus

<400> SEQUENCE: 228
agctatgtaa tgatc 15

<210> SEQ ID NO 229
<211> LENGTH: 45
<212> TYPE: DNA
<213> ORGANISM: Oryctolagus cuniculus

<400> SEQUENCE: 229
atcacttgga gtgctggtac atactacgcg agctgggcga aaggc 45

<210> SEQ ID NO 230
<211> LENGTH: 24
<212> TYPE: DNA
<213> ORGANISM: Oryctolagus cuniculus

<400> SEQUENCE: 230
ggtggtggta gtatttatga tatt 24

<210> SEQ ID NO 231
<211> LENGTH: 336
<212> TYPE: DNA
<213> ORGANISM: Artificial Sequence
<220> FEATURE:
<223> OTHER INFORMATION: Chemically Synthesized

<400> SEQUENCE: 231
gacatccaga tgacccagtc tccttccacc ctgtctgcat ctgtaggaga cagagtcacc 60
atcacttgcc agtccagtca gagtgtctat aagaacaact acttatcctg gtatcagcag 120
aaaccaggaa aagcccctaa gctcctgatc tatgatgcat ccaatctgcc atctggagtc 180
ccatcaaggt tcagcggcag tggatctgga acagaattca ctctcaccat cagcagcctg 240
cagcctgatg attttgcaac ttattactgc ctaggcgatt atgatgatga tgctgataat 300
gctttcggcg gaggaaccaa ggtggaaatc aaacgt 336

<210> SEQ ID NO 232
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 232
gacatccaga tgacccagtc tccttccacc ctgtctgcat ctgtaggaga cagagtcacc 60
atcacttgcc agtccagtca gagtgtctat aagaacaact acttatcctg gtatcagcag 120
aaaccaggaa aagcccctaa gctcctgatc tatgatgcat ccaatctgcc atctggagtc 180
ccatcaaggt tcagcggcag tggatctgga acagaattca ctctcaccat cagcagcctg 240
cagcctgatg attttgcaac ttattactgc ctaggcgatt atgatgatga tgctgataat 300
gctttcggcg gaggaaccaa ggtggaaatc aaacgtacgg tagcggcccc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgttag 657

<210> SEQ ID NO 233
<211> LENGTH: 345
<212> TYPE: DNA
<213> ORGANISM: Artificial Sequence
<220> FEATURE:
<223> OTHER INFORMATION: Chemically Synthesized

<400> SEQUENCE: 233
gaggtgcagc tggtggagtc tgggggaggc ttggtccagc ctggggggtc cctgagactc 60
tcctgtgcag cctctggatt caccgtcagt agctatgtaa tgatctgggt ccgtcaggct 120
ccagggaagg ggctggagta catcggaatc acttggagtg ctggtacata ctacgcgagc 180
agtgcgaaag gccgattcac catctccaga gacaattcca agaacaccct gtatcttcaa 240
atgaacagcc tgagagctga ggacactgct gtgtattact gtgctggagg tggtggtagt 300
atctatgata tttggggcca agggaccctc gtcaccgtct cgagc 345

<210> SEQ ID NO 234
<211> LENGTH: 1338
<212> TYPE: DNA
<213> ORGANISM: Artificial Sequence
<220> FEATURE:
<223> OTHER INFORMATION: Chemically Synthesized

<400> SEQUENCE: 234
gaggtgcagc tggtggagtc tgggggaggc ttggtccagc ctggggggtc cctgagactc 60
tcctgtgcag cctctggatt caccgtcagt agctatgtaa tgatctgggt ccgtcaggct 120
ccagggaagg ggctggagta catcggaatc acttggagtg ctggtacata ctacgcgagc 180
agtgcgaaag gccgattcac catctccaga gacaattcca agaacaccct gtatcttcaa 240
atgaacagcc tgagagctga ggacactgct gtgtattact gtgctggagg tggtggtagt 300
atctatgata tttggggcca agggaccctc gtcaccgtct cgagcgcctc caccaagggc 360
ccatcggtct tccccctggc accctcctcc aagagcacct ctgggggcac agcggccctg 420
ggctgcctgg tcaaggacta cttccccgaa ccggtgacgg tgtcgtggaa ctcaggcgcc 480
ctgaccagcg gcgtgcacac cttcccggct gtcctacagt cctcaggact ctactccctc 540
agcagcgtgg tgaccgtgcc ctccagcagc ttgggcaccc agacctacat ctgcaacgtg 600
aatcacaagc ccagcaacac caaggtggac aagagagttg agcccaaatc ttgtgacaaa 660
actcacacat gcccaccgtg cccagcacct gaactcctgg ggggaccgtc agtcttcctc 720
ttccccccaa aacccaagga caccctcatg atctcccgga cccctgaggt cacatgcgtg 780
gtggtggacg tgagccacga agaccctgag gtcaagttca actggtacgt ggacggcgtg 840
gaggtgcata atgccaagac aaagccgcgg gaggagcagt acgccagcac gtaccgtgtg 900
gtcagcgtcc tcaccgtcct gcaccaggac tggctgaatg gcaaggagta caagtgcaag 960
gtctccaaca aagccctccc agcccccatc gagaaaacca tctccaaagc caaagggcag 1020
ccccgagaac cacaggtgta caccctgccc ccatcccggg aggagatgac caagaaccag 1080
gtcagcctga cctgcctggt caaaggcttc tatcccagcg acatcgccgt ggagtgggag 1140
agcaatgggc agccggagaa caactacaag accacgcctc ccgtgctgga ctccgacggc 1200
tccttcttcc tctacagcaa gctcaccgtg gacaagagca ggtggcagca ggggaacgtc 1260
ttctcatgct ccgtgatgca tgaggctctg cacaaccact acacgcagaa gagcctctcc 1320
ctgtctccgg gtaaatga 1338

<210> SEQ ID NO 235
<211> LENGTH: 39
<212> TYPE: DNA
<213> ORGANISM: Oryctolagus cuniculus

<400> SEQUENCE: 235
cagtccagtc agaatgttta taagaacaac tacttatcc 39

<210> SEQ ID NO 236
<211> LENGTH: 21
<212> TYPE: DNA
<213> ORGANISM: Oryctolagus cuniculus

<400> SEQUENCE: 236
aaggcatcca ctctggcatc t 21

<210> SEQ ID NO 237
<211> LENGTH: 32
<212> TYPE: DNA
<213> ORGANISM: Oryctolagus cuniculus

<400> SEQUENCE: 237
gcaggcggtt ataccagtag tagtgataat gc 32

<210> SEQ ID NO 238
<211> LENGTH: 15
<212> TYPE: DNA
<213> ORGANISM: Oryctolagus cuniculus

<400> SEQUENCE: 238
agctatgtaa tgatc 15

<210> SEQ ID NO 239
<211> LENGTH: 45
<212> TYPE: DNA
<213> ORGANISM: Artificial Sequence
<220> FEATURE:
<223> OTHER INFORMATION: Chemically Synthesized

<400> SEQUENCE: 239
atcacttgga gtgctggtac atactacgcg agcagtgcga aaggc 45

<210> SEQ ID NO 240
<211> LENGTH: 24
<212> TYPE: DNA
<213> ORGANISM: Oryctolagus cuniculus

<400> SEQUENCE: 240
ggtggtggta gtatctatga tatt 24

<210> SEQ ID NO 241
<211> LENGTH: 333
<212> TYPE: DNA
<213> ORGANISM: Oryctolagus cuniculus

<400> SEQUENCE: 241
gcctatgata tgacccagac tccagcctct gtggaggtag ctgtgggagg cacagtcacc 60
atcaagtgcc aggccagtca gagcatttac agcaatttag cctggtatca gcagagacca 120
gggcagcctc ccaagctcct gatctatgat gcatccactc tggaatctgg ggtcccatcg 180
cggttcaaag gcagtggatc tgggacagag tacactctca ccatcagcgg cgtggagtgt 240
gccgatgctg cctcttacta ctgtcaacag ggttttactg ttagtgatat tgataatgct 300
ttcggcggag ggaccgaggt ggtggtcaaa cgt 333

<210> SEQ ID NO 242
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 242
gcctatgata tgacccagac tccagcctct gtggaggtag ctgtgggagg cacagtcacc 60
atcaagtgcc aggccagtca gagcatttac agcaatttag cctggtatca gcagagacca 120
gggcagcctc ccaagctcct gatctatgat gcatccactc tggaatctgg ggtcccatcg 180
cggttcaaag gcagtggatc tgggacagag tacactctca ccatcagcgg cgtggagtgt 240
gccgatgctg cctcttacta ctgtcaacag ggttttactg ttagtgatat tgataatgct 300
ttcggcggag ggaccgaggt ggtggtcaaa cgtacggtag cggccccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg ttag 654

<210> SEQ ID NO 243
<211> LENGTH: 354
<212> TYPE: DNA
<213> ORGANISM: Oryctolagus cuniculus

<400> SEQUENCE: 243
cagtcggtgg aggagtccgg gggtcgcctg gtcacgcctg ggacacccct gacactcacc 60
tgcacagtct ctggattctc cctcagtaac tatgcagtgg gctgggtccg ccaggctcca 120
gggaaggggc tggaatggat cggaatcatt ggtcgtaatg gtaacacatg gtacgcgagc 180
tgggcaagag gccgattcac catctccaaa acctcgacca cggtggatct gaaaatcacc 240
agtccgacaa gcgaggacac ggccacatat ttctgtgcca gaggatatgg ccgtagtgtt 300
gcttattacg tctttaacat ctggggccca ggcaccctcg tcaccgtctc gagc 354

<210> SEQ ID NO 244
<211> LENGTH: 1347
<212> TYPE: DNA
<213> ORGANISM: Artificial Sequence
<220> FEATURE:
<223> OTHER INFORMATION: Chemically Synthesized

<400> SEQUENCE: 244
cagtcggtgg aggagtccgg gggtcgcctg gtcacgcctg ggacacccct gacactcacc 60
tgcacagtct ctggattctc cctcagtaac tatgcagtgg gctgggtccg ccaggctcca 120
gggaaggggc tggaatggat cggaatcatt ggtcgtaatg gtaacacatg gtacgcgagc 180
tgggcaagag gccgattcac catctccaaa acctcgacca cggtggatct gaaaatcacc 240

-continued

```
agtccgacaa gcgaggacac ggccacatat ttctgtgcca gaggatatgg ccgtagtgtt    300

gcttattacg tctttaacat ctggggccca ggcaccctcg tcaccgtctc gagcgcctcc    360

accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcaccca gacctacatc    600

tgcaacgtga atcacaagcc cagcaacacc aaggtggaca agagagttga gcccaaatct    660

tgtgacaaaa ctcacacatg cccaccgtgc ccagcacctg aactcctggg gggaccgtca    720

gtcttcctct tccccccaaa acccaaggac accctcatga tctcccggac ccctgaggtc    780

acatgcgtgg tggtggacgt gagccacgaa gaccctgagg tcaagttcaa ctggtacgtg    840

gacggcgtgg aggtgcataa tgccaagaca aagccgcggg aggagcagta cgccagcacg    900

taccgtgtgg tcagcgtcct caccgtcctg caccaggact ggctgaatgg caaggagtac    960

aagtgcaagg tctccaacaa agccctccca gcccccatcg agaaaaccat ctccaaagcc   1020

aaagggcagc cccgagaacc acaggtgtac accctgcccc catcccggga ggagatgacc   1080

aagaaccagg tcagcctgac ctgcctggtc aaaggcttct atcccagcga catcgccgtg   1140

gagtgggaga gcaatgggca gccggagaac aactacaaga ccacgcctcc cgtgctggac   1200

tccgacggct ccttcttcct ctacagcaag ctcaccgtgg acaagagcag gtggcagcag   1260

gggaacgtct tctcatgctc cgtgatgcat gaggctctgc acaaccacta cacgcagaag   1320

agcctctccc tgtctccggg taaatga                                        1347
```

<210> SEQ ID NO 245
<211> LENGTH: 33
<212> TYPE: DNA
<213> ORGANISM: Oryctolagus cuniculus

<400> SEQUENCE: 245

```
caggccagtc agagcattta cagcaattta gcc                                  33
```

<210> SEQ ID NO 246
<211> LENGTH: 21
<212> TYPE: DNA
<213> ORGANISM: Oryctolagus cuniculus

<400> SEQUENCE: 246

```
gatgcatcca ctctggaatc t                                                21
```

<210> SEQ ID NO 247
<211> LENGTH: 36
<212> TYPE: DNA
<213> ORGANISM: Oryctolagus cuniculus

<400> SEQUENCE: 247

```
caacagggtt ttactgttag tgatattgat aatgct                                36
```

<210> SEQ ID NO 248
<211> LENGTH: 15
<212> TYPE: DNA
<213> ORGANISM: Oryctolagus cuniculus

<400> SEQUENCE: 248

```
aactatgcag tgggc                                                       15
```

<210> SEQ ID NO 249
<211> LENGTH: 48
<212> TYPE: DNA
<213> ORGANISM: Oryctolagus cuniculus

<400> SEQUENCE: 249
atcattggtc gtaatggtaa cacatggtac gcgagctggg caagaggc 48

<210> SEQ ID NO 250
<211> LENGTH: 39
<212> TYPE: DNA
<213> ORGANISM: Oryctolagus cuniculus

<400> SEQUENCE: 250
ggatatggcc gtagtgttgc ttattacgtc tttaacatc 39

<210> SEQ ID NO 251
<211> LENGTH: 333
<212> TYPE: DNA
<213> ORGANISM: Artificial Sequence
<220> FEATURE:
<223> OTHER INFORMATION: Chemically Synthesized

<400> SEQUENCE: 251
gacatccaga tgacccagtc tccttccacc ctgtctgcat ctgtaggaga cagagtcacc 60
atcacttgcc aggccagtca gagcatttac agcaatcttg cctggtatca gcagaaacca 120
ggaaaagccc ctaagctcct gatctatgat gcatccactc tggaatctgg agtcccatca 180
aggttcagcg gcagtggatc tgggacagag tacactctca ccatcagcag cctgcagcct 240
gatgattttg caacttacta ctgccaacag ggttttactg ttagtgatat tgataatgct 300
ttcggcggag gaaccaaggt ggaaatcaaa cgt 333

<210> SEQ ID NO 252
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 252
gacatccaga tgacccagtc tccttccacc ctgtctgcat ctgtaggaga cagagtcacc 60
atcacttgcc aggccagtca gagcatttac agcaatcttg cctggtatca gcagaaacca 120
ggaaaagccc ctaagctcct gatctatgat gcatccactc tggaatctgg agtcccatca 180
aggttcagcg gcagtggatc tgggacagag tacactctca ccatcagcag cctgcagcct 240
gatgattttg caacttacta ctgccaacag ggttttactg ttagtgatat tgataatgct 300
ttcggcggag gaaccaaggt ggaaatcaaa cgtacggtag cggccccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg ttag 654

<210> SEQ ID NO 253
<211> LENGTH: 363
<212> TYPE: DNA
<213> ORGANISM: Artificial Sequence
<220> FEATURE:

<223> OTHER INFORMATION: Chemically Synthesized

<400> SEQUENCE: 253
gaggtgcagc tggtggagtc tgggggaggc ttggtccagc ctggggggtc cctgagactc 60
tcctgtgcag cctctggatt caccgtcagt aactatgcag tgggctgggt ccgtcaggct 120
ccagggaagg ggctggagtg ggtcggaatc attggtcgta atggtaacac atggtacgcg 180
agctctgcaa gaggccgatt caccatctcc agagacaatt ccaagaacac cctgtatctt 240
caaatgaaca gcctgagagc tgaggacact gctgtgtatt actgtgctag aggatatggc 300
cgtagtgttg cttattacgt ctttaacatc tggggcccag ggaccctcgt caccgtctcg 360
agc 363

<210> SEQ ID NO 254
<211> LENGTH: 1356
<212> TYPE: DNA
<213> ORGANISM: Artificial Sequence
<220> FEATURE:
<223> OTHER INFORMATION: Chemically Synthesized

<400> SEQUENCE: 254
gaggtgcagc tggtggagtc tgggggaggc ttggtccagc ctggggggtc cctgagactc 60
tcctgtgcag cctctggatt caccgtcagt aactatgcag tgggctgggt ccgtcaggct 120
ccagggaagg ggctggagtg ggtcggaatc attggtcgta atggtaacac atggtacgcg 180
agctctgcaa gaggccgatt caccatctcc agagacaatt ccaagaacac cctgtatctt 240
caaatgaaca gcctgagagc tgaggacact gctgtgtatt actgtgctag aggatatggc 300
cgtagtgttg cttattacgt ctttaacatc tggggcccag ggaccctcgt caccgtctcg 360
agcgcctcca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtgcacacct tcccggctgt cctacagtcc 540
tcaggactct actccctcag cagcgtggtg accgtgccct ccagcagctt gggcacccag 600
acctacatct gcaacgtgaa tcacaagccc agcaacacca aggtggacaa gagagttgag 660
cccaaatctt gtgacaaaac tcacacatgc ccaccgtgcc cagcacctga actcctgggg 720
ggaccgtcag tcttcctctt ccccccaaaa cccaaggaca ccctcatgat ctcccggacc 780
cctgaggtca catgcgtggt ggtggacgtg agccacgaag accctgaggt caagttcaac 840
tggtacgtgg acggcgtgga ggtgcataat gccaagacaa agccgcggga ggagcagtac 900
gccagcacgt accgtgtggt cagcgtcctc accgtcctgc accaggactg gctgaatggc 960
aaggagtaca agtgcaaggt ctccaacaaa gccctcccag cccccatcga gaaaaccatc 1020
tccaaagcca aagggcagcc ccgagaacca caggtgtaca ccctgccccc atcccgggag 1080
gagatgacca agaaccaggt cagcctgacc tgcctggtca aaggcttcta tcccagcgac 1140
atcgccgtgg agtgggagag caatgggcag ccggagaaca actacaagac cacgcctccc 1200
gtgctggact ccgacggctc cttcttcctc tacagcaagc tcaccgtgga caagagcagg 1260
tggcagcagg ggaacgtctt ctcatgctcc gtgatgcatg aggctctgca caaccactac 1320
acgcagaaga gcctctccct gtctccgggt aaatga 1356

<210> SEQ ID NO 255
<211> LENGTH: 33
<212> TYPE: DNA
<213> ORGANISM: Oryctolagus cuniculus

<400> SEQUENCE: 255
caggccagtc agagcattta cagcaatctt gcc 33

<210> SEQ ID NO 256
<211> LENGTH: 21
<212> TYPE: DNA
<213> ORGANISM: Oryctolagus cuniculus

<400> SEQUENCE: 256
gatgcatcca ctctggaatc t 21

<210> SEQ ID NO 257
<211> LENGTH: 36
<212> TYPE: DNA
<213> ORGANISM: Oryctolagus cuniculus

<400> SEQUENCE: 257
caacagggtt ttactgttag tgatattgat aatgct 36

<210> SEQ ID NO 258
<211> LENGTH: 15
<212> TYPE: DNA
<213> ORGANISM: Oryctolagus cuniculus

<400> SEQUENCE: 258
aactatgcag tgggc 15

<210> SEQ ID NO 259
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 259
atcattggtc gtaatggtaa cacatggtac gcgagctctg caagaggc 48

<210> SEQ ID NO 260
<211> LENGTH: 39
<212> TYPE: DNA
<213> ORGANISM: Oryctolagus cuniculus

<400> SEQUENCE: 260
ggatatggcc gtagtgttgc ttattacgtc tttaacatc 39

<210> SEQ ID NO 261
<211> LENGTH: 336
<212> TYPE: DNA
<213> ORGANISM: Oryctolagus cuniculus

<400> SEQUENCE: 261
gccgatgttg tgatgaccca gactccagcc tccgtgtctc aacctgtggg aggcacagtc 60
accatcaagt gccaggccag tgaggacatt tataacttat tggcctggta tcagcagaaa 120
ccagggcagc ctcccaagct cctgatctat tctgcatcca ctctggcatc tggggtccca 180
tcgcggttca aaggcagtgg atctgggaca gagtacactc tcaccatcag cggcctggag 240
tgtgccgatg ctgccactta ctactgtcaa aacaattatc ttgttactac ttatggtgtt 300
gctttcggcg gagggaccga ggtggtggtc aaacgt 336

<210> SEQ ID NO 262

-continued

<211> LENGTH: 657
<212> TYPE: DNA
<213> ORGANISM: Artificial Sequence
<220> FEATURE:
<223> OTHER INFORMATION: Chemically Synthesized

<400> SEQUENCE: 262
gccgatgttg tgatgaccca gactccagcc tccgtgtctc aacctgtggg aggcacagtc 60
accatcaagt gccaggccag tgaggacatt tataacttat tggcctggta tcagcagaaa 120
ccagggcagc ctcccaagct cctgatctat tctgcatcca ctctggcatc tggggtccca 180
tcgcggttca aaggcagtgg atctgggaca gagtacactc tcaccatcag cggcctggag 240
tgtgccgatg ctgccactta ctactgtcaa aacaattatc ttgttactac ttatggtgtt 300
gctttcggcg gagggaccga ggtggtggtc aaacgtacgg tagcggcccc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgttag 657

<210> SEQ ID NO 263
<211> LENGTH: 360
<212> TYPE: DNA
<213> ORGANISM: Oryctolagus cuniculus

<400> SEQUENCE: 263
caggagcagc tgaaggagtc cgggggtcgc ctggtcacgc ctgggacacc cctgacactc 60
acctgtacag tctctggatt ctccctcagt agctatgcaa tgatctgggt ccgccaggct 120
ccagggaagg ggctggaata catcggatac attgatactg atactagcgc atactacgcg 180
agctgggtga aaggccgatt caccatctcc agaacctcga ccacggtgga tctcaaaatc 240
actagtccga caaccgagga cacggccacc tatttctgtg ccagatctta tgctgcttat 300
ggtggttatc ctgctacttt tgatccctgg ggcccaggca ccctggtcac cgtctcgagc 360

<210> SEQ ID NO 264
<211> LENGTH: 1353
<212> TYPE: DNA
<213> ORGANISM: Artificial Sequence
<220> FEATURE:
<223> OTHER INFORMATION: Chemically Synthesized

<400> SEQUENCE: 264
caggagcagc tgaaggagtc cgggggtcgc ctggtcacgc ctgggacacc cctgacactc 60
acctgtacag tctctggatt ctccctcagt agctatgcaa tgatctgggt ccgccaggct 120
ccagggaagg ggctggaata catcggatac attgatactg atactagcgc atactacgcg 180
agctgggtga aaggccgatt caccatctcc agaacctcga ccacggtgga tctcaaaatc 240
actagtccga caaccgagga cacggccacc tatttctgtg ccagatctta tgctgcttat 300
ggtggttatc ctgctacttt tgatccctgg ggcccaggca ccctggtcac cgtctcgagc 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagag agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacgcc 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctac agcaagctca ccgtggacaa gagcaggtgg 1260
cagcagggga acgtcttctc atgctccgtg atgcatgagg ctctgcacaa ccactacacg 1320
cagaagagcc tctccctgtc tccgggtaaa tga 1353

<210> SEQ ID NO 265
<211> LENGTH: 33
<212> TYPE: DNA
<213> ORGANISM: Oryctolagus cuniculus

<400> SEQUENCE: 265
caggccagtg aggacattta taacttattg gcc 33

<210> SEQ ID NO 266
<211> LENGTH: 21
<212> TYPE: DNA
<213> ORGANISM: Oryctolagus cuniculus

<400> SEQUENCE: 266
tctgcatcca ctctggcatc t 21

<210> SEQ ID NO 267
<211> LENGTH: 36
<212> TYPE: DNA
<213> ORGANISM: Oryctolagus cuniculus

<400> SEQUENCE: 267
caaaacaatt atcttgttac tacttatggt gttgct 36

<210> SEQ ID NO 268
<211> LENGTH: 15
<212> TYPE: DNA
<213> ORGANISM: Oryctolagus cuniculus

<400> SEQUENCE: 268
agctatgcaa tgatc 15

<210> SEQ ID NO 269
<211> LENGTH: 48
<212> TYPE: DNA
<213> ORGANISM: Oryctolagus cuniculus

<400> SEQUENCE: 269
tacattgata ctgatactag cgcatactac gcgagctggg tgaaaggc 48

<210> SEQ ID NO 270

<211> LENGTH: 36
<212> TYPE: DNA
<213> ORGANISM: Oryctolagus cuniculus

<400> SEQUENCE: 270
tcttatgctg cttatggtgg ttatcctgct actttt 36

<210> SEQ ID NO 271
<211> LENGTH: 333
<212> TYPE: DNA
<213> ORGANISM: Artificial Sequence
<220> FEATURE:
<223> OTHER INFORMATION: Chemically Synthesized

<400> SEQUENCE: 271
gacatccaga tgacccagtc tccatcctcc ctgtctgcat ctgtaggaga cagagtcacc 60
atcacttgcc aggccagtga ggacatttac aacttattgg cctggtatca gcagaaacca 120
gggaaagtcc ctaagctcct gatctattct gcatccactc tggcatctgg ggtcccatct 180
cgtttcagtg gcagtggatc tgggacagat tacactctca ccatcagcag cctgcagcct 240
gaagatgttg caacttatta ctgtcaaaac aactatcttg ttactactta tggtgttgct 300
ttcggcggag gaaccaaggt ggaaatcaaa cgt 333

<210> SEQ ID NO 272
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 272
gacatccaga tgacccagtc tccatcctcc ctgtctgcat ctgtaggaga cagagtcacc 60
atcacttgcc aggccagtga ggacatttac aacttattgg cctggtatca gcagaaacca 120
gggaaagtcc ctaagctcct gatctattct gcatccactc tggcatctgg ggtcccatct 180
cgtttcagtg gcagtggatc tgggacagat tacactctca ccatcagcag cctgcagcct 240
gaagatgttg caacttatta ctgtcaaaac aactatcttg ttactactta tggtgttgct 300
ttcggcggag gaaccaaggt ggaaatcaaa cgtacggtag cggccccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg ttag 654

<210> SEQ ID NO 273
<211> LENGTH: 366
<212> TYPE: DNA
<213> ORGANISM: Artificial Sequence
<220> FEATURE:
<223> OTHER INFORMATION: Chemically Synthesized

<400> SEQUENCE: 273
caggtacagc tggtggagtc tggtggaggc gtggtccagc ctgggaggtc cctgagactc 60
tcctgtgcag cttctggatt caccttcagt agctatgcaa tgatctgggt ccgccaggct 120
ccagggaagg ggctggaata catcggatac attgatactg atactagcgc atactacgca 180
agcagtgtga aaggccgatt caccatctcc agagacaatt ccaagaacac gctgtacctg 240
caaatgtcta gcctgagagc cgaggacacg gctgtgtatt actgtgctag atcttatgct 300
gcttatggtg gttatcctgc tacttttgat ccctggggcc aaggtaccct cgtcaccgtc 360
tcgagc 366

<210> SEQ ID NO 274
<211> LENGTH: 1359
<212> TYPE: DNA
<213> ORGANISM: Artificial Sequence
<220> FEATURE:
<223> OTHER INFORMATION: Chemically Synthesized

<400> SEQUENCE: 274
caggtacagc tggtggagtc tggtggaggc gtggtccagc ctgggaggtc cctgagactc 60
tcctgtgcag cttctggatt caccttcagt agctatgcaa tgatctgggt ccgccaggct 120
ccagggaagg ggctggaata catcggatac attgatactg atactagcgc atactacgca 180
agcagtgtga aaggccgatt caccatctcc agagacaatt ccaagaacac gctgtacctg 240
caaatgtcta gcctgagagc cgaggacacg gctgtgtatt actgtgctag atcttatgct 300
gcttatggtg gttatcctgc tacttttgat ccctggggcc aaggtaccct cgtcaccgtc 360
tcgagcgcct ccaccaaggg cccatcggtc ttccccctgg caccctcctc caagagcacc 420
tctgggggca cagcggccct gggctgcctg gtcaaggact acttccccga accggtgacg 480
gtgtcgtgga actcaggcgc cctgaccagc ggcgtgcaca ccttcccggc tgtcctacag 540
tcctcaggac tctactccct cagcagcgtg gtgaccgtgc cctccagcag cttgggcacc 600
cagacctaca tctgcaacgt gaatcacaag cccagcaaca ccaaggtgga caagagagtt 660
gagcccaaat cttgtgacaa aactcacaca tgcccaccgt gcccagcacc tgaactcctg 720
gggggaccgt cagtcttcct cttcccccca aaacccaagg acaccctcat gatctcccgg 780
acccctgagg tcacatgcgt ggtggtggac gtgagccacg aagaccctga ggtcaagttc 840
aactggtacg tggacggcgt ggaggtgcat aatgccaaga caaagccgcg ggaggagcag 900
tacgccagca cgtaccgtgt ggtcagcgtc ctcaccgtcc tgcaccagga ctggctgaat 960
ggcaaggagt acaagtgcaa ggtctccaac aaagccctcc cagcccccat cgagaaaacc 1020
atctccaaag ccaaagggca gccccgagaa ccacaggtgt acaccctgcc cccatcccgg 1080
gaggagatga ccaagaacca ggtcagcctg acctgcctgg tcaaaggctt ctatcccagc 1140
gacatcgccg tggagtggga gagcaatggg cagccggaga acaactacaa gaccacgcct 1200
cccgtgctgg actccgacgg ctccttcttc ctctacagca agctcaccgt ggacaagagc 1260
aggtggcagc aggggaacgt cttctcatgc tccgtgatgc atgaggctct gcacaaccac 1320
tacacgcaga agagcctctc cctgtctccg ggtaaatga 1359

<210> SEQ ID NO 275
<211> LENGTH: 33
<212> TYPE: DNA
<213> ORGANISM: Oryctolagus cuniculus

<400> SEQUENCE: 275
caggccagtg aggacattta caacttattg gcc 33

<210> SEQ ID NO 276
<211> LENGTH: 21
<212> TYPE: DNA
<213> ORGANISM: Oryctolagus cuniculus

<400> SEQUENCE: 276
tctgcatcca ctctggcatc t 21

<210> SEQ ID NO 277
<211> LENGTH: 36
<212> TYPE: DNA
<213> ORGANISM: Oryctolagus cuniculus

<400> SEQUENCE: 277
caaaacaact atcttgttac tacttatggt gttgct 36

<210> SEQ ID NO 278
<211> LENGTH: 15
<212> TYPE: DNA
<213> ORGANISM: Oryctolagus cuniculus

<400> SEQUENCE: 278
agctatgcaa tgatc 15

<210> SEQ ID NO 279
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 279
tacattgata ctgatactag cgcatactac gcaagcagtg tgaaaggc 48

<210> SEQ ID NO 280
<211> LENGTH: 42
<212> TYPE: DNA
<213> ORGANISM: Oryctolagus cuniculus

<400> SEQUENCE: 280
tcttatgctg cttatggtgg ttatcctgct acttttgatc cc 42

<210> SEQ ID NO 281
<211> LENGTH: 333
<212> TYPE: DNA
<213> ORGANISM: Oryctolagus cuniculus

<400> SEQUENCE: 281
gcctatgata tgacccagac tccagcctcc gtgtctgcag ctgtgggagg cacagtcacc 60
atcaagtgcc aggccagtga gaacattggt agctacttag cctggtatca gcagaaacca 120
gggcagcctc ccgaactcct gatctacagg gcgtccactc tggcatctgg ggtcccatcg 180
cggttcaaag gcagtggatc tgggacacag ttcactctca ccatcagcgg cgtggagtgt 240
gccgatgctg ccacttacta ctgtcaacag ggttataata gtgagaatct tgataatgct 300
ttcggcggag ggaccgaggt ggtggtcaaa cgt 333

<210> SEQ ID NO 282
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 282
gcctatgata tgacccagac tccagcctcc gtgtctgcag ctgtgggagg cacagtcacc 60
atcaagtgcc aggccagtga gaacattggt agctacttag cctggtatca gcagaaacca 120
gggcagcctc ccgaactcct gatctacagg gcgtccactc tggcatctgg ggtcccatcg 180
cggttcaaag gcagtggatc tgggacacag ttcactctca ccatcagcgg cgtggagtgt 240
gccgatgctg ccacttacta ctgtcaacag ggttataata gtgagaatct tgataatgct 300
ttcggcggag ggaccgaggt ggtggtcaaa cgtacggtag cggccccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg ttag 654

<210> SEQ ID NO 283
<211> LENGTH: 345
<212> TYPE: DNA
<213> ORGANISM: Oryctolagus cuniculus

<400> SEQUENCE: 283
cagtcggtgg aggagtccgg gggtcgcctg gtcacgcctg ggacacccct gacactcacc 60
tgcacagtct ctggaatcga cctcagtatg tattcaatgg gctgggtccg ccaggctcca 120
gggaaggggc tggaatacat cggatggatt agttatggtg gtactgcata ttacgcgagc 180
tgggcgaagg gccgattcac catctccaaa acctcgacca cggtggagct gaagatcacc 240
agtccgacaa tcgaggacac ggccacctat ttctgtgcca gagagactcc tgttaattat 300
tatttggaca tttggggcca ggggaccctc gtcaccgtct cgagc 345

<210> SEQ ID NO 284
<211> LENGTH: 1338
<212> TYPE: DNA
<213> ORGANISM: Artificial Sequence
<220> FEATURE:
<223> OTHER INFORMATION: Chemically Synthesized

<400> SEQUENCE: 284
cagtcggtgg aggagtccgg gggtcgcctg gtcacgcctg ggacacccct gacactcacc 60
tgcacagtct ctggaatcga cctcagtatg tattcaatgg gctgggtccg ccaggctcca 120
gggaaggggc tggaatacat cggatggatt agttatggtg gtactgcata ttacgcgagc 180
tgggcgaagg gccgattcac catctccaaa acctcgacca cggtggagct gaagatcacc 240
agtccgacaa tcgaggacac ggccacctat ttctgtgcca gagagactcc tgttaattat 300
tatttggaca tttggggcca ggggaccctc gtcaccgtct cgagcgcctc caccaagggc 360
ccatcggtct tccccctggc accctcctcc aagagcacct ctgggggcac agcggccctg 420
ggctgcctgg tcaaggacta cttccccgaa ccggtgacgg tgtcgtggaa ctcaggcgcc 480
ctgaccagcg gcgtgcacac cttcccggct gtcctacagt cctcaggact ctactccctc 540
agcagcgtgg tgaccgtgcc ctccagcagc ttgggcaccc agacctacat ctgcaacgtg 600
aatcacaagc ccagcaacac caaggtggac aagagagttg agcccaaatc ttgtgacaaa 660
actcacacat gcccaccgtg cccagcacct gaactcctgg ggggaccgtc agtcttcctc 720
ttccccccaa aacccaagga caccctcatg atctcccgga cccctgaggt cacatgcgtg 780
gtggtggacg tgagccacga agaccctgag gtcaagttca actggtacgt ggacggcgtg 840
gaggtgcata atgccaagac aaagccgcgg gaggagcagt acgccagcac gtaccgtgtg 900
gtcagcgtcc tcaccgtcct gcaccaggac tggctgaatg gcaaggagta caagtgcaag 960
gtctccaaca aagccctccc agcccccatc gagaaaacca tctccaaagc caaagggcag 1020
ccccgagaac cacaggtgta caccctgccc ccatcccggg aggagatgac caagaaccag 1080
gtcagcctga cctgcctggt caaaggcttc tatcccagcg acatcgccgt ggagtgggag 1140
agcaatgggc agccggagaa caactacaag accacgcctc ccgtgctgga ctccgacggc 1200
tccttcttcc tctacagcaa gctcaccgtg gacaagagca ggtggcagca ggggaacgtc 1260
ttctcatgct ccgtgatgca tgaggctctg cacaaccact acacgcagaa gagcctctcc 1320
ctgtctccgg gtaaatga 1338

<210> SEQ ID NO 285
<211> LENGTH: 33
<212> TYPE: DNA
<213> ORGANISM: Oryctolagus cuniculus

<400> SEQUENCE: 285
caggccagtg agaacattgg tagctactta gcc 33

<210> SEQ ID NO 286
<211> LENGTH: 21
<212> TYPE: DNA
<213> ORGANISM: Oryctolagus cuniculus

<400> SEQUENCE: 286
agggcgtcca ctctggcatc t 21

<210> SEQ ID NO 287
<211> LENGTH: 36
<212> TYPE: DNA
<213> ORGANISM: Oryctolagus cuniculus

<400> SEQUENCE: 287
caacagggtt ataatagtga gaatcttgat aatgct 36

<210> SEQ ID NO 288
<211> LENGTH: 15
<212> TYPE: DNA
<213> ORGANISM: Oryctolagus cuniculus

<400> SEQUENCE: 288
atgtattcaa tgggc 15

<210> SEQ ID NO 289
<211> LENGTH: 48
<212> TYPE: DNA
<213> ORGANISM: Oryctolagus cuniculus

<400> SEQUENCE: 289
tggattagtt atggtggtac tgcatattac gcgagctggg cgaagggc 48

<210> SEQ ID NO 290
<211> LENGTH: 30
<212> TYPE: DNA
<213> ORGANISM: Oryctolagus cuniculus

<400> SEQUENCE: 290
gagactcctg ttaattatta tttggacatt 30

<210> SEQ ID NO 291
<211> LENGTH: 333

<212> TYPE: DNA
<213> ORGANISM: Artificial Sequence
<220> FEATURE:
<223> OTHER INFORMATION: Chemically Synthesized

<400> SEQUENCE: 291
gcctatgata tgacccagtc tccatcctcc ctgtctgcat ctgtaggaga cagagtcacc 60
atcacttgcc aggccagtga gaacattggt agctacttag cctggtatca gcagaaacca 120
gggaaagtcc ctaagctcct gatctatagg gcttccactc tggcatctgg ggtcccatct 180
cgtttcagtg gcagtggatc tgggacagat ttcactctca ccatcagcag cctgcagcct 240
gaagatgttg caacttatta ctgtcaacag ggttacaata gtgagaatct tgataatgct 300
ttcggcggag gaaccaaggt ggaaatcaaa cgt 333

<210> SEQ ID NO 292
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 292
gcctatgata tgacccagtc tccatcctcc ctgtctgcat ctgtaggaga cagagtcacc 60
atcacttgcc aggccagtga gaacattggt agctacttag cctggtatca gcagaaacca 120
gggaaagtcc ctaagctcct gatctatagg gcttccactc tggcatctgg ggtcccatct 180
cgtttcagtg gcagtggatc tgggacagat ttcactctca ccatcagcag cctgcagcct 240
gaagatgttg caacttatta ctgtcaacag ggttacaata gtgagaatct tgataatgct 300
ttcggcggag gaaccaaggt ggaaatcaaa cgtacggtag cggccccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg ttag 654

<210> SEQ ID NO 293
<211> LENGTH: 354
<212> TYPE: DNA
<213> ORGANISM: Artificial Sequence
<220> FEATURE:
<223> OTHER INFORMATION: Chemically Synthesized

<400> SEQUENCE: 293
caggtacagc tggtggagtc tggtggaggc gtggtccagc ctgggaggtc cctgagactc 60
tcctgtgcag cttctggatt caccttcagt atgtattcaa tgggctgggt ccgccaggct 120
ccagggaagg ggctggaata catcggatgg attagttatg gtggtactgc atactacgct 180
agcagcgcta agggccgatt caccatctcc agagacaatt ccaagaacac gctgtacctg 240
caaatgtcta gcctgagagc cgaggacacg gctgtgtatt actgtgctag agagactcct 300
gttaattact acttggacat ttggggccaa ggtaccctcg tcaccgtctc gagc 354

<210> SEQ ID NO 294
<211> LENGTH: 1347
<212> TYPE: DNA
<213> ORGANISM: Artificial Sequence
<220> FEATURE:

-continued

<223> OTHER INFORMATION: Chemically Synthesized

<400> SEQUENCE: 294

```
caggtacagc tggtggagtc tggtggaggc gtggtccagc ctgggaggtc cctgagactc      60
tcctgtgcag cttctggatt caccttcagt atgtattcaa tgggctgggt ccgccaggct     120
ccagggaagg ggctggaata catcggatgg attagttatg gtggtactgc atactacgct     180
agcagcgcta agggccgatt caccatctcc agagacaatt ccaagaacac gctgtacctg     240
caaatgtcta gcctgagagc cgaggacacg gctgtgtatt actgtgctag agagactcct     300
gttaattact acttggacat ttggggccaa ggtaccctcg tcaccgtctc gagcgcctcc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct tgggcaccca gacctacatc     600
tgcaacgtga atcacaagcc cagcaacacc aaggtggaca agagagttga gcccaaatct     660
tgtgacaaaa ctcacacatg cccaccgtgc ccagcacctg aactcctggg gggaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta cgccagcacg     900
taccgtgtgg tcagcgtcct caccgtcctg caccaggact ggctgaatgg caaggagtac     960
aagtgcaagg tctccaacaa agccctccca gcccccatcg agaaaaccat ctccaaagcc    1020
aaagggcagc cccgagaacc acaggtgtac accctgcccc catcccggga ggagatgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaatga                                        1347
```

<210> SEQ ID NO 295
<211> LENGTH: 33
<212> TYPE: DNA
<213> ORGANISM: Oryctolagus cuniculus

<400> SEQUENCE: 295

```
caggccagtg agaacattgg tagctactta gcc                                   33
```

<210> SEQ ID NO 296
<211> LENGTH: 21
<212> TYPE: DNA
<213> ORGANISM: Oryctolagus cuniculus

<400> SEQUENCE: 296

```
agggcttcca ctctggcatc t                                                21
```

<210> SEQ ID NO 297
<211> LENGTH: 36
<212> TYPE: DNA
<213> ORGANISM: Oryctolagus cuniculus

<400> SEQUENCE: 297

```
caacagggtt acaatagtga gaatcttgat aatgct                                36
```

<210> SEQ ID NO 298
<211> LENGTH: 15
<212> TYPE: DNA
<213> ORGANISM: Oryctolagus cuniculus

<400> SEQUENCE: 298
atgtattcaa tgggc 15

<210> SEQ ID NO 299
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 299
tggattagtt atggtggtac tgcatactac gctagcagcg ctaagggc 48

<210> SEQ ID NO 300
<211> LENGTH: 30
<212> TYPE: DNA
<213> ORGANISM: Oryctolagus cuniculus

<400> SEQUENCE: 300
gagactcctg ttaattacta cttggacatt 30

<210> SEQ ID NO 301
<211> LENGTH: 327
<212> TYPE: DNA
<213> ORGANISM: Oryctolagus cuniculus

<400> SEQUENCE: 301
gcattcgaat tgacccagac tccatcctcc gtggaggcag ctgtgggagg cacagtcacc 60
atcaagtgcc aggccagtca gaacattgtt accaatttag cctggtatca acagaaacca 120
gggcagcctc ccaagctcct gatctatggt gcatccactc tggcatctgg ggtctcatcg 180
cggttcaaag gcagtggatc tgggacacag ttcactctca ccatcagcga cctggagtgt 240
gccgatgctg ccacttattt ctgtcagagc tatgatggtt ttaatagtgc tgggttcggc 300
ggagggaccg aggtggtggt caaacgt 327

<210> SEQ ID NO 302
<211> LENGTH: 648
<212> TYPE: DNA
<213> ORGANISM: Artificial Sequence
<220> FEATURE:
<223> OTHER INFORMATION: Chemically Synthesized

<400> SEQUENCE: 302
gcattcgaat tgacccagac tccatcctcc gtggaggcag ctgtgggagg cacagtcacc 60
atcaagtgcc aggccagtca gaacattgtt accaatttag cctggtatca acagaaacca 120
gggcagcctc ccaagctcct gatctatggt gcatccactc tggcatctgg ggtctcatcg 180
cggttcaaag gcagtggatc tgggacacag ttcactctca ccatcagcga cctggagtgt 240
gccgatgctg ccacttattt ctgtcagagc tatgatggtt ttaatagtgc tgggttcggc 300
ggagggaccg aggtggtggt caaacgtacg gtagcggccc catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgttag 648

<210> SEQ ID NO 303
<211> LENGTH: 360
<212> TYPE: DNA
<213> ORGANISM: Oryctolagus cuniculus

<400> SEQUENCE: 303
cagtcgctgg aggagtccgg gggtcgcctg gtcacgcctg ggacacccct gacactcacc 60
tgcacagcct ctggattctc cctcagtggc tacgacatga gctgggtccg ccaggctcca 120
ggaaaggggc tggaatacat cggactcatt agttatgatg gtaacacata ctacgcgacc 180
tgggcgaaag gccgattcac catctccaaa acctcgacca cggtggatct gaaaatcacc 240
agtccgacaa ccgaggacac ggccacctat ttctgtgcca gaagtcttta tgctggtcct 300
aatgctggta tcggaccgtt taacatctgg ggccagggga ccctcgtcac cgtctcgagc 360

<210> SEQ ID NO 304
<211> LENGTH: 1353
<212> TYPE: DNA
<213> ORGANISM: Artificial Sequence
<220> FEATURE:
<223> OTHER INFORMATION: Chemically Synthesized

<400> SEQUENCE: 304
cagtcgctgg aggagtccgg gggtcgcctg gtcacgcctg ggacacccct gacactcacc 60
tgcacagcct ctggattctc cctcagtggc tacgacatga gctgggtccg ccaggctcca 120
ggaaaggggc tggaatacat cggactcatt agttatgatg gtaacacata ctacgcgacc 180
tgggcgaaag gccgattcac catctccaaa acctcgacca cggtggatct gaaaatcacc 240
agtccgacaa ccgaggacac ggccacctat ttctgtgcca gaagtcttta tgctggtcct 300
aatgctggta tcggaccgtt taacatctgg ggccagggga ccctcgtcac cgtctcgagc 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagag agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacgcc 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctac agcaagctca ccgtggacaa gagcaggtgg 1260
cagcagggga acgtcttctc atgctccgtg atgcatgagg ctctgcacaa ccactacacg 1320
cagaagagcc tctccctgtc tccgggtaaa tga 1353

<210> SEQ ID NO 305
<211> LENGTH: 33
<212> TYPE: DNA
<213> ORGANISM: Oryctolagus cuniculus

<400> SEQUENCE: 305
caggccagtc agaacattgt taccaattta gcc 33

<210> SEQ ID NO 306
<211> LENGTH: 21
<212> TYPE: DNA
<213> ORGANISM: Oryctolagus cuniculus

<400> SEQUENCE: 306
ggtgcatcca ctctggcatc t 21

<210> SEQ ID NO 307
<211> LENGTH: 30
<212> TYPE: DNA
<213> ORGANISM: Oryctolagus cuniculus

<400> SEQUENCE: 307
cagagctatg atggttttaa tagtgctggg 30

<210> SEQ ID NO 308
<211> LENGTH: 15
<212> TYPE: DNA
<213> ORGANISM: Oryctolagus cuniculus

<400> SEQUENCE: 308
ggctacgaca tgagc 15

<210> SEQ ID NO 309
<211> LENGTH: 48
<212> TYPE: DNA
<213> ORGANISM: Oryctolagus cuniculus

<400> SEQUENCE: 309
ctcattagtt atgatggtaa cacatactac gcgacctggg cgaaaggc 48

<210> SEQ ID NO 310
<211> LENGTH: 45
<212> TYPE: DNA
<213> ORGANISM: Oryctolagus cuniculus

<400> SEQUENCE: 310
agtctttatg ctggtcctaa tgctggtatc ggaccgttta acatc 45

<210> SEQ ID NO 311
<211> LENGTH: 327
<212> TYPE: DNA
<213> ORGANISM: Artificial Sequence
<220> FEATURE:
<223> OTHER INFORMATION: Chemically Synthesized

<400> SEQUENCE: 311
gcattccaga tgacccagtc tccatcctcc ctgtctgcat ctgtaggaga cagagtcacc 60
atcacttgcc aggccagtca gaacattgtt accaacttag cctggtatca gcagaaacca 120
gggaaagtcc ctaagctcct gatctatggt gcatccactc tggcatctgg ggtcccatct 180
cgtttcagtg gcagtggatc tgggacagat ttcactctca ccatcagcag cctgcagcct 240
gaagatgttg caacttatta ctgtcagagc tatgatggtt tcaatagtgc tggtttcggc 300
ggaggaacca aggtggaaat caaacgt 327

<210> SEQ ID NO 312
<211> LENGTH: 648
<212> TYPE: DNA
<213> ORGANISM: Artificial Sequence
<220> FEATURE:
<223> OTHER INFORMATION: Chemically Synthesized

<400> SEQUENCE: 312
gcattccaga tgacccagtc tccatcctcc ctgtctgcat ctgtaggaga cagagtcacc 60
atcacttgcc aggccagtca gaacattgtt accaacttag cctggtatca gcagaaacca 120
gggaaagtcc ctaagctcct gatctatggt gcatccactc tggcatctgg ggtcccatct 180
cgtttcagtg gcagtggatc tgggacagat ttcactctca ccatcagcag cctgcagcct 240
gaagatgttg caacttatta ctgtcagagc tatgatggtt tcaatagtgc tggtttcggc 300
ggaggaacca aggtggaaat caaacgtacg gtagcggccc catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgttag 648

<210> SEQ ID NO 313
<211> LENGTH: 369
<212> TYPE: DNA
<213> ORGANISM: Artificial Sequence
<220> FEATURE:
<223> OTHER INFORMATION: Chemically Synthesized

<400> SEQUENCE: 313
caggtacagc tggtggagtc tggtggaggc gtggtccagc ctgggaggtc cctgagactc 60
tcctgtgcag cttctggatt ctccctcagt ggctacgaca tgagctgggt ccgtcaggct 120
ccaggcaagg gactggagtg ggtgggactc attagttatg atggtaacac atactacgcg 180
acctccgcga aaggccgatt caccatctcc agagacaatt ccaagaacac gctgtacctg 240
caaatgtcta gcctgagagc cgaggacacg gctgtgtatt actgtgctag aagtctttat 300
gctggtccta atgctggtat cggaccgttt aacatctggg gccaaggtac cctcgtcacc 360
gtctcgagc 369

<210> SEQ ID NO 314
<211> LENGTH: 1362
<212> TYPE: DNA
<213> ORGANISM: Artificial Sequence
<220> FEATURE:
<223> OTHER INFORMATION: Chemically Synthesized

<400> SEQUENCE: 314
caggtacagc tggtggagtc tggtggaggc gtggtccagc ctgggaggtc cctgagactc 60
tcctgtgcag cttctggatt ctccctcagt ggctacgaca tgagctgggt ccgtcaggct 120
ccaggcaagg gactggagtg ggtgggactc attagttatg atggtaacac atactacgcg 180
acctccgcga aaggccgatt caccatctcc agagacaatt ccaagaacac gctgtacctg 240

-continued

```
caaatgtcta gcctgagagc cgaggacacg gctgtgtatt actgtgctag aagtctttat    300

gctggtccta atgctggtat cggaccgttt aacatctggg gccaaggtac cctcgtcacc    360

gtctcgagcg cctccaccaa gggcccatcg gtcttccccc tggcaccctc ctccaagagc    420

acctctgggg gcacagcggc cctgggctgc ctggtcaagg actacttccc cgaaccggtg    480

acggtgtcgt ggaactcagg cgccctgacc agcggcgtgc acaccttccc ggctgtccta    540

cagtcctcag gactctactc cctcagcagc gtggtgaccg tgccctccag cagcttgggc    600

acccagacct acatctgcaa cgtgaatcac aagcccagca acaccaaggt ggacaagaga    660

gttgagccca aatcttgtga caaaactcac acatgcccac cgtgcccagc acctgaactc    720

ctggggggac cgtcagtctt cctcttcccc ccaaaaccca aggacaccct catgatctcc    780

cggacccctg aggtcacatg cgtggtggtg gacgtgagcc acgaagaccc tgaggtcaag    840

ttcaactggt acgtggacgg cgtggaggtg cataatgcca agacaaagcc gcgggaggag    900

cagtacgcca gcacgtaccg tgtggtcagc gtcctcaccg tcctgcacca ggactggctg    960

aatggcaagg agtacaagtg caaggtctcc aacaaagccc tcccagcccc catcgagaaa   1020

accatctcca aagccaaagg gcagccccga gaaccacagg tgtacaccct gcccccatcc   1080

cgggaggaga tgaccaagaa ccaggtcagc ctgacctgcc tggtcaaagg cttctatccc   1140

agcgacatcg ccgtggagtg ggagagcaat gggcagccgg agaacaacta caagaccacg   1200

cctcccgtgc tggactccga cggctccttc ttcctctaca gcaagctcac cgtggacaag   1260

agcaggtggc agcaggggaa cgtcttctca tgctccgtga tgcatgaggc tctgcacaac   1320

cactacacgc agaagagcct ctccctgtct ccgggtaaat ga                      1362


<210> SEQ ID NO 315
<211> LENGTH: 33
<212> TYPE: DNA
<213> ORGANISM: Oryctolagus cuniculus

<400> SEQUENCE: 315

caggccagtc agaacattgt taccaactta gcc                                  33


<210> SEQ ID NO 316
<211> LENGTH: 21
<212> TYPE: DNA
<213> ORGANISM: Oryctolagus cuniculus

<400> SEQUENCE: 316

ggtgcatcca ctctggcatc t                                               21


<210> SEQ ID NO 317
<211> LENGTH: 29
<212> TYPE: DNA
<213> ORGANISM: Oryctolagus cuniculus

<400> SEQUENCE: 317

cagagctatg atggtttcaa tagtgctgg                                       29


<210> SEQ ID NO 318
<211> LENGTH: 15
<212> TYPE: DNA
<213> ORGANISM: Oryctolagus cuniculus

<400> SEQUENCE: 318

ggctacgaca tgagc                                                      15
```

<210> SEQ ID NO 319
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 319
ctcattagtt atgatggtaa cacatactac gcgacctccg cgaaaggc 48

<210> SEQ ID NO 320
<211> LENGTH: 45
<212> TYPE: DNA
<213> ORGANISM: Oryctolagus cuniculus

<400> SEQUENCE: 320
agtctttatg ctggtcctaa tgctggtatc ggaccgttta acatc 45

<210> SEQ ID NO 321
<211> LENGTH: 336
<212> TYPE: DNA
<213> ORGANISM: Oryctolagus cuniculus

<400> SEQUENCE: 321
gccgccgtgc tgacccagac tccatctccc gtgtctgcag ctgtgggagg cacagtcagc 60
atcagttgcc agtccagtca gaatgtttat aagaacaact acttatcctg gtatcagcag 120
aaaccagggc agcctcccaa gctcctgatc tacaaggcat ccactctggc atctggggtc 180
ccatcgcggt tcaaaggcgg tggatctggg acagatttca ctctcaccat cagcgacgtg 240
cagtgtgacg ctgctgccac ttactactgt gcaggcggtt ataccagtag tagtgataat 300
gctttcggcg gagggaccga ggtggtggtc aaacgt 336

<210> SEQ ID NO 322
<211> LENGTH: 656
<212> TYPE: DNA
<213> ORGANISM: Artificial Sequence
<220> FEATURE:
<223> OTHER INFORMATION: Chemically Synthesized

<400> SEQUENCE: 322
gccgccgtgc tgacccagac tccatctccc gtgtctgcag ctgtgggagg cacagtcagc 60
atcagttgcc agtccagtca gaatgtttat aagaacaact acttatcctg gtatcagcag 120
aaaccagggc agcctcccaa gctcctgatc tacaaggcat ccactctggc atctggggtc 180
ccatcgcggt tcaaaggcgg tggatctggg acagatttca ctctcaccat cagcgacgtg 240
cagtgtgacg ctgctgccac ttactactgt gcaggcggtt ataccagtag tagtgataat 300
gctttcggcg gagggaccga ggtggtggtc aaacgtacgg tagcggcccc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgtta 656

<210> SEQ ID NO 323
<211> LENGTH: 351
<212> TYPE: DNA
<213> ORGANISM: Oryctolagus cuniculus

<400> SEQUENCE: 323
cagtcggtgg aggcgtccgg gggtcgcctg gtcacgcctg ggacacccct gacactcacc 60
tgcacagcct ctggattctc cctcagtacc tactggatga gctgggtccg ccaggctcca 120
gggaaggggc tggaatggat cggagacatt tattttagta atgaagaaac aaactacgcg 180
agctgggcga aaggccgatt taccatctcc aaaacctcga ccacggtgga tctgaatgtc 240
atcagtccga caaccgagga cacggccacc tatttctgtg ccagaggttc tcctgatgtt 300
gatattggta tagatatgtg gggcccgggc accctcgtca ccgtctcgag c 351

<210> SEQ ID NO 324
<211> LENGTH: 1344
<212> TYPE: DNA
<213> ORGANISM: Artificial Sequence
<220> FEATURE:
<223> OTHER INFORMATION: Chemically Synthesized

<400> SEQUENCE: 324
cagtcggtgg aggcgtccgg gggtcgcctg gtcacgcctg ggacacccct gacactcacc 60
tgcacagcct ctggattctc cctcagtacc tactggatga gctgggtccg ccaggctcca 120
gggaaggggc tggaatggat cggagacatt tattttagta atgaagaaac aaactacgcg 180
agctgggcga aaggccgatt taccatctcc aaaacctcga ccacggtgga tctgaatgtc 240
atcagtccga caaccgagga cacggccacc tatttctgtg ccagaggttc tcctgatgtt 300
gatattggta tagatatgtg gggcccgggc accctcgtca ccgtctcgag cgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660
gacaaaactc acacatgccc accgtgccca gcacctgaac tcctgggggg accgtcagtc 720
ttcctcttcc ccccaaaacc caaggacacc ctcatgatct cccggacccc tgaggtcaca 780
tgcgtggtgg tggacgtgag ccacgaagac cctgaggtca agttcaactg gtacgtggac 840
ggcgtggagg tgcataatgc caagacaaag ccgcgggagg agcagtacgc cagcacgtac 900
cgtgtggtca gcgtcctcac cgtcctgcac caggactggc tgaatggcaa ggagtacaag 960
tgcaaggtct ccaacaaagc cctcccagcc cccatcgaga aaaccatctc caaagccaaa 1020
gggcagcccc gagaaccaca ggtgtacacc ctgcccccat cccgggagga gatgaccaag 1080
aaccaggtca gcctgacctg cctggtcaaa ggcttctatc ccagcgacat cgccgtggag 1140
tgggagagca atgggcagcc ggagaacaac tacaagacca cgcctcccgt gctggactcc 1200
gacggctcct tcttcctcta cagcaagctc accgtggaca agagcaggtg gcagcagggg 1260
aacgtcttct catgctccgt gatgcatgag gctctgcaca accactacac gcagaagagc 1320
ctctccctgt ctccgggtaa atga 1344

<210> SEQ ID NO 325
<211> LENGTH: 39
<212> TYPE: DNA
<213> ORGANISM: Oryctolagus cuniculus

<400> SEQUENCE: 325

-continued cagtccagtc agaatgttta taagaacaac tacttatcc 39

<210> SEQ ID NO 326
<211> LENGTH: 21
<212> TYPE: DNA
<213> ORGANISM: Oryctolagus cuniculus

<400> SEQUENCE: 326
aaggcatcca ctctggcatc t 21

<210> SEQ ID NO 327
<211> LENGTH: 33
<212> TYPE: DNA
<213> ORGANISM: Oryctolagus cuniculus

<400> SEQUENCE: 327
gcaggcggtt ataccagtag tagtgataat gct 33

<210> SEQ ID NO 328
<211> LENGTH: 15
<212> TYPE: DNA
<213> ORGANISM: Oryctolagus cuniculus

<400> SEQUENCE: 328
acctactgga tgagc 15

<210> SEQ ID NO 329
<211> LENGTH: 51
<212> TYPE: DNA
<213> ORGANISM: Oryctolagus cuniculus

<400> SEQUENCE: 329
gacatttatt ttagtaatga agaaacaaac tacgcgagct gggcgaaagg c 51

<210> SEQ ID NO 330
<211> LENGTH: 33
<212> TYPE: DNA
<213> ORGANISM: Oryctolagus cuniculus

<400> SEQUENCE: 330
ggttctcctg atgttgatat tggtatagat atg 33

<210> SEQ ID NO 331
<211> LENGTH: 336
<212> TYPE: DNA
<213> ORGANISM: Artificial Sequence
<220> FEATURE:
<223> OTHER INFORMATION: Chemically Synthesized

<400> SEQUENCE: 331
gacatccaga tgacccagtc tccatcctcc ctgtctgcat ctgtaggaga cagagtcacc 60
atcacttgcc agtccagtca gaatgtttat aagaacaact acttatcctg gtatcagcag 120
aaaccaggga aagtccctaa gctcctgatc tataaggcat ccactctggc atctggggtc 180
ccatctcgtt tcagtggcag tggatctggg acagatttca ctctcaccat cagcagcctg 240
cagcctgaag atgttgcaac ttattactgt gcaggcggtt ataccagtag tagtgataat 300
gctttcggcg gaggaaccaa ggtggaaatc aaacgt 336

<210> SEQ ID NO 332
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 332
gacatccaga tgacccagtc tccatcctcc ctgtctgcat ctgtaggaga cagagtcacc 60
atcacttgcc agtccagtca gaatgtttat aagaacaact acttatcctg gtatcagcag 120
aaaccaggga aagtccctaa gctcctgatc tataaggcat ccactctggc atctggggtc 180
ccatctcgtt tcagtggcag tggatctggg acagatttca ctctcaccat cagcagcctg 240
cagcctgaag atgttgcaac ttattactgt gcaggcggtt ataccagtag tagtgataat 300
gctttcggcg gaggaaccaa ggtggaaatc aaacgtacgg tagcggcccc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgttag 657

<210> SEQ ID NO 333
<211> LENGTH: 360
<212> TYPE: DNA
<213> ORGANISM: Artificial Sequence
<220> FEATURE:
<223> OTHER INFORMATION: Chemically Synthesized

<400> SEQUENCE: 333
gaggtgcagc tggtggagtc tgggggaggc ttggtccagc ctggggggtc cctgagactc 60
tcctgtgcag cctctggatt caccgtcagt acctactgga tgagctgggt ccgtcaggct 120
ccagggaagg ggctggagtg ggtcggagac atttacttta gtaatgaaga aacaaactac 180
gcgagcagcg cgaaaggccg attcaccatc tccagagaca attccaagaa caccctgtat 240
cttcaaatga acagcctgag agctgaggac actgctgtgt attactgtgc tagaggttct 300
cctgatgttg atattggtat agatatgtgg ggcccaggga ccctcgtcac cgtctcgagc 360

<210> SEQ ID NO 334
<211> LENGTH: 1353
<212> TYPE: DNA
<213> ORGANISM: Artificial Sequence
<220> FEATURE:
<223> OTHER INFORMATION: Chemically Synthesized

<400> SEQUENCE: 334
gaggtgcagc tggtggagtc tgggggaggc ttggtccagc ctggggggtc cctgagactc 60
tcctgtgcag cctctggatt caccgtcagt acctactgga tgagctgggt ccgtcaggct 120
ccagggaagg ggctggagtg ggtcggagac atttacttta gtaatgaaga aacaaactac 180
gcgagcagcg cgaaaggccg attcaccatc tccagagaca attccaagaa caccctgtat 240
cttcaaatga acagcctgag agctgaggac actgctgtgt attactgtgc tagaggttct 300
cctgatgttg atattggtat agatatgtgg ggcccaggga ccctcgtcac cgtctcgagc 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600

-continued

```
tacatctgca acgtgaatca caagcccagc aacaccaagg tggacaagag agttgagccc    660

aaatcttgtg acaaaactca cacatgccca ccgtgcccag cacctgaact cctgggggga    720

ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgcgggagga gcagtacgcc    900

agcacgtacc gtgtggtcag cgtcctcacc gtcctgcacc aggactggct gaatggcaag    960

gagtacaagt gcaaggtctc caacaaagcc ctcccagccc ccatcgagaa aaccatctcc   1020

aaagccaaag ggcagccccg agaaccacag gtgtacaccc tgcccccatc ccgggaggag   1080

atgaccaaga accaggtcag cctgacctgc ctggtcaaag gcttctatcc cagcgacatc   1140

gccgtggagt gggagagcaa tgggcagccg gagaacaact acaagaccac gcctcccgtg   1200

ctggactccg acggctcctt cttcctctac agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtaaa tga                                1353


<210> SEQ ID NO 335
<211> LENGTH: 39
<212> TYPE: DNA
<213> ORGANISM: Oryctolagus cuniculus

<400> SEQUENCE: 335

cagtccagtc agaatgttta taagaacaac tacttatcc                             39


<210> SEQ ID NO 336
<211> LENGTH: 21
<212> TYPE: DNA
<213> ORGANISM: Oryctolagus cuniculus

<400> SEQUENCE: 336

aaggcatcca ctctggcatc t                                                21


<210> SEQ ID NO 337
<211> LENGTH: 33
<212> TYPE: DNA
<213> ORGANISM: Oryctolagus cuniculus

<400> SEQUENCE: 337

gcaggcggtt ataccagtag tagtgataat gct                                   33


<210> SEQ ID NO 338
<211> LENGTH: 15
<212> TYPE: DNA
<213> ORGANISM: Oryctolagus cuniculus

<400> SEQUENCE: 338

acctactgga tgagc                                                       15


<210> SEQ ID NO 339
<211> LENGTH: 51
<212> TYPE: DNA
<213> ORGANISM: Artificial Sequence
<220> FEATURE:
<223> OTHER INFORMATION: Chemically Synthesized

<400> SEQUENCE: 339

gacatttact ttagtaatga agaaacaaac tacgcgagca gcgcgaaagg c               51
```

<210> SEQ ID NO 340
<211> LENGTH: 33
<212> TYPE: DNA
<213> ORGANISM: Oryctolagus cuniculus

<400> SEQUENCE: 340
ggttctcctg atgttgatat tggtatagat atg 33

<210> SEQ ID NO 341
<211> LENGTH: 336
<212> TYPE: DNA
<213> ORGANISM: Oryctolagus cuniculus

<400> SEQUENCE: 341
gcagccgtgc tgacccagac accatcgccc gtgtctgcag ctgtgggaga cacagtcacc 60
atcaagtgcc agtccagtca gagtgtttat aagaacaact acttatcctg gtatcagcag 120
aaaccagggc agcctcccaa gctcctgatc tatgatgcat ccaatctgcc atctggggtc 180
ccatcacggt tcagcggcag tggatctggg acacagttca ctctcaccat cagcggcgtg 240
cagtgtgacg atgctgccac ttactactgt ctaggcgatt atgatgatga tactgataat 300
ggtttcggcg gagggaccga ggtggtggtc aaacgt 336

<210> SEQ ID NO 342
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 342
gcagccgtgc tgacccagac accatcgccc gtgtctgcag ctgtgggaga cacagtcacc 60
atcaagtgcc agtccagtca gagtgtttat aagaacaact acttatcctg gtatcagcag 120
aaaccagggc agcctcccaa gctcctgatc tatgatgcat ccaatctgcc atctggggtc 180
ccatcacggt tcagcggcag tggatctggg acacagttca ctctcaccat cagcggcgtg 240
cagtgtgacg atgctgccac ttactactgt ctaggcgatt atgatgatga tactgataat 300
ggtttcggcg gagggaccga ggtggtggtc aaacgtacgg tagcggcccc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgttag 657

<210> SEQ ID NO 343
<211> LENGTH: 336
<212> TYPE: DNA
<213> ORGANISM: Oryctolagus cuniculus

<400> SEQUENCE: 343
cagtcggtgg aggagtccgg gggtcgcctg gtcacgcctg ggacacccct gacactcacc 60
tgcacagtct ctggaatcga cctcagtagc tatgcaatga tctgggtccg ccaggctcca 120
gggaaggggc tggaatacat cggaatcatt tggagtggtg gcacctacta cgcgacctgg 180
gcgaaaggcc gattcaccat ctccaaaacc tcgaccacgg tggatctgca aatcaccagt 240
ccgacaaccg aggacgcggc cacctatttc tgtgccgcag gtggtggtag tatttatgat 300
gtttggggcc cgggcaccct ggtcaccgtc tcgagc 336

<210> SEQ ID NO 344
<211> LENGTH: 1329
<212> TYPE: DNA
<213> ORGANISM: Artificial Sequence
<220> FEATURE:
<223> OTHER INFORMATION: Chemically Synthesized

<400> SEQUENCE: 344
cagtcggtgg aggagtccgg gggtcgcctg gtcacgcctg ggacacccct gacactcacc 60
tgcacagtct ctggaatcga cctcagtagc tatgcaatga tctgggtccg ccaggctcca 120
gggaaggggc tggaatacat cggaatcatt tggagtggtg gcacctacta cgcgacctgg 180
gcgaaaggcc gattcaccat ctccaaaacc tcgaccacgg tggatctgca aatcaccagt 240
ccgacaaccg aggacgcggc cacctatttc tgtgccgcag gtggtggtag tatttatgat 300
gtttggggcc cgggcaccct ggtcaccgtc tcgagcgcct ccaccaaggg cccatcggtc 360
ttccccctgg caccctcctc caagagcacc tctgggggca cagcggccct gggctgcctg 420
gtcaaggact acttccccga accggtgacg gtgtcgtgga actcaggcgc cctgaccagc 480
ggcgtgcaca ccttcccggc tgtcctacag tcctcaggac tctactccct cagcagcgtg 540
gtgaccgtgc cctccagcag cttgggcacc cagacctaca tctgcaacgt gaatcacaag 600
cccagcaaca ccaaggtgga caagagagtt gagcccaaat cttgtgacaa aactcacaca 660
tgcccaccgt gcccagcacc tgaactcctg gggggaccgt cagtcttcct cttcccccca 720
aaacccaagg acaccctcat gatctcccgg acccctgagg tcacatgcgt ggtggtggac 780
gtgagccacg aagaccctga ggtcaagttc aactggtacg tggacggcgt ggaggtgcat 840
aatgccaaga caaagccgcg ggaggagcag tacgccagca cgtaccgtgt ggtcagcgtc 900
ctcaccgtcc tgcaccagga ctggctgaat ggcaaggagt acaagtgcaa ggtctccaac 960
aaagccctcc cagcccccat cgagaaaacc atctccaaag ccaaagggca gccccgagaa 1020
ccacaggtgt acaccctgcc cccatcccgg gaggagatga ccaagaacca ggtcagcctg 1080
acctgcctgg tcaaaggctt ctatcccagc gacatcgccg tggagtggga gagcaatggg 1140
cagccggaga acaactacaa gaccacgcct cccgtgctgg actccgacgg ctccttcttc 1200
ctctacagca agctcaccgt ggacaagagc aggtggcagc aggggaacgt cttctcatgc 1260
tccgtgatgc atgaggctct gcacaaccac tacacgcaga agagcctctc cctgtctccg 1320
ggtaaatga 1329

<210> SEQ ID NO 345
<211> LENGTH: 39
<212> TYPE: DNA
<213> ORGANISM: Oryctolagus cuniculus

<400> SEQUENCE: 345
cagtccagtc agagtgttta taagaacaac tacttatcc 39

<210> SEQ ID NO 346
<211> LENGTH: 21
<212> TYPE: DNA
<213> ORGANISM: Oryctolagus cuniculus

<400> SEQUENCE: 346
gatgcatcca atctgccatc t 21

<210> SEQ ID NO 347
<211> LENGTH: 33
<212> TYPE: DNA
<213> ORGANISM: Oryctolagus cuniculus

<400> SEQUENCE: 347
ctaggcgatt atgatgatga tactgataat ggt 33

<210> SEQ ID NO 348
<211> LENGTH: 15
<212> TYPE: DNA
<213> ORGANISM: Oryctolagus cuniculus

<400> SEQUENCE: 348
agctatgcaa tgatc 15

<210> SEQ ID NO 349
<211> LENGTH: 45
<212> TYPE: DNA
<213> ORGANISM: Oryctolagus cuniculus

<400> SEQUENCE: 349
atcatttgga gtggtggcac ctactacgcg acctgggcga aaggc 45

<210> SEQ ID NO 350
<211> LENGTH: 24
<212> TYPE: DNA
<213> ORGANISM: Oryctolagus cuniculus

<400> SEQUENCE: 350
ggtggtggta gtatttatga tgtt 24

<210> SEQ ID NO 351
<211> LENGTH: 336
<212> TYPE: DNA
<213> ORGANISM: Oryctolagus cuniculus

<400> SEQUENCE: 351
gccctggtga tgacccagac tccatcctcc acgtctgaac cagtgggagg cacagtcacc 60
atcaattgcc aggctagtca gaatattggt aacgacctat cctggtatca gcagaaacca 120
gggcagcctc ccgagctcct aatctattct acatccaaac tggcaactgg ggtcccaaag 180
cggttcagtg gcagcagatc tgggacacag ttcactctca ccatcagcga cctggagtgt 240
gacgatgctg ccacttacta ctgtctaggt gtttatagtt atattagtga tgatggtaat 300
gctttcggcg gagggaccga ggtggtggtc aaacgt 336

<210> SEQ ID NO 352
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 352
gccctggtga tgacccagac tccatcctcc acgtctgaac cagtgggagg cacagtcacc 60
atcaattgcc aggctagtca gaatattggt aacgacctat cctggtatca gcagaaacca 120
gggcagcctc ccgagctcct aatctattct acatccaaac tggcaactgg ggtcccaaag 180
cggttcagtg gcagcagatc tgggacacag ttcactctca ccatcagcga cctggagtgt 240
gacgatgctg ccacttacta ctgtctaggt gtttatagtt atattagtga tgatggtaat 300

-continued

```
gctttcggcg gagggaccga ggtggtggtc aaacgtacgg tagcggcccc atctgtcttc    360

atcttcccgc catctgatga gcagttgaaa tctggaactg cctctgttgt gtgcctgctg    420

aataacttct atcccagaga ggccaaagta cagtggaagg tggataacgc cctccaatcg    480

ggtaactccc aggagagtgt cacagagcag gacagcaagg acagcaccta cagcctcagc    540

agcaccctga cgctgagcaa agcagactac gagaaacaca aagtctacgc ctgcgaagtc    600

acccatcagg gcctgagctc gcccgtcaca aagagcttca acaggggaga gtgttag       657
```

<210> SEQ ID NO 353
<211> LENGTH: 360
<212> TYPE: DNA
<213> ORGANISM: Oryctolagus cuniculus

<400> SEQUENCE: 353

```
cagtcggtgg aggagttcgg gggtcgcctg gtcacgcctg ggacacccct gacactcacc     60

tgcaccgtct ctggattctc cctcaataac tatgcaatga cctgggtccg ccaggctcca    120

gggaaggggc tggagtggat cgggatcatt ggtagtattg gtaccacata ctacgcgagc    180

tgggcgaaag gccgattctt catctccaaa acctcgacca ctgtggatct gaaaatcatt    240

agtccgacaa ccgaggacac ggccacctat ttctgtgcca gagatgctgg cgttactgtt    300

gatggttatg gctactactt taacatctgg ggcccaggca ccctcgtcac cgtctcgagc    360
```

<210> SEQ ID NO 354
<211> LENGTH: 1353
<212> TYPE: DNA
<213> ORGANISM: Artificial Sequence
<220> FEATURE:
<223> OTHER INFORMATION: Chemically Synthesized

<400> SEQUENCE: 354

```
cagtcggtgg aggagttcgg gggtcgcctg gtcacgcctg ggacacccct gacactcacc     60

tgcaccgtct ctggattctc cctcaataac tatgcaatga cctgggtccg ccaggctcca    120

gggaaggggc tggagtggat cgggatcatt ggtagtattg gtaccacata ctacgcgagc    180

tgggcgaaag gccgattctt catctccaaa acctcgacca ctgtggatct gaaaatcatt    240

agtccgacaa ccgaggacac ggccacctat ttctgtgcca gagatgctgg cgttactgtt    300

gatggttatg gctactactt taacatctgg ggcccaggca ccctcgtcac cgtctcgagc    360

gcctccacca agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagag agttgagccc    660

aaatcttgtg acaaaactca cacatgccca ccgtgcccag cacctgaact cctgggggga    720

ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgcgggagga gcagtacgcc    900

agcacgtacc gtgtggtcag cgtcctcacc gtcctgcacc aggactggct gaatggcaag    960

gagtacaagt gcaaggtctc caacaaagcc ctcccagccc ccatcgagaa aaccatctcc   1020

aaagccaaag ggcagccccg agaaccacag gtgtacaccc tgcccccatc ccgggaggag   1080

atgaccaaga accaggtcag cctgacctgc ctggtcaaag gcttctatcc cagcgacatc   1140
```

gccgtggagt gggagagcaa tgggcagccg gagaacaact acaagaccac gcctcccgtg 1200
ctggactccg acggctcctt cttcctctac agcaagctca ccgtggacaa gagcaggtgg 1260
cagcagggga acgtcttctc atgctccgtg atgcatgagg ctctgcacaa ccactacacg 1320
cagaagagcc tctccctgtc tccgggtaaa tga 1353

<210> SEQ ID NO 355
<211> LENGTH: 33
<212> TYPE: DNA
<213> ORGANISM: Oryctolagus cuniculus

<400> SEQUENCE: 355
caggctagtc agaatattgg taacgaccta tcc 33

<210> SEQ ID NO 356
<211> LENGTH: 21
<212> TYPE: DNA
<213> ORGANISM: Oryctolagus cuniculus

<400> SEQUENCE: 356
tctacatcca aactggcaac t 21

<210> SEQ ID NO 357
<211> LENGTH: 39
<212> TYPE: DNA
<213> ORGANISM: Oryctolagus cuniculus

<400> SEQUENCE: 357
ctaggtgttt atagttatat tagtgatgat ggtaatgct 39

<210> SEQ ID NO 358
<211> LENGTH: 15
<212> TYPE: DNA
<213> ORGANISM: Oryctolagus cuniculus

<400> SEQUENCE: 358
aactatgcaa tgacc 15

<210> SEQ ID NO 359
<211> LENGTH: 48
<212> TYPE: DNA
<213> ORGANISM: Oryctolagus cuniculus

<400> SEQUENCE: 359
atcattggta gtattggtac cacatactac gcgagctggg cgaaaggc 48

<210> SEQ ID NO 360
<211> LENGTH: 45
<212> TYPE: DNA
<213> ORGANISM: Oryctolagus cuniculus

<400> SEQUENCE: 360
gatgctggcg ttactgttga tggttatggc tactacttta acatc 45

<210> SEQ ID NO 361
<211> LENGTH: 336
<212> TYPE: DNA
<213> ORGANISM: Oryctolagus cuniculus

<400> SEQUENCE: 361
gccatcgaaa tgacccagac tccattctcc gtgtctgcag ctgtgggagg cacagtcacc 60
atcaagtgcc aggccagtca gaccattagc aactacttag cctggtatca gcagaaacca 120
gggcagcctc ccaagctcct gatctatggt gcatccaatc tggaatctgg ggtcccatcg 180
cggttcaaag gcagtggatc tgggacacag ttcactctca ccatcagcga cctggagtgt 240
gacgatgctg ccacttacta ctgtcaacag ggttatacta tcagtaatgt tgataacaat 300
gttttcggcg gagggaccga ggtggtggtc aaacgt 336

<210> SEQ ID NO 362
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 362
gccatcgaaa tgacccagac tccattctcc gtgtctgcag ctgtgggagg cacagtcacc 60
atcaagtgcc aggccagtca gaccattagc aactacttag cctggtatca gcagaaacca 120
gggcagcctc ccaagctcct gatctatggt gcatccaatc tggaatctgg ggtcccatcg 180
cggttcaaag gcagtggatc tgggacacag ttcactctca ccatcagcga cctggagtgt 240
gacgatgctg ccacttacta ctgtcaacag ggttatacta tcagtaatgt tgataacaat 300
gttttcggcg gagggaccga ggtggtggtc aaacgtacgg tagcggcccc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgttag 657

<210> SEQ ID NO 363
<211> LENGTH: 345
<212> TYPE: DNA
<213> ORGANISM: Oryctolagus cuniculus

<400> SEQUENCE: 363
cagtcgctgg aggagtccgg gggtcgcctg gtcacgcctg gggggatccct gacactcacc 60 tgcgcagcct ctggattctc cctcactggc tacaacttgg tctgggtccg ccaggctcca 120
gggaaggggc tggagtggat cggattcatt agttatggtg ataccacata ctacgcgagc 180
tgggcgaaag gccgattcac catctccaaa acctcgacca cggtgactct gacgatcacc 240
gatctgcaac cttcagacac gggcacctat ttctgtgcca gagagactgc taatacttat 300
gattatggca tctggggccc aggcaccctc gtcaccgtct cgagc 345

<210> SEQ ID NO 364
<211> LENGTH: 1338
<212> TYPE: DNA
<213> ORGANISM: Artificial Sequence
<220> FEATURE:
<223> OTHER INFORMATION: Chemically Synthesized

<400> SEQUENCE: 364
cagtcgctgg aggagtccgg gggtcgcctg gtcacgcctg gggggatccct gacactcacc 60 tgcgcagcct ctggattctc cctcactggc tacaacttgg tctgggtccg ccaggctcca 120
gggaaggggc tggagtggat cggattcatt agttatggtg ataccacata ctacgcgagc 180
tgggcgaaag gccgattcac catctccaaa acctcgacca cggtgactct gacgatcacc 240

```
gatctgcaac cttcagacac gggcacctat ttctgtgcca gagagactgc taatacttat    300

gattatggca tctggggccc aggcaccctc gtcaccgtct cgagcgcctc caccaagggc    360

ccatcggtct tcccccctggc accctcctcc aagagcacct ctgggggcac agcggccctg    420

ggctgcctgg tcaaggacta cttccccgaa ccggtgacgg tgtcgtggaa ctcaggcgcc    480

ctgaccagcg gcgtgcacac cttcccggct gtcctacagt cctcaggact ctactccctc    540

agcagcgtgg tgaccgtgcc ctccagcagc ttgggcaccc agacctacat ctgcaacgtg    600

aatcacaagc ccagcaacac caaggtggac aagagagttg agcccaaatc ttgtgacaaa    660

actcacacat gcccaccgtg cccagcacct gaactcctgg ggggaccgtc agtcttcctc    720

ttccccccaa aacccaagga caccctcatg atctcccgga cccctgaggt cacatgcgtg    780

gtggtggacg tgagccacga agaccctgag gtcaagttca actggtacgt ggacggcgtg    840

gaggtgcata atgccaagac aaagccgcgg gaggagcagt acgccagcac gtaccgtgtg    900

gtcagcgtcc tcaccgtcct gcaccaggac tggctgaatg gcaaggagta caagtgcaag    960

gtctccaaca aagccctccc agcccccatc gagaaaacca tctccaaagc caaagggcag   1020

ccccgagaac cacaggtgta caccctgccc ccatcccggg aggagatgac caagaaccag   1080

gtcagcctga cctgcctggt caaaggcttc tatcccagcg acatcgccgt ggagtgggag   1140

agcaatgggc agccggagaa caactacaag accacgcctc ccgtgctgga ctccgacggc   1200

tccttcttcc tctacagcaa gctcaccgtg gacaagagca ggtggcagca ggggaacgtc   1260

ttctcatgct ccgtgatgca tgaggctctg cacaaccact acacgcagaa gagcctctcc   1320

ctgtctccgg gtaaatga                                                 1338
```

```
<210> SEQ ID NO 365
<211> LENGTH: 33
<212> TYPE: DNA
<213> ORGANISM: Oryctolagus cuniculus

<400> SEQUENCE: 365

caggccagtc agaccattag caactactta gcc                                  33


<210> SEQ ID NO 366
<211> LENGTH: 21
<212> TYPE: DNA
<213> ORGANISM: Oryctolagus cuniculus

<400> SEQUENCE: 366

ggtgcatcca atctggaatc t                                               21


<210> SEQ ID NO 367
<211> LENGTH: 39
<212> TYPE: DNA
<213> ORGANISM: Oryctolagus cuniculus

<400> SEQUENCE: 367

caacagggtt atactatcag taatgttgat aacaatgtt                            39


<210> SEQ ID NO 368
<211> LENGTH: 15
<212> TYPE: DNA
<213> ORGANISM: Oryctolagus cuniculus

<400> SEQUENCE: 368

ggctacaact tggtc                                                      15
```

<210> SEQ ID NO 369
<211> LENGTH: 48
<212> TYPE: DNA
<213> ORGANISM: Oryctolagus cuniculus

<400> SEQUENCE: 369
ttcattagtt atggtgatac cacatactac gcgagctggg cgaaaggc 48

<210> SEQ ID NO 370
<211> LENGTH: 30
<212> TYPE: DNA
<213> ORGANISM: Oryctolagus cuniculus

<400> SEQUENCE: 370
gagactgcta atacttatga ttatggcatc 30

<210> SEQ ID NO 371
<211> LENGTH: 336
<212> TYPE: DNA
<213> ORGANISM: Artificial Sequence
<220> FEATURE:
<223> OTHER INFORMATION: Chemically Synthesized

<400> SEQUENCE: 371
gacatccaga tgacccagtc tccttccacc ctgtctgcat ctgtaggaga cagagtcacc 60
atcacttgtc aggctagtca gaccattagc aactacttag cctggtatca gcagaaacca 120
ggaaaagccc ctaagctcct gatctatggt gcatccaatc tggaatctgg agtcccatca 180
aggttcagcg gcagtggatc tggaacagaa ttcactctca ccatcagcag cctgcagcct 240
gatgattttg caacttacta ctgtcaacag ggttatacta tcagtaatgt tgataacaat 300
gttttcggcg gaggaaccaa ggtggaaatc aaacgt 336

<210> SEQ ID NO 372
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 372
gacatccaga tgacccagtc tccttccacc ctgtctgcat ctgtaggaga cagagtcacc 60
atcacttgtc aggctagtca gaccattagc aactacttag cctggtatca gcagaaacca 120
ggaaaagccc ctaagctcct gatctatggt gcatccaatc tggaatctgg agtcccatca 180
aggttcagcg gcagtggatc tggaacagaa ttcactctca ccatcagcag cctgcagcct 240
gatgattttg caacttacta ctgtcaacag ggttatacta tcagtaatgt tgataacaat 300
gttttcggcg gaggaaccaa ggtggaaatc aaacgtacgg tagcggcccc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgttag 657

<210> SEQ ID NO 373
<211> LENGTH: 354
<212> TYPE: DNA
<213> ORGANISM: Artificial Sequence
<220> FEATURE:
<223> OTHER INFORMATION: Chemically Synthesized

<400> SEQUENCE: 373
gaggtgcagc tggtggagtc tgggggaggc ttggtccagc ctggggggtc cctgagactc 60
tcctgtgcag cctctggatt caccgtcagt ggctacaact tggtctgggt ccgtcaggct 120
ccagggaagg ggctggagtg ggtcggattc attagttatg gtgataccac atactacgct 180
agctctgcta aaggccgatt caccatctcc agagacaatt ccaagaacac cctgtatctt 240
caaatgaaca gcctgagagc tgaggacact gctgtgtatt actgtgctag agagactgct 300
aatacttatg attatggcat ctggggccaa gggaccctcg tcaccgtctc gagc 354

<210> SEQ ID NO 374
<211> LENGTH: 1347
<212> TYPE: DNA
<213> ORGANISM: Artificial Sequence
<220> FEATURE:
<223> OTHER INFORMATION: Chemically Synthesized

<400> SEQUENCE: 374
gaggtgcagc tggtggagtc tgggggaggc ttggtccagc ctggggggtc cctgagactc 60
tcctgtgcag cctctggatt caccgtcagt ggctacaact tggtctgggt ccgtcaggct 120
ccagggaagg ggctggagtg ggtcggattc attagttatg gtgataccac atactacgct 180
agctctgcta aaggccgatt caccatctcc agagacaatt ccaagaacac cctgtatctt 240
caaatgaaca gcctgagagc tgaggacact gctgtgtatt actgtgctag agagactgct 300
aatacttatg attatggcat ctggggccaa gggaccctcg tcaccgtctc gagcgcctcc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcaccca gacctacatc 600
tgcaacgtga atcacaagcc cagcaacacc aaggtggaca agagagttga gcccaaatct 660
tgtgacaaaa ctcacacatg cccaccgtgc ccagcacctg aactcctggg gggaccgtca 720
gtcttcctct tccccccaaa acccaaggac accctcatga tctcccggac ccctgaggtc 780
acatgcgtgg tggtggacgt gagccacgaa gaccctgagg tcaagttcaa ctggtacgtg 840
gacggcgtgg aggtgcataa tgccaagaca aagccgcggg aggagcagta cgccagcacg 900
taccgtgtgg tcagcgtcct caccgtcctg caccaggact ggctgaatgg caaggagtac 960
aagtgcaagg tctccaacaa agccctccca gcccccatcg agaaaaccat ctccaaagcc 1020
aaagggcagc cccgagaacc acaggtgtac accctgcccc catcccggga ggagatgacc 1080
aagaaccagg tcagcctgac ctgcctggtc aaaggcttct atcccagcga catcgccgtg 1140
gagtgggaga gcaatgggca gccggagaac aactacaaga ccacgcctcc cgtgctggac 1200
tccgacggct ccttcttcct ctacagcaag ctcaccgtgg acaagagcag gtggcagcag 1260
gggaacgtct tctcatgctc cgtgatgcat gaggctctgc acaaccacta cacgcagaag 1320
agcctctccc tgtctccggg taaatga 1347

<210> SEQ ID NO 375
<211> LENGTH: 33
<212> TYPE: DNA
<213> ORGANISM: Oryctolagus cuniculus

<400> SEQUENCE: 375
caggctagtc agaccattag caactactta gcc 33

<210> SEQ ID NO 376
<211> LENGTH: 21
<212> TYPE: DNA
<213> ORGANISM: Oryctolagus cuniculus

<400> SEQUENCE: 376
ggtgcatcca atctggaatc t 21

<210> SEQ ID NO 377
<211> LENGTH: 39
<212> TYPE: DNA
<213> ORGANISM: Oryctolagus cuniculus

<400> SEQUENCE: 377
caacagggtt atactatcag taatgttgat aacaatgtt 39

<210> SEQ ID NO 378
<211> LENGTH: 15
<212> TYPE: DNA
<213> ORGANISM: Oryctolagus cuniculus

<400> SEQUENCE: 378
ggctacaact tggtc 15

<210> SEQ ID NO 379
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 379
ttcattagtt atggtgatac cacatactac gctagctctg ctaaaggc 48

<210> SEQ ID NO 380
<211> LENGTH: 30
<212> TYPE: DNA
<213> ORGANISM: Oryctolagus cuniculus

<400> SEQUENCE: 380
gagactgcta atacttatga ttatggcatc 30

<210> SEQ ID NO 381
<211> LENGTH: 336
<212> TYPE: DNA
<213> ORGANISM: Oryctolagus cuniculus

<400> SEQUENCE: 381
gccgccgtgc tgacccagac tccatctccc gtgtctgcag ctgtgggagg cacagtcagc 60
atcagttgcc agtccagtca gaatgtttat aagaacaact atttatcctg gtatcagcag 120
aaaccagggc agcctcccaa gctcctgatc tacaaggctt ccactctggc atctggggtc 180
ccatcgcggt tcaaaggcag tggatctggg acagatttca ctctcaccat cagcgacgtg 240
cagtgtgacg ctgctgccac ttactactgt gcaggcggtt atagtagtag tagtgataat 300
gctttcggcg gagggaccga ggtggtggtc aaacgt 336

<210> SEQ ID NO 382
<211> LENGTH: 657

<212> TYPE: DNA
<213> ORGANISM: Artificial Sequence
<220> FEATURE:
<223> OTHER INFORMATION: Chemically Synthesized

<400> SEQUENCE: 382
gccgccgtgc tgacccagac tccatctccc gtgtctgcag ctgtgggagg cacagtcagc 60
atcagttgcc agtccagtca gaatgtttat aagaacaact atttatcctg gtatcagcag 120
aaaccagggc agcctcccaa gctcctgatc tacaaggctt ccactctggc atctggggtc 180
ccatcgcggt tcaaaggcag tggatctggg acagatttca ctctcaccat cagcgacgtg 240
cagtgtgacg ctgctgccac ttactactgt gcaggcggtt atagtagtag tagtgataat 300
gctttcggcg gagggaccga ggtggtggtc aaacgtacgg tagcggcccc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgttag 657

<210> SEQ ID NO 383
<211> LENGTH: 351
<212> TYPE: DNA
<213> ORGANISM: Oryctolagus cuniculus

<400> SEQUENCE: 383
cagtcggtgg aggcgtccgg gggtcgtctg gtcatgcctg gaggatccct gacactcacc 60
tgcacagcct ctggattctc cctcagtacc tactggatgt cctgggtccg ccaggctcca 120
gggaaggggc tggaatggat cggagacatt tattttagta atgaggaaac aaactacgcg 180
acctgggcga aaggccgatt taccatctcc aaaacctcga ccacggtgga tctgaatgtc 240
atcagtccga caaccgagga cacggccacc tatttctgtg caagaggttc tcctgatgtt 300
gagattgcta tagatatgtg gggccagggc accctcgtca ccgtctcgag c 351

<210> SEQ ID NO 384
<211> LENGTH: 1344
<212> TYPE: DNA
<213> ORGANISM: Artificial Sequence
<220> FEATURE:
<223> OTHER INFORMATION: Chemically Synthesized

<400> SEQUENCE: 384
cagtcggtgg aggcgtccgg gggtcgtctg gtcatgcctg gaggatccct gacactcacc 60
tgcacagcct ctggattctc cctcagtacc tactggatgt cctgggtccg ccaggctcca 120
gggaaggggc tggaatggat cggagacatt tattttagta atgaggaaac aaactacgcg 180
acctgggcga aaggccgatt taccatctcc aaaacctcga ccacggtgga tctgaatgtc 240
atcagtccga caaccgagga cacggccacc tatttctgtg caagaggttc tcctgatgtt 300
gagattgcta tagatatgtg gggccagggc accctcgtca ccgtctcgag cgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600

-continued

```
aacgtgaatc acaagcccag caacaccaag gtggacaaga gagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacgc cagcacgtac    900

cgtgtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggagga gatgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa atga                                          1344
```

<210> SEQ ID NO 385
<211> LENGTH: 39
<212> TYPE: DNA
<213> ORGANISM: Oryctolagus cuniculus

<400> SEQUENCE: 385

```
cagtccagtc agaatgttta taagaacaac tatttatcc                            39
```

<210> SEQ ID NO 386
<211> LENGTH: 21
<212> TYPE: DNA
<213> ORGANISM: Oryctolagus cuniculus

<400> SEQUENCE: 386

```
aaggcttcca ctctggcatc t                                               21
```

<210> SEQ ID NO 387
<211> LENGTH: 33
<212> TYPE: DNA
<213> ORGANISM: Oryctolagus cuniculus

<400> SEQUENCE: 387

```
gcaggcggtt atagtagtag tagtgataat gct                                  33
```

<210> SEQ ID NO 388
<211> LENGTH: 15
<212> TYPE: DNA
<213> ORGANISM: Oryctolagus cuniculus

<400> SEQUENCE: 388

```
acctactgga tgtcc                                                      15
```

<210> SEQ ID NO 389
<211> LENGTH: 51
<212> TYPE: DNA
<213> ORGANISM: Oryctolagus cuniculus

<400> SEQUENCE: 389

```
gacatttatt ttagtaatga ggaaacaaac tacgcgacct gggcgaaagg c              51
```

<210> SEQ ID NO 390
<211> LENGTH: 33

<212> TYPE: DNA
<213> ORGANISM: Oryctolagus cuniculus

<400> SEQUENCE: 390
ggttctcctg atgttgagat tgctatagat atg 33

<210> SEQ ID NO 391
<211> LENGTH: 336
<212> TYPE: DNA
<213> ORGANISM: Artificial Sequence
<220> FEATURE:
<223> OTHER INFORMATION: Chemically Synthesized

<400> SEQUENCE: 391
gacatccaga tgacccagtc tccatcctcc ctgtctgcat ctgtaggaga cagagtcacc 60
atcacttgcc agtccagtca gaatgtttat aagaacaact acttatcctg gtatcagcag 120
aaaccaggga aagtccctaa gctcctgatc tataaggcat ccactctggc atctggggtc 180
ccatctcgtt tcagtggcag tggatctggg acagatttca ctctcaccat cagcagcctg 240
cagcctgaag atgttgcaac ttattactgt gcaggcggtt ataccagtag tagtgataat 300
gctttcggcg gaggaaccaa ggtggaaatc aaacgt 336

<210> SEQ ID NO 392
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 392
gacatccaga tgacccagtc tccatcctcc ctgtctgcat ctgtaggaga cagagtcacc 60
atcacttgcc agtccagtca gaatgtttat aagaacaact acttatcctg gtatcagcag 120
aaaccaggga aagtccctaa gctcctgatc tataaggcat ccactctggc atctggggtc 180
ccatctcgtt tcagtggcag tggatctggg acagatttca ctctcaccat cagcagcctg 240
cagcctgaag atgttgcaac ttattactgt gcaggcggtt ataccagtag tagtgataat 300
gctttcggcg gaggaaccaa ggtggaaatc aaacgtacgg tagcggcccc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgttag 657

<210> SEQ ID NO 393
<211> LENGTH: 360
<212> TYPE: DNA
<213> ORGANISM: Artificial Sequence
<220> FEATURE:
<223> OTHER INFORMATION: Chemically Synthesized

<400> SEQUENCE: 393
gaggtgcagc tggtggagtc tgggggaggc ttggtccagc ctgggggtc cctgagactc 60 tcctgtgcag cctctggatt caccgtcagt acctactgga tgagctgggt ccgtcaggct 120
ccagggaagg ggctggagtg ggtcggagac atttacttta gtaatgaaga aacaaactac 180
gcgaccagcg cgaaaggccg attcaccatc tccagagaca attccaagaa caccctgtat 240
cttcaaatga acagcctgag agctgaggac actgctgtgt attactgtgc tagaggttct 300
cctgatgttg agattgctat agatatgtgg ggccaaggga ccctcgtcac cgtctcgagc 360

<210> SEQ ID NO 394
<211> LENGTH: 1353
<212> TYPE: DNA
<213> ORGANISM: Artificial Sequence
<220> FEATURE:
<223> OTHER INFORMATION: Chemically Synthesized

<400> SEQUENCE: 394
gaggtgcagc tggtggagtc tgggggaggc ttggtccagc ctggggggtc cctgagactc 60
tcctgtgcag cctctggatt caccgtcagt acctactgga tgagctgggt ccgtcaggct 120
ccagggaagg ggctggagtg ggtcggagac atttacttta gtaatgaaga aacaaactac 180
gcgaccagcg cgaaaggccg attcaccatc tccagagaca attccaagaa caccctgtat 240
cttcaaatga acagcctgag agctgaggac actgctgtgt attactgtgc tagaggttct 300
cctgatgttg agattgctat agatatgtgg ggccaaggga ccctcgtcac cgtctcgagc 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagag agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacgcc 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctac agcaagctca ccgtggacaa gagcaggtgg 1260
cagcagggga acgtcttctc atgctccgtg atgcatgagg ctctgcacaa ccactacacg 1320
cagaagagcc tctccctgtc tccgggtaaa tga 1353

<210> SEQ ID NO 395
<211> LENGTH: 39
<212> TYPE: DNA
<213> ORGANISM: Oryctolagus cuniculus

<400> SEQUENCE: 395
cagtccagtc agaatgttta taagaacaac tacttatcc 39

<210> SEQ ID NO 396
<211> LENGTH: 21
<212> TYPE: DNA
<213> ORGANISM: Oryctolagus cuniculus

<400> SEQUENCE: 396
aaggcatcca ctctggcatc t 21

```
<210> SEQ ID NO 397
<211> LENGTH: 33
<212> TYPE: DNA
<213> ORGANISM: Oryctolagus cuniculus

<400> SEQUENCE: 397

gcaggcggtt ataccagtag tagtgataat gct                                  33


<210> SEQ ID NO 398
<211> LENGTH: 15
<212> TYPE: DNA
<213> ORGANISM: Oryctolagus cuniculus

<400> SEQUENCE: 398

acctactgga tgagc                                                      15


<210> SEQ ID NO 399
<211> LENGTH: 51
<212> TYPE: DNA
<213> ORGANISM: Artificial Sequence
<220> FEATURE:
<223> OTHER INFORMATION: Chemically Synthesized

<400> SEQUENCE: 399

gacatttact ttagtaatga agaaacaaac tacgcgacca gcgcgaaagg c              51


<210> SEQ ID NO 400
<211> LENGTH: 33
<212> TYPE: DNA
<213> ORGANISM: Artificial Sequence
<220> FEATURE:
<223> OTHER INFORMATION: Chemically Synthesized

<400> SEQUENCE: 400

ggttctcctg atgttgagat tgctatagat atg                                  33


<210> SEQ ID NO 401
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 401

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Gly Phe Thr Val Ser Asp
                85                  90                  95

Ile Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125
```

Lys Ser Gly Thr Ala Ser Val Val Cys Leu Leu Asn Asn Phe Tyr Pro
130 135 140

Arg Glu Ala Lys Val Gln Trp Lys Val Asp Asn Ala Leu Gln Ser Gly
145 150 155 160

Asn Ser Gln Glu Ser Val Thr Glu Gln Asp Ser Lys Asp Ser Thr Tyr
165 170 175

Ser Leu Ser Ser Thr Leu Thr Leu Ser Lys Ala Asp Tyr Glu Lys His
180 185 190

Lys Val Tyr Ala Cys Glu Val Thr His Gln Gly Leu Ser Ser Pro Val
195 200 205

Thr Lys Ser Phe Asn Arg Gly Glu Cys
210 215

<210> SEQ ID NO 402
<211> LENGTH: 451
<212> TYPE: PRT
<213> ORGANISM: Artificial Sequence
<220> FEATURE:
<223> OTHER INFORMATION: Chemically Synthesized

<400> SEQUENCE: 402

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Val Ser Asn Tyr
20 25 30

Ala Val Gly Trp Val Arg Gln Ala Pro Gly Lys Gly Leu Glu Trp Val
35 40 45

Gly Ile Ile Gly Arg Asn Gly Asn Thr Trp Tyr Ala Ser Ser Ala Arg
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Gly Tyr Gly Arg Ser Val Ala Tyr Tyr Val Phe Asn Ile Trp Gly
100 105 110

Pro Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Ala Arg Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

-continued

```
Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 403
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 403

gacatccaga tgacccagtc tccttccacc ctgtctgcat ctgtaggaga cagagtcacc     60

atcacttgcc aggccagtca gagcatttac agcaatcttg cctggtatca gcagaaacca    120

ggaaaagccc ctaagctcct gatctatgat gcatccactc tggaatctgg agtcccatca    180

aggttcagcg gcagtggatc tgggacagag tacactctca ccatcagcag cctgcagcct    240

gatgattttg caacttacta ctgccaacag ggttttactg ttagtgatat tgataatgct    300

ttcggcggag gaaccaaggt ggaaatcaaa cgtacggtag cggccccatc tgtcttcatc    360

ttcccgccat ctgatgagca gttgaaatct ggaactgcct ctgttgtgtg cctgctgaat    420

aacttctatc ccagagaggc caaagtacag tggaaggtgg ataacgccct ccaatcgggt    480

aactcccagg agagtgtcac agagcaggac agcaaggaca gcacctacag cctcagcagc    540

accctgacgc tgagcaaagc agactacgag aaacacaaag tctacgcctg cgaagtcacc    600

catcagggcc tgagctcgcc cgtcacaaag agcttcaaca ggggagagtg ttag          654


<210> SEQ ID NO 404
<211> LENGTH: 1356
<212> TYPE: DNA
<213> ORGANISM: Artificial Sequence
<220> FEATURE:
<223> OTHER INFORMATION: Chemically Synthesized

<400> SEQUENCE: 404

gaggtgcagc tggtggagtc tgggggaggc ttggtccagc ctggggggtc cctgagactc     60
```

```
tcctgtgcag cctctggatt caccgtcagt aactatgcag tgggctgggt ccgtcaggct    120

ccagggaagg ggctggagtg ggtcggaatc attggtcgta atggtaacac atggtacgcg    180

agctctgcaa gaggccgatt caccatctcc agagacaatt ccaagaacac cctgtatctt    240

caaatgaaca gcctgagagc tgaggacact gctgtgtatt actgtgctag aggatatggc    300

cgtagtgttg cttactacgt ctttaacatc tggggcccag ggaccctcgt caccgtctcg    360

agcgcctcca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacgc gagagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

gccagcacgt accgtgtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca caggtgtaca ccctgccccc atcccgggag   1080

gagatgacca agaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtgga caagagcagg   1260

tggcagcagg ggaacgtctt ctcatgctcc gtgatgcatg aggctctgca caaccactac   1320

acgcagaaga gcctctccct gtctccgggt aaatga                              1356
```

```
<210> SEQ ID NO 405
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 405

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Gly Phe Thr Val Ser Asp
                85                  90                  95

Ile Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125
```

```
Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 406
<211> LENGTH: 228
<212> TYPE: PRT
<213> ORGANISM: Artificial Sequence
<220> FEATURE:
<223> OTHER INFORMATION: Chemically Synthesized

<400> SEQUENCE: 406

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Ala Val Gly Trp Val Arg Gln Ala Pro Gly Lys Gly Leu Glu Trp Val
        35                  40                  45

Gly Ile Ile Gly Arg Asn Gly Asn Thr Trp Tyr Ala Ser Ser Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Gly Arg Ser Val Ala Tyr Tyr Val Phe Asn Ile Trp Gly
            100                 105                 110

Pro Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Ala Arg Val Glu Pro Lys Ser Cys
    210                 215                 220

Asp Lys Thr His
225


<210> SEQ ID NO 407
<211> LENGTH: 217
<212> TYPE: PRT
<213> ORGANISM: Artificial Sequence
<220> FEATURE:
```

<223> OTHER INFORMATION: Chemically Synthesized

<400> SEQUENCE: 407

Asp Ile Gln Met Thr Gln Ser Pro Ser Thr Leu Ser Ala Ser Val Gly
1 5 10 15

Asp Arg Val Thr Ile Thr Cys Gln Ala Ser Gln Ser Ile Tyr Ser Asn
20 25 30

Leu Ala Trp Tyr Gln Gln Lys Pro Gly Lys Ala Pro Lys Leu Leu Ile
35 40 45

Tyr Asp Ala Ser Thr Leu Glu Ser Gly Val Pro Ser Arg Phe Ser Gly
50 55 60

Ser Gly Ser Gly Thr Glu Tyr Thr Leu Thr Ile Ser Ser Leu Gln Pro
65 70 75 80

Asp Asp Phe Ala Thr Tyr Tyr Cys Gln Gln Gly Phe Thr Val Ser Asp
85 90 95

Ile Asp Asn Ala Phe Gly Gly Gly Thr Lys Val Glu Ile Lys Arg Thr
100 105 110

Val Ala Ala Pro Ser Val Phe Ile Phe Pro Pro Ser Asp Glu Gln Leu
115 120 125

Lys Ser Gly Thr Ala Ser Val Val Cys Leu Leu Asn Asn Phe Tyr Pro
130 135 140

Arg Glu Ala Lys Val Gln Trp Lys Val Asp Asn Ala Leu Gln Ser Gly
145 150 155 160

Asn Ser Gln Glu Ser Val Thr Glu Gln Asp Ser Lys Asp Ser Thr Tyr
165 170 175

Ser Leu Ser Ser Thr Leu Thr Leu Ser Lys Ala Asp Tyr Glu Lys His
180 185 190

Lys Val Tyr Ala Cys Glu Val Thr His Gln Gly Leu Ser Ser Pro Val
195 200 205

Thr Lys Ser Phe Asn Arg Gly Glu Cys
210 215

<210> SEQ ID NO 408
<211> LENGTH: 228
<212> TYPE: PRT
<213> ORGANISM: Artificial Sequence
<220> FEATURE:
<223> OTHER INFORMATION: Chemically Synthesized

<400> SEQUENCE: 408

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Val Ser Asn Tyr
20 25 30

Ala Val Gly Trp Val Arg Gln Ala Pro Gly Lys Gly Leu Glu Trp Val
35 40 45

Gly Ile Ile Gly Arg Asn Gly Asn Thr Trp Tyr Ala Ser Ser Ala Arg
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Gly Tyr Gly Arg Ser Val Ala Tyr Tyr Val Phe Asn Ile Trp Gly
100 105 110

Pro Gly Thr Leu Val Thr Val Ser Ser Ala Ser Thr Lys Gly Pro Ser
115 120 125

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Ala Arg Val Glu Pro Lys Ser Cys
    210                 215                 220

Asp Lys Thr His
225
```

<210> SEQ ID NO 409
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 409

```
gacatccaga tgacccagtc tccttccacc ctgtctgcat ctgtaggaga cagagtcacc     60

atcacttgcc aggccagtca gagcatttac agcaatcttg cctggtatca gcagaaacca    120

ggaaaagccc ctaagctcct gatctatgat gcatccactc tggaatctgg agtcccatca    180

aggttcagcg gcagtggatc tgggacagag tacactctca ccatcagcag cctgcagcct    240

gatgattttg caacttacta ctgccaacag ggttttactg ttagtgatat tgataatgct    300

ttcggcggag gaaccaaggt ggaaatcaaa cgtacggtag cggccccatc tgtcttcatc    360

ttcccgccat ctgatgagca gttgaaatct ggaactgcct ctgttgtgtg cctgctgaat    420

aacttctatc ccagagaggc caaagtacag tggaaggtgg ataacgccct ccaatcgggt    480

aactcccagg agagtgtcac agagcaggac agcaaggaca gcacctacag cctcagcagc    540

accctgacgc tgagcaaagc agactacgag aaacacaaag tctacgcctg cgaagtcacc    600

catcagggcc tgagctcgcc cgtcacaaag agcttcaaca ggggagagtg ttag          654
```

<210> SEQ ID NO 410
<211> LENGTH: 687
<212> TYPE: DNA
<213> ORGANISM: Artificial Sequence
<220> FEATURE:
<223> OTHER INFORMATION: Chemically Synthesized

<400> SEQUENCE: 410

```
gaggtgcagc tggtggagtc tgggggaggc ttggtccagc ctggggggtc cctgagactc     60

tcctgtgcag cctctggatt caccgtcagt aactatgcag tgggctgggt ccgtcaggct    120

ccagggaagg ggctggagtg ggtcggaatc attggtcgta atggtaacac atggtacgcg    180

agctctgcaa gaggccgatt caccatctcc agagacaatt ccaagaacac cctgtatctt    240

caaatgaaca gcctgagagc tgaggacact gctgtgtatt actgtgctag aggatatggc    300

cgtagtgttg cttactacgt ctttaacatc tggggcccag ggaccctcgt caccgtctcg    360

agcgcctcca ccaagggccc atcggtcttc cccctggcac cctcctccaa gagcacctct    420

gggggcacag cggccctggg ctgcctggtc aaggactact tccccgaacc ggtgacggtg    480
```

tcgtggaact caggcgccct gaccagcggc gtgcacacct tcccggctgt cctacagtcc 540
tcaggactct actccctcag cagcgtggtg accgtgccct ccagcagctt gggcacccag 600
acctacatct gcaacgtgaa tcacaagccc agcaacacca aggtggacgc gagagttgag 660
cccaaatctt gtgacaaaac tcactag 687

<210> SEQ ID NO 411
<211> LENGTH: 120
<212> TYPE: PRT
<213> ORGANISM: Homo sapiens

<400> SEQUENCE: 411

Ser Ser Ser His Pro Ile Phe His Arg Gly Glu Phe Ser Val Cys Asp
1 5 10 15

Ser Val Ser Val Trp Val Gly Asp Lys Thr Thr Ala Thr Asp Ile Lys
20 25 30

Gly Lys Glu Val Met Val Leu Gly Glu Val Asn Ile Asn Asn Ser Val
35 40 45

Phe Lys Gln Tyr Phe Phe Glu Thr Lys Cys Arg Asp Pro Asn Pro Val
50 55 60

Asp Ser Gly Cys Arg Gly Ile Asp Ser Lys His Trp Asn Ser Tyr Cys
65 70 75 80

Thr Thr Thr His Thr Phe Val Lys Ala Leu Thr Met Asp Gly Lys Gln
85 90 95

Ala Ala Trp Arg Phe Ile Arg Ile Asp Thr Ala Cys Val Cys Val Leu
100 105 110

Ser Arg Lys Ala Val Arg Arg Ala
115 120

<210> SEQ ID NO 412
<211> LENGTH: 105
<212> TYPE: PRT
<213> ORGANISM: Homo sapiens

<400> SEQUENCE: 412

Val Ala Ala Pro Ser Val Phe Ile Phe Pro Pro Ser Asp Glu Gln Leu
1 5 10 15

Lys Ser Gly Thr Ala Ser Val Val Cys Leu Leu Asn Asn Phe Tyr Pro
20 25 30

Arg Glu Ala Lys Val Gln Trp Lys Val Asp Asn Ala Leu Gln Ser Gly
35 40 45

Asn Ser Gln Glu Ser Val Thr Glu Gln Asp Ser Lys Asp Ser Thr Tyr
50 55 60

Ser Leu Ser Ser Thr Leu Thr Leu Ser Lys Ala Asp Tyr Glu Lys His
65 70 75 80

Lys Val Tyr Ala Cys Glu Val Thr His Gln Gly Leu Ser Ser Pro Val
85 90 95

Thr Lys Ser Phe Asn Arg Gly Glu Cys
100 105

<210> SEQ ID NO 413
<211> LENGTH: 330
<212> TYPE: PRT
<213> ORGANISM: Homo sapiens

<400> SEQUENCE: 413

Ala Ser Thr Lys Gly Pro Ser Val Phe Pro Leu Ala Pro Ser Ser Lys

-continued

```
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```